US007955814B2

(12) United States Patent
De Kreij et al.

(10) Patent No.: US 7,955,814 B2
(45) Date of Patent: *Jun. 7, 2011

(54) METHOD

(75) Inventors: Arno De Kreij, Lausanne (CH); Susan Mampusti Madrid, Vedbaek (DK); Jørn Dalgaard Mikkelsen, Hvidovre (DK); Jørn Borch Søe, Tilst (DK); Mark Turner, Høsholm (DK); Jonathan Goodwins, Indres et Loire (FR)

(73) Assignee: Danisco A/S, Copenhagen (DK)

( * ) Notice: Subject to any disclaimer, the term of this patent is extended or adjusted under 35 U.S.C. 154(b) by 968 days.

This patent is subject to a terminal disclaimer.

(21) Appl. No.: 11/671,953

(22) Filed: Feb. 6, 2007

(65) Prior Publication Data

US 2008/0063783 A1 Mar. 13, 2008

Related U.S. Application Data

(63) Continuation-in-part of application No. 11/182,408, filed on Jul. 15, 2005, which is a continuation-in-part of application No. PCT/IB2004/000655, filed on Jan. 15, 2004.

(60) Provisional application No. 60/489,441, filed on Jul. 23, 2003.

(30) Foreign Application Priority Data

| Jan. 17, 2003 | (GB) | .................................. | 0301117.8 |
| Jan. 17, 2003 | (GB) | .................................. | 0301118.6 |
| Jan. 17, 2003 | (GB) | .................................. | 0301119.4 |
| Jan. 17, 2003 | (GB) | .................................. | 0301120.2 |
| Jan. 17, 2003 | (GB) | .................................. | 0301121.0 |
| Jan. 17, 2003 | (GB) | .................................. | 0301122.8 |
| Dec. 24, 2003 | (GB) | .................................. | 0330016.7 |

(51) Int. Cl.
*C12Q 1/48* (2006.01)
*C12N 9/10* (2006.01)

(52) U.S. Cl. .............................. 435/15; 435/193; 426/49
(58) Field of Classification Search .................... 435/15, 435/193; 426/49
See application file for complete search history.

(56) References Cited

U.S. PATENT DOCUMENTS

| 2,888,385 A | 5/1959 | Grandel |
| 3,260,606 A | 7/1966 | Azuma |
| 3,368,903 A | 2/1968 | Johnson |
| 3,520,702 A | 7/1970 | Menzi |
| 3,634,195 A | 1/1972 | Melaschouris |
| 3,652,397 A | 3/1972 | Pardun |
| 3,677,902 A | 7/1972 | Aunstrup |
| 3,817,837 A | 6/1974 | Rubenstein et. al. |
| 3,850,752 A | 11/1974 | Wilhelmus et al. |
| 3,852,260 A | 12/1974 | Knutsen |
| 3,939,350 A | 2/1976 | Kronick et al. |
| 3,973,042 A | 8/1976 | Kosikowski |
| 3,996,345 A | 12/1976 | Ullman et al. |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada |
| 4,275,149 A | 6/1981 | Litman et al. |
| 4,277,437 A | 7/1981 | Maggio |
| 4,366,241 A | 12/1982 | Tom et al. |
| 4,399,218 A | 8/1983 | Gauhl |
| 4,567,046 A | 1/1986 | Inoue |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,816,567 A | 3/1989 | Cabilly et al. |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |
| 4,916,064 A | 4/1990 | Derez |
| 5,112,624 A | 5/1992 | Johna |

(Continued)

FOREIGN PATENT DOCUMENTS

AR 331094 2/1995

(Continued)

OTHER PUBLICATIONS

Verenium Corporation leaflet Purifine Enzyme, "Convert Gums to Oils Significantly Increase oil Yields no increase in Free Fatty Acids", San Diego, Jan. 2008.
AOCS Introduction to the Processing of Fats and Oils, four modules on CD-ROM American Oil Chemists Society, 2003, pp. 111-16-111-19.
Anguita et al., Appl. Environ. Microbiol., 1983, vol. 59, No. 8, pp. 2411-2417.
Sutrisno et al., Journal of Bioscience and Bioengineering, 2001 vol. 91, No. 6, pp. 599-602.
Kalscheuer et al., Applied and Environmental Microbiology, 2004, vol. 70, No. 12, pp. 7119-7125.

(Continued)

*Primary Examiner* — Tekchand Saidha
(74) *Attorney, Agent, or Firm* — Vedder Price P.C.; Thomas J. Kowalski; Heidi Lunasin

(57) ABSTRACT

A method for the in situ production of an emulsifier in a foodstuff, wherein a lipid acyltransferase is added to the foodstuff. Preferably the emulsifier is produced without an increase or without a substantial increase in the free fatty acid content of the foodstuff. Preferably, the lipid acyltransferase is one which is capable of transferring an acyl group from a lipid to one or more of the following acyl acceptors: a sterol, a stanol, a carbohydrate, a protein or a sub-unit thereof, glycerol. Preferably, in addition to an emulsifier one or more of a stanol ester or a stanol ester or a protein ester or a carbohydrate ester or a diglyceride or a monoglyceride may be produced. One or more of these may function as an additional emulsifier.

22 Claims, 121 Drawing Sheets

U.S. PATENT DOCUMENTS

| | | |
|---|---|---|
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda |
| 5,264,367 A | 11/1993 | Aalrust |
| 5,273,898 A | 12/1993 | Ishii |
| 5,288,619 A | 2/1994 | Brown |
| 5,290,694 A | 3/1994 | Nakanishi |
| 5,310,679 A | 5/1994 | Artiss et al. |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,674,707 A | 10/1997 | Hintz et al. |
| 5,677,160 A | 10/1997 | Oester |
| 5,695,802 A | 12/1997 | Van Den Ouweland |
| 5,716,654 A | 2/1998 | Groenendaal |
| 5,741,665 A | 4/1998 | Kato et al. |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,824,354 A | 10/1998 | Ritter et al. |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen |
| 6,143,545 A | 11/2000 | Clausen |
| 6,146,869 A | 11/2000 | Harris |
| 6,156,548 A | 12/2000 | Christensen |
| 6,180,406 B1 | 1/2001 | Stemmer |
| 6,254,645 B1 | 7/2001 | Kellis |
| 6,254,903 B1 | 7/2001 | Schuster et al. |
| 6,344,328 B1 | 2/2002 | Short |
| 6,350,604 B1 | 2/2002 | Hirayama |
| 6,358,543 B1 | 3/2002 | Soe |
| 6,361,974 B1 | 3/2002 | Short |
| 6,365,204 B1 | 4/2002 | Spendler |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,726,942 B2 | 4/2004 | Soe et al. |
| 6,730,346 B2 | 5/2004 | Rey |
| 6,815,190 B1 | 11/2004 | Abo |
| 6,852,346 B2 | 2/2005 | Soe |
| 6,866,837 B2 | 3/2005 | Reubi et al. |
| 6,936,289 B2 | 8/2005 | Olsen et al. |
| 6,964,944 B1 | 11/2005 | Callisen et al. |
| 6,967,035 B2 | 11/2005 | Bojsen et al. |
| 7,226,771 B2 | 6/2007 | Gramatikova et al. |
| 7,718,204 B2 | 5/2010 | Soe et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2002/0182734 A1 | 12/2002 | Diaz-Torres et al. |
| 2003/0003561 A1 | 1/2003 | Vind |
| 2003/0028923 A1 | 2/2003 | Lardizabal |
| 2003/0040450 A1 | 2/2003 | Rey |
| 2003/0074695 A1 | 4/2003 | Farese |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0142441 A1 | 7/2004 | Weiss et al. |
| 2004/0235106 A1 | 11/2004 | Kapeller-Libermann |
| 2004/0235119 A1 | 11/2004 | Hoppe et al. |
| 2005/0059130 A1 | 3/2005 | Bojsen |
| 2005/0059131 A1 | 3/2005 | Bisgard-Frantzen |
| 2005/0118697 A1 | 6/2005 | Budolfsen |
| 2005/0142647 A1 | 6/2005 | Wassell |
| 2006/0040357 A1 | 2/2006 | Bardaru et al. |
| 2006/0075518 A1 | 4/2006 | Yaver et al. |
| 2006/0141457 A1 | 6/2006 | Lindqvist et al. |
| 2007/0026106 A1 | 2/2007 | Kreij et al. |
| 2007/0122525 A1 | 5/2007 | Kreij |
| 2008/0063783 A1 | 3/2008 | Kreij et al. |
| 2008/0070287 A1 | 3/2008 | Soe |
| 2008/0131936 A1 | 6/2008 | Miasnikov et al. |
| 2008/0187643 A1 | 8/2008 | Horlacher |

FOREIGN PATENT DOCUMENTS

| | | |
|---|---|---|
| AR | 249546 | 12/1996 |
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| CN | 036151 | 2/2002 |
| CN | 172509 | 6/2003 |
| CN | 97181706.5 | 10/2003 |
| CN | 101200754 | 12/2007 |
| DE | 2817087 | 11/1978 |
| DE | 19620649 | 11/1997 |
| DE | 69129988 | 3/1999 |
| DE | 69330066 | 10/2001 |
| DE | 10018787 | 5/2002 |
| DE | 69527835 | 4/2003 |
| DE | 69528070 | 6/2003 |
| DE | 69333065 | 7/2003 |
| DE | 69904161 | 7/2003 |
| DE | 69716711 | 9/2003 |
| DE | 69333065 | 4/2004 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | PA0543/98 | 4/1998 |

| | | | | | | |
|---|---|---|---|---|---|---|
| DK | PA199801572 | 11/1998 | | EP | 1193314 | 4/2002 |
| DK | PA5677000 | 12/1998 | | EP | 0746618 | 8/2002 |
| DK | PA199801604 | 12/1998 | | EP | 1233676 | 8/2002 |
| DK | PA199901736 | 12/1999 | | EP | 0648263 | 9/2002 |
| DK | PA200000989 | 6/2000 | | EP | 0784674 | 9/2002 |
| DK | PA200000991 | 6/2000 | | EP | 1073339 | 11/2002 |
| DK | PA200100285 | 2/2001 | | EP | 1275711 | 1/2003 |
| DK | PA200100843 | 5/2001 | | EP | 1285969 | 2/2003 |
| DK | EP659049 | 6/2001 | | EP | 1298205 | 4/2003 |
| DK | EP0784674 | 11/2002 | | EP | 0635053 | 6/2003 |
| DK | EP0869167 | 1/2003 | | EP | 0675944 | 6/2003 |
| DK | EP1073339 | 1/2003 | | EP | 0817838 | 6/2003 |
| DK | PA200300634 | 4/2003 | | EP | 1280919 | 6/2003 |
| DK | 5559215 | 7/2003 | | EP | 0746608 | 8/2003 |
| DK | EP0746608 | 10/2003 | | EP | 0851913 | 5/2004 |
| DK | EP1042458 | 3/2004 | | EP | 1262562 | 6/2004 |
| EP | 0064855 | 11/1982 | | EP | 1433852 | 6/2004 |
| EP | 0010296 | 12/1982 | | EP | 0977869 | 7/2004 |
| EP | 0109244 | 5/1984 | | EP | 0743017 | 9/2004 |
| EP | 0130064 | 1/1985 | | EP | 0675949 | 10/2004 |
| EP | 0140542 | 5/1985 | | EP | 0880590 | 10/2004 |
| EP | 0167309 | 1/1986 | | EP | 0897423 | 10/2004 |
| EP | 0171995 | 2/1986 | | EP | 1466980 | 10/2004 |
| EP | 0205208 | 12/1986 | | EP | 0839186 | 11/2004 |
| EP | 0206390 | 12/1986 | | EP | 1162889 | 2/2005 |
| EP | 0214761 | 3/1987 | | EP | 1532863 | 5/2005 |
| EP | 0257388 | 3/1988 | | EP | 1559788 | 8/2005 |
| EP | 0260573 | 3/1988 | | EP | 1363506 | 11/2005 |
| EP | 0334462 | 9/1989 | | EP | 1 624 047 A1 | 2/2006 |
| EP | 0195311 | 6/1990 | | EP | 1 624 047 B1 | 10/2006 |
| EP | 0375102 | 6/1990 | | EP | 1762622 | 3/2007 |
| EP | 0426211 | 5/1991 | | EP | 1 788 080 | 5/2007 |
| EP | 0445692 | 9/1991 | | ES | 535608 | 9/1984 |
| EP | 0449375 | 10/1991 | | ES | 535602 | 10/1984 |
| EP | 0468731 | 1/1992 | | ES | 535609 | 3/1985 |
| EP | 0493045 | 7/1992 | | GB | 1086550 | 10/1967 |
| EP | 0583265 | 10/1992 | | GB | 1442418 | 7/1976 |
| EP | 0513709 | 11/1992 | | GB | 1577933 | 10/1980 |
| EP | 0542351 | 5/1993 | | GB | 2264429 | 9/1993 |
| EP | 0558112 | 9/1993 | | GB | 0028701.1 | 11/2000 |
| EP | 0258068 | 11/1993 | | GB | 2358784 | 8/2001 |
| EP | 0238023 | 12/1993 | | GB | 0301117.8 | 1/2003 |
| EP | 0575133 | 12/1993 | | GB | 0301118.6 | 1/2003 |
| EP | 0580252 | 1/1994 | | GB | 0301119.4 | 1/2003 |
| EP | 0258068 | 8/1994 | | GB | 0301120.2 | 1/2003 |
| EP | 0622446 | 11/1994 | | GB | 0301121.1 | 1/2003 |
| EP | 0652289 | 5/1995 | | GB | 0301122.8 | 1/2003 |
| EP | 0654527 | 5/1995 | | GB | 2379165 | 3/2003 |
| EP | 0396162 | 9/1995 | | GB | 2267033 | 11/2003 |
| EP | 0687414 | 12/1995 | | GB | 0330016.7 | 12/2003 |
| EP | 0585988 | 3/1996 | | JP | 59183881 | 4/1960 |
| EP | 0721981 | 7/1996 | | JP | 54-76892 | 6/1979 |
| EP | 0752008 | 1/1997 | | JP | 5476892 | 6/1979 |
| EP | 0776604 | 6/1997 | | JP | 55131340 | 10/1980 |
| EP | 0531104 | 8/1997 | | JP | 57-189638 | 11/1982 |
| EP | 0808903 | 11/1997 | | JP | 57-189637 | 12/1982 |
| EP | 0682116 | 12/1997 | | JP | 60078529 | 5/1985 |
| EP | 0812910 | 12/1997 | | JP | 62118883 | 11/1985 |
| EP | 0305216 | 3/1998 | | JP | 63042691 | 8/1986 |
| EP | 0847701 | 6/1998 | | JP | 62061590 | 3/1987 |
| EP | 0548228 | 8/1998 | | JP | 62285749 | 12/1987 |
| EP | 0866796 | 9/1998 | | JP | 10203974 | 8/1988 |
| EP | 0702712 | 12/1998 | | JP | 1252294 | 10/1989 |
| EP | 0882797 | 12/1998 | | JP | 2-49593 | 2/1990 |
| EP | 0897667 | 2/1999 | | JP | 2-153997 | 6/1990 |
| EP | 0913092 | 5/1999 | | JP | 04075592 | 3/1992 |
| EP | 0913468 | 5/1999 | | JP | 6014773 | 3/1992 |
| EP | 0321811 | 12/1999 | | JP | 4121186 | 4/1992 |
| EP | 1131416 | 6/2000 | | JP | 15626492 | 6/1992 |
| EP | 0739985 | 11/2000 | | JP | 04200339 | 7/1992 |
| EP | 1057415 | 12/2000 | | JP | 4300839 | 10/1992 |
| EP | 1071734 | 1/2001 | | JP | 4327536 | 11/1992 |
| EP | 0659049 | 3/2001 | | JP | 5211852 | 8/1993 |
| EP | 1103606 | 5/2001 | | JP | 6345800 | 12/1994 |
| EP | 1108360 | 6/2001 | | JP | 8268882 | 4/1995 |
| EP | 1138763 | 10/2001 | | JP | 7231788 | 9/1995 |
| EP | 1145637 | 10/2001 | | JP | 7330794 | 12/1995 |
| EP | 0191217 | 2/2002 | | JP | 8143457 | 6/1996 |
| EP | 0869167 | 2/2002 | | JP | 8266213 | 10/1996 |

| | | | | | |
|---|---|---|---|---|---|
| JP | 9040689 | 2/1997 | WO | WO 98/31790 | 7/1998 |
| JP | 10155493 | 6/1998 | WO | 98/41623 | 9/1998 |
| JP | 10155493 A | 6/1998 | WO | 98/44804 | 10/1998 |
| JP | 11 228986 | 8/1999 | WO | 98/45453 | 10/1998 |
| JP | 11290078 | 10/1999 | WO | 98/50532 | 11/1998 |
| JP | 2000226335 | 8/2000 | WO | 98/51163 | 11/1998 |
| JP | 03/024096 | 7/2001 | WO | 98/59028 | 12/1998 |
| JP | 3553958 | 5/2004 | WO | 99/33964 | 7/1999 |
| KR | 93-700773 | 3/1993 | WO | 99/34011 | 7/1999 |
| KR | 94-10252 | 10/1994 | WO | 99/37782 | 7/1999 |
| KR | 95-700043 | 1/1995 | WO | 99/42566 | 8/1999 |
| KR | 95-702583 | 6/1995 | WO | 99/50399 | 10/1999 |
| KR | 96-704602 | 8/1996 | WO | 99/53001 | 10/1999 |
| KR | 2001-7012115 | 9/2001 | WO | 99/53769 | 10/1999 |
| KR | 2003-7008997 | 10/2003 | WO | 99/55883 | 11/1999 |
| NL | 0784674 | 12/2002 | WO | 00/05396 | 2/2000 |
| NL | 0869167 | 1/2003 | WO | 00/28044 | 5/2000 |
| NL | 1073339 | 2/2003 | WO | 00/32758 | 6/2000 |
| NL | 0746608 | 11/2003 | WO | 00/34450 | 6/2000 |
| PH | 31068 | 11/1984 | WO | 00/36114 | 6/2000 |
| RU | 2140751 | 6/1997 | WO | 00/43036 | 7/2000 |
| RU | 2235775 | 11/1999 | WO | 00/49164 | 8/2000 |
| RU | 2001117497 | 6/2001 | WO | 00/58517 | 10/2000 |
| SE | 9802548 | 7/1998 | WO | 00/59307 | 10/2000 |
| TR | 200101551 | 12/1999 | WO | 00/60063 | 10/2000 |
| WO | 88/02775 | 4/1988 | WO | 00/61771 | 10/2000 |
| WO | 88/03365 | 5/1988 | WO | 00/71808 | 11/2000 |
| WO | 2008/901969 | 3/1989 | WO | 00/75295 | 12/2000 |
| WO | 89/06803 | 7/1989 | WO | 01/16308 | 3/2001 |
| WO | 91/00920 | 1/1991 | WO | 01/27251 | 4/2001 |
| WO | 91/06661 | 5/1991 | WO | 01/29222 | 4/2001 |
| WO | 91/14772 | 10/1991 | WO | WO 00/23461 | 4/2001 |
| WO | WO 91/17243 | 11/1991 | WO | 01/34835 | 5/2001 |
| WO | 92/05249 | 4/1992 | WO | WO 01/39544 | 5/2001 |
| WO | 92/14830 | 9/1992 | WO | 01/39602 | 6/2001 |
| WO | 92/18645 | 10/1992 | WO | 01/42433 | 6/2001 |
| WO | 93/01285 | 1/1993 | WO | 01/47363 | 7/2001 |
| WO | 93/11249 | 6/1993 | WO | 01/66711 | 9/2001 |
| WO | 93/12812 | 7/1993 | WO | 01/78524 | 10/2001 |
| WO | 94/01541 | 1/1994 | WO | WO 01/75083 | 10/2001 |
| WO | 94/04035 | 3/1994 | WO | 01/83559 | 11/2001 |
| WO | 94/14940 | 7/1994 | WO | 01/83770 | 11/2001 |
| WO | 94/14951 | 7/1994 | WO | 01/92502 | 12/2001 |
| WO | 94/26883 | 11/1994 | WO | 02/00852 | 1/2002 |
| WO | 95/06720 | 3/1995 | WO | 02/03805 | 1/2002 |
| WO | 95/09909 | 4/1995 | WO | 02/06457 | 1/2002 |
| WO | 95/22606 | 8/1995 | WO | WO 02/06508 | 1/2002 |
| WO | 95/22615 | 8/1995 | WO | 02/24881 | 3/2002 |
| WO | 95/22625 | 8/1995 | WO | 02/30207 | 4/2002 |
| WO | 95/29996 | 11/1995 | WO | WO 02/39828 | 5/2002 |
| WO | 95/30744 | 11/1995 | WO | 02/055679 | 7/2002 |
| WO | 96/09772 | 4/1996 | WO | 02/062973 | 8/2002 |
| WO | 96/13578 | 5/1996 | WO | 02/065854 | 8/2002 |
| WO | 96/13579 | 5/1996 | WO | 02/066622 | 8/2002 |
| WO | 96/13580 | 5/1996 | WO | 02/094123 | 11/2002 |
| WO | 96/27002 | 9/1996 | WO | WO 0306644 | 1/2003 |
| WO | 96/28542 | 9/1996 | WO | 03/020923 | 3/2003 |
| WO | 96/30502 | 10/1996 | WO | WO 03/020923 | 3/2003 |
| WO | 96/32472 | 10/1996 | WO | WO 03/020941 | 3/2003 |
| WO | 96/39851 | 12/1996 | WO | WO 2006/031699 | 3/2003 |
| WO | 97/04079 | 2/1997 | WO | 03/040091 | 5/2003 |
| WO | 97/05219 | 2/1997 | WO | 03/060112 | 7/2003 |
| WO | 97/07202 | 2/1997 | WO | 03/070013 | 8/2003 |
| WO | 97/11083 | 3/1997 | WO | 03/089620 | 10/2003 |
| WO | 97/14713 | 4/1997 | WO | WO 03/089620 | 10/2003 |
| WO | 97/27237 | 7/1997 | WO | 03/097825 | 11/2003 |
| WO | 97/27276 | 7/1997 | WO | WO 03/97835 | 11/2003 |
| WO | 97/41212 | 11/1997 | WO | 03/099016 | 12/2003 |
| WO | 97/41735 | 11/1997 | WO | 03/100044 | 12/2003 |
| WO | 97/41736 | 11/1997 | WO | 03/102118 | 12/2003 |
| WO | WO 98/00029 | 1/1998 | WO | WO 03/100044 | 12/2003 |
| WO | 98/08939 | 3/1998 | WO | 2004/004467 | 1/2004 |
| WO | 98/14594 | 4/1998 | WO | 2004/018660 | 3/2004 |
| WO | WO 98/13479 | 4/1998 | WO | 2004/053039 | 6/2004 |
| WO | WO 98/16112 | 4/1998 | WO | 2004/053152 | 6/2004 |
| WO | 98/18912 | 5/1998 | WO | 2004/059075 | 7/2004 |
| WO | 98/26057 | 6/1998 | WO | WO 2004/064537 | 8/2004 |
| WO | WO 98/23162 | 6/1998 | WO | WO 2004/084638 | 10/2004 |
| WO | 98/31790 | 7/1998 | WO | 2004/097012 | 11/2004 |

| | | |
|---|---|---|
| WO | 2004/111216 | 12/2004 |
| WO | 2005/003339 | 1/2005 |
| WO | 2005/005977 | 1/2005 |
| WO | 97/07205 | 2/2005 |
| WO | 2005/056782 | 6/2005 |
| WO | 2005/066347 | 7/2005 |
| WO | 2005/066351 | 7/2005 |
| WO | 2005069762 | 8/2005 |
| WO | WO 2005069762 | 8/2005 |
| WO | 2005/080540 | 9/2005 |
| WO | 2005/087918 | 9/2005 |
| WO | WO 2005/111203 | 11/2005 |
| WO | 2006/008508 | 1/2006 |
| WO | 2006/008653 | 1/2006 |
| WO | 2006018205 | 2/2006 |
| WO | WO 200618205 | 2/2006 |
| WO | 2006/032279 | 3/2006 |
| WO | WO 2006/045354 | 5/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2009/002480 | 12/2008 |
| WO | WO 2009/024736 | 2/2009 |
| WO | WO 2009/024862 | 2/2009 |
| WO | WO 2009/081094 | 7/2009 |

OTHER PUBLICATIONS

Brunel et al., J. Biotechnology, Jul. 1, 2004, vol. 111, No. 1, pp. 41-50.
Delphine Briand et al., "Substrate Specificity of the Lipase from *Candida parapsilosis*", Lipids, 1995, vol. 30, No. 8.
"Definition of Recombined Milk", International Dairy Federation, 1979, doc. 116, p. 5.
Stryer, L., Biochemistry, 1981, $2^{nd}$ Edition, W H Freeman and Co., San Francisco, p. 16.
Jennifer L. Seffernick et al., "Melamine Deaminase and Atrazine Chlorohydrolase: 98 Percent Identical but Functionally Different", Journal of Bacteriology, Apr. 2001, vol. 183, No. 8, pp. 2405-2410.
Andrzej Witkowski et al., "Conversion of a β-Ketoacyl Synthase to a Malonyl Decarboxylase by Replacement of the Active-Site Cysteine with Glutamine", Biochemistry, 1999, vol. 38, No. 6, pp. 11643-11650.
"AOCS Introduction to the Processing of Fats and Oils", American Oil Chemists Society, 2003, pp. III 16-19.
Hajime Seino et al., "Enzymatic Synthesis of Carbohydrate Esters of Fatty Acid (10 Esterification of Sucrose, Glucose, Fructose and Sorbitol", JAOCS, Nov. 1984, vol. 61, No. 11.
Roberto A. Chica et al., "Semi-rational approaches to engineering enzyme activity: combining the benefits of directed evolution and rational design", Biotechnology, 2005, vol. 16, pp. 378-384.
Anna Maria V. Garzillo et al., "Production, purification and characterization of glucose oxidase from Penicillium variabile P16[1]", Biotechnol. Appln. Biochem., 1995, vol. 22, pp. 169-178.
Patent Abstracts of Japan; Publication No. 04-370055; Publication Date Dec. 12, 1992.
Patent Abstracts of Japan; Publication No. 07-079687; Publication Date Mar. 28, 1995.
Patent Abstracts of Japan; Publication No. 48-16612; Publication Date May 23, 1973.
"Purifine Enzyme", Verenium Corporation leaftlet, Jan. 2008.
Sequence alignment of database accession No. Q44268 with Seq. ID No. 16, (1996).
Sequence alignment of database accession No. Q44268 with Seq. ID No. 70, (1996).
S. Sen et al., "Developments in Directed Evolution for Improving Enzyme Functions", Appl. Biotechnol., 2007, vol. 143, No. 3, pp. 212-223.
Buckley J. Thomas, "Substrate specificity of bacterial glycerophospholipid: Cholesterol Acyltransferase", Biochemistry, 1982, vol. 21, pp. 6699-6703.
Nerland A.H., "The Nucleotide Sequence of the Gene Encoding GCAT from Aeromonas salmonicida SSP. Salmonicida", Journal of Fish Diseases, 1996, vol. 19, No. 2, pp. 145-150, XP008049669.
Nerland A.H., "Glycerophospholipid-cholesterol acyltransferase precursor", SwissProt, Feb. 11, 2005, XP002318368.
U.S. Appl. No. 60/039,791, filed Mar. 4, 1997, Clausen.
U.S. Appl. No. 60/189,780, filed Mar. 16, 2000, Soe.
U.S. Appl. No. 60/489,441, filed Jul. 23, 2003, Kreij.
Acker, L. "Die Lipide des Getreides, ihre Zusammense und inre Bedeutung", Getreide Mehl Brot (1974) 28:181-187.
Adamzcak, Marek, et al., "Application of Enzymatic Glycerolysis for Production of Monoglycerides from Waste Fats", Polish Journal of Food and Nutrition Science, Mar. 1994, p. 129-133.
Adhikari, B., et al., "Stickiness in Foods: A Review of Mechanisms and Test Methods", International Journal of Food Properties, vol. 4, No. 1, 2001, 1pg.
Agarwal et al., "Lipase Activity of Some Fungi Isolated from Groundnut", Current Science, Dec. 5, 1984, vol. 53, No. 23, p. 1253.
Aires-Barros M.R. et al., Isolation and purification of lipases, in "Lipases their structure, biochemistry and application", editors Woolley et al., Cambridge University Press, 1994, ISBN 0521445469 NZAS-00354436 p. 242-270.
Aisaka, Kazuo et al., "Production of Lipoprotein Lipase and Lipase by Rhizopus japonicu", Agri. Biol. Chem., vol. 43, No. 10, pp. 2125-2129, 1979.
Akoh, Casimir C., et al., "GDSL family of serine esterases/lipases" Progress in Lipid Research, vol. 43, 2004, pp. 534-552.
Allan Svendsen et al., "Biochemical properties of cloned lipases from the Pseudomonas family", Biochimica et Biophysica Acta, vol. 1259, 1995, pp. 9-17.
Al-Obaidy, K A, "Dough and Gluten Characteristics of Good and Poor Quality Flours: Lipid-Protein Bindings affected by Mixing time, water absorption, chemicals and heat," Dissertation Abstracts International B (1987) vol. 47(9) 3597, order No. DA8624641, pp. 266.
Amano Enzyme Inc., http://www.amano-enzyme.co.jp/english/productuse/oil_fat.html. Date of visit: Jun. 21, 2004; (Copyright 2003) pp. 1-2.
Amano Enzymes "Enzymes for Gastrointestinal Digestion" Oct. 1997, pp. 1-2.
Amano Enzymes, Amano Enzyme Europe Ltd, Sep. 1994, pp. 1-4.
Amin, Neelam S., et al., "Direct transformation of site-saturation libraries in Bacillus subtilis", BioTechniques, Dec. 2003, vol. 35 p. 1134-1140.
Andersson, L., et al., "Hydrolysis of galactolipids by human pancreatic lipolytic enzymes and duidenal contents", Journal of Lipid Research, 1995, vol. 36, pp. 1392-1400.
Sander, Andreas, et al., "Herstellung und Anwendungsmoelichkeiten von Eiweiss-Fettsaeurekondensaten/Production and application of acylated proten hydrolysates", Fett/Lipid 99 (1997) Nr. 4, pp. 115-120.
An-I Yeh et al., "Effects of Oxido-reductants on rheological properties of wheat flour dough and comparison with some characteristics of extruded noodles", Cereal Chemistry, 1999, vol. 76, No. 5, pp. 614-620.
Arbige, Michael A et al, "Novel lipase for cheddar cheese flavor development" Food Technology, vol. 40, 1996, p. 91-98.
Archer, David B., et al., "Proteolytic degradation of heterologous proteins expressed in *Aspergillus niger*", Biotechnology Letter, vol. 14, No. 5, May 1992, pp. 357-362.
Arcos J.A. et al, "Quantative Enzymatic Production of 6.O-Acylglucose Esters", Biotechnology and Bioengineering 1998 vol. 57, No. 5, p. 505-509.
Arpigny Jean Louis et al, "Bacterial lipolytic enzymes: Classification and properties", Biochemical Journal, vol. 343, No. 1, Oct. 1, 1999, pp. 177-183, XP002375631.
Assignment Document for Enzymatisk detergent additiv, detergent og vaskemetode, executed Aug. 13, 1986 p. 1-3.
Atomi H, et al., "Microbial lipases-from screening to design", In: Barnes PJ, ed. Oils-Fats-Lipids, 21st World Congress Int Soc Fat Res. England: Bridgwater, 1995: pp. 49-50, vol. 1. NZAS-0016055-NZAS-0016056.
August C.A.P.A. et al. "The use of genetic engineering to obtain efficient production of porcine pancreatic phospholipase A2", Biochimica et Biophysica Acta, vol. 1089, 1991, pp. 345-351.

Aunstrup, Knud et al., "Production of Microbiol Enzymes", Microbiol Technology, Academic Press, 1979, 2nd edition, vol. 1, chap. 9, p. 281-309.
Ausubel, Frederick M., et al. (editors), "Short Protocols in Molecular Biology—A Compendium of Methods from Current Protocols in Molecular Biology", 1995, John Wiley & Sons, Inc, NZAS-0028441-NZAS-002844.
Bachmatova, I., et al., "Lipase of Pseudomonas mendocina 3121-1 and its Substrate Specificty", Biologija, 1995, p. 57-59.
"Fat Splitting, Esterification, and Interesterification", in Bailey's Industrial Oils and Fat Products, vol. 2, 4th Edition, John Wiley and Sons, New York pp. 97-173, 1982.
Balcao V.M et. al., "Bioreactors with immobilized lipase: State of the art," Enzyme Microb Technhol, May 1, 1996; 18(6):392-416.
Balcao, V. et. al. "Lipase Catalyzed Modification of Milkfat," (1998), Biotechnology Advances, vol. 16, No. 2, pp. 309-341.
Ballance, D.J., et al., "Transformation of Aspergillus Nidulans by the orotidine-5'-phosphate decarboxylase gene of neurospora crassa", Biochemical and biophysical Research Communications, vol. 112, No. 1, 1983, pp. 284-289.
Ballance, "Transformation Systems for Filamentous Fungi and an Overview of Fungal Gene Structure", Molecular Industrial Mycology, Systems and Applications for Filamentous Fungi, Leong and Berka (eds.), Marcel Dekker Inc, New York 1991, pp. 1-29.
Barbesgaard, Peder et al, "On the safety of *Aspergillus oryzae*: a review," Applied Microbiology and Biotechnology (1992) 36: 569-572.
Barnes, P.J., "Lipids in Cereal Technology", Food and Science Technology, Academic Press, 1983, pp. 167-171.
Basrl, M., et al., "Amidination of Lipase with Hyrdophobic Imidoesters", JAOCS, vol. 69, No. 6, Jun. 1992, p. 579-582.
Bateman A et. al., "HMM-based databases in InterPro," Briefings in Bioinformatics vol. 3,No. 3, pp. 236-245 (2002).
Bateman A et al, (2002), "The Pfam Protein Families Database," Nucleic Acids Res. vol. 30, No. 1, p. 276-280.
Becker T. "Separation and Purification Processes for Recovery of Industrial Enzymes" in R.K. Singh, S.S.H. Rizvi (eds): Bioseparation processes in Foods, Marcel Dekker, New York (1995) pp. 427-445.
Bekkers et al, "The use of genetic engineering to obtain efficient production of porcine pancreatic phospholipase A2 by *Saccharomyces cerevisiae*," (1991) Biochim Biophys Acta vol. 1089 No. 3, p. 345-51.
Bengtsson Olivecrona Gunilla et al. "Phospholipase activity of milk lipoprotein lipase," Methods in Enzymology, vol. 197, 1991 p. 345-356.
Bentley S D et al, Complete genome sequence of the model actinomycete Streptomyces coelicolor A3(2), Nature vol. 417, 2002, pp. 141-147.
Berger K.G. (1990) "Recent developments in palm oil." Oleagineux, vol. 45, p. 437-443.
Berks, Ben C., "A common export pathway for proteins binding complex redox cofactors?" Molecular Microbiology, 1996, vol. 22, pp. 393-404.
Beucage S.L. et al, (1981), "Deoxynucleoside Phosphoramidites—A New class of Key Intermediates for Deoxypolynucleotide Synthesis," Tetrahedron Letters 22, p. 1859-1869.
Bieleski R.L., Sugar Alcohols, in Loewus F A & Tanner W (eds), Plant Carbohydrates I. Intercellular Carbohydrates Encyclopedia Plant Physiol. N.S., 1982, 13A, chapter 5, p. 158-192, Springer, Berlin.
Bilyk, Alexander, et al., "Lipase-catalyzed triglyceride Hydrolysis in Organic Solvent", pp. 320-323, J, vol. 68, No. 5, May 1991.
Biocatalysts, Limited, Product Sheet for Lipomod(TM) 627P-L627P, published Jan. 9, 2004, Pontypridd UK, p. 1.
Jakobsen, Soren, "Biotekkomet falder hardt til jorden", Borsens, p. 6, Aug. 28, 2002. NZAS-0564031.
Birch et al., "Evidence of Multiple Extracellular Phospholipase Activities of Aspergillus fumigatus", Infection and Immunity, Mar. 1996, vol. 64, No. 3, 1996.
Birgitte Hugh-Jensen et al., "*Rhizomucor miehei* Triglyceride Lipase is Processed and Secreted from Transformed *Aspergillus oryzae*", Lipids, vol. 24, No. 9, 1989.

Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.
Bjorkling, F., et al., "Lipase Catalyzed Organic Synthesis", S. Servie (ed.), Microbial Reagents in Organic Synthesis, pp. 249-260, 1992.
Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.
Bjorkling, Frederik, et al., "Lipase -mediated Formation of Peroxycarboxylic acids used in Catalytic Epoxidation of Alkenes", J. Chem. Soc., Chemical Communications, Issue 19, 1990.
Bjurlin et al. Identification of carboxylesterase activities of commercial triacylglycerol hydrolase (lipase) preparations, Eur. J. Lipid Sci. Technol. 104 (2002) 143-155.
Blain JA et al, The Nature of Mycelial Lipolytic enzymes in filamentous fungi, Fems Microbiol. Lett., 1978, vol. 3, 85-87.
Blecker et al, Improved emulsifying and foaming of whey proteins after enzymic fat hydrolysis, (1997) J Food Science, vol. 62, No. 1.
Blumenthal, Cynthia Z., "Production of toxic metabolites in *Aspergillus niger, Aspergillus oryzae*, and *Trichoderma reesei*: justification of mycotoxin testing in food grade enzyme preparations derived from the three fungi", Regulatory Toxicology and Pharmacology, vol. 39, 2004, p. 214-228.
Boel, Esper, et al.; "*Rhizomucor miehei Triglyceride lipase* is Synthesized as a Precursor"; Novo Research Institute; vol. 23; No. 7; Jul. 1988.
Bornscheuer U T et al, "Optimizing lipases and related enzymes for efficient application," Trends in Biotechnology, Elsevier Publications, Cambridge GB, vol. 20, No. 10, Oct. 1, 2002, pp. 433-437.
Bornscheuer, Uwe T., "Lipase-catalyzed syntheses of monoacylglycerols", Enzyme and Microbiol Technology, vol. 17, pp. 578-586, 1995.
Brady, Leo, et al., "A serine protease triad forms the catalytic centre of a triacylglycerol lipase", Nature, vol. 343, 1990, p. 767-770.
Brockerhoff, Hans, et al., "Lipolytic Enzymes", Academic Press, 1974, 1 page.
Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.
Brzozowski, A.M., et al., "A model for interfacial activation in lipases from the structure of a fungal lipase-inhibitor complex", Nature, vol. 351, 1991, pp. 491-494.
Buckley J. Thomas et al, "Purification and Partial Characterization of a Bacterial Phospholipid: Cholesterol Acyltransferase," Journal of Biological Chemistry, vol. 257, No. 6, pp. 3320-3325, 1982.
Buckley, "Mechanism of action of a bacterial glycerophospholipid cholesterol acyltransferase," Biochemistry 1983, 22, 5490-5493.
Bulkacz J et al, "Phospholipase A activity in supernatants from cultures of *Bacteroides melaninogenicus*," Biochim. Biophys. Acta (1981) vol. 664, pp. 148-155.
Van Den Berg. G, Regulatory status and use of lipase in various countries, Bulletin of the IDF 294/1994—The use of lipases in cheesemaking, pp. 19-20, (1994).
Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.
Butcher, Bronwyn G., et al., "The divergent chromosomal ars operon of *Acidithiobacillus ferrooxidans* is regulated by an atypical ArsR protein," Microbiology, 2002, vol. 148, pp. 3983-3992.
Buxton et al, "Transformation of *Aspergillus niger* using the argB gene of *Aspergillus nidulans*," Gene, 1985, 37:207-214.
Cao, Shu-Gui, et al., "Enzymatic Preparation of Monoglycerides via Glycerolysis of Fats and Oils Catalyzed by Lipase from Pseudomonas Species" National Laboratory of Enzyme Engineering. Monoglycerides, Enzyme Engine, Annals New York Academy of Sciences, 1996, vol. 799, issue 1, p. 670-677.
Carriere et al, "Pancreatic Lipase Structure-Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) "New Chemical methods for Synthesizing polynucleotides," Nuc Acids Res Symp Ser 215-223.

Casimir C A et al "GDSL family of serine esterases/lipases," Progress in Lipid Research, 2004, pp. 534-552.

Castello, P., et al., "Technological and Biochemical effects of exogenous lipases in breadmaking", 2nd European Symposium on enzymes in Grain Processing, Dec. 8-10, 1999, Helsinki, p. 193-199. Published by VTT, Espoo, 2000.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.

Chakravarti DN et al, Biol. Abstracts, 1981, vol. 72, abstract No. 012592.

Cheng Cheng et al., "Transformation of *Trichoderma viride* using the *Neurospora crassa* pyr4 gene and its use in the expression of a Taka-amylase a gene from *Aspergillus oryzae*", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from Arabidopsis", Phytochemical Analysis, vol. 9, pp. 53-57, 1998.

Christophersen, Claus, et al., "Enzymatic Characterisation of Novamyl a Thermostable α-Amylase", Starch/Sturke, vol. 50, 1998, p. 39-45.

Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.

Chung OK et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science and Technology, vol. 103, 2001, pp. 333-340.

Clausen, Kim, "New enzyme for degumming", Oils and Fats International, vol. 17, No. 4, Jun. 2001, pp. 24-25.

Cloning of rad51 and rad52 homologues from *Aspergillus oryzae* and the effect of their overexpression on homologous recombination, Novozymes internal document Feb. 9, 2001.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-0β-D-Glucosylk- and Galactosyl-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998, p. 657-660.

Council Directive of Dec. 21, 1988 (89/107/EEC).

Council Regulation (EC) No. 2991/94 5/12/94 Official Journal of the European Communities, Sep. 12, 1994, No. L316/2-7.

Courtin, Christophe M., et al., "Recent Advances in Enzymes in Grain Processing", Laboratory of Food Chemistry, Leuven, Belgium, 2003, p. 267-274, ISBN 90-9016671-8.

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan. Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.

Daboussi et al, "Heterologous expression of the *Aspergillus nidulans* regulatory gene nirA in *Fusarium oxysporum*," (1991) Gene vol. 109, No. 1, p. 155-60.

Daboussi et al., "Transformation of seven species of filamentous fungi using the nitrate reductase gene of *Aspergillus nidulans*", Curr. Genet., 15:453-456, 1989.

Daftary R.D. et al., Functional Bread-making Properties of Wheat Flour Lipids, Functional Bread-Making Properties of Lipids chapter 2, in Food Technology, Mar. 1968m vol. 22, No. 327, p. 79-82, NZAS-0487568.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three Neocallimastic patriciarum esterases associated with the degradation of complex polysaccharides are members of a new family of hydrolases", Microbiology, vol. 142, pp. 2605-2614, 1997.

Danisco, "Unique Chance for Better Bread" *Direct, A Newsletter from Danisco Ingredients* (1996).

Danisco, Hexose oxidase—nyt enzym med mange mulingheder (advert) Mar. 15, 1999.

Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.

Accession No., P10480 "Glycerophosphospholipid-cholesterol acyltransferase" created Jul. 1, 1989, available at www.ncbi.nlm.nih.gov/entrez.

Database accession No. Q44268 -& Database UniProt 'Online! Nov. 1, 1996.

Database accession No. Q9F7Y6 Database UniProt 'Online!, Mar. 1, 2001.

Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 1997, pp. 81-84.

Database FSTA International Food Information Service (IFIS), Frankfurt/Main, De Nicolas J: "Action of oxidoreductases in breadmaking. Maturation of soft wheat flours and kneading of doughs." XP002077286 see abstract & Annales De Technologie Agricole, vol. 28, No. 4, 1979, pp. 445-468.

Database FSTA International Food Information Service (IFIS), Frankfurt/Main, De Qi SI J: "New enzymes for the baking industry" XP002077284 see abstract & Food Tech Europe vol. 3, No. 1, 1996, pp. 60-64, Novo Nordisk Ferment Ltd.

Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.

Database Uniprotkb Jun. 1, 2003, S. Omura et al: "putative secreted hydrolase from streptomyces avermitilis" XP002376340 retrieved from EBI, Hinxton, UK Database accession No. Q828T4 abstract.

Database Uniprotkb May 1, 2000, S.D. Bentley et al: "Putative Secreted Hydrolase from Streptomyces coelicolor" XP002376339 retrieved from EBI, Hinxton, UK Database accession No. Q9S2A5 abstract.

Davies, Progress in Industrial Microbiology, Martinelli and Kinghorn (eds.), Elsevier, Amsterdam 1994, 29:525-560.

De Haas GH et al, "Purification and Properties of Phospholipase A from Porcine Pancreas" Biochim. Biophys. ACTA, 1968, vol. 139, pp. 103-117.

Declaration by Clive Graham Phipps Walter (Dec C) Jul. 4, 2003.

Declaration by Dr Jorn Borch Soe (Dec F) Dec. 2, 2003.

Declaration by Dr Mark Turner (Dec G) Feb. 4, 2005, pp. 1-6.

Declaration by Henrik Pedersen (Dec A) Jul. 7, 2003, pp. 1-3.

Declaration by Henrik Pedersen, Masoud Rajabi Zargahi and Clive Graham Phipps Walter (Dec. 2) Feb. 7, 2005, pp. 1-26, D46.

Declaration by Janne Brunstedt (Dec D) Jul. 4, 2003.

Declaration by Kazuko Kato, Henrik Pedersen, Masoud Rajabi Zaghari, Clive Phipps Walter, and Janne Brunstedt (Dec I) Feb. 7, 2005.

Declaration by Kim Borch Oct. 17, 2005.

Declaration by Luise Erlandsen Oct. 21, 2005.

Declaration by Masoud Rajabi Zargahi (Dec B) Jul. 7, 2003.

Declaration by Masoud Rajabi Zargahi (Dec E) Jul. 15, 2003.

Declaration by Tina Spendler Oct. 14, 2005.

Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.

Dellaporta, et al.; "A Plant DNA Minipreparation Version II"; Plant Molecular Biology Reporter(1983); vol. 1(4); pp. 19-21.

Derewenda et al, "The crystal and molecular structure of the *Rhizomuxor miehei* Triacylglyceride Lipase at 1.9 Å Resolution", J. Mol. Biol. 1992, 227:818-839.

Derewenda, Urszula, et al., "Catalysis at the Interface: The Anatomy of a Conformational Change in a Triglyceride Lipase", Biochemistry, vol. 31, pp. 1532-1541, 1992.

Dictionary of Biochemistry and Molecular Biology, Stenesh, J. Second Edition, John Wiley, 1975, p. 16, ISBN 0471840890, p. 1-3.

Dinkci. N, Mucor miehei den elde edilen lipaz, Ege Univeraitesi Ziraat Fakultesi Dergisi Cilt, 37, Saiy 2-3, 2000, 141-148.

Direct, "The Road to Success: New Stabilizers Rouses Big Interest," A Newsletter from Danisco Ingredients, Sep. 1996, p. 1-4.

Directive 2000/36/EC. Http://europa.eu.int/scadplus/leg/en/lvb/121122b.htm. Dato: 16.06.04.

Drost-Lustenberger, C and Spendler T Lipopan F BG—Application and Mechanism of a new lipase for baking, Novozymes. Spanish version of EP869167, Novozymes, Oct. 7, 1998.

Drost-Lustenberger, C. et al., Novozymes, "Lipopan F BG—application and mechanism of a new lipase for bread baking" Cereal Food (2003), Novozymes internal draft.

Drost-Lustenberger, Cornelia, et al., "Lipopan F BG-unlocking the natural strengthening potential in dough", Cereal Food, 2004. Novozymes internal draft, p. 1-6.

Duan, Rui Dong, Fat Digestion and Absorption (2000), p. 25-46, publisher AOCS Press, Champaign III CODEN 69ACBA Conference; general review written in English.

Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.

Ducancel, Frederic, et al., "Complete amino acid sequence of a PLA2 from the tiger snake Notechis sculatus scutatus as deduced from a complementary DNA", Nucleic Acids Research, vol. 16, No. 18, 1988.

Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.

Dugruix, A. , et al., Preparation and Handling of Biological Macromolecules, Oxford University Press (1992) p. 31-39.

Dutilh & Groger, "Improvement of Product Attributes of Mayonnaise by Enzymic Hydrolysis of Egg Yolk with Phospholipase A2", 1981 J. Sci. Food Agric. 32, 451-458.

Eddine et al, "Cloning and expression analysis of NhL1, a gene encoding an extracellular lipase from the fungal pea pathogen Nextria haematococca MP VI (Fusarium solani f. sp. pisi) that is expressed in planta", Mol. Genet. Genomics (2001) 265: 215-224.

EFEMA Index of Food Emulsifiers, Mono- and diglycerides of fatty acids, Jan. 2004, 4th Edition, p. 1-3 and 51-55.

Efthymiou CC et al., "Development of domestic feta cheese", Journal of Dairy Science 1964, vol. 47, No. 6, p. 593-598.

Ellaiah et al., "Production of lipase by immobilized cells of *Aspergillus niger*", Process Biochemistry, vol. 39, 2004, pp. 525-528.

Elyk, Alexander, et al., "Lipase-Catalyzed", JAOCS, vol. 08, No. 5, May 1991, pp. 320-323.

Engelhorn and Raab, "Rapid Electroblotting of Small DNA Fragments from Polyacrylamide Gels", Biotechniques (1991) 11(5):594-6.

Engelhorn et al., "Rapid Electroblotting of Small DNA Fragments from Polyacrylamide Gels"; Biotechniques(1991); vol. 11(5); pp. 594-596.

Nagodawithana, T. "Enzymes in food processing" (3rd Ed.), Academic press 1993, p. 205-219.

EPO, Mobay Chemical Corporation—Decision of the Technical Board of Appeal 3.3.1 dated Jul. 1, 1982, *Official Journal EPO*, Oct. 1982, pp. 394-402.

Ettinger, William F. et al., "Structure of Cutinase Gene, cDNA, and the Derived Amino Acid Sequence from Phytopathogenic Fungi", Biochemistry, vol. 26, pp. 7883-7892, 1987.

Euromonitor International, "The World Market for Dairy Products—Introduction, Executive Summary, Operating Environment, World Market Overview, Key Trends and Developments" in *Euromonitor, Strategy 2000*, Feb. 2001.

European Parliament and Council Directive No. 95/2/EC of Feb. 20, 1995 on food additives other than colours and sweeteners. OJ No. L61 Mar. 18, 1995 p. 1-53.

European Parliament and Council Directive No. 98/72/EC of Oct. 15, 1998 amending Directive 95/2/EC on food additives other than colours and sweeteners. OJ No. L295 Nov. 4, 1998 p. 18-30.

European Journal of Biochemistry, vol. 166, 1987, Published by Springer International on behalf of the Federation of European Biochemical Societies.

Ezra, David, et al., "Coronamycins, peptide antibiotics produced by a verticillate *Streptomyces sp.* (MSU-2110) endophytic on *Monstera sp.*", Microbiology, 2004, vol. 150, p. 785-793.

Fauvel, et al.; "Purification of Two Lipases With High Phospholipase A, Activity from Guinea-Pig Pancreas"; Biochimica et Biophysica Acta(1981); vol. 663; pp. 446-456.

Fernandez-Garcia et al., "The use of lipolytic and proteolytic enzymees in the manufacture of manchego type cheese from ovine and bovine milk", 1994 J. Dairy Sci. 77: 2139-2149.

Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.

Ferrer et al, 2000, "Purification and properties of a lipase from *Penicillium chrysogenum* isolated from industrial wastes," J. Chem. Technol. Biotechnol. 75, 569-576.

Finizym Technical Information, Novo Enzymes, 1981.

Fødevarenubusteriet (2003). Bekendtgørelse om indhold af transfedtsyrer I olier og fedtstoffer. Bekendtgørelse nr. 160 af Nov. 3, 2003.

Food Enzymes: Stalingase L, Gist-brocades Food Ingredients, p. 1-2 (Date after 2000).

Vafiades D, "Embracing Enzymes", Food R&D, Dairy Fields ingredient technology section, Mar. 1996 p. 39-44.

Forman, Todd, "Enzymes Used in Bread Baking: An Application Update", Technical Bulletin, vol. XXVI, Issue Oct. 10, 2004.

Fox, et al.; "Isolation and some Properties of Extracellular Heat-Stable Lipases: from *Pseudomonas Fluorescens* Strain AFT 36"; Journal of Dairy Research (1988); vol. 50; pp. 77-89.

Frenken N. et al (1992) "cloning of the Pseudomonas glumae Lipase Gene and Determination of the Active Site Residues," Appl. Envir. Microbiol. 58 3787-3791.

Freshzyme™, Novozymes Product Sheet Baking/2000-11814, NZAS-0265916. Mar. 12, 2001, p. 1-3.

Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.

Frost & Sullivan leaflet for report #7954-88 U.S. Market for Enzymes for Food Applications, May 2001, NZAS-0413133.

Fugman, Douglas A et al "Lipoprotein Lipase and phospholipase A2-Catalyzed hydrolysis of phospholipid vesicles with an encapsulated fluorescent dye," Biochemica et Biophysica acia 795 (1984) 191-195.

Galliard T and Dennis S (1974) Phospholipase, Galactolipase, and Acyl Transferase Activities of a Lipolytic Enzyme from Potatoe, Phytochemistry vol. 13, pp. 1731-1735.

Galliard, "The Enzymic Breakdown of Lipids in Potato Tuber by Phospholipid- and Galactolipid-Acyl Hydrolase Activities and by Lipoxygenase", Phytochemistry, 1970, vol. 9, pp. 1725-1734.

Gan, Z. et al., "Rapid Communication—Antisera agains: Wheat Diacylgalactosylglycerol (MGDG) and Diacyldigalactosylglycerol (DGDG)", Journal of Cereal Science, vol. 18, pp. 207-210, 1993.

Ganghro AB & Dahot MU, Sci Int. (Lahore), 1992, vol. 4, pp. 169-172.

Gemel J et al., "Comparison of galactoplipase activity and free fatty acid levels in chloroplasts of chill-sensitve and chill-resistant plants", European Journal of Biochemistry, vol. 166, 1987, Published by Springer International on behalf of the Federation of European Biochemical Societies, p. 229-233.

Geus et al (1987) Nucleic Acids Research 15(9) p. 3743-3759.

Gilbert, E. Jane, et al., "Purification and properties of extracellular lipase from Pseudomonal aeruginosa EF2", Journal of General Microbiology, 1991, vol. 137, pp. 2223-2229.

Gillian, B., Turgeon et al., "*Cochliobolus heterostrophus* using the *Aspergillus nidulans* amdS gene", Mol Gen Genet, 201: 450-453, 1985.

Godfrey, Tony, et al., "Industrial Enzymology Second Edition", Macmillan Press, 1996, ISBN 0333594649, Chapter 2.17, Olive and other Edible Oils, p. 299-300.

Goodey et al, "Expression and secretion of foreign polypeptides in Yeast," Yeast Biotechnology, Berry et al (eds.), Allen and Unwin, London 1987, pp. 401-429.

Graille J, "Possible applications of acyltransferases in Oleotechnology," Lipid Technology, vol. 5, No. 1, 1993, pp. 11-16.

GRAS Notification dated Apr. 11, 2001 by Novozymes for LecitaseR and LipopanTM F. Gregg L. et al., A lipases preparation produced by *Aspergillus oryzae* expressing the gene encoding a lipases from Fusarium oxyporum. Novo Nordisk A/S product Sheet for Lecitase Novo, Oct. 2000.

Greenough et al (1996) "Safety evaluation of a lipase expressed in *Aspergillus oryzae*," Food Chem Toxicology 34:161-166 and PubMed abstract in respect thereof.

Greenough R J et al, "Safety Evaluation of a Lipase Expressed in *Aspergillus oryzae*," Food and Chemical Toxicology, vol. 34(2), 1996, pp. 161-166.

Haas and Berka, 1991, "cloning, expression and characterization of a cDNA encoding a lipase from Phizopus delemar," Gene, 109:107-113.

Haas, et al., "Enzymatic Phosphatidylcholine Hydrolysis in Organic Solvents: An Examination of Selected Commercially Available Lipases", JAOCS, vol. 71, No. 5, May 1994, pp. 483-490.

Haas, et al.; "Lipases of the Genera *Rhizopus* and *Rhizomucor*: Versatile Catalysts in Nature and the Laboratory"; Food Biotechnology Micro-organisims (1995); pp. 549-588.

Haggag H F et al. Egypt J Food Sci vol. 22, No. 1 pp. 99-107 (1994).

Marion D et al., "Lipids, Lipid-protein interactions and the quality of baked cereal products", chapter 6 in Hamer, Rob J., et al., "Interaction: The Keys to Cereal Quality", American Association of Cereal Chemists, S Paul, Minnesota, 1998, ISBN 0913250996, p. 131-167.

Hanlin, Richard T., "Illustrated Genera of Ascomycetes"; The American Phytopathological Society, 1992, St Paul, Minnesota, p. 48, 49, 234, 235, 244, 245.

Hansen, Chr., Danisco and Novozymes, Apr. 3, 2002, Food Ingredients day, R&D—the main ingredients for growth.

Hara, et al.; "Comparative Study of Comercially Available Lipases in Hydrolysis Reaction of Phosphatidylcholine"; JAOCS (1997); vol. 74; No. 9, pp. 1129-1132.

Hawker, Kim L., et al., "Heterologous expression and regulation of the *Neurospora crassa* nit-4 pathway-specific regularotry gene for nitrate assimilation in *Aspergillus nidulans*", Gene., vol. 100, pp. 237-240, 1991.

Hedin, Eva M.K., et al., "Selective reduction and chemical modification of oxidized lipase cysteine mutants", Journal of Chemistry (2002) vol. 89, p. 529-539.

Helmsing, "Purification and Properties of Galactolipase", Biochim., Biophys., Acta, vol. 178, pp. 519-533, 1969.

Henderson, H.E., et al., "Structure-function relationships of lipoprotein lipase: mutation analysis and mutagenesis of the loop region", Journal of Lipid Research, vol. 34, 1993, pp. 1593-1602.

Henke, Erik, et al., "Activity of Lipases and Esterases towards Tertiary Alcohols: Insights into Structure-Function Relationships", Angew. Chem. Int. Ed., 2002, vol. 41, No. 17.

Hernquist L & Anjou K (1993) Diglycerides as a stabilizer of the β'-crystal form in margarines and fats, in Fette Seifen Anstrichmittel 2:64-66.

Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.

Hilton S et al, "Purification and spectral study of a microbial fatty acyltransferase:activation by limited proteolysis," Biochemistry vol. 29, No. 38, 1990, pp. 9072-9078.

Hilton S, Buckley JT, "Studies on the reaction mechanism of a microbial lipase/acyltransferase using chemical modification and site-directed mutagenesis," J Biol Chem. Jan. 15, 1991; 266(2): 997-1000.

Hirayama O et al, "Purification and properities of a lipid acylhydrolase from potatoe tubers," Biochim Biophys Acta. 1975, vol. 384(1), p. 127-37.

Hirose, Yoshihiko et al., "Characteristics of Immobilized Lipase PS on Chemically Modified Ceramics", Amano Pharmaceutical, p. 239 (Date Unknown).

Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Höfelmann et al, J. Food Sci., 1985, 50:1721-1731.

Holmquist et al., "Lipases from *Rhizomucor miehei* and Humicola lanuginosa: Modification of the Lid covering the active site alters enantioselectivity", Journal of Protein Chemistry, vol. 12, No. 6, 1993.

Holmquist et al., "Trp89 in the Lid of Humicola lanuginosa Lipase is Important for Efficient Hydrolysis of Tributyrin", Lipids, vol. 29, No. 9, 1994.

Horn T et al, Synthesis of oligonucleotides on cellulose. Part II: design and synthetic strategy to the synthesis of 22 oligodeoxynucleotides coding for Gastric Inhibitory Polypeptide (GIP), Nuc Acids Res Symp Ser No. 7, pp. 225-232 (1980).

Hoshino, et al.; "Calcium Ion Regulates the Release of Lipase of *Fusarium oxysporum*"; J. Biochem (1991); vol. 110; pp. 457-461.

Hoshino, Tamotsu, et al., "Purfication and Some Characteristics of Extracellular Lipase from *Fusarium oxysporum*", Biosci. Biotech. Biochem., vol. 56, No. 4, pp. 660-664, 1992.

Hossen, Monjur and Hernandez, Ernesto, "Phospolipase D-Catalyzed Synthesis of Novel Phospholipid-Phytosterol Conjugates", Lipids, vol. 39, Aug. 2004, pp. 777-782.

Hou, Ching T, "pH dependence and thermostability of lipases from cultures from the ARS Culture Collection", Journal of Industrial Microbiology, vol. 13, No. 4, 1994, pp. 242-248.

Hübner et al., "Interactions at the lipid-water interface", Chemistry and physics of Lipids, vol. 96, 1998, pp. 99-123.

Hugh-Jensen, Birgitte, et al., "*Rhizomucor miehei* Triglyceride Lipase is Processed and Secreted from Transformed *Aspergillus oryzae*", Lipids, vol. 24, No. 9, pp. 781-785, 1989.

Humum et al., "Enzyme Catalysed Synthesis in Ambient Temperature Ionic Liquids", Biocatalysis and Biotransformation, 2001, vol. 19, pp. 331-338, NZAS-0215170.

Icard-Verniere, Christele, et al., "Effects of mixing conditions on pasta dough development on biochemical changes", Cereal Chemistry, 1999, vol. 76, No. 4, pp. 558-565.

Igrejas, Gilberto, et al., "Genetic and Environmental Effects on Puroindoline-a and Puroindoline-b Content and their Relationship to Technological Properties in French Bread Wheats", Journal of Cereal Science, vol. 34, 2001, pp. 37-47.

Ikeda H et al, "Complete genome sequence and comparative analysis of the industrial microorganism *Streptomyces avermitilis*", Nature Biotech, vol. 21, pp. 526-531, May 2003.

Godfrey, Tony, et al., editors, Industrial enzymology (2nd Ed.), The Macmillan press, pp. 299-300, (1996).

Ishihara et al., "Studies on Lipase from *Mucor Javanicus*I. Purification and Properties", Biochimica et Biophysica Acta vol. 388, pp. 413-422, (1975).

Isobe and Nokihara, "Primary structure determination of mono- and diacylglycerol lipase from *Penicillium camembertti*", Febs. Lett., Federation of European Biochemical Societies, vol. 320, No. 2, pp. 101-106, (1993).

Isobe K et al, "A new enzymatic method for glycoaldehyde production from ethylene glycol", Journal of Molecular Catalysis B: Enzymatic 1 (1995), pp. 37-43.

Iwai and Tsujisaka, "Fungal lipase", (in Lipases, Borgström and Brockman (eds.), Elsevier, Amsterdam, 1984, pp. 443-468.

Iwai, Mieko, et al., "Hydrolytic and Esterifying Actions of Crystalline Lipase of *Aspergillus niger*", J. Gen. Appl. Microbiol., 1964, vol. 10, No. 1, p. 13-21.

Izco et al., "Capillary electrophoresis: Evaluation of the effect of added enzymes on casein proteolysis during the ripening of a ewe's-milk cheese", Adv Food Sci, vol. 21, No. ¾, pp. 110-116, (1999).

Jacob, Jules S., et al., "The Effects of Galactolipid Depletion on the Structure of a Photosynthetic Membrane", The Journal of Cell Biology, vol. 103, Oct. 1986, pp. 1337-1347.

Jacobsberg B. & Oh C.H. (1976) Studies in Palm Oil Crystallisation, in Journal of the American Oil Chemist Society 53: pp. 609-616.

Jan-Willem F. A. Simons et al., "Cloning, purification and characterisation of the lipase from *Staphylococcus epidermidis*", Eur. J. Biochem., vol. 253, pp. 675-683, 1998.

Jeng-yen Lin, Matthew, "Wheat Polar Lipids—A Theseis Submitted to the Graduate Faculty of the North Dakota State University of Agriculture and Applied Science", May 1972, pp. 34-45.

Jensen B et al "Effect and Activity of Lipases in Dough and Bread" (translation), 48th Conference on Baking technology and 3rd Conference on Cake & Pastry Technology, Nov. 4-6, 1997, pp. 67-76.

Jensen, B., et al., "Effekt and Wirksamkeit von Lipasen in Teig und Brot" 48th Conference on Baking technology and 3rd Conference on Cake & Pastry Technology, Nov. 4-6, 1997, pp. 67-76.

Owens J., "Lecithinase Positive Bacteria in Milk", Process Biochemistry, Jan. 1978, vol. 13, pp. 13-14, 30.

Joerger et al., "Alteration of Chain Length Selectivity of a Rhizopus delemar Lipase through Site-Directed Mutagenesis", Lipids, vol. 29, No. 6, 1994, pp. 377-384.

Jong et al.; "American Type Culture Collection Catalogue of Filamentous Fungi"; Eighteenth edition (1991) p. 80.

List of Cultures, Fungi and Yeasts, 32 edition, Institute of the Royal Netherlands Academy of Arts and Sciences, p. 38. (1990).

JCM Catalogue of Strains, Fifth Edition, "Filamentous Fungi & Yeasts", p. 246, (1992).

List of Cultures, 1992 Microorganisms Ninth Edition, Institute for Fermentation, Osaka, Japan, p. 325, (1992).

Joshi, et al.; "Specificity of Fungal Lipase in Hydrolytic Cleavage of Oil"; Acta Microbiologica Hungarica (1987); vol. 34(2); pp. 111-114.

Joshi, Sunita, et al., "Specificity of Lipase isolated from Fusarium oxysporum", Department of Chemistry, Indian Institute of Technology, vol. 25, No. 1 & 2, pp. 76-78, (Jan.-Jun. 1985).

Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.

Kaniuga Z, "Galactolipase and chilling sensitivity of plants", Acta Biochim Pol. (1997), vol. 44(1), pp. 21-35.

Kapur J & Sood ML, J. "Effect of pH and Temperature on Lipase and Phospholipase of Adult *Haemonchus contortus* (Nematoda: Trichostrongylidae)" J. Parasit., 1986, vol. 72, No. 2, pp. 346-347.

Kasai, Naoya, et al., "Chiral C3 epoxides and halophydrins: Their preparation and synthetic application", Journal of Molecular Catalysis B: Enzymatic, vol. 4, 1998, pp. 237-252.

Kasai, Naoya, et al., "Optically Active Chlorohydrins as Chiral C3 and C4 Building Units: Microbial Resolution and Synthetic Applications", Chirality, vol. 10, pp. 682-692, (1998).

Kawamura, F., et al., "Construction of a *Bacillus subtilis* Double Mutant Deficient in Extracellular Alkaline and Neutral Proteases", J. of Bacteriology, vol. 160, No. 1, Oct. 1984, pp. 442-444.

Keller, R.C.A., et al., "Competitive Adsorption Behaviour of Wheat Flour Components and Emulsifiers at an Air-Water Interface", Journal of Cereal Science, vol. 25, 1997, pp. 175-183.

Keum J S et al., "Effect of Commercial Protease and Lipase on the Ripening of Cheddar Cheese", Korean J Dairy Sci 15 (2): pp. 103-117, (1993).

Kim, Hyung Kwoun, et al., Expression and characterization of Ca2+-independent lipase from Bacillus pumilus B26, Biochimica et Biophysica Acta, vol. 1583, 2002, pp. 205-212.

Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.

Kimura, Yoshiharu, et al., "Application of Immobilized Lipase to Hydrolysis of Triacylglyceride", Eur J. Appl Microbiol Biotechnol, 1983, vol. 17, pp. 107-112.

Kindstedt et al., Rapid Quantative test for free oil (Oiling off) in melted Mozzarella cheese, J. Dairy Sci., 1990, vol. 73, p. 867-873.

King et al, "The production of proteins and peptides from *Saccharomyces cervisiae*", Molecular and Cell Biology of Yeasts, Walton and Yarronton (eds.), Blackie, Glasgow, 1989, pp. 107-133.

Kirk, Ole, et al., "Fatty Acid Specificity in Lipase-Catalyzed Synthesis of Glucoside Esters" Biocatalysis, 1992, vol. 6, pp. 127-134.

Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.

Klein, Robert R., et al., "Additive Effects of Acyl-Binding Site Mutations on the Fatty Acid Selectivity of Rhizopus delemar Lipase", JAOCS, vol. 74, No. 11, 1997, p. 1401-1407.

Kocak et al., Effect of lipase enzyme (palatase A 750 L) on the ripening of tulum cheese, Tr. J. of Agriculture and Forestry, 1995, vol. 19, p. 171-177.

Kocak et al., Effect of added fungal lipase on the ripening of Kasar cheese, Milchwissenschaft 51(1), 1996, p. 13-17.

Kochubei et al., Role of lipids in the organization of the closest surroundings of the reaction centers, Molekulyarnaya Biologiya vol. 12, No. 1, pp. 47-54, Jan.-Feb. 1978.

Kochubei S M et al, "Nature of Longwave Fluorescence of Particles Enriched with Photosytem I", Biophysics (1981), vol. 26(2), pp. 299-304.

Kochubei S M et al, "Differences in the Structure of Long Wave Fluorescence Molecular Aggregates in Photosytems I and II" Institute of Plant Physiology, Academy of Sciences of the Ukranian SSR, Kiev, (Translated from Molekulyarnaya Biologiya vol. 9, No. 2, pp. 190-193, Mar.-Apr. 1975) pp. 150-153, (1975).

Kochubei SM et al, "Role of Lipids in the Organization of the Closest Surroundings of the Reaction Centers of Photosytem 1", Institute of Plant Physiology, Academy of Sciences of the Ukranian SSR, Kiev, (Translated from Molekulyarnaya Biologiya vol. 12, No. 1, pp. 47-54, Jan.-Feb. 1978) pp. 32-37, (1978).

Kolkovski et al., "The Effect of Dietary Enzymes with Age on Protein and Lipid Assimilation and Deposition in *Sparus Aurata* Larvae", in Fish Nutrition in Practice, Biarritz (France), Jun. 24-27, 1991, Ed. INRA Paris, 1993, les Colloques, No. 61, p. 569-578.

Kostal, Jan, et al., "Enhanced Arsenic Accumulation in Engineered Bacterial Cells Expressing ArsR", Applied and Environmental Microbiology, Aug. 2004, vol. 70, No. 8, pp. 4582-4587.

Kouker, et al.; "Specific and Sensitive Plate Assay for Bacterial Lipases"; Applied and Environmental Microbiology (1987); vol. 53(1); pp. 211-213.

Krishna, Sajja Hari, et al., "Enantioselective transesterification of a tertiary alcohol by lipase A from Candida antarctica", Tetrahedron: Asymmetry, vol. 13, 2002, pp. 2693-2696.

Kristensen A.C.J., "Preparation of margarine and spreads by enzyme-generated emulsifiers", Master thesis, The Royal Veterinary and Agricultural University, Frederiksberg, Copenhagen, (Jan. 2004) pp. 1-154.

Krog, Niels J., "Dynamic and Unique Monoglycerides", Cereal Foods World, The American Association of Cereal Chemists, Jan. 1979, vol. 24, No. 1, p. 10.

Krupa, Zbigniew et al., "Requirement of Galactolipids for Photosystem J Activity in Lyophilized Spinach Chloroplasts", Biochimica et Biophysica Acta, 408, pp. 26-34, 1975.

Kuipers, Oscar P., et al., "Enhanced Activity and Altered Specificity of Phospholipase A2 by Deletion of a Surface Loop", Science, vol. 244, 1989, p82-85 NZAS-0668767.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from *Torulaspora delbrueckii*", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, pp. 1072-1076, 1994.

Larchenkova LP et al. "Effect of starter and souring temperature on reproduction of *E coli* and lactobacili in milk," International Dairy Congress XXI, vol. 1, book 2. Moscow, Jul. 12-16, 1982, Brief Communications, p. 539.

Larsen N G et al, "The Effect of Ball-milling on Phospholipid Extractability and the Breadmaking Quality of Flour", Journal of Cereal Science (1990), vol. 12(2), p. 155-164.

Lecointe et al., "Ester Synthesis in Aqueous Media in the Presence of Various Lipases" Biotechnology Letters, vol. 18, No. 8 (Aug.) pp. 869-874, (1996).

Lee, Keun Hyeung, et al., "Identification and characterization of the antimicrobial peptide corresponding to C-terminal B-sheet domain of tenecin 1, an antibacterial protein of larvae of *Tenebrio molitor*", Biochem. J., 1996, vol. 334, pp. 99-105.

Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.

Leidich et al., "Cloning and Disruption of caPLB1, a Phospholipase B Gene Involved in the Pathogenicity of *Candida albicans*", The Journal of Biological Chemistry, vol. 273, No. 40, pp. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, "Inhibition of Listeria monocytogenes by monoacylglycerols synthesized from coconut oil and milkfat by lipase-catalyzed glycerolysis." Journal of Agricultural Food Chemistry (1993), vol. 41, No. 8, pp. 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M JY et al, "Effect on quality of bread and pasta products" Cereal Chemistry (1974), vol. 51(1), pp. 34-45.

Lin S et al, "Purification and characterization of a glycerol oxidase from *Penicillium* sp. TS-622" Enzyme and Microbial Technology 18 (1996), pp. 383-387.

"Lipase A Amano" Technical Bulletin No. Lez-1 (Product Specification from Armano Pharmaceutical Co Ltd Nagoya Japan), Dec. 16, 1985, pp. 1-6.

Lipase A "Amano" 6 Assay Note from Armano Pharmaceutical Co Ltd Nagoya Japan, Aug. 27, 1985, p. 1.

Lipase A "Amano" 6 product sheet, Amano Enzyme Inc, Apr. 1, 1999, pp. 1-2.

Lipase SP677 as a Baking Enzyme, from Novo Nordisk, Denmark, Mar. 17, 1994, pp. 1-5.

Lipomod L338P Data Sheet, Biocatalysts Limited, Aug. 15, 2003, pp. 1-2.

Lipopan F: Keep the quality—cut your costs 2000 Novozymes A/S. www.enzymes.novo.dk/cgl-bin/bvisapi.dll/biotimes/one_article. jsp?id=16947&lang=en&t=b1, pp. 1-2. (2000).

Litthauer, Derek, et al., "*Pseudomonas luteola* lipase: A new member of the 320-residue Pseudomonas lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Longhi, Sonia, et al., "Atomic Resolution (1.0 Å) Crystal Structure of *Fusarium solani* Cutinase: Stereochemical Analysis" J. Mol. Biol. vol. 268, pp. 779-799, 1997.

Lozano et al., "Over-stabilization of Candida antarctica lipase B by ionic liquids in ester synthesis", Biotechnology Letters, vol. 23, pp. 1529-1533, 2001.

Lustenberger, Cornelia et al., Abstract of "Application of lipase in Asian Noodles and Non-durum Pasta" AACC 2000 Annual Meeting, Nov. 5-9, 2000, pp. 1-2, available at http://aaccnet.org/meetings/2000/Abstracts/a00ma031.htm.

Luzi, Paola et al "Structure and organization of the human galactocerebrosidase (GALC) gene",Genomics (1995), vol. 26, No. 2, p. 407-409.

Madsen J.S. & Qvist K.B., "Hydrolysis of milk protein by *Bacillus licheniformis* protease specific for acidic amino acid residues" Journal of Food Science, vol. 62, pp. 579-582, (1997).

Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.

Maria Teres Neves Petersen, PhD, "Total Internal Reflection Fluorescence Flow System with Electrochemical Control", TIRF-EC Flow System, University of Aalborg, pp. 1-13, Sep. 2002.

Marion D et al., "Lipids, Lipid-protein Interactions and the Quality of Baked Cereal Products" from Interactions the Keys to Cereal Quality, Chapter 6, Editors Hamer & Hoseney, American Association of Cereal Chemists, Inc., St. Paul, Minnesota, pp. 131-167, (1998). ISBN 0 913250-99-6.

Marion D et al., Wheat Lipids and Lipid-binding proteins: structure and function, in "Wheat Structure Biochemistry & Functionality", editor Schofield JP, 2000, Royal Society of Chemistry Special publication 212 pp. 245-260 ISBN 085404777-8 (It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of Humicola lanuginosa lipase", Protein Engineering, vol. 9, No. 6, 1996, pp. 519-524.

Martinez, Chrislaine, et al., "Engineering cysteine mutants to obtain crystallographic phases with a cutinase from *Fusarium solani* pisi", Protein Engineering, vol. 6, No. 2, pp. 157-165, 1993.

Martinez, Diego, et al., "Genome sequence of the lignocellulose degrading fungus *Phanerochaete chrysosporium* strain RP78", Nature Biotechnology, Nature Publishing Group, pp. 1-6, published online on May 2, 2004.

Mase et al., "Purification and Characterization of a new Lipase from Fusarium sp. TM-30", Biosci. Biotech. Biochem., vol. 59, No. 9, pp. 1771-1772, 1995.

Mason, "Use of Lipolytic Enzyme From *Aeromonas* in Detergents", Research Disclosure, Kenneth Mason Publications, Westbourne GB no 390, Oct. 1996, pp. 661-662.

Masuda, Naoko, et al., "Primary structure of protein moiety of *Penicillium notatum* phospholipase B deduced from the Cdna", Eur. J. Biochem., vol. 202, pp. 783-787, 1991.

Matos, A.R., et al., "A patatin-like protein with galactolipase activity is induced by drought stress in *Vigna unguiculata* leaves", Biochemical Society Transactions, Lipid Catabolism: Lipid Degradation, vol. 28, part 6, p. 779-781, Jun. 30, 2000.

Matos, AR et al, "A novel patatin-like gene stimulated by drought stress encodes a galactolipid acyl hydrolase", FEBS Letters, 491, pp. 188-192, (First published online Feb. 9, 2001).

Matsuda H et al, "Purification and properties of a lipolytic acylhydrolase from potato leaves", Biochimica et Biophysica Acta, vol. 573(1), p. 155-165, (1979).

Matsuoka, et al.; "Purification and properties of a Phospholipase C That has High Activity toward Sphingomyelin from *Aspergillus Saitoi*"; Biotechonology and Applied Biochemistry (1987); vol. 9, pp. 401-409.

Matthes et al, "Simultaneous rapid chemical synthesis of over one hundred oligonucleotides on a microscale" The EMBO Journal, vol. 3, No. 4, pp. 801-805, (1984).

Reetz M.T., Max-Planck-Institut fur Kohlenforschung et al., "Controlling the enantioselectivity of enzymes by directed evolution: Practical and theoretical ramifications", PNAS, Apr. 20, 2004, vol. 101, No. 16, pp. 5716-5722. NZAS-0441867.

McAuley, Katherine E., et al., "Structure of a feruloyl esterase from *Aspergillus niger*", Acta Crystallographica, Section D, D60, Biological Crystallography, pp. 878-887, 2004.

McCoy M G et al, "Characterization of the lipolytic activity of endothelial lipase", Journal of Lipid Research (2002), vol. 43, pp. 921-929.

McNeill G.P. & Berger R.G., Enzymatic glycerolysis of palm oil fractions and palm oil based model mixture: Relationship between fatty acid composition and monoglyceride yield, in Food Biotechnology 7: pp. 75-87, (1993).

McNeill, Gerald P., et al., "Further Improvements in the Yield of Monoglycerides During Enzymatic Glycerolysis of Fats and Oils", JAOCS, Jan. 1991, vol. 68, No. 1, pp. 6-10. NZAS-0213370.

McNeill, Gerald P., et al., "High-Yield Enzymatic Glycerolysis of Fats and Oils", JAOCS, vol. 68, No. 1, pp. 1-5, Jan. 1991.

McNeill, Gerald P., et al., "Selective Distribution of Saturated Fatty Acids into the Monoglyceride Fraction During Enzymatic Glycerolysis", JAOCS, vol. 69, No. 11, pp. 1098-1103, Nov. 1992.

McNeill, Gerald P., et al., "Solid Phase Enzymatic Glycerolysis of Beef Tallow Resulting in a High Yield of Monoglyceride", JAOCS, vol. 67, No. 11, pp. 779-783, (Nov. 1990).

Memo: From Charlotte Johanson, "Short introduction/ status on Ferulic Acid Esterases and Acetyl Xylan Esterases", Protein Biochemistry, pp. 1-2, Jan. 9, 2004.

Meyer, V., et al., "Transcriptional regulation of the Antifungal Protein in *Aspergillus giganteus*", Mol Genet Genomics, 2002, vol. 266, pp. 747-757.

Meyers, Robert A., "Molecular Biology and Biotechnology—A Comprehensive Desk Reference" VCH Publishers, pp. 731-737, (1995). ISBN1560815698, NZAS-015769.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from *Phanerochaete chrysosporium* and Bjerkandera sp. BOS55", Enzyme and Microbial Technology, vol. 32, pp. 769-775 (2003).

Miller, Byron S., et al., "A Comparison of Cereal, Fungal, and Bacterial Alpha-Amylases as Supplements for Breadmaking", Food Technology, pp. 38-42, (Jan. 1953). NZAS 0225991.

Mine Y, "Application of the enzymatic methods to the determination of contaminated yolk in egg white", Food Research International, vol. 29, No. 1, pp. 81-84, (1996).

Ministerio da Ciencia e Tecnologia, *Diario Oficial da Uniao*, No. 134, p. 6, Jul. 15, 2003. ISSN 1677-7042, NZNA-0046369.

Mogensen, Jesper E., et al., "Activation, Inhibition, and Destabilization of Thermomyces lanuginosus Lipase by Detergents", Biochemistry, vol. 44, pp. 1719-1730, 2005.

Molecular Biological Methods for Bacillus—Chapter 3 Plasmids (Ed. C.R. Harwood and S.M. Cutting) John Wiley and Sons Ltd, Chichester, UK, p. 75-174, 1990.

Mœlgaard, Anne, et al., "Rhamnogalacturonan acetylesterase elucidates the structure and function of a new family of hydrolases", Structure, vol. 9, No. 4, pp. 373-383, 2000. NZNA-0056695.

Umanskii M.S. et al., Effect on quality of Kostroma cheese of bacterial cultures selected on phospholipase activity, Molochnaya Promyshlennost 1980 No. 11 21-25, 47—abstract from Food Sci & Tech Abs.

Monick John A., Alcohols, Their Chemistry, Properties and Manufacture, Reinhold Book Cooperation, pp. 3, 6, 14, 47, 48, (1968).

"Mono- and Diglycerides of Edible Fatty Acids", in Monographs for Emulsifiers for Foods, 2nd Edition, The European Food Emulsifier Manufacturers' Association (EFEMA), pp. 47-51, Nov. 1985.

Moore, Charles M., et al., "Metal ion homeostasis in *Bacillus subtilis*", Current Opinion in Microbiology, vol. 8, pp. 188-195, 2005.

Morgan, Keith R., et al., "Stalling in Starch Breads: The Effect of Antistaling α-Amylase", Starch/Stärke, vol. 49, pp. 59-66,1997.

Morgan-Jones, Gareth; "Notes on Coelomycetes.II. Concerning the *Fusicoccum Anamorph* of Botryosphaneria Ribis"; Mycotoxon, vol. 30, pp. 117-125; Oct.-Dec. 1987.

Morinaga et al., "Improvement of Oligonucleotide-Directed Site-Specific Mutagenesis Using Double-Stranded Plasmid DNA", Biotechnology 2, pp. 636-639, (1984).

Morten, T. & A., Letter, Rodovre, Jul. 2004.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Mototake, et al., "Transesterification of Oil by Fatty Acid-Modified Lipase", Technical Research Institute, JAOCS, Jun. 1993, vol. 70, No. 6, p. 571-574 NZAS-0457255.

Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedron, vol. 50, No. 7, pp. 1993-2002, (1994).

Mustranta, Annikka, et al., "Comparison of Lipases and Phosphlipases in the Hydrolysis of Phospholipids", Process Biochemistry, vol. 30, No. 5, pp. 393-401, 1995.

General Conditions of the company limited by shares N.V. Nederlandsch Octrooibureau, Terms and Conditions, Jan. 2004. NZAS-0012567.

Nagano, et al.; "Cloning and Nucleotide Sequence of cDNA Encoding a Lipase from *Fusarium keteroporum*"; J. Biochem (1994); vol. 116; pp. 535-540.

Nagao T. et al, "C-Terminal Peptide of *Fusarium heterosporum* Lipase is Necessary for its Increasing Thermostability", J. Biochem., vol. 124, 1124-1129, 1998.

Nagao, T., et al, "Amino Acid Residues Contributing to Stabilization of *Fusarium heterosporum* Lipase", J. of Bioscience and Bioengineering, vol. 89, No. 5, pp. 446-450, 2000.

Nagao, T., et al, "Review: Increase in stability of *Fusarium heterosporum* lipase", J. of Molecular Catalysis B: Enzymatic 17 (2002) pp. 125-132.

Nagao, T., et al, "Use of Thermostable *Fusarium heterosporum* Lipase for Production of Structured Lipid Containing Oleic and Palmitic Acids in Organic Solvent-Free System", JAOCS vol. 78, No. 2, pp. 167-172, (2001).

Nagao, Toshihiro et al., "Cloning and Nucleotide Sequence of CDNA Encoding a Lipase from *Fusarium heterosporum*", J. Biochem., vol. 116, pp. 535-540, 1994.

Nagao, Toshihiro et al., "Expression of Lipase cDNA from *Fusarium heterosporum* by *Saccharomyces cereviisiae*: High-Level Production and Purification", Journal of Fermentation and Bioengineering, 1996, vol. 81, No. 6, pp. 488-492.

Godtfredsen S E, "Lipases", in "Enzymes in food processing" (3rd Ed.), Nagodawithana T and Red G (editors), Academic Press, New York, 1993, ISBN 0125136307, chapter 8, p. 205-219 NZAS-0665885.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. of Molecular Biology 48, 443-453.

Nelson and Long, Analytical Biochemistry (1989), 180, p. 147-151.

Nerland A H, Journal of Fish Diseases, vol. 19, No. 2, 1996, pp. 145-150.

Néron, et al., "Effects of lipase and the phosphlipase on the lipids hydrolysis during mixing in correlation with the oxygen consumption by wheat flour dough during kneading", poster 125 Ko at AACC/Tia, San Diego, Calfornia, Sep. 20-22, 2004, available at http://www.cnam.fr/biochimie.

Ness, Jon. E., et al., "DNA shuffling of subgenomic sequences of subtilisin" Nature Biotechnology, vol. 17, Sep. 1999.

Nestle Research Center, Brochure for "Food Colloids 2006" in Montreux, Switzerland, Apr. 23-26, 2006.

Neugnot Virginie et al, European Journal of Biochemistry, 2002, vol. 269, pp. 1734-1745.

Newport, G., et al., "KEX2 Influences *Candida albicans* Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nielsen et al., "Lipases A and B from the yeast *Candida antarctica*", in "Biotechnological Applications of Cold-Adapted Organisms" Margesin R & Shimmer F (editors), Springer, 1999, ISBN 3540649727 p. 49-61 NZAS-0214451.

Nierle W et al, Fette Seifen Anstrichmittel (Wheat Lipids: Function and Effect in Flour Processing) (1981), vol. 83(10), p. 391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi M et al, Tetrahedron Letters (1991), vol. 31(1), p. 1331-4.

Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".

Novozymes Memo—Test of lipases for EP1193314B1, Jul. 6, 2005, p. 1-5.

Novozymes Report 2002 Annual Report, "Successfor new baking enzyme," p. 1-2.

Novozymes journal BioTimes, "Biowhitening—a new concept for steamed bread", Jan. 2005 http://www.biotimes.com/en/Articles/2005/March/Pages/Biowhitening-anewconceptforsteamedbread.aspx, p. 1-2.

Novozymes, "Breakthrough: Less Fattening Fried Food" *BioTimes*, Jun. 2001, No. 2, p. 1-12.

Novozymes, "Enzymes for dough strengthening", 2001, p. 16-21.

Novozymes, "Lipopan F BG-application and mechanism of a new lipase for bread baking" (Draft) *Cereal Food* (2003) (Author: Drost-Lustenberger, C. et al.), p. 1-29.

Novozymes, "Product Sheet for Lipopan F BG", *Cereal Food*, (2001), p. 1-3.

Novozymes, "Product Sheet for Lipopan FS BG", *Cereal Food* (2002), p. 1-3.

Novozymes, "Product Sheet for Lipopan S BG", *Cereal Food* (2002), p. 1-3.

Novozymes, "Product Sheet for Noopazyme", Cereal Food (2002) p. 1-3.

Novozymes, "Product Sheet for Novozym 27016," Baking (2000), p. 1-6.

Novozymes, "Product Sheet for Novozym 27019," Baking (2000), p. 1-6.

Novozymes, "Product Sheet for Novozym 27080," Cereal Food (2003), p. 1-3.

Novozymes, "Revolutionizing baking", *BioTimes* (Dec. 2002) pp. 6-7.

Novozymes, "Strong sales for lipase that makes dough stronger" *BioTimes*, Dec. 2003, p. 1-2.

Novozymes, "The perfect roll every time for steers", *BioTimes*, Sep. 2003, p. 1-2.

Novozymes, "The value of innovation", *BioTimes*, Mar. 2004, p. 8-9.

Novozymes, "The vital role of technical service in baking", *BioTimes*, Jun. 2004, p. 8-9.

Novozymes brochure "Enzymes at work" 2004, p. 1-60.

Nylander et al., "Interaction between lipids and lipases A collection of papers presented at the European Meeting on lipid and lipase interaction at Lund University" Sep. 2000.

Ognjenovic Radomir et al, Acceleration of ripening of semi-hard cheese by proteolytic and lipolytic enzymes, Proceedings for Natural Sciences, 1996, vol. 91, p. 5-17.

Ohm, J.B., et al., "Relationships of Free Lipids with Quality Factors in Hard Winter Wheat Flours", Cereal Chem., vol. 79, No. 2, pp. 274-278, 2002.

Ohta, S. et al., "Application of Enzymatic Modification of Phospholipids on Breadmaking", Abstract from AACC 68th Annual Meeting in Kansas City, MO, Oct. 30th-Nov. 3, 1983, published in Cerial Foods World, p. 561.

Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.

Okiy D.A. (1977) "Partial glycerides and palm oil Crystallisation," in Journal of Science and Food Agriculture vol. 28, p. 955.

Okiy D.A. (1978) "Interaction of triglycerides and diglycerides of palm oil," in Oleagineux, vol. 33 p. 625-628.

Okiy D.A., Wright, W.B., Berger, K.G. & Morton I.D. (1978), The physical properties of modified palm oil, in Journal of Science of Food and Agriculture 29:1061-1068.

Oluwatosin, Yemisi E., et al., "Phenotype: a Possible Role for the Kex2 Endoprotease in Vacuolar Acidification", Molecular and Cellular Biology, 1998, pp. 1534-1543.

Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.

O'Mahony et al. "Hydrolysis of the lipoprotein fractions of milk by Phospholipase C," Journal of Dairy Science, 1972, vol. 55, No. 4, p. 408-412.

Orberg, Marie-Louise, "Self-assembly Structures Formed by Wheat Polar Lipids and their Interaction with Lipases", Master of Scient Thesis, Apr. 2005.

Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.

Osman, Mohamed, et al., "Lipolytic activity of *Alternaria altemata* and *Fusarium oxysporum* and certain properties of their lipids", Microbios Letters, vol. 39, pp. 131-135, 1988.

O'Sullivan et al, "A Galactolipase activity associated with the thylakoids of Wheat Leaves (*Triticum aestivum* L.)," J Plant Physiol, vol. 313, (1987) p. 393-404.

Outtrup, Günther H., et al., "Properties and Application of a Thermostable Maltogenic Amylase Produced by a Strain of Bacillus Modified by Recombinant-DNA Techniques", Starch/Starke (2003) vol. 36, No. 12, pp. 405-411.

Palomo, Jose M., et al., "Enzymatic production of (3S, 4R)-(–)-4-(4'-fluorophenyl)-6-oxo-piperidin-3-carboxylic acid using a commerical preparation of lipase A from *Candida antarctica*: the role of a contaminant esterase" Tetrahedron: Asymmetry, vol. 13, 2002, pp. 2653-2659.

Palomo, Jose M., et al., "Enzymatic resolution of (±)-glycidyl butyrate in aquenous media. Strong modulation of the properties of the lipase from *Rhizopus oryzae* via immobilization techniques", Tetrahedron: Asymmetry, vol. 15, 2004, pp. 1157-1161.

Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.

Pariza, Michael, et al., "Evaluating the safety of Microbiol Enzyme Preparations Used in Food Processing: Update for a New Century", Regulatory Toxicology and Pharmacology (2001) vol. 33, pp. 173-186.

Patent Abstracts of Japan vol. 016, No. 528 (C-1001), Oct. 29, 1992 & JP 04 200339 A see abstract.

Patent Abstracts of Japan vol. 095, No. 001, Feb. 28, 1995 & JP 06 296467 A see abstract.
Peelman F, et al, "A proposed architecture for lecithin cholesterol acyl transferase (LCAT): Identification of catalytic triad and molecular modeling," Protein Science Mar. 1998; 7(3): 587-99.
Penninga et al, "Site-directed mutations in Tyrosine 195 of Cyclodextrin Glycosyltransferase from *Bacillus circulans* Strain 251 affect qctivity and product Specificity," Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the *Humicola lanuginosa* Lipase", Biochemistry, 1998, vol. 37, pp. 12375-12383.
Peters, G.H., et al.; "Dynamics of *Rhizomucor miehei* lipase in a lipid or aqueous environment: Functional role of glycines"; Draft for Biophys. J, Nov. 1996, vol. 71, No. 5, p. 2245-2255 NZAS-0031441.
Peters, G.H., et al.; "Essential motions in lipases and their relationship to the biological function", Proceedings of the German Conference on Bioinformatics, GCB '96, Leipzig, Germany, Sep. 30-Oct. 2, 1996, poster, p. 280-282 NZAS-0031438.
Peters, Günther H., et al., "Theoretical Investigation of the Dynamics of the Active Site Lid in *Rhizomucor miehei* Lipase", Biophysical Journal, vol. 71, 1996, pp. 119-129.
Harborne J.B. et al. (editors), Phytochemical Dictionary: A Handbook of Bioactive Compounds from Plants, Taylor & Francis, 1993, ISBN 978050667363 Chapter 4, "Sugar Alcohols and Cyclitols", p. 20-23.
Picon et al., "Release of Encapsulated Proeinase from Dehydration-Rehydration Liposomes by a Co-encapsulated Phospholipase," Biotechnology Letters, Oct. 1995, vol. 17, No. 10, pp. 1051-1056.
Plijter J and JHGM Mutsaers, "The surface rheological properties of dough and the influence of lipase on it, Gist-brocades," Bakery Ingredients Division, Oct. 1994.
Plou et al, "Enzymatic acylation of di- and trisaccharides with fatty acids: choosing approiate enzyme, support and solvent," J. Biotechnology 92 (2002) 55-66.
Ponte J G, "Note on the Separation and Baking properties of Polar and Nonpolar Wheat Flour Lipids," Cereal Chemistry (1969), vol. 46(3), p. 325-29.
Poulsen, C.H., et al., "Effect and Functionality of Lipases in Dough and Bread", in Angelino SAGF, Hamer RJ, van Hartingsveldt W, Heidekamp F, van der Lugt JP (editors), First European Symposium on Enzymes and Grain Processing, Zeist, The Netherlands, TNO Nutrition and Food Research Institute, ISBN 90-75202-04-0, p. 204-214. Proceedings of ESEGP-1, Noordwijkerhout, The Netherlands, Dec. 2-4, 1996. NZAS-0158559.
Poulsen, Charlotte, et al. "Purification and Characterization of a Hexose Oxidase with Excellent Strenghening Effects in Bread" Cereal Chem. (1998) vol. 75(1); pp. 51-57.
Punt, P. et. al., "Transformation of Filamentous Fungi Based on Hygromycin B and Phleomycin Resistance Markers," Meth. Enzym., 1992, 216:447-457.
Pyler, E.J., "Baking Science and Technology," Third Edition vol. 1, 1988, p. 1-602.
Pyler, E.J., "Baking Science and Technology," Third Edition vol. II, 1988, p. 1-784.
Queener et al. (1994), "Improved Expression of a Hybrid: *Streptomyces clavuligerus* cefE Gene in *Penicillium chrysogenum*," Ann N Y Acad Sci. 721, p. 178-193.
Rambosek, J., "Recombinant DNA in Filamentous Fungi: Progress and Prospects," CRC Crit. Rev. Biotechnol., 1987, vol. 6, No. 4, p. 357-393.
Rapp, Peter, et al., "Formation of extracellular lipases by filamentous fungi, yeasts, and bacteria", Enzyme Microb. Technol., 1992, vol. 14, November.
Rapp, Peter; "Production, regulation, and some properties of lipase activity from *Fusarium oxysporum* f. sp. *vasinfectum*"; Enzyme and Microbial Technology(1995); vol. 17; pp. 832-838.
Reetz M.T et. al., "Overexpression, immobilization and biotechnological application of Pseudomonas lipases," Chem Phys Lipids. Jun. 1998; 93(1-2): 3-14.

Reetz Manfred T, "Lipases as practical biocatalysts," Current Opinion in Chemical Biology, Apr. 2002, vol. 6, No. 2, pp. 145-150.
Reiser J et al.(1990). "Transfer and Expression of Heterologous Genes in Yeasts other than *Saccharomyces cerevisiae*," Adv Biochem Eng Biotechnol. 43, p. 75-102.
Richardson & Hyslop, "Enzymes", pp. 371-476 in "Food Chemistry Second Edition, Revised and Expanded", 1985, second edition, Owen R. Fennema (ed), Marcel Dekker, Inc, New York and Basel.
Richardson and Hyslop, "Enzymes: XI—Enzymes Added to Foods During Processing" in *Food Chemistry*, Marcel Dekker, Inc., New York, NY 1985.
Arskog and Joergensen, "Baking performance of prior art lipases from *Candida cylindracea* and *Aspergillus foeditus* and their actiivty on galactolipids in dough", Novozymes Report 2005.
Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) . "Heterologous gene expression in *Aspergillus niger*: a glucoamylase-porcine pancreatic prophospholipase A2 fusion protein is secreted and processed to yield mature enzyme," Gene 122(1), 155-161.
Roberts, et al.; "Extracellular Lipase Production by Fungi from Sunflower Seed"; Mycologia(1987); vol. 79(2); pp. 265-273.
Robertson et al, "Influence of Active Site and Tyrosine Modification on the Secretion and Activity of the *Aeromonas hydrophila* Lipase/Acyltransferase," Journal of Biological Chemistry, 1994, vol. 259, No. 3, p. 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is a Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in *Vigna unguiculata* leaves and influence of drought stress", Physiologia Plantarum, vol. 104, pp. 577-586, 1998.
Sahsah, Y., et al., "Purification and characterization of a soluble lipolytic acylhydrolase from Cowpea (*vigna unguiculata* L.) leaves", Biochimica et Biophysica Acta, vol. 1215, pp. 66-73, 1994.
Saiki R.K. et al, "Primer-Directed Enzymatic Amplification of DNA with a Thermostable DNA Polymerase," Science (1988) 239, pp. 487-491.
Saito, Kunihiko, et al., "Phospholipase B from *Penicillium notatum*", Methods in Enzymology, 1991, vol. 197, p. 446-456 NZAS-0418833.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Sambrook et al, Chapters 1, 7, 9, 11, 12 and 13—Molecular Cloning a laboratory manual, vol. 3, p. 1.113.104, Cold Spring Harbor Laboratory Press (1989).
Sambrook, J., et al. "Molecular Cloning: A Laboratory Manual, Second Edition", Plasmid Vectors, 1989, p. 1-462.

Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.

Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).

Saxena, et al.; "Purification Strategies for Microbial Lipases"; Journal of Microbilogical Methods (2003); pp. 1-18.

Scheib et al.; "Stereoselectivity of Mucorales lipases toward triradylglycerols—A simple solution to a complex problem"; Protein Science (1999); vol. 8; pp. 215-221.

Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.

Schofield, J. David, "Wheat Structure, Biochemistry and Functionality", Department of Food Science and Technology, Apr. 2000, p. 243-260.

Scopes, Robert K., "Section 8.4: Ultrafiltration" in *Protein Purification Principles and Practice, Third Edition* (1994) Springer-Verlag, New York, p. 267-269.

Shehata, A. "Manufacture of Blue Cheese by Direct Acidification Methods," University of Wisconsin, Nov. 30, 2005, p. 1-90.

Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.

Shillcock, Julian C., et al., "Tension-induced fusion of bilayer membranes and vesicles", Advance Online Publication Feb. 13, 2005, Nat. Mater., 2005, vol. 4, No. 3, p. 225-228 NZAS-0231181.

Shimada et al, "Enzymatic Purification of Polyunsaturated Fatty Acids," J. of Bioscience and Bioengineering vol. 91, No. 6, 529-538 (2001).

Shimada et al, "Purification and Characterization of a Novel Solvent-Tolerant Lipase from *Fusarium heterosporum*," J. of Fermentation and Bioengineering vol. 75, No. 5, 349-352 (1993).

Shimada et al, "Enrichment of Polyunsaturated Fatty Acids with *Geotrichum candidum* Lipase," JAOCS vol. 71, No. 9, (Sep. 1994), p. 951-954.

Shin, et al.; "Butyl-Toyopearl 650 as a New Hydrophobic Adsorbent for Water-Soluable Enzyme Proteins"; Analytical Biochemistry(1984); vol. 138; pp. 259-261.

Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969, p. 93-103.

Si, Joan Qi, "Enzymes, Baking, Bread-Making", Encyclopedia of Bioprocess Technology, Wiley, 1999, ISBN 0471138223 NZAS-0255053, p. 1-18.

Si, Joan Qi, "Synergistic Effect of Enzymes for Breadbaking", Novo Nordisk publication A-06513b, p. 1-18, based on presentation No. 300 at AACC Annual Meeting 1996, Baltimore. Also Encyclopedia of Bioprocess Technology, Wiley, 1999, ISBN 0471138223.

Si, Joan Qi, et al. "Enzymes for bread, noodles and non-durum pasta", Cereal Food 2002 p. 1:3-3:4. Also in Enzymes in Food Technology, RJ Whitehurst & BA Law, Enzymes in Food Technology, Sheffield Academic Press, ISBN 1-84127-223-X, p. 19-54.

Si, Joan Qi, et al., "Novamyl—A true Anti-Staling Enzyme", Cereal Food, Oct. 2001, p. 1-20.

Si, Joan Qi, et al., "Synergistic Effect of Enzymes for Breadbaking", Cereal Food, Oct. 2001, p. 1:21, based on presentation No. 300 at AACC Annual Meeting 1996, Baltimore. Also Encyclopedia of Bioprocess Technology, Wiley, 1999, ISBN 0471138223.

Si, Joan Qi; "New Enzymes for the Baking Industry"; Food Tech Europe (1996) pp. 60-64.

Sias B et al, "Human Pancreatic Lipase-Related Protein 2 Is a Galactolipase," Biochemistry, (2004), vol. 43(31), p. 10138-48.

Siew W.L. et. al. (1999) "Influence of diglycerides on crystalisation of palm oil," in Journal of Science of Food and Agriculture 79:722-726.

Siew W.L. & Ng W.L. (2000) Differential scanning thermograms of palm oil triglycerides in the presence of diglycerides, in Journal of Oil Palm Research 12:107.

Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.

Skovgaard, et al.;"Comparison of Intra- and extracellualr isozyme banding patterns of *Fusarium oxysporum*"; Mycol. Res. (1998); vol. 102(9); pp. 1077-1084.

Slotboom et al, "Hydrolysis of Phosphoglycerides by Purified Lipase Preparation," Chem. Phys. Lipids vol. 4 (1970) 15-29.

Smith, George P.; "The Progeny of sexual PCR"; Nature; vol. 370; No. 18; Aug. 4, 1994 p. 324-325.

Smith, Timothy L., et al., "The promoter of the glucoamylase-encoding gene of *Aspergillus niger* functions in *Ustilago maydis*", Gene. 88, 259-262, 1990.

Soe, J.B., "Analyses of Monoglycerides and Other Emulsifiers by Gaschromatography", Fette, Seifen, Anstrichmittel, 1983, 85 Jahrgang, nr. 2, p. 72-76NZNA-0005896.

Solares, Laura F., et al., "Enzymatic resolution of new carbonate intermediates for the synthesis of (S)-(+)-zopiclone", Tetrahedron: Asymmetry, vol. 13, 2002, pp. 2577-2582.

Sols and De Le Fuente, "On the substrate specificity of glucose oxidase", Biochem et Biophysica Acta (1957) 24:206-7.

Sonntag N. O.V. (1982a) Glycerolysis of Fats and methyl esters—status, review and critique, in Journal of American Oil Chemist Society 59:795-802A.

Soragni, Elisabetta, et al., "A nutrient-regulated, dual localization phospholipase A2 in the symbiotic fungus" The EMBO Journal, vol. 20, No. 18, pp. 5079-5090, 2001.

Sosland, Josh, "Alive and kicking", Milling & Baking News, Feb. 24, 2004. http://www.bakingbusiness.com/co_articles.asp?ArticleID=70026 downloaded Sep. 16, 2004 p. 1-13.

Soumanou, Mohamed M., et al., "Two-Step Enzymatic Reaction for the Synthesis of Pure Structured Triacylglycerides", JAOCS, vol. 75, No. 6, 1998.

Spendler, et al., "Functionality and mechanism of a new 2nd generation lipase for baking industry"—Abstract. 2001 AACC Annual Meeting; Symposia at Charlotte, NC. Oct. 14-18, 2001.

Spradling J.E., "Tailoring Enzyme Systems for Food Processing, in"Biocatalysis in Agricultural Biotechnology, ACS Symposium Series 389, ed. Whitaker, John R. et al., 1989, ISBN 0-8412-1571-5 p. 24-43 NZAS-0213683.

Sreekrishna K et al (1988) "High level expression of heterologous proteins in methylotrophic yeast *Pichia pastoris*," J Basic Microbiol. 28(4), 265-78.

Stadler et al., "Understanding Lipase Action and Selectivity", CCACAA, vol. 68, No. 3, pp. 649-674, 1995.

Steinstraesser, et al., "Activity of Novispirin G10 against *Pseudomonas aeruginosa* in Vitro and in Infected Burns", Antimicrobial Agents and Chemotherapy, Jun. 2002, vol. 46, No. 6, pp. 1837-1844.

Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.

Stemmer, Willem P.C.; "Rapid evolution of a protein in vitro by DNA shuffling"; Affymax Research Institute, Nature, vol. 370, Aug. 4, 1994.

Sternberg, M., "Purification of Industrial Enzymes with Polyacrylic Acids", Process Biochemistry, Sep. 1976.

Strickland, James A., et al., "Inhibition of Diabrotica Larval Growth by Patatin, the Lipid Acyl Hydrolase from Potato Tubers", Plant Physiol, vol. 109, pp. 667-674, 1995.

Sudbery et al (1988) Biochem Soc Trans. 16(6), 1081-3.

Sugatani, Junko, et al., "Studies of a Phospholipase B from *Penicillium notatum* Substrate Specificity and Properties of Active Site", Biochimica et Biophysica Acta, vol. 620, 1980, pp. 372-386.

Sugimoto et al., Agric. Biol. Chem. 47(6), 1201-1206 (1983).

Sugiyama et al., "Molecular cloning of a second phospholipase B gene, caPLB2 from *Candida albicans*", Medical Mycology, vol. 37, 1999.

Svendsen, A. "Engineered lipases for practical use", Inform (1994) 5(5):619-623.

Svendsen, Allan, "Lipase protein engineering" Biochimica et Biophysica Acta, vol. 1543, 2000, pp. 223-238.

Svendsen, Allan, et al., "Biochemical properties of cloned lipases from the Pseudomonas family", Biochimica et Biophysica Acta, vol. 1259, 1995, pp. 9-17.

Sweigard, James A., et al., "Cloning and analysis of CUT1, a cutinase gene from *Magnaporthe grisea*", Mol. Gen. Genet., 232:174-182, 1992.

Swinkels et al (1993) Antonie van Leeuwenhoek 64, 187-201.

Sztajer H et al Acta Biotechnol, vol. 8, 1988, pp. 169-175.

Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.

Terasaki, Masaru, et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.

The New Enzyme Operatives, Ingredient Technology, 50, Aug. 1997.

Thommy L-G; Carlson, "Law and Order in Wheat Flour Dough; Colloidal Aspects of the Wheat Flour Dough and its Lipid and Protein Constituents in Aqueous Media", Fortroligt, Lund 1981.

Thornton et al 1988 Biochem. Et Biophys. Acta. 959, 153-159.

Tiss, Aly, et al., "Effects of Gum Arabic on Lipase Interfacial Binding and Activity", Analytical Biochemistry, vol. 294, pp. 36-43, 2001.

Toida J et al, Bioscience, Biotechnology, and Biochemistry, Jul. 1995, vol. 59, No. 7, pp. 1199-1203.

Tombs and Blake, Biochim. Biophys (1982) 700:81-89.

Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.

Torossian and Bell (Biotechnol. Appl. Biochem., 1991, 13:205-211.

Tsao et al. (1973) J Supramol Struct. 1(6), 490-7.

Tsuchiya, Atsushi et al, Cloning and Nucelotide Sequence of the Mono-and Diacylglycerol Lipase Gene (mdlB) of *Aspergillus oryzae*, Fems Microbiology Letters (1996) vol. 143, pp. 63-67.

Tsuneo Yamane et al., "Glycerolysis of Fat by Lipase", Laboratory of Bioreaction Engineering, vol. 35, No. 8, 1986.

Tsychiya, Atsushi, et al., "Cloning and nucleotide sequence of the mono- and diacylglycerol lipase gene (mdlB) of *Aspergillus oryzae*", FEMS Microbiology Letters, vol. 143, pp. 63-67, 1996.

Turnbull, K.M., et al., "Early expression of grain hardness in the developing wheat endosperm", Planta, 2003, vol. 216, pp. 699-706.

Turner, Nigel A., et al., "At what temperature can enzymes maintain their catalytic activity?", Enzyme and Microbial Technology, vol. 27, 2000, pp. 108-113.

Turner, Progress in Industrial Microbiology, Martinelli and Kinghorn (eds.), Elsevier, Amsterdam, 1994, 29:641-666.

Uppenberg, Jonas, et al., "Crystallographic and Molecular-Modeling Studies of Lipase B from *Candida antarctia* Reveal a Stereospecificity Pocket for Secondary alcohols", Biochemistry, 1995, vol. 34, pp. 16838-16851.

Uppenberg, Jonas, et al., "The Sequence, crystal structure determination and refinement of two crystal forms of lipase B from *Candida antarctica*", Structure 1994, vol. 2, No. 4.

Upton C et al TIBS Trends in Biochemical Sciences, Elsevier Publication (1995), vol. 20, pp. 178-179.

Uusitalo et al. (1991) J Biotechnol. 17(1), 35-49.

Uwajima T et al, Agricultural and Biological Chemistry, 43(12), pp. 2633-2634, 1979.

Uwajima T et al, Agricultural and Biological Chemistry, 44(9), pp. 2039-2045, 1980.

Vaidehi, et al.; "Lipase Activity of Some Fungi Isolated from Groundnut"; Current Science (1984); vol. 53(23); p. 1253.

van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.

Van Den Berg. G, Regulatory status and use of lipase in various countries, Bulletin of the IDF 294, p. 19-20, 1994.

van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.

van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.

van Nieuqenhuyzen W., "Lecithins Open Doors to baked goods", International Food Ingredients, 1998, No. 2, p. 32-36.

van Oort, Maarten G et al, Biochemistry 1989 9278-9285.

Vaysse et al J. of Biotechnology 53 (1997) 41-46.

Villenueva, Inform, vol. 8, No. 6, Jun. 1997.

Vujaklija, Dušica, et al., "A novel streptomycete lipase: cloning, sequencing and high-level expression of the *Streptomyces rimosus* GDS (L)-lipase gene", Arch. Microbiol, vol. 178, pp. 124-130, 2002.

Wahnelt S.V., Meusel D, & Tülsner M, (1991) Zur kenntnis des diglyceride influsses auf das kristallisationsverhalten von Felten, in Fat Science Technology 4:117-121.

Waninge, Rianne, et al., "Milk membrane lipid vesicle structures studied with Cryo-TEM", Colloids and Surfaces B: Biointerfaces 31 (2003), pp. 257-264.

Warmuth et al, 1992, Bio Forum 9, 282-283.

Watanabe et al. Bio sci Biochem 63(5) 820-826, 1999.

Watanabe, Yasuo et al., "Cloning and sequencing of phospholipase B gene from the yeast *Torulaspora delbrueckii*", FEMS Microbiology Letters, vol. 124, 1994, pp. 29-34.

Webb EC, Enzyme Nomenclature, 1992, p. 310.

Weber et al. J Agric Food Chem 1985, 33, 1093-1096.

Wen-Chen Suen et al., "Improved activity and thermostability of *Candida antarctica* lipase B by DNA family shuffling", Protein Engineering, Design & Selection, vol. 17, No. 2, pp. 133-140, 2004.

Wen-Chen Suen et al., "Improved activity and thermostability of *Candida antarctica* lipase B by DNA family shuffling", Protein Engineering, Design & Selection, vol. 17, No. 2, pp. 133-140, 2004.

West S.; "Olive and Other Edible Oils"; Industrial Enzymology (1996); pp. 295-299.

Whitaker, John R., et al., "Biocatalysis in Agricultural Biotechnology", ACS Symposium Series, American Chemical Society, 1989, p. 25-43.

Whitehead, Michael, et al., "Transformation of a nitrate reductase deficient mutant of *Penicillium chrysogenum* with the corresponding *Aspergillus niger* and *A. nidulans* niaD genes", Mol Gen Genet, 216: 408-411, 1989.

Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.

Williams K.R. et al., "Protein Analysis by Integrated Sample Preparation, Chemistry, and Mass Spectrometry", in Molecular Biology and Biotechnology—A Comprehensive Desk Reference, VCH, 1995, ISBN 1-56081-569-8 edited by Meyers R.A., p. 731-737.

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

Helmerich G. et al., Strukur-Wirkungsbeziehehungen von Phospholipiden in Backwaren, Wirkung von Phospholipiden, Getreide Mehl und Brot, 2003, vol. 57, No. 5, p. 270-273 NZAS-0301096.

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From *Saccharomyces cerevisiae*", Biochimica et Biophysica Acta, vol. 795, 1984, pp. 117-124.

Kelley R.L. and Reddy C.A., Glucose Oxidase of *Phanerochaete chrysosporium*, in "Biomass, Part B, Lignin, Pectin, and Chitin", Wood et al., Eds., Methods in Enzymology (1988) vol. 161, Academic Press, San Diego, p. 307-316.

Woolley et al., "Lipases their structure, biochemistry and application", Cambridge University Press (1994) p. 242-270.

WPI Acc No. 93-298906(38) and JP05211852 Preparation of low fat content cream-by adding lipase to mixture of fat and water, Nisshin Oil and Fat Corp. Aug. 24, 1993.
Xu, Jun, et al., "Intron requirement for AFP gene expression in *Trichoderma viride*", Microbiology, 2003, vol. 149, pp. 3093-3097.
Yamaguchi et al, 1991, Gene 103:61-67.
Yamane et al., "High-Yield Diacylglycerol Formation by Solid-Phase Enzymatic Glycerolysis of Hydrogenated Beef Tallow", JAOCS, vol. 71, No. 3, Mar. 1994.
Yamano Y et al., Surface activity of lysophosphatidyl choline from soybean, 4th World Surfactants Congress, 1996, p. 24-34.
Yamauchi, Asao et al., "Evolvability of random polypetides through functional selection within a small library", Protein Engineering, vol. 15, No. 7, pp. 619-626, 2002.
Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.
Yount, Nannette Y., et al., "Multidimensional signatures in antimicrobial peptides" PNAS (2004) vol. 101, No. 10, p. 7363-7368.
Zaks, Aleksey, et al., "Enzyme-catalyzed processes in organic solvents", Proc. Natl. Acad. Sci. USA, vol. 82, pp. 3192-3196, May 1985.
Zaks, Aleksey, et al., "The Effect of Water on Enzyme Action in Organic Media", The Journal of Biological Chemistry, vol. 263, No. 17, Issue of Jun. 15, pp. 8017-8021, 1988.
Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.
Zangenbert, Niels Honberg, et al., "A dynamic in vitro lipolysis model II. Evaluation of the model", European Journal of Pharmaceutical Sciences, vol. 14, 2001, pp. 237-244.
Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.
Zaks, Aleksey, et al., "Enzyme-catalyzed processes in organic solvents", Proc. Natl. Acad. Sci. USA, vol. 82, pp. 3192-3196, May 1985.
AACC Method 54-21 Farinograph Method for Flour, from Physical Dough Tests supplied by The British Library, Nov. 3, 1999.
Anderson D, "A Primer in Oils Processing Technology" in Bailey's Industrial Oil and Fat Products, Sixth edition, John Wiley, 2005, vol. 5, chapter 1, p. 1-56. ISBN 978047138401.
"AOAC Official method 999.10 (Lead, Cadmium, Zinc, Copper, and Iron in Foods Atomic absorption Spectrophotometry after Microwave Digestion), First Action 1999 NMKL-AOAC Method", AOAC International, pp. 1-3, 2002.
AOCS Method 2c-25 "1997 Moisture and Volatile Matter Air Oven Method" Sampling and Analysis of Commercial Fats and Oils, obtained from The British Library, p. 1, 1997.
AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.
Archer D.B. & Peberdy, The Molecular Biology of Secreted Enzyme Production by Fungi, Critical Reviews in Biotechnology, 1997, vol. 17, No. 4, p. 273-306.
Arskog and Joergensen, "Baking performance of prior art lipases from *Candida cylindracea* and *Aspergillus foeditus* and their activity on galactolipids in dough", Novozymes Report Jul. 18, 2005, pp. 1-2.
Arskog and Joergensen, "Baking performance of prior art lipases from *Humicola Lanuginosa, Aspergillus tubigensis, Rhizopus delemar* and *Rhizomucor miehei*, and their activity on galactolipids in dough", Novozymes Report Jul. 17, 2005, pp. 1-8.
Aust K., "Applications of lecithin in bakery foods," AIB Research Technical Bulletin, vol. XV, issue 12, Dec. 1993, p. 1-6.
Banas A. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, pp. 34626-34634.

Beggs J.D., Transformation of yeast by a replicating hybrid plasmid, Nature (London), 1978, vol. 275, p. 104.
Bessette, "Efficient folding or proteins with multiple disulphide bonds in the *Escherida coli cytoplasm*", Proc. Natl. Acad. Sci. USA, 1999, vol. 96, p. 13703-13708.
Bo Yang et al., "Optimization of Enzymatic Degumming Process for Rapseed Oil," JAOCS, 2006, vol. 83, No. 7, p. 653-658.
Bru R., López-Nicolás J.M., García-Carmona F., (1995) "Aggregation of polyunsaturated fatty acid in the presence of cyclodextrins", Colloids and Surfaces A: Physiochemical and Engineering Aspects. 97, p. 263-269.
Buchold H. et. al., "Enzymatische Phosphatidentfernung aus Pflanzenolen'" Technologies, 1993, vol. 95, No. 8, p. 300-304, ISSN:0931-5985.
Bylund G. (ed), 1995, Dairy Processing Handbook, Chapter 2, p. 17-42, Lund, Sweden.
Bylund G. (ed), 1995, Dairy Processing Handbook, Chapter 9, p. 227-246, Lund, Sweden.
Ceci L.N. et al, Oil recovery and lecithin production using water degumming sludge of crude soybean oils, Journal of the Science of Food and Agriculture, 2008, vol. 88, No. 14, p. 2460-2466.
Cereghino et al., Heterologous protein expression in the methylotrophic yeast *Pichia pastoris*, FEMS Microbiology Review, 2000, vol. 24, No. 1, p. 45-66.
Christou P., Genetic engineering of crop legumes and cereals: current status and recent advances, Agro-Food-Industry Hi-Tech, Mar./Apr. 1994, p. 17-27.
Davis R.H. and de Serres, Genetic and Microbiological Research Techniques for *Neurospora crassa*, Methods Enzymology, 1971, vol. 17A, p. 79-143.
EC 1.1.3.10 (downloaded—Jul. 12, 2010 from http://www.chem.qmul.ac.uk/iubmb/enzyme/EC1/1/3/10.html).
EC 1.1.3.4 (downloaded—Jul. 12, 2010 from http://www.chem.qmul.ac.uk/iubmb/enzyme/EC1/1/3/4.html).
EC 1.1.3.5 (downloaded—Nov. 16, 2009 from http://www.chem.qmul.ac.uk/iubmb/enzyme/EC1/1/3/5.html).
EC 2.3.1.43 (downloaded Apr. 21, 2009 from http://www.chem.qmul.ac.uk/iubmb/enzyme/EC2/3/1/43.html).
EC 2.4.1.19 (Downloaded Jul. 12, 2010 from http://www.chem.qmul.ac.uk/iubmb/enzyme/EC2/4/1/19.html).
EC 3.1.1.26 (downloaded—Dec. 18, 2008 from http://www.chem.qmul.ac.uk/iubmb/enzyme/EC3/1/1/26.html).
EC 3.1.1.3 (downloaded—Dec. 18, 2008 from http://www.chem.qmul.ac.uk/iubmb/enzyme/EC3/1/1/3.html).
EC 3.1.1.32 (downloaded—May 22, 2008 from http://www.chem.qmul.ac.uk/iubmb/enzyme/EC3/1/1/32.html).
EC 3.1.1.4 Phospholipase A2 enzyme Enzyme Entry 1983 (downloaded Apr. 21, 2009 from http://www.chem.qmul.ac.uk/iubmb/enzyme/EC3/1/1/4.html).
EC 3.1.1.5 (downloaded Dec. 18, 2008 from http://www.chem.qmul.ac.uk/iubmb/enzyme/EC3/1/1/5.html).
EC 3.2.1.3 (downloaded Jul. 12, 2010 from http://www.chem.qmul.ac.uk/iubmb/enzyme/EC3/2/1/3.html).
EC 3.2.1.32 (Downloaded Jul. 12, 2010 from http://www.chem.qmul.ac.uk/iubmb/enzyme/EC3/2/1/32.html).
EC 3.2.1.60 (downloaded Apr. 28, 2009 from http://www.chem.qmul.ac.uk/iubmb/enzyme/EC3/2/1/60.html).
Eliasson A-C. and Larssen K., "Chapter 2: Physiochemical Behavior of the Components of Wheat Flour", *Cereals in Breadmaking: a molecular colloidal approach*, Marcel Dekker Inc, 1993, ISBN0824788168, p. 31-45.
Genbank accession code NC_003888.1:8327480..8328367 (downloaded Apr. 21, 2009), p. 1.
Genbank accession No. AL646052 (downloaded Apr. 21, 2009), pp. 1-2.
Genbank accession No. AL939131.1:265480..266367 (downloaded Apr. 21, 2009), p. 1.
Genbank accession No. CAC42140 (downloaded Apr. 21, 2009), pp. 1-2.
Genbank accession No. NP_003888.1 (downloaded Apr. 21, 2009), pp. 1.
Genbank accession No. NP_631558.1 (downloaded Apr. 21, 2009), pp. 1.

Genbank accession No. P41734 (downloaded Apr. 21, 2009), pp. 1-4.
NCBI Accession No. Z75034 (downloaded Apr. 21, 2009) p. 1-2.
Hammond E.G. et al., "Soybean Oil" in Bailey's Industrial Oil and Fat Products, Sixth edition, John Wiley, 2005, vol. 3, chapter 13, p. 577-653. ISBN 9780471384011.
Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.
Hinnen A. et al., Transformation of yeast, Proceedings of the National Academy of Sciences USA, Apr. 1978, vol. 75, No. 4, p. 1929-1933.
Hollenberg C.P. et al., Production of recombinant proteins by methylotrophic yeasts, Current Opinion in Biotechnology Oct. 1997, vol. 8, No. 5, pp. 554-560.
Horwell DC, "The 'peptoid' approach to the design of non-peptide, small molecular agonists and antagonists of neuropeptides", Trends Biotechnol., 1995, vol. 13, No. 4, pp. 132-134.
Hossen, Monjur, "Enzyme catalyzed synthesis of structured phospholipids with conjugated linoleic acid and plant sterols, " A Dissertation by MD Monjur Hossen, May 2005, p. 1-152.
HUI, Bailey's Industrial Oil and Fat Products, 5th edition vol. 2 Edible Oil and Fat Products: Oils and Oilseeds, Wiley Interscience (1996), pp. 513-516. ISBN 0471594261.
Ito H. et al., "Transformation of Intact Yeast Cells Treated with Alkali Cations," J. Bacteriology, 1983, vol. 153, p. 163-168.
Jost R. et. al., "Milk and Dairy Products," Nestle Product Technology Center, 2007, Wiley-VCH, pp. 1-62, Konolfingen, Switzerland.
Kane, "Effects of rare codon clusters on high-level expression of heterolgous proteins in *E.coli*" Current Opinion Biotechnology, 1995, vol. 6, p. 494-500.
Kimmel, A. et al. "Preparation of cDNA and the Generation of cDNA Libraries: Overview," Methods in Enzymology, 1987, vol. 152, p. 307-316.
LaVallie T.M., 2-Methoxyestradiol Inhibits Proliferation and Induces Apoptosis Independently of Estrogen Receptors α and β, Current Opinion in Biotechnology, 1995, vol. 6, No. 5, pp. 501-506.
Leon et al., "A new approach to study starchy changes occurring the double-baking process and during bread storage," Z. Lebensn Unters Forsch A, 1997, vol. 204 pp. 316-320.
McIntyre et al., "Distribution of Glycerophospholipid-Cholesterol Acyltransferase in Selected Bacterial Species," Journal of Bacteriology, Jul. 1979, vol. 139, No. pp. 132-136.
NCBI protein accession code AAK84028.1 GI:15082088, (downloaded Dec. 18, 2009), pp. 1-2.
NCBI protein accession code CAB39707.1 GI:4529178, (downloaded Dec. 18, 2009), pp. 1-2.
NCBI protein accession code CAB62724.1 GI:6562793, (downloaded Dec. 18, 2009), pp. 1-2.
NCBI protein accession code CAB88833.1 GI:7635996, (downloaded Dec. 18, 2009), pp. 1-2.
NCBI protein accession code CAB89450.1; GI:7672261, (downloaded Dec. 18, 2009), pp. 1-2.
NCBI protein accession code CAC01477.1 GI:9716139, (downloaded Dec. 18, 2009), pp. 1-2.
NCBI's Genbank database accession No. 1IVN_A; GID:33357066, (downloaded Oct. 14, 2010), pp. 1-2.
Oil Mill Gazetteer, "Enzymatic Degumming Improves Oil Refining in China," Jul. 2005 vol. 111, p. 2-4.
Phospholipase C, E.C.3.1.4.3,, (downloaded Sep. 8, 2009 from http://www.chem.qmul.ac.uk/iubmb/enzyme/EC3/1/4/3.html), p. 1.
Poldermans B and Schoppink P, "Controlling the baking process and product quality with enzymes", Cereal Foods World, Mar. 1999, 44 (3), p. 132-135.
Potrykus I., Gene Transfer to Plants: assessment of published approaches and results, Annu. Rev. Plant Physiol. Plant Mol. Biol., 1991, vol. 42, p. 205-225.
PreSens Manual HydroPlate® HP96U and HydroPlate® HP96C, pp. 1-15, Aug. 17, 2004.
Simon RJ et al.,"Peptides: a modular approach to drug discovery", Proc. Natl. Acad. Sci. USA, 1992, vol. 89, No. 20, pp. 9367-9371.
Szuhaj B.F., "Lecithins" in Bailey's Industrial Oil and Fat Products, Sixth edition, John Wiley, 2005, vol. 2, chapter 13, p. 361-456. ISBN 9780471384011.
Tanji M.et al., "Lipase hydrolysis of milk fat and its soft fractions", Research Bulletin of Obihiro University, 2001, vol. 22, No. 2, p. 89-94.
Tilden E.B. and Hudson C.S., Preparation and Properties of the Amylases Produced by Bacillus Macerans and Bacillus Polymyxa, J. Bacteriology, 1942, vol. 43, p. 527-544.
Torres C.F. et al., A two steps enzymatic procedure to obtain sterol esters, tocopherols and fatty acid ethyl esters from soybean oil deodorizer distillate, Process Biochemistry, 2007, vol. 42, No., 9, p. 1335-1341.
Trueman L.J., "Heterologous Expression in Yeast," Methods Molecular Biology, vol. 49, p. 341-354 (1995).
Turner G. Vectors for generic manipulation, in Martinelli S.D, Kinghorn J.R. (editors), *Aspergillus*: 50 years on. Progress in industrial microbiology, 1994, vol. 29, p. 641-666.
Notification of Reasons for Refusal: JP Application No. 526105, Feb. 12, 2003 (Translation).
Notification of Reasons for Refusal: JP Application No. 526105, Jun. 4, 2002 (Translation).
Written Argument: JP Application No. 97181706.5, (Dec. 9, 1997) (Translation).
U.S. Appl. No. 60/083,277, filed Apr. 28, 1998, Spender, Tina et al.

SEQ ID No. 1

```
  1 ivafGDSlTd geayygdsdg ggwgagladr Ltallrlrar prgvdvfnrg isGrtsdGrl
 61 ivDalvallF laqslglpnL pPYLsgdflr GANFAsagAt Ilptsgpfli QvqFkdfksq
121 vlelrqalgl lqellrllpv ldakspdlvt imiGtNDlit saffgpkste sdrnvsvpef
181 kdnlrqlikr Lrsnngarii vlitlvilnl gplGClPlkl alalassknv dasgclerln
241 eavadfneal relaiskled qlrkdglpdv kgadvpyvDl ysifqdldgi qnpsayvyGF
301 ettkaCCGyG gryNynrvCG naglcnvtak aCnpssylls flfwDgfHps ekGykavAea
361 1
```

FIG. 1

SEQ ID No. 2

```
  1 mkkwfvcllg lvaltvqaad srpafsrivm fgdslsdtgk myskmrgylp ssppyyegrf
 61 sngpvwleql tnefpgltia neaeggptav aynkiswnpk yqvinnldye vtqflqkdsf
121 kpddlvilwv gandylaygw nteqdakrvr daisdaanrm vlngakeill fnlpdlgqnp
181 sarsqkvvea ashvsayhnq lllnlarqla ptgmvklfei dkqfaemlrd pqnfglsdqr
241 nacyggsyvw kpfasrsast dsqlsafnpq erlaiagnpl laqavaspma arsastlnce
301 gkmfwdqvhp ttvvhaalse paatfiesqy eflah
```

FIG. 2

SEQ ID No. 3

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

FIG. 3

SEQ ID No. 4

FIG. 4

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wieplllfghs lvpvhpnalg errmaehtmd vlgld
```

SEQ ID No. 5

```
  1 mpkpalrrvm tatvaavgtl algltdatah aapagatptl dyvalgdsys agsgvlpvdp
 61 anlclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aigahlndav rraaeetgat
241 yvdfsgvsdg hdaceapgtr wiepllfghs lvpvhpnalg errmaehtmd vlgld
```

FIG. 5

SEQ ID No. 6

```
  1 mdyekfllfg dsitefafnt rpiedgkdqy algaalvney trkmdilqrg fkgytsrwal
 61 kilpeilkhe snivmatifl gandacsagp qsvplpefid nirqmvsImk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

FIG. 6

Alignment of pfam00657.6 consensus sequence with P10480

```
           *->ivafGDSlTdg...............eayygdsdgggwgagladrL
              iv+fGDSl+d+++   ++ ++  +++++++  +++s+g   w ++l + +
P10480   28   IVMFGDSLSDTgkmyskmrgylpssppYYEGRFSNGPVWLEQLTNEF   74 tall..rlrarprgvdvfnrgisGrtsdGrlivDalvallFlaqslglpn
              + l   + ++++++++ +n+   +
P10480   75   PGLTiaNEAEGGPTAVAYNKISWNPK----------------------  100

LpPYLsgdflrGANFAsagAtIlptsgpfliQvqFkdfksqvlelrqalg
                                                             ++  ++
P10480  101   ------------------------------------------YQVINN  106 llqellrllpvldakspdlvtimiGtNDlitsaffgpkstesdrnvsvpe
              l++e+ ++l +++ k+ dlv++++G+ND+        ++ ++ ++++++
P10480  107   LDYEVTQFLQKDSFKPDDLVILWVGANDY--------LAYGWNTEQDAKR  148 fkdnlrqlikrLrsnngariivlitlvilnlgplGClPlklalalasskn
              ++d ++++++r+   nga+       ++++nl+  lG+ P+
P10480  149   VRDAISDAANRMV-LNGAK-----EILLFNLPDLGQNPS----------  181 vdasgclerlneavadfnealrelaiskledqlrkdglpdvkgadvpyvD
              ++++ +e +  ++a++n++l +la      +ql+++g+++++++d ++++
P10480  182   ARSQKVVEAASHVSAYHNQLLLNLA-----RQLAPTGMVKLFEIDKQFAE  226 lysifqdldgiqnpsayv.y....GFe.ttkaCCGyGgr.yNyn.rv.CG
              +  +q+++ + + +a++++    +++ +++a++++++  +N+++r+ ++
P10480  227   MLRDPQNFGLSDQRNACYgGsyvwKPFaSRSASTDSQLSaFNPQeRLaIA  276 nag.l.c.nvtakaC.npssyll.sflfwDgfHpsekGykavAeal<-*
              +++ l +  ++++a++ +s+ ++++++fwD++Hp+   ++a+ e
P10480  277   GNPlLaQaVASPMAArSASTLNCeGKMFWDQVIPTTVVHAALSEPA     322
```

FIG. 7A

Alignment of pfam00657.6 consensus sequence with AAG09804

```
                *->ivafGDSlTdg...............eayygdsdgggwgagladrL
                   iv+fGDSl+d+++   ++ ++  ++++++++  +++s+g   w ++l + +
AAG09804     28    IVMFGDSLSDTgkmyskmrgylpssppYYEGRFSNGPVWLEQLTKQF   74 tallrlrarprgvdvfnrgisGrtsdGrlivDalvallFlaqslglpnLp
                   +g+++    n +  +G+t
AAG09804     75    ----------PGLTIANEAEGGAT--------------------------   88

PYLsgdflrGANFAsagAtIlptsgpfliQvqFkdfksqvlelrqa....
                                                     ++++ + ++++ +
AAG09804     89    ------------------------------------AVAYNKISWNpkyq  102

..lgllqellrllpvldakspdlvtimiGtNDlitsaffgpkstesdrnv
                     ++l++e+ ++l +++ k+ dlv++++G+ND+       ++ ++ ++
AAG09804    103    vyNNLDYEVTQFLQKDSFKPDDLVILWVGANDY--------LAYGWNTEQ  144 svpefkdnlrqlikrLrsnngariivlitlvilnlgplGClPlklalala
                   ++++++d +++++++r+    nga+     +++++nl+ lG+ P+
AAG09804    145    DAKRVRDAISDAANRMV-LNGAK-----QILLFNLPDLGQNPS-------  181 ssknvdasgclerlneavadfnealrelaiskledqlrkdglpdvkgadv
                        ++++ +e + ++a++n++l +la      +ql+++g+++++++d
AAG09804    182    ----ARSQKVVEAVSHVSAYHNKLLLNLA------RQLAPTGMVKLFEIDK  222 pyvDlysifqdldgiqnpsayv.y....GFe.ttkaCCGyGgr.yNyn.r
                   +++++    +q+++ + ++ +++++   +++ t++ +++ +++ + +++r
AAG09804    223    QFAEMLRDPQNFGLSDVENPCYdGgyvwKPFaTRSVSTDRQLSaFSPQeR  272 v.CGnag.l.c.nvtakaC.npssyll.sflfwDgfHpsekGykavAeal
                   + +++++ l +  +++a++  +s    ++++++fwD+++Hp+    ++a+ e+
AAG09804    273    LaIAGNPlLaQaVASPMARrSASPLNCeGKMFWDQVHPTTVVHAALSERA  322

<-*

AAG09804      -    -
```

Alignment of pfam00657.6 consensus sequence with NP 631558

FIG. 7B

```
            *->ivafGDSlTdgeayygdsdgggwgagladrLtallrlrarprgvdvf
               +va+GDS ++g         +g +  +++L     + + + ++   +
NP_631558   42  YVALGDSYSAG---------SGVLPVDPANL----LCLRSTANYPHV  75 nrgisGrtsdGrlivD.a.l.vallFlaqslglpnLpPYLsgdflrGANF
             + ++G++       D + + +
NP_631558   76 IADTTGAR-----LTDvTcGaAQ--------------------------  93

AsagAtIlptsgpfliQvqFkdfksqvlelrqalgllqellrllpvldak
                                 +++        ++ +   ++ +++
NP_631558   94 ------------------------TADFTRAQYPGVAPQLDALGT 114 spdlvtimiGtNDl...............itsaffgpkstesdrnvsvp
            + dlvt+ iG+ND ++ + +  ++ +    ++ + +k   ++ + +++
NP_631558  115 GTDLVTLTIGGNDNstfinaitacgtagvlSGGKGSPCKDRHGTSFDDEI 164 efkdn..lrqlikrLrs.nngariivlitlvilnlg..........plG
            e +++ l++++ +r+++ +ar+ +l ++i+++ +++   + +    G
NP_631558  165 EANTYpaLKEALLGVRArAPHARVAALGYPWITPATadpscflklplAAG 214

ClPlklalalasssknvdasgclerlneavadfnealrelaiskledqlrk
              P+              l+ ++a  n a+r  a
NP_631558  215 DVPY-------------------LRAIQAHLNDAVRRAA---------- 234 dglpdvkgadvpyvDlysifqdldgiqnpsayvyGFettkaCCGyGgryN
            ++ + +yvD+ ++
NP_631558  235 ------EETGATYVDFSGVSDG--------------------------- 250 ynrvCGnaglcnvtakaC.npssyll.sflfwDgf...HpsekGykavAe
                           ++aC+ p +++ + lf + + + Hp++ G +++Ae
NP_631558  251 --------------HDACeAPGTRWIePLLFGHSLvpvHPNALGERRMAE 286 al<-*
             +
NP_631558  287 HT   288
```

FIG. 7C

Alignment of pfam00657.6 consensus sequence with CAC42140

```
            *->ivafGDSlTdgeayygdsdgggwgagladrLtallrlrarprgvdvf
               +va+GDS ++g         +g +  +++L    + + + ++    +
CAC42140  42   YVALGDSYSAG---------SGVLPVDPANL----LCLRSTANYPHV  75 nrgisGrtsdGrlivD.a.l.vallFlaqslglpnLpPYLsgdflrGANF
               + ++G++          D + + +
CAC42140  76   IADTTGAR-----LTDvTcGaAQ--------------------------  93

AsagAtIlptsgpfliQvqFkdfksqvlelrqalgllqellrllpvldak
                                         +++     ++ +  ++ +++
CAC42140  94   ------------------------TADFTRAQYPGVAPQLDALGT 114 spdlvtimiGtNDl...............itsaffgpkstesdrnvsvp
               + dlvt+ iG+ND ++  +  + ++ +   ++  + +k  ++ + +++
CAC42140  115  GTDLVTLTIGGNDNstfinaitacgtagvlSGGKGSPCKDRHGTSFDDEI 164 efkdn..lrqlikrLrs.nngariivlitlvilnlg..........plG
               e  +++ l++++ +r+++ +ar+ +l ++i+++  +++    + + G
CAC42140  165  EANTYpaLKEALLGVRArAPHARVAALGYPWITPATadpscflklplAAG 214

ClPlklalalasssknvdasgclerlneavadfnealrelaiskledqlrk
               P+                    1+ ++a  n  a+r  a
CAC42140  215  DVPY-------------------LRAIQAHLNDAVRRAA---------- 234 dglpdvkgadvpyvDlysifqdldgiqnpsayvyGFettkaCCGyGgryN
                                 ++ + +yvD+ ++
CAC42140  235  ------EETGATYVDFSGVSDG--------------------------- 250 ynrvCGnaglcnvtakaC.npssyll.sflfwDgf...HpsekGykavAe
                                  ++aC+ p +++ +   lf + + + Hp++  G +++Ae
CAC42140  251  --------------HDACeAPGTRWIePLLFGHSLvpvHPNALGERRMAE 286
```

FIG. 7D

```
              al<-*
              +
   CAC42140  287 HT   288

Alignment of pfam00657.6 consensus sequence with P41734
           *->ivafGDSlTdg....eayygdsdgggwgagladrLtallrlrarprg
              ++fGDS+T+   +++ + +  d+   ga+l + +       +r+
      P41734    6   FLLFGDSITEFafntRPIEDGKDQYALGAALVNEY---------TRK  43
```

FIG. 7E

```
           vdvfnrgisGrtsdGrlivDalvallFlaqslglpnLpPYLsgdflrGAN
           +d+   rg++G+t
P41734  44 MDILQRGFKGYT--------------------------------------- 55

FAsagAtIlptsgpfliQvqFkdfksqvlelrqalgllqellrllpvlda
                               +r+al++l+e+l+         +
P41734  56 -----------------------SRWALKILPEILKH-----E 70 kspdlvtimiGtNDlitsaffgpkstesdrnvsvpefkdnlrqlikrLrs
           +  + ti++G+ND+         ++ +++ v++pef+dn+rq++++++s
P41734  71 SNIVMATIFLGANDA---------CSAGPQSVPLPEFIDNIRQMVSLMKS 111 nngariivlitlvilnlgplGClPlklalalassknvdasgclerlneav
           ++++ii++++lv   ++                ++ k ++ +  + r+ne +
P41734 112 YHIRPIIIGPGLVDREKW-------------EKEKSEEIALGYFRTNENF 148 adfnealrelaiskledqlrkdglpdvkgadvpyvDlysifqdldgiqnp
           a +  al +la                ++ +vp+v l+++fq+ +g++++
P41734 149 AIYSDALAKLA----------------NEEKVPFVALNKAFQQEGGDAWQ 182 sayvyGFettkaCCGyGgryNynrvCGnaglcnvtakaCnpssyllsflf
           +                                              l+
P41734 183 Q---------------------------------------------LL 185 wDgfHpsekGykavAeal<-*
           Dg+H+s kGyk+++++l
P41734 186 TDGLHFSGKGYKIFHDEL    203
```

*FIG. 7F*

```
A.sal   1   MKKWFVCLLGLIALTVQAADTRPAFSRIVMFGDSLSDTGKMYSKMRGYLPSSPPYYEGRF  60
                       +           +

A.hyd   1   MKKWFVCLLGLVALTVQAADSRPAFSRIVMFGDSLSDTGKMYSKMRGYLPSSPPYYEGRF  60

A. sal  61  SNGPVWLEQLTKQFPGLTIANEAEGGATAVAYNKISWNPKYQVINNLDYEVTQFLQKDSF  120
                        ++             +

A. hyd  61  SNGPVWLEQLTNEFPGLTIANEAEGGPTAVAYNKISWNPKYQVINNLDYEVTQFLQKDSF  120

A. sal  121 KPDDLVILWVGANDYLAYGWNTEQDAKRVRDAISDAANRMVLNGAKQILLFNLPDLGQNP  180
                                                              +

A. hyd  121 KPDDLVILWVGANDYLAYGWNTEQDAKRVRDAISDAANRMVLNGAKEILLFNLPDLGQNP  180

A. sal  181 SARSQKVVEAVSHVSAYHNKLLLNLARQLAPTGMVKLFEIDKQFAEMLRDPQNFGLSDVE  240
                      +      +                                        ++

A.hyd   181 SARSQKVVEAASHVSAYHNQLLLNLARQLAPTGMVKLFEIDKQFAEMLRDPQNFGLSDQR  240

A. sal  241 NPCYDGGYVWKPFATRSVSTDRQLSAFSPQERLAIAGNPLLAQAVASPMARRSASPLNCE  300
               + ++ +    + + +   +                         + +

A. hyd  241 NACYGGSYVWKPFASRSASTDSQLSAFNPQERLAIAGNPLLAQAVASPMAARSASTLNCE  300

A. sal  301 GKMFWDQVHPTTVVHAALSERAATFIETQYEFLAH  335
                        +       +

A. hyd  301 GKMFWDQVHPTTVVHAALSEPAATFIESQYEFLAH  335
```

FIG. 8

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCGCTTC
181  TCCAACGGGC CCGTCTGGCT GGAGCAGCTG ACCAACGAGT TCCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC CGGATCTGGG CCAGAACCCC
541  TCGGCCCGCA GCCAGAAGGT GGTCGAGGCG GCCAGCCATG TCTCCGCCTA CCACAACCAG
601  CTGCTGCTGA ACCTGGCACG CCAGCTGGCT CCCACCGGCA TGGTGAAGCT GTTCGAGATC
661  GACAAGCAGT TTGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCCGG CAACCCGCTG
841  CTGGCCCAGG CCGTCGCCAG CCCCATGGCT GCCCGCAGCG CCAGCACCCT CAACTGTGAG
901  GGCAAGATGT TCTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

FIG. 9

```
  1 ATGAAAAAAT GGTTTGTTTG TTTATTGGGG TTGATCGCGC TGACAGTTCA GGCAGCCGAC
 61 ACTCGCCCCG CCTTCTCCCG GATCGTGATG TTCGGCGACA GCCTCTCCGA TACCGGCAAA
121 ATGTACAGCA AGATGCGCGG TTACCTCCCC TCCAGCCCGC CCTACTATGA GGGCCGTTTC
181 TCCAACGGAC CCGTCTGGCT GGAGCAGCTG ACCAAGCAGT TCCCGGGTCT GACCATCGCC
241 AACGAAGCGG AAGGCGGTGC CACTGCCGTG GCTTACAACA AGATCTCCTG GAATCCCAAG
301 TATCAGGTCT ACAACAACCT GGACTACGAG GTCACCCAGT TCTTGCAGAA AGACAGCTTC
361 AAGCCGGACG ATCTGGTGAT CCTCTGGGTC GGTGCCAATG ACTATCTGGC ATATGGCTGG
421 AATACGGAGC AGGATGCCAA GCGAGTTCGC GATGCCATCA GCGATGCGGC CAACCGCATG
481 GTACTGAACG GTGCCAAGCA GATACTGCTG TTCAACCTGC CGGATCTGGG CCAGAACCCG
541 TCAGCCCGCA GTCAGAAGGT GGTCGAGGCG GTCAGCCATG TCTCCGCCTA TCACAACAAG
601 CTGCTGCTGA ACCTGGCACG CCAGCTGGCC CCCACCGGCA TGGTAAAGCT GTTCGAGATC
661 GACAAGCAAT TGCCGAGAT GCTGCGTGAT CCGCAGAACT TCGGCCTGAG CGACGTCGAG
721 AACCCCTGCT ACGACGGCGG CTATGTGTGG AAGCCGTTTG CCACCCGCAG CGTCAGCACC
781 GACCGCCAGC TCTCCGCCTT CAGTCCGCAG GAACGCCTCG CCATCGCCGG CAACCCGCTG
841 CTGGCACAGG CCGTTGCCAG TCCTATGGCC CGCCGCAGCG CCAGCCCCCT CAACTGTGAG
901 GGCAAGATGT TCTGGGATCA GGTACACCCG ACCACTGTCG TGCACGCAGC CCTGAGCGAG
961 CGCGCCGCCA CCTTCATCGA GACCCAGTAC GAGTTCCTCG CCCACGGATG A
```

FIG. 10

```
  1 ATGCCGAAGC CTGCCCTTCG CCGTGTCATG ACCGCGACAG TCGCCGCCGT CGGCACGCTC
 61 GCCCTCGGCC TCACCGACGC CACCGCCCAC GCCGCGCCCG CCCAGGCCAC TCCGACCCTG
121 GACTACGTCG CCCTCGGCGA CAGCTACAGC GCCGGCTCCG GCGTCCTGCC CGTCGACCCC
181 GCCAACCTGC TCTGTCTGCG CTCGACGGCC AACTACCCCC ACGTCATCGC GGACACGACG
241 GGCGCCCGCC TCACGGACGT CACCTGCGGC GCCGCGCAGA CCGCCGACTT CACGCGGGCC
301 CAGTACCCGG GCGTCGCACC CCAGTTGGAC GCGCTCGGCA CCGGCACGGA CCTGGTCACG
361 CTCACCATCG GCGGCAACGA CAACAGCACC TTCATCAACG CCATCACGGC CTGCGGCACG
421 GCGGGTGTCC TCAGCGGCGG CAAGGGCAGC CCCTGCAAGG ACAGGCACGG CACCTCCTTC
481 GACGACGAGA TCGAGGCCAA CACGTACCCC GCGCTCAAGG AGGCGCTGCT CGGCGTCCGC
541 GCCAGGGCTC CCCACGCCAG GGTGGCGGCT CTCGGCTACC CGTGGATCAC CCCGGCCACC
601 GCCGACCCGT CCTGCTTCCT GAAGCTCCCC CTCGCCGCCG GTGACGTGCC CTACCTGCGG
661 GCCATCCAGG CACACCTCAA CGACGCGGTC CGGCGGGCCG CCGAGGAGAC CGGAGCCACC
721 TACGTGGACT TCTCCGGGGT GTCCGACGGC CACGACGCCT GCGAGGCCCC CGGCACCCGC
781 TGGATCGAAC CGCTGCTCTT CGGGCACAGC CTCGTTCCCG TCCACCCCAA CGCCCTGGGC
841 GAGCGGCGCA TGGCCGAGCA CACGATGGAC GTCCTCGGCC TGGACTGA
```

FIG. 11

```
  1  TCAGTCCAGG CCGAGGACGT CCATCGTGTG CTCGGCCATG CGCCGCTCGC CCAGGGCGTT
 61  GGGGTGGACG GGAACGAGGC TGTGCCCGAA GAGCAGCGGT TCGATCCAGC GGGTGCCGGG
121  GGCCTCGCAG GCGTCGTGGC CGTCGGACAC CCCGGAGAAG TCCACGTAGG TGGCTCCGGT
181  CTCCTCGGCG GCCCGCCGGA CCGCGTCGTT GAGGTGTGCC TGGATGGCCC GCAGGTAGGG
241  CACGTCACCG GCGGCGAGGG GGAGCTTCAG GAAGCAGGAC GGGTCGGCGG TGGCCGGGGT
301  GATCCACGGG TAGCCGAGAG CCGCCACCCT GGCGTGGGGA GCCCTGGCGC GGACGCCGAG
361  CAGCGCCTCC TTGAGCGCGG GGTACGTGTT GGCCTCGATC TCGTCGTCGA AGGAGGTGCC
421  GTGCCTGTCC TTGCAGGGGC TGCCCTTGCC GCCGCTGAGG ACACCCGCCG TGCCGCAGGC
481  CGTGATGGCG TTGATGAAGG TGCTGTTGTC GTTGCCGCCG ATGGTGAGCG TGACCAGGTC
541  CGTGCCGGTG CCGAGCGCGT CCAACTGGGG TGCGACGCCC GGGTACTGGG CCCGCGTGAA
601  GTCGGCGGTC TGCGCGGCGC CGCAGGTGAC GTCCGTGAGG CGGGCGCCCG TCGTGTCCGC
661  GATGACGTGG GGGTAGTTGG CCGTCGAGCG CAGACAGAGC AGGTTGGCGG GGTCGACGGG
721  CAGGACGCCG GAGCCGGCGC TGTAGCTGTC GCCGAGGGCG ACGTAGTCCA GGGTCGGAGT
781  GGCCTGGGCG GGCGCGGCGT GGGCGGTGGC GTCGGTGAGG CCGAGGGCGA GCGTGCCGAC
841  GGCGGCGACT GTCGCGGTCA TGACACGGCG AAGGGCAGGC TTCGGCAT
```

FIG. 12

```
  1 ATGGATTACG AGAAGTTTCT GTTATTTGGG GATTCCATTA CTGAATTTGC TTTTAATACT
 61 AGGCCCATTG AAGATGGCAA AGATCAGTAT GCTCTTGGAG CCGCATTAGT CAACGAATAT
121 ACGAGAAAAA TGGATATTCT TCAAAGAGGG TTCAAAGGGT ACACTTCTAG ATGGGCGTTG
181 AAAATACTTC CTGAGATTTT AAAGCATGAA TCCAATATTG TCATGGCCAC AATATTTTTG
241 GGTGCCAACG ATGCATGCTC AGCAGGTCCC CAAAGTGTCC CCTCCCCGA ATTTATCGAT
301 AATATTCGTC AAATGGTATC TTTGATGAAG TCTTACCATA TCCGTCCTAT TATAATAGGA
361 CCGGGGCTAG TAGATAGAGA GAAGTGGGAA AAAGAAAAAT CTGAAGAAAT AGCTCTCGGA
421 TACTTCCGTA CCAACGAGAA CTTTGCCATT TATTCCGATG CCTTAGCAAA ACTAGCCAAT
481 GAGGAAAAAG TTCCCTTCGT GGCTTTGAAT AAGGCGTTTC AACAGGAAGG TGGTGATGCT
541 TGGCAACAAC TGCTAACAGA TGGACTGCAC TTTTCCGGAA AAGGGTACAA AATTTTTCAT
601 GACGAATTAT TGAAGGTCAT TGAGACATTC TACCCCCAAT ATCATCCCAA AAACATGCAG
661 TACAAACTGA AAGATTGGAG AGATGTGCTA GATGATGGAT CTAACATAAT GTCTTGA
```

FIG. 13

(SEQ ID No. 12)

```
              10         20         30         40         50         60
              |          |          |          |          |          |
       MNLRQWMGAA TAALALGLAA CGGGGTDQSG NPNVAKVQRM VVFGDSLSDI GTYTPVAQAV 70         80         90        100        110        120
              |          |          |          |          |          |
       GGGKFTTNPG PIWAETVAAQ LGVTLTPAVM GYATSVQNCP KAGCFDYAQG GSRVTDPNGI 130        140        150        160        170        180
              |          |          |          |          |          |
       GHNGGAGALT YPVQQQLANF YAASNNTFNG NNDVVFVLAG SNDIFFWTTA AATSGSGVTP 190        200        210        220        230        240
              |          |          |          |          |          |
       AIATAQVQQA ATDLVGYVKD MIAKGATQVY VFNLPDSSLT PDGVASGTTG QALLHALVGT 250        260        270        280        290        300
              |          |          |          |          |          |
       FNTTLQSGLA GTSARIIDFN AQLTAAIQNG ASFGFANTSA RACDATKINA LVPSAGGSSL 310        320        330        340
              |          |          |          |
       FCSANTLVAS GADQSYLFAD GVHPTTAGHR LIASNVLARL LADNVAH
```

*FIG. 14*

(SEQ ID No. 13)

```
atgaacctgc gtcaatggat gggcgccgcc acggctgccc ttgccttggg cttggccgcg      60
tgcgggggcg gtgggaccga ccagagcggc aatcccaatg tcgccaaggt gcagcgcatg     120
gtggtgttcg gcgacagcct gagcgatatc ggcacctaca cccccgtcgc gcaggcggtg     180
ggcggcggca agttcaccac caacccgggc ccgatctggg ccgagaccgt ggccgcgcaa     240
ctgggcgtga cgctcacgcc ggcggtgatg ggctacgcca cctccgtgca gaattgcccc     300
aaggccggct gcttcgacta tgcgcagggc ggctcgcgcg tgaccgatcc gaacggcatc     360
ggccacaacg gcggcgcggg ggcgctgacc tacccggttc agcagcagct cgccaacttc     420
tacgcggcca gcaacaacac attcaacggc aataacgatg tcgtcttcgt gctggccggc     480
agcaacgaca ttttcttctg gaccactgcg gcggccacca gcggctccgg cgtgacgccc     540
gccattgcca cggcccaggt gcagcaggcc gcgacggacc tggtcggcta tgtcaaggac     600
atgatcgcca agggtgcgac gcaggtctac gtgttcaacc tgcccgacag cagcctgacg     660
ccggacggcg tggcaagcgg cacgaccggc caggcgctgc tgcacgcgct ggtgggcacg     720
ttcaacacga cgctgcaaag cgggctggcc ggcacctcgg cgcgcatcat cgacttcaac     780
gcacaactga ccgcggcgat ccagaatggc gcctcgttcg gcttcgccaa caccagcgcc     840
cgggcctgcg acgccaccaa gatcaatgcc ctggtgccga gcgccggcgg cagctcgctg     900
ttctgctcgg ccaacacgct ggtggcttcc ggtgcggacc agagctacct gttcgccgac     960
ggcgtgcacc cgaccacggc cggccatcgc ctgatcgcca gcaacgtgct ggcgcgcctg    1020
ctggcggata acgtcgcgca ctga                                           1044
```

FIG. 15

(SEQ ID No. 20)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

FIG. 16

(SEQ ID No. 21)

```
  1 gtgatcgggt cgtacgtggc ggtgggggac agcttcaccg agggcgtcgg cgaccccggc
 61 cccgacgggg cgttcgtcgg ctgggccgac cggctcgccg tactgctcgc ggaccggcgc
121 cccgagggcg acttcacgta cacgaacctc gccgtgcgcg gcaggctcct cgaccagatc
181 gtggcggaac aggtcccgcg ggtcgtcgga ctcgcgcccg acctcgtctc gttcgcggcg
241 ggcggcaacg acatcatccg gcccggcacc gatcccgacg aggtcgccga gcggttcgag
301 ctggcggtgg ccgcgctgac cgccgcggcc ggaaccgtcc tggtgaccac cgggttcgac
361 acccgggggg tgcccgtcct caagcacctg cgcggcaaga tcgccacgta caacgggcac
421 gtccgcgcca tcgccgaccg ctacggctgc ccggtgctcg acctgtggtc gctgcggagc
481 gtccaggacc gcagggcgtg ggacgccgac cggctgcacc tgtcgccgga ggggcacacc
541 cgggtggcgc tgcgcgcggg gcaggccctg gcctgcgcg tcccggccga ccctgaccag
601 ccctggccgc ccctgccgcc gcgcggcacg ctcgacgtcc ggcgcgacga cgtgcactgg
661 gcgcgcgagt acctggtgcc gtggatcggg cgccggctgc ggggcgagtc gtcgggcgac
721 cacgtgacgg ccaaggggac gctgtcgccg gacgccatca agacgcggat cgccgcggtg
781 gcctga
```

FIG. 17

(SEQ ID No. 22)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

FIG. 18

(SEQ ID No. 23)

```
  1 atgcagacga accccgcgta caccagtctc gtcgccgtcg gcgactcctt caccgagggc
 61 atgtcggacc tgctgcccga cggctcctac cgtggctggg ccgacctcct cgccacccgg
121 atggcggccc gctcccccgg cttccggtac gccaacctgg cggtgcgcgg␣aagctgatc
181 ggacagatcg tcgacgagca ggtggacgtg gccgccgcca tgggagccga cgtgatcacg
241 ctggtcggcg ggctcaacga cacgctgcgg cccaagtgcg acatggcccg ggtgcgggac
301 ctgctgaccc aggccgtgga acggctcgcc ccgcactgcg agcagctggt gctgatgcgc
361 agtcccggtc gccagggtcc ggtgctggag cgcttccggc ccgcatgga  ggccctgttc
421 gccgtgatcg acgacctggc cgggcggcac ggcgccgtgg tcgtcgacct gtacggggcc
481 cagtcgctgg ccgaccctcg gatgtgggac gtggaccggc tgcacctgac cgccgagggc
541 caccgccggg tcgcggaggc ggtgtggcag tcgctcggcc acgagcccga ggaccccgag
601 tggcacgcgc cgatcccggc gacgccgccg cggggtgg tgacgcgcag gaccgcggac
661 gtccggttcg cccggcagca cctgctgccc tggataggcc gcaggctgac cgggcgctcg
721 tccggggacg gcctgccggc caagcgcccg gacctgctgc cctacgagga ccccgcacgg
781 tga
```

FIG. 19

(SEQ ID No. 24)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 irvvgatitp fggygytea retmrgevne eirsgrvfdt vvdfdkalrd pydprrmrsd
421 ydsgdhlhpg dkgyarmgav idlaaikgaa pvka
```

FIG. 20

(SEQ ID No. 25)

```
   1 atgacccggg gtcgtgacgg gggtgcgggg gcgccccca ccaagcaccg tgcctgctc
  61 gcggcgatcg tcaccctgat agtggcgatc tccgcggcca tatacgccgg agcgtccgcg
 121 gacgacggca gcagggacca cgcgctgcag gccggaggcc gtctcccacg aggagacgcc
 181 gccccccgt ccaccggtgc gctgggcca gccacccggc cgcacccggc cggccccgag
 241 ccgggcaccg agacgaccgg cctggcgggc cgctccgtgc gcaacgtcgt gcacacctcg
 301 gtcgcggca ccctcgatcg gatcacccc tgaacctgt acgggcagtc gccgctgacc
 361 gtcacacacg cctcgcacgc cggcgcagc gggcccgaca ccgccgcgc gatcgccgac
 421 accatgcgcc ggctcacctt cggcggcgga tcatccggg tcatcccgg gggcgccag
 481 gtgatgagcg acacccgcg cctcgccatc ccctacgggg gccggttga cgaactcgcc
 541 tactccccca tcccgtccgg gccgtgacc taccatccgc agccccggca ggtcaccacg
 601 ctggccgacg gcgaccgcac ccgcgacgtc acgcgccgtcg cgtacacgac cccacgccc
 661 tactgccgct acctcgccct cgacgtgctg agccacgg aggccgacgg caggtgtg
 721 gcgttcggcg actccatcac cgacggcgca cgcagccaag gcgacaacg ccaccgctgg
 781 acggacgtcc tcgccgcacg cctgcacgag gcggcgggcg acggcggga cacgccccgc
 841 tacagcgtcg tcaacgagg catcagcggc aaccggctcc ttccagcggg gcgggggcgg
 901 cggcccgaca accgcccgcc cctgagccgg actgagcggg accgtgctgga acgaccaac
 961 gtcaaggccg tcgtcgtcgt cctcggcgtc aacgacgtcc tgaacagccc ggaactcgcc
1021 gacgcgcacg ccatcctgac cggcctgcgc accctcgtcg acgggcgca cgcccgggga
1081 ctgcgggtcg tcgccgcggct gatcacgccg ttcggcggct acgggcgcta cacggaggcc
1141 cgcgagacga tgcgcgagga tgcaacgag gtcaacgag gagatccgtt cggcgggt cttcgacacg
1201 gtcgtcgact tcgacaaggc cctgcgcgac ccgtacgacc cgcgccggt gcgctccgac
1261 tacgacagcg gcgaccacct gcacccccggc gacaaggggt acgcgcgcat gggcgcggtc
1321 atcgacctgg ccgcgctgaa gggcgcggcg ccggtcaagg cgtag
```

FIG. 21

(SEQ ID No. 26)

```
  1 mtsmsrarva rriaagaayg gggiglagaa avglvvaevq larrrvgvgt ptrvpnaqgl
 61 yggtlptagd pplrlmmlgd staagqvhr agqtpgalla sglaavaerp vrlgsvaqpg
121 acsddidrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeeaas
301 eagtevaaam ptgprgpwal lkrrrrrrvs eaepsspsgv
```

FIG. 22

(SEQ ID No. 27)

```
   1 atgacgagca tgtcgagggc gagggtggcg cggccggatcg cggccggcgc ggcgtacggc
  61 gcggccggca tcgccctggc ggagcgccgg gcggtcggtc cggtgttggc cgaggtgcag
 121 ctgccagac gcagggtggg gtgggcacg ccgaccccgg tccgaacgc gcaggggactg
 181 tacggcggca ccctgcccac ccgccgcgac ccgccgctgc ggctgatgat gctgggcgac
 241 tccacggcg ccgggcaggg cgtgcaccgg gccggcaga gccgggcgc gctgggcgcg
 301 tccgggctcg cggcgcctggc ggagcgccgg gtgcgcctgg ggtcggctcg cagccgggg
 361 gcgtgctcgg acgacctgg cggcagtg gcgtggtgc tcgcccgagcc ggaccggtg
 421 cccgacatct gcgtgatcat ggtcggcgcc aacgacgtca cccaccggcg gccggcgacc
 481 cgctcggtgc ggcaccctgtc ctcggcggta ccgggcctgc gcaacggccgg tgcggaggtg
 541 gtggtcggca cctgtccgga cctgggcacg atcgagcggg tgcggcagcc gctgcgctgg
 601 ctggcccggc gggcctcacg gcagctcgcg gcgcacaga ccatcggcgc cgtcgagcag
 661 gcgggcgca cgtgtgcct ggcgacctg ctggtccgg agttccgcca gaaccccgg
 721 gagctcttcg gccccgacaa ctaccaccc tccgccgagg gtacgccac ggccgccgatg
 781 gcgtactgc cctcggtgtg cgccgcctc ggcctgtggc cggccgacga ggagcacccg
 841 gacgcggctgc gccgcgaggg cttcctgccg gtggcgcgcg gcgcggcgcc tgcgtcc
 901 gaggcgggta cggaggtgcg cctacgggg cctacggccatg ctctacgccg ctgggcctg
 961 ctgaagcgcc ggagacggcc gaggcggaac cgtccagcc gtccagcgtt
1021 tga
```

FIG. 23

(SEQ ID No. 28)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraaqre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

FIG. 24

(SEQ ID No. 29)

```
  1 atggtcgag ggacggacca gcggacgcgg tacggccgtc gccgggcgcg tgtcgcgctc
 61 gcgccctga ccgccgccgt cctgggcgtg ggcgtggcgg gctgcgactc cgtgggcggc
121 gactcacccg ctccttccgg cagcccgtcg aagcggacga ggacggcgcc cgcctggtcc
181 accagcccgg cgtccgtcgc cgccgtgggc gactccatca cgcgcggctt cgacgcctgt
241 gcggtgctgt cggactgccc ggaggtgtcg tgggcgaccg gcagcagcgc gaaggtcgac
301 tcgctggccg tacggctgct ggggaaggcg gacgcggccg agcacagctg gaactacgcg
361 gtcaccgggg cccggatggc ggacctgacc gctcaggtga cgcgggcggc gcagcgcgag
421 ccggagctgg tggcggtgat ggccggggcg aacgacgcgt gccgttccac gacctcgacg
481 atgacgccgg tggcggactt ccgggcgcag ttcgaggagg cgatggccac cctgcgcaag
541 aagctcccca aggcgcaggt gtacgtgtcg agcatcccgg acctcaagcg gctctggtcc
601 cagggcccga ccaacccgct gggcaagcag gtgtggaagc tcggcctgtg ccgtcgatg
661 ctgggcgacg cgactccct ggactcggcg gcgacctgc ggcgcaacac ggtgcgcgac
721 cggtggcgg cgtactcgga ggtgctgcgg gaggtctgcg gcaaggaccg gcggtgccgc
781 agcgacgacg gcgcggtgca cgagttccgg ttcggcacgg cgaaggaccg gcactgggac
841 tggttccacc cgagtgtgga cggccaggcc cggctggcgg agatcgccta ccgcgcggtc
901 accgcgaaga atccctga
```

FIG. 25

(SEQ ID No. 30)

```
  1 mrlsrraata sallltpala lfgasaavsa priqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl pagldqvyda idsrapaaqv vvlgyprfyk
181 lggscavgls eksraainaa addinavtak raadhgfafg dvnttfaghe lcsgapwlhs
241 vtlpvensyh ptanggskgy lpvlnsat
```

FIG. 26

(SEQ ID No. 31)

```
   1 ttcatcacaa cgatgtcaca acaccggcca tccggtcat ccctgatcgt gggaatgggt
  61 gacaagcctt cccgtgacga aagggtcctg ctacatcaga aatgacagaa atcctgctca
 121 gggaggttcc atgagactgt cccgacggcg ggccacggcg tccgcgctcc tcctcaccc
 181 ggcgctcgcg ctcttcggcg cgagcgccgc cgtgtccggc cgcgaatcc agccaccga
 241 ctacgtggcc ctcggcgact cctactcctc ggggtcggc ctgtggcagt acgacagcag
 301 cagtggctcc tgtaagcgca gcaccaagtc ggcgccggcc ctgtggccg cctcgcacac
 361 cggtacgcgg ttcaacttca cgcctgttc acaggagacg tgctggcaa cctcgcacaa
 421 gcagctgacc ccggtcaact ccggcaccga cctggtcagc acaccatcg gcggcaacga
 481 cgcgggcttc gccgacacca tgaccacctg caacctccag ggcgagagcg cgtgcctggc
 541 gcgaatcgcc aaggcgcgcg cctacatcca gcagacgctg cccgcccagc tggaccaggt
 601 ctacgacgcc atcgacagcc gggccccgc agcccaggtc gtcgtcctgg gctacccgcg
 661 cttctacaag ctgggcggca gctgcgcgt cggtctctcg gagaagtccc gcgcggccat
 721 caacgccgcc gccgacgaca tcaacgccgt caccgccaag cgcgccgccg accacggctt
 781 cgcctttcggg gacgtcaaca cgaccttcgc cgggcacgag ctgtgctccg gcgccccctg
 841 gctgcacagc gtcacccttc cgtggagaa ctcctaccac cccacggcca acggacagtc
 901 caagggctac ctgccgtcc tgaactccgc cacctgatct cgcggctact ccgcccctga
 961 cgaagtcccg cccccggcg gggcttcgcc gtaggtgcgc gtaccgccgt cgcccgtcgc
1021 gccggtggcc ccgccgtacg tgccgccgcc cccggacgcg gtcggttc
```

FIG. 27

(SEQ ID No. 32)

```
  1 MKKWFVCLLG LVALTVQAAD SRPAFSRIVM FGDSLSDTGK MYSKMRGYLP
 51 SSPPYYEGRF SNGPVWLEQL TKQFPGLTIA NEAEGGATAV AYNKISWNPK
101 YQVINNLDYE VTQFLQKDSF KPDDLVILWV GANDYLAYGW NTEQDAKRVR
151 DAISDAANRM VLNGAKQILL FNLPDLGQNP SARSQKVVEA VSHVSAYHNQ
201 LLLNLARQLA PTGMVKLFEI DKQFAEMLRD PQNFGLSDVE NPCYDGGYVW
251 KPFATRSVST DRQLSAFSPQ ERLAIAGNPL LAQAVASPMA RRSASPLNCE
301 GKMFWDQVHP TTVVHAALSE RAATFIANQY EFLAH*
```

FIG. 28

(SEQ ID No. 33)

```
   1 ATGAAAAAAT GGTTTGTGTG TTTATTGGGA TTGGTCGCGC TGACAGTTCA
     TACTTTTTTA CCAAACACAC AAATAACCCT AACCAGCGCG ACTGTCAAGT

51 GGCAGCCGAC AGTCGCCCCG CCTTTTCCCG GATCGTGATG TTCGGCGACA
     CCGTCGGCTG TCAGCGGGGC GGAAAAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAACAGT TCCCGGGTCT GACCATCGCC AACGAAGCGG
     CCTCGTCGAC TGGTTTGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC CTATGGCTGG AACACGGAGC AGGATGCCAA GCGGGTTCGC
     TGATAGACCG GATACCGACC TTGTGCCTCG TCCTACGGTT CGCCCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCTCGCA
     CTATGACGAC AAGTTGGACG GCCTAGACCC GGTCTTGGGC AGTCGAGCGT

551 GTCAGAAGGT GGTCGAGGCG GTCAGCCATG TCTCCGCCTA TCACAACCAG
     CAGTCTTCCA CCAGCTCCGC CAGTCGGTAC AGAGGCGGAT AGTGTTGGTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGC GAACCAGTAC GAGTTCCTCG
     GGACTCGCTC GCGCGGCGGT GGAAGTAGCG CTTGGTCATG CTCAAGGAGC

1001 CCCAC TGA
     GGGTG ACT
```

FIG. 29

(SEQ ID No. 34)
```
  1 MKKWFVCLLG LIALTVQAAD TRPAFSRIVM FGDSLSDTGK MYSKMRGYLP
 51 SSPPYYEGRF SNGPVWLEQL TKQFPGLTIA NEAEGGATAV AYNKISWNPK
101 YQVINNLDYE VTQFLQKDSF KPDDLVILWV GANDYLAYGW NTEQDAKRVR
151 DAISDAANRM VLNGAKQILL FNLPDLGQNP SARSQKVVEA VSHVSAYHNK
201 LLLNLARQLA PTGMVKLFEI DKQFAEMLRD PQNFGLSDVE NPCYDGGYVW
251 KPFATRSVST DRQLSAFSPQ ERLAIAGNPL LAQAVASPMA RRSASPLNCE
301 GKMFWDQVHP TTVVHAALSE RAATFIETQY EFLAHG*
```

FIG. 30

(SEQ ID No. 35)

```
   1 ATGAAAAAAT GGTTTGTTTG TTTATTGGGG TTGATCGCGC TGACAGTTCA
     TACTTTTTTA CCAAACAAAC AAATAACCCC AACTAGCGCG ACTGTCAAGT

51 GGCAGCCGAC ACTCGCCCCG CCTTCTCCCG GATCGTGATG TTCGGCGACA
     CCGTCGGCTG TGAGCGGGGC GGAAGAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GCAGACCGA

201 GGAGCAGCTG ACCAAGCAGT TCCCGGGTCT GACCATCGCC AACGAAGCGG
     CCTCGTCGAC TGGTTCGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC ATATGGCTGG AATACGGAGC AGGATGCCAA GCGAGTTCGC
     TGATAGACCG TATACCGACC TTATGCCTCG TCCTACGGTT CGCTCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCCCGCA
     CTATGACGAC AAGTTGGACG GCCTAGACCC GGTCTTGGGC AGTCGGGCGT

551 GTCAGAAGGT GGTCGAGGCG GTCAGCCATG TCTCCGCCTA TCACAACAAG
     CAGTCTTCCA CCAGCTCCGC CAGTCGGTAC AGAGGCGGAT AGTGTTGTTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGA GACCCAGTAC GAGTTCCTCG
     GGACTCGCTC GCGCGGCGGT GGAAGTAGCT CTGGGTCATG CTCAAGGAGC

1001 CCCACGGATG A
     GGGTGCCTAC T
```

FIG. 31

```
                    1         10        20        30        40        50
                    |---------+---------+---------+---------+---------|
          satA      ADTRPAFSRIVNFGDSLSDTGKHYSKHRGYLPSSPPYYEGRFSN--G
          R.sol     QSGNPNYAKVQRHYYFGDSLSDIGT-------YTPYAQAYGGGKFTTNPG
       Consensus    ...adnraafqRiVnFGDSLSDiGk.......YlPsaqaygeGrFsn..G 51        60        70        80        90        100
                    |---------+---------+---------+---------+---------|
          satA      PYHLEQLTKQFPGLTIANEAEGGATAYAYNKISHNPKYQVINNLDYEYTQ
          R.sol     PIHAETVAAQL-GYTLTPAYNGYATSYQNCPKAGCFDYAQGGSRYTDPNG
       Consensus    P!HaEqlaaQl.GlTianaaeGgATaVannkiagnfdYaqgnnrdt#pnq 101       110       120       130       140       150
                    |---------+---------+---------+---------+---------|
          satA      FLQKDSFKPDDLVILHVGANDYLAYG--HNTEQDAKRYRDAISDAANRHY
          R.sol     IGHNGGAGALTYPYQQQLANFYAASNNTFNGNNDYVFYLAGSNDIFFHTT
       Consensus    igqndgagaddlp!qqqgANdYaAsn..fNg##DakrYraainDaanrHt 151       160       170       180       190       200
                    |---------+---------+---------+---------+---------|
          satA      LNGAKQILLFNLPDLGQNPSARSQKVVEAYSHYSAYHNKL-LLNLARQLA
          R.sol     AAATSGSGVTPAIATAQYQQAATDLVGYYKDHIAKGATQVYYFNLPDSSL
       Consensus    aaaakqiglfnaialaQnqqAas#lVgeakdh!aaganql.llNLarqla 201       210       220       230       240       250
                    |---------+---------+---------+---------+---------|
          satA      PTGHYKLFEIDKQFAEHLRDPQNFGLSDYENPCYDGGYVHKPFATRSYST
          R.sol     TPDGYASGTTGQALLHALYGTFNTTLQSGLAGTSARIIDFNAQLTAAIQN
       Consensus    ppdgYalgeidqalaeaLrdpqNfgLqdgeagcsargidfnaqaTaa!qn 251       260       270       280       290       300
                    |---------+---------+---------+---------+---------|
          satA      DRQLSAFSPQERLAIAG--NPLLAQAYASPH---ARRSASPLNCEGKHFH
          R.sol     GASFGFANTSARACDATKINALVPSAGGSSLFCSANTLVASGADQSYLFA
       Consensus    daqlgaanpqaRaadAg..NaLlaqAgaSp$...Arrlaapgad#gk$Fa 301       310       320       330
                    |---------+---------+---------|
          satA      DQYHPTTVYHAALSERAATFIETQYEFLAH
          R.sol     DGYHPTTAGHRLIASNYLARLLA--DHYAH              FIG. 32
       Consensus    DqYHPTTagHaaiaeraaariea..#nlAH
```

FIG. 33A

```
Pfam        *->ivafGDSltdggg..............ayygdsdgggwgagladrltsla..rlrargrgvdv
Sriml    38 YVALGDSYSSGVG...........agSYDSSSGSCKRSTKSYPALWAAS..-----HTGTRF  81
Scoe1     5 YVAVGDSFTEG--..............--VGDPGPDGAFVGWADRLAVLL..ADRRPEGDFTY  47
Scoe2    10 LVAVGDSFTEG--..............--MSDLLPDGSYRGWADLLATRM..--AARSPGFRY  50
Scoe3   239 VVAFGDSITDG--..............ARSQSDANHRWTDVLAARLHEAA..GDGRDTPRYSV 283
Scoe4    75 LMMLGDSTAAG--..............------QGVHRAGQTPGALLASG..LAAVAERPVRL 113
Scoe5    66 VAAVGDSITRGFD...........acAVLSDCPEVSWATGSSAKVDSLAvrLLGKADAAEHS 116
Ahyd1    28 IVMFGDSLSDTGKmyskmrgylpssppyYEGRFSNGPVWLEQLTNEFPGLTiaNEAEGGPTAVA  91
Asal1    28 IVMFGDSLSDTGKmyskmrgylpssppyYEGRFSNGPVWLEQLTKQF----..-------PGLTI  79
Ahyd2    40 IVMFGDSLSDTGKmyskmrgylpssppyYEGRFSNGPVWLEQLTKQFPGLTiaNEAEGGATAVA 103

Pfam        fnrgisGrtsdDGrlvvDarlvatllFlaqflGlnlpPYLsgdflrGANFAsagAtIlgtslipflni
Sriml    82 NFTACSGAR---------------------------------------  90
Scoe1    48 TNLAVRGRL---------------------------------------  56
Scoe2    51 ANLAVRGKL---------------------------------------  59
Scoe3   284 VNEGISGNR--------------------------------------- 292
Scoe4   114 GSVAQPGAC--------------------------------------- 122
Scoe5   117 WNYAVTGAR--------------------------------------- 125
Ahyd1    92 YNKISWNPK--------------------------------------- 100
Asal1    80 ANEAEGGAT---------------------------------------  88
Ahyd2   104 YNKISWNPK--------------------------------------- 112

Pfam        QvqFkdfkskvlelrqa......lgllqellrlvpvldakspdlvtimiGtNDl...itvakfgpks
Sriml    91 ----------------......---TGDVLAKQLTPVNSGTDLVSITIGGNDAgfaDTMTTCNLQG 131
Scoe1    57 ----------------......--LDQIVAEQVPRVVGLAPDLVSFAAGGNDI...-----I----  86
Scoe2    60 ----------------......--IGQIVDEQVDVAAAMGADVITLVGGLNDT...----------  88
Scoe3   293 --------LLTSRPGRPA......DNPSGLSRFQRDVLERTNVKAVVVVLGVNDV...---------- 333
Scoe4   123 ---------------......SDDLDRQVALVLAEPDRVPDICVIMVGANDV...---------- 153
Scoe5   126 ----------------......---MADLTAQVTRAAQREPELVAVMAGANDA...--------CR 155
Ahyd1   101 -------------YQVI......NNLDYEVTQFLQKDSFKPDDLVILWVGANDY...--------LA 137
Asal1    89 -------AVAYNKISWNpkyqvyNNLDYEVTQFLQKDSFKPDDLVILWVGANDY...--------LA 137
Ahyd2   113 -------------YQVI......NNLDYEVTQFLQKDSFKPDDLVILWVGANDY...--------LA 149
```

TO FIG. 33B

FROM FIG. 33A

```
Pfam         .......tksdrnvsvpefrdnlrklikrLrsangariiilitlvllnlpl..........plGCl
Sriml  132   esaclarIAKARAYIQQTLPAQLDQVYDAIDSRAPAA-----QVVVLGYP-..........----- 176
Scoe1   87   .......---RPGTDPDEVAERFELAVAALT-AAAGTVLVTTGFDTRGVP-..........----- 125
Scoe2   89   .......---------LRPKCDMARVRDLLTQAVERLAPHCEQLVLMRSP-..........----- 122
Scoe3  334   .......LNSPELADRDAILTGLRTLVDRAHARGLRVVGATITPFGGYGG-..........----- 376
Scoe4  154   .......---THRMPATRSVRHLSSAVRRLR-TAGAEVVVGTCPDLGTIE-..........----- 192
Scoe5  156   .......STTSAMTPVADFRAQFEEAMATLR-KKLPKAQVYVSSIPDLKRLwsqgrtnplgkQVWKL 214
Ahyd1  138   .......YGWNTEQDAKRVRDAISDAANRMV-LNGAK-----EILLFNLP-..........----- 174
Asal1  138   .......YGWNTEQDAKRVRDAISDAANRMV-LNGAK-----QILLFNLP-..........----- 174
Ahyd2  150   .......YGWNTEQDAKRVRDAISDAANRMV-LNGAK-----QILLFNLP-..........----- 186

Pfam         pq.klalalasssknvdatgclerlneavadyneaLrelaei.ek.l.q.aqlrkdglpdlkeanvpy
Sriml  177   --.RFYKLGGSCAVGLSEKSRAAINAAADDINAVTAKRA--.--.-.-.-----------ADHGFAF 219
Scoe1  126   --.------------VLKHLRGKIATYNGHVRAIA--.--.-.-.-----------DRYGCPV 152
Scoe2  123   --.-----------GRQGPVLERFRPRMEALFAVIDDLA--.--.-.-.-----------GRHGAVV 154
Scoe3  377   --.YTEARETMRQEVNEEIRSGRVFDTVVDFDKALRDPY--.--.-.-.----------------- 412
Scoe4  193   --.---------------------------RVRQPLRWLaRRaSrQlAAAQTIGAVEQGGRTVSL 227
Scoe5  215   GLcPSMLGDADSLDSAATLRRNTVRDRVADYNEVLREVC--.--.-.AkDRRCRSDDGAVHEFRFGT 273
Ahyd1  175   --.----DLGQNPSARSQKVVEAASHVSAYHNQLLLNLA--.--.-.-.RQLAPTGMVKLFEIDKQF 224
Asal1  175   --.----DLGQNPSARSQKVVEAVSHVSAYHNKLLLNLA--.--.-.-.RQLAPTGMVKLFEIDKQF 224
Ahyd2  187   --.----DLGQNPSARSQKVVEAVSHVSAYHNQLLLNLA--.--.-.-.RQLAPTGMVKLFEIDKQF 236

Pfam         VDlysifqdldgiqnpsayv.y....GFeet.kaCCGyGgr.yNyn.rv.CGnag.l.ck.vtakaC
Sriml  220   GDVNT--------------.-....-----.---------.----.--.-TFAgHElCSGAPwL.HS.VT---- 242
Scoe1  153   LDLWSLRSVQDRRA------.-....-----.---------.----.--.-----.-.---.------ 166
Scoe2  155   VDLYGAQSLADPRM------.-....-----.---------.----.--.-----.-.---.------ 168
Scoe3  413   ------------------.-....-----.---------.----.--.-----.-.---.------ 413
Scoe4  228   GDLLGPEFAQNPREL-----.-....-----.---------.----.--.-----.-.---.------ 242
Scoe5  274   DQL----------------.-....-----.---------.----.--.-----.-.---.------ 276
Ahyd1  225   AEMLRDPQNFGLSDQRNACYgGsyvwKPFASrSASTDSQLSaFNPQeRLaIAGNPllaQAvASPMAA 291
Asal1  225   AEMLRDPQNFGLSDVENPCYdGgyvwKPFATrSVSTDRQLSaFSPQeRLaIAGNPllaQAvASPMAR 291
Ahyd2  237   AEMLRDPQNFGLSDVENPCYdGgyvwKPFATrSVSTDRQLSaFSPQeRLaIAGNPllaQAvASPMAR 303
```

FROM FIG. 33B

```
Pfam         .dassyll.atlfwDgf.HpsekGykavAeal<-*
Sriml  243  .--------.--LPVENSyHPTANGQSKGYLPV     263
Scoe1  167  .--------.--WDADRL.HLSPEGHTRVALRA     186
Scoe2  169  .--------.--WDVDRL.HLTAEGHRRVAEAV     188
Scoe3  413  .-DPRRMRsDYDSGDHL.HPGDKGYARMGAVI     441
Scoe4  243  .--------.--FGPDNY.HPSAEGYATAAMAV     262
Scoe5  277  .--------.--SHWDWF.HPSVDGQARLAEIA     296
Ahyd1  292  rSASTLNCeGKMFWDQV.HPTTVVHAALSEPA     322
Asal1  292  rSASPLNCeGKMFWDQV.HPTTVVHAALSERA     322
Ahyd2  304  rSASPLNCeGKMFWDQV.HPTTVVHAALSERA     334
```

FIG. 33C

```
Pfam        *->ivafGDSltdggg..............ayygdsdgggwgagladrltsla..rlrargrgvdv
Sriml   38    YVALGDSYSSGVG...........agSYDSSSGSCKRSTKSYPALWAAS..------HTGTRF  81
Scoe1    5    YVAVGDSFTEG--..............--VGDPGPDGAFVGWADRLAVLL..ADRRPEGDFTY  47
Scoe2   10    LVAVGDSFTEG--..............--MSDLLPDGSYRGWADLLATRM..--AARSPGFRY  50
Ahyd1   28    IVMFGDSLSDTGKmyskmrgylpssppyYEGRFSNGPVWLEQLTNEFPGLTiaNEAEGGPTAVA  91
Asal1   28    IVMFGDSLSDTGKmyskmrgylpssppyYEGRFSNGPVWLEQLTKQF----..-------PGLTI  79
Ahyd2   40    IVMFGDSLSDTGKmyskmrgylpssppyYEGRFSNGPVWLEQLTKQFPGLTiaNEAEGGATAVA 103

Pfam        fnrgisGrtsdGrlvvDarlvatllFlaqflGlnlpPYLsgdflrGANFAsagAtIlgtslipflni
Sriml   82   NFTACSGAR--------------------------------------------------  90
Scoe1   48   TNLAVRGRL--------------------------------------------------  56
Scoe2   51   ANLAVRGKL--------------------------------------------------  59
Ahyd1   92   YNKISWNPK-------------------------------------------------- 100
Asal1   80   ANEAEGGAT--------------------------------------------------  88
Ahyd2  104   YNKISWNPK-------------------------------------------------- 112

Pfam        QvqFkdfkskvlelrqa......lgllqellrlvpvldakspdlvtimiGtNDl...itvakfgpks
Sriml   91   ----------------......---TGDVLAKQLTPVNSGTDLVSITIGGNDAgfaDTMTTCNLQG 131
Scoe1   57   ----------------......--LDQIVAEQVPRVVGLAPDLVSFAAGGNDI...-----I----  86
Scoe2   60   ----------------......--IGQIVDEQVDVAAAMGADVITLVGGLNDT...----------  88
Ahyd1  101   ------------YQVI......NNLDYEVTQFLQKDSFKPDDLVILWVGANDY...--------LA 137
Asal1   89   -------AVAYNKISWNpkyqvyNNLDYEVTQFLQKDSFKPDDLVILWVGANDY...--------LA 137
Ahyd2  113   ------------YQVI......NNLDYEVTQFLQKDSFKPDDLVILWVGANDY...--------LA 149
```

FROM FIG. 34B

```
Pfam        .......tksdrnvsvpefrdnlrklikrLrsangariiilitlvllnlplplGCl
Sriml 132   esaclarIAKARAYIQQTLPAQLDQVYDAIDSRAPAA-----QVVVLGYP------ 176
Scoe1  87   .......---RPGTDPDEVAERFELAVAALT-AAAGTVLVTTGFDTRGVP------ 125
Scoe2  89   .......---------LRPKCDMARVRDLLTQAVERLAPHCEQLVLMRSP------ 122
Ahyd1 138   .......YGWNTEQDAKRVRDAISDAANRMV-LNGAK-----EILLFNLP------ 174
Asal1 138   .......YGWNTEQDAKRVRDAISDAANRMV-LNGAK-----QILLFNLP------ 174
Ahyd2 150   .......YGWNTEQDAKRVRDAISDAANRMV-LNGAK-----QILLFNLP------ 186

Pfam        pqklalalassknvdatgclerlneavadynealrelaeieklqaqlrkdglpdlkeanvpy
Sriml 177   --RFYKLGGSCAVGLSEKSRAAINAAADDINAVTAKRA------------------ADHGFAF 219
Scoe1 126   -------------------VLKHLRGKIATYNGHVRAIA------------------DRYGCPV 152
Scoe2 123   ---------------GRQGPVLERFRPRMEALFAVIDDLA------------------GRHGAVV 154
Ahyd1 175   ------DLGQNPSARSQKVVEAASHVSAYHNQLLLNLA------RQLAPTGMVKLFEIDKQF 224
Asal1 175   ------DLGQNPSARSQKVVEAVSHVSAYHNKLLLNLA------RQLAPTGMVKLFEIDKQF 224
Ahyd2 187   ------DLGQNPSARSQKVVEAVSHVSAYHNQLLLNLA------RQLAPTGMVKLFEIDKQF 236

Pfam        VDlysifqdldgiqnpsayv.y....GFeet.kaCCGyGgr.yNyn.rv.CGnag.l.ck.vtakaC
Sriml 220   GDVNT---------------.-....-----.---------.-TFAgHElCSGAPwL.HS.VT---- 242
Scoe1 153   LDLWSLRSVQDRRA------.-....-----.---------.----.--.-----.-.--.------ 166
Scoe2 155   VDLYGAQSLADPRM------.-....-----.---------.----.--.-----.-.--.------ 168
Ahyd1 225   AEMLRDPQNFGLSDQRNACYgGsyvwKPFASrSASTDSQLSaFNPQeRLaIAGNPlLaQAvASPMAA 291
Asal1 225   AEMLRDPQNFGLSDVENPCYdGgyvwKPFATrSVSTDRQLSaFSPQeRLaIAGNPlLaQAvASPMAR 291
Ahyd2 237   AEMLRDPQNFGLSDVENPCYdGgyvwKPFATrSVSTDRQLSaFSPQeRLaIAGNPlLaQAvASPMAR 303

▼
Pfam        .dassyll.atlfwDgf.HpsekGykavAeal<-*
Sriml 243   .-------.--LPVENSyHPTANGQSKGYLPV    263
Scoe1 167   .-------.--WDADRL.HLSPEGHTRVALRA    186
Scoe2 169   .-------.--WDVDRL.HLTAEGHRRVAEAV    188
Ahyd1 292   rSASTLNCeGKMFWDQV.HPTTVVHAALSEPA    322
Asal1 292   rSASPLNCeGKMFWDQV.HPTTVVHAALSERA    322
Ahyd2 304   rSASPLNCeGKMFWDQV.HPTTVVHAALSERA    334
```

FIG. 34B

A. hydrophila enzyme    A. salmonicida enzyme

Transferase activity for #178 as a function of % water in the assay.

1 2 3 4 5 6 7 8

(SEQ ID No. 36)

```
  1 MFKFKKNFLV GLSAALMSIS LFSATASAAS ADSRPAFSRI VMFGDSLSDT
 51 GKMYSKMRGY LPSSPPYYEG RFSNGPVWLE QLTKQFPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLF EIDKQFAEML RDPQNFGLSD
251 VENPCYDGGY VWKPFATRSV STDRQLSAFS PQERLAIAGN PLLAQAVASP
301 MARRSASPLN CEGKMFWDQV HPTTVVHAAL SERAATFIAN QYEFLAH**
```

*FIG. 71*

```
   1 ATGTTTAAGT TTAAAAAGAA TTTCTTAGTT GGATTATCGG CAGCTTTAAT
     TACAAATTCA AATTTTTCTT AAAGAATCAA CCTAATAGCC GTCGAAATTA
  51 GAGTATTAGC TTGTTTTCGG CAACCGCCTC TGCAGCTAGC GCCGACAGCC
     CTCATAATCG AACAAAAGCC GTTGGCGGAG ACGTCGATCG CGGCTGTCGG
 101 GTCCCGCCTT TTCCCGGATC GTGATGTTCG GCGACAGCCT CTCCGATACC
     CAGGGCGGAA AAGGGCCTAG CACTACAAGC CGCTGTCGGA GAGGCTATGG
 151 GGCAAAATGT ACAGCAAGAT GCGCGGTTAC CTCCCCTCCA GCCCGCCCTA
     CCGTTTTACA TGTCGTTCTA CGCGCCAATG GAGGGGAGGT CGGGCGGGAT
 201 CTATGAGGGC CGTTTCTCCA ACGGACCCGT CTGGCTGGAG CAGCTGACCA
     GATACTCCCG GCAAAGAGGT TGCCTGGGCA GACCGACCTC GTCGACTGGT
 251 AACAGTTCCC GGGTCTGACC ATCGCCAACG AAGCGGAAGG CGGTGCCACT
     TTGTCAAGGG CCCAGACTGG TAGCGGTTGC TTCGCCTTCC GCCACGGTGA
 301 GCCGTGGCTT ACAACAAGAT CTCCTGGAAT CCCAAGTATC AGGTCATCAA
     CGGCACCGAA TGTTGTTCTA GAGGACCTTA GGGTTCATAG TCCAGTAGTT
 351 CAACCTGGAC TACGAGGTCA CCCAGTTCTT GCAGAAAGAC AGCTTCAAGC
     GTTGGACCTG ATGCTCCAGT GGGTCAAGAA CGTCTTTCTG TCGAAGTTCG
 401 CGGACGATCT GGTGATCCTC TGGGTCGGTG CCAATGACTA TCTGGCCTAT
     GCCTGCTAGA CCACTAGGAG ACCCAGCCAC GGTTACTGAT AGACCGGATA
 451 GGCTGGAACA CGGAGCAGGA TGCCAAGCGG GTTCGCGATG CCATCAGCGA
     CCGACCTTGT GCCTCGTCCT ACGGTTCGCC CAAGCGCTAC GGTAGTCGCT
 501 TGCGGCCAAC CGCATGGTAC TGAACGGTGC CAAGCAGATA CTGCTGTTCA
     ACGCCGGTTG GCGTACCATG ACTTGCCACG GTTCGTCTAT GACGACAAGT
 551 ACCTGCCGGA TCTGGGCCAG AACCCGTCAG CTCGCAGTCA GAAGGTGGTC
     TGGACGGCCT AGACCCGGTC TTGGGCAGTC GAGCGTCAGT CTTCCACCAG
 601 GAGGCGGTCA GCCATGTCTC CGCCTATCAC AACCAGCTGC TGCTGAACCT
     CTCCGCCAGT CGGTACAGAG GCGGATAGTG TTGGTCGACG ACGACTTGGA
 651 GGCACGCCAG CTGGCCCCCA CCGGCATGGT AAAGCTGTTC GAGATCGACA
     CCGTGCGGTC GACCGGGGGT GGCCGTACCA TTTCGACAAG CTCTAGCTGT
 701 AGCAATTTGC CGAGATGCTG CGTGATCCGC AGAACTTCGG CCTGAGCGAC
     TCGTTAAACG GCTCTACGAC GCACTAGGCG TCTTGAAGCC GGACTCGCTG
 751 GTCGAGAACC CCTGCTACGA CGGCGGCTAT GTGTGGAAGC CGTTTGCCAC
     CAGCTCTTGG GGACGATGCT GCCGCCGATA CACACCTTCG GCAAACGGTG
 801 CCGCAGCGTC AGCACCGACC GCCAGCTCTC CGCCTTCAGT CCGCAGGAAC
     GGCGTCGCAG TCGTGGCTGG CGGTC GAGAG GCGGAAGTCA GGCGTCCTTG
 851 GCCTCGCCAT CGCCGGCAAC CCGCTGCTGG CACAGGCCGT TGCCAGTCCT
     CGGAGCGGTA GCGGCCGTTG GGCGACGACC GTGTCCGGCA ACGGTCAGGA
 901 ATGGCCCGCC GCAGCGCCAG CCCCCTCAAC TGTGAGGGCA AGATGTTCTG
     TACCGGGCGG CGTCGCGGTC GGGGGAGTTG ACACTCCCGT TCTACAAGAC
 951 GGATCAGGTA CACCCGACCA CTGTCGTGCA CGCAGCCCTG AGCGAGCGCG
     CCTAGTCCAT GTGGGCTGGT GACAGCACGT GCGTCGGGAC TCGCTCGCGC
1001 CCGCCACCTT CATCGCGAAC CAGTACGAGT TCCTCGCCCA CTGATGA
     GGCGGTGGAA GTAGCGCTTG GTCATGCTCA AGGAGCGGGT GACTACT
```

FIG. 72

SEQ ID No. 62

```
  1 ADTRPAFSRI VMFGDSLSDT GKMYSKMRGY LPSSPPYYEG RFSNGPVWLE QLTKQFPGLT
 61 IANEAEGGAT AVAYNKISWD PKYQVINNLD YEVTQFLQKD SFKPDDLVIL WVGANDYLAY
121 GWNTEQDAKR VRDAISDAAN RMVLNGAKQI LLFNLPDLGQ NPSARSQKVV EAVSHVSAYH
181 NKLLLNLARQ LAPTGMVKLF EIDKQFAEML RDPQNFGLSD VENPCYDGGY VWKPFATRSV
241 STDRQLSAFS PQERLAIAGN PLLAQAVASP MARRSASPLN CEGKMFWDQV HPTTVVHAAL
301 SERAATFIET QYEFLAHG
```

FIG. 74

SEQ ID No 63 which is the amino acid sequence of a lipid acyltransferase from *Candida parapsilosis*;

```
MRYFAIAFLL  INTISAFVLA  PKKPSQDDFY  TPPQGYEAQP  LGSILKTRNV  PNPLTNVFTP  VKVQNAWQLL
VRSEDTFGNP  NAIVTTIIQP  FNAKKDKLVS  YQTFEDSGKL  DCAPSYAIQY  GSDISTLTTQ  GEMYYISALL
DQGYYVVTPD  YEGPKSTFTV  GLQSGRATLN  SLRATLKSGN  LTGVSSDAET  LLWGYSGGSL  ASGWAAAIQK
EYAPELSKNL  LGAALGGFVT  NITATAEAVD  SGPFAGIISN  ALAGIGNEYP  DFKNYLLKKV  SPLLSITYRL
GNTHCLLDGG  IAYFGKSFFS  RIIRYFPDGW  DLVNQEPIKT  ILQDNGLVYQ  PKDLTPQIPL  FIYHGTLDAI
VPIVNSRKTF  QQWCDWGLKS  GEYNEDLTNG  HITESIVGAP  AALTWIINRF  NGQPPVDGCQ  HNVRASNLEY
PGTPQSIKNY  FEAALHAILG  FDLGPDVKRD  KVTLGGLLKL  ERFAF
```

FIG. 75

SEQ ID No 64 which is the amino acid sequence of a lipid acyltransferase from *Candida parapsilosis*;

```
MRYFAIAFLL  INTISAFVLA  PKKPSQDDFY  TPPQGYEAQP  LGSILKTRNV  PNPLTNVFTP  VKVQNAWQLL
VRSEDTFGNP  NAIVTTIIQP  FNAKKDKLVS  YQTFEDSGKL  DCAPSYAIQY  GSDISTLTTQ  GEMYYISALL
DQGYYVVTPD  YEGPKSTFTV  GLQSGRATLN  SLRATLKSGN  LTGVSSDAET  LLWGYSGGSL  ASGWAAAIQK
EYAPELSKNL  LGAALGGFVT  NITATAEAVD  SGPFAGIISN  ALAGIGNEYP  DFKNYLLKKV  SPLLSITYRL
GNTHCLLDGG  IAYFGKSFFS  RIIRYFPDGW  DLVNQEPIKT  ILQDNGLVYQ  PKDLTPQIPL  FIYHGTLDAI
VPIVNSRKTF  QQWCDWGLKS  GEYNEDLTNG  HITESIVGAP  AALTWIINRF  NGQPPVDGCQ  HNVRASNLEY
PGTPQSIKNY  FEAALHAILG  FDLGPDVKRD  KVTLGGLLKL  ERFAFHHHHH  H
```

FIG. 76

SEQ ID No. 65

```
1    migsyvavgd sftegvgdpg pdgafvgwad rlavlladrr pegdftytnl avrgrlldqi
61   vaeqvprvvg lapdlvsfaa ggndiirpgt dpdevaerfe lavaaltaaa gtvlvttgfd
121  trgvpvlkhl rgkiatyngh vraiadrygc pvldlwslrs vqdrrawdad rlhlspeght
181  rvalragqal glrvpadpdq pwpplppgrt ldvrrddvhw areylvpwig rrlrgessgd
241  hvtakgtlsp daiktriaav a
```

SEQ ID No. 66

ZP_00058717

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIG. 79

SEQ ID No. 67

```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

SEQ ID No. 68

```
  1 mrttviaasa llllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIG. 80

SEQ ID No. 69

ZP_00094165

```
  1 mgqvklfarr capvllalag lapaatvare aplaegaryv algssfaagp gvgpnapgsp
 61 ercgrgtlny phllaealkl dlvdatcsga tthhvlgpwn evppqidsvn gdtrlvtlti
121 ggndvsfvgn ifaaacekma spdprcgkwr eiteeewqad eermrsivrq iharaplarv
181 vvvdyitvlp psgtcaamai spdrlaqsrs aakrlarita rvareegasl lkfshisrrh
241 hpcsakpwsn glsapaddgi pvhpnrlgha eaaaalvklv klmk //
```

FIG. 81

SEQ ID No. 70

NP_625998.

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
```

*FIG. 82*

SEQ ID No. 71

NP_827753.

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

*FIG. 83*

SEQ ID No. 72

MRLTRSLSAASVIVFALLLALLGISPAQAAGPAYVALGDSYSSGNGAGSYIDSSGDCHRSN

NAYPARWAAANAPSSFTFAACSGAVTTDVINNQLGALNASTGLVSITIGGNDAGFADAMTT

CVTSSDSTCLNRLATATNYINTTLLARLDAVYSQIKARAPNARVVVLGYPRMYLASNPWYC

LGLSNTKRAAINTTADTLNSVISSRATAHGFRFGDVRPTFNNHELFFGNDWLHSLTLPVWE

SYHPTSTGHQSGYLPVLNANSST

FIG. 84

SEQ ID No. 73

ADSRPAFSRIVMFGDSLSDTGKMYSKMRGYLPSSPPYYEGRFSNGPVWLEQLTNEFPGLTIANEAE
GGPTAVAYNKISWNPKYQVINNLDYEVTQFLQKDSFKPDDLVILWVGANDYLAYGWNTEQDAKRVR
DAISDAANRMVLNGAKEILLFNLPDLGQNPSARSQKVVEAASHVSAYHNQLLLNLARQLAPTGMVK
LFEIDKQFAEMLRDPQNFGLSDQRNACYGGSYVWKPFASRSASTDSQLSAFNPQERLAIAGNPLLA
QAVASPMAARSASTLNCEGKMFWDQVHPTTVVHAALSEPAATFIESQYEFLAH

FIG. 85

SEQ ID No. 74

```
  1  ADTRPAFSRI VMFGDSLSDT GKMYSKMRGY LPSSPPYYEG RFSNGPVWLE QLTKQFPGLT
 61  IANEAEGGAT AVAYNKISWN PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIG. 86

SEQ ID No. 75

```
ACAGGCCGATGCACGGAACCGTACCTTTCCGCAGTGAAGCGCTCTCCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT
```

FIG. 87

SEQ ID No. 76

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIG. 88

SEQ ID No. 77

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIG. 89

SEQ ID No. 78

```
   1 ggtggtgaac cagaacaccc ggtcgtcggc gtgggcgtcc aggtgcaggt gcaggttctt
  61 caactgctcc agcaggatgc cgccgtggcc gtgcacgatg gccttgggca ggcctgtggt
 121 ccccgacgag tacagcaccc atagcggatg gtcgaacggc agcggggtga actccagttc
 181 cgcgccttcg cccgcggctt cgaactccgc ccaggacagg gtgtcggcga cagggccgca
 241 gcccaggtac ggcaggacga cggtgtgctg caggctgggc atgccgtcgc gcagggcttt
 301 gagcacgtca cggcggtcga agtccttacc gccgtagcgg tagccgtcca cggccagcag
 361 cactttcggt tcgatctgcg cgaaccggtc gaggacgctg cgcaccccga agtcggggga
 421 acaggacgac caggtcgcac cgatcgcggc gcaggcgagg aatgcggccg tcgcctcggc
 481 gatgttcggc aggtaggcca cgacccggtc gccggggccc accccgaggc tgcggagggc
 541 cgcagcgatc gcggcggtgc gggtccgcag ttctccccag gtccactcgg tcaacggccg
 601 gagttcggac gcgtgccgga tcgccacggc tgatgggtca cggtcgcgga agatgtgctc
 661 ggcgtagttg agggtggcgc cggggaacca gacggcgccg ggcatggcgt cggaggcgag
 721 cactgtggtg tacggggtgg cggcgcgcac ccggtagtac tcccagatcg cggaccagaa
 781 tccttcgagg tcggttaccg accagcgcca cagtgcctcg tagtccggtg cgtccacacc
 841 gcggtgctcc cgcacccagc gggtgaacgc ggtgaggttg gcgcgttctt tgcgctcctc
 901 gtcgggactc cacaggatcg gcggctgcgg cttgagtgtc atgaaacgcg accccttcgt
 961 ggacggtgcg gatgcggtga gcgtcgggtg cctcccctaa cgctccccgg tgacggagtg
1021 ttgtgcacca catctagcac gcgggacgcg gaaaccgtat ggagaaaaca cctacaaccc
1081 cggccggacg gtgggtttcg gccacactta ggggtcgggt gcctgcttgc cgggcagggc
1141 agtcccgggg tgctgtggtg cgggcgggag ggctgtcgct tcgaggtgtg ccggcgggac
1201 actccgggcc tcagccgtac ccgcaacggg gacagttctc ctcccttccg ggctggatgg
1261 tcccttcccc cgaaatgcgg cgagatctcc cagtcagccc ggaaaacacc cgctgtgccc
1321 aggtactctt tgcttcgaac agacaggccg gacggtccac ggggaggtt tgtgggcagc
1381 ggaccacgtg cggcgaccag acgacggttg ttcctcggta tccccgctct tgtacttgtg
1441 acagcgctca cgctggtctt ggctgtcccg acggggcgcg agacgctgtg gcgcatgtgg
1501 tgtgaggcca cccaggactg gtgcctgggg gtgccggtcg actcccgcgg acagcctgcg
1561 gaggacggcg agtttctgct gctttctccg gtccaggcag cgacctgggg gaactattac
1621 gcgctcgggg attcgtactc ttcgggggac ggggcccgcg actactatcc cggcaccgcg
1681 gtgaagggcg gttgctggcg gtccgctaac gcctatccgg agctggtcgc cgaagcctac
1741 gacttcgccg gacacttgtc gttcctggcc tgcagcggcc agcgcggcta cgccatgctt
1801 gacgctatcg acgaggtcgg ctcgcagctg gactggaact ccctcacac gtcgctggtg
1861 acgatcggga tcggcggcaa cgatctgggg ttctccacg ttttgaagac ctgcatggtg
1921 cgggtgccgc tgctggacag caaggcgtgc acggaccagg aggacgctat ccgcaagcgg
1981 atggcgaaat tcgagacgac gtttgaagag ctcatcagcg aagtgcgcac ccgcgcgccg
2041 gacgcccgga tccttgtcgt gggctacccc cggatttttc cggaggaacc gaccggcgcc
2101 tactacacgc tgaccgcgag caaccagcgg tggctcaacg aaaccattca ggagttcaac
2161 cagcagctcg ccgaggctgt cgcggtccac gacgaggaga ttgccgcgtc gggcggggtg
2221 ggcagcgtgg agttcgtgga cgtctaccac gcgttggacg gccacgagat cggctcggac
2281 gagccgtggg tgaacggggt gcagttgcgg gacctcgcca ccggggtgac tgtggaccgc
2341 agtaccttcc accccaacgc cgctgggcac cgggcggtcg gtgagcgggt catcgagcag
2401 atcgaaaccg gcccgggccg tccgctctat gccactttcg cggtggtggc ggggcgacc
2461 gtggacactc tcgcgggcga ggtggggtga cccggcttac cgtccggccc gcaggtctgc
2521 gagcactgcg gcgatctggt ccactgccca gtgcagttcg tcttcggtga tgaccagcgg
2581 cggggagagc cggatcgttg agccgtgcgt gtctttgacg agcacacccc gctgcaggag
2641 ccgttcgcac agttctcttc cggtggccag agtcgggtcg acgtcgatcc cagcccacag
2701 gccgatgctg cgggccgcga ccacgccgtt gccgaccagt tggtcgaggc gggcgcgcag
2761 cacgggggcg agggcgcgga catggtccag gtaagggcc tcgcggacga ggctcaccac
2821 ggcagtgccg accgcgcagg cgagggcgtt gccgccgaag tgctgccgt gctggccggg
2881 gcggatcacg tcgaagactt ccgcgtcgcc taccgccgcc gccacgggca ggatgccgcc
2941 gcccagcgct tgccgaaca ggtagatatc ggcgtcgact ccgctgtggt cgcaggcccg
```

FIG. 90

SEQ ID No. 79

```
  1 vgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvplids kactdqedai rkrmakfett feelisevrt rapdarilvv gyprifpeep
241 tgayytltas ngrwlnetiq efnqqlaeav avhdeeiaas ggvgsvefvd vyhaldghel
301 gsdepwvngv qlrdlatgvt vdrstfhpna aghravgerv leqietgpgr plyatfavva
361 gatvdtlage vg
```

FIG. 91

SEQ ID No. 80

```
  1 mrttviaasa llllagcadg areetagapp gessggiree gaeaststitd vyialgdsya
 61 amggrdgplr gepfclrssg nypeilhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiggqt dayplhptsa gheamaaavr dalglepvqp
```

FIG. 92

SEQ ID No. 81

FIG. 93

```
   1 ttctggggtg ttatggggtt gttatcggct cgtcctgggt ggatcccgcc aggtggggta
  61 ttcacggggg acttttgtgt ccaacagccg agaatgagtg ccctgagcgg tgggaatgag
 121 gtgggcgggg ctgtgtcgcc atgaggggc ggcgggctct gtggtgcccc gcgaccccg
 181 gccccggtga gcggtgaatg aaatccggct gtaatcagca tcccgtgccc acccgtcgg
 241 ggaggtcagc gcccggagtg tctacgcagt cggatcctct cggactcggc catgctgtcg
 301 gcagcatcgc gctcccgggt cttggcgtcc ctcggctgtt ctgcctgctg tccctggaag
 361 gcgaaatgat caccggggag tgatacaccg gtggtctcat cccggatgcc cacttcggcg
 421 ccatccggca attcgggcag ctccgggtgg aagtaggtgg catccgatgc gtcggtgacg
 481 ccatagtggg cgaagatctc atcctgctcg agggtgctca ggccactctc cggatcgata
 541 tcgggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aatgggtgg tgggagccct ggtcgcggtt
 961 ccgtgggagg cgccgtgccc cgcaggatcg tcggcatcgg cggatctggc cggtaccccg
1021 cggtgaataa aatcattctg taaccttcat cacggttggt tttaggtatc cgccccttc
1081 gtcctgaccc cgtccccggc gcgcgggagc ccgcgggttg cggtagacag gggagacgtg
1141 gacaccatga ggacaacggt catcgcagca agcgcattac tccttctcgc cggatgcgcg
1201 gatgggccc gggaggagac cgccggtgca ccgccgggtg agtcctccgg gggcatccgg
1261 gaggaggggg cggaggcgtc gacaagcatc accgacgtct acatcgccct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg ccaggggcg
1441 gtgaccgggg atctgctcga acccaggacg ctgggggagc gcacgctgcc ggcgcaggtg
1501 gatgcgctga cggaggacac caccctggtc accctctcca tcggggggcaa tgacctcgga
1561 ttcgggggagg tggcgggatg catccgggaa cggatcgccg gggagaacgc tgatgattgc
1621 gtggacctgc tgggggaaac catcgggggag cagctcgatc agcttccccc gcagctggac
1681 cgcgtgcacg aggctatccg ggaccgcgcc ggggacgcgc aggttgtggt caccggttac
1741 ctgccgctcg tgtctgccgg ggactgcccc gaactgggg atgtctccga ggcggatcgt
1801 cgttgggcgg ttgagctgac cggcagatc aacgagaccg tgcgcgaggc ggccgaacga
1861 cacgatgccc tctttgtcct gcccgacgat gccgatgagc acaccagttg tgcaccccca
1921 cagcagcgct gggcggatat ccaggccaa cagaccgatc cctatccgct gcacccgacc
1981 tccgccggcc atgaggcgat ggccgccgcc gtccgggacg cgctgggcct ggaaccggtc
2041 cagccgtagc gccgggcgcg cgcttgtcga cgaccaaccc atgccaggct gcagtcacat
2101 ccgcacatag cgcgcgcggg cgatggagta cgcaccatag aggatgagcc cgatgccgac
2161 gatgatgagc agcacactgc cgaagggttg ttccccgagg gtgcgcagag ccgagtccag
2221 acctgcgcc tgctccggat catgggccca accggcgatg acgatcaaca ccccaggat
2281 cccgaaggcg ataccacggg cgacataacc ggctgttccg gtgatgatga tcgcggtccc
2341 gacctgccct gaccccgcac ccgcctccag atcctcccg aaatcccggg tggccccctt
2401 ccagaggttg tagacacccg ccccagtac caccagcccg gcgaccacaa ccagcaccac
2461 accccaggt tgggatagga cggtggcggt gacatcggtg gcggtctccc catcggaggt
2521 gctgccgccc cgggcgaagg tggaggtggt caccgccagg gagaagtaga ccatggccat
2581 gaccgccccc ttggccctt ccttgaggtc ctcgcccgcc agcagctggc tcaattgcca
2641 gagtcccagg gccgccaggg cgatgacggc aacccacagg aggaactgcc cacccggagc
2701 ctccgcgatg gtggccaggg cacctgaatt cgaggcctca tcacccgaac cgccggatcc
2761 agtggcgatg cgcaccgcga tccacccgat gaggatgtgc agtatgccca ggacaatgaa
2821 accacctctg gccagggtgg tcagcgcggg gtggtcctcg gcctggtcgg cagcccgttc
2881 gatcgtccgt ttcgcggatc tggtgtcgcc cttatccata gctcccattg aaccgccttg
2941 aggggtgggc ggccactgtc agggcggatt gtgatctgaa ctgtgatgtt ccatcaaccc
```

SEQ ID No. 82

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
```

*FIG. 94*

SEQ ID No. 83

```
   1 cccggcggcc cgtgcaggag cagcagccgg cccgcgatgt cctcgggcgt cgtcttcatc
  61 aggccgtcca tcgcgtcggc gaccggcgcc gtgtagttgg cccggacctc gtcccaggtg
 121 cccgcggcga tctggcgggt ggtgcggtgc gggccgcgcc gaggggagac gtaccagaag
 181 cccatcgtca cgttctccgg ctgcggttcg ggctcgtccg ccgctccgtc cgtcgcctcg
 241 ccgagcacct tctcggcgag gtcggcgctg tcgccgtca ccgtgacgtc ggcgccccgg
 301 ctccagcgcg agatcagcag cgtccagccg tcgccctccg ccagcgtcgc gctgcggtcg
 361 tcgtcgcggg cgatccgcag cacgcgcgcg ccgggcggca gcagcgtggc gccggaccgt
 421 acgcggtcga tgttcgccgc gtgcgagtac ggctgctcac ccgtggcgaa acggccgagg
 481 aacagcgcgt cgacgacgtc ggacggggag tcgctgtcgt ccacgttgag ccggatcggc
 541 agggcttcgt gcgggttcac ggacatgtcg ccatgatcgg gcacccggcc gccgcgtgca
 601 cccgctttcc cgggcacgca cgacaggggc tttctcgccg tcttccgtcc gaacttgaac
 661 gagtgtcagc catttcttgg catggacact tccagtcaac gcgcgtagct gctaccacgg
 721 ttgtggcagc aatcctgcta agggaggttc catgagacgt ttccgacttg tcggcttcct
 781 gagttcgctc gtcctcgccg ccggcgccgc cctcaccggg gcagcgaccg cccaggcggc
 841 ccaacccgcc gccgccgacg gctatgtggc cctcggcgac tcctactcct ccggggtcgg
 901 agcgggcagc tacatcagct cgagcggcga ctgcaagcgc agcacgaagg cccatcccta
 961 cctgtgggcg ccgcccact cgccctccac gttcgacttc accgcctgtt ccggcgcccg
1021 tacgggtgat gttctctccg gacagctcgg cccgctcagc tccggcaccg gcctcgtctc
1081 gatcagcatc ggcggcaacg acgccggttt cgccgacacc atgacgacct gtgtgctcca
1141 gtccgagagc tcctgcctgt cgcggatcgc caccgccgag gcgtacgtcg actcgacgct
1201 gcccggcaag ctcgacggcg tctactcggc aatcagcgac aaggcgccga acgcccacgt
1261 cgtcgtcatc ggctacccgc gcttctacaa gctcggcacc acctgcatcg gcctgtccga
1321 gaccaagcgg acggcgatca caaggcctc cgaccacctc aacaccgtcc tcgcccagcg
1381 cgccgccgcc cacggcttca ccttcggcga cgtacgcacc accttcaccg gccacgagct
1441 gtgctccggc agccctggc tgcacagcgt caactggctg aacatcggcg agtcgtacca
1501 ccccaccgcg gccggccagt ccggtggcta cctgccggtc ctcaacggcg ccgcctgacc
1561 tcaggcggaa ggagaagaag aaggagcgga gggagacgag gagtgggagg ccccgcccga
1621 cggggtcccc gtccccgtct ccgtctccgt cccggtcccg caagtcaccg agaacgccac
1681 cgcgtcggac gtggcccgca ccggactccg cacctccacg cgcacggcac tctcgaacgc
1741 gccggtgtcg tcgtgcgtcg tcaccaccac gccgtcctgg cgcgagcgct cgccgcccga
1801 cgggaaggac agcgtccgcc accccggatc ggagaccgac ccgtccgcgg tcacccaccg
1861 gtagccgacc tccgcgggca gccgcccgac cgtgaacgtc gccgtgaacg cgggtgcccg
1921 gtcgtgcggc ggcggacagg cccccgagta gtgggtgcgc gagcccacca cggtcacctc
1981 caccgactgc gctgcggggc
```

*FIG. 95*

SEQ ID No. 84

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

SEQ ID No. 85

FIG. 97

```
   1 ccaccgccgg gtcggcggcg agtctcctgg cctcggtcgc ggagaggttg gccgtgtagc
  61 cgttcagcgc ggcgccgaac gtcttcttca ccgtgccgcc gtactcgttg atcaggccct
 121 tgcccttgct cgacgcggcc ttgaagccgg tgcccttctt gagcgtgacg atgtagctgc
 181 ccttgatcgc ggtgggggag ccggcggcga gcaccgtgcc ctcggccggg gtggcctggg
 241 cgggcagtgc ggtgaatccg cccacgaggg cgccggtcgc cacggcggtt atcgcggcga
 301 tccggatctt cttgctacgc agctgtgcca tacgagggag tcctcctctg ggcagcggcg
 361 cgcctgggtg gggcgcacgg ctgtgggggg tgcgcgcgtc atcacgcaca cggccctgga
 421 gcgtcgtgtt ccgccctggg ttgagtaaag cctcggccat ctacggggt ggctcaaggg
 481 agttgagacc ctgtcatgag tctgacatga gcacgcaatc aacggggccg tgagcacccc
 541 ggggcgaccc cggaaagtgc cgagaagtct tggcatggac acttcctgtc aacacgcgta
 601 gctggtacga cggttacggc agagatcctg ctaaagggag gttccatgag acgttcccga
 661 attacggcat acgtgacctc actcctcctc gccgtcggct cgccctcac cggggcagcg
 721 acggcgcagg cgtccccagc cgccgcggcc acgggctatg tggccctcgg cgactcgtac
 781 tcgtccggtg tcggcgccgg cagctacctc agctccagcg gcgactgcaa gcgcagttcg
 841 aaggcctatc cgtacctctg gcaggccgcg cattcaccct cgtcgttcag tttcatggct
 901 tgctcgggcg ctcgtacggg tgatgtcctg gccaatcagc tcggcaccct gaactcgtcc
 961 accggcctgg tctccctcac catcggaggc aacgacgcgg gcttctccga cgtcatgacg
1021 acctgtgtgc tccagtccga cagcgcctgc ctctcccgca tcaacacggc gaaggcgtac
1081 gtcgactcca ccctgccccgg ccaactcgac agcgtgtaca cggcgatcag cacgaaggcc
1141 ccgtcggccc atgtggccgt gctgggctac ccccgcttct acaaactggg cggctcctgc
1201 ctcgcgggcc tctcggagac caagcggtcc gccatcaacg acgcggccga ctatctgaac
1261 agcgccatcg ccaagcgcgc cgccgaccac ggcttcacct tcggcgacgt caagagcacc
1321 ttcaccggcc atgagatctg ctccagcagc acctggctgc acagtctcga cctgctgaac
1381 atcggccagt cctaccaccc gaccgcggcc ggccagtccg gcggctatct gccggtcatg
1441 aacagcgtgg cctgagctcc cacggcctga attttttaagg cctgaatttt taaggcgaag
1501 gtgaaccgga agcggaggcc ccgtccgtcg gggtctccgt cgcacaggtc accgagaacg
1561 gcacggagtt ggacgtcgtg cgcaccgggt cgcgcacctc gacggcgatc tcgttcgaga
1621 tcgttccgct cgtgtcgtac gtggtgacga cacctgcttc tgctgggtc tttccgccgc
1681 tcgccgggaa ggacagcgtc ttccagcccg gatccgggac ctcgcccttc ttggtcaccc
1741 agcggtactc cacctcgacc ggcacccggc ccaccgtgaa ggtcgccgtg aacgtgggcg
1801 cctgggcggt gggcggcggg caggcaccgg agtagtcggt gtgcacgccg gtgaccgtca
1861 ccttcacgga ctggccggc ggggtcgtcg taccgccgcc gccaccgccg cctccggag
1921 tggagcccga gctgtggtcg cccccgccgt cggcgttgtc gtcctcgggg gttttcgaac
```

SEQ ID No. 86

```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

SEQ ID No. 87

```
  1    ctgcagacac ccgccccgcc ttctcccgga tcgtcatgtt cggcgactcc ctcagcgaca
 61    ccggcaagat gtactccaag atgcgcggct acctgccgtc ctccccgccg tactacgagg
121    gccgcttctc gaacggcccg gtctggctgg agcagctgac gaagcagttc cccggcctga
181    cgatcgccaa cgaggccgag gggggcgcga ccgcagtcgc ctacaacaag atctcctgga
241    acccgaagta ccaggtcatt aacaacctcg actacgaggt cacccagttc ttgcagaagg
301    actcgttcaa gcccgacgac ctggtcatcc tgtgggtggg cgccaacgac tacctggcct
361    acggttggaa cacggagcag gacgccaagc gggtgcgcga cgccatctcg gacgcggcaa
421    accgcatggt cctgaacggc gcgaagcaga tcctgctgtt caacctgccc gacctgggcc
481    agaacccgtc cgcccgctcc cagaaggtcg tcgaggccgt ctcgcacgtg tccgcctacc
541    acaacaagct gctcctcaac ctcgcccggc agctcgcccc gacgggcatg gtcaagctgt
601    tcgagatcga caagcagttc gcggagatgc tgcgcgaccc ccagaacttc ggcctgagcg
661    acgtggagaa cccgtgctac gacggcggct acgtgtggaa gccgttcgcc acccggtccg
721    tctcgaccga ccggcagctg tcggccttct cgccccagga gcgcctggcg atcgctggca
781    acccgctcct ggcacaggcg gtagcttcgc cgatggcccg ccgctcggcc tcgcccctca
841    actgcgaggg caagatgttc tgggaccagg tccaccccac caccgtggtc cacgccgccc
901    tctcggagcg cgccgccacc ttcatcgaga cccagtacga gttcctcgcc cactagtcta
961    gaggatcc
```

FIG. 99

SEQ ID No. 88

```
  1 ATGAAACAAC AAAAACGGCT TTACGCCCGA TTGCTGACGC TGTTATTTGC
    TACTTTGTTG TTTTTGCCGA AATGCGGGCT AACGACTGCG ACAATAAACG

51 GCTCATCTTC TTGCTGCCTC ATTCTGCAGC TTCAGCAGCA GATACAAGAC
    CGAGTAGAAG AACGACGGAG TAAGACGTCG AAGTCGTCGT CTATGTTCTG

101 CGGCGTTTAG CCGGATCGTC ATGTTTGGAG ATAGCCTGAG CGATACGGGC
    GCCGCAAATC GGCCTAGCAG TACAAACCTC TATCGGACTC GCTATGCCCG

151 AAAATGTATA GCAAAATGAG AGGCTATCTT CCGTCAAGCC CGCCGTATTA
    TTTTACATAT CGTTTTACTC TCCGATAGAA GGCAGTTCGG GCGGCATAAT

201 TGAAGGCCGC TTTAGCAATG GACCGGTCTG GCTGGAACAA CTGACGAAAC
    ACTTCCGGCG AAATCGTTAC CTGGCCAGAC CGACCTTGTT GACTGCTTTG

251 AATTTCCGGG ACTGACGATC GCTAATGAAG CAGAAGGAGG AGCAACAGCG
    TTAAAGGCCC TGACTGCTAG CGATTACTTC GTCTTCCTCC TCGTTGTCGC

301 GTCGCCTATA ACAAAATCAG CTGGGACCCG AAATATCAGG TCATCAACAA
    CAGCGGATAT TGTTTTAGTC GACCCTGGGC TTTATAGTCC AGTAGTTGTT

351 CCTGGACTAT GAAGTCACAC AGTTTCTTCA GAAAGACAGC TTTAAACCGG
    GGACCTGATA CTTCAGTGTG TCAAAGAAGT CTTTCTGTCG AAATTTGGCC

401 ATGATCTGGT CATCCTTTGG GTCGGCGCCA ATGATTATCT GGCGTATGGC
    TACTAGACCA GTAGGAAACC CAGCCGCGGT TACTAATAGA CCGCATACCG

451 TGGAACACAG AACAAGATGC CAAAAGAGTC AGAGATGCCA TCAGCGATGC
    ACCTTGTGTC TTGTTCTACG GTTTTCTCAG TCTCTACGGT AGTCGCTACG

501 CGCTAATAGA ATGGTCCTGA ACGGCGCCAA ACAAATCCTG CTGTTTAACC
    GCGATTATCT TACCAGGACT TGCCGCGGTT TGTTTAGGAC GACAAATTGG
```

FROM FIG. 100

```
 551 TGCCGGATCT GGGACAAAAT CCGAGCGCCA GAAGCCAAAA AGTCGTCGAA
     ACGGCCTAGA CCCTGTTTTA GGCTCGCGGT CTTCGGTTTT TCAGCAGCTT

601 GCAGTCAGCC ATGTCAGCGC CTATCATAAC AAACTGCTGC TGAACCTGGC
     CGTCAGTCGG TACAGTCGCG GATAGTATTG TTTGACGACG ACTTGGACCG

651 AAGACAATTG GCACCGACGG GAATGGTTAA ATTGTTTGAA ATTGACAAAC
     TTCTGTTAAC CGTGGCTGCC CTTACCAATT TAACAAACTT TAACTGTTTG

701 AGTTTGCCGA AATGCTGAGA GATCCGCAAA ATTTTGGCCT GAGCGATGTC
     TCAAACGGCT TTACGACTCT CTAGGCGTTT TAAAACCGGA CTCGCTACAG

751 GAAAACCCGT GCTATGATGG CGGATATGTC TGGAAACCGT TTGCCACAAG
     CTTTTGGGCA CGATACTACC GCCTATACAG ACCTTTGGCA AACGGTGTTC

801 AAGCGTCAGC ACGGATAGAC AACTGTCAGC GTTTAGCCCG CAAGAAAGAC
     TTCGCAGTCG TGCCTATCTG TTGACAGTCG CAAATCGGGC GTTCTTTCTG

851 TGGCAATCGC CGGAAATCCG CTTTTGGCAC AAGCAGTTGC TTCACCGATG
     ACCGTTAGCG GCCTTTAGGC GAAAACCGTG TTCGTCAACG AAGTGGCTAC

901 GCAAGAAGAT CAGCAAGCCC GCTGAATTGC GAAGGCAAAA TGTTTTGGGA
     CGTTCTTCTA GTCGTTCGGG CGACTTAACG CTTCCGTTTT ACAAAACCCT

951 TCAGGTCCAT CCGACAACAG TTGTCCATGC TGCCCTTTCA GAAAGAGCGG
     AGTCCAGGTA GGCTGTTGTC AACAGGTACG ACGGGAAAGT CTTTCTCGCC

1001 CGACGTTTAT CGAAACACAG TATGAATTTC TGGCCCATGG CTGA
     GCTGCAAATA GCTTTGTGTC ATACTTAAAG ACCGGGTACC GACT
```

FIG. 100A

SEQ ID No. 89

MRLTRSLSAASVIVFALLLALLGISPAQAAGPAYVALGDSYSSGNGAGSYIDSSGDCHRSN

NAYPARWAAANAPSSFTFAACSGAVTTDVINNQLGALNASTGLVSITIGGNDAGFADAMTT

CVTSSDSTCLNRLATATNYINTTLLARLDAVYSQIKARAPNARVVVLGYPRMYLASNPWYC

LGLSNTKRAAINTTADTLNSVISSRATAHGFRFGDVRPTFNNHELFFGNDWLHSLTLPVWE

SYHPTSTGHQSGYLPVLNANSST

FIG. 101

SEQ ID No. 90

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFRSASP
241  RSASPLNCEG KMFWDQVHPT TVVHAALSER AATFIETQYE FLAHG
```

FIG. 102

1. L131
2. S.avermitilis
3. T.fusca
4. Consensus

```
                      1                                                50
1   (1)   --------MRLTRSLSAASVIVFALLLALLGISPAQAAG-----------
2   (1)   --------MRRSRITAYVTSLLLAVGCALTGAATAQASPA----------
3   (1)   VGSGPRAATRRRLFLGIPALVLVTALTLVLAVPTGRETLWRMWCEATQDW
4   (1)           MRRSRFLA  ALILLTLA AL GAA ARAAP 51                                               100
1  (32)   ---------------------------P-AYVALGDSYSSGNGAGSYID
2  (33)   --------------------------AAATGYVALGDSYSSGVGAGSYLS
3  (51)   CLGVPVDSRGQPAEDGEFLLLSPVQAATWGNYYALGDSYSSGDGARDYYP
4  (51)                         A A  YVALGDSYSSG GAGSY 101                                               150
1  (53)   SSGD----CHRSNNAYPARWAAANAP---SSFTFAACSGAVTTDVIN----
2  (57)   SSGD----CKRSSKAYPYLWQAAHSP---SSFSFMACSGARTGDVLA----
3 (101)   GTAVKGGCWRSANAYPELVAEAYDFA--GHLSFLACSGQRGYAMLDAIDE
4 (101)   SSGD    C RSTKAYPALWAAAHA    SSFSF ACSGARTYDVLA 151                                               200
1  (93)   --NQLGALNAST--GLVSITIGGNDAGFADAMTTCVTS------SDSTCL
2  (97)   --NQLGTLNSST--GLVSLTIGGNDAGFSDVMTTCVLQ------SDSACL
3 (149)   VGSQLDWNSPHT--SLVTIGIGGNDLGFSTVLKTCMVR------VPLLDS
4 (151)        QL LNS T   LVSITIGGNDAGFAD MTTCVL      SDSACL
```

FROM FIG. 103

```
                  201                                              250
1  (133)  NRLATATNYINTTLLA-------RLDAVYSQIKARAPNARVVVLGYPRMY
2  (137)  SRINTAKAYVDSTLPG-------QLDSVYTAISTKAPSAHVAVLGYPRFY
3  (191)  KACTDQEDAIRKRMAKF----ETTFEELISEVRTRAPDARILVVGYPRIF
4  (201)   RIA AK YI   TLPA       RLDSVYSAI TRAP ARVVVLGYPRIY 251                                              300
1  (176)  LASNPWYCLGLSNTKRAAINTTADTLNSVISSRATAH-----------GF
2  (180)  KLGG-SCLAGLSETKRSAINDAADYLNSAIAKRAADH-----------GF
3  (237)  PEEPTGAYYTLTASNQRWLNETIQEFNQQLAEAVAVHDEEIAASGGVGSV
4  (251)      SG    LGLS TKRAAINDAAD LNSVIAKRAADH           GF 301                                              350
1  (215)  RFGDVRPTFNNHELFFGNDWLHSLTLP----------------VWESYH
2  (218)  TFGDVKSTFTGHEICSSSTWLHSLDLLN----------------IGQSYH
3  (287)  EFVDVYHALDGHEIGSDEPWVNGVQLRDLATG---------VTVDRSTFH
4  (301)  TFGDV  TF GHELCSA  PWLHSLTLP                V  SYH 351                                              395
1  (248)  PTSTGHQSGYLPVLNANSST-------------------------
2  (252)  PTAAGQSGGYLPVMNSVA---------------------------
3  (328)  PNAAGHRAVGERVIEQIETGPGRPLYATFAVVAGATVDTLAGEVG
4  (351)  PTA GHAAGYLPVLNSI T
```

```
IDEO    TTVYL AGDSTMAKn- - - - - - - - - - - - - - - - - - - - - - - - - - - - - - - - - - - -GGGSGTNGWGEYL
        slslSlSl sl slslh?h?h?h?                                                                h1h1h1h1h1
IIVN    ADTLLI LGDSLSAG- - - - - - - - - - - - - - - - - - - - - - - - - - - - - - - - - - - - YRMSASAAWPALL
        slslSlSl sl slslh h h h                                                                  h1h1h1h1h1
P10480  IVM FGDSLSDTgkmyskmrgy lpssppy yeGRFSNGPVWLEQL IDEO    ASYLS A TV- - - - - - - - - - VND AVAGRS- - -ARSYTREGRFENIADVV
        h1h1h1   h1h1                 s2s2 s2 s2        h3  h3h3 h3h3h3h3h3h3h3h3h3h3h3h3
IIVN    NDKWq s k- - - - - - - - -tsv VNA SISGDT- - - - -SQQGLARLPALLKQ
        h1h1h1    s22s2?              s2?s2s2s2s2 s2 s2 s2                h3h3h3h3h3h3h3h3h3h3h3h3h3
P10480  TNEFP G LTianeaeggp tava YNK ISWNPKy qvINNLDYEVTQFLQKDSF IDEO    TAGDY V IVEFGHNDGg s lstd n gr tdcsgtg aEvCYSVYDGVNETILTFP
        s4s4 s4 s4s4s4                                                   h4h4h4h4h4
IIVN    HQPRW V LVELGGNDG- - - - - ? ? ? ? ? ? ? ? ? s2s2?s?s?s?s?s?h4h4h4h4
        h3 s4s4s4 s4 s4s4
P10480  KPDDLV ILWVGANDY- - - - - - - - - - - - - - - - - - - - - - -LAYGWNTEQDAKRVR

TO FIG. 115A
```

```
FROM FIG. 115

1DEO  A Y L E N A  A K L F T - A K G A K - - - - -  V I L S S Q T P - - - - - N N P W E T G T F F V N S P T R
      h4h4h4h4h4 h4 h4h4h4h4h4     h4                s5 s5 s5 s5 s5

1IVN  Q T L R Q I  L Q D V K a A N A E P  l l m q i R L P A N Y G R - - - - - - - - - - - - - - - - - - - R Y
      h4h4h4h4h4 h4 h4h4h4h4h4     s5s5s5 s5s5s5s5?s5?s5?s5?                                              h5

P10480 D A I S D  A A N R M V - L N G A K - - - - -  E I L L F N L P d  l g g n P S A R S Q K V V E A A S H V

1DEO  F V E Y A E  L A A E V A - - - - - - - - - -  - - G V E Y V  D H W S Y V D S I Y E T L G N A t v n
      h5h5h5h5h5 h5 h5h5h5h5h5                        s6s6s6s6?h6h6h6h6h6h6h6h6h6h6h6       h h h h

1IVN  N E A F S  A I Y P K L a k e - - - - - - - -  - f D V P L L  P F F M E E V Y L K P Q W - - - - - - -
      h5h5h5h5h5 h5 h5h5h5h5h5                        s6s6s6s6?                      s

```
1DEO     ----------------------------------------
1IVN     ----------------------------------------
P10480 ggsyvw kpfasrsastd sqls a fnpqerlai agnpllaqavaspmaarsa 1DEO     - - - - -   s y F P I D H T H T S   P A G A   E V V   A E A F L K A   V V C T G T S L K S V L T T T S F E G
                                                s?s?s? h7h7h7h7 h7 h7 h7h7h7h7h7h7 h7h7h7h7  h?h?h?
1IVN     - - - - -  - - -  M Q D D G I H P N   R D A Q   P F I   A D W M A K Q   L Q P L V N H D S L E
                                         s s s                                     h7h7h7 h7 h7 h7h7h7h7h7h7h7 h7h7h7h7
P10480 stlnce gkMFWDQVHPT TVVH A A L  SEPAATF IESQYEFLAH-
```

```
1DEOm    T T V Y L   A G D S T M A K n - - - - - - - - - - - - - - - - - - - - - - - G G G S G T N G W G E Y L
         slslsl sl slslh?h?h?h?                                                       h1h1h1h1h1
1IVNm  A D T L L I   L G D S L S A G - - - - - - - - - - - - - - - - - - - - Y R M S A S A A W P A L L
       slslsl sl slslh h h h                                                  h1h1h1h1h1h1
P10480m    I V M F G D S L S D T g k m   y s k m r g y l   p   s   p p y y e G R F S N G P V W L E Q L 1DEOm    A S Y I L S   A   T V - - - - - - - - - - - - - - V N D A   V   A G R   S - - - - - - A R S Y T R E G R F E E N I A
         h1h1h1 s2 s2 s2                                   s2s2s2s2s2                           h3h3h3h3h3h3h3h3h3h3h3h3
1IVNm  N D K W q s k - - - - - - - - - - - - - t s V V N A S   H   S G D   T - - - - - - - S Q Q G L A   R L P A L L
       h1h1h1 s2?s2?                           s2s2s2s2s2s2s2                                  h3h3h3h3 h3h3h3h3h3h3
P10480mT N E F P G L T i a n e a e g g p   t a v a Y N K I   s   W   N P   K           y q v I N N L D Y E V T Q F L Q 1DEOm    D   V V T   A   G D Y V I V E F G H N   D G g s l s t d   n c. - d c s g t g a E v C Y S V V Y D G V N E T I
         h3h3                              s4 s4s4s4s4s4           c.c.c.c.c.c.        c. s?s?s?s?s?s?s?s?s?s?
1IVNm    K Q H Q P                       R W V L V E L G G N   c. c. c. c. c. D G - - - - - - - - - L R G F Q P
         h3h3h3                          s4s4s4s4s4                                                 h4
P10480mK D S F K   P D D L V I L W V G A N   D Y - - - - - - - - - - L A Y G W N T E Q D A 1DEOm    L T F P A   Y   L E N A A K L F T A K   G A K V I L S S   Q   T P N   N P W E T G T F V N S P T R
         h4h4h4h4 h4 h4h4h4h4h4h4h4h4h4h4           s5s5s5s5s5s5
1IVNm    Q Q T E Q T   L R Q I L Q D V K a A   N A E P l l m q i R L P   A N Y G R - - - - - - - - R Y N E A
         h4h4h4h4h4 h4 h4h4h4h4h4h4h4h4h4       s5s5s5s5s5s5s5s5s5?s5?                                 h5h5h5h5h5h5h5
P10480mK R V R D   A   I S D A A N R M V L N   G A K E I L L E N   L P d   l g q n P S A R S Q K V V E A A S H V S A
```

FROM FIG. 116A

```
1DEOm    F V E Y A   E L A A E V A - - - - - - - G V E Y   V D H W S Y V D S I Y E T L G N A t v n - -
         h5h5h5 h5 h5h5h5h5h5h5h5                  s6 s6 s6?h6h6h6h6h6h6h6h6h6h6h6 h h h h
1IVNm    F S A I Y   P K L A k e - - - - - - - - f D V P L L P F F M E E V Y       L K P Q W - - -
         h5h5h5h5h5 h5 h5h5h5                                 h6 h6 h6 h6h6     s
P10480m  Y H N Q L   L N L A r q l a p t g m v k l f e i D K   Q F A E M L R D P Q N F G L S D Q R N a c y g g
                                             h5  s6s6s6s6?

1DEOm    - - - - -   - - - - - - - - - - - - - - - - - - - - - - - - - - - - - - - - - - - - - - -
1IVNm    - - - - -   - - - - - - - - - - - - - - - - - - - - - - - - - - - - - - - - - - - - - - -
P10480m  s y v w k   p f a s r s a s t d s q   l s a f n p q e   r l   a i   a g n p l l a q a v a s p m a a r s a s t

1DEOm    - - - - -   y F P I D H T H T S P A   G A E V V A E A F   L K A   V V C T G T S L K S V L T T T S F E E G T C
                       s?s?s?s?h7          h7h7h7h7h7h7h7h7  h7  h7 h7  h7 h7h7h7h7h7       h?h?h?
1IVNm    - - - - -   - M Q D D G I H P N R D   A Q P F I A D W M A K   Q L Q P L V N H D S L E
         s                                 h7h7h7h7h7h7h7 h7 h7 h7 h7
P10480m  l n c e q   k M F W D Q V H P T T V   V H A A L S E P A A T F   I E S Q Y E F L A H -
```

FIG. 117A

```
1DEO      T T V Y L  A G D S T M A K n - - - - - - - - - - - - - - - G G G S G T N G W G E Y L
          slslsls1 sl slslh?h?h?H?                                                 Hlhlhlhlhl
1IVN    A D T L L I  L G D S L S A G - - - - - - - - - - - - - - - - Y R M S A S A A W P A L L
          slslsls1 sl slslh h h                                                    hlhlhlhlhl
P10480     I V M F G D S L S D T g k m y s k m r - g y l ps spp y y e G R F S N G P V W L E Q L 1DEOm     T T V Y L  A G D S T M A K n - - - - - - - - - - - - - - - G G G S G T N G W G E Y L
          slslsls1 sl slslh?h?h?H?                                                 Hlhlhlhlhl
1IVNm   A D T L L I  L G D S L S A G - - - - - - - - - - - - - - - - Y R M S A S A A W P A L L
          slslsls1 sl slslh h h                                                    hlhlhlhlhl
P10480m    I V M F G D S L S D T g k m y s k m r - g y l ps spp y y e G R F S N G P V W L E Q L 1DEO    A S Y L S A T V - - - - - - - - - - - - - - A V A G R S - - - A R S Y T R E G R F E E N I A D V V
        hlhlhl     s2 s2                             h3  h3h3h3h3h3h3h3h3h3h3h3h3h3h3h3h3h3
1IVN    N D K W q s k - - s2s2 s2 s2 s2 V N D S I S G D T - - - - - - - S Q Q G L A R L P A L L K Q
        hlhlhl    s2?S2?   - t s v v N A s2 s2                           h3h3h3h3h3h3h3h3h3h3h3
P10480  T N E F P G L T i a n e a e g g p t a v a Y N K I S W N P K y q v I N N L D Y E V T Q F L Q K D S F 1DEOm   A S Y L S A T V - - - - - - - - - - - - - - A V A G R S - - -     A R S Y T R E G R F E E N I A
        hlhlhl     s2 s2                             h3                   h3h3h3h3h3h3h3h3h3h3h3h3h3
1IVNm   N D K W q s k - - s2s2 s2 s2 s2 V N D S I S G D T - - - - - - -     S Q Q G L A     R L P A L L
        hlhlhl    s2?S2?   - t s v v N A s2 s2                                               h3h3h3h3h3
P10480m T N E F P G L T i a n e a e g g p t a v a Y N K I S W N P K         y q v I N N L D Y E V T Q F L Q
```

```
            FROM FIG. 117A

1DEO      T A G D Y   V   I V E F G H N D G g s l s t d n g r t d c s g t g a E v C Y S V Y D G V N E T I L T F P
          s4s4 s4     s4s4s4                                                                  ?s?s?s?s?s?s?h4h4h4h4
1IVN      H Q P R W   V   L V E L G G N D G - - - ? ? ? ? ? ? ? ? ? ? ? ? - - - L R G F Q P Q Q T E
          h3  s4s4s4  s4  s4s4                                                                h4h4h4h4h4
P10480    K P D D L   V   I L W V G A N D Y - - - - - - - - - - - - - - - - - L A Y G W N T E Q D A K R V R

1DEOm     D   V V T   A   G D Y V I V E F G H N D G g s l s d n g r t d c s g t g a E v C Y S V Y D G V N E T I
          h3h3             s4s4s4s4s4                   ? ? ? ? ? ? ? ? ? ? ? s?s?s?s?s?s?s?s?s?s?
1IVNm     K Q H Q P       R W V L V E L G G N   ? ? l ? ? ? ? ? ? ? s ? ? ? - - - L R G F Q P
          h3h3h3           s4s4s4s4s4                                                         h4
P10480m K D S F K   P   D D L V I L W V G A N   D Y - - - - - - - - - - - - - L A Y G W N T E Q D A

1DEO      A Y L E N   A   A K L F T - A K G A K     - - - - - V I L S S   Q T P - - N N P W E T G T F V N S P T R
          h4h4h4h4h4 h4  h4h4h4h4h4 h4          s5         s5 s5 s5 s5
1IVN      Q T L R Q   I   L Q D V K a A N A E P   l l m q i R L P A N   Y G R - - - - - - - - - - - - - R Y
          h4h4h4h4h4 h4  h4h4h4h4h4                s5s5s5 s5s5s5s5?s5?s5?s5?                                H5
P10480    D A I S D   A   A N R M V - L N G A K   - - - E I L L F N L P d l g q n P S A R S Q K V V E A A S H V

1DEOm     L T F P A   Y   L E N A A K L F T A K   G A K V I L S   S   Q T P N N P W E T G T F V N S P P T R
          h4h4h4h4h4 h4  h4h4h4h4h4h4h4h4h4    s5s5s5 s5 s5 s5 s5

FROM FIG. 117B

```
1IVNm    Q Q T E Q T L R Q I L Q D V K a A N A E P l l m q i R L P A N   Y G R - - - - - - - - R Y N E A
         h4h4h4h4h4h4h4h4h4h4h4h4h4              s5s5s5s5s5s5?s5?s5?                             h5h5h5h5h5
P10480m  K R V R D A I S D A A N R M V L N G A K E I L F N L P p   d   l g   q n P S A R S Q K V V E A A S H V S A

1DEO     F V E Y A E L A A A E V A - - - - - - - - -                                   G   V E   Y V   D H W S Y V D S I Y E T L G N A t v n
         h5h5h5h5h5h5h5h5h5h5h5h5h5                                                        s6 s6 s6s6?h6h6h6h6h6h6h6h6h6h6 h h h
1IVN     N E A F S A I Y P K L A k e - - - - - - - -                                   f D   V P   L L   P F F M E E V Y L K P Q W - - - -
         h5h5h5h5h5h5h5h5h5h5h5h5h5                                                        s6 s6 s6s6?                  s
P10480   S A Y H N Q L L L N L A r g l a p t g m v k l f e - i                          D K   Q F   A   E M L R D P Q N F G L S D Q R N a c y

1DEOm    F V E Y A E L A A A E V A - - - - - - - - -                                   G   V E   Y V   D H   W S Y V D S I Y E T L G N A t v n
         h5h5h5h5h5h5h5h5h5h5h5h5h5                                                        s6 s6 s6?h6h6 h6h6h6h6h6h6h6h6h6 h h h
1IVNm    F S A I Y P K L A k e - - - - - - - -                                        - f D V P   L L   P F   F M E E V Y     L K P Q W - - - -
         h5h5h5h5h5h5h5h5h5                                                                                              s
P10480m  Y H N Q L L L N L A r g l a p t g m v k l f e i D K                            Q F   A E M   L R D P Q N F G L S D Q R N a c y g g

1DEO     - - - - - - - - - - - - - - - - - - - - - - - - - - - - - - - - - - - - - - - - - - - -
1IVN     - - - - - - - - - - - - - - - - - - - - - - - - - - - - - - - - - - - - - - - - - - - -
P10480   g g s y v v w k p f a s r s a s t d s q l s a f n p g e r l a i a g n p l l a g a v a s p m a a r s a
1DEOm    - - - - - - - - - - - - - - - - - - - - - - - - - - - - - - - - - - - - - - - - - - - -
1IVNm    - - - - - - - - - - - - - - - - - - - - - - - - - - - - - - - - - - - - - - - - - - - -
P10480m  s y v v w k p f a s r s a s t d s q l s a f n p g e r l a i a g n p l l a g a v a s p m a a r s a s t
```

FROM FIG. 117C

```
1DEO     - - - - - s y F P I D H T S P A G A E V V A E A F L K A V V C T G T S L K S V L T T T S F E G
                   h                s?s?s?h7h7h7h7h7h7 h7 h7 h7 h7 h7h7h7h7                    h?h?h?
1IVN     - - - - - - - M Q D D G I H P N R D A Q P F I A D W M A K Q L Q P L V N H D S L E
         s t l n c e g k M F W D Q V H P T T V V H A A L S   E P A T F F I E S Q Y E F L A H -
P10480                     s s                  h7h7h7h7h7h7h7h7 h7 h7 h7 h7 h7h7h7h7
1DEOm    - - - - - s y F P I D H T S P A G A E V V A E A F L K A V V C T G T S L K S V L T T T S F E G T C
                   h                s?s?s?h7h7h7h7h7h7 h7 h7 h7 h7 h7h7h7h7                    h?h?h?
1IVNm    - - - - - - - M Q D D G I H P N R D A Q P F I A D W M A K Q L Q P L V N H D S L E
         s s s                                  h7h7h7h7h7h7h7h7 h7 h7 h7 h7 h7h7h7h7
P10480ml n c e g k M F W D Q V H P T T V V H A A L S E P A A T F F I E   S Q Y E F L A H -
```

FIG. 118

```
                      10        20        30        40        50        60
               ....*....|....*....|....*....|....*....|....*....|....*....|
1IVN_A       4 LLILGDSLSAG-------------------YRMSASAAWPALLNDKWgsk----------  34
P10480      28 IVMFGDSLSDTgkmyskmrgylpsspPyyegGRFSNGPVWLEQITNEFPGLTianeaeggp  87

70        80        90       100       110       120
               ....*....|....*....|....*....|....*....|....*....|....*....|
1IVN_A      35 -tsvVNASISGDT---------------------SQQGLARLPALLKQHQPRW-------  65
P10480      88 tavaYNKISWNPKyq---------------------vINNLDYEVTQFLQRDSFKPDDL 125

130       140       150       160       170       180
               ....*....|....*....|....*....|....*....|....*....|....*....|
1IVN_A      66 VLVELGGNDG-----------------------------LRGFQPQQTEQT--------  87
P10480     126 VILWVGANDY-------------------LA--YGWNTEQDAKRVRDA----------- 152

190       200       210       220       230       240
               ....*....|....*....|....*....|....*....|....*....|....*....|
1IVN_A      88 LRQILQDVKaANAEPllmqiRLPANYGR--------EILLFNLPdlg------------ 115
P10480     153 ISDAANRMV-LNGAK-------------------------------------qnP    180

250       260       270       280       290       300
               ....*....|....*....|....*....|....*....|....*....|....*....|
1IVN_A     116 ---------RYNEAFSAIYPKLAke-----------------fDVPLLPFFME------ 142
P10480     181 SARSQKVVEAASHVSAYHNQLLLNLArqlaptg-----mvklfeiDKQFAEMLRD     230

310       320       330       340       350       360
               ....*....|....*....|....*....|....*....|....*....|....*....|
1IVN_A     143 EVYLKPQW------------------------------------------------- 150
P10480     231 PQNFGLSDQRNacyggsyvwkpfasrsastdsqlsafnpqerlaiagnpllaqavaspma 290

370       380       390       400
               ....*....|....*....|....*....|....*....|
1IVN_A     151 -------MQDDGI------HPNRDAQPFIADWM         170
P10480     291 arsastlncegkMFWDQV--------HPTTVHAALSEPA   322
```

FIG. 119

```
P10480     (1)  MKKWFVCLLGLVALTVQAADSRPAFSRIVMFGDSLSDTGKMYSKMRGYLP
A. sal     (1)  ---------------------ADTRPAFSRIVMFGDSLSDTGKMYSKMRGYLP
A. hyd     (1)  ---------------------ADSRPAFSRIVMFGDSLSDTGKMYSKMRGYLP
Consensus  (1)                         AD RPAFSRIVMFGDSLSDTGKMYSKMRGYLP
                                                                     50

P10480    (51)  SSPPYYEGRFSNGPVWLEQITNEFPGLTIANEAEGGPTAVAYNKISWNPK
A. sal    (33)  SSPPYYEGRFSNGPVWLEQITKQFPGLTIANEAEGGATAVAYNKISWNPK
A. hyd    (33)  SSPPYYEGRFSNGPVWLEQITKQFPGLTIANEAEGGATAVAYNKISWNPK
Consensus (51)  SSPPYYEGRFSNGPVWLEQLT**FPGLTIANEAEGG*TAVAYNKISWNPK
                                                                    150

P10480   (101)  YQVINNLDYEVTQFLQKDSFKPDDLVILWVGANDYLAYGWNTEQDAKRVR
A. sal    (83)  YQVINNLDYEVTQFLQKDSFKPDDLVILWVGANDYLAYGWNTEQDAKRVR
A. hyd    (83)  YQVINNLDYEVTQFLQKDSFKPDDLVILWVGANDYLAYGWNTEQDAKRVR
Consensus(101)  YQVINNLDYEVTQFLQKDSFKPDDLVILWVGANDYLAYGWNTEQDAKRVR
                                                                    200

P10480   (151)  DAISDAANRMVLNGAKEILLFNLPDLGQNPSARSQKVVEAASHVSAYHNQ
A. sal   (133)  DAISDAANRMVLNGAKQILLFNLPDLGQNPSARSQKVVEAVSHVSAYHNK
A. hyd   (133)  DAISDAANRMVLNGAKQILLFNLPDLGQNPSARSQKVVEAVSHVSAYHNQ
Consensus(151)  DAISDAANRMVLNGAK*ILLFNLPDLGQNPSARSQKVVEA*SHVSAYHN*
                                                                    250

P10480   (201)  LLLNLARQLAPTGMVKLFEIDKQFAEMLRDPQNFGLSDQRNACYGGSYVW
A. sal   (183)  LLLNLARQLAPTGMVKLFEIDKQFAEMLRDPQNFGLSDVENPCYDGGYVW
A. hyd   (183)  LLLNLARQLAPTGMVKLFEIDKQFAEMLRDPQNFGLSDVENPCYDGGYVW
Consensus(201)  LLLNLARQLAPTGMVKLFEIDKQFAEMLRDPQNFGLSD**N*CY*G*YVW
                                                                    300

P10480   (251)  KPFASRSASTDSQLSAFNPQERLAIAGNPLLAQAVASPMAARSASTLNCE
A. sal   (233)  KPFATRSVSTDRQLSAFSPQERLAIAGNPLLAQAVASPMARRSASPLNCE
A. hyd   (233)  KPFATRSVSTDRQLSAFSPQERLAIAGNPLLAQAVASPMARRSASPLNCE
Consensus(251)  KPFA*RS*STD*QLSAF*PQERLAIAGNPLLAQAVASPMA*RSAS*LNCE
                                                                    336

P10480   (301)  GKMFWDQVHPTTVVHAALSEPAATFIESQYEFLAH-
A. sal   (283)  GKMFWDQVHPTTVVHAALSERAATFIETQYEFLAHG
A. hyd   (283)  GKMFWDQVHPTTVVHAALSERAATFIANQYEFLAH-
Consensus(301)  GKMFWDQVHPTTVVHAALSEAATFIQYEFLAH*
```

$$\frac{d_t}{d} = \frac{S_t}{S} = 1 + \sqrt{(1+2(h/d))}$$

S = W / area of dropped weight.

Example. W = 4 kg  Area of base = 2 cm x 2 cm. static deflection = d = 0.5 cm.

Static stress = 4 kg x 9.806 / 2 x 2 = 9.806 N/sq cm.

H = 5.0 cm.  St / S = 1 + √(1 + 2 x 5 / 0.5) = 5.582

Force of impact = 5.582 x 4 x 9.806 = 218.97 N.  Stress = 218.97 / 2 x 2 = 54.74 N/sq cm.

```
                                                -35
  1  GCTTTTCTTT TGGAAGAAAA TATAGGGAAA ATGGTACTTG TTAAAAATTC GGAATATTTA
     CGAAAAGAAA ACCTTCTTTT ATATCCCTTT TACCATGAAC AATTTTTAAG CCTTATAAAT
       -10                                       M K Q Q K R L ·
 61  TACAATATCA TATGTTTCAC ATTGAAAGGG GAGGAGAATC ATGAAACAAC AAAAACGGCT
     ATGTTATAGT ATACAAAGTG TAACTTTCCC CTCCTCTTAG TACTTTGTTG TTTTTGCCGA
     · Y A R   L L T   L F A   L I F   L L P   H S A ·
121  TTACGCCCGA TTGCTGACGC TGTTATTTGC GCTCATCTTC TTGCTGCCTC ATTCTGCAGC
     AATGCGGGCT AACGACTGCG ACAATAAACG CGAGTAGAAG AACGACGGAG TAAGACGTCG
     · S A A   D T R   P A F S   R I V   M F G D   S L S ·
181  TTCAGCAGCA GATACAAGAC CGGCGTTTAG CCGGATCGTC ATGTTTGGAG ATAGCCTGAG
     AAGTCGTCGT CTATGTTCTG GCCGCAAATC GGCCTAGCAG TACAAACCTC TATCGGACTC
     · D T G   K M Y S   K M R   G Y L   P S S   P Y Y ·
241  CGATACGGGC AAAATGTATA GCAAAATGAG AGGCTATCTT CCGTCAAGCC CGCCGTATTA
     GCTATGCCCG TTTTACATAT CGTTTTACTC TCCGATAGAA GGCAGTTCGG GCGGCATAAT
     · E G R   F S N G   P V W   L E Q   L T K Q   F P G ·
301  TGAAGGCCGC TTTAGCAATG GACCGGTCTG GCTGGAACAA CTGACGAAAC AATTTCCGGG
     ACTTCCGGCG AAATCGTTAC CTGGCCAGAC CGACCTTGTT GACTGCTTTG TTAAAGGCCC
     · L T I   A N E A   E G G   A T A   V A Y N   K I S ·
361  ACTGACGATC GCTAATGAAG CAGAAGGAGG AGCAACAGCG GTCGCCTATA ACAAAATCAG
     TGACTGCTAG CGATTACTTC GTCTTCCTCC TCGTTGTCGC CAGCGGATAT TGTTTTAGTC
     · W D P   K Y Q   V I N N   L D Y   E V T Q   F L Q ·
421  CTGGGACCCG AAATATCAGG TCATCAACAA CCTGGACTAT GAAGTCACAC AGTTTCTTCA
     GACCCTGGGC TTTATAGTCC AGTAGTTGTT GGACCTGATA CTTCAGTGTG TCAAAGAAGT
     · K D S   F K P D   D L V   I L W   V G A N   D Y L ·
481  GAAAGACAGC TTTAAACCGG ATGATCTGGT CATCCTTTGG GTCGGCGCCA ATGATTATCT
     CTTTCTGTCG AAATTTGGCC TACTAGACCA GTAGGAAACC CAGCCGCGGT TACTAATAGA
     · A Y G   W N T E   Q D A   K R V   R D A I   S D A ·
541  GGCGTATGGC TGGAACACAG AACAAGATGC CAAAAGAGTC AGAGATGCCA TCAGCGATGC
     CCGCATACCG ACCTTGTGTC TTGTTCTACG GTTTTCTCAG TCTCTACGGT AGTCGCTACG
     · A N R   M V L N   G A K   Q I L   F N L   P D L ·
601  CGCTAATAGA ATGGTCCTGA ACGGCGCCAA ACAAATCCTG CTGTTTAACC TGCCGGATCT
     GCGATTATCT TACCAGGACT TGCCGCGGTT TGTTTAGGAC GACAAATTGG ACGGCCTAGA
     · G Q N   P S A R   S Q K   V V E   A V S H   V S A ·
661  GGGACAAAAT CCGAGCGCCA GAAGCCAAAA AGTCGTCGAA GCAGTCAGCC ATGTCAGCGC
     CCCTGTTTTA GGCTCGCGGT CTTCGGTTTT TCAGCAGCTT CGTCAGTCGG TACAGTCGCG
     · Y H N   K L L L   N L A   R Q L   A P T   G M V K ·
721  CTATCATAAC AAACTGCTGC TGAACCTGGC AAGACAATTG GCACCGACGG GAATGGTTAA
     GATAGTATTG TTTGACGACG ACTTGGACCG TTCTGTTAAC CGTGGCTGCC CTTACCAATT
     · L F E   I D K Q   F A E   M L R   D P Q N   F G L ·
781  ATTGTTTGAA ATTGACAAAC AGTTTGCCGA AATGCTGAGA GATCCGCAAA ATTTTGGCCT
     TAACAAACTT TAACTGTTTG TCAAACGGCT TTACGACTCT CTAGGCGTTT TAAAACCGGA
     · S D V   E N P C   Y D G   G Y V   W K P   F A T R ·
841  GAGCGATGTC GAAAACCCGT GCTATGATGG CGGATATGTC TGGAAACCGT TTGCCACAAG
     CTCGCTACAG CTTTTGGGCA CGATACTACC GCCTATACAG ACCTTTGGCA AACGGTGTTC
     · S V S   T D R Q   L S A   F S P   Q E R L   A I A ·
901  AAGCGTCAGC ACGGATAGAC AACTGTCAGC GTTTAGCCCG CAAGAAAGAC TGGCAATCGC
     TTCGCAGTCG TGCCTATCTG TTGACAGTCG CAAATCGGGC GTTCTTTCTG ACCGTTAGCG
     · G N P   L L A Q   A V A   S P M   A R R S   A S P ·
961  CGGAAATCCG CTTTTGGCAC AAGCAGTTGC TTCACCGATG GCAAGAAGAT CAGCAAGCCC
     GCCTTTAGGC GAAAACCGTG TTCGTCAACG AAGTGGCTAC CGTTCTTCTA GTCGTTCGGG
     · L N C   E G K M   F W D   Q V H   P T T V   H A ·
1021 GCTGAATTGC GAAGGCAAAA TGTTTTGGGA TCAGGTCCAT CCGACAACAG TTGTCCATGC
     CGACTTAACG CTTCCGTTTT ACAAAACCCT AGTCCAGGTA GGCTGTTGTC AACAGGTACG
     · A L S   E R A A T   F I   E T Q   Y E F L   A H G ·
1081 TGCCCTTTCA GAAAGAGCGG CGACGTTTAT CGAAACACAG TATGAATTTC TGGCCCATGG
     ACGGGAAAGT CTTTCTCGCC GCTGCAAATA GCTTTGTGTC ATACTTAAAG ACCGGGTACC
     · stop
1141 CTGAGTTAAC AGAGGACGGA TTTCCTGAAG GAAATCCGTT TTTTTATTTT AAGCTTGGAG
     GACTCAATTG TCTCCTGCCT AAAGGACTTC CTTTAGGCAA AAAAATAAAA TTCGAACCTC
1201 ACAAGGTAAA GGATAAAACC TCGAG
     TGTTCCATTT CCTATTTTGG AGCTC
```

FIG. 139

SEQUENCE LISTING

```
<160> NUMBER OF SEQ ID NOS: 111

<210> SEQ ID NO 1
<211> LENGTH: 361
<212> TYPE: PRT
<213> ORGANISM: Artificial Sequence
<220> FEATURE:
<223> OTHER INFORMATION: Description of Artificial Sequence: Synthetic
      pfam00657 consensus sequence

<400> SEQUENCE: 1

Ile Val Ala Phe Gly Asp Ser Leu Thr Asp Gly Glu Ala Tyr Tyr Gly
 1               5                  10                  15

Asp Ser Asp Gly Gly Gly Trp Gly Ala Gly Leu Ala Asp Arg Leu Thr
            20                  25                  30

Ala Leu Leu Arg Leu Arg Ala Arg Pro Arg Gly Val Asp Val Phe Asn
        35                  40                  45

Arg Gly Ile Ser Gly Arg Thr Ser Asp Gly Arg Leu Ile Val Asp Ala
    50                  55                  60

Leu Val Ala Leu Leu Phe Leu Ala Gln Ser Leu Gly Leu Pro Asn Leu
65                  70                  75                  80

Pro Pro Tyr Leu Ser Gly Asp Phe Leu Arg Gly Ala Asn Phe Ala Ser
                85                  90                  95
```

-continued

```
Ala Gly Ala Thr Ile Leu Pro Thr Ser Gly Pro Phe Leu Ile Gln Val
            100                 105                 110

Gln Phe Lys Asp Phe Lys Ser Gln Val Leu Glu Leu Arg Gln Ala Leu
            115                 120                 125

Gly Leu Leu Gln Glu Leu Leu Arg Leu Leu Pro Val Leu Asp Ala Lys
        130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
        195                 200                 205

Asn Leu Gly Pro Leu Gly Cys Leu Pro Leu Lys Leu Ala Leu Ala Leu
210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
            260                 265                 270

Ala Asp Val Pro Tyr Val Asp Leu Tyr Ser Ile Phe Gln Asp Leu Asp
        275                 280                 285

Gly Ile Gln Asn Pro Ser Ala Tyr Val Tyr Gly Phe Glu Thr Thr Lys
    290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
            340                 345                 350

Gly Tyr Lys Ala Val Ala Glu Ala Leu
        355                 360

<210> SEQ ID NO 2
<211> LENGTH: 335
<212> TYPE: PRT
<213> ORGANISM: Aeromonas hydrophila

<400> SEQUENCE: 2

Met Lys Lys Trp Phe Val Cys Leu Leu Gly Leu Val Ala Leu Thr Val
  1               5                  10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110
```

```
Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
        130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285

Met Ala Ala Arg Ser Ala Ser Thr Leu Asn Cys Glu Gly Lys Met Phe
    290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 3
<211> LENGTH: 336
<212> TYPE: PRT
<213> ORGANISM: Aeromonas salmonicida

<400> SEQUENCE: 3

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160
```

Val Leu Asn Gly Ala Lys Gln Ile Leu Leu Phe Asn Leu Pro Asp Leu
               165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
                275                 280                 285

Met Ala Arg Arg Ser Ala Ser Pro Leu Asn Cys Glu Gly Lys Met Phe
            290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 4
<211> LENGTH: 295
<212> TYPE: PRT
<213> ORGANISM: Streptomyces coelicolor

<400> SEQUENCE: 4

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
            20                  25                  30

Pro Ala Gln Ala Thr Pro Thr Leu Asp Tyr Val Ala Leu Gly Asp Ser
        35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                    245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
                275                 280                 285

Met Asp Val Leu Gly Leu Asp
290                 295

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
                20                  25                  30

Pro Ala Gln Ala Thr Pro Thr Leu Asp Tyr Val Ala Leu Gly Asp Ser
            35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                    85                  90                  95

Phe Thr Arg Ala Gln Tyr Pro Gly Val Ala Pro Gln Leu Asp Ala Leu
                100                 105                 110

Gly Thr Gly Thr Asp Leu Val Thr Leu Thr Ile Gly Gly Asn Asp Asn
            115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
    195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                    245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
                275                 280                 285

```
Met Asp Val Leu Gly Leu Asp
    290             295

<210> SEQ ID NO 6
<211> LENGTH: 238
<212> TYPE: PRT
<213> ORGANISM: Saccharomyces cerevisiae

<400> SEQUENCE: 6

Met Asp Tyr Glu Lys Phe Leu Leu Phe Gly Asp Ser Ile Thr Glu Phe
 1               5                  10                  15

Ala Phe Asn Thr Arg Pro Ile Glu Asp Gly Lys Asp Gln Tyr Ala Leu
            20                  25                  30

Gly Ala Ala Leu Val Asn Glu Tyr Thr Arg Lys Met Asp Ile Leu Gln
        35                  40                  45

Arg Gly Phe Lys Gly Tyr Thr Ser Arg Trp Ala Leu Lys Ile Leu Pro
    50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Ile Gly Pro Gly Leu Val Asp Arg Glu Lys
        115                 120                 125

Trp Glu Lys Glu Lys Ser Glu Glu Ile Ala Leu Gly Tyr Phe Arg Thr
    130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220

Asp Trp Arg Asp Val Leu Asp Asp Gly Ser Asn Ile Met Ser
225                 230                 235

<210> SEQ ID NO 7
<211> LENGTH: 1005
<212> TYPE: DNA
<213> ORGANISM: Aeromonas hydrophila

<400> SEQUENCE: 7
atgaaaaaat ggtttgtgtg tttattggga ttggtcgcgc tgacagttca ggcagccgac      60
agccgtcccg ccttctcccg gatcgtgatg tttggcgaca gcctctccga taccggcaag     120
atgtacagca gatgcgcgg ttacctcccc tccagccccc cctactatga gggccgcttc     180
tccaacgggc ccgtctggct ggagcagctg accaacgagt tcccgggcct gaccatagcc     240
aacgaggcgg aaggcggacc gaccgccgtg gcttacaaca gatctcctg gaatcccaag     300 tatcaggtca tcaacaacct ggactacgag gtcacccagt tcctgcaaaa agacagcttc     360
aagccggacg atctggtgat cctctgggtc ggcgccaacg actatctggc ctatggctgg     420
aacacagagc aggatgccaa gcgggtgcgc gacgccatca gcgatgcggc caaccgcatg     480
```

-continued

```
gtgctgaacg cgccaagga gatactgctg ttcaacctgc cggatctggg ccagaacccc      540
tcggcccgca gccagaaggt ggtcgaggcg gccagccatg tctccgccta ccacaaccag      600
ctgctgctga acctggcacg ccagctggct cccaccggca tggtgaagct gttcgagatc      660
gacaagcagt ttgccgagat gctgcgtgat ccgcagaact tcggcctgag cgaccagagg      720
aacgcctgct acggtggcag ctatgtatgg aagccgtttg cctcccgcag cgccagcacc      780
gacagccagc tctccgcctt caacccgcag gagcgcctcg ccatcgccgg caacccgctg      840
ctggcccagg ccgtcgccag ccccatggct gcccgcagcg ccagcaccct caactgtgag      900
ggcaagatgt tctgggatca ggtccacccc accactgtcg tgcacgccgc cctgagcgag      960
cccgccgcca ccttcatcga gagccagtac gagttcctcg cccac                    1005
```

<210> SEQ ID NO 8
<211> LENGTH: 1011
<212> TYPE: DNA
<213> ORGANISM: Aeromonas salmonicida
<400> SEQUENCE: 8

```
atgaaaaaat ggtttgtttg tttattgggg ttgatcgcgc tgacagttca ggcagccgac       60
actcgccccg ccttctcccg gatcgtgatg ttcggcgaca gcctctccga taccggcaaa      120
atgtacagca agatgcgcgg ttacctcccc tccagcccgc cctactatga gggccgtttc      180
tccaacggac ccgtctggct ggagcagctg accaagcagt tcccgggtct gaccatcgcc      240
aacgaagcgg aaggcggtgc cactgccgtg gcttacaaca agatctcctg gaatcccaag      300
tatcaggtct acaacaacct ggactacgag gtcacccagt tcttgcagaa agacagcttc      360
aagccggacg atctggtgat cctctgggtc ggtgccaatg actatctggc atatggctgg      420
aatacggagc aggatgccaa gcgagttcgc gatgccatca gcgatgcggc caaccgcatg      480
gtactgaacg gtgccaagca gatactgctg ttcaacctgc cggatctggg ccagaacccg      540
tcagcccgca gtcagaaggt ggtcgaggcg gtcagccatg tctccgccta tcacaacaag      600
ctgctgctga acctggcacg ccagctggcc cccaccggca tggtaaagct gttcgagatc      660
gacaagcaat ttgccgagat gctgcgtgat ccgcagaact tcggcctgag cgacgtcgag      720
aacccctgct acgacggcgg ctatgtgtgg aagccgtttg ccaccgcag cgtcagcacc      780 gaccgccagc tctccgcctt cagtccgcag gaacgcctcg ccatcgccgg caacccgctg      840
ctggcacagg ccgttgccag tcctatggcc cgccgcagcg ccagcccct caactgtgag      900 ggcaagatgt tctgggatca ggtacacccg accactgtcg tgcacgcagc cctgagcgag      960
cgcgccgcca ccttcatcga gacccagtac gagttcctcg cccacggatg a             1011
```

<210> SEQ ID NO 9
<211> LENGTH: 888
<212> TYPE: DNA
<213> ORGANISM: Streptomyces coelicolor
<400> SEQUENCE: 9

```
atgccgaagc ctgcccttcg ccgtgtcatg accgcgacag tcgccgccgt cggcacgctc       60
gccctcggcc tcaccgacgc caccgcccac gccgcgcccg cccaggccac tccgaccctg      120
gactacgtcg ccctcggcga cagctacagc gccggctccg gcgtcctgcc cgtcgacccc      180
gccaacctgc tctgtctgcg ctcgacggca aactaccccc acgtcatcgc ggacacgacg      240
ggcgcccgcc tcacgacgt cacctgcggc gccgcgcaga ccgccgactt cacgcgggcc      300
cagtacccgg gcgtcgcacc ccagttggac gcgctcggca ccggcacgga cctggtcacg      360
```

```
ctcaccatcg gcggcaacga caacagcacc ttcatcaacg ccatcacggc ctgcggcacg      420
gcgggtgtcc tcagcggcgg caagggcagc ccctgcaagg acaggcacgg cacctccttc      480
gacgacgaga tcgaggccaa cacgtacccc gcgctcaagg aggcgctgct cggcgtccgc      540
gccagggctc cccacgccag ggtggcggct ctcggctacc cgtggatcac cccggccacc      600
gccgacccgt cctgcttcct gaagctcccc ctcgccgccg gtgacgtgcc ctacctgcgg      660
gccatccagg cacacctcaa cgacgcgtc cggcgggccg ccgaggagac cggagccacc       720
tacgtggact ctccggggt gtccgacggc cacgacgcct gcgaggcccc cggcacccgc       780
tggatcgaac cgctgctctt cgggcacagc ctcgttcccg tccaccccaa cgccctgggc      840
gagcggcgca tggccgagca cacgatggac gtcctcggcc tggactga                  888
```

```
<210> SEQ ID NO 10
<211> LENGTH: 888
<212> TYPE: DNA
<213> ORGANISM: Streptomyces coelicolor

<400> SEQUENCE: 10
tcagtccagg ccgaggacgt ccatcgtgtg ctcggccatg cgccgctcgc ccagggcgtt       60
ggggtggacg ggaacgaggc tgtgcccgaa gagcagcggt tcgatccagc gggtgccggg      120
ggcctcgcag gcgtcgtggc cgtcggacac cccgagaag tccacgtagg tggctccggt       180
ctcctcggcg gcccgccgga ccgcgtcgtt gaggtgtgcc tggatggccc gcaggtaggg      240
cacgtcaccg gcggcgaggg ggagcttcag gaagcaggac gggtcggcgg tggccggggt     300
gatccacggg tagccgagag ccgccaccct ggcgtgggga gccctggcgc ggacgccgag      360
cagcgcctcc ttgagcgcgg ggtacgtgtt ggcctcgatc tcgtcgtcga aggaggtgcc      420
gtgcctgtcc ttgcaggggc tgcccttgcc gccgctgagg acacccgccg tgccgcaggc      480
cgtgatggcg ttgatgaagg tgctgttgtc gttgccgccg atggtgagcg tgaccaggtc      540
cgtgccggtg ccgagcgcgt ccaactgggg tgcgacgccc gggtactggg cccgcgtgaa      600
gtcggcggtc tgcgcggcgc cgcaggtgac gtccgtgagg cgggcgcccg tcgtgtccgc      660
gatgacgtgg gggtagttgg ccgtcgagcg cagacagagc aggttggcgg ggtcgacggg      720
caggacgccg gagccggcgc tgtagctgtc gccgagggcg acgtagtcca gggtcggagt      780
ggcctgggcg ggcgcggcgt gggcggtggc gtcggtgagg ccgagggcga gcgtgccgac      840
ggcggcgact gtcgcggtca tgacacggcg aagggcaggc ttcggcat                  888
```

```
<210> SEQ ID NO 11
<211> LENGTH: 717
<212> TYPE: DNA
<213> ORGANISM: Saccharomyces cerevisiae

<400> SEQUENCE: 11
atggattacg agaagtttct gttatttggg gattccatta ctgaatttgc ttttaatact       60
aggcccattg aagatggcaa agatcagtat gctcttggag ccgcattagt caacgaatat      120
acgagaaaaa tggatattct tcaaagaggg ttcaagggt acacttctag atgggcgttg       180
aaaatacttc ctgagatttt aaagcatgaa tccaatattg tcatggccac aatattttg       240 ggtgccaacg atgcatgctc agcaggtccc caaagtgtcc cctcccga   atttatcgat      300 aatattcgtc aaatggtatc tttgatgaag tcttaccata tccgtcctat tataatagga      360
ccggggctag tagatagaga gaagtgggaa aaagaaaaat ctgaagaaat agctctcgga      420
tacttccgta ccaacgagaa ctttgccatt tattccgatg ccttagcaaa actagccaat      480
```

```
gaggaaaaag ttcccttcgt ggctttgaat aaggcgtttc aacaggaagg tggtgatgct    540
tggcaacaac tgctaacaga tggactgcac ttttccggaa aagggtacaa aatttttcat    600
gacgaattat tgaaggtcat tgagacattc taccccaat atcatcccaa aaacatgcag     660
tacaaactga aagattggag agatgtgcta gatgatggat ctaacataat gtcttga       717
```

<210> SEQ ID NO 12
<211> LENGTH: 347
<212> TYPE: PRT
<213> ORGANISM: Ralstonia solanacearum

<400> SEQUENCE: 12

```
Met Asn Leu Arg Gln Trp Met Gly Ala Thr Ala Ala Leu Ala Leu
  1               5                  10                  15

Gly Leu Ala Ala Cys Gly Gly Gly Thr Asp Gln Ser Gly Asn Pro
                 20                  25                  30

Asn Val Ala Lys Val Gln Arg Met Val Val Phe Gly Asp Ser Leu Ser
             35                  40                  45

Asp Ile Gly Thr Tyr Thr Pro Val Ala Gln Ala Val Gly Gly Gly Lys
         50                  55                  60

Phe Thr Thr Asn Pro Gly Pro Ile Trp Ala Glu Thr Val Ala Ala Gln
 65                  70                  75                  80

Leu Gly Val Thr Leu Thr Pro Ala Val Met Gly Tyr Ala Thr Ser Val
                 85                  90                  95

Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Gly Ala Gly Ala
        115                 120                 125

Leu Thr Tyr Pro Val Gln Gln Gln Leu Ala Asn Phe Tyr Ala Ala Ser
    130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Ala Thr Ser Gly Ser
                165                 170                 175

Gly Val Thr Pro Ala Ile Ala Thr Ala Gln Val Gln Gln Ala Ala Thr
            180                 185                 190

Asp Leu Val Gly Tyr Val Lys Asp Met Ile Ala Lys Gly Ala Thr Gln
        195                 200                 205

Val Tyr Val Phe Asn Leu Pro Asp Ser Ser Leu Thr Pro Asp Gly Val
    210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
            260                 265                 270

Phe Gly Phe Ala Asn Thr Ser Ala Arg Ala Cys Asp Ala Thr Lys Ile
        275                 280                 285

Asn Ala Leu Val Pro Ser Ala Gly Gly Ser Ser Leu Phe Cys Ser Ala
    290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335
```

Leu Ala Arg Leu Leu Ala Asp Asn Val Ala His
            340                 345

<210> SEQ ID NO 13
<211> LENGTH: 1044
<212> TYPE: DNA
<213> ORGANISM: Ralstonia solanacearum

<400> SEQUENCE: 13

| | | | | | |
|---|---|---|---

```
<220> FEATURE:
<223> OTHER INFORMATION: Description of Artificial Sequence: Synthetic
      peptide

<400> SEQUENCE: 16

Gly Gly Asn Asp Ala
  1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Asp Ser Tyr
  1

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Asn Asp Leu
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: variable amino acid

<400> SEQUENCE: 19

Gly Gly Asn Asp Xaa
  1               5

<210> SEQ ID NO 20
<211> LENGTH: 261
<212> TYPE: PRT
<213> ORGANISM: Streptomyces coelicolor

<400> SEQUENCE: 20

Met Ile Gly Ser Tyr Val Ala Val Gly Asp Ser Phe Thr Glu Gly Val
  1               5                  10                  15

Gly Asp Pro Gly Pro Asp Gly Ala Phe Val Gly Trp Ala Asp Arg Leu
                 20                  25                  30

Ala Val Leu Leu Ala Asp Arg Arg Pro Glu Gly Asp Phe Thr Tyr Thr
             35                  40                  45

Asn Leu Ala Val Arg Gly Arg Leu Leu Asp Gln Ile Val Ala Glu Gln
         50                  55                  60

Val Pro Arg Val Val Gly Leu Ala Pro Asp Leu Val Ser Phe Ala Ala
 65                  70                  75                  80

Gly Gly Asn Asp Ile Ile Arg Pro Gly Thr Asp Pro Asp Glu Val Ala
                 85                  90                  95
```

```
Glu Arg Phe Glu Leu Ala Val Ala Ala Leu Thr Ala Ala Ala Gly Thr
                100                 105                 110

Val Leu Val Thr Thr Gly Phe Asp Thr Arg Gly Val Pro Val Leu Lys
            115                 120                 125

His Leu Arg Gly Lys Ile Ala Thr Tyr Asn Gly His Val Arg Ala Ile
        130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Leu Pro Pro Arg
        195                 200                 205

Gly Thr Leu Asp Val Arg Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 21
<211> LENGTH: 786
<212> TYPE: DNA
<213> ORGANISM: Streptomyces coelicolor

<400> SEQUENCE: 21
gtgatcgggt cgtacgtggc ggtgggggac agcttcaccg agggcgtcgg cgaccccggc      60
cccgacgggg cgttcgtcgg ctgggccgac cggctcgccg tactgctcgc ggaccggcgc     120
cccgagggcg acttcacgta cacgaacctc gccgtgcgcg gcaggctcct cgaccagatc     180
gtggcggaac aggtcccgcg ggtcgtcgga ctcgcgcccg acctcgtctc gttcgcggcg     240
ggcggcaacg acatcatccg gcccggcacc gatcccgacg aggtcgccga gcggttcgag     300
ctggcggtgg ccgcgctgac cgccgcggcc ggaaccgtcc tggtgaccac cgggttcgac     360
acccgggggg tgcccgtcct caagcacctg cgcggcaaga tcgccacgta caacgggcac     420
gtccgcgcca tcgccgaccg ctacggctgc ccggtgctcg acctgtggtc gctgcggagc     480
gtccaggacc gcagggcgtg ggacgccgac cggctgcacc tgtcgccgga ggggcacacc     540
cgggtggcgc tgcgcgcggg gcaggccctg ggcctgcgcg tcccggccga ccctgaccag     600
ccctggccgc ccctgccgcc gcgcggcacg ctcgacgtcc ggcgcgacga cgtgcactgg     660
gcgcgcgagt acctggtgcc gtggatcggg cgccggctgc ggggcgagtc gtcgggcgac     720
cacgtgacgg ccaaggggac gctgtcgccg gacgccatca agacgcggat cgccgcggtg     780
gcctga                                                               786

<210> SEQ ID NO 22
<211> LENGTH: 260
<212> TYPE: PRT
<213> ORGANISM: Streptomyces coelicolor

<400> SEQUENCE: 22

Met Gln Thr Asn Pro Ala Tyr Thr Ser Leu Val Ala Val Gly Asp Ser
1               5                   10                  15
```

Phe Thr Glu Gly Met Ser Asp Leu Leu Pro Asp Gly Ser Tyr Arg Gly
            20                  25                  30

Trp Ala Asp Leu Leu Ala Thr Arg Met Ala Ala Arg Ser Pro Gly Phe
        35                  40                  45

Arg Tyr Ala Asn Leu Ala Val Arg Gly Lys Leu Ile Gly Gln Ile Val
    50                  55                  60

Asp Glu Gln Val Asp Val Ala Ala Met Gly Ala Asp Val Ile Thr
65                  70                  75                  80

Leu Val Gly Gly Leu Asn Asp Thr Leu Arg Pro Lys Cys Asp Met Ala
                85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
        115                 120                 125

Leu Glu Arg Phe Arg Pro Arg Met Glu Ala Leu Phe Ala Val Ile Asp
    130                 135                 140

Asp Leu Ala Gly Arg His Gly Ala Val Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Arg Val Ala Glu Ala Val Trp Gln Ser Leu
            180                 185                 190

Gly His Glu Pro Glu Asp Pro Glu Trp His Ala Pro Ile Pro Ala Thr
        195                 200                 205

Pro Pro Pro Gly Trp Val Thr Arg Arg Thr Ala Asp Val Arg Phe Ala
    210                 215                 220

Arg Gln His Leu Leu Pro Trp Ile Gly Arg Leu Thr Gly Arg Ser
225                 230                 235                 240

Ser Gly Asp Gly Leu Pro Ala Lys Arg Pro Asp Leu Leu Pro Tyr Glu
                245                 250                 255

Asp Pro Ala Arg
            260

<210> SEQ ID NO 23
<211> LENGTH: 783
<212> TYPE: DNA
<213> ORGANISM: Streptomyces coelicolor

<400> SEQUENCE: 23
atgcagacga accccgcgta caccagtctc gtcgccgtcg gcgactcctt caccgagggc      60
atgtcggacc tgctgcccga cggctcctac cgtggctggg ccgacctcct cgccacccgg     120
atggcggccc gctcccccgg cttccggtac gccaacctgg cggtgcgcgg aagctgatc      180 ggacagatcg tcgacgagca ggtggacgtg gccgccgcca tgggagccga cgtgatcacg     240
ctggtcggcg gctcaacga cacgctgcgg cccaagtgcg acatggcccg gtgcgggac       300 ctgctgaccc aggccgtgga acggctcgcc ccgcactgcg agcagctggt gctgatgcgc     360
agtcccggtc gccagggtcc ggtgctggag cgcttccggc cccgcatgga ggccctgttc     420
gccgtgatcg acgacctggc cgggcggcac ggcgccgtgg tcgtcgacct gtacggggcc     480
cagtcgctgg ccgaccctcg gatgtgggac gtggaccggc tgcacctgac cgccgagggc     540
caccgccggg tcgcggaggc ggtgtggcag tcgctcggcc acgagcccga ggaccccgag     600
tggcacgcgc cgatcccggc gacgccgccg cggggtggg tgacgcgcag gaccgcggac     660
gtccggttcg cccggcagca cctgctgccc tggataggcc gcaggctgac cgggcgctcg     720

```
tccggggacg gcctgccggc caagcgcccg gacctgctgc cctacgagga ccccgcacgg    780
tga                                                                  783
```

<210> SEQ ID NO 24
<211> LENGTH: 454
<212> TYPE: PRT
<213> ORGANISM: Streptomyces coelicolor

<400> SEQUENCE: 24

```
Met Thr Arg Gly Arg Asp Gly Ala Gly Ala Pro Pro Thr Lys His
  1               5                  10                  15

Arg Ala Leu Leu Ala Ala Ile Val Thr Leu Ile Val Ala Ile Ser Ala
             20                  25                  30

Ala Ile Tyr Ala Gly Ala Ser Ala Asp Asp Gly Ser Arg Asp His Ala
         35                  40                  45

Leu Gln Ala Gly Gly Arg Leu Pro Arg Gly Asp Ala Ala Pro Ala Ser
     50                  55                  60

Thr Gly Ala Trp Val Gly Ala Trp Ala Thr Ala Pro Ala Ala Glu
 65                  70                  75                  80

Pro Gly Thr Glu Thr Thr Gly Leu Ala Gly Arg Ser Val Arg Asn Val
                 85                  90                  95

Val His Thr Ser Val Gly Gly Thr Gly Ala Arg Ile Thr Leu Ser Asn
            100                 105                 110

Leu Tyr Gly Gln Ser Pro Leu Thr Val Thr His Ala Ser Ile Ala Leu
        115                 120                 125

Ala Ala Gly Pro Asp Thr Ala Ala Ile Ala Asp Thr Met Arg Arg
    130                 135                 140

Leu Thr Phe Gly Gly Ser Ala Arg Val Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
        195                 200                 205

Asp Val Thr Ala Val Ala Tyr Thr Thr Pro Thr Pro Tyr Trp Arg Tyr
    210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
                245                 250                 255

Asn His Arg Trp Thr Asp Val Leu Ala Ala Arg Leu His Glu Ala Ala
            260                 265                 270

Gly Asp Gly Arg Asp Thr Pro Arg Tyr Ser Val Val Asn Glu Gly Ile
        275                 280                 285

Ser Gly Asn Arg Leu Leu Thr Ser Arg Pro Gly Arg Pro Ala Asp Asn
    290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
                325                 330                 335

Pro Glu Leu Ala Asp Arg Asp Ala Ile Leu Thr Gly Leu Arg Thr Leu
            340                 345                 350

Val Asp Arg Ala His Ala Arg Gly Leu Arg Val Val Gly Ala Thr Ile
```

```
                355             360             365
Thr Pro Phe Gly Gly Tyr Gly Tyr Thr Glu Ala Arg Glu Thr Met
    370             375             380

Arg Gln Glu Val Asn Glu Glu Ile Arg Ser Gly Arg Val Phe Asp Thr
385             390             395             400

Val Val Asp Phe Asp Lys Ala Leu Arg Asp Pro Tyr Asp Pro Arg Arg
            405             410             415

Met Arg Ser Asp Tyr Asp Ser Gly His Leu His Pro Gly Asp Lys
        420             425             430

Gly Tyr Ala Arg Met Gly Ala Val Ile Asp Leu Ala Ala Leu Lys Gly
        435             440             445

Ala Ala Pro Val Lys Ala
    450
```

<210> SEQ ID NO 25
<211> LENGTH: 1365
<212> TYPE: DNA
<213> ORGANISM: Streptomyces coelicolor

<400> SEQUENCE: 25

```
atgacccggg gtcgtgacgg gggtgcgggg gcgcccccca ccaagcaccg tgccctgctc      60
gcggcgatcg tcaccctgat agtggcgatc tccgcggcca tatacgccgg agcgtccgcg     120
gacgacggca gcagggacca cgcgctgcag gccggaggcc gtctcccacg aggagacgcc     180
gcccccgcgt ccaccggtgc ctgggtgggc gcctgggcca ccgcaccggc cgcggccgag     240
ccgggcaccg agacgaccgg cctggcgggc cgctccgtgc gcaacgtcgt gcacacctcg     300
gtcggcggca ccggcgcgcg gatcaccctc tcgaacctgt acgggcagtc gccgctgacc     360
gtcacacacg cctcgatcgc cctggccgcc gggcccgaca ccgccgccgc gatcgccgac     420
accatgcgcc ggctcacctt cggcggcagc gcccgggtga tcatcccggc gggcggccag     480
gtgatgagcg acaccgcccg cctcgccatc ccctacgggg cgaacgtcct ggtcaccacg     540
tactcccccca tcccgtccgg gccggtgacc taccatccgc aggcccggca gaccagctac     600
ctggccgacg gcgaccgcac ggcggacgtc accgccgtcg cgtacaccac ccccacgccc     660
tactggcgct acctgaccgc cctcgacgtg ctgagccacg aggccgacgg cacggtcgtg     720
gcgttcggcg actccatcac cgacggcgcc cgctcgcaga gcgacgccaa ccaccgctgg     780
accgacgtcc tcgccgcacg cctgcacgag gcggcgggcg acggccggga cacgccccgc     840
tacagcgtcg tcaacgaggg catcagcggc aacggctcc tgaccagcag gccggggcgg     900
ccggccgaca cccgagcgg actgagccgg ttccagcggg acgtgctgga acgcaccaac     960
gtcaaggccg tcgtcgtcgt cctcggcgtc aacgacgtcc tgaacagccc ggaactcgcc    1020
gaccgcgacg ccatcctgac cggcctgcgc accctcgtcg accgggcgca cgcccgggga    1080
ctgcgggtcg tcggcgccac gatcacgccg ttcggcggct acggcggcta caccgaggcc    1140
cgcgagacga tgcggcagga ggtcaacgag gagatccgct ccggccgggt cttcgacacg    1200
gtcgtcgact cgacaaggc cctgcgcgac ccgtacgacc cgcgccggat cgctccgac    1260
tacgacagcg gcgaccacct gcacccccgg cgacaagggg t acgcgcgcat gggcgcggtc    1320
atcgacctgg ccgcgctgaa gggcgcggcg ccggtcaagg cgtag              1365
```

<210> SEQ ID NO 26
<211> LENGTH: 340
<212> TYPE: PRT
<213> ORGANISM: Streptomyces coelicolor

```
<400> SEQUENCE: 26

Met Thr Ser Met Ser Arg Ala Arg Val Ala Arg Ile Ala Ala Gly
 1               5                  10                  15

Ala Ala Tyr Gly Gly Gly Ile Gly Leu Ala Gly Ala Ala Val
             20                  25                  30

Gly Leu Val Val Ala Glu Val Gln Leu Ala Arg Arg Val Gly Val
         35                  40                  45

Gly Thr Pro Thr Arg Val Pro Asn Ala Gln Gly Leu Tyr Gly Gly Thr
         50                  55                  60

Leu Pro Thr Ala Gly Asp Pro Leu Arg Leu Met Met Leu Gly Asp
 65                  70                  75                  80

Ser Thr Ala Ala Gly Gln Gly Val His Arg Ala Gly Gln Thr Pro Gly
                     85                  90                  95

Ala Leu Leu Ala Ser Gly Leu Ala Ala Val Ala Glu Arg Pro Val Arg
                100                 105                 110

Leu Gly Ser Val Ala Gln Pro Gly Ala Cys Ser Asp Asp Leu Asp Arg
            115                 120                 125

Gln Val Ala Leu Val Leu Ala Glu Pro Asp Arg Val Pro Asp Ile Cys
130                 135                 140

Val Ile Met Val Gly Ala Asn Asp Val Thr His Arg Met Pro Ala Thr
145                 150                 155                 160

Arg Ser Val Arg His Leu Ser Ser Ala Val Arg Arg Leu Arg Thr Ala
                165                 170                 175

Gly Ala Glu Val Val Gly Thr Cys Pro Asp Leu Gly Thr Ile Glu
            180                 185                 190

Arg Val Arg Gln Pro Leu Arg Trp Leu Ala Arg Ala Ser Arg Gln
195                 200                 205

Leu Ala Ala Gln Thr Ile Gly Ala Val Glu Gln Gly Gly Arg Thr
210                 215                 220

Val Ser Leu Gly Asp Leu Leu Gly Pro Glu Phe Ala Gln Asn Pro Arg
225                 230                 235                 240

Glu Leu Phe Gly Pro Asp Asn Tyr His Pro Ser Ala Glu Gly Tyr Ala
                245                 250                 255

Thr Ala Ala Met Ala Val Leu Pro Ser Val Cys Ala Ala Leu Gly Leu
                260                 265                 270

Trp Pro Ala Asp Glu Glu His Pro Asp Ala Leu Arg Arg Glu Gly Phe
                275                 280                 285

Leu Pro Val Ala Arg Ala Ala Glu Ala Ala Ser Glu Ala Gly Thr
        290                 295                 300

Glu Val Ala Ala Ala Met Pro Thr Gly Pro Arg Gly Pro Trp Ala Leu
305                 310                 315                 320

Leu Lys Arg Arg Arg Arg Arg Val Ser Glu Ala Glu Pro Ser Ser
                325                 330                 335

Pro Ser Gly Val
            340

<210> SEQ ID NO 27
<211> LENGTH: 1023
<212> TYPE: DNA
<213> ORGANISM: Streptomyces coelicolor

<400> SEQUENCE: 27
atgacgagca tgtcgagggc gagggtggcg cggcggatcg cggccggcgc ggcgtacggc      60
ggcggcggca tcggcctggc gggagcggcg gcggtcggtc tggtggtggc cgaggtgcag     120
```

-continued

```
ctggccagac gcagggtggg ggtgggcacg ccgacccggg tgccgaacgc gcagggactg    180
tacggcggca ccctgcccac ggccggcgac ccgccgctgc ggctgatgat gctgggcgac    240
tccacggccg ccgggcaggg cgtgcaccgg gccgggcaga cgccgggcgc gctgctggcg    300
tccgggctcg cggcggtggc ggagcggccg gtgcggctgg ggtcggtcgc ccagccgggg    360
gcgtgctcgg acgacctgga ccggcaggtg gcgctggtgc tcgccgagcc ggaccgggtg    420
cccgacatct gcgtgatcat ggtcggcgcc aacgacgtca cccaccggat gccggcgacc    480
cgctcggtgc ggcacctgtc ctcggcggta cggcggctgc gcacggccgg tgcggaggtg    540
gtggtcggca cctgtccgga cctgggcacg atcgagcggg tgcggcagcc gctgcgctgg    600
ctggcccggc gggcctcacg gcagctcgcg gcggcacaga ccatcggcgc cgtcgagcag    660
ggcgggcgca cggtgtcgct gggcgacctg ctgggtccgg agttcgcgca gaacccgcgg    720
gagctcttcg gccccgacaa ctaccacccc tccgccgagg ggtacgccac ggccgcgatg    780
gcggtactgc cctcggtgtg cgccgcgctc ggcctgtggc cggccgacga ggagcacccg    840
gacgcgctgc gccgcgaggg cttcctgccg gtggcgcgcg cggcggcgga ggcggcgtcc    900
gaggcgggta cggaggtcgc cgccgccatg cctacggggc ctcgggggcc ctgggcgctg    960
ctgaagcgcc ggagacggcg tcgggtgtcg gaggcggaac cgtccagccc gtccggcgtt    1020
tga                                                                 1023
```

<210> SEQ ID NO 28
<211> LENGTH: 305
<212> TYPE: PRT
<213> ORGANISM: Streptomyces coelicolor

<400> SEQUENCE: 28

```
Met Gly Arg Gly Thr Asp Gln Arg Thr Arg Tyr Gly Arg Arg Arg Ala
  1               5                  10                  15

Arg Val Ala Leu Ala Ala Leu Thr Ala Ala Val Leu Gly Val Gly Val
             20                  25                  30

Ala Gly Cys Asp Ser Val Gly Gly Asp Ser Pro Ala Pro Ser Gly Ser
         35                  40                  45

Pro Ser Lys Arg Thr Arg Thr Ala Pro Ala Trp Asp Thr Ser Pro Ala
     50                  55                  60

Ser Val Ala Ala Val Gly Asp Ser Ile Thr Arg Gly Phe Asp Ala Cys
 65                  70                  75                  80

Ala Val Leu Ser Asp Cys Pro Glu Val Ser Trp Ala Thr Gly Ser Ser
                 85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
        115                 120                 125

Leu Thr Ala Gln Val Thr Arg Ala Ala Gln Arg Glu Pro Glu Leu Val
    130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
        195                 200                 205

Lys Gln Val Trp Lys Leu Gly Leu Cys Pro Ser Met Leu Gly Asp Ala
```

```
            210                 215                 220
Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Asp Gly Ala Val His Glu Phe Arg Phe Gly
            260                 265                 270

Thr Asp Gln Leu Ser His Trp Asp Trp Phe His Pro Ser Val Asp Gly
                275                 280                 285

Gln Ala Arg Leu Ala Glu Ile Ala Tyr Arg Ala Val Thr Ala Lys Asn
            290                 295                 300

Pro
305

<210> SEQ ID NO 29
<211> LENGTH: 918
<212> TYPE: DNA
<213> ORGANISM: Streptomyces coelicolor

<400> SEQUENCE: 29
atgggtcgag ggacggacca gcggacgcgg tacggccgtc gccgggcgcg tgtcgcgctc      60
gccgccctga ccgccgccgt cctgggcgtg ggcgtggcgg gctgcgactc cgtgggcggc     120
gactcacccg ctccttccgg cagcccgtcg aagcggacga ggacggcgcc cgcctgggac     180
accagcccgg cgtccgtcgc cgccgtgggc gactccatca cgcgcggctt cgacgcctgt     240
gcggtgctgt cggactgccc ggaggtgtcg tgggcgaccg gcagcagcgc gaaggtcgac     300
tcgctggccg tacggctgct ggggaaggcg gacgcggccg agcacagctg gaactacgcg     360
gtcaccgggg cccggatggc ggacctgacc gctcaggtga cgcgggcggc gcagcgcgag     420
ccggagctgg tggcggtgat ggccggggcg aacgacgcgt gccggtccac gacctcggcg     480
atgacgccgg tggcggactt ccgggcgcag ttcgaggagg cgatggccac cctgcgcaag     540
aagctcccca aggcgcaggt gtacgtgtcg agcatcccgg acctcaagcg gctctggtcc     600
cagggccgca ccaacccgct gggcaagcag gtgtggaagc tcggcctgtg cccgtcgatg     660
ctgggcgacg cggactccct ggactcggcg gcgaccctgc ggcgcaacac ggtgcgcgac     720
cgggtggcga actacaacga ggtgctgcgg gaggtctgcg cgaaggaccg cgggtgccgc     780
agcgacgacg gcgcggtgca cgagttccgg ttcggcacgg accagttgag ccactgggac     840
tggttccacc cgagtgtgga cggccaggcc cggctggcgg agatcgccta ccgcgcggtc     900
accgcgaaga atccctga                                                  918

<210> SEQ ID NO 30
<211> LENGTH: 268
<212> TYPE: PRT
<213> ORGANISM: Streptomyces rimosus

<400> SEQUENCE: 30

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Val Ser Ala Pro Arg
                20                  25                  30

Ile Gln Ala Thr Asp Tyr Val Ala Leu Gly Asp Ser Tyr Ser Ser Gly
            35                  40                  45

Val Gly Ala Gly Ser Tyr Asp Ser Ser Ser Gly Ser Cys Lys Arg Ser
        50                  55                  60
```

```
Thr Lys Ser Tyr Pro Ala Leu Trp Ala Ala Ser His Thr Gly Thr Arg
 65                  70                  75                  80

Phe Asn Phe Thr Ala Cys Ser Gly Ala Arg Thr Gly Asp Val Leu Ala
                 85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
        115                 120                 125

Leu Gln Gly Glu Ser Ala Cys Leu Ala Arg Ile Ala Lys Ala Arg Ala
130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Leu Gly Tyr Pro
                165                 170                 175

Arg Phe Tyr Lys Leu Gly Gly Ser Cys Ala Val Gly Leu Ser Glu Lys
                180                 185                 190

Ser Arg Ala Ala Ile Asn Ala Ala Ala Asp Asp Ile Asn Ala Val Thr
                195                 200                 205

Ala Lys Arg Ala Ala Asp His Gly Phe Ala Phe Gly Asp Val Asn Thr
210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
                245                 250                 255

Ser Lys Gly Tyr Leu Pro Val Leu Asn Ser Ala Thr
                260                 265

<210> SEQ ID NO 31
<211> LENGTH: 1068
<212> TYPE: DNA
<213> ORGANISM: Streptomyces rimosus

<400> SEQUENCE: 31
ttcatcacaa cgatgtcaca acaccggcca tccgggtcat ccctgatcgt gggaatgggt      60
gacaagcctt cccgtgacga aagggtcctg ctacatcaga aatgacagaa atcctgctca     120
gggaggttcc atgagactgt cccgacgcgc ggccacggcg tccgcgctcc tcctcacccc     180
ggcgctcgcg ctcttcggcg cgagcgccgc cgtgtccgcg ccgcgaatcc aggccaccga     240
ctacgtggcc ctcggcgact cctactcctc ggggtcggc gcgggcagct acgacagcag     300
cagtggctcc tgtaagcgca gcaccaagtc ctacccggcc ctgtgggccg cctcgcacac     360
cggtacgcgg ttcaacttca ccgcctgttc gggcgcccgc acaggagacg tgctggccaa     420
gcagctgacc ccggtcaact ccggcaccga cctggtcagc attaccatcg gcggcaacga     480
cgcgggcttc gccgacacca tgaccacctg caacctccag ggcgagagcg cgtgcctggc     540
gcggatcgcc aaggcgcgcg cctacatcca gcagacgctg cccgcccagc tggaccaggt     600
ctacgacgcc atcgacagcc gggcccccgc agcccaggtc gtcgtcctgg gctaccgcg     660 cttctacaag ctgggcggca gctgcgccgt cggtctctcg gagaagtccc gcgcggccat     720
caacgccgcc gccgacgaca tcaacgccgt caccgccaag cgcgccgccg accacggctt     780
cgccttcggg gacgtcaaca cgaccttcgc cgggcacgag ctgtgctccg gcgcccctg     840 gctgcacagc gtcaccccttc ccgtggagaa ctcctaccac cccacggcca acggacagtc     900
caagggctac ctgcccgtcc tgaactccgc cacctgatct cgcggctact ccgcccctga     960
cgaagtcccg ccccggggcg gggcttcgcc gtaggtgcgc gtaccgccgt cgcccgtcgc    1020
```
gccggtggcc cgccgtacg tgccgccgcc cccggacgcg gtcggttc            1068

<210> SEQ ID NO 32
<211> LENGTH: 335
<212> TYPE: PRT
<213> ORGANISM: Aeromonas hydrophila

<400> SEQUENCE: 32

Met Lys Lys Trp Phe Val Cys Leu Leu Gly Leu Val Ala Leu Thr Val
 1               5                  10                  15

Gln Ala Ala Asp Ser Arg Pro Ala Phe Ser Arg Ile Val Met Phe Gly
             20                  25                  30

Asp Ser Leu Ser Asp Thr Gly Lys Met Tyr Ser Lys Met Arg Gly Tyr
         35                  40                  45

Leu Pro Ser Ser Pro Tyr Tyr Glu Gly Arg Phe Ser Asn Gly Pro
     50                  55                  60

Val Trp Leu Glu Gln Leu Thr Lys Gln Phe Pro Gly Leu Thr Ile Ala
 65                  70                  75                  80

Asn Glu Ala Glu Gly Gly Ala Thr Ala Val Ala Tyr Asn Lys Ile Ser
                 85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Gln Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335

<210> SEQ ID NO 33
<211> LENGTH: 1008
<212> TYPE: DNA
<213> ORGANISM: Aeromonas hydrophila

<400> SEQUENCE: 33

```
atgaaaaaat ggtttgtgtg tttattggga ttggtcgcgc tgacagttca ggcagccgac     60
agtcgccccg ccttttcccg gatcgtgatg ttcggcgaca gcctctccga taccggcaaa    120
atgtacagca agatgcgcgg ttacctcccc tccagcccgc cctactatga gggccgtttc    180
tccaacggac ccgtctggct ggagcagctg accaaacagt tcccgggtct gaccatcgcc    240
aacgaagcgg aaggcggtgc cactgccgtg gcttacaaca agatctcctg gaatcccaag    300
tatcaggtca tcaacaacct ggactacgag gtcacccagt tcttgcagaa agacagcttc    360
aagccggacg atctggtgat cctctgggtc ggtgccaatg actatctggc ctatggctgg    420
aacacggagc aggatgccaa gcgggttcgc gatgccatca gcgatgcggc caaccgcatg    480
gtactgaacg gtgccaagca gatactgctg ttcaacctgc cggatctggg ccagaacccg    540
tcagctcgca gtcagaaggt ggtcgaggcg gtcagccatg tctccgccta tcacaaccag    600
ctgctgctga acctggcacg ccagctggcc cccaccggca tggtaaagct gttcgagatc    660
gacaagcaat tgccgagat gctgcgtgat ccgcagaact tcggcctgag cgacgtcgag    720
aaccctgct acgacggcgg ctatgtgtgg aagccgtttg ccacccgcag cgtcagcacc    780
gaccgccagc tctccgcctt cagtccgcag gaacgcctcg ccatcgccgg caaccgctg    840
ctggcacagg ccgttgccag tcctatggcc cgccgcagcg ccagccccct caactgtgag    900
ggcaagatgt tctgggatca ggtacacccg accactgtcg tgcacgcagc cctgagcgag    960
cgcgccgcca ccttcatcgc gaaccagtac gagttcctcg cccactga                1008
```

<210> SEQ ID NO 34
<211> LENGTH: 336
<212> TYPE: PRT
<213> ORGANISM: Aeromonas salmonicida

<400> SEQUENCE: 34

```
Met Lys Lys Trp Phe Val Cys Leu Leu Gly Leu Ile Ala Leu Thr Val
  1               5                  10                  15
Gln Ala Ala Asp Thr Arg Pro Ala Phe Ser Arg Ile Val Met Phe Gly
             20                  25                  30
Asp Ser Leu Ser Asp Thr Gly Lys Met Tyr Ser Lys Met Arg Gly Tyr
         35                  40                  45
Leu Pro Ser Ser Pro Pro Tyr Tyr Glu Gly Arg Phe Ser Asn Gly Pro
     50                  55                  60
Val Trp Leu Glu Gln Leu Thr Lys Gln Phe Pro Gly Leu Thr Ile Ala
 65                  70                  75                  80
Asn Glu Ala Glu Gly Gly Ala Thr Ala Val Ala Tyr Asn Lys Ile Ser
                 85                  90                  95
Trp Asn Pro Lys Tyr Gln Val Ile Asn Asn Leu Asp Tyr Glu Val Thr
            100                 105                 110
Gln Phe Leu Gln Lys Asp Ser Phe Lys Pro Asp Asp Leu Val Ile Leu
        115                 120                 125
Trp Val Gly Ala Asn Asp Tyr Leu Ala Tyr Gly Trp Asn Thr Glu Gln
    130                 135                 140
Asp Ala Lys Arg Val Arg Asp Ala Ile Ser Asp Ala Ala Asn Arg Met
145                 150                 155                 160
Val Leu Asn Gly Ala Lys Gln Ile Leu Leu Phe Asn Leu Pro Asp Leu
                165                 170                 175
Gly Gln Asn Pro Ser Ala Arg Ser Gln Lys Val Val Glu Ala Val Ser
            180                 185                 190
```

```
            His Val Ser Ala Tyr His Asn Lys Leu Leu Asn Leu Ala Arg Gln
                195                 200                 205

Leu Ala Pro Thr Gly Met Val Lys Leu Phe Glu Ile Asp Lys Gln Phe
                210                 215                 220

Ala Glu Met Leu Arg Asp Pro Gln Asn Phe Gly Leu Ser Asp Val Glu
            225                 230                 235                 240

Asn Pro Cys Tyr Asp Gly Gly Tyr Val Trp Lys Pro Phe Ala Thr Arg
                            245                 250                 255

Ser Val Ser Thr Asp Arg Gln Leu Ser Ala Phe Ser Pro Gln Glu Arg
                            260                 265                 270

Leu Ala Ile Ala Gly Asn Pro Leu Leu Ala Gln Ala Val Ala Ser Pro
                        275                 280                 285

Met Ala Arg Arg Ser Ala Ser Pro Leu Asn Cys Glu Gly Lys Met Phe
                290                 295                 300

Trp Asp Gln Val His Pro Thr Thr Val Val His Ala Ala Leu Ser Glu
            305                 310                 315                 320

Arg Ala Ala Thr Phe Ile Glu Thr Gln Tyr Glu Phe Leu Ala His Gly
                            325                 330                 335

<210> SEQ ID NO 35
<211> LENGTH: 1011
<212> TYPE: DNA
<213> ORGANISM: Aeromonas salmonicida

<400> SEQUENCE: 35
atgaaaaaat ggtttgtttg tttattgggg ttgatcgcgc tgacagttca ggcagccgac      60
actcgccccg ccttctcccg gatcgtgatg ttcggcgaca gcctctccga taccggcaaa     120
atgtacagca gatgcgcgg ttacctcccc tccagcccgc cctactatga gggccgtttc     180
tccaacggac ccgtctggct ggagcagctg accaagcagt tcccgggtct gaccatcgcc     240
aacgaagcgg aaggcggtgc cactgccgtg gcttacaaca gatctcctg gaatcccaag     300 tatcaggtca tcaacaacct ggactacgag gtcacccagt tcttgcagaa agacagcttc     360
aagccggacg atctggtgat cctctgggtc ggtgccaatg actatctggc atatggctgg     420
aatacggagc aggatgccaa gcgagttcgc gatgccatca gcgatgcggc caaccgcatg     480
gtactgaacg gtgccaagca gatactgctg ttcaacctgc cggatctggg ccagaacccg     540
tcagcccgca gtcagaaggt ggtcgaggcg gtcagccatg tctccgccta tcacaacaag     600
ctgctgctga acctggcacg ccagctggcc cccaccggca tggtaaagct gttcgagatc     660
gacaagcaat tgccgagat gctgcgtgat ccgcagaact tcggcctgag cgacgtcgag     720 aaccctgct acgacggcgg ctatgtgtgg aagccgtttg ccaccgcag cgtcagcacc     780 gaccgccagc tctccgcctt cagtccgcag gaacgcctcg ccatcgccgg caaccgctg     840 ctggcacagg ccgttgccag tcctatggcc cgccgcagcg ccagcccct caactgtgag     900 ggcaagatgt tctgggatca ggtacacccg accactgtcg tgcacgcagc cctgagcgag     960
cgcgccgcca ccttcatcga gacccagtac gagttcctcg cccacggatg a           1011

<210> SEQ ID NO 36
<211> LENGTH: 347
<212> TYPE: PRT
<213> ORGANISM: Aeromonas hydrophila

<400> SEQUENCE: 36

Met Phe Lys Phe Lys Lys Asn Phe Leu Val Gly Leu Ser Ala Ala Leu
            1               5                   10                  15
```

-continued

Met Ser Ile Ser Leu Phe Ser Ala Thr Ala Ser Ala Ala Ser Ala Asp
            20                  25                  30

Ser Arg Pro Ala Phe Ser Arg Ile Val Met Phe Gly Asp Ser Leu Ser
        35                  40                  45

Asp Thr Gly Lys Met Tyr Ser Lys Met Arg Gly Tyr Leu Pro Ser Ser
    50                  55                  60

Pro Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
            85                  90                  95

Gly Gly Ala Thr Ala Val Ala Tyr Asn Lys Ile Ser Trp Asn Pro Lys
        100                 105                 110

Tyr Gln Val Ile Asn Asn Leu Asp Tyr Glu Val Thr Gln Phe Leu Gln
    115                 120                 125

Lys Asp Ser Phe Lys Pro Asp Asp Leu Val Ile Leu Trp Val Gly Ala
130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
            165                 170                 175

Ala Lys Gln Ile Leu Leu Phe Asn Leu Pro Asp Leu Gly Gln Asn Pro
        180                 185                 190

Ser Ala Arg Ser Gln Lys Val Val Glu Ala Val Ser His Val Ser Ala
    195                 200                 205

Tyr His Asn Gln Leu Leu Leu Asn Leu Ala Arg Gln Leu Ala Pro Thr
210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
            245                 250                 255

Asp Gly Gly Tyr Val Trp Lys Pro Phe Ala Thr Arg Ser Val Ser Thr
        260                 265                 270

Asp Arg Gln Leu Ser Ala Phe Ser Pro Gln Glu Arg Leu Ala Ile Ala
    275                 280                 285

Gly Asn Pro Leu Leu Ala Gln Ala Val Ala Ser Pro Met Ala Arg Arg
290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
            325                 330                 335

Phe Ile Ala Asn Gln Tyr Glu Phe Leu Ala His
        340                 345

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtgatggtgg gcgaggaact cgtactg                                      27

<210> SEQ ID NO 38
<211> LENGTH: 35
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 38
agcatatgaa aaatggtttt gtttgtttat tgggg                               35

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttggatccga attcatcaat ggtgatggtg atggtgggc                           39

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
taatacgact cactatag                                                  18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctagttattg ctcagcgg                                                  18

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtcatatgaa aaatggtttt gtgtgtttat tgggattggt c                        41

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atggtgatgg tgggcgagga actcgtactg                                     30

<210> SEQ ID NO 44
<211> LENGTH: 41
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 44
gtcatatgaa aaatggttt gtgtgttat tgggattggt c                        41

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttggatccga attcatcaat ggtgatggtg atggtgggc                         39

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atgccatggc cgacagccgt cccgcc                                       26

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttggatccga attcatcaat ggtgatg                                      27

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttgctagcgc cgacagccgt cccgcc                                       26

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttggatccga attcatcaat ggtgatg                                      27

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 50
ttgccatggc cgacactcgc cccgcc                                          26

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttggatccga attcatcaat ggtgatg                                         27

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttgctagcgc cgacactcgc cccgcc                                          26

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttggatccga attcatcaat ggtgatg                                         27

<210> SEQ ID NO 54
<211> LENGTH: 1047
<212> TYPE: DNA
<213> ORGANISM: Aeromonas hydrophila

<400> SEQUENCE: 54
atgtttaagt ttaaaagaa tttcttagtt ggattatcgg cagctttaat gagtattagc      60
ttgttttcgg caaccgcctc tgcagctagc gccgacagcc gtcccgcctt ttcccggatc     120
gtgatgttcg gcgacagcct ctccgatacc ggcaaaatgt acagcaagat gcgcggttac     180
ctcccctcca gcccgcccta tatgagggc cgtttctcca acggacccgt ctggctggag      240
cagctgacca aacagttccc gggtctgacc atcgccaacg aagcggaagg cggtgccact     300
gccgtggctt acaacaagat ctcctggaat cccaagtatc aggtcatcaa caacctggac     360
tacgaggtca cccagttctt gcagaaagac agcttcaagc cggacgatct ggtgatcctc     420
tgggtcggtg ccaatgacta tctggcctat ggctggaaca cggagcagga tgccaagcgg     480
gttcgcgatg ccatcagcga tgcggccaac cgcatggtac tgaacggtgc caagcagata     540
ctgctgttca acctgccgga tctgggccag aacccgtcag ctcgcagtca aaggtggtc      600 gaggcggtca gccatgtctc cgcctatcac aaccagctgc tgctgaacct ggcacgccag     660
ctggccccca ccggcatggt aaagctgttc gagatcgaca agcaatttgc cgagatgctg     720
cgtgatccgc agaacttcgg cctgagcgac gtcgagaacc cctgctacga cggcggctat     780
gtgtggaagc cgtttgccac ccgcagcgtc agcaccgacc gccagctctc cgccttcagt     840
```

```
ccgcaggaac gcctcgccat cgccggcaac ccgctgctgg cacaggccgt tgccagtcct    900
atggcccgcc gcagcgccag ccccctcaac tgtgagggca agatgttctg ggatcaggta    960
cacccgacca ctgtcgtgca cgcagccctg agcgagcgcg ccgccacctt catcgcgaac   1020
cagtacgagt tcctcgccca ctgatga                                       1047
```

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 55

His His His His His His
  1               5

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
agcatatgaa aaatggttt gtttgtttat tgggg                                 35
```

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
taatacgact cactatag                                                   18
```

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
ctagttattg ctcagcgg                                                   18
```

<210> SEQ ID NO 59
<211> LENGTH: 102
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
cccccgctcga ggcttttctt ttggaagaaa atatagggaa aatggtactt gttaaaaatt    60
cggaatattt atacaatatc atatgtttca cattgaaagg gg                       102
```

<210> SEQ ID NO 60
<211> LENGTH: 35
<212> TYPE: DNA

<213> ORGANISM: Artificial Sequence
<220> FEATURE:
<223> OTHER INFORMATION: Description of Artificial Sequence: Synthetic primer

<400> SEQUENCE: 60
tggaatctcg aggttttatc ctttaccttg tctcc    35

<210> SEQ ID NO 61
<211> LENGTH: 295
<212> TYPE: PRT
<213> ORGANISM: Aeromonas hydrophila

<400> SEQUENCE: 61

```
Ile Val Met Phe Gly Asp Ser Leu Ser Asp Thr Gly Lys Met Tyr Ser
  1               5                  10                  15

Lys Met Arg Gly Tyr Leu Pro Ser Ser Pro Tyr Tyr Glu Gly Arg
             20                  25                  30

Phe Ser Asn Gly Pro Val Trp Leu Glu Gln Leu Thr Asn Glu Phe Pro
         35                  40                  45

Gly Leu Thr Ile Ala Asn Glu Ala Glu Gly Gly Pro Thr Ala Val Ala
     50                  55                  60

Tyr Asn Lys Ile Ser Trp Asn Pro Lys Tyr Gln Val Ile Asn Asn Leu
 65                  70                  75                  80

Asp Tyr Glu Val Thr Gln Phe Leu Gln Lys Asp Ser Phe Lys Pro Asp
                 85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
    290                 295
```

<210> SEQ ID NO 62
<211> LENGTH: 318
<212> TYPE: PRT
<213> ORGANISM: Aeromonas salmonicida

```
<400> SEQUENCE: 62

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His Gly
305                 310                 315

<210> SEQ ID NO 63
<211> LENGTH: 465
<212> TYPE: PRT
<213> ORGANISM: Candida parapsilosis

<400> SEQUENCE: 63

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
```

```
              50                  55                  60
Asn Ala Trp Gln Leu Leu Val Arg Ser Glu Asp Thr Phe Gly Asn Pro
 65                  70                  75                  80

Asn Ala Ile Val Thr Thr Ile Ile Gln Pro Phe Asn Ala Lys Lys Asp
                 85                  90                  95

Lys Leu Val Ser Tyr Gln Thr Phe Glu Asp Ser Gly Lys Leu Asp Cys
                100                 105                 110

Ala Pro Ser Tyr Ala Ile Gln Tyr Gly Ser Asp Ile Ser Thr Leu Thr
                115                 120                 125

Thr Gln Gly Glu Met Tyr Tyr Ile Ser Ala Leu Leu Asp Gln Gly Tyr
                130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
                180                 185                 190

Trp Gly Tyr Ser Gly Gly Ser Leu Ala Ser Gly Trp Ala Ala Ala Ile
                195                 200                 205

Gln Lys Glu Tyr Ala Pro Glu Leu Ser Lys Asn Leu Leu Gly Ala Ala
                210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
                260                 265                 270

Leu Leu Ser Ile Thr Tyr Arg Leu Gly Asn Thr His Cys Leu Leu Asp
                275                 280                 285

Gly Gly Ile Ala Tyr Phe Gly Lys Ser Phe Ser Arg Ile Ile Arg
                290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
                340                 345                 350

Ile Val Asn Ser Arg Lys Thr Phe Gln Gln Trp Cys Asp Trp Gly Leu
                355                 360                 365

Lys Ser Gly Glu Tyr Asn Glu Asp Leu Thr Asn Gly His Ile Thr Glu
                370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
                420                 425                 430

Ala Ala Leu His Ala Ile Leu Gly Phe Asp Leu Gly Pro Asp Val Lys
                435                 440                 445

Arg Asp Lys Val Thr Leu Gly Gly Leu Leu Lys Leu Glu Arg Phe Ala
450                 455                 460

Phe
465
```

-continued

<210> SEQ ID NO 64
<211> LENGTH: 471
<212> TYPE: PRT
<213> ORGANISM: Candida parapsilosis

<400> SEQUENCE: 64

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
    50                  55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Leu Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

```
Ser Ile Val Gly Ala Pro Ala Leu Thr Trp Ile Ile Asn Arg Phe
385                 390                 395                 400

Asn Gly Gln Pro Pro Val Asp Gly Cys Gln His Asn Val Arg Ala Ser
            405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
            435                 440                 445

Arg Asp Lys Val Thr Leu Gly Gly Leu Leu Lys Leu Glu Arg Phe Ala
450                 455                 460

Phe His His His His His His
465                 470
```

<210> SEQ ID NO 65
<211> LENGTH: 261
<212> TYPE: PRT
<213> ORGANISM: Streptomyces coelicolor

<400> SEQUENCE: 65

```
Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Leu Pro Pro Arg
        195                 200                 205

Gly Thr Leu Asp Val Arg Arg Asp Asp Val His Trp Ala Arg Glu Tyr
    210                 215                 220

Leu Val Pro Trp Ile Gly Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260
```

<210> SEQ ID NO 66
<211> LENGTH: 548

```
<212> TYPE: PRT
<213> ORGANISM: Thermobifida fusca

<400> SEQUENCE: 66
```

| | | | | | | | | | | | | | | |
|---|---|---|---|---|---|---|---|---|---|---|---|---|---|---|
| Met | Leu | Pro | His | Pro | Ala | Gly | Glu | Arg | Gly | Glu | Val | Gly | Ala | Phe | Phe |
| 1 | | | | 5 | | | | | 10 | | | | | 15 | |
| Ala | Leu | Leu | Val | Gly | Thr | Pro | Gln | Asp | Arg | Arg | Leu | Arg | Leu | Glu | Cys |
| | | | 20 | | | | | 25 | | | | | 30 | | |
| His | Glu | Thr | Arg | Pro | Leu | Arg | Gly | Arg | Cys | Gly | Cys | Gly | Glu | Arg | Arg |
| | | 35 | | | | | 40 | | | | | 45 | | | |
| Val | Pro | Pro | Leu | Thr | Leu | Pro | Gly | Asp | Gly | Val | Leu | Cys | Thr | Thr | Ser |
| | 50 | | | | | 55 | | | | | 60 | | | | |
| Ser | Thr | Arg | Asp | Ala | Glu | Thr | Val | Trp | Arg | Lys | His | Leu | Gln | Pro | Arg |
| 65 | | | | | 70 | | | | | 75 | | | | | 80 |
| Pro | Asp | Gly | Gly | Phe | Arg | Pro | His | Leu | Gly | Val | Gly | Cys | Leu | Leu | Ala |
| | | | | 85 | | | | | 90 | | | | | 95 | |
| Gly | Gln | Gly | Ser | Pro | Gly | Val | Leu | Trp | Cys | Gly | Arg | Glu | Gly | Cys | Arg |
| | | | | 100 | | | | | 105 | | | | | 110 | |
| Phe | Glu | Val | Cys | Arg | Arg | Asp | Thr | Pro | Gly | Leu | Ser | Arg | Thr | Arg | Asn |
| | | | 115 | | | | | 120 | | | | | 125 | | |
| Gly | Asp | Ser | Ser | Pro | Pro | Phe | Arg | Ala | Gly | Trp | Ser | Leu | Pro | Pro | Lys |
| | 130 | | | | | 135 | | | | | 140 | | | | |
| Cys | Gly | Glu | Ile | Ser | Gln | Ser | Ala | Arg | Lys | Thr | Pro | Ala | Val | Pro | Arg |
| 145 | | | | | 150 | | | | | 155 | | | | | 160 |
| Tyr | Ser | Leu | Leu | Arg | Thr | Asp | Arg | Pro | Asp | Gly | Pro | Arg | Gly | Arg | Phe |
| | | | | 165 | | | | | 170 | | | | | 175 | |
| Val | Gly | Ser | Gly | Pro | Arg | Ala | Ala | Thr | Arg | Arg | Arg | Leu | Phe | Leu | Gly |
| | | | | 180 | | | | | 185 | | | | | 190 | |
| Ile | Pro | Ala | Leu | Val | Leu | Val | Thr | Ala | Leu | Thr | Leu | Val | Leu | Ala | Val |
| | | | 195 | | | | | 200 | | | | | 205 | | |
| Pro | Thr | Gly | Arg | Glu | Thr | Leu | Trp | Arg | Met | Trp | Cys | Glu | Ala | Thr | Gln |
| | 210 | | | | | 215 | | | | | 220 | | | | |
| Asp | Trp | Cys | Leu | Gly | Val | Pro | Val | Asp | Ser | Arg | Gly | Gln | Pro | Ala | Glu |
| 225 | | | | | 230 | | | | | 235 | | | | | 240 |
| Asp | Gly | Glu | Phe | Leu | Leu | Leu | Ser | Pro | Val | Gln | Ala | Ala | Thr | Trp | Gly |
| | | | | 245 | | | | | 250 | | | | | 255 | |
| Asn | Tyr | Tyr | Ala | Leu | Gly | Asp | Ser | Tyr | Ser | Ser | Gly | Asp | Gly | Ala | Arg |
| | | | | 260 | | | | | 265 | | | | | 270 | |
| Asp | Tyr | Tyr | Pro | Gly | Thr | Ala | Val | Lys | Gly | Gly | Cys | Trp | Arg | Ser | Ala |
| | | | 275 | | | | | 280 | | | | | 285 | | |
| Asn | Ala | Tyr | Pro | Glu | Leu | Val | Ala | Glu | Ala | Tyr | Asp | Phe | Ala | Gly | His |
| | 290 | | | | | 295 | | | | | 300 | | | | |
| Leu | Ser | Phe | Leu | Ala | Cys | Ser | Gly | Gln | Arg | Gly | Tyr | Ala | Met | Leu | Asp |
| 305 | | | | | 310 | | | | | 315 | | | | | 320 |
| Ala | Ile | Asp | Glu | Val | Gly | Ser | Gln | Leu | Asp | Trp | Asn | Ser | Pro | His | Thr |
| | | | | 325 | | | | | 330 | | | | | 335 | |
| Ser | Leu | Val | Thr | Ile | Gly | Ile | Gly | Gly | Asn | Asp | Leu | Gly | Phe | Ser | Thr |
| | | | 340 | | | | | 345 | | | | | 350 | | |
| Val | Leu | Lys | Thr | Cys | Met | Val | Arg | Val | Pro | Leu | Leu | Asp | Ser | Lys | Ala |
| | | 355 | | | | | 360 | | | | | 365 | | | |
| Cys | Thr | Asp | Gln | Glu | Asp | Ala | Ile | Arg | Lys | Arg | Met | Ala | Lys | Phe | Glu |
| | 370 | | | | | 375 | | | | | 380 | | | | |
| Thr | Thr | Phe | Glu | Glu | Leu | Ile | Ser | Glu | Val | Arg | Thr | Arg | Ala | Pro | Asp |
| 385 | | | | | 390 | | | | | 395 | | | | | 400 |

```
Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
            420                 425                 430

Glu Thr Ile Gln Glu Phe Asn Gln Gln Leu Ala Glu Ala Val Ala Val
        435                 440                 445

His Asp Glu Glu Ile Ala Ala Ser Gly Gly Val Gly Ser Val Glu Phe
    450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
        515                 520                 525

Tyr Ala Thr Phe Ala Val Val Ala Gly Ala Thr Val Asp Thr Leu Ala
    530                 535                 540

Gly Glu Val Gly
545

<210> SEQ ID NO 67
<211> LENGTH: 372
<212> TYPE: PRT
<213> ORGANISM: Thermobifida fusca

<400> SEQUENCE: 67

Met Gly Ser Gly Pro Arg Ala Ala Thr Arg Arg Leu Phe Leu Gly
  1               5                  10                  15

Ile Pro Ala Leu Val Leu Val Thr Ala Leu Thr Leu Val Leu Ala Val
                 20                  25                  30

Pro Thr Gly Arg Glu Thr Leu Trp Arg Met Trp Cys Glu Ala Thr Gln
             35                  40                  45

Asp Trp Cys Leu Gly Val Pro Val Asp Ser Arg Gly Gln Pro Ala Glu
         50                  55                  60

Asp Gly Glu Phe Leu Leu Leu Ser Pro Val Gln Ala Ala Thr Trp Gly
 65                  70                  75                  80

Asn Tyr Tyr Ala Leu Gly Asp Ser Tyr Ser Ser Gly Asp Gly Ala Arg
                 85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220
```

```
Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
            245                 250                 255

Glu Thr Ile Gln Glu Phe Asn Gln Gln Leu Ala Glu Ala Val Ala Val
                260                 265                 270

His Asp Glu Glu Ile Ala Ala Ser Gly Gly Val Gly Ser Val Glu Phe
            275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
            325                 330                 335

Gly Glu Arg Val Ile Glu Gln Ile Gly Thr Gly Pro Gly Arg Pro Leu
                340                 345                 350

Tyr Ala Thr Phe Ala Val Val Ala Gly Ala Thr Val Asp Thr Leu Ala
            355                 360                 365

Gly Glu Val Gly
370

<210> SEQ ID NO 68
<211> LENGTH: 300
<212> TYPE: PRT
<213> ORGANISM: Corynebacterium efficiens

<400> SEQUENCE: 68

Met Arg Thr Thr Val Ile Ala Ala Ser Ala Leu Leu Leu Ala Gly
1               5                   10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile
            35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
                100                 105                 110

Thr Leu Pro Ala Gln Val Asp Ala Leu Thr Glu Asp Thr Thr Leu Val
            115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220
```

```
Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
            245                 250                 255

Pro Pro Gln Gln Arg Trp Ala Asp Ile Gln Gly Gln Thr Asp Ala
                260                 265                 270

Tyr Pro Leu His Pro Thr Ser Ala Gly His Glu Ala Met Ala Ala Ala
            275                 280                 285

Val Arg Asp Ala Leu Gly Leu Glu Pro Val Gln Pro
290                 295                 300
```

<210> SEQ ID NO 69
<211> LENGTH: 284
<212> TYPE: PRT
<213> ORGANISM: Novosphingobium aromaticivorans

<400> SEQUENCE: 69

```
Met Gly Gln Val Lys Leu Phe Ala Arg Arg Cys Ala Pro Val Leu Leu
1               5                   10                  15

Ala Leu Ala Gly Leu Ala Pro Ala Ala Thr Val Ala Arg Glu Ala Pro
            20                  25                  30

Leu Ala Glu Gly Ala Arg Tyr Val Ala Leu Gly Ser Ser Phe Ala Ala
        35                  40                  45

Gly Pro Gly Val Gly Pro Asn Ala Pro Gly Ser Pro Glu Arg Cys Gly
    50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His His Val Leu
                85                  90                  95

Gly Pro Trp Asn Glu Val Pro Pro Gln Ile Asp Ser Val Asn Gly Asp
            100                 105                 110

Thr Arg Leu Val Thr Leu Thr Ile Gly Gly Asn Asp Val Ser Phe Val
        115                 120                 125

Gly Asn Ile Phe Ala Ala Ala Cys Glu Lys Met Ala Ser Pro Asp Pro
    130                 135                 140

Arg Cys Gly Lys Trp Arg Glu Ile Thr Glu Glu Trp Gln Ala Asp
145                 150                 155                 160

Glu Glu Arg Met Arg Ser Ile Val Arg Gln Ile His Ala Arg Ala Pro
                165                 170                 175

Leu Ala Arg Val Val Val Val Asp Tyr Ile Thr Val Leu Pro Pro Ser
            180                 185                 190

Gly Thr Cys Ala Ala Met Ala Ile Ser Pro Asp Arg Leu Ala Gln Ser
        195                 200                 205

Arg Ser Ala Ala Lys Arg Leu Ala Arg Ile Thr Ala Arg Val Ala Arg
    210                 215                 220

Glu Glu Gly Ala Ser Leu Leu Lys Phe Ser His Ile Ser Arg Arg His
225                 230                 235                 240

His Pro Cys Ser Ala Lys Pro Trp Ser Asn Gly Leu Ser Ala Pro Ala
                245                 250                 255

Asp Asp Gly Ile Pro Val His Pro Asn Arg Leu Gly His Ala Glu Ala
            260                 265                 270

Ala Ala Ala Leu Val Lys Leu Val Lys Leu Met Lys
        275                 280
```

<210> SEQ ID NO 70
<211> LENGTH: 268

```
<212> TYPE: PRT
<213> ORGANISM: Streptomyces coelicolor

<400> SEQUENCE: 70

Met Arg Arg Phe Arg Leu Val Gly Phe Leu Ser Ser Leu Val Leu Ala
 1               5                  10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Ala Glu Ala
130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205

Gln Arg Ala Ala Ala His Gly Phe Thr Phe Gly Asp Val Arg Thr Thr
210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265

<210> SEQ ID NO 71
<211> LENGTH: 269
<212> TYPE: PRT
<213> ORGANISM: Streptomyces avermitilis

<400> SEQUENCE: 71

Met Arg Arg Ser Arg Ile Thr Ala Tyr Val Thr Ser Leu Leu Leu Ala
 1               5                  10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
```

```
                            85                  90                  95
Asn Gln Leu Gly Thr Leu Asn Ser Ser Thr Gly Leu Val Ser Leu Thr
                100                 105                 110
Ile Gly Gly Asn Asp Ala Gly Phe Ser Asp Val Met Thr Thr Cys Val
            115                 120                 125
Leu Gln Ser Asp Ser Ala Cys Leu Ser Arg Ile Asn Thr Ala Lys Ala
        130                 135                 140
Tyr Val Asp Ser Thr Leu Pro Gly Gln Leu Asp Ser Val Tyr Thr Ala
145                 150                 155                 160
Ile Ser Thr Lys Ala Pro Ser Ala His Val Ala Val Leu Gly Tyr Pro
                165                 170                 175
Arg Phe Tyr Lys Leu Gly Gly Ser Cys Leu Ala Gly Leu Ser Glu Thr
            180                 185                 190
Lys Arg Ser Ala Ile Asn Asp Ala Ala Asp Tyr Leu Asn Ser Ala Ile
        195                 200                 205
Ala Lys Arg Ala Ala Asp His Gly Phe Thr Phe Gly Asp Val Lys Ser
    210                 215                 220
Thr Phe Thr Gly His Glu Ile Cys Ser Ser Thr Trp Leu His Ser
225                 230                 235                 240
Leu Asp Leu Leu Asn Ile Gly Gln Ser Tyr His Pro Thr Ala Ala Gly
                245                 250                 255
Gln Ser Gly Gly Tyr Leu Pro Val Met Asn Ser Val Ala
            260                 265

<210> SEQ ID NO 72
<211> LENGTH: 267
<212> TYPE: PRT
<213> ORGANISM: Streptomyces sp.

<400> SEQUENCE: 72

Met Arg Leu Thr Arg Ser Leu Ser Ala Ala Ser Val Ile Val Phe Ala
1               5                   10                  15
Leu Leu Leu Ala Leu Leu Gly Ile Ser Pro Ala Gln Ala Ala Gly Pro
                20                  25                  30
Ala Tyr Val Ala Leu Gly Asp Ser Tyr Ser Ser Gly Asn Gly Ala Gly
            35                  40                  45
Ser Tyr Ile Asp Ser Ser Gly Asp Cys His Arg Ser Asn Asn Ala Tyr
        50                  55                  60
Pro Ala Arg Trp Ala Ala Ala Asn Ala Pro Ser Ser Phe Thr Phe Ala
65                  70                  75                  80
Ala Cys Ser Gly Ala Val Thr Thr Asp Val Ile Asn Asn Gln Leu Gly
                85                  90                  95
Ala Leu Asn Ala Ser Thr Gly Leu Val Ser Ile Thr Ile Gly Gly Asn
                100                 105                 110
Asp Ala Gly Phe Ala Asp Ala Met Thr Thr Cys Val Thr Ser Ser Asp
            115                 120                 125
Ser Thr Cys Leu Asn Arg Leu Ala Thr Ala Thr Asn Tyr Ile Asn Thr
        130                 135                 140
Thr Leu Leu Ala Arg Leu Asp Ala Val Tyr Ser Gln Ile Lys Ala Arg
145                 150                 155                 160
Ala Pro Asn Ala Arg Val Val Val Leu Gly Tyr Pro Arg Met Tyr Leu
                165                 170                 175
Ala Ser Asn Pro Trp Tyr Cys Leu Gly Leu Ser Asn Thr Lys Arg Ala
            180                 185                 190
Ala Ile Asn Thr Thr Ala Asp Thr Leu Asn Ser Val Ile Ser Ser Arg
```

```
              195                 200                 205
Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 73
<211> LENGTH: 317
<212> TYPE: PRT
<213> ORGANISM: Aeromonas hydrophila

<400> SEQUENCE: 73

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
                20                  25                  30

Ser Ser Pro Pro Tyr Tyr Glu Gly Arg Phe Ser Asn Gly Pro Val Trp
            35                  40                  45

Leu Glu Gln Leu Thr Asn Glu Phe Pro Gly Leu Thr Ile Ala Asn Glu
    50                  55                  60

Ala Glu Gly Gly Pro Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
    115                 120                 125

Lys Arg Val Arg Asp Ala Ile Ser Asp Ala Ala Asn Arg Met Val Leu
130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Asn Leu Ala Arg Gln Leu Ala
            180                 185                 190

Pro Thr Gly Met Val Lys Leu Phe Glu Ile Asp Lys Gln Phe Ala Glu
    195                 200                 205

Met Leu Arg Asp Pro Gln Asn Phe Gly Leu Ser Asp Gln Arg Asn Ala
    210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270

Ala Arg Ser Ala Ser Thr Leu Asn Cys Glu Gly Lys Met Phe Trp Asp
    275                 280                 285

Gln Val His Pro Thr Thr Val Val His Ala Ala Leu Ser Glu Pro Ala
290                 295                 300

Ala Thr Phe Ile Glu Ser Gln Tyr Glu Phe Leu Ala His
```

<210> SEQ ID NO 74
<211> LENGTH: 318
<212> TYPE: PRT
<213> ORGANISM: Aeromonas salmonicida

<400> SEQUENCE: 74

| Ala | Asp | Thr | Arg | Pro | Ala | Phe | Ser | Arg | Ile | Val | Met | Phe | Gly | Asp | Ser |
|---|---|---|---|---|---|---|---|---|---|---|---|---|---|---|---|
| 1 | | | | 5 | | | | | 10 | | | | | 15 | |

| Leu | Ser | Asp | Thr | Gly | Lys | Met | Tyr | Ser | Lys | Met | Arg | Gly | Tyr | Leu | Pro |
| | | | 20 | | | | | 25 | | | | | 30 | | |

| Ser | Ser | Pro | Pro | Tyr | Tyr | Glu | Gly | Arg | Phe | Ser | Asn | Gly | Pro | Val | Trp |
| | | 35 | | | | | 40 | | | | | 45 | | | |

| Leu | Glu | Gln | Leu | Thr | Lys | Gln | Phe | Pro | Gly | Leu | Thr | Ile | Ala | Asn | Glu |
| | 50 | | | | | 55 | | | | | 60 | | | | |

| Ala | Glu | Gly | Gly | Ala | Thr | Ala | Val | Ala | Tyr | Asn | Lys | Ile | Ser | Trp | Asn |
| 65 | | | | | 70 | | | | | 75 | | | | | 80 |

| Pro | Lys | Tyr | Gln | Val | Ile | Asn | Asn | Leu | Asp | Tyr | Glu | Val | Thr | Gln | Phe |
| | | | | 85 | | | | | 90 | | | | | 95 | |

| Leu | Gln | Lys | Asp | Ser | Phe | Lys | Pro | Asp | Asp | Leu | Val | Ile | Leu | Trp | Val |
| | | | 100 | | | | | 105 | | | | | 110 | | |

| Gly | Ala | Asn | Asp | Tyr | Leu | Ala | Tyr | Gly | Trp | Asn | Thr | Glu | Gln | Asp | Ala |
| | | | | 115 | | | | | 120 | | | | | 125 | |

| Lys | Arg | Val | Arg | Asp | Ala | Ile | Ser | Asp | Ala | Ala | Asn | Arg | Met | Val | Leu |
| | 130 | | | | | 135 | | | | | 140 | | | | |

| Asn | Gly | Ala | Lys | Gln | Ile | Leu | Leu | Phe | Asn | Leu | Pro | Asp | Leu | Gly | Gln |
| 145 | | | | | 150 | | | | | 155 | | | | | 160 |

| Asn | Pro | Ser | Ala | Arg | Ser | Gln | Lys | Val | Val | Glu | Ala | Val | Ser | His | Val |
| | | | | 165 | | | | | 170 | | | | | 175 | |

| Ser | Ala | Tyr | His | Asn | Lys | Leu | Leu | Leu | Asn | Leu | Ala | Arg | Gln | Leu | Ala |
| | | | 180 | | | | | 185 | | | | | 190 | | |

| Pro | Thr | Gly | Met | Val | Lys | Leu | Phe | Glu | Ile | Asp | Lys | Gln | Phe | Ala | Glu |
| | | | | 195 | | | | | 200 | | | | | 205 | |

| Met | Leu | Arg | Asp | Pro | Gln | Asn | Phe | Gly | Leu | Ser | Asp | Val | Glu | Asn | Pro |
| | 210 | | | | | 215 | | | | | 220 | | | | |

| Cys | Tyr | Asp | Gly | Gly | Tyr | Val | Trp | Lys | Pro | Phe | Ala | Thr | Arg | Ser | Val |
| 225 | | | | | 230 | | | | | 235 | | | | | 240 |

| Ser | Thr | Asp | Arg | Gln | Leu | Ser | Ala | Phe | Ser | Pro | Gln | Glu | Arg | Leu | Ala |
| | | | | 245 | | | | | 250 | | | | | 255 | |

| Ile | Ala | Gly | Asn | Pro | Leu | Leu | Ala | Gln | Ala | Val | Ala | Ser | Pro | Met | Ala |
| | | | 260 | | | | | 265 | | | | | 270 | | |

| Arg | Arg | Ser | Ala | Ser | Pro | Leu | Asn | Cys | Glu | Gly | Lys | Met | Phe | Trp | Asp |
| | | | | 275 | | | | | 280 | | | | | 285 | |

| Gln | Val | His | Pro | Thr | Thr | Val | Val | His | Ala | Ala | Leu | Ser | Glu | Arg | Ala |
| | 290 | | | | | 295 | | | | | 300 | | | | |

| Ala | Thr | Phe | Ile | Glu | Thr | Gln | Tyr | Glu | Phe | Leu | Ala | His | Gly |
| 305 | | | | | 310 | | | | | 315 | | | |

<210> SEQ ID NO 75
<211> LENGTH: 1371
<212> TYPE: DNA
<213> ORGANISM: Streptomyces thermosacchari

<400> SEQUENCE: 75

```
acaggccgat gcacggaacc gtacctttcc gcagtgaagc gctctccccc catcgttcgc      60
```

-continued

```
cgggacttca tccgcgattt tggcatgaac acttccttca acgcgcgtag cttgctacaa    120
gtgcggcagc agacccgctc gttggaggct cagtgagatt gacccgatcc ctgtcggccg    180
catccgtcat cgtcttcgcc ctgctgctcg cgctgctggg catcagcccg gcccaggcag    240
ccggcccggc ctatgtggcc ctgggggatt cctattcctc gggcaacggc gccggaagtt    300
acatcgattc gagcggtgac tgtcaccgca gcaacaacgc gtaccccgcc cgctgggcgg    360
cggccaacgc accgtcctcc ttcaccttcg cggcctgctc gggagcggtg accacggatg    420
tgatcaacaa tcagctgggc gccctcaacg cgtccaccgg cctggtgagc atcaccatcg    480
gcggcaatga cgcgggcttc gcggacgcga tgacccctg cgtcaccagc tcggacagca    540
cctgcctcaa ccggctggcc accgccacca actacatcaa caccaccctg ctcgcccggc    600
tcgacgcggt ctacagccag atcaaggccc gtgcccccaa cgcccgcgtg gtcgtcctcg    660
gctacccgcg catgtacctg cctcgaacc cctggtactg cctgggcctg agcaacacca    720
agcgcgcggc catcaacacc accgccgaca ccctcaactc ggtgatctcc tcccgggcca    780
ccgcccacgg attccgattc ggcgatgtcc gcccgacctt caacaaccac gaactgttct    840
tcggcaacga ctggctgcac tcactcaccc tgccggtgtg ggagtcgtac cacccccacca   900 gcacgggcca tcagagcggc tatctgccgg tcctcaacgc caacagctcg acctgatcaa    960
cgcacggccg tgcccgcccc gcgcgtcacg ctcggcgcgg gcgccgcagc gcgttgatca   1020
gcccacagtg ccggtgacgg tcccaccgtc acggtcgagg gtgtacgtca cggtggcgcc   1080
gctccagaag tggaacgtca gcaggaccgt ggagccgtcc ctgacctcgt cgaagaactc   1140
cggggtcagc gtgatcaccc ctcccccgta gccggggcg aaggcggcgc cgaactcctt   1200
gtaggacgtc cagtcgtgcg gcccggcgtt gccaccgtcc gcgtagaccg cttccatggt   1260
cgccagccgg tccccgcgga actcggtggg gatgtccgtg cccaaggtgg tcccggtggt   1320
gtccgagagc accgggggct cgtaccggat gatgtgcaga tccaaagaat t            1371
```

<210> SEQ ID NO 76
<211> LENGTH: 267
<212> TYPE: PRT
<213> ORGANISM: Streptomyces thermosacchari

<400> SEQUENCE: 76

Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg

-continued

```
            145                 150                 155                 160
Ala Pro Asn Ala Arg Val Val Leu Gly Tyr Pro Arg Met Tyr Leu
                165                 170                 175

Ala Ser Asn Pro Trp Tyr Cys Leu Gly Leu Ser Asn Thr Lys Arg Ala
                180                 185                 190

Ala Ile Asn Thr Thr Ala Asp Thr Leu Asn Ser Val Ile Ser Ser Arg
                195                 200                 205

Ala Thr Ala His Gly Phe Arg Phe Gly Asp Val Arg Pro Thr Phe Asn
                210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
                260                 265

<210> SEQ ID NO 77
<211> LENGTH: 548
<212> TYPE: PRT
<213> ORGANISM: Thermobifida fusca

<400> SEQUENCE: 77

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
                20                  25                  30

His Glu Thr Arg Pro Leu Arg Gly Arg Cys Gly Cys Gly Glu Arg Arg
                35                  40                  45

Val Pro Pro Leu Thr Leu Pro Gly Asp Gly Val Leu Cys Thr Thr Ser
                50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
                100                 105                 110

Phe Glu Val Cys Arg Arg Asp Thr Pro Gly Leu Ser Thr Arg Asn
                115                 120                 125

Gly Asp Ser Ser Pro Pro Phe Arg Ala Gly Trp Ser Leu Pro Pro Lys
130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Arg Leu Phe Leu Gly
                180                 185                 190

Ile Pro Ala Leu Val Leu Val Thr Ala Leu Thr Leu Val Leu Ala Val
                195                 200                 205

Pro Thr Gly Arg Glu Thr Leu Trp Arg Met Trp Cys Glu Ala Thr Gln
                210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
```

```
                260             265              270
Asp Tyr Tyr Pro Gly Thr Ala Val Lys Gly Gly Cys Trp Arg Ser Ala
        275                 280                 285
Asn Ala Tyr Pro Glu Leu Val Ala Glu Ala Tyr Asp Phe Ala Gly His
        290                 295                 300
Leu Ser Phe Leu Ala Cys Ser Gly Gln Arg Gly Tyr Ala Met Leu Asp
305                 310                 315                 320
Ala Ile Asp Glu Val Gly Ser Gln Leu Asp Trp Asn Ser Pro His Thr
                325                 330                 335
Ser Leu Val Thr Ile Gly Ile Gly Gly Asn Asp Leu Gly Phe Ser Thr
                340                 345                 350
Val Leu Lys Thr Cys Met Val Arg Val Pro Leu Leu Asp Ser Lys Ala
            355                 360                 365
Cys Thr Asp Gln Glu Asp Ala Ile Arg Lys Arg Met Ala Lys Phe Glu
            370                 375                 380
Thr Thr Phe Glu Glu Leu Ile Ser Glu Val Arg Thr Arg Ala Pro Asp
385                 390                 395                 400
Ala Arg Ile Leu Val Val Gly Tyr Pro Arg Ile Phe Pro Glu Glu Pro
                405                 410                 415
Thr Gly Ala Tyr Tyr Thr Leu Thr Ala Ser Asn Gln Arg Trp Leu Asn
                420                 425                 430
Glu Thr Ile Gln Glu Phe Asn Gln Gln Leu Ala Glu Ala Val Ala Val
                435                 440                 445
His Asp Glu Glu Ile Ala Ala Ser Gly Gly Val Gly Ser Val Glu Phe
            450                 455                 460
Val Asp Val Tyr His Ala Leu Asp Gly His Glu Ile Gly Ser Asp Glu
465                 470                 475                 480
Pro Trp Val Asn Gly Val Gln Leu Arg Asp Leu Ala Thr Gly Val Thr
                485                 490                 495
Val Asp Arg Ser Thr Phe His Pro Asn Ala Ala Gly His Arg Ala Val
                500                 505                 510
Gly Glu Arg Val Ile Glu Gln Ile Glu Thr Gly Pro Gly Arg Pro Leu
            515                 520                 525
Tyr Ala Thr Phe Ala Val Val Ala Gly Ala Thr Val Asp Thr Leu Ala
            530                 535                 540
Gly Glu Val Gly
545

<210> SEQ ID NO 78
<211> LENGTH: 3000
<212> TYPE: DNA
<213> ORGANISM: Thermobifida fusca

<400> SEQUENCE: 78
ggtggtgaac cagaacaccc ggtcgtcggc gtgggcgtcc aggtgcaggt gcaggttctt        60
caactgctcc agcaggatgc cgccgtggcc gtgcacgatg ccttgggca ggcctgtggt       120 ccccgacgag tacagcaccc atagcggatg gtcgaacggc agcggggtga actccagttc       180
cgcgccttcg cccgcggctt cgaactccgc ccaggacagg gtgtcggcga cagggccgca       240
gcccaggtac ggcaggacga cggtgtgctg caggctgggc atgccgtcgc gcagggcttt       300
gagcacgtca cggcggtcga agtccttacc gccgtagcgg tagccgtcca ggccagcag       360 cactttcggt tcgatctgcg cgaaccggtc gaggacgctg cgcacccga gtcgggggga       420 acaggacgac caggtcgcac cgatcgcggc gcaggcgagg aatgcggccg tcgcctcggc       480
```

```
gatgttcggc aggtaggcca cgacccggtc gccggggccc accccgaggc tgcggagggc    540
cgcagcgatc gcggcggtgc gggtccgcag ttctccccag gtccactcgg tcaacggccg    600
gagttcggac gcgtgccgga tcgccacggc tgatgggtca cggtcgcgga agatgtgctc    660
ggcgtagttg agggtggcgc cggggaacca gacggcgccg gcatggcgt cggaggcgag     720 cactgtggtg tacggggtgg cggcgcgcac ccggtagtac tcccagatcg cggaccagaa    780
tccttcgagg tcggttaccg accagcgcca cagtgcctcg tagtccggtg cgtccacacc    840
gcggtgctcc cgcacccagc gggtgaacgc ggtgaggttg gcgcgttctt tgcgctcctc    900
gtcgggactc cacaggatcg gcggctgcgg cttgagtgtc atgaaacgcg accccttcgt    960
ggacggtgcg gatgcggtga gcgtcgggtg cctcccctaa cgctccccgg tgacggagtg   1020
ttgtgcacca catctagcac gcgggacgcg gaaaccgtat ggagaaaaca cctacaaccc   1080
cggccggacg gtgggtttcg gccacactta ggggtcgggt gcctgcttgc cgggcagggc   1140
agtcccgggg tgctgtggtg cgggcgggag ggctgtcgct tcgaggtgtg ccggcgggac   1200
actccgggcc tcagccgtac ccgcaacggg gacagttctc ctcccttccg ggctggatgg   1260
tcccttcccc cgaaatgcgg cgagatctcc cagtcagccc ggaaaacacc cgctgtgccc   1320
aggtactctt tgcttcgaac agacaggccg gacggtccac gggggaggtt tgtgggcagc   1380
ggaccacgtg cggcgaccag acgacggttg ttcctcggta tccccgctct tgtacttgtg   1440
acagcgctca cgctggtctt ggctgtcccg acggggcgcg agacgctgtg gcgcatgtgg   1500
tgtgaggcca cccaggactg gtgcctgggg gtgccggtcg actccgcgg acagcctgcg    1560 gaggacggcg agtttctgct gctttctccg gtccaggcag cgacctgggg gaactattac   1620
gcgctcgggg attcgtactc ttcggggggac ggggcccgcg actactatcc cggcaccgcg   1680
gtgaagggcg gttgctggcg gtccgctaac gcctatccgg agctggtcgc cgaagcctac   1740
gacttcgccg gacacttgtc gttcctggcc tgcagcggcc agcgcggcta cgccatgctt   1800
gacgctatcg acgaggtcgg ctcgcagctg gactggaact cccctcacac gtcgctggtg   1860
acgatcggga tcggcggcaa cgatctgggg ttctccacgg ttttgaagac ctgcatggtg   1920
cgggtgccgc tgctggacag caaggcgtgc acggaccagg aggacgctat ccgcaagcgg   1980
atggcgaaat tcgagacgac gtttgaagag ctcatcagcg aagtgcgcac ccgcgcgccg   2040
gacgcccgga tccttgtcgt gggctacccc cggatttttc cggaggaacc gaccggcgcc   2100
tactacacgc tgaccgcgag caaccagcgg tggctcaacg aaaccattca ggagttcaac   2160
cagcagctcg ccgaggctgt cgcggtccac gacgaggaga ttgccgcgtc gggcggggtg   2220
ggcagcgtgg agttcgtgga cgtctaccac gcgttggacg gccacgagat cggctcggac   2280
gagccgtggg tgaacggggt gcagttgcgg gacctcgcca ccggggtgac tgtgaccgc    2340 agtaccttcc accccaacgc cgctgggcac cgggcggtcg gtgagcgggt catcgagcag   2400
atcgaaaccg gcccggggccg tccgctctat gccactttcg cggtggtggc gggggcgacc   2460
gtggacactc tcgcgggcga ggtggggtga cccggcttac cgtccggccc gcaggtctgc   2520
gagcactgcg gcgatctggt ccactgccca gtgcagttcc tcttcggtga tgaccagcgg   2580
cggggagagc cggatcgttg agccgtgcgt gtctttgacg agcacacccc gctgcaggag   2640
ccgttcgcac agttctcttc cggtggccag agtcgggtcg acgtcgatcc cagcccacag   2700
gccgatgctg cgggccgcga ccacgccgtt gccgaccagt tggtcgaggc gggcgcgcag   2760 cacggggggcg agggcgcgga catggtccag gtaaggggccg tcgcggacga ggctcaccac   2820
ggcagtgccg accgcgcagg cgagggcgtt gccgccgaag gtgctgccgt gctggccggg   2880
```

```
gcggatcacg tcgaagactt ccgcgtcgcc taccgccgcc gccacgggca ggatgccgcc   2940
gcccagcgct tgccgaaca  ggtagatatc ggcgtcgact ccgctgtggt cgcaggcccg   3000
```

<210> SEQ ID NO 79
<211> LENGTH: 372
<212> TYPE: PRT
<213> ORGANISM: Thermobifida fusca

<400> SEQUENCE: 79

```
Val Gly Ser Gly Pro Arg Ala Ala Thr Arg Arg Leu Phe Leu Gly
 1               5                  10                  15

Ile Pro Ala Leu Val Leu Val Thr Ala Leu Thr Leu Val Leu Ala Val
             20                  25                  30

Pro Thr Gly Arg Glu Thr Leu Trp Arg Met Trp Cys Glu Ala Thr Gln
         35                  40                  45

Asp Trp Cys Leu Gly Val Pro Val Asp Ser Arg Gly Gln Pro Ala Glu
     50                  55                  60

Asp Gly Glu Phe Leu Leu Ser Pro Val Gln Ala Ala Thr Trp Gly
 65                  70                  75                  80

Asn Tyr Tyr Ala Leu Gly Asp Ser Tyr Ser Ser Gly Asp Gly Ala Arg
                 85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365
```

Gly Glu Val Gly
    370

<210> SEQ ID NO 80
<211> LENGTH: 300
<212> TYPE: PRT
<213> ORGANISM: Corynebacterium efficiens

<400> SEQUENCE: 80

Met Arg Thr Thr Val Ile Ala Ala Ser Ala Leu Leu Leu Ala Gly
 1               5                  10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile
        35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Thr Asp Ala
            260                 265                 270

Tyr Pro Leu His Pro Thr Ser Ala Gly His Glu Ala Met Ala Ala Ala
        275                 280                 285

Val Arg Asp Ala Leu Gly Leu Glu Pro Val Gln Pro
    290                 295                 300

<210> SEQ ID NO 81
<211> LENGTH: 3000
<212> TYPE: DNA
<213> ORGANISM: Corynebacterium efficiens

<400> SEQUENCE: 81
ttctggggtg ttatggggtt gttatcggct cgtcctgggt ggatcccgcc aggtggggta      60
ttcacggggg acttttgtgt ccaacagccg agaatgagtg ccctgagcgg tgggaatgag     120

```
gtgggcgggg ctgtgtcgcc atgagggggc ggcgggctct gtggtgcccc gcgacccccg    180
gccccggtga gcggtgaatg aaatccggct gtaatcagca tcccgtgccc accccgtcgg    240
ggaggtcagc gcccggagtg tctacgcagt cggatcctct cggactcggc catgctgtcg    300
gcagcatcgc gctcccgggt cttggcgtcc ctcggctgtt ctgcctgctg tccctggaag    360
gcgaaatgat caccggggag tgatacaccg gtggtctcat cccggatgcc cacttcggcg    420
ccatccggca attcgggcag ctccgggtgg aagtaggtgg catccgatgc gtcggtgacg    480
ccatagtggg cgaagatctc atcctgctcg agggtgctca ggccactctc cggatcgata    540 tcggggggcgt ccttgatggc gtccttgctg aaaccgaggt gcagcttgtg ggcttccaat    600
ttcgcaccac ggagcgggac gaggctgaa tgacggccga agagcccgtg gtggacctca    660
acgaaggtgg gtagtcccgt gtcatcattg aggaacacgc cctccaccgc acccagcttg    720
tggccggagt gtcgtaggc gctggcatcc agaagggaaa cgatctcata tttgtcggtg    780
tgctcagaca tgatcttcct ttgctgtcgg tgtctggtac taccacggta gggctgaatg    840
caactgttat ttttctgtta ttttaggaat tggtccatat cccacaggct ggctgtggtc    900
aaatcgtcat caagtaatcc ctgtcacaca aatgggtgg tgggagccct ggtcgcggtt    960
ccgtgggagg cgccgtgccc cgcaggatcg tcggcatcgg cggatctggc cggtaccccg   1020
cggtgaataa aatcattctg taaccttcat cacggttggt tttaggtatc cgccccttc    1080 gtcctgaccc cgtccccggc gcgcgggagc ccgcgggttg cggtagacag gggagacgtg   1140
gacaccatga ggacaacggt catcgcagca agcgcattac tccttctcgc cggatgcgcg   1200
gatgggcccc gggaggagac cgccggtgca ccgccgggtg agtcctccgg gggcatccgg   1260
gaggaggggg cggaggcgtc gacaagcatc accgacgtct acatcgccct cggggattcc   1320
tatgcggcga tgggcgggcg ggatcagccg ttacggggtg agccgttctg cctgcgctcg   1380
tccggtaatt acccggaact cctccacgca gaggtcaccg atctcacctg ccagggggcg   1440
gtgaccgggg atctgctcga acccaggacg ctggggagc gcacgctgcc ggcgcaggtg   1500
gatgcgctga cggaggacac caccctggtc accctctcca tcggggggcaa tgacctcgga   1560 ttcggggagg tggcgggatg catccgggaa cggatcgccg gggagaacgc tgatgattgc   1620
gtggacctgc tgggggaaac catcggggag cagctcgatc agcttccccc gcagctggac   1680
cgcgtgcacg aggctatccg ggaccgcgcc ggggacgcgc aggttgtggt caccggttac   1740
ctgccgctcg tgtctgccgg ggactgcccc gaactggggg atgtctccga ggcggatcgt   1800
cgttgggcgg ttgagctgac cgggcagatc aacgagaccg tgcgcgaggc ggccgaacga   1860
cacgatgccc tctttgtcct gcccgacgat gccgatgagc acaccagttg tgcacccca    1920 cagcagcgct gggcggatat ccagggccaa cagaccgatg cctatccgct gcacccgacc   1980
tccgccggcc atgaggcgat ggccgccgcc gtccgggacg cgctgggcct ggaaccggtc   2040
cagccgtagc gccgggcgcg cgcttgtcga cgaccaaccc atgccaggct gcagtcacat   2100
ccgcacatag cgcgcgcggg cgatggagta cgcaccatag aggatgagcc cgatgccgac   2160
gatgatgagc agcacactgc cgaagggttg ttccccgagg gtgcgcagag ccgagtccag   2220
acctgcggcc tgctccggat catgggccca accggcgatg acgatcaaca ccccaggat   2280 cccgaaggcg ataccacggg cgacataacc ggctgttccg gtgatgatga tcgcggtccc   2340
gacctgccct gaccccgcac ccgcctccag atcctcccgg aaatcccggg tggccccctt   2400
ccagaggttg tagacacccg cccccagtac caccagcccg gcgaccacaa ccagcaccac   2460
accccagggt tgggataggga cggtggcggt gacatcggtg gcggtctccc catcggaggt   2520
```

-continued

```
gctgccgccc cgggcgaagg tggaggtggt caccgccagg gagaagtaga ccatggccat    2580
gaccgccccc ttggcccttt ccttgaggtc ctcgcccgcc agcagctggc tcaattgcca    2640
gagtcccagg gccgccaggg cgatgacggc aacccacagg aggaactgcc caccccggagc   2700 ctccgcgatg gtggccaggg cacctgaatt cgaggcctca tcacccgaac cgccggatcc    2760
agtggcgatg cgcaccgcga tccacccgat gaggatgtgc agtatgccca ggacaatgaa    2820
accacctctg gccagggtgg tcagcgcggg gtggtcctcg gcctggtcgg cagcccgttc    2880
gatcgtccgt ttcgcggatc tggtgtcgcc cttatccata gctcccattg aaccgccttg    2940
aggggtgggc ggccactgtc agggcggatt gtgatctgaa ctgtgatgtt ccatcaaccc    3000
```

<210> SEQ ID NO 82
<211> LENGTH: 268
<212> TYPE: PRT
<213> ORGANISM: Streptomyces coelicolor

<400> SEQUENCE: 82

```
Met Arg Arg Phe Arg Leu Val Gly Phe Leu Ser Ser Leu Val Leu Ala
  1               5                  10                  15

Ala Gly Ala Ala Leu Thr Gly Ala Ala Thr Ala Gln Ala Ala Gln Pro
             20                  25                  30

Ala Ala Ala Asp Gly Tyr Val Ala Leu Gly Asp Ser Tyr Ser Ser Gly
         35                  40                  45

Val Gly Ala Gly Ser Tyr Ile Ser Ser Ser Gly Asp Cys Lys Arg Ser
     50                  55                  60

Thr Lys Ala His Pro Tyr Leu Trp Ala Ala Ala His Ser Pro Ser Thr
 65                  70                  75                  80

Phe Asp Phe Thr Ala Cys Ser Gly Ala Arg Thr Gly Asp Val Leu Ser
                 85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Glu Ala
    130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205

Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265
```

<210> SEQ ID NO 83
<211> LENGTH: 2000
<212> TYPE: DNA

<213> ORGANISM: Streptomyces coelicolor

<400> SEQUENCE: 83

| | | | | | |
|---|---|---|---|---|---|
| cccggcggcc | cgtgcaggag | cagcagccgg | cccgcgatgt | cctcgggcgt | cgtcttcatc | 60 |
| aggccgtcca | tcgcgtcggc | gaccggcgcc | gtgtagttgg | cccggacctc | gtcccaggtg | 120 |
| cccgcggcga | tctggcgggt | ggtgcggtgc | gggccgcgcc | gagggagac | gtaccagaag | 180 |
| cccatcgtca | cgttctccgg | ctgccggttcg | ggctcgtccg | ccgctccgtc | cgtcgcctcg | 240 |
| ccgagcacct | tctcggcgag | gtcggcgctg | gtcgccgtca | ccgtgacgtc | ggcgccccgg | 300 |
| ctccagcgcg | agatcagcag | cgtccagccg | tcgccctccg | ccagcgtcgc | gctgcggtcg | 360 |
| tcgtcgcggg | cgatccgcag | cacgcgcgcg | ccgggcggca | gcagcgtggc | gccggaccgt | 420 |
| acgcggtcga | tgttcgccgc | gtgcgagtac | ggctgctcac | ccgtggcgaa | acggccgagg | 480 |
| aacagcgcgt | cgacgacgtc | ggacggggag | tcgctgtcgt | ccacgttgag | ccggatcggc | 540 |
| agggcttcgt | gcgggttcac | ggacatgtcg | ccatgatcgg | gcaccggcc | gccgcgtgca | 600 |
| cccgctttcc | cgggcacgca | cgacaggggc | tttctcgccg | tcttccgtcc | gaacttgaac | 660 |
| gagtgtcagc | catttcttgg | catggacact | tccagtcaac | gcgcgtagct | gctaccacgg | 720 |
| ttgtggcagc | aatcctgcta | agggaggttc | catgagacgt | ttccgacttg | tcggcttcct | 780 |
| gagttcgctc | gtcctcgccg | ccggcgccg | cctcaccggg | gcagcgaccg | cccaggcggc | 840 |
| ccaacccgcc | gccgccgacg | gctatgtggc | cctcggcgac | tcctactcct | ccggggtcgg | 900 |
| agcgggcagc | tacatcagct | cgagcggcga | ctgcaagcgc | agcacgaagg | cccatcccta | 960 |
| cctgtgggcg | gccgcccact | cgccctccac | gttcgacttc | accgcctgtt | ccggcgcccg | 1020 |
| tacgggtgat | gttctctccg | gacagctcgg | cccgctcagc | tccggcaccg | gctcgtctc | 1080 |
| gatcagcatc | ggcggcaacg | acgccggttt | cgccgacacc | atgacgacct | gtgtgctcca | 1140 |
| gtccgagagc | tcctgcctgt | cgcggatcgc | caccgccgag | gcgtacgtcg | actcgacgct | 1200 |
| gcccggcaag | ctcgacggcg | tctactcggc | aatcagcgac | aaggcgccga | acgcccacgt | 1260 |
| cgtcgtcatc | ggctacccgc | gcttctacaa | gctcggcacc | acctgcatcg | gcctgtccga | 1320 |
| gaccaagcgg | acggcgatca | acaaggcctc | cgaccacctc | aacaccgtcc | tcgcccagcg | 1380 |
| cgccgccgcc | cacggcttca | ccttcggcga | cgtacgcacc | accttcaccg | gccacgagct | 1440 |
| gtgctccggc | agcccctggc | tgcacagcgt | caactggctg | aacatcggcg | agtcgtacca | 1500 |
| ccccaccgcg | gccggccagt | ccggtggcta | cctgccggtc | ctcaacggcg | ccgcctgacc | 1560 |
| tcaggcggaa | ggagaagaag | aaggagcgga | gggagacgag | gagtgggagg | ccccgcccga | 1620 |
| cggggtcccc | gtccccgtct | ccgtctccgt | cccggtcccg | caagtcaccg | agaacgccac | 1680 |
| cgcgtcggac | gtgcccgca | ccggactccg | cacctccacg | cgcacggcac | tctcgaacgc | 1740 |
| gccggtgtcg | tcgtgcgtcg | tcaccaccac | gccgtcctgg | cgcgagcgct | cgccgcccga | 1800 |
| cgggaaggac | agcgtccgcc | accccggatc | ggagaccgac | ccgtccgcgg | tcacccaccg | 1860 |
| gtagccgacc | tccgcgggca | gccgcccgac | cgtgaacgtc | gccgtgaacg | cgggtgcccg | 1920 |
| gtcgtgcggc | ggcggacagg | cccccgagta | gtgggtgcgc | gagcccacca | cggtcacctc | 1980 |
| caccgactgc | gctgcggggc | | | | | 2000 |

<210> SEQ ID NO 84
<211> LENGTH: 269
<212> TYPE: PRT
<213> ORGANISM: Streptomyces avermitilis

<400> SEQUENCE: 84

```
Met Arg Arg Ser Arg Ile Thr Ala Tyr Val Thr Ser Leu Leu Leu Ala
  1               5                  10                  15

Val Gly Cys Ala Leu Thr Gly Ala Ala Thr Ala Gln Ala Ser Pro Ala
             20                  25                  30

Ala Ala Ala Thr Gly Tyr Val Ala Leu Gly Asp Ser Tyr Ser Ser Gly
         35                  40                  45

Val Gly Ala Gly Ser Tyr Leu Ser Ser Ser Gly Asp Cys Lys Arg Ser
     50                  55                  60

Ser Lys Ala Tyr Pro Tyr Leu Trp Gln Ala Ala His Ser Pro Ser Ser
 65                  70                  75                  80

Phe Ser Phe Met Ala Cys Ser Gly Ala Arg Thr Gly Asp Val Leu Ala
                 85                  90                  95

Asn Gln Leu Gly Thr Leu Asn Ser Ser Thr Gly Leu Val Ser Leu Thr
             100                 105                 110

Ile Gly Gly Asn Asp Ala Gly Phe Ser Asp Val Met Thr Thr Cys Val
         115                 120                 125

Leu Gln Ser Asp Ser Ala Cys Leu Ser Arg Ile Asn Thr Ala Lys Ala
         130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
                180                 185                 190

Lys Arg Ser Ala Ile Asn Asp Ala Ala Asp Tyr Leu Asn Ser Ala Ile
            195                 200                 205

Ala Lys Arg Ala Ala Asp His Gly Phe Thr Phe Gly Asp Val Lys Ser
210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265

<210> SEQ ID NO 85
<211> LENGTH: 1980
<212> TYPE: DNA
<213> ORGANISM: Streptomyces avermitilis

<400> SEQUENCE: 85
ccaccgccgg gtcggcggcg agtctcctgg cctcggtcgc ggagaggttg gccgtgtagc      60
cgttcagcgc ggcgccgaac gtcttcttca ccgtgccgcc gtactcgttg atcaggccct     120
tgcccttgct cgacgcggcc ttgaagccgg tgcccttctt gagcgtgacg atgtagctgc     180
ccttgatcgc ggtgggggag ccggcggcga gcaccgtgcc ctcggccggg gtggcctggg     240
cgggcagtgc ggtgaatccg cccacgaggg cgccggtcgc cacggcggtt atcgcggcga     300
tccggatctt cttgctacgc agctgtgcca tacgagggag tcctcctctg ggcagcggcg     360
cgcctgggtg gggcgcacgg ctgtgggggg tgcgcgcgtc atcacgcaca cggccctgga     420
gcgtcgtgtt ccgccctggg ttgagtaaag cctcggccat ctacggggt ggctcaaggg     480 agttgagacc ctgtcatgag tctgacatga gcacgcaatc aacggggccg tgagcacccc     540
ggggcgaccc cggaaagtgc cgagaagtct tggcatggac acttcctgtc aacacgcgta     600
gctggtacga cggttacggc agagatcctg ctaaagggag gttccatgag acgttcccga     660
```

```
attacggcat acgtgacctc actcctcctc gccgtcggct gcgccctcac cggggcagcg    720
acggcgcagg cgtccccagc cgccgcggcc acgggctatg tggccctcgg cgactcgtac    780
tcgtccggtg tcggcgccgg cagctacctc agctccagcg gcgactgcaa gcgcagttcg    840
aaggcctatc cgtacctctg gcaggccgcg cattcaccct cgtcgttcag tttcatggct    900
tgctcgggcg ctcgtacggg tgatgtcctg gccaatcagc tcggcaccct gaactcgtcc    960
accggcctgg tctccctcac catcggaggc aacgacgcgg gcttctccga cgtcatgacg   1020
acctgtgtgc tccagtccga cagcgcctgc ctctcccgca tcaacacggc gaaggcgtac   1080
gtcgactcca ccctgcccgg ccaactcgac agcgtgtaca cggcgatcag cacgaaggcc   1140
ccgtcggccc atgtggccgt gctgggctac ccccgcttct acaaactggg cggctcctgc   1200
ctcgcgggcc tctcggagac caagcggtcc gccatcaacg acgcggccga ctatctgaac   1260
agcgccatcg ccaagcgcgc cgccgaccac ggcttcacct cggcgacgt caagagcacc   1320 ttcaccggcc atgagatctg ctccagcagc acctggctgc acagtctcga cctgctgaac   1380
atcggccagt cctaccaccc gaccgcggcc ggccagtccg gcggctatct gccggtcatg   1440
aacagcgtgg cctgagctcc cacggcctga atttttaagg cctgaatttt taaggcgaag   1500
gtgaaccgga agcggaggcc ccgtccgtcg gggtctccgt cgcacaggtc accgagaacg   1560
gcacggagtt ggacgtcgtg cgcaccgggt cgcgcacctc gacggcgatc tcgttcgaga   1620
tcgttccgct cgtgtcgtac gtggtgacga cacctgctt ctgctgggtc tttccgccgc   1680
tcgccgggaa ggacagcgtc ttccagcccg gatccgggac ctcgcccttc ttggtcaccc   1740
agcggtactc cacctcgacc ggcacccggc ccaccgtgaa ggtcgccgtg aacgtgggcg   1800
cctgggcggt gggcggcggg caggcaccgg agtagtcggt gtgcacgccg gtgaccgtca   1860
ccttcacgga ctgggccggc ggggtcgtcg taccgccgcc gccaccgccg cctcccggag   1920
tggagcccga gctgtggtcg cccccgccgt cggcgttgtc gtcctcgggg gttttcgaac   1980
```

<210> SEQ ID NO 86
<211> LENGTH: 372
<212> TYPE: PRT
<213> ORGANISM: Thermobifida fusca

<400> SEQUENCE: 86

```
Met Gly Ser Gly Pro Arg Ala Ala Thr Arg Arg Leu Phe Leu Gly
  1               5                  10                  15

Ile Pro Ala Leu Val Leu Val Thr Ala Leu Thr Leu Val Leu Ala Val
                 20                  25                  30

Pro Thr Gly Arg Glu Thr Leu Trp Arg Met Trp Cys Glu Ala Thr Gln
             35                  40                  45

Asp Trp Cys Leu Gly Val Pro Val Asp Ser Arg Gly Gln Pro Ala Glu
         50                  55                  60

Asp Gly Glu Phe Leu Leu Ser Pro Val Gln Ala Ala Thr Trp Gly
     65                  70                  75              80

Asn Tyr Tyr Ala Leu Gly Asp Ser Tyr Ser Gly Asp Gly Ala Arg
                 85                  90                  95

Asp Tyr Tyr Pro Gly Thr Ala Val Lys Gly Gly Cys Trp Arg Ser Ala
                100                 105                 110

Asn Ala Tyr Pro Glu Leu Val Ala Glu Ala Tyr Asp Phe Ala Gly His
            115                 120                 125

Leu Ser Phe Leu Ala Cys Ser Gly Gln Arg Gly Tyr Ala Met Leu Asp
        130                 135                 140
```

```
Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Val Gly Val Ser Val Glu Phe
        275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365

Gly Glu Val Gly
    370

<210> SEQ ID NO 87
<211> LENGTH: 968
<212> TYPE: DNA
<213> ORGANISM: Thermobifida fusca

<400> SEQUENCE: 87
ctgcagacac ccgccccgcc ttctcccgga tcgtcatgtt cggcgactcc ctcagcgaca      60
ccggcaagat gtactccaag atgcgcggct acctgccgtc ctccccgccg tactacgagg     120
gccgcttctc gaacggcccg gtctggctgg agcagctgac gaagcagttc cccggcctga     180
cgatcgccaa cgaggccgag gggggcgcga ccgcagtcgc ctacaacaag atctcctgga     240
acccgaagta ccaggtcatt aacaacctcg actacgaggt cacccagttc ttgcagaagg     300
actcgttcaa gcccgacgac ctggtcatcc tgtgggtggg cgccaacgac tacctggcct     360
acggttggaa cacggagcag gacgccaagc gggtgcgcga cgccatctcg gacgcggcaa     420
accgcatggt cctgaacggc gcgaagcaga tcctgctgtt caacctgccc gacctgggcc     480
agaacccgtc cgcccgctcc cagaaggtcg tcgaggccgt ctcgcacgtg tccgcctacc     540
acaacaagct gctcctcaac ctcgcccggc agctcgcccc gacgggcatg gtcaagctgt     600
tcgagatcga caagcagttc gcggagatgc tgcgcgaccc ccagaacttc ggcctgagcg     660
acgtggagaa cccgtgctac gacggcggct acgtgtggaa gccgttcgcc acccggtccg     720
tctcgaccga ccggcagctg tcggccttct cgccccagga gcgcctggcg atcgctggca     780
acccgctcct ggcacaggcg gtagcttcgc cgatggcccg ccgctcggcc tcgcccctca     840
```

-continued

```
actgcgaggg caagatgttc tgggaccagg tccaccccac caccgtggtc cacgccgccc    900
tctcggagcg cgccgccacc ttcatcgaga cccagtacga gttcctcgcc cactagtcta    960
gaggatcc                                                             968
```

<210> SEQ ID NO 88
<211> LENGTH: 1044
<212> TYPE: DNA
<213> ORGANISM: Aeromonas salmonicida

<400> SEQUENCE: 88

```
atgaaacaac aaaaacggct ttacgcccga ttgctgacgc tgttatttgc gctcatcttc     60
ttgctgcctc attctgcagc ttcagcagca gatacaagac cggcgtttag ccggatcgtc    120
atgtttggag atagcctgag cgatacgggc aaaatgtata gcaaaatgag aggctatctt    180
ccgtcaagcc cgccgtatta tgaaggccgc tttagcaatg gaccggtctg gctggaacaa    240
ctgacgaaac aatttccggg actgacgatc gctaatgaag cagaaggagg agcaacagcg    300
gtcgcctata caaaaatcag ctgggacccg aaatatcagg tcatcaacaa cctggactat    360
gaagtcacac agtttcttca gaaagacagc tttaaaccgg atgatctggt catcctttgg    420
gtcggcgcca atgattatct ggcgtatggc tggaacacag aacaagatgc caaaagagtc    480
agagatgcca tcagcgatgc cgctaataga atggtcctga acggcgccaa acaaatcctg    540
ctgtttaacc tgccggatct gggacaaaat ccgagcgcca gaagccaaaa agtcgtcgaa    600
gcagtcagcc atgtcagcgc ctatcataac aaactgctgc tgaacctggc aagacaattg    660
gcaccgacgg gaatggttaa attgtttgaa attgacaaac agtttgccga atgctgaga     720
gatccgcaaa attttggcct gagcgatgtc gaaaacccgt gctatgatgg cggatatgtc    780
tggaaaccgt ttgccacaag aagcgtcagc acggatagaa aactgtcagc gtttagcccg    840
caagaaagac tggcaatcgc cggaaatccg ctttttggcac aagcagttgc ttcaccgatg    900
gcaagaagat cagcaagccc gctgaattgc gaaggcaaaa tgttttggga tcaggtccat    960
ccgacaacag ttgtccatgc tgcccttttca gaaagagcgg cgacgtttat cgaaacacag   1020
tatgaatttc tggcccatgg ctga                                           1044
```

<210> SEQ ID NO 89
<211> LENGTH: 267
<212> TYPE: PRT
<213> ORGANISM: Streptomyces sp.

<400> SEQUENCE: 89

```
Met Arg Leu Thr Arg Ser Leu Ser Ala Ala Ser Val Ile Val Phe Ala
  1               5                  10                  15

Leu Leu Leu Ala Leu Leu Gly Ile Ser Pro Ala Gln Ala Ala Gly Pro
             20                  25                  30

Ala Tyr Val Ala Leu Gly Asp Ser Tyr Ser Ser Gly Asn Gly Ala Gly
         35                  40                  45

Ser Tyr Ile Asp Ser Ser Gly Asp Cys His Arg Ser Asn Asn Ala Tyr
     50                  55                  60

Pro Ala Arg Trp Ala Ala Asn Ala Pro Ser Ser Phe Thr Phe Ala
 65                  70                  75                  80

Ala Cys Ser Gly Ala Val Thr Thr Asp Val Ile Asn Asn Gln Leu Gly
                 85                  90                  95

Ala Leu Asn Ala Ser Thr Gly Leu Val Ser Ile Thr Ile Gly Gly Asn
            100                 105                 110
```

```
Asp Ala Gly Phe Ala Asp Ala Met Thr Thr Cys Val Thr Ser Ser Asp
            115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 90
<211> LENGTH: 285
<212> TYPE: PRT
<213> ORGANISM: Aeromonas salmonicida

<400> SEQUENCE: 90

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
                20                  25                  30

Ser Ser Pro Pro Tyr Tyr Glu Gly Arg Phe Ser Asn Gly Pro Val Trp
            35                  40                  45

Leu Glu Gln Leu Thr Lys Gln Phe Pro Gly Leu Thr Ile Ala Asn Glu
        50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220
```

```
Cys Tyr Asp Gly Gly Tyr Val Trp Lys Pro Phe Arg Ser Ala Ser Pro
225                 230                 235                 240

Arg Ser Ala Ser Pro Leu Asn Cys Glu Gly Lys Met Phe Trp Asp Gln
            245                 250                 255

Val His Pro Thr Thr Val Val His Ala Ala Leu Ser Glu Arg Ala Ala
        260                 265                 270

Thr Phe Ile Glu Thr Gln Tyr Glu Phe Leu Ala His Gly
    275                 280                 285
```

<210> SEQ ID NO 91
<211> LENGTH: 295
<212> TYPE: PRT
<213> ORGANISM: Aeromonas salmonicida

<400> SEQUENCE: 91

```
Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Lys Gln Phe Pro
        35                  40                  45

Gly Leu Thr Ile Ala Asn Glu Ala Glu Gly Gly Ala Thr Ala Val Ala
    50                  55                  60

Tyr Asn Lys Ile Ser Trp Asn Pro Lys Tyr Gln Val Tyr Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Gln Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Val Ser His Val Ser Ala Tyr His Asn Lys Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Val Glu Asn Pro Cys Tyr Asp Gly Gly Tyr Val Trp Lys
    210                 215                 220

Pro Phe Ala Thr Arg Ser Val Ser Thr Asp Arg Gln Leu Ser Ala Phe
225                 230                 235                 240

Ser Pro Gln Glu Arg Leu Ala Ile Ala Gly Asn Pro Leu Leu Ala Gln
                245                 250                 255

Ala Val Ala Ser Pro Met Ala Arg Arg Ser Ala Ser Pro Leu Asn Cys
            260                 265                 270

Glu Gly Lys Met Phe Trp Asp Gln Val His Pro Thr Thr Val Val His
        275                 280                 285

Ala Ala Leu Ser Glu Arg Ala
    290                 295
```

<210> SEQ ID NO 92
<211> LENGTH: 247

```
<212> TYPE: PRT
<213> ORGANISM: Streptomyces coelicolor

<400> SEQUENCE: 92

Tyr Val Ala Leu Gly Asp Ser Tyr Ser Ala Gly Ser Gly Val Leu Pro
 1               5                  10                  15

Val Asp Pro Ala Asn Leu Leu Cys Leu Arg Ser Thr Ala Asn Tyr Pro
            20                  25                  30

His Val Ile Ala Asp Thr Thr Gly Ala Arg Leu Thr Asp Val Thr Cys
        35                  40                  45

Gly Ala Ala Gln Thr Ala Asp Phe Thr Arg Ala Gln Tyr Pro Gly Val
    50                  55                  60

Ala Pro Gln Leu Asp Ala Leu Gly Thr Gly Thr Asp Leu Val Thr Leu
65                  70                  75                  80

Thr Ile Gly Gly Asn Asp Asn Ser Thr Phe Ile Asn Ala Ile Thr Ala
                85                  90                  95

Cys Gly Thr Ala Gly Val Leu Ser Gly Gly Lys Gly Ser Pro Cys Lys
            100                 105                 110

Asp Arg His Gly Thr Ser Phe Asp Asp Glu Ile Glu Ala Asn Thr Tyr
        115                 120                 125

Pro Ala Leu Lys Glu Ala Leu Leu Gly Val Arg Ala Arg Ala Pro His
    130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
            180                 185                 190

Ala Glu Glu Thr Gly Ala Thr Tyr Val Asp Phe Ser Gly Val Ser Asp
        195                 200                 205

Gly His Asp Ala Cys Glu Ala Pro Gly Thr Arg Trp Ile Glu Pro Leu
    210                 215                 220

Leu Phe Gly His Ser Leu Val Pro Val His Pro Asn Ala Leu Gly Glu
225                 230                 235                 240

Arg Arg Met Ala Glu His Thr
                245

<210> SEQ ID NO 93
<211> LENGTH: 247
<212> TYPE: PRT
<213> ORGANISM: Streptomyces coelicolor

<400> SEQUENCE: 93

Tyr Val Ala Leu Gly Asp Ser Tyr Ser Ala Gly Ser Gly Val Leu Pro
 1               5                  10                  15

Val Asp Pro Ala Asn Leu Leu Cys Leu Arg Ser Thr Ala Asn Tyr Pro
            20                  25                  30

His Val Ile Ala Asp Thr Thr Gly Ala Arg Leu Thr Asp Val Thr Cys
        35                  40                  45

Gly Ala Ala Gln Thr Ala Asp Phe Thr Arg Ala Gln Tyr Pro Gly Val
    50                  55                  60

Ala Pro Gln Leu Asp Ala Leu Gly Thr Gly Thr Asp Leu Val Thr Leu
65                  70                  75                  80

Thr Ile Gly Gly Asn Asp Asn Ser Thr Phe Ile Asn Ala Ile Thr Ala
                85                  90                  95

Cys Gly Thr Ala Gly Val Leu Ser Gly Gly Lys Gly Ser Pro Cys Lys
```

```
                    100                 105                 110
Asp Arg His Gly Thr Ser Phe Asp Asp Glu Ile Glu Ala Asn Thr Tyr
                115                 120                 125

Pro Ala Leu Lys Glu Ala Leu Leu Gly Val Arg Ala Arg Ala Pro His
            130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
                180                 185                 190

Ala Glu Glu Thr Gly Ala Thr Tyr Val Asp Phe Ser Gly Val Ser Asp
                195                 200                 205

Gly His Asp Ala Cys Glu Ala Pro Gly Thr Arg Trp Ile Glu Pro Leu
                210                 215                 220

Leu Phe Gly His Ser Leu Val Pro Val His Pro Asn Ala Leu Gly Glu
225                 230                 235                 240

Arg Arg Met Ala Glu His Thr
                245

<210> SEQ ID NO 94
<211> LENGTH: 198
<212> TYPE: PRT
<213> ORGANISM: Saccharomyces cerevisiae

<400> SEQUENCE: 94

Phe Leu Leu Phe Gly Asp Ser Ile Thr Glu Phe Ala Phe Asn Thr Arg
1               5                   10                  15

Pro Ile Glu Asp Gly Lys Asp Gln Tyr Ala Leu Gly Ala Ala Leu Val
            20                  25                  30

Asn Glu Tyr Thr Arg Lys Met Asp Ile Leu Gln Arg Gly Phe Lys Gly
        35                  40                  45

Tyr Thr Ser Arg Trp Ala Leu Lys Ile Leu Pro Glu Ile Leu Lys His
    50                  55                  60

Glu Ser Asn Ile Val Met Ala Thr Ile Phe Leu Gly Ala Asn Asp Ala
65                  70                  75                  80

Cys Ser Ala Gly Pro Gln Ser Val Pro Leu Pro Glu Phe Ile Asp Asn
                85                  90                  95

Ile Arg Gln Met Val Ser Leu Met Lys Ser Tyr His Ile Arg Pro Ile
            100                 105                 110

Ile Ile Gly Pro Gly Leu Val Asp Arg Glu Lys Trp Glu Lys Glu Lys
        115                 120                 125

Ser Glu Glu Ile Ala Leu Gly Tyr Phe Arg Thr Asn Glu Asn Phe Ala
    130                 135                 140

Ile Tyr Ser Asp Ala Leu Ala Lys Leu Ala Asn Glu Glu Lys Val Pro
145                 150                 155                 160

Phe Val Ala Leu Asn Lys Ala Phe Gln Gln Glu Gly Gly Asp Ala Trp
                165                 170                 175

Gln Gln Leu Leu Thr Asp Gly Leu His Phe Ser Gly Lys Gly Tyr Lys
            180                 185                 190

Ile Phe His Asp Glu Leu
        195

<210> SEQ ID NO 95
<211> LENGTH: 317
<212> TYPE: PRT
```

<213> ORGANISM: Aeromonas salmonicida

<400> SEQUENCE: 95

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His
305                 310                 315

<210> SEQ ID NO 96
<211> LENGTH: 320
<212> TYPE: PRT
<213> ORGANISM: Ralstonia solanacearum

<400> SEQUENCE: 96

Gln Ser Gly Asn Pro Asn Val Ala Lys Val Gln Arg Met Val Val Phe
1               5                   10                  15

Gly Asp Ser Leu Ser Asp Ile Gly Thr Tyr Thr Pro Val Ala Gln Ala
            20                  25                  30

Val Gly Gly Gly Lys Phe Thr Thr Asn Pro Gly Pro Ile Trp Ala Glu
        35                  40                  45

```
Thr Val Ala Ala Gln Leu Gly Val Thr Leu Thr Pro Ala Val Met Gly
 50                  55                  60

Tyr Ala Thr Ser Val Gln Asn Cys Pro Lys Ala Gly Cys Phe Asp Tyr
 65                  70                  75                  80

Ala Gln Gly Gly Ser Arg Val Thr Asp Pro Asn Gly Ile Gly His Asn
                 85                  90                  95

Gly Gly Ala Gly Ala Leu Thr Tyr Pro Val Gln Gln Leu Ala Asn
            100                 105                 110

Phe Tyr Ala Ala Ser Asn Asn Thr Phe Asn Gly Asn Asn Asp Val Val
            115                 120                 125

Phe Val Leu Ala Gly Ser Asn Asp Ile Phe Phe Trp Thr Ala Ala
            130                 135                 140

Ala Thr Ser Gly Ser Gly Val Thr Pro Ala Ile Ala Thr Ala Gln Val
145                 150                 155                 160

Gln Gln Ala Ala Thr Asp Leu Val Gly Tyr Val Lys Asp Met Ile Ala
                165                 170                 175

Lys Gly Ala Thr Gln Val Tyr Val Phe Asn Leu Pro Asp Ser Ser Leu
                180                 185                 190

Thr Pro Asp Gly Val Ala Ser Gly Thr Thr Gly Gln Ala Leu Leu His
                195                 200                 205

Ala Leu Val Gly Thr Phe Asn Thr Thr Leu Gln Ser Gly Leu Ala Gly
            210                 215                 220

Thr Ser Ala Arg Ile Ile Asp Phe Asn Ala Gln Leu Thr Ala Ala Ile
225                 230                 235                 240

Gln Asn Gly Ala Ser Phe Gly Phe Ala Asn Thr Ser Ala Arg Ala Cys
                245                 250                 255

Asp Ala Thr Lys Ile Asn Ala Leu Val Pro Ser Ala Gly Gly Ser Ser
                260                 265                 270

Leu Phe Cys Ser Ala Asn Thr Leu Val Ala Ser Gly Ala Asp Gln Ser
            275                 280                 285

Tyr Leu Phe Ala Asp Gly Val His Pro Thr Thr Ala Gly His Arg Leu
            290                 295                 300

Ile Ala Ser Asn Val Leu Ala Arg Leu Leu Ala Asp Asn Val Ala His
305                 310                 315                 320

<210> SEQ ID NO 97
<211> LENGTH: 367
<212> TYPE: PRT
<213> ORGANISM: Artificial Sequence
<220> FEATURE:
<223> OTHER INFORMATION: Description of Artificial Sequence: Synthetic
      Pfam00657.11 consensus sequence

<400> SEQUENCE: 97

Ile Val Ala Phe Gly Asp Ser Leu Thr Asp Gly Gly Ala Tyr Tyr
 1               5                  10                  15

Gly Asp Ser Asp Gly Gly Gly Trp Gly Ala Gly Leu Ala Asp Arg Leu
                20                  25                  30

Thr Ser Leu Ala Arg Leu Arg Ala Arg Gly Arg Gly Val Asp Val Phe
            35                  40                  45

Asn Arg Gly Ile Ser Gly Arg Thr Ser Asp Gly Arg Leu Val Val Asp
 50                  55                  60

Ala Arg Leu Val Ala Thr Leu Leu Phe Leu Ala Gln Phe Leu Gly Leu
 65                  70                  75                  80

Asn Leu Pro Pro Tyr Leu Ser Gly Asp Phe Leu Arg Gly Ala Asn Phe
                 85                  90                  95
```

Ala Ser Ala Gly Ala Thr Ile Leu Gly Thr Ser Leu Ile Pro Phe Leu
            100                 105                 110

Asn Ile Gln Val Gln Phe Lys Asp Phe Lys Ser Lys Val Leu Glu Leu
            115                 120                 125

Arg Gln Ala Leu Gly Leu Leu Gln Glu Leu Leu Arg Leu Val Pro Val
        130                 135                 140

Leu Asp Ala Lys Ser Pro Asp Leu Val Thr Ile Met Ile Gly Thr Asn
145                 150                 155                 160

Asp Leu Ile Thr Val Ala Lys Phe Gly Pro Lys Ser Thr Lys Ser Asp
                165                 170                 175

Arg Asn Val Ser Val Pro Glu Phe Arg Asp Asn Leu Arg Lys Leu Ile
                180                 185                 190

Lys Arg Leu Arg Ser Ala Asn Gly Ala Arg Ile Ile Leu Ile Thr
                195                 200                 205

Leu Val Leu Leu Asn Leu Pro Leu Pro Leu Gly Cys Leu Pro Gln Lys
        210                 215                 220

Leu Ala Leu Ala Leu Ala Ser Ser Lys Asn Val Asp Ala Thr Gly Cys
225                 230                 235                 240

Leu Glu Arg Leu Asn Glu Ala Val Ala Asp Tyr Asn Glu Ala Leu Arg
                245                 250                 255

Glu Leu Ala Glu Ile Glu Lys Leu Gln Ala Gln Leu Arg Lys Asp Gly
                260                 265                 270

Leu Pro Asp Leu Lys Glu Ala Asn Val Pro Tyr Val Asp Leu Tyr Ser
        275                 280                 285

Ile Phe Gln Asp Leu Asp Gly Ile Gln Asn Pro Ser Ala Tyr Val Tyr
        290                 295                 300

Gly Phe Glu Glu Thr Lys Ala Cys Cys Gly Tyr Gly Gly Arg Tyr Asn
305                 310                 315                 320

Tyr Asn Arg Val Cys Gly Asn Ala Gly Leu Cys Lys Val Thr Ala Lys
                325                 330                 335

Ala Cys Asp Ala Ser Ser Tyr Leu Leu Ala Thr Leu Phe Trp Asp Gly
                340                 345                 350

Phe His Pro Ser Glu Lys Gly Tyr Lys Ala Val Ala Glu Ala Leu
        355                 360                 365

<210> SEQ ID NO 98
<211> LENGTH: 367
<212> TYPE: PRT
<213> ORGANISM: Artificial Sequence
<220> FEATURE:
<223> OTHER INFORMATION: Description of Artificial Sequence: Synthetic
      Pfam00657.11 consensus sequence

<400> SEQUENCE: 98

Ile Val Ala Phe Gly Asp Ser Leu Thr Asp Gly Gly Gly Ala Tyr Tyr
1               5                   10                  15

Gly Asp Ser Asp Gly Gly Gly Trp Gly Ala Gly Leu Ala Asp Arg Leu
                20                  25                  30

Thr Ser Leu Ala Arg Leu Arg Ala Arg Gly Arg Gly Val Asp Val Phe
            35                  40                  45

Asn Arg Gly Ile Ser Gly Arg Thr Ser Asp Gly Arg Leu Val Val Asp
        50                  55                  60

Ala Arg Leu Val Ala Thr Leu Leu Phe Leu Ala Gln Phe Leu Gly Leu
65                  70                  75                  80

Asn Leu Pro Pro Tyr Leu Ser Gly Asp Phe Leu Arg Gly Ala Asn Phe
                85                  90                  95

```
Ala Ser Ala Gly Ala Thr Ile Leu Gly Thr Ser Leu Ile Pro Phe Leu
            100                 105                 110

Asn Ile Gln Val Gln Phe Lys Asp Phe Lys Ser Lys Val Leu Glu Leu
            115                 120                 125

Arg Gln Ala Leu Gly Leu Leu Gln Glu Leu Leu Arg Leu Val Pro Val
        130                 135                 140

Leu Asp Ala Lys Ser Pro Asp Leu Val Thr Ile Met Ile Gly Thr Asn
145                 150                 155                 160

Asp Leu Ile Thr Val Ala Lys Phe Gly Pro Lys Ser Thr Lys Ser Asp
                165                 170                 175

Arg Asn Val Ser Val Pro Glu Phe Arg Asp Asn Leu Arg Lys Leu Ile
                180                 185                 190

Lys Arg Leu Arg Ser Ala Asn Gly Ala Arg Ile Ile Leu Ile Thr
        195                 200                 205

Leu Val Leu Leu Asn Leu Pro Leu Pro Leu Gly Cys Leu Pro Gln Lys
    210                 215                 220

Leu Ala Leu Ala Leu Ala Ser Ser Lys Asn Val Asp Ala Thr Gly Cys
225                 230                 235                 240

Leu Glu Arg Leu Asn Glu Ala Val Ala Asp Tyr Asn Glu Ala Leu Arg
                245                 250                 255

Glu Leu Ala Glu Ile Glu Lys Leu Gln Ala Gln Leu Arg Lys Asp Gly
            260                 265                 270

Leu Pro Asp Leu Lys Glu Ala Asn Val Pro Tyr Val Asp Leu Tyr Ser
        275                 280                 285

Ile Phe Gln Asp Leu Asp Gly Ile Gln Asn Pro Ser Ala Tyr Val Tyr
    290                 295                 300

Gly Phe Glu Glu Thr Lys Ala Cys Cys Gly Tyr Gly Gly Arg Tyr Asn
305                 310                 315                 320

Tyr Asn Arg Val Cys Gly Asn Ala Gly Leu Cys Lys Val Thr Ala Lys
                325                 330                 335

Ala Cys Asp Ala Ser Ser Tyr Leu Leu Ala Thr Leu Phe Trp Asp Gly
            340                 345                 350

Phe His Pro Ser Glu Lys Gly Tyr Lys Ala Val Ala Glu Ala Leu
        355                 360                 365

<210> SEQ ID NO 99
<211> LENGTH: 267
<212> TYPE: PRT
<213> ORGANISM: Streptomyces thermosacchari

<400> SEQUENCE: 99

Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
            35                  40                  45

Ser Tyr Ile Asp Ser Ser Gly Asp Cys His Arg Ser Asn Asn Ala Tyr
        50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110
```

```
Asp Ala Gly Phe Ala Asp Ala Met Thr Thr Cys Val Thr Ser Ser Asp
            115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Leu Gly Tyr Pro Arg Met Tyr Leu
                165                 170                 175

Ala Ser Asn Pro Trp Tyr Cys Leu Gly Leu Ser Asn Thr Lys Arg Ala
                180                 185                 190

Ala Ile Asn Thr Thr Ala Asp Thr Leu Asn Ser Val Ile Ser Ser Arg
            195                 200                 205

Ala Thr Ala His Gly Phe Arg Phe Gly Asp Val Arg Pro Thr Phe Asn
            210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 100
<211> LENGTH: 269
<212> TYPE: PRT
<213> ORGANISM: Streptomyces avermitilis

<400> SEQUENCE: 100

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
                20                  25                  30

Ala Ala Ala Thr Gly Tyr Val Ala Leu Gly Asp Ser Tyr Ser Ser Gly
            35                  40                  45

Val Gly Ala Gly Ser Tyr Leu Ser Ser Ser Gly Asp Cys Lys Arg Ser
    50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
            115                 120                 125

Leu Gln Ser Asp Ser Ala Cys Leu Ser Arg Ile Asn Thr Ala Lys Ala
130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
            165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Ala Asp Tyr Leu Asn Ser Ala Ile
            195                 200                 205

Ala Lys Arg Ala Ala Asp His Gly Phe Thr Phe Gly Asp Val Lys Ser
            210                 215                 220
```

```
Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
            245                 250                 255

Gln Ser Gly Gly Tyr Leu Pro Val Met Asn Ser Val Ala
        260                 265

<210> SEQ ID NO 101
<211> LENGTH: 372
<212> TYPE: PRT
<213> ORGANISM: Thermobifida fusca

<400> SEQUENCE: 101

Val Gly Ser Gly Pro Arg Ala Ala Thr Arg Arg Leu Phe Leu Gly
 1               5                  10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
 50                  55                  60

Asp Gly Glu Phe Leu Leu Leu Ser Pro Val Gln Ala Ala Thr Trp Gly
 65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335
```

```
Gly Glu Arg Val Ile Glu Gln Ile Thr Gly Pro Gly Arg Pro Leu
            340                 345                 350
Tyr Ala Thr Phe Ala Val Val Ala Gly Ala Thr Val Asp Thr Leu Ala
            355                 360                 365
Gly Glu Val Gly
    370
```

<210> SEQ ID NO 102
<211> LENGTH: 230
<212> TYPE: PRT
<213> ORGANISM: Aspergillus aculeatus

<400> SEQUENCE: 102

```
Thr Thr Val Tyr Leu Ala Gly Asp Ser Thr Met Ala Lys Asn Gly Gly
  1               5                  10                  15
Gly Ser Gly Thr Asn Gly Trp Gly Glu Tyr Leu Ala Ser Tyr Leu Ser
                 20                  25                  30
Ala Thr Val Val Asn Asp Ala Val Ala Gly Arg Ser Ala Arg Ser Tyr
             35                  40                  45
Thr Arg Glu Gly Arg Phe Glu Asn Ile Ala Asp Val Val Thr Ala Gly
         50                  55                  60
Asp Tyr Val Ile Val Glu Phe Gly His Asn Asp Gly Gly Ser Leu Ser
 65                  70                  75                  80
Thr Asp Asn Gly Arg Thr Asp Cys Ser Gly Thr Gly Ala Glu Val Cys
                 85                  90                  95
Tyr Ser Val Tyr Asp Gly Val Asn Glu Thr Ile Leu Thr Phe Pro Ala
                100                 105                 110
Tyr Leu Glu Asn Ala Ala Lys Leu Phe Thr Ala Lys Gly Ala Lys Val
            115                 120                 125
Ile Leu Ser Ser Gln Thr Pro Asn Asn Pro Trp Glu Thr Gly Thr Phe
        130                 135                 140
Val Asn Ser Pro Thr Arg Phe Val Glu Tyr Ala Glu Leu Ala Ala Glu
145                 150                 155                 160
Val Ala Gly Val Glu Tyr Val Asp His Trp Ser Tyr Val Asp Ser Ile
                165                 170                 175
Tyr Glu Thr Leu Gly Asn Ala Thr Val Asn Ser Tyr Phe Pro Ile Asp
            180                 185                 190
His Thr His Thr Ser Pro Ala Gly Ala Glu Val Val Ala Glu Ala Phe
        195                 200                 205
Leu Lys Ala Val Val Cys Thr Gly Thr Ser Leu Lys Ser Val Leu Thr
    210                 215                 220
Thr Thr Ser Phe Glu Gly
225                 230
```

<210> SEQ ID NO 103
<211> LENGTH: 184
<212> TYPE: PRT
<213> ORGANISM: Escherichia coli

<400> SEQUENCE: 103

```
Ala Asp Thr Leu Leu Ile Leu Gly Asp Ser Leu Ser Ala Gly Tyr Arg
  1               5                  10                  15
Met Ser Ala Ser Ala Ala Trp Pro Ala Leu Leu Asn Asp Lys Trp Gln
                 20                  25                  30
Ser Lys Thr Ser Val Val Asn Ala Ser Ile Ser Gly Asp Thr Ser Gln
             35                  40                  45
```

```
Gln Gly Leu Ala Arg Leu Pro Ala Leu Leu Lys Gln His Gln Pro Arg
     50                  55                  60

Trp Val Leu Val Glu Leu Gly Gly Asn Asp Gly Leu Arg Gly Phe Gln
 65                  70                  75                  80

Pro Gln Gln Thr Glu Gln Thr Leu Arg Gln Ile Leu Gln Asp Val Lys
                 85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180

<210> SEQ ID NO 104
<211> LENGTH: 308
<212> TYPE: PRT
<213> ORGANISM: Aeromonas hydrophila

<400> SEQUENCE: 104

Ile Val Met Phe Gly Asp Ser Leu Ser Asp Thr Gly Lys Met Tyr Ser
  1               5                  10                  15

Lys Met Arg Gly Tyr Leu Pro Ser Ser Pro Tyr Tyr Glu Gly Arg
                 20                  25                  30

Phe Ser Asn Gly Pro Val Trp Leu Glu Gln Leu Thr Asn Glu Phe Pro
             35                  40                  45

Gly Leu Thr Ile Ala Asn Glu Ala Glu Gly Gly Pro Thr Ala Val Ala
         50                  55                  60

Tyr Asn Lys Ile Ser Trp Asn Pro Lys Tyr Gln Val Ile Asn Asn Leu
 65                  70                  75                  80

Asp Tyr Glu Val Thr Gln Phe Leu Gln Lys Asp Ser Phe Lys Pro Asp
                 85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Thr Asp Ser Gln Leu Ser Ala Phe
225                 230                 235                 240
```

```
Asn Pro Gln Glu Arg Leu Ala Ile Ala Gly Asn Pro Leu Leu Ala Gln
            245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
            275                 280                 285

Ala Ala Leu Ser Glu Pro Ala Ala Thr Phe Ile Glu Ser Gln Tyr Glu
            290                 295                 300

Phe Leu Ala His
305

<210> SEQ ID NO 105
<211> LENGTH: 232
<212> TYPE: PRT
<213> ORGANISM: Aspergillus aculeatus

<400> SEQUENCE: 105

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
    130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
        195                 200                 205

Leu Lys Ala Val Val Cys Thr Gly Thr Ser Leu Lys Ser Val Leu Thr
    210                 215                 220

Thr Thr Ser Phe Glu Gly Thr Cys
225                 230

<210> SEQ ID NO 106
<211> LENGTH: 184
<212> TYPE: PRT
<213> ORGANISM: Escherichia coli

<400> SEQUENCE: 106

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
```

```
                    20                  25                  30
Ser Lys Thr Ser Val Val Asn Ala Ser Ile Ser Gly Asp Thr Ser Gln
            35                  40                  45

Gln Gly Leu Ala Arg Leu Pro Ala Leu Leu Lys Gln His Gln Pro Arg
        50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180
```

<210> SEQ ID NO 107
<211> LENGTH: 308
<212> TYPE: PRT
<213> ORGANISM: Aeromonas hydrophila

<400> SEQUENCE: 107

```
Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Gly Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
```

```
                210                 215                 220
Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala Ala Thr Phe Ile Glu Ser Gln Tyr Glu
    290                 295                 300

Phe Leu Ala His
305

<210> SEQ ID NO 108
<211> LENGTH: 167
<212> TYPE: PRT
<213> ORGANISM: Escherichia coli

<400> SEQUENCE: 108

Leu Leu Ile Leu Gly Asp Ser Leu Ser Ala Gly Tyr Arg Met Ser Ala
1               5                   10                  15

Ser Ala Ala Trp Pro Ala Leu Leu Asn Asp Lys Trp Gln Ser Lys Thr
            20                  25                  30

Ser Val Val Asn Ala Ser Ile Ser Gly Asp Thr Ser Gln Gln Gly Leu
        35                  40                  45

Ala Arg Leu Pro Ala Leu Leu Lys Gln His Gln Pro Arg Trp Val Leu
    50                  55                  60

Val Glu Leu Gly Gly Asn Asp Gly Leu Arg Gly Phe Gln Pro Gln Gln
65                  70                  75                  80

Thr Glu Gln Thr Leu Arg Gln Ile Leu Gln Asp Val Lys Ala Ala Asn
                85                  90                  95

Ala Glu Pro Leu Leu Met Gln Ile Arg Leu Pro Ala Asn Tyr Gly Arg
            100                 105                 110

Arg Tyr Asn Glu Ala Phe Ser Ala Ile Tyr Pro Lys Leu Ala Lys Glu
        115                 120                 125

Phe Asp Val Pro Leu Leu Pro Phe Phe Met Glu Glu Val Tyr Leu Lys
    130                 135                 140

Pro Gln Trp Met Gln Asp Asp Gly Ile His Pro Asn Arg Asp Ala Gln
145                 150                 155                 160

Pro Phe Ile Ala Asp Trp Met
                165

<210> SEQ ID NO 109
<211> LENGTH: 295
<212> TYPE: PRT
<213> ORGANISM: Aeromonas hydrophila

<400> SEQUENCE: 109

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Glu Gly Gly Pro Thr Ala Val Ala
    50                  55                  60
```

```
Tyr Asn Lys Ile Ser Trp Asn Pro Lys Tyr Gln Val Ile Asn Asn Leu
 65                  70                  75                  80

Asp Tyr Glu Val Thr Gln Phe Leu Gln Lys Asp Ser Phe Lys Pro Asp
             85                  90                  95

Asp Leu Val Ile Leu Trp Val Gly Ala Asn Asp Tyr Leu Ala Tyr Gly
        100                 105                 110

Trp Asn Thr Glu Gln Asp Ala Lys Arg Val Arg Asp Ala Ile Ser Asp
    115                 120                 125

Ala Ala Asn Arg Met Val Leu Asn Gly Ala Lys Glu Ile Leu Leu Phe
130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
    290                 295

<210> SEQ ID NO 110
<211> LENGTH: 1225
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (101)..(1141)

<400> SEQUENCE: 110
gcttttcttt tggaagaaaa tatagggaaa atggtacttg ttaaaaattc ggaatattta      60
tacaatatca tatgtttcac attgaaaggg gaggagaatc atg aaa caa caa aaa      115
                                              Met Lys Gln Gln Lys
                                                1               5 cgg ctt tac gcc cga ttg ctg acg ctg tta ttt gcg ctc atc ttc ttg      163
Arg Leu Tyr Ala Arg Leu Leu Thr Leu Leu Phe Ala Leu Ile Phe Leu
             10                  15                  20 ctg cct cat tct gca gct tca gca gca gat aca aga ccg gcg ttt agc      211
Leu Pro His Ser Ala Ala Ser Ala Ala Asp Thr Arg Pro Ala Phe Ser
         25                  30                  35 cgg atc gtc atg ttt gga gat agc ctg agc gat acg ggc aaa atg tat      259
Arg Ile Val Met Phe Gly Asp Ser Leu Ser Asp Thr Gly Lys Met Tyr
     40                  45                  50 agc aaa atg aga ggc tat ctt ccg tca agc ccg ccg tat tat gaa ggc      307
Ser Lys Met Arg Gly Tyr Leu Pro Ser Ser Pro Pro Tyr Tyr Glu Gly
```

```
              55                  60                  65
cgc ttt agc aat gga ccg gtc tgg ctg gaa caa ctg acg aaa caa ttt      355
Arg Phe Ser Asn Gly Pro Val Trp Leu Glu Gln Leu Thr Lys Gln Phe
 70                  75                  80                  85 ccg gga ctg acg atc gct aat gaa gca gaa gga gga gca aca gcg gtc      403
Pro Gly Leu Thr Ile Ala Asn Glu Ala Glu Gly Gly Ala Thr Ala Val
                 90                  95                 100 gcc tat aac aaa atc agc tgg gac ccg aaa tat cag gtc atc aac aac      451
Ala Tyr Asn Lys Ile Ser Trp Asp Pro Lys Tyr Gln Val Ile Asn Asn
                105                 110                 115 ctg gac tat gaa gtc aca cag ttt ctt cag aaa gac agc ttt aaa ccg      499
Leu Asp Tyr Glu Val Thr Gln Phe Leu Gln Lys Asp Ser Phe Lys Pro
                120                 125                 130 gat gat ctg gtc atc ctt tgg gtc ggc gcc aat gat tat ctg gcg tat      547
Asp Asp Leu Val Ile Leu Trp Val Gly Ala Asn Asp Tyr Leu Ala Tyr
135                 140                 145 ggc tgg aac aca gaa caa gat gcc aaa aga gtc aga gat gcc atc agc      595
Gly Trp Asn Thr Glu Gln Asp Ala Lys Arg Val Arg Asp Ala Ile Ser
150                 155                 160                 165 gat gcc gct aat aga atg gtc ctg aac ggc gcc aaa caa atc ctg ctg      643
Asp Ala Ala Asn Arg Met Val Leu Asn Gly Ala Lys Gln Ile Leu Leu
                170                 175                 180 ttt aac ctg ccg gat ctg gga caa aat ccg agc gcc aga agc caa aaa      691
Phe Asn Leu Pro Asp Leu Gly Gln Asn Pro Ser Ala Arg Ser Gln Lys
                185                 190                 195 gtc gtc gaa gca gtc agc cat gtc agc gcc tat cat aac aaa ctg ctg      739
Val Val Glu Ala Val Ser His Val Ser Ala Tyr His Asn Lys Leu Leu
                200                 205                 210 ctg aac ctg gca aga caa ttg gca ccg acg gga atg gtt aaa ttg ttt      787
Leu Asn Leu Ala Arg Gln Leu Ala Pro Thr Gly Met Val Lys Leu Phe
215                 220                 225 gaa att gac aaa cag ttt gcc gaa atg ctg aga gat ccg caa aat ttt      835
Glu Ile Asp Lys Gln Phe Ala Glu Met Leu Arg Asp Pro Gln Asn Phe
230                 235                 240                 245 ggc ctg agc gat gtc gaa aac ccg tgc tat gat ggc gga tat gtc tgg      883
Gly Leu Ser Asp Val Glu Asn Pro Cys Tyr Asp Gly Gly Tyr Val Trp
                250                 255                 260 aaa ccg ttt gcc aca aga agc gtc agc acg gat aga caa ctg tca gcg      931
Lys Pro Phe Ala Thr Arg Ser Val Ser Thr Asp Arg Gln Leu Ser Ala
                265                 270                 275 ttt agc ccg caa gaa aga ctg gca atc gcc gga aat ccg ctt ttg gca      979
Phe Ser Pro Gln Glu Arg Leu Ala Ile Ala Gly Asn Pro Leu Leu Ala
                280                 285                 290 caa gca gtt gct tca ccg atg gca aga aga tca gca agc ccg ctg aat     1027
Gln Ala Val Ala Ser Pro Met Ala Arg Arg Ser Ala Ser Pro Leu Asn
295                 300                 305 tgc gaa ggc aaa atg ttt tgg gat cag gtc cat ccg aca aca gtt gtc     1075
Cys Glu Gly Lys Met Phe Trp Asp Gln Val His Pro Thr Thr Val Val
310                 315                 320                 325 cat gct gcc ctt tca gaa aga gcg gcg acg ttt atc gaa aca cag tat     1123
His Ala Ala Leu Ser Glu Arg Ala Ala Thr Phe Ile Glu Thr Gln Tyr
                330                 335                 340 gaa ttt ctg gcc cat ggc tgagttaaca gaggacggat ttcctgaagg            1171
Glu Phe Leu Ala His Gly
                345 aaatccgttt tttatttta agcttggaga caaggtaaag gataaaacct cgag           1225

<210> SEQ ID NO 111
<211> LENGTH: 347
<212> TYPE: PRT
```

-continued

<213> ORGANISM: Artificial Sequence
<220> FEATURE:
<223> OTHER INFORMATION: Description of Artificial Sequence: Synthetic construct

<400> SEQUENCE: 111

```
Met Lys Gln Gln Lys Arg Leu Tyr Ala Arg Leu Leu Thr Leu Leu Phe
 1               5                   10                  15
Ala Leu Ile Phe Leu Leu Pro His Ser Ala Ala Ser Ala Ala Asp Thr
            20                  25                  30
Arg Pro Ala Phe Ser Arg Ile Val Met Phe Gly Asp Ser Leu Ser Asp
        35                  40                  45
Thr Gly Lys Met Tyr Ser Lys Met Arg Gly Tyr Leu Pro Ser Ser Pro
    50                  55                  60
Pro Tyr Tyr Glu Gly Arg Phe Ser Asn Gly Pro Val Trp Leu Glu Gln
65                  70                  75                  80
Leu Thr Lys Gln Phe Pro Gly Leu Thr Ile Ala Asn Glu Ala Glu Gly
                85                  90                  95
Gly Ala Thr Ala Val Ala Tyr Asn Lys Ile Ser Trp Asp Pro Lys Tyr
            100                 105                 110
Gln Val Ile Asn Asn Leu Asp Tyr Glu Val Thr Gln Phe Leu Gln Lys
        115                 120                 125
Asp Ser Phe Lys Pro Asp Asp Leu Val Ile Leu Trp Val Gly Ala Asn
    130                 135                 140
Asp Tyr Leu Ala Tyr Gly Trp Asn Thr Glu Gln Asp Ala Lys Arg Val
145                 150                 155                 160
Arg Asp Ala Ile Ser Asp Ala Ala Asn Arg Met Val Leu Asn Gly Ala
                165                 170                 175
Lys Gln Ile Leu Leu Phe Asn Leu Pro Asp Leu Gly Gln Asn Pro Ser
            180                 185                 190
Ala Arg Ser Gln Lys Val Val Glu Ala Val Ser His Val Ser Ala Tyr
        195                 200                 205
His Asn Lys Leu Leu Leu Asn Leu Ala Arg Gln Leu Ala Pro Thr Gly
    210                 215                 220
Met Val Lys Leu Phe Glu Ile Asp Lys Gln Phe Ala Glu Met Leu Arg
225                 230                 235                 240
Asp Pro Gln Asn Phe Gly Leu Ser Asp Val Glu Asn Pro Cys Tyr Asp
                245                 250                 255
Gly Gly Tyr Val Trp Lys Pro Phe Ala Thr Arg Ser Val Ser Thr Asp
            260                 265                 270
Arg Gln Leu Ser Ala Phe Ser Pro Gln Glu Arg Leu Ala Ile Ala Gly
        275                 280                 285
Asn Pro Leu Leu Ala Gln Ala Val Ala Ser Pro Met Ala Arg Arg Ser
    290                 295                 300
Ala Ser Pro Leu Asn Cys Glu Gly Lys Met Phe Trp Asp Gln Val His
305                 310                 315                 320
Pro Thr Thr Val Val His Ala Ala Leu Ser Glu Arg Ala Ala Thr Phe
                325                 330                 335
Ile Glu Thr Gln Tyr Glu Phe Leu Ala His Gly
            340                 345
```

METHOD

REFERENCE TO RELATED APPLICATIONS

This application is a continuation-in-part of U.S. patent application Ser. No. 11/182,408, filed Jul. 15, 2005, which is a is a continuation-in-part of International Patent Application PCT/IB2004/000655 filed Jan. 15, 2004 and published as WO 2004/064537 on Aug. 5, 2004 which claims priority to Great Britain Application Numbers 0301117.8, 0301118.6, 0301119.4, 0301120.2, 0301121.0, 0301122.8, all of which were filed Jan. 17, 2003, U.S. Patent Application No. 60/489,441 filed Jul. 23, 2003, and Great Britain Application Number 0330016.7 filed Dec. 24, 2003.

Reference is also made to the following related applications: U.S. application Ser. No. 09/750,990 filed on 20 Jul. 1999 and U.S. application Ser. No. 10/409,391 filed Apr. 8, 2003, International Patent Application Nos. PCT/IB2005/000575 filed Jan. 15, 2004 and published as WO2004/064987 on Aug. 5, 2004, PCT/IB2004/004378 filed Dec. 23, 2004 and published as WO 2005/066347 on Jul. 21, 2005, PCT/IB2004/004374 filed Dec. 23, 2004 and published as WO 2005/066351 on Jul. 21, 2005 and PCT/GB05/002823 filed Jul. 18, 2005 and published as WO2006/008508 on Jan. 26, 2006.

Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference.

FIELD OF INVENTION

The present invention relates to a method for the in situ production of an emulsifier within a foodstuff by use of a lipid acyltransferase.

The present invention further relates to a method for the in situ production of an emulsifier within a foodstuff by use of a lipid acyltransferase, wherein the method is such that the emulsifier is produced without increasing or without substantially increasing the free fatty acids in the foodstuff.

The present invention yet further relates to a method for the in situ production of at least two emulsifiers within a foodstuff by use of a lipid acyltransferase.

The present invention also relates to a method for the in situ production of a carbohydrate ester and/or a sterol ester and/or a stanol ester and/or a protein ester and/or glycerol ester and/or a hydroxy acid ester within a foodstuff by use of a lipid acyltransferase.

The present invention relates to a food enzyme composition and/or a feed enzyme composition, which contains a lipid acyltransferase, and the use of such a composition in the methods of the present invention.

The present invention further relates to a method of identifying suitable lipid acyltransferases in accordance with the present invention and to lipid acyltransferases so identified.

The present invention yet further relates to an immobilised lipid acyltransferase.

TECHNICAL BACKGROUND

The beneficial use of phospholipases and lipases (referred to as lipolytic enzymes, (EC. 3.1.1.x) used in food and/or feed industrial applications has been known for many years.

For instance, in EP 0 585 988 it is claimed that lipase addition to dough resulted in an improvement in the antistaling effect. It is suggested that a lipase obtained from *Rhizopus arrhizus* when added to dough can improve the quality of the resultant bread when used in combination with shortening/fat. WO94/04035 teaches that an improved softness can be obtained by adding a lipase to dough without the addition of any additional fat/oil to the dough. Castello, P. ESEGP 89-10 December 1999 Helsinki, shows that exogenous lipases can modify bread volume.

Lipolytic enzymes hydrolyse one or more of the fatty acids from lipids present in the food which can result in the formation of powerful emulsifier molecules within the foodstuff which provide commercially valuable functionality. The molecules which contribute the most significant emulsifier characteristics are the partial hydrolysis products, such as lyso-phospholipids, lyso-glycolipids, and mono-glyceride molecules. The polar lipid hydrolysis products, such as lyso-phospholipids and lyso-glycolipids are particularly advantageous. In bread making, such in situ derived emulsifiers can give equivalent functionality as emulsifiers, such as DATEM.

However, the activity of lipolytic enzymes also results in accumulation of free fatty acids, which can lead to detrimental functionality in the foodstuff. This inherent activity of lipolytic enzymes limits their functionality.

Numerous solutions to this problem have been attempted in the art. However, these result in a significant increase in free fatty acids in the foodstuff, particularly food stuffs with high water content, including, but not limited to bread doughs and egg yolk.

Phospholipases, particularly phospholipase A2 (E.C. 3.1.1.4), have been used for many years for the treatment of egg or egg-based products (see U.S. Pat. No. 4,034,124 and Dutihl & Groger 1981 J. Sci. Food Agric. 32, 451-458 for example). The phospholipase activity during the treatment of egg or egg-based products results in the accumulation of polar lysolecithin, which can act as an emulsifier. Phospholipase treatment of egg or egg-based products can improve the stability, thermal stability under heat treatment such as pasteurization and result in substantial thickening. Egg-based products may include, but are not limited to cake, mayonnaise, salad dressings, sauces, ice creams and the like. Use of phospholipases results in the accumulation of free fatty acids. The accumulation of free fatty acids can result in significant off-flavour. In addition, the accumulation of free fatty acids can result in enhanced susceptibility to oxidation, and hence result in poor shelf-life, product discoloration and alteration of other critical food characteristics such as flavour and texture. Recently, lipolytic enzymes with broader substrate specificity have been marketed for treatment of egg yolk and related food products. These have the advantage that, unlike most of the phospholipase A2s, they do not originate from a mammalian source. However, they result in significant accumulation of free fatty acids, not only due to the hydrolysis of phospholipids, but also triglycerides.

As mentioned above, another area where lipases have been extensively used is in the bakery industry. The use of phospholipases in baking dates bake to the early 1980s.

The substrate for lipases in wheat flour is 1.5-3% endogenous wheat lipids, which are a complex mixture of polar and non-polar lipids. The polar lipids can be divided into glycolipids and phospholipids. These lipids are built up of glycerol esterified with two fatty acids and a polar group. The polar group contributes to surface activity of these lipids.

Enzymatic cleavage of one of the fatty acids in these lipids leads to lipids with a much higher surface activity. It is well known that emulsifiers, such as DATEM, with high surface activity are very functional when added to dough.

However, the use of lipases (E.C. 3.1.1.X) in dough products may have a detrimental impact on yeast activity, and/or a negative effect on bread volume. The negative effect on bread volume is often explained by overdosing. Overdosing can lead to a decrease in gluten elasticity which results in a dough which is too stiff and thus results in reduced bread volumes. In addition, or alternatively, such lipases can degrade shortening, oil or milk fat added to the dough, resulting in off-flavour in the dough and baked product. Overdosing and off flavour have been attributed to the accumulation of free fatty acids in the dough.

In EP 1 193 314, EP 0 977 869 and also in WO 01/39602, the use of lipolytic enzymes active on glycolipids was reported to be particularly beneficial in application in bread making as the partial hydrolysis products the lyso-glycolipids were found to have very high emulsifier functionality, apparently resulting in a higher proportion of positive emulsifier functionality compared to the detrimental accumulation of free fatty acids. However, the enzymes were also found to have significant non selective activity on triglyceride which resulted in unnecessarily high free fatty acid.

The same finding was reported in WO 00/32758, which disclosed lipolytic enzyme variants with enhanced activity on phospholipids and/or glycolipids, in addition to variants which had a preference for long rather than short chain fatty acids. This latter feature, also disclosed in WO 01/39602, was deemed of particular importance to prevent the off-flavours associated with the accumulation of free short chain fatty acids. However, significant free fatty acids are produced.

The problem of high triglyceride activity was addressed in WO02/094123, where the use of lipolytic enzymes active on the polar lipids (i.e. glycolipids and phospholipids) in a dough, but substantially not active on triglycerides or 1-mono-glycerides is taught. However, significant free fatty acids are produced.

Some lipolytic enzymes have low or no activity on the lyso form of polar lipids (e.g. glycolipids/phospholipids). The use of such enzymes has been deemed preferable as they ensure the accumulation of the highly polar lyso-lipids, resulting in optimal functionality. Free fatty acids do however accumulate. This selective functionality is characteristic of phospholipase A2 enzymes, and the glycolipases disclosed in EP 0 977 869, EP 1 193 314, and WO01/39602. Variant enzymes of less selective lipolytic enzymes have been produced which have a lower activity on the lyso-polar lipids when compared to the parent enzyme (WO03/060112). However, significant free fatty acids are produced.

WO00/05396 teaches a process for preparing a foodstuff comprising an emulsifier, wherein food material is contacted with an enzyme such that an emulsifier is generated by the enzyme from a fatty acid ester and a second functional ingredient is generated from a second constituent. WO00/05396 teaches the use of in particular a lipase or esterase enzyme. Nowhere in WO00/05396 is the specific use of a lipid acyltransferase taught. In addition, in foodstuffs with high water content, the use of the esterases and lipases as taught in WO00/05396 would result in significant accumulation of free fatty acids.

A disadvantage associated with the use of lipases, including phospholipases and glycolipases, may be caused by the build-up of free fatty acids released from the lipids. Over the past couple of decades the use of lipolytic enzymes in foodstuffs has been limited due to the balance between the detrimental accumulation of free fatty acids and the production of the lyso-lipids which provide positive functionality. Although numerous strategies in the art have been attempted, some of which provided significant improvements in functionality, none have completely addressed and solved the fundamental problem in the art, i.e. the significant accumulation of free fatty acids in foodstuffs prepared using lipolytic enzymes in situ.

The presence of high levels of free fatty acids (FFA) in raw materials or food products is generally recognised as a quality defect and food processors and customers will usually include a maximum FFA level in the food specifications. The resulting effects of excess FFA levels can be in organoleptic and/or functional defects.

A result of lipolysis is hydrolytic rancidity, with the formation of characteristic "soapy" flavour. This "soapy" taste is especially acute with fatty acids of intermediate chain length (C8-C12) which, although not present in high concentrations, may be important constituents of, for example, dairy products or vegetable oils. A more common organoleptic defect is due to the combined effects of lipolytic enzymes and oxidation processes. Unsaturated fatty acids are more susceptible to enzymatic oxidation when unesterified than when esterified in acyl lipids.

Functional defects in food due to high FFA levels are recognised, but less readily explained. Without wishing to be bound by theory, the hydrolysis of unchanged lipids to carboxylic acids will increase [H+] and produce carbonyl groups that can combine with other compounds or metal ions. Free fatty acids also combine proteins by hydrophobic interactions and can complex with starch during cooking. FFA may also interfere with the action of surface-active agents, such as polar lipids and emulsifiers. (Lipid in Cereal Technology, P. J. Barnes, Academic Press 1983.)

WO03/100044 discloses a class of acyl transferases known as PDATs (or ATWAX). These enzymes use a monoglyceride or a diglyceride as the acceptor molecule, and phosphatidylcholine (PC) as the donor molecule to produce the following products: lyso phosphatidylcholine and triacylglycerol and/or diacylglycerol.

In one embodiment, the present invention relates to improvements in the incorporation of whey proteins into food products, providing for improved yields without impairing the qualities—such as the texture—of the food compositions and products.

Cheese compositions are typically prepared from dairy liquids by processes that include treating the liquid with a coagulating or clotting agent. The coagulating agent may be a curding enzyme, an acid or a suitable bacterial culture, or it may include such a culture. The curd that results generally incorporates transformed casein, fats including natural butter fat, and flavourings that arise especially when a bacterial culture is used. The curd may be separated from the liquid whey, which contains soluble proteins not affected by the coagulation and that therefore are not incorporated into the curd.

Whey is thus a by-product of manufacturing in commercial processes that produce food products—such as cheeses. Traditionally, whey is disposed of as unused waste or used as fertiliser or animal feed or processed into a food ingredient.

The inability of whey proteins to be substantially retained in the curd is an important factor contributing to a lack of efficiency in the conventional production of dairy products—such as cheese curds—and to a reduction in overall yield relating to the incorporation of all the protein solids that are present in the starting dairy liquids into resulting cheese curds.

There have been numerous attempts to include whey proteins in cheese e.g. by heat treatment of the milk, heat treatment of whey, or by filtration—such as ultrafiltration.

There are also several descriptions of the use of specific proteases to induce aggregation of whey proteins. A serine protease derived from *Bacillus licheniformis* has been shown to have the ability to induce aggregation of whey proteins (U.S. Pat. No. 5,523,237).

However, there remains many difficulties associated with adding whey proteins in processes such as the manufacture of cheeses. For example, incorporation of whey protein into cheeses is associated with a deterioration in the taste and mouth-feel of the product, and furthermore tends to interfere with curding and subsequent processing of the product. Proteases that have been previously reported that can be added to cheese milk for hydrolysis of whey proteins result in significant hydrolysis of the caseins as described by Madsen, J. S. & Qvist, K. B. (1997) Hydrolysis of milk protein by a *Bacillus licheniformis* protease specific for acidic amino acid residues. *J. Food Sci.* 62, 579-582.

Thus, there is a need in the art for methods and compositions that provide for the improved incorporation of whey protein into food products while maintaining organoleptic and other desirable properties. Such optimisation would result in increased efficiency, higher yields of food products, and reduced overall material costs.

Lipase:cholesterol acyltransferases have been known for some time (see for example Buckley—Biochemistry 1983, 22, 5490-5493). In particular, glycerophospholipid:cholesterol acyl transferases (GCATs) have been found, which like the plant and/or mammalian lecithin:cholesterol acyltransferases (LCATs), will catalyse fatty acid transfer between phosphatidylcholine and cholesterol.

Upton and Buckley (TIBS 20, May 1995 p 178-179) and Brumlik and Buckley (J. of Bacteriology April 1996 p 2060-2064) teach a lipase/acyltransferase from *Aeromonas hydrophila* which has the ability to carry out acyl transfer to alcohol acceptors in aqueous media.

SUMMARY ASPECTS OF THE PRESENT INVENTION

According to a first aspect of the present invention there is provided a method of in situ production of an emulsifier in a foodstuff, wherein the method comprises the step of adding to the foodstuff a lipid acyltransferase as defined herein.

In a further aspect, the present invention provides a method of in situ production of an emulsifier in a foodstuff, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of in situ production of an emulsifier and either a sterol ester and/or a stanol ester in a foodstuff, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of in situ production of an emulsifier and either a sterol ester and/or a stanol ester in a foodstuff, wherein the method comprises the step of adding a lipid acyltransferase to the foodstuff.

According to another aspect of the present invention there is provided a method for the in situ production of at least two emulsifiers in a foodstuff, wherein the method comprises the step of adding to the foodstuff a lipid acyltransferase.

According to a further aspect of the present invention there is provided a method of in situ production of at least two emulsifiers and either a sterol ester and/or a stanol ester in a foodstuff, wherein the method is such that the emulsifiers are produced without increasing or without substantially increasing the free fatty acids in the foodstuff, and wherein the method comprises the step of adding a lipid acyltransferase to the foodstuff.

According to a further aspect of the present invention there is provided a method of in situ production of at least two emulsifiers and either a sterol ester and/or a stanol ester in a foodstuff, wherein the method comprises the step of adding a lipid acyltransferase to the foodstuff.

In a further aspect, the present invention provides a method for the in situ production of a carbohydrate ester in a foodstuff, wherein the method comprises the step of adding a lipid acyltransferase to the foodstuff.

In another aspect, the present invention provides a method for the in situ production of a carbohydrate ester together with an emulsifier in a foodstuff, wherein the method comprises the step of adding a lipid acyltransferase to the foodstuff.

In another aspect, the present invention provides a method of in situ production of an emulsifier, and one or more of a carbohydrate ester; a sterol ester; a stanol ester; a protein ester; a monoglyceride or a diglyceride in a foodstuff, and wherein the method comprises the step of adding a lipid acyltransferase to the foodstuff.

According to a further aspect of the present invention there is provided a method of production of a foodstuff comprising an emulsifier, wherein the method comprises the step of adding to the foodstuff a lipid acyltransferase as defined herein.

In a further aspect, the present invention provides a method of production of a foodstuff comprising an emulsifier, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of the production of a foodstuff comprising an emulsifier and either a sterol ester and/or a stanol ester, wherein the method is such that the emulsifier is produced without increasing or without substantially increasing the free fatty acids in the foodstuff, and wherein the method comprises the step of adding a lipid acyltransferase to the foodstuff.

In another aspect, the present invention provides a method of the production of a foodstuff comprising an emulsifier and either a sterol ester and/or a stanol ester, wherein the method comprises the step of adding a lipid acyltransferase to the foodstuff.

According to a further aspect of the present invention there is provided a method for the production of a foodstuff comprising at least two emulsifiers, wherein the method comprises the step of adding to the foodstuff a lipid acyltransferase.

According to a further aspect of the present invention there is provided a method of the production of a foodstuff comprising at least two emulsifiers and either a sterol ester and/or a stanol ester, wherein the method is such that the emulsifiers are produced without increasing or without substantially increasing the free fatty acids in the foodstuff, and wherein the method comprises the step of adding a lipid acyltransferase to the foodstuff.

According to a further aspect of the present invention there is provided a method of the production of a foodstuff comprising at least two emulsifiers and either a sterol ester and/or a stanol ester, wherein the method comprises the step of adding a lipid acyltransferase to the foodstuff.

In a further aspect, the present invention provides a method for the production of a foodstuff comprising a carbohydrate ester, wherein the method comprises the step of adding a lipid acyltransferase to the foodstuff.

In another aspect, the present invention provides a method for the production of a foodstuff comprising a carbohydrate ester and an emulsifier, wherein the method comprises the step of adding a lipid acyltransferase to the foodstuff.

In another aspect, the present invention provides a method of the production of a foodstuff comprising an emulsifier and one or more of a carbohydrate ester; a sterol ester; a stanol ester; a protein ester; a monoglyceride or a diglyceride, and wherein the method comprises the step of adding a lipid acyltransferase to the foodstuff.

In another aspect, the present invention provides use of a lipid acyltransferase to prepare from a food material a foodstuff comprising an emulsifier, wherein the emulsifier is generated from constituents of the food material by the lipid acyltransferase.

In a further aspect, the present invention provides use of a lipid acyltransferase to prepare from a food material a foodstuff comprising an emulsifier, wherein the emulsifier is produced without increasing or without substantially increasing the free fatty acids in the foodstuff, and wherein the emulsifier is generated from constituents of the food material by the lipid acyltransferase.

In another aspect, the present invention provides use of a lipid acyltransferase to prepare from a food material a foodstuff comprising an emulsifier and either a sterol ester and/or a stanol ester, wherein the emulsifier is produced without increasing or without substantially increasing the free fatty acids in the foodstuff, and wherein the emulsifier and/or sterol ester and/or stanol ester is/are generated from constituents of the food material by the lipid acyltransferase.

In another aspect, the present invention provides use of a lipid acyltransferase to prepare from a food material a foodstuff comprising an emulsifier and either a sterol ester and/or a stanol ester, wherein the emulsifier and/or sterol ester and/or stanol ester is/are generated from constituents of the food material by the lipid acyltransferase.

In another aspect, the present invention provides use of a lipid acyltransferase to prepare from a food material a foodstuff comprising at least two emulsifiers, wherein the two emulsifiers are generated from constituents of the food material by the lipid acyltransferase.

According to a further aspect of the present invention there is provided use of a lipid acyltransferase to prepare from a food material a foodstuff comprising at least two emulsifiers and either a sterol ester and/or a stanol ester, wherein the emulsifiers are produced without increasing or without substantially increasing the free fatty acids in the foodstuff, and wherein one or both of the emulsifiers and/or the sterol ester and/or the stanol ester is/are generated from constituents of the food material by the lipid acyltransferase.

According to a further aspect of the present invention there is provided use of a lipid acyltransferase to prepare from a food material a foodstuff comprising at least two emulsifiers and either a sterol ester and/or a stanol ester, wherein one or both of the emulsifiers and/or the sterol ester and/or the stanol ester is/are generated from constituents of the food material by the lipid acyltransferase.

In a further aspect, the present invention provides use of a lipid acyltransferase to prepare from a food material a foodstuff comprising a carbohydrate ester, wherein the carbohydrate ester is generated from constituents of the food material by the lipid acyltransferase.

In another aspect, the present invention provides use of a lipid acyltransferase to prepare from a food material a foodstuff comprising at least a carbohydrate ester and a further emulsifier, wherein the carbohydrate ester and the emulsifier are generated from constituents of the food material by the lipid acyltransferase.

In another aspect, the present invention provides use of a lipid acyltransferase to prepare from a food material a foodstuff comprising an emulsifier and one or more of a carbohydrate ester; a sterol ester; a stanol ester; a protein ester; a monoglyceride or a diglyceride, and wherein the emulsifier and/or the carbohydrate ester and/or the sterol ester and/or the stanol ester and/or the protein ester and/or the monoglyceride and/or the diglyceride is/are generated from constituents of the food material by the lipid acyltransferase.

In accordance with a further aspect of the present invention there is provided a method of the in situ production of an emulsifier, preferably a lysolecithin and a sterol ester in a egg based foodstuff, wherein the method is such that the emulsifier is produced without increasing or without substantially increasing the free fatty acids in the foodstuff, and wherein the method comprises the step of adding a lipid acyltransferase to the foodstuff.

In accordance with a further aspect of the present invention there is provided a method of the in situ production of an emulsifier, preferably a lysolecithin, and a sterol ester in an egg based foodstuff, wherein the method comprises the step of adding a lipid acyltransferase to the foodstuff.

In another aspect, the present invention provides a method of production of a egg based foodstuff comprising an emulsifier, preferably a lysolecithin, and a sterol ester in an egg based foodstuff, wherein the emulsifier is produced without increasing or without substantially increasing the free fatty acids in the foodstuff, and wherein the method comprises the step of adding a lipid acyltransferase to the foodstuff.

In another aspect, the present invention provides a method of production of an egg based foodstuff comprising an emulsifier, preferably a lysolecithin, and a sterol ester in an egg based foodstuff, wherein the method comprises the step of adding a lipid acyltransferase to the foodstuff.

In a further aspect, the present invention further provides a foodstuff obtainable by, preferably obtained by, a method according to the present invention.

In another aspect the present invention further relates to a food enzyme composition and/or a feed enzyme composition, which contains a lipid acyltransferase, and the use of such a composition in the methods of the present invention.

In accordance with a further aspect of the present invention there is provided a method of identifying a suitable lipid acyltransferase for use in accordance with the present invention, comprising the steps of testing an enzyme of interest using one or more of the "Transferase Assay in a Low Water environment", the "Transferase Assay in High Water Egg Yolk" or the "Transferase Assay in Buffered Substrate", and selecting a lipid acyltransferase if it is one which has one or more of the following characteristics: (a) when tested using the "Transferase Assay in a Low Water Environment", measured after a time period selected from 30, 20 or 120 minutes, has a relative transferase activity of at least 1%; (b) when tested using the "Transferase Assay in High Water Egg Yolk" in an egg yolk with 54% water, has up to 100% relative transferase activity; or (c) when tested using the "Transferase Assay in Buffered Substrate" has at least 2% acyltransferase activity.

The present invention yet further provides a lipid acyltransferase identified using a method according to the present invention.

In accordance with a further aspect, the present invention provides an immobilised lipid acyltransferase enzyme as defined herein.

DETAILED ASPECTS OF THE PRESENT INVENTION

The term "lipid acyltransferase" as used herein means an enzyme which as well as having lipase activity (generally classified as E.C. 3.1.1.x in accordance with the Enzyme Nomenclature Recommendations (1992) of the Nomenclature Committee of the International Union of Biochemistry and Molecular Biology) also has acyltransferase activity (generally classified as E.C. 2.3.1.x), whereby the enzyme is capable of transferring an acyl group from a lipid to one or more acceptor substrates, such as one or more of the following: a sterol; a stanol; a carbohydrate; a protein; a protein subunit; glycerol.

The lipid acyltransferase for use in the methods and/or uses of the present invention may be one as described in WO2004/064537 or WO2004/064987, or PCT/IB2004/004378 or GB0513859.9, or PCT/GB05/002823. These documents are incorporated herein by reference.

The lipid acyltransferase for use in the methods and/or uses of the present invention may be a natural lipid acyltransferase or may be a variant lipid acyltransferase.

Preferably, the lipid acyltransferase for use in the methods and/or uses of the present invention is capable of transferring an acyl group from a lipid (as defined herein) to one or more of the following acyl acceptor substrates: a sterol, a stanol, a carbohydrate, a protein or subunits thereof, or a glycerol.

For some aspects the "acyl acceptor" according to the present invention may be any compound comprising a hydroxy group (—OH), such as for example, polyvalent alcohols, including glycerol; sterol; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water.

In one embodiment, the acyl acceptor is preferably not a monoglyceride and/or a diglyceride.

In one aspect, preferably the enzyme is capable of transferring an acyl group from a lipid to a sterol and/or a stanol.

In one aspect, preferably the enzyme is capable of transferring an acyl group from a lipid to a carbohydrate.

In one aspect, preferably the enzyme is capable of transferring an acyl group from a lipid to a protein or a subunit thereof. Suitably the protein subunit may be one or more of the following: an amino acid, a protein hydrolysate, a peptide, a dipeptide, an oligopeptide, a polypeptide.

Suitably in the protein or protein subunit the acyl acceptor may be one or more of the following constituents of the protein or protein subunit: a serine, a threonine, a tyrosine, or a cysteine.

When the protein subunit is an amino acid, suitably the amino acid may be any suitable amino acid. Suitably the amino acid may be one or more of a serine, a threonine, a tyrosine, or a cysteine for example.

In one aspect, preferably the enzyme is capable of transferring an acyl group from a lipid to glycerol.

In one aspect, preferably the enzyme is capable of transferring an acyl group from a lipid to a hydroxy acid.

In one aspect, preferably the enzyme is capable of transferring an acyl group from a lipid to a polyvalent alcohol.

In one aspect, the lipid acyltransferase may, as well as being able to transfer an acyl group from a lipid to a sterol and/or a stanol, additionally be able to transfer the acyl group from a lipid to one or more of the following: a carbohydrate, a protein, a protein subunit, glycerol.

Preferably, the lipid substrate upon which the lipid acyltransferase according to the present invention acts is one or more of the following lipids: a phospholipid, such as a lecithin, e.g. phosphatidylcholine, a triacylglyceride, a cardiolipin, a diglyceride, or a glycolipid, such as digalactosyldiglyceride (DGDG) for example. This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the lipid substrate upon which the lipid acyltransferase acts is a phospholipid, such as lecithin, for example phosphatidylcholine.

For some aspects, preferably the lipid substrate is a glycolipid, such as DGDG for example.

Preferably the lipid substrate is a food lipid, that is to say a lipid component of a foodstuff.

For some aspects, preferably the lipid acyltransferase according to the present invention is incapable, or substantially incapable, of acting on a triglyceride and/or a 1-monoglyceride and/or 2-monoglyceride.

Suitably, the lipid substrate or lipid acyl donor may be one or more lipids present in one or more of the following substrates: fats, including lard, tallow and butter fat; oils including oils extracted from or derived from palm oil, sunflower oil, soya bean oil, safflower oil, cotton seed oil, ground nut oil, corn oil, olive oil, peanut oil, coconut oil, and rape seed oil. Lecithin from soya, rape seed or egg yolk is also a suitable lipid substrate. The lipid substrate may be an oat lipid or other plant based material containing galactolipids.

In one aspect the lipid acyl donor is preferably lecithin (such as phosphatidylcholine) in egg yolk.

For some aspects of the present invention, the lipid may be selected from lipids having a fatty acid chain length of from 8 to 22 carbons.

For some aspects of the present invention, the lipid may be selected from lipids having a fatty acid chain length of from 16 to 22 carbons, more preferably of from 16 to 20 carbons.

For some aspects of the present invention, the lipid may be selected from lipids having a fatty acid chain length of no greater than 14 carbons, suitably from lipids having a fatty acid chain length of from 4 to 14 carbons, suitably 4 to 10 carbons, suitably 4 to 8 carbons.

Suitably, the lipid acyltransferase according to the present invention may exhibit one or more of the following lipase activities: glycolipase activity (E.C. 3.1.1.26), triacylglycerol lipase activity (E.C. 3.1.1.3), phospholipase A2 activity (E.C. 3.1.1.4) or phospholipase A1 activity (E.C. 3.1.1.32). The term "glycolipase activity" as used herein encompasses "galactolipase activity".

Suitably, the lipid acyltransferase according to the present invention may have at least one or more of the following activities: glycolipase activity (E.C. 3.1.1.26) and/or phospholipase A1 activity (E.C. 3.1.1.32) and/or phospholipase A2 activity (E.C. 3.1.1.4).

For some aspects, the lipid acyltransferase according to the present invention may have at least glycolipase activity (E.C. 3.1.1.26).

Suitably, for some aspects the lipid acyltransferase according to the present invention may be capable of transferring an acyl group from a glycolipid and/or a phospholipid to one or more of the following acceptor substrates: a sterol, a stanol, a carbohydrate, a protein, glycerol.

For some aspects, preferably the lipid acyltransferase according to the present invention is capable of transferring an acyl group from a glycolipid and/or a phospholipid to a sterol and/or a stanol to form at least a sterol ester and/or a stanol ester.

For some aspects, preferably the lipid acyltransferase according to the present invention is capable of transferring an acyl group from a glycolipid and/or a phospholipid to a carbohydrate to form at least a carbohydrate ester.

For some aspects, preferably the lipid acyltransferase according to the present invention is capable of transferring an acyl group from a glycolipid and/or a phospholipid to a protein to form at least protein ester (or a protein fatty acid condensate).

For some aspects, preferably the lipid acyltransferase according to the present invention is capable of transferring an acyl group from a glycolipid and/or a phospholipid to glycerol to form at least a diglyceride and/or a monoglyceride.

In one embodiment the acyl acceptor is glycerol. The glycerol may be naturally comprised in the foodstuff and/or food material comprising the acyl donor (i.e. the phospholipid for example) —such as butter fat, milk or cream for instance. Alternatively the glycerol may be added to the foodstuff and/or food material comprising the acyl donor (i.e. the phospholipids for example) —such as butterfat, milk or cream— either prior to, during or subsequent to the addition of lipid acyl transferase enzyme.

For some aspects, preferably the lipid acyltransferase according to the present invention does not exhibit triacylglycerol lipase activity (E.C. 3.1.1.3) or significant triacylglycerol lipase activity (E.C. 3.1.1.3).

In some aspects, the lipid acyltransferase may be capable of transferring an acyl group from a lipid to a sterol and/or a stanol. Thus, in one embodiment the "acyl acceptor" according to the present invention may be either a sterol or a stanol or a combination of both a sterol and a stanol.

In one embodiment suitably the sterol and/or stanol may comprise one or more of the following structural features:
 i) a 3-beta hydroxy group or a 3-alpha hydroxy group; and/or
 ii) A:B rings in the cis position or A:B rings in the trans position or $C_5$-$C_6$ is unsaturated.

Suitable sterol acyl acceptors include cholesterol and phytosterols, for example alpha-sitosterol, beta-sitosterol, stigmasterol, ergosterol, campesterol, 5,6-dihydrosterol, brassicasterol, alpha-spinasterol, beta-spinasterol, gamma-spinasterol, deltaspinasterol, fucosterol, dimosterol, ascosterol, serebisterol, episterol, anasterol, hyposterol, chondrillasterol, desmosterol, chalinosterol, poriferasterol, clionasterol, sterol glycosides, and other natural or synthetic isomeric forms and derivatives.

In one aspect of the present invention suitably more than one sterol and/or stanol may act as the acyl acceptor, suitably more than two sterols and/or stanols may act as the acyl acceptor. In other words, in one aspect of the present invention, suitably more than one sterol ester and/or stanol ester may be produced. Suitably, when cholesterol is the acyl acceptor one or more further sterols or one or more stanols may also act as the acyl acceptor. Thus, in one aspect, the present invention provides a method for the in situ production of both a cholesterol ester and at least one sterol or stanol ester in combination. In other words, the lipid acyltransferase for some aspects of the present invention may transfer an acyl group from a lipid to both cholesterol and at least one further sterol and/or at least one stanol.

In one aspect, preferably the sterol acyl acceptor is one or more of the following: alpha-sitosterol, beta-sitosterol, stigmasterol, ergosterol and campesterol.

In one aspect, preferably the sterol acyl acceptor is cholesterol. When it is the case that cholesterol is the acyl acceptor for the lipid acyltransferase, the amount of free cholesterol in the foodstuff is reduced as compared with the foodstuff prior to exposure to the lipid acyltransferase and/or as compared with an equivalent foodstuff which has not been treated with the lipid acyltransferase.

Advantageously, preferably the level of cholesterol in the foodstuff (for example a dairy product, such as cheese, milk, cream, butterfat or ice cream for instance) is reduced compared with a control foodstuff (for example a dairy product, such as cheese, milk, cream, butterfat or ice cream for instance), e.g. one which has not been treated with a lipid acyltransferase in accordance with the present invention).

In another embodiment the acyl acceptor is cholesterol. The cholesterol may be naturally comprised in the foodstuff and/or food material comprising the acyl donor (i.e. the phospholipid for example) —such as butter fat, milk or cream for instance. Alternatively the cholesterol may be added to the foodstuff and/or food material comprising the acyl donor (i.e. the phospholipids for example) —such as butterfat, milk or cream—either prior to, during or subsequent to the addition of lipid acyl transferase enzyme.

Suitable stanol acyl acceptors include phytostanols, for example beta-sitostanol or ss-sitostanol.

In one aspect, preferably the sterol and/or stanol acyl acceptor is a sterol and/or a stanol other than cholesterol.

In some aspects, the foodstuff prepared in accordance with the present invention may be used to reduce blood serum cholesterol and/or to reduce low density lipoprotein. Blood serum cholesterol and low density lipoproteins have both been associated with certain diseases in humans, such as atherosclerosis and/or heart disease for example. Thus, it is envisaged that the foodstuffs prepared in accordance with the present invention may be used to reduce the risk of such diseases.

Thus, in one aspect the present invention provides the use of a foodstuff according to the present invention for use in the treatment and/or prevention of atherosclerosis and/or heart disease.

In a further aspect, the present invention provides a medicament comprising a foodstuff according to the present invention.

In a further aspect, the present invention provides a method of treating and/or preventing a disease in a human or animal patient which method comprising administering to the patient an effective amount of a foodstuff according to the present invention.

Suitably, the sterol and/or the stanol "acyl acceptor" may be found naturally within the foodstuff. Alternatively, the sterol and/or the stanol may be added to the foodstuff. When it is the case that a sterol and/or a stanol is added to the foodstuff, the sterol and/or stanol may be added before, simultaneously with, and/or after the addition of the lipid acyltransferase according to the present invention. Suitably, the present invention may encompass the addition of exogenous sterols/stanols, particularly phytosterols/phytostanols, to the foodstuff prior to or simultaneously with the addition of the enzyme according to the present invention.

For some aspects, one or more sterols present in the foodstuff may be converted to one or more stanols prior to or at the same time as the lipid acyltransferase is added according to the present invention. Any suitable method for converting sterols to stanols may be employed. For example, the conversion may be carried out by chemical hydrogenation for example. The conversion may be conducted prior to the addition of the lipid acyltransferase in accordance with the present invention or simultaneously with the addition of the lipid acyltransferase in accordance with the present invention. Suitably enzymes for the conversion of sterol to stanols are taught in WO00/061771.

Suitably the present invention may be employed to produce phytostanol esters in situ in a foodstuff. Phytostanol esters have increased solubility through lipid membranes, bioavailability and enhanced health benefits (see for example WO92/99640).

In some embodiments of the present invention the stanol ester and/or the sterol ester may be a flavouring and/or a texturiser. In which instances, the present invention encompasses the in situ production of flavourings and/or texturisers.

For some aspects of the present invention, the lipid acyltransferase according to the present invention may utilise a carbohydrate as the acyl acceptor. The carbohydrate acyl acceptor may be one or more of the following: a monosaccharide, a disaccharide, an oligosaccharide or a polysaccharide. Preferably, the carbohydrate is one or more of the following: glucose, fructose, anhydrofructose, maltose, lactose, sucrose, galactose, xylose, xylooligosacharides, arabinose, maltooligosaccharides, tagatose, microthecin, ascopyrone P, ascopyrone T, cortalcerone.

Suitably, the carbohydrate "acyl acceptor" may be found naturally within the foodstuff. Alternatively, the carbohydrate may be added to the foodstuff. When it is the case that the carbohydrate is added to the foodstuff, the carbohydrate may be added before, simultaneously with, and/or after the addition of the lipid acyltransferase according to the present invention.

Carbohydrate esters can function as valuable emulsifiers in foodstuffs. Thus, when it is the case that the enzyme functions to transfer the acyl group to a sugar, the invention encompasses the production of a second in situ emulsifier in the foodstuff.

In some embodiments, the lipid acyltransferase may utilise both a sterol and/or stanol and a carbohydrate as an acyl acceptor.

The utilisation of lipid acyltransferase which can transfer the acyl group to a carbohydrate as well as to a sterol and/or a stanol is particularly advantageous for foodstuffs comprising eggs. In particular, the presence of sugars, in particular glucose, in eggs and egg products is often seen as disadvantageous. Egg yolk may comprise up to 1% glucose. Typically, egg or egg based products may be treated with glucose oxidase to remove some or all of this glucose. However, in accordance with the present invention this unwanted sugar can be readily removed by "esterifying" the sugar to form a sugar ester.

For some aspects of the present invention, the lipid acyltransferase according to the present invention may utilise a protein as the acyl acceptor. Suitably, the protein may be one or more of the proteins found in a food product, for example in a dairy product and/or a meat product. By way of example only, suitable proteins may be those found in curd or whey, such as lactoglobulin. Other suitable proteins include ovalbumin from egg, gliadin, glutenin, puroindoline, lipid transfer proteins from grains, and myosin from meat.

Thus in accordance with the present invention, one or more of the following advantageous properties can be achieved: in situ production of an emulsifier without an increase in free fatty acids; a reduction in the accumulation of free fatty acids in the foodstuff; a reduction in free cholesterol levels in the foodstuff, an increase in sterol esters and/or stanol esters; a reduction in blood serum cholesterol and/or low density lipoproteins; an increase in carbohydrate esters; a reduction in unwanted free carbohydrates.

An advantage of the present invention is that the emulsifier(s) is/are prepared in situ in the foodstuff without an increase, or a substantial, increase, in the free fatty acid content of the foodstuff. The production of free fatty acids can be detrimental to foodstuffs. In particular, free fatty acids have been linked with off-odours and/or off-flavours in foodstuffs, as well other detrimental effects, including a soapy taste in cheese for instance. Preferably, the method according to the present invention results in the in situ preparation of an emulsifier(s) wherein the accumulation of free fatty acids is reduced and/or eliminated. Without wishing to be bound by theory, in accordance with the present invention the fatty acid which is removed from the lipid is transferred by the lipid acyltransferase to an acyl acceptor, for example a sterol and/or a stanol. Thus, the overall level of free fatty acids in the foodstuff does not increase or increases only to an insignificant degree. This is in sharp contradistinction to the situation when lipases (E.C. 3.1.1.x) are used to produce emulsifiers in situ. In particular, the use of lipases can result in an increased amount of free fatty acid in the foodstuff, which can be detrimental. In accordance with the present invention, the accumulation of free fatty acids is reduced and/or eliminated when compared with the amount of free fatty acids which would have been accumulated had a lipase enzyme, in particular a phospholipase A enzyme, been used in place of the lipid acyltransferase in accordance with the present invention.

The utilisation of a lipid acyltransferase which can transfer the acyl group to a sterol and/or stanol may be particularly advantageous for foodstuffs comprising eggs. In particular, it has been found that an egg-based product with significantly better properties can be obtained following treatment with a lipid acyltransferase as defined herein compared with egg-based products treated with conventional phospholipases, such as LipopanF® (Novozymes A/S, Denmark)), Lecitase Ultra® (Novozymes A/S, Denmark) or Lipomod 22 L from Biocatalysts, for instance.

In another aspect the acyl acceptor may be ascorbic acid or comprises ascorbic acid. Therefore ascorbic acid bay be added to the foodstuff and/or food material, or aqueous emulsion, possibly in combination with an appropriate level of glycerol and optionally sterol/stanols. Ascorbic ester is an antioxidant. The use of ascorbic acid may be especially preferred when used in a foodstuff as the anti-oxidant properties can act as a preservation agent, e.g. to prevent or reduce oxidation of lipids. In this way the use of ascorbic acid in the foodstuff and/or food material of the present invention can prevent or reduce rancidity in the modified foodstuff and/or food material. Therefore the use of asorbic acid may be particularly useful for use in dairy products where rancidity can be a problem, for example in cheese. The amount of ascorbic acid added may be very low, e.g. at a level of up to $\frac{1}{5}^{th}$, such as up to $\frac{1}{10}^{th}$ or up to $\frac{1}{100}^{th}$ the amounts recommended for the addition of glycerol as herein defined. Preferably, the range of ascorbic acid should be 0.02-0.5 wt %. In a preferable embodiment the ascorbic acid is added in the form of an ascorbyl-palmitate, e.g. for use as an anti-oxidant in oil, and the dosage is preferably between 0.1 and 0.2 wt % corresponding to preferably between 0.04-0.08 wt % ascorbic acid.

In a preferred embodiment the modified foodstuff and/or food material treated in accordance with the present invention comprises lysophospholipid, preferably lysolecithin, preferably the foodstuff and/or food material treated in accordance with the present invention comprises at least 0.001 wt %, such as 0.005 wt %, including at least 0.01 wt %, lysophospholipid, preferably lysolecithin, more preferably at least 0.05 wt %, or at least 0.1 wt %, lysophospholipid, preferably lysolecithin. Higher concentrations of lysophospholipid, preferably lysolecethin, are also envisaged, such as at least 0.5 wt %, or at least 1 wt %, lysophospholipid, preferably lysolecithin, including at least 2 wt %, or at least 5%, lysophospholipid, preferably lysolecithin.

In a preferred embodiment the food stuff and/or food material treated in accordance with the present invention comprises one or more of the following glycerophosphatylcholine/phosphatylethanolamine phosphatylinositol and phosphatylserine, preferably the foodstuff and/or the food material treated in accordance with the present invention comprises at least 0.001 wt % of one or more of the following glycerophosphatylcholine/phosphatylethanolamine phosphatylinositol and phosphatylserine, such as 0.005 wt %, including at least 0.01 wt %, more preferably at least 0.05 wt %, or at least 0.1 wt %, one or more of the following glycerophosphatylcholine/phosphatylethanolamine phosphatylinositol and phosphatylserine. Higher concentrations of one or more of the following glycerophosphatylcholine/phosphatylethanolamine phosphatylinositol and phosphatylserine, are also envisaged, such as at least 0.5 wt %, or at least 1 wt %, including at least 2 wt %, or at least 5%, It is preferable that the modified foodstuff and/or food material described in the above paragraph comprises glycerophosphatylcholine.

When the modified foodstuff and/or food material comprises glycerophosphatylcholine, the modified foodstuff and/or food material may comprise of less than 0.001 wt % lysophospholipid, such as lysolecithin. This may comprise less than 0.0005 wt % lysophospholipid, including the embodiment where the modified foodstuff and/or food material comprises no lysophospholipid.

In a preferred embodiment the modified foodstuff and/or food material comprises at least 0.001 wt % monoglyceride such as 0.005 wt %, including at least 0.01 wt % monoglyceride, more preferably at least 0.05 wt % monoglyceride, or at least 0.1 wt % monoglyceride. Higher concentrations of monoglyceride, are also envisaged, such as at least 0.5 wt % monoglyceride, or at least 1 wt % monoglyceride, including at least 2 wt % monoglyceride, or at least 5%, monoglyceride.

In a preferred embodiment the modified foodstuff and/or food material comprises at least 0.001 wt % sterol ester such as 0.005 wt %, including at least 0.01 wt % sterol ester, more preferably at least 0.05 wt % sterol ester, or at least 0.1 wt % sterol ester. Higher concentrations of sterol ester, are also envisaged, such as at least 0.5 wt % sterol ester.

In one embodiment, i.e. where the acyl acceptor is glycerol for instance, the functional ingredient of the present invention is generated by a reaction selected from alcoholysis, preferably glycerolysis.

A preferred temperature for the modification of the foodstuff and/or food material according to processes of the invention may depend on several factors including the temperature optima and stability of the enzyme used, the melting point and viscosity of the foodstuff and/or food material, the volume of the foodstuff and/or food material to be modified, the heat stability of the foodstuff and/or food material.

For example, in one embodiment the enzyme modification may occur between 10-70° C., such as 10 to 32° C., or 10 to 34° C. including between 10-20° C., more preferably between 20-60° C., such as between 30-60° C., or 36-60° C., such as 37-60° C., including between 40-60° C.

For the enzyme modification of milk and/or cream for example it may be preferable to use a temperature of less than about 50° C., such as between about 10 to 34° C. for example, or between about 36-49° C. for example, or between about 40-49° C. for example, or between about 40 to 45° C. for example, or between about 45-49° C. for example. Suitable temperatures of between 20-50° C. may be used, such as between 30-40° C. for example.

In some embodiments, an advantage of the use of a lipid acyltransferase herein disclosed may be that it has a high thermal stability and may therefore be used in the treatment of a foodstuff and/or food material at a temperature where the viscosity of said foodstuff and/or food material is low. The high thermal stability may also allow lower dosages of enzyme to be used.

Suitably, for some embodiments the lipid acyltransferase may have a temperature optima of between about 50 to about 70° C. for example. Suitably, for some embodiments a lipid acyltransferase may have a temperature stability, as measured using the PLU assay, wherein said acyltransferase retains at least about 25%, such as at least about 50% of its activity after 1 hour at 55° C.

The process for the treatment of the foodstuff and/or food material according to the invention may occur over any suitable time period. This may depend for example on the temperature used and enzyme dosage. By way of example only the time period may be between about 1 minute and about 4 hours, such as between about 5 minutes to about 2 hours, or between about 10 minutes to about 1 hour, or between about 5 minutes to about 30 minutes or between about 1 minute to about 29 minutes or between about 31 minutes to about 60 minutes. Suitably the time period may be between about 5 minutes and 1 hour.

The enzyme dosage may be in any suitable dosage, for example the enzyme dosage, when added in terms of PLU activity, may be dosed between about 1-10,000 PLU/kg foodstuff and/or food material, such as between 5-5000 PLU/kg foodstuff and/or food material, such as between 100-1000 PLU/kg foodstuff and/or food material, or 1000 to 3000 PLU/kg foodstuff and/or food material. 50 to 1000 PLU/kg foodstuff and/or food material may be preferable in some embodiments for a lipid acyl transferase.

Preferably, the lipid acyltransferase enzyme according to the present invention may be characterised using the following criteria:
(i) the enzyme possesses acyl transferase activity which may be defined as ester transfer activity whereby the acyl part of an original ester bond of a lipid acyl donor is transferred to an acyl acceptor to form a new ester; and
(ii) the enzyme comprises the amino acid sequence motif GDSX, wherein X is one or more of the following amino acid residues L, A, V, I, F, Y, H, Q, T, N, M or S.

Preferably, X of the GDSX motif is L or Y. More preferably, X of the GDSX motif is L. Thus, preferably the enzyme according to the present invention comprises the amino acid sequence motif GSDL (SEQ ID NO: 14).

The GDSX motif is comprised of four conserved amino acids. Preferably, the serine within the motif is a catalytic serine of the lipid acyltransferase enzyme. Suitably, the serine of the GDSX motif may be in a position corresponding to Ser-16 in *Aeromonas hydrophila* lipolytic enzyme taught in Brumlik & Buckley (Journal of Bacteriology April 1996, Vol. 178, No. 7, p 2060-2064).

To determine if a protein has the GDSX motif according to the present invention, the sequence is preferably compared with the hidden markov model profiles (HMM profiles) of the pfam database.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft D H (2002) Brief Bioinform 3; 236-245. (abstracts available from National Center fro Biotechnology Information website maintained in conjunction with the National Library of Medicine and the National Institutes of Health.

For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several servers which are currently located websites maintained by the Sanger Institute (UK) in conjunction with Wellcome Trust Institute, the HHMI Janelia Farm Research Campus, the Institut National de la Recherche Agronomique, and the Center for Genomics and Bioinformatics of the Karolinska Institutet, among others.

The database offers a search facility where one can enter a protein sequence. Using the default parameters of the database the protein sequence will then be analysed for the presence of Pfam domains. The GDSX domain is an established domain in the database and as such its presence in any query sequence will be recognised. The database will return the alignment of the Pfam00657 consensus sequence to the query sequence.

A multiple alignment, including *Aeromonas salmonicida* or *Aeromonas hydrophila* can be obtained by:
a) manual
obtain an alignment of the protein of interest with the Pfam00657 consensus sequence and obtain an alignment of P10480 with the Pfam00657 consensus sequence following the procedure described above;
or
b) through the database
After identification of the Pfam00657 consensus sequence the database offers the option to show an alignment of the query sequence to the seed alignment of the Pfam00657 consensus sequence. P10480 is part of this seed alignment and is indicated by GCAT_AERHY. Both the query sequence and P10480 will be displayed in the same window.

The *Aeromonas hydrophila* reference sequence:

The residues of *Aeromonas hydrophila* GDSX lipase are numbered in the NCBI file P10480, the numbers in this text refer to the numbers given in that file which in the present invention is used to determine specific amino acids residues which, in a preferred embodiment are present in the lipid acyltransferase enzymes of the invention.

The Pfam alignment was performed (FIGS. 33 and 34): The following conserved residues can be recognised and in a preferable embodiment may be present in the enzymes for use in the compositions and methods of the invention;

| Block 1 - GDSX block | | | | | | | |
|---|---|---|---|---|---|---|---|
| hid | hid | hid | hid | Gly | Asp | Ser | hid |
| 28 | 29 | 30 | 31 | 32 | 33 | 34 | 35 |

| Block 2 - GANDY block | | | | | |
|---|---|---|---|---|---|
| hid | Gly | hid | Asn | Asp | hid |
| 130 | 131 | 132 | 133 | 134 | 135 |

| Block 3 - HPT block |
|---|
| His |
| 309 |

Where 'hid' means a hydrophobic residue selected from Met, Ile, Leu, Val, Ala, Gly, Cys, His, Lys, Trp, Tyr, Phe.

Preferably the lipid acyltransferase enzyme for use in the compositions/methods of the invention can be aligned using the Pfam00657 consensus sequence.

Preferably, a positive match with the hidden markov model profile (HMM profile) of the pfam00657 domain family indicates the presence of the GDSL (SEQ ID NO: 14) or GDSX domain according to the present invention.

Preferably when aligned with the Pfam00657 consensus sequence the lipid acyltransferase for use in the compositions/methods of the invention have at least one, preferably more than one, preferably more than two, of the following, a GDSx block, a GANDY (SEQ ID NO: 15) block, a HPT block. Suitably, the lipid acyltransferase may have a GDSx block and a GANDY (SEQ ID NO: 15) block. Alternatively, the enzyme may have a GDSx block and a HPT block. Preferably the enzyme comprises at least a GDSx block.

Preferably, residues of the GANDY (SEQ ID NO: 15) motif are selected from GANDY (SEQ ID NO: 15), GGNDA (SEQ ID NO: 16), GGNDL (SEQ ID NO: 18), most preferably GANDY (SEQ ID NO: 15).

Preferably, when aligned with the Pfam00657 consensus sequence the enzyme for use in the compositions/methods of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophilia* polypeptide sequence, namely SEQ ID No. 32: 28hid, 29hid, 30hid, 31hid, 32gly, 33Asp, 34Ser, 35hid, 130hid, 131Gly, 132Hid, 133Asn, 134Asp, 135hid, 309His The pfam00657 GDSX domain is a unique identifier which distinguishes proteins possessing this domain from other enzymes.

The pfam00657 consensus sequence is presented in FIG. 1 as SEQ ID No. 1. This is derived from the identification of the pfam family 00657, database version 6, which may also be referred to as pfam00657.6 herein.

The consensus sequence may be updated by using further releases of the pfam database.

For example, FIGS. 33 and 34 show the pfam alignment of family 00657, from database version 11, which may also be referred to as pfam00657.11 herein.

The presence of the GDSx, GANDY (SEQ ID NO: 15) and HPT blocks are found in the pfam family 00657 from both releases of the database. Future releases of the pfam database can be used to identify the pfam family 00657.

Preferably, the lipid acyltransferase enzyme according to the present invention may be characterised using the following criteria:
  (i) the enzyme possesses acyl transferase activity which may be defined as ester transfer activity whereby the acyl part of an original ester bond of a lipid acyl donor is transferred to an acyl acceptor to form a new ester;
  (ii) the enzyme comprises the amino acid sequence motif GDSX, wherein X is one or more of the following amino acid residues L, A, V, I, F, Y, H, Q, T, N, M or S;
  (iii) the enzyme comprises His-309 or comprises a histidine residue at a position corresponding to His-309 in the *Aeromonas hydrophila* lipolytic enzyme shown in FIG. 2 (SEQ ID No. 2 or SEQ ID No. 32).

Preferably, the amino acid residue of the GDSX motif is L.

In SEQ ID No. 2 or SEQ ID No. 32 the first 18 amino acid residues form a signal sequence. His-309 of the full length sequence, that is the protein including the signal sequence, equates to His-291 of the mature part of the protein, i.e. the sequence without the signal sequence.

Preferably, the lipid acyltransferase enzyme according to the present invention comprises the following catalytic triad: Ser-34, Asp-306 and His-309 or comprises a serine residue, an aspartic acid residue and a histidine residue, respectively, at positions corresponding to Ser-34, Asp-306 and His-309 in the *Aeromonas hydrophila* lipolytic enzyme shown in FIG. 2 (SEQ ID No. 2) or FIG. 28 (SEQ ID No. 32). As stated above, in the sequence shown in SEQ ID No. 2 or SEQ ID No. 32 the first 18 amino acid residues form a signal sequence. Ser-34, Asp-306 and His-309 of the full length sequence, that is the protein including the signal sequence, equate to Ser-16, Asp-288 and His-291 of the mature part of the protein, i.e. the sequence without the signal sequence. In the pfam00657 consensus sequence, as given in FIG. 1 (SEQ ID No. 1) the active site residues correspond to Ser-7, Asp-345 and His-348.

Preferably, the lipid acyltransferase enzyme according to the present invention may be characterised using the following criteria:
  (i) the enzyme possesses acyl transferase activity which may be defined as ester transfer activity whereby the acyl part of an original ester bond of a first lipid acyl donor is transferred to an acyl acceptor to form a new ester; and
  (ii) the enzyme comprises at least Gly-32, Asp-33, Ser-34, Asp-306 and His-309 or comprises glycine, aspartic acid, serine, aspartic acid and histidine residues at positions corresponding to Gly-32, Asp-33, Ser-34, Asp-306 and His-309, respectively, in the *Aeromonas hydrophila* lipolytic enzyme shown in FIG. 2 (SEQ ID No. 2) or FIG. 28 (SEQ ID No. 32).

Suitably, the lipid acyltransferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter*, Vibrionaceae, *Xylella, Sulfolobus, Aspergillus, Schizosaccharomyces, Listeria, Neisseria, Mesorhizobium, Ralstonia, Xanthomonas* and *Candida*.

Suitably, the lipid acyltransferase enzyme according to the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Lactobacillus helveticus, Desulfitobacterium dehalogenans, Bacillus* sp, *Campylobacter jejuni*, Vibrionaceae, *Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis* and *Candida parapsilosis*.

In one aspect, preferably the lipid acyltransferase enzyme according to the present invention is obtainable, preferably obtained, from one or more of *Aeromonas hydrophila* or *Aeromonas salmonicida*.

Suitably, the lipid acyltransferase enzyme according to the present invention may be encoded by any one of the following nucleotide sequences:
  (a) the nucleotide sequence shown as SEQ ID No. 7 (see FIG. 9);
  (b) the nucleotide sequence shown as SEQ ID No. 8 (see FIG. 10);
  (c) the nucleotide sequence shown as SEQ ID No. 9 (see FIG. 11);
  (d) the nucleotide sequence shown as SEQ ID No. 10 (see FIG. 12);
  (e) the nucleotide sequence shown as SEQ ID No. 11 (see FIG. 13);
  (f) the nucleotide sequence shown as SEQ ID No. 13 (see FIG. 15);
  (g) the nucleotide sequence shown as SEQ ID No. 21 (see FIG. 17);
  (h) the nucleotide sequence shown as SEQ ID No. 23 (see FIG. 19);
  (i) the nucleotide sequence shown as SEQ ID No. 25 (see FIG. 21);
  (j) the nucleotide sequence shown as SEQ ID No. 27 (see FIG. 23);
  (k) the nucleotide sequence shown as SEQ ID No. 29 (see FIG. 25);
  (l) the nucleotide sequence shown as SEQ ID No. 31 (see FIG. 27);
  (m) the nucleotide sequence shown as SEQ ID No. 33 (see FIG. 29);
  (n) the nucleotide sequence shown as SEQ ID No. 35 (see FIG. 31);
  (o) the nucleotide sequence shown as SEQ ID No. 46 (see FIG. 95);
  (p) the nucleotide sequence shown as SEQ ID No. 75 (see FIG. 87);
  (q) the nucleotide sequence shown as SEQ ID No. 77 (see FIG. 89);
  (r) the nucleotide sequence shown as SEQ ID No. 78 (see FIG. 90);
  (s) the nucleotide sequence shown as SEQ ID No. 81 (see FIG. 93);
  (t) the nucleotide sequence shown as SEQ ID No. 83 (see FIG. 37);
  (u) the nucleotide sequence shown as SEQ ID No. 87 (see FIG. 99);
  (v) the nucleotide sequence shown as SEQ ID No. 88 (see FIG. 100);
  (w) or a nucleotide sequence which has 70% or more, preferably 75% or more, identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 46, SEQ ID No. 75, SEQ ID No. 77, SEQ ID No. 78, SEQ ID No. 81, SEQ ID No. 83, SEQ ID No.87, or SEQ ID No. 88.^^

Suitably the lipid acyltransferase encoded by the nucleotide sequence of any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 46, SEQ ID No. 75, SEQ ID No. 77, SEQ ID No. 78, SEQ ID No. 81, SEQ ID No. 83, SEQ ID No.87, or SEQ ID No. 88 or by a nucleotide sequence which has 70% or more, preferably 75% or more, identity with any one of the sequences shown as SEQ ID No. 7, SEQ ID No. 8, SEQ ID No. 9, SEQ ID No. 10, SEQ ID No. 11, SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 46, SEQ ID No. 75, SEQ ID No. 77, SEQ ID No. 78, SEQ ID No. 81, SEQ ID No. 83, SEQ ID No.87, or SEQ ID No. 88 may be post-transcriptionally and/or post-translationally modified.

Suitably the nucleotide sequence may have 80% or more, preferably 85% or more, more preferably 90% or more and even more preferably 95% or more identity with any one of the sequences shown as SEQ ID No. 7, SEQ ID No. 8, SEQ ID No. 9, SEQ ID No. 10, SEQ ID No. 1, SEQ ID No. 13, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 46, SEQ ID No. 75, SEQ ID No. 77, SEQ ID No. 78, SEQ ID No. 81, SEQ ID No. 83, SEQ ID No.87, or SEQ ID No. 88.

In one embodiment, the nucleotide sequence encoding a lipid acyltransferase enzyme for use in the methods and uses of the present invention is a nucleotide sequence which has 70% or more, preferably 75% or more, identity with any one of the sequences shown as: SEQ ID No. 88, SEQ ID No. 7, SEQ ID No. 8, SEQ ID No. 33, and SEQ ID No. 34. Suitably the nucleotide sequence may have 80% or more, preferably 85% or more, more preferably 90% or more and even more preferably 95% or more identity with any one of the sequences shown as: SEQ ID No. 88, SEQ ID No. 7, SEQ ID No. 8, SEQ ID No. 33, and SEQ ID No. 34.

In one embodiment, the nucleotide sequence encoding a lipid acyltransferase enzyme for use in the methods and uses of the present invention is a nucleotide sequence which has 70% or more, 75% or more, 80% or more, preferably 85% or more, more preferably 90% or more and even more preferably 95% or more identity the sequence shown as SEQ ID No. 88.

Suitably, the lipid acyltransferase enzyme according to the present invention may comprise one or more of the following amino acid sequences:

(i) the amino acid sequence shown as SEQ ID No. 2 (see FIG. 2)
(ii) the amino acid sequence shown as SEQ ID No. 3 (see FIG. 3)
(iii) the amino acid sequence shown as SEQ ID No. 4 (see FIG. 4)
(iv) the amino acid sequence shown as SEQ ID No. 5 (see FIG. 5)
(v) the amino acid sequence shown as SEQ ID No. 6 (see FIG. 6)
(vi) the amino acid sequence shown as SEQ ID No. 12 (see FIG. 14)
(vii) the amino acid sequence shown as SEQ ID No. 20 (FIG. 16)
(viii) the amino acid sequence shown as SEQ ID No. 22 (FIG. 18)
(ix) the amino acid sequence shown as SEQ ID No. 24 (FIG. 20)
(x) the amino acid sequence shown as SEQ ID No. 26 (FIG. 22)
(xi) the amino acid sequence shown as SEQ ID No. 28 (FIG. 24)
(xii) the amino acid sequence shown as SEQ ID No. 30 (FIG. 26)
(xiii) the amino acid sequence shown as SEQ ID No. 32 (FIG. 28)
(xiv) the amino acid sequence shown as SEQ ID No. 34 (FIG. 30)
(xv) the amino acid sequence shown as SEQ ID No. 62 (FIG. 74)
(xvi) the amino acid sequence shown as SEQ ID No. 90 (FIG. 102) or
an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 62 or SEQ ID No. 90.

Suitably, the lipid acyltransferase enzyme according to the present invention may comprise either the amino acid sequence shown as SEQ ID No. 2 or as SEQ ID No. 3 or SEQ ID No. 32 or SEQ ID No. 34 or SEQ ID No. 62 or SEQ ID No. 90 or may comprise an amino acid sequence which has 75% or more, preferably 80% or more, preferably 85% or more, preferably 90% or more, preferably 95% or more, identity with the amino acid sequence shown as SEQ ID No. 2 or the amino acid sequence shown as SEQ ID No. 3 or the amino acid sequence shown as SEQ ID No. 32 or the amino acid sequence shown as SEQ ID No. 34 or the amino acid sequence shown as SEQ ID No.62 or the amino acid sequence shown as SEQ ID No.90.

For the purposes of the present invention, the degree of identity is based on the number of sequence elements which are the same. The degree of identity in accordance with the present invention for amino acid sequences may be suitably determined by means of computer programs known in the art, such as Vector NTI 10 (Invitrogen Corp.). For pairwise alignment the score used is preferably BLOSUM62 with Gap opening penalty of 10.0 and Gap extension penalty of 0.1.

Suitably the lipid acyltransferase enzyme according to the present invention comprises an amino acid sequence which has 80% or more, preferably 85% or more, more preferably 90% or more and even more preferably 95% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, or SEQ ID No. 34.

Suitably, the lipid acyltransferase enzyme according to the present invention may comprise one or more of SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34 or SEQ ID No. 62 before being post-translationally modified. The present invention also encompasses the use of a lipid acyltransferase enzyme which has been post-translationally modified, wherein the originally translated enzyme or pro-enzyme comprises one or more of SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, or SEQ ID No. 62.

In one embodiment the lipid acyltransferase enzyme according to the present invention may be a fragment of one or more of the amino acid sequences SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 62 or SEQ ID No. 90. In one embodiment preferably the amino acid sequence fragment has 70% or more, preferably 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 62 or SEQ ID No. 90 when determined over the whole of the sequence shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 62 or SEQ ID No. 90 respectively.

In one embodiment, suitably the lipid acyl transferase in accordance with the present invention comprises (or consists of) the amino acid sequence shown in SEQ ID No. 90 or comprises (or consists of) an amino acid sequence which has at least 70%, at least 75%, at least 85%, at least 90%, at least 95%, at least 98% identity to SEQ ID No. 90.

Suitably, the lipid acyltransferase enzyme according to the present invention comprises one or more of the following amino acid sequences:
(a) an amino acid sequence shown as amino acid residues 1-100 of SEQ ID No. 2 or SEQ ID No. 32;
(b) an amino acid sequence shown as amino acids residues 101-200 of SEQ ID No. 2 or SEQ ID No. 32;
(c) an amino acid sequence shown as amino acid residues 201-300 of SEQ ID No. 2 or SEQ ID No. 32; or
(d) an amino acid sequence which has 75% or more, preferably 85% or more, more preferably 90% or more, even more preferably 95% or more identity to any one of the amino acid sequences defined in (a)-(c) above.

Suitably, the lipid acyltransferase enzyme according to the present invention comprises one or more of the following amino acid sequences:
(a) an amino acid sequence shown as amino acid residues 28-39 of SEQ ID No. 2 or SEQ ID No. 32;
(b) an amino acid sequence shown as amino acids residues 77-88 of SEQ ID No. 2 or SEQ ID No. 32;
(c) an amino acid sequence shown as amino acid residues 126-136 of SEQ ID No. 2 or SEQ ID No. 32;
(d) an amino acid sequence shown as amino acid residues 163-175 of SEQ ID No. 2 or SEQ ID No. 32;
(e) an amino acid sequence shown as amino acid residues 304-311 of SEQ ID No. 2 or SEQ ID No. 32; or
(f) an amino acid sequence which has 75% or more, preferably 85% or more, more preferably 90% or more, even more preferably 95% or more identity to any one of the amino acid sequences defined in (a)-(e) above.

In one aspect, the lipid acyl transferase for use in the method and uses of the present invention may be the lipid acyl transferase from *Candida parapsilosis* as taught in EP 1 275 711. Thus in one aspect the lipid acyl transferase for use in the method and uses of the present invention may be a lipid acyl transferase comprising one of the amino acid sequences taught in SEQ ID No. 63 or SEQ ID No. 64.

Much by preference, the lipid acyltransferase for use in the method and uses of the present invention may be a lipid acyl transferase (lipid acyltransferase) comprising the amino acid sequence shown as SEQ ID No. 62, or the amino acid sequence shown as SEQ ID No. 90 or an amino acid sequence which has 75% or more, preferably 85% or more, more preferably 90% or more, even more preferably 95% or more, even more preferably 98% or more, or even more preferably 99% or more identity to SEQ ID No. 62 or SEQ ID No. 90. This enzyme may be considered a variant enzyme.

In one aspect, the lipid acyltransferase according to the present invention may be a lecithin:cholesterol acyltransferases (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the lipid acyltransferase enzyme according to the present invention may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NICMB 41204 and NCIMB 41205, respectively.

Highly preferred lipid acyltransferase (in particular a phospholipid glycerol acyl transferase) for use in the methods of the invention include those isolated from *Aeromonas* spp., preferably *Aeromonas hydrophila* or *A. salmonicida*, most preferable *A. salmonicida*. Most preferred lipid acyl transferases for use in the present invention are encoded by one of SEQ ID No.s 2, 3, 32, 34, 62 or 90. It will be recognised by the skilled person that it is preferable that the signal peptides of the acyl transferase has been cleaved during expression of the transferase. The signal peptide of SEQ ID 2, 3, 32, 34, 62 and 90 are amino acids 1-18. Therefore the most preferred regions are amino acids 19-335 for SEQ ID No. 32 and SEQ ID No. 2 (*A. hydrophilia*) and amino acids 19-336 for SEQ ID No. 3, SEQ ID No. 34, SEQ ID No. 62 and SEQ ID No. 90. (*A. salmonicida*). When used to determine the homology of identity of the amino acid sequences, it is preferred that the alignments as herein described use the mature sequence. The mature sequence may be on which has the signal peptide removed and/or may be one which has been post-translationally modified.

Therefore the most preferred regions for determining homology (identity) are amino acids 19-335 for SEQ ID No.s 32 and 2 (*A. hydrophilia*) and amino acids 19-336 for SEQ ID No.s 3, 34 and 62. (*A. salmonicida*). SEQ ID No.s 73 and 74 are "mature" (i.e. without signal peptide) protein sequences of the highly preferred lipid acyl transferases from *A. hydrophilia* and *A. salmonicida* respectively. SEQ ID Nos. 73 and 74 may or may not undergo further post-translational modification.

A lipid acyl transferase for use in the invention may also be isolated from *Thermobifida*, preferably *T. fusca*, most preferably that encoded by SEQ ID No. 67.

A lipid acyl transferase for use in the invention may also be isolated from *Streptomyces*, preferable *S. avermitis*, most preferably that encoded by SEQ ID No. 71. Other possible enzymes for use in the present invention from *Streptomyces* include those encoded by SEQ ID Nos. 4, 5, 20, 22, 24, 26, 28, 30, 70, 72.

An enzyme for use in the invention may also be isolated from *Corynebacterium*, preferably *C. efficiens*, most preferably that encoded by SEQ ID No. 68.

Suitably, the lipid acyltransferase for use in the methods and uses according to the present invention may be a lipid acyltransferase comprising any one of the amino acid sequences shown as SEQ ID Nos. 76, 77, 79, 80, 82, 84, or 86 or an amino acid sequence which has at least 70%, 75%, 80%, 85%, 90%, 95%, 96%, 97% or 98% identity therewith, or encoded by any one of the nucleotide sequences shown as SEQ ID Nos. 75, 78, 81, 83, 85, or 87 or a nucleotide sequence which has at least 70%, 75%, 80%, 85%, 90%, 95%, 96%, 97% or 98% identity therewith.

In one embodiment the lipid acyltransferase for use in the methods and uses according to the present invention is preferably a lipid acyltransferase encoded by a nucleic acid selected from the group consisting of:
 a) a nucleic acid comprising a nucleotide sequence shown in SEQ ID No. 75;
 b) a nucleic acid which is related to the nucleotide sequence of SEQ ID No. 75 by the degeneration of the genetic code; and
 c) a nucleic acid comprising a nucleotide sequence which has at least 70% identity with the nucleotide sequence shown in SEQ ID No. 75.

In one embodiment, the lipid acyltransferase for use in the methods and uses according to the present invention is preferably a lipid acyltransferase comprising an amino acid sequence as shown in SEQ ID No. 76 or an amino acid sequence which has at least 60% identity thereto.

In a further embodiment the lipid acyltransferase for use in the methods and uses according to the present invention may be a lipid acyltransferase comprising any one of the amino acid sequences shown as SEQ ID No. 76, 77, 79, 80, 82, 84 or 86 or an amino acid sequence which has at least 70%, 75%, 80%, 85%, 90%, 95%, 96%, 97% or 98% identity therewith, or encoded by any one of the nucleotide sequences shown as SEQ ID No. 78, 81, 83, 85 or 87 or a nucleotide sequence which has at least 70%, 75%, 80%, 85%, 90%, 95%, 96%, 97% or 98% identity therewith.

In a further embodiment the lipid acyltransferase for use in the methods and uses according to the present invention may be a lipid acyltransferase comprising any one of amino sequences shown as SEQ ID No. 77, 79, 80, 84 or 86 or an amino acid sequence which has at least 70%, 75%, 80%, 85%, 90%, 95%, 96%, 97% or 98% identity therewith for the uses described herein.

In a further embodiment the lipid acyltransferase for use in the methods and uses according to the present invention may be a lipid acyltransferase comprising any one of amino sequences shown as SEQ ID No. 77, 79, or 86 or an amino acid sequence which has at least 70%, 75%, 80%, 85%, 90%, 95%, 96%, 97% or 98% identity therewith for the uses described herein.

More preferably in one embodiment the lipid acyltransferase for use in the methods and uses according to the present invention may be a lipid acyltransferase comprising the amino acid sequence shown as SEQ ID No. 86 or an amino acid sequence which has at least 70%, 75%, 80%, 85%, 90%, 95%, 96%, 97% or 98% identity therewith.

In another embodiment the lipid acyl transferase for use in the methods and uses according to the present invention may be a lipid acyltransferase comprising the amino acid sequence shown as SEQ ID No. 82 or 83 or an amino acid sequence which has at least 80%, 85%, 90%, 95%, 96%, 97% or 98% identity therewith.

In another embodiment the lipid acyl transferase for use in the methods and uses according to the present invention may be a lipid acyltransferase comprising the amino acid sequence shown as SEQ ID No. 80 or an amino acid sequence which has at least 70%, 75%, 80%, 85%, 90%, 95%, 96%, 97% or 98% identity therewith.

In one embodiment the lipid acyl transferase for use in the methods and uses according to the present invention may be a encoded by a nucleic acid selected from the group consisting of:
 a) a nucleic acid comprising a nucleotide sequence shown in SEQ ID No. 75;
 b) a nucleic acid which is related to the nucleotide sequence of SEQ ID No. 75 by the degeneration of the genetic code; and
 c) a nucleic acid comprising a nucleotide sequence which has at least 70% identity with the nucleotide sequence shown in SEQ ID No. 75.

In one embodiment the lipid acyltransferase according to the present invention may be a lipid acyltransferase obtainable, preferably obtained, from the *Streptomyces* strains L130 or L131 deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Suitable lipid acyltransferases for use in accordance with the present invention and/or in the methods of the present invention may comprise any one of the following amino acid sequences and/or be encoded by the following nucleotide sequences:
a polynucleotide encoding a lipid acyltransferase according to the present invention (SEQ ID No. 62);
an amino acid sequence of a lipid acyltransferase according to the present invention (SEQ ID No. 63);
a polynucleotide encoding a lipid acyltransferase according to the present invention (SEQ ID No. 90).

A suitable lipid acyl-transferase enzyme for use in the methods of the invention may also be identified by alignment to the L131 (SEQ ID No. 76) sequence using Align X, the Clustal W pairwise alignment algorithm of Vector NTI using default settings.

An alignment of the L131 and homologues from *S. avermitilis* and *T. fusca* illustrates that the conservation of the GDSx motif (GDSY (SEQ ID NO: 17) in L131 and *S. avermitilis* and *T. fusca*), the GANDY (SEQ ID NO: 15) box, which is either GGNDA (SEQ ID NO: 16) or GGNDL (SEQ ID NO: 18), and the HPT block (considered to be the conserved catalytic histidine). These three conserved blocks are highlighted in FIG. 103.

When aligned to either the pfam Pfam00657 consensus sequence and/or the L131 sequence herein disclosed (SEQ ID No 76) it is possible to identify three conserved regions, the GDSx block, the GANDY (SEQ ID NO: 15) block and the HTP block.

When aligned to either the pfam Pfam00657 consensus sequence and/or the L131 sequence herein disclosed (SEQ ID No 76)
 i) The lipid acyl-transferase enzyme of the invention, or for use in methods of the invention, has preferably a GDSx motif, more preferably a GDSx motif selected from GDSL (SEQ ID NO: 14) or GDSY (SEQ ID NO: 17) motif.

and/or ii) The lipid acyl-transferase enzyme of the invention, or for use in methods of the invention, has preferably a GANDY (SEQ ID NO: 15) block, more preferably a GANDY (SEQ ID NO: 15) block comprising amino GGNDx (SEQ ID NO: 19), more preferably GGNDA (SEQ ID NO: 16) or GGNDL (SEQ ID NO: 18).

and/or iii) The enzyme of the invention, or for use in methods of the invention, has preferable an HTP block.

and preferably iv) The lipid acyl-transferase enzyme of the invention, or for use in methods of the invention, has preferably a GDSx or GDSY (SEQ ID NO: 17) motif, and a GANDY (SEQ ID NO: 15) block comprising amino GGNDx (SEQ ID NO: 19), preferably GGNDA (SEQ ID NO: 16) or GGNDL (SEQ ID NO: 18), and a HTP block (conserved histadine).

Variant Lipid Acyl Transferase

In a preferred embodiment the lipid acyl transferase is a variant lipid acyl transferase. Suitable methods for the production of lipid acyl transferases for use in the invention are disclosed in WO2005/066347. Variants which have an increased activity on phospholipids, such as increased hydrolytic activity and/or increased transferase, preferably increased transferase activity on phospholipids.

Preferably the variant lipid acyltransferase is prepared by one or more amino acid modifications of the lipid acyl transferases as herein defined.

Suitably, when the lipid acyltransferase for use in the methods or uses of the present invention, may be a variant lipid acyltransferase, in which case the enzyme may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7 (as defined WO2005/066347 and hereinbelow).

For instance the variant lipid acyltransferase enzyme for use in the methods or uses of the present invention may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues detailed in set 2 or set 4 or set 6 or set 7 (as defined in WO2005/066347 and hereinbelow) identified by said parent sequence being structurally aligned with the structural model of P10480 defined herein, which is preferably obtained by structural alignment of P10480 crystal structure coordinates with 1IVN.PDB and/or 1DEO.PDB as defined WO2005/066347 and hereinbelow.

In a further embodiment the variant lipid acyltransferase enzyme for use in the methods or uses of the present invention may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues taught in set 2 identified when said parent sequence is aligned to the pfam consensus sequence (SEQ ID No. 1—FIG. 2) and modified according to a structural model of P10480 to ensure best fit overlap as defined WO2005/066347 and hereinbelow.

Suitably the variant lipid acyltransferase enzyme may comprise an amino acid sequence, which amino acid sequence is shown as SEQ ID No. 73, SEQ ID No. 2, SEQ ID No. 3, SEQ ID No. 4, SEQ ID No. 5, SEQ ID No. 6, SEQ ID No. 12, SEQ ID No. 65, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 89, SEQ ID No. 66, SEQ ID No. 67, SEQ ID No. 68, SEQ ID No. 69, SEQ ID No. 71, or SEQ ID No. 72 except for one or more amino acid modifications at any one or more of the amino acid residues defined in set 2 or set 4 or set 6 or set 7 (as defined WO2005/066347 and hereinbelow) identified by sequence alignment with SEQ ID No. 73.

Alternatively the variant lipid acyltransferase enzyme may be a variant enzyme comprising an amino acid sequence, which amino acid sequence is shown as SEQ ID No. 73, SEQ ID No. 2, SEQ ID No. 3, SEQ ID No. 4, SEQ ID No. 5, SEQ ID No. 6, SEQ ID No. 12, SEQ ID No. 65, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 89, SEQ ID No. 66, SEQ ID No. 67, SEQ ID No. 68, SEQ ID No. 69, SEQ ID No. 71, or SEQ ID No. 72 except for one or more amino acid modifications at any one or more of the amino acid residues defined in set 2 or set 4 or set 6 or set 7 as defined WO2005/066347 and hereinbelow, identified by said parent sequence being structurally aligned with the structural model of P10480 defined herein, which is preferably obtained by structural alignment of P10480 crystal structure coordinates with 1IVN.PDB and/or 1DEO.PDB as taught within WO2005/066347 and hereinbelow.

Alternatively, the variant lipid acyltransferase enzyme may be a variant enzyme comprising an amino acid sequence, which amino acid sequence is shown as SEQ ID No. 73, SEQ ID No. 2, SEQ ID No. 3, SEQ ID No. 4, SEQ ID No. 5, SEQ ID No. 6, SEQ ID No. 12, SEQ ID No. 89, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 89, SEQ ID No. 66, SEQ ID No. 67, SEQ ID No. 68, SEQ ID No. 69, SEQ ID No. 71, or SEQ ID No. 72 except for one or more amino acid modifications at any one or more of the amino acid residues taught in set 2 identified when said parent sequence is aligned to the pfam consensus sequence (SEQ ID No. 1) and modified according to a structural model of P10480 to ensure best fit overlap as taught within WO2005/066347 and hereinbelow.

Preferably, the parent enzyme is an enzyme which comprises, or is homologous to, the amino acid sequence shown as SEQ ID No. 73 and/or SEQ ID No. 34 and/or SEQ ID No. 74.

Preferably, the variant enzyme is an enzyme which comprises an amino acid sequence, which amino acid sequence is shown as SEQ ID No. 73 or SEQ ID No. 74 except for one or more amino acid modifications at any one or more of the amino acid residues defined in set 2 or set 4 or set 6 or set 7 as defined in WO2005/066347 and hereinbelow.

DEFINITION OF SETS

Amino Acid Set 1:

Amino acid set 1 (note that these are amino acids in 1IVN —FIG. 53 and FIG. 54) Gly8, Asp9, Ser10, Leu11, Ser12, Tyr15, Gly44, Asp45, Thr46, Glu69, Leu70, Gly71, Gly72, Asn73, Asp74, Gly75, Leu76, Gln106, Ile107, Arg108, Leu109, Pro110, Tyr113, Phe121, Phe139, Phe140, Met141, Tyr145, Met151, Asp154, His157, Gly155, Ile156, Pro158

The highly conserved motifs, such as GDSx and catalytic residues, were deselected from set 1 (residues underlined). For the avoidance of doubt, set 1 defines the amino acid residues within 10 Å of the central carbon atom of a glycerol in the active site of the 1IVN model.

Amino Acid Set 2:

Amino acid set 2 (note that the numbering of the amino acids refers to the amino acids in the P10480 mature sequence) Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289 and Val290.

Table of selected residues in Set 1 compared with Set 2:

| IVN model | | | P10480 |
|---|---|---|---|
| | A.hyd homologue | | Mature sequence |
| IVN | PFAM | Structure | Residue Number |
| Gly8 | Gly32 | | |
| Asp9 | Asp33 | | |
| Ser10 | Ser34 | | |
| Leu11 | Leu35 | | Leu17 |
| Ser12 | Ser36 | | Ser18 |
| | | | Lys22 |
| | | | Met23 |
| Tyr15 | Gly58 | | Gly40 |
| Gly44 | Asn98 | | Asn80 |
| Asp45 | Pro99 | | Pro81 |
| Thr46 | Lys100 | | Lys82 |
| | | | Asn87 |
| | | | Asn88 |
| Glu69 | Trp129 | | Trp111 |
| Leu70 | Val130 | | Val112 |
| Gly71 | Gly131 | | |
| Gly72 | Ala132 | | Ala114 |
| Asn73 | Asn133 | | |
| Asp74 | Asp134 | | |
| Gly75 | Tyr135 | | Tyr117 |
| Leu76 | Leu136 | | Leu118 |
| Gln106 | | Pro174 | Pro156 |
| Ile107 | | Gly177 | Gly159 |
| Arg108 | | Gln178 | Gln160 |
| Leu109 | | Asn179 | Asn161 |

| IVN model | | | P10480 |
|---|---|---|---|
| | A.hyd homologue | | Mature sequence |
| IVN | PFAM | Structure | Residue Number |
| Pro110 | | 180 to 190 | Pro162 |
| Tyr113 | | | Ser163 |
| | | | Ala164 |
| | | | Arg165 |
| | | | Ser166 |
| | | | Gln167 |
| | | | Lys168 |
| | | | Val169 |
| | | | Val170 |
| | | | Glu171 |
| | | | Ala172 |
| Phe121 | His198 | Tyr197 | Tyr179 |
| | | His198 | His180 |
| | | Asn199 | Asn181 |
| Phe139 | Met227 | | Met209 |
| Phe140 | Leu228 | | Leu210 |
| Met141 | Arg229 | | Arg211 |
| Tyr145 | Asn233 | | Asn215 |
| | | | Lys284 |
| Met151 | Met303 | | Met285 |
| Asp154 | Asp306 | | |
| Gly155 | Gln307 | | Gln289 |
| Ile156 | Val308 | | Val290 |
| His157 | His309 | | |
| Pro158 | Pro310 | | |

Amino Acid Set 3:

Amino acid set 3 is identical to set 2 but refers to the *Aeromonas salmonicida* (SEQ ID No. 3) coding sequence, i.e. the amino acid residue numbers are 18 higher in set 3 as this reflects the difference between the amino acid numbering in the mature protein (SEQ ID No. 73) compared with the protein including a signal sequence (SEQ ID No. 36).

The mature proteins of *Aeromonas salmonicida* GDSX (SEQ ID No. 3) and *Aeromonas hydrophila* GDSX (SEQ ID No. 73) differ in five amino acids. These are Thr3Ser, Gln182Lys, Glu309Ala, Ser310Asn, Gly318-, where the salmonicida residue is listed first and the hydrophila residue is listed last. The hydrophila protein is only 317 amino acids long and lacks a residue in position 318. The *Aeromonas salmonicidae* GDSX has considerably high activity on polar lipids such as galactolipid substrates than the *Aeromonas hydrophila* protein. Site scanning was performed on all five amino acid positions.

Amino Acid Set 4:
Amino acid set 4 is S3, Q182, E309, S310, and -318.
Amino Acid Set 5:
F13S, D15N, S18G, S18V, Y30F, D116N, D116E, D157 N, Y226F, D228N Y230F.
Amino Acid Set 6:
Amino acid set 6 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, -318.

The numbering of the amino acids in set 6 refers to the amino acids residues in P10480 (SEQ ID No. 36) —corresponding amino acids in other sequence backbones can be determined by homology alignment and/or structural alignment to P10480 and/or 1IVN.

Amino Acid Set 7:
Amino acid set 7 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val69, Val170, Glu171, Ala172, Tyr179, His180, Asn181, Gln182, Met209, Leu210, Arg211, Asn215, Lys284, Met285, Gln289, Val290, Glu309, Ser310, -318, Y30X (where X is selected from A, C, D, E, G, H, I, K, L, M, N, P, Q, R, S, T, V, or W), Y226X (where X is selected from A, C, D, E, G, H, I, K, L, M, N, P, Q, R, S, T, V, or W), Y230X (where X is selected from A, C, D, E, G, H, I, K, L, M, N, P, Q, R, S, T, V, or W), S18X (where X is selected from A, C, D, E, F, H, I, K, L, M, N, P, Q, R, T, W or Y), D157X (where X is selected from A, C, E, F, G, H, I, K, L, M, P, Q, R, S, T, V, W or Y).

The numbering of the amino acids in set 7 refers to the amino acids residues in P10480 (SEQ ID No. 36) —corresponding amino acids in other sequence backbones can be determined by homology alignment and/or structural alignment to P10480 and/or 1IVN).

Suitably, the variant enzyme comprises one or more of the following amino acid modifications compared with the parent enzyme:
S3E, A, G, K, M, Y, R, P, N, T or G
E309Q, R or A, preferably Q or R
-318Y, H, S or Y, preferably Y.

Preferably, X of the GDSX motif is L. Thus, preferably the parent enzyme comprises the amino acid motif GDSL (SEQ ID NO: 14).

Suitably, said first parent lipid acyltransferase may comprise any one of the following amino acid sequences: SEQ ID No. 73, SEQ ID No. 2, SEQ ID No. 3, SEQ ID No. 4, SEQ ID No. 5, SEQ ID No. 6, SEQ ID No. 12, SEQ ID No. 65, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 89, SEQ ID No. 66, SEQ ID No. 67, SEQ ID No. 68, SEQ ID No. 69, SEQ ID No. 71 or SEQ ID No. 72.

Suitably, said second related lipid acyltransferase may comprise any one of the following amino acid sequences: SEQ ID No. 2, SEQ ID No. 73, SEQ ID No. 3, SEQ ID No. 4, SEQ ID No. 5, SEQ ID No. 6, SEQ ID No. 12, SEQ ID No. 65, SEQ ID No. 22, SEQ ID No. 24, SEQ ID No. 26, SEQ ID No. 28, SEQ ID No. 30, SEQ ID No. 32, SEQ ID No. 34, SEQ ID No. 36, SEQ ID No. 89, SEQ ID No. 66, SEQ ID No. 67, SEQ ID No. 68, SEQ ID No. 69, SEQ ID No. 71 or SEQ ID No. 72.

The variant enzyme must comprise at least one amino acid modification compared with the parent enzyme. In some embodiments, the variant enzyme may comprise at least 2, preferably at least 3, preferably at least 4, preferably at least 5, preferably at least 6, preferably at least 7, preferably at least 8, preferably at least 9, preferably at least 10 amino acid modifications compared with the parent enzyme.

When referring to specific amino acid residues herein the numbering is that obtained from alignment of the variant sequence with the reference sequence shown as SEQ ID No. 73 or SEQ ID No. 74.

In one aspect preferably the variant enzyme comprises one or more of the following amino acid substitutions:
S3A, C, D, E, F, G, H, I, K, L, M, N, P, Q, R, T, V, W, or Y; and/or
L17A, C, D, E, F, G, H, I, K, M, N, P, Q, R, S, T, V, W, or Y; and/or
S18A, C, D, E, F, H, I, K, L, M, N, P, Q, R, T, W, or Y; and/or
K22A, C, D, E, F, G, H, I, L, M, N, P, Q, R, S, T, V, W, or Y; and/or
M23A, C, D, E, F, G, H, I, K, L, N, P, Q, R, S, T, V, W, or Y; and/or
Y30A, C, D, E, G, H, I, K, L, M, N, P, Q, R, S, T, V, or W; and/or
G40A, C, D, E, F, H, I, K, L, M, N, P, Q, R, S, T, V, W, or Y; and/or
N80A, C, D, E, F, G, H, I, K, L, M, P, Q, R, S, T, V, W, or Y; and/or
P81A, C, D, E, F, G, H, I, K, L, M, N, Q, R, S, T, V, W, or Y; and/or
K82A, C, D, E, F, G, H, I, L, M, N, P, Q, R, S, T, V, W, or Y; and/or
N87A, C, D, E, F, G, H, I, K, L, M, P, Q, R, S, T, V, W, or Y; and/or
N88A, C, D, E, F, G, H, I, K, L, M, P, Q, R, S, T, V, W, or Y; and/or
W111A, C, D, E, F, G, H, I, K, L, M, N, P, Q, R, S, T, V, W or Y; and/or
V112A, C, D, E, F, G, H, I, K, L, M, N, P, Q, R, S, T, W, or Y; and/or
A114C, D, E, F, G, H, I, K, L, M, N, P, Q, R, S, T, V, W, or Y; and/or
Y 117A, C, D, E, F, G, H, I, K, L, M, N, P, Q, R, S, T, V, or W; and/or
L118A, C, D, E, F, G, H, I, K, M, N, P, Q, R, S, T, V, W, or Y; and/or
P156A, C, D, E, F, G, H, I, K, L, M, N, Q, R, S, T, V, W, or Y; and/or
D157A, C, E, F, G, H, I, K, L, M, P, Q, R, S, T, V, W, or Y; and/or
G159A, C, D, E, F, H, I, K, L, M, N, P, Q, R, S, T, V, W, or Y; and/or
Q160A, C, D, E, F, G, H, I, K, L, M, N, P, R, S, T, V, W, or Y; and/or
N161A, C, D, E, F, G, H, I, K, L, M P, Q, R, S, T, V, W, or Y; and/or
P162A, C, D, E, F, G, H, I, K, L, M, N, Q, R, S, T, V, W, or Y; and/or
S163A, C, D, E, F, G, H, I, K, L, M, N, P, Q, R, T, V, W, or Y; and/or
A164C, D, E, F, G, H, I, K, L, M, N, P, Q, R, S, T, V, W, or Y; and/or
R165A, C, D, E, F, G, H, I, K, L, M, N, P, Q, S, T, V, W, or Y; and/or
S166A, C, D, E, F, G, H, I, K, L, M, N, P, Q, R, T, V, W, or Y; and/or
Q167A, C, D, E, F, G, H, I, K, L, M, N, P, R, S, T, V, W, or Y; and/or
K168A, C, D, E, F, G, H, I, L, M, N, P, Q, R, S, T, V, W, or Y; and/or V169A, C, D, E, F, G, H, I, K, L, M, N, P, Q, R, S, T, W, or Y; and/or
V170A, C, D, E, F, G, H, I, K, L, M, N, P, Q, R, S, T, W, or Y; and/or
E171A, C, D, F, G, H, I, K, L, M, N, P, Q, R, S, T, V, W, or Y; and/or
A172C, D, E, F, G, H, I, K, L, M, N, P, Q, R, S, T, V, W, or Y; and/or
Y179A, C, D, E, F, G, H, I, K, L, M, N, P, Q, R, S, T, V, or W; and/or
H180A, C, D, E, F, G, I, K, L, M, P, Q, R, S, T, V, W, or Y; and/or
N181A, C, D, E, F, G, H, I, K, L, M, P, Q, R, S, T, V, W, or Y; and/or
Q182A, C, D, E, F, G, H, I, K, L, M, N, P, R, S, T, V, W, or Y, preferably K; and/or
M209A, C, D, E, F, G, H, I, K, L, N, P, Q, R, S, T, V, W, or Y; and/or
L210 A, C, D, E, F, G, H, I, K, M, N, P, Q, R, S, T, V, W, or Y; and/or
R211A, C, D, E, F, G, H, I, K, L, M, N, P, Q, R, S, T, V, W, or Y; and/or
N215 A, C, D, E, F, G, H, I, K, L, M, N, P, Q, R, S, T, V, W, or Y; and/or
Y226A, C, D, E, G, H, I, K, L, M, N, P, Q, R, S, T, V, or W; and/or
Y230A, C, D, E, G, H, I, K, L, M, N, P, Q, R, S, T, V or W; and/or
K284A, C, D, E, F, G, H, I, L, M, N, P, Q, R, S, T, V, W, or Y; and/or
M285A, C, D, E, F, G, H, I, K, L, N, P, Q, R, S, T, V, W, or Y; and/or
Q289A, C, D, E, F, G, H, I, K, L, M, N, P, R, S, T, V, W, or Y; and/or
V290A, C, D, E, F, G, H, I, K, L, M, N, P, Q, R, S, T, W, or Y; and/or
E309A, C, D, F, G, H, I, K, L, M, N, P, Q, R, S, T, V, W, or Y; and/or
S310A, C, D, E, F, G, H, I, K, L, M, N, P, Q, R, T, V, W, or Y.

In addition or alternatively thereto there may be one or more C-terminal extensions. Preferably the additional C-terminal extension is comprised of one or more aliphatic amino acids, preferably a non-polar amino acid, more preferably of I, L, V or G. Thus, the present invention further provides for a variant enzyme comprising one or more of the following C-terminal extensions: 318I, 318L, 318V, 318G.

Preferred variant enzymes may have a decreased hydrolytic activity against a phospholipid, such as phosphatidylcholine (PC), may also have an increased transferase activity from a phospholipid.

Preferred variant enzymes may have an increased transferase activity from a phospholipid, such as phosphatidylcholine (PC), these may also have an increased hydrolytic activity against a phospholipid.

Modification of one or more of the following residues may result in a variant enzyme having an increased absolute transferase activity against phospholipid: S3, D157, S310, E309, Y179, N215, K22, Q289, M23, H180, M209, L210, R211, P81, V112, N80, L82, N88; N87

Specific preferred modifications which may provide a variant enzyme having an improved transferase activity from a phospholipid may be selected from one or more of the following:
S3A, C, D, E, F, G, H, I, K, L, M, N, P, Q, R, T, V, W or Y; preferably N, E, K, R, A, P or M, most preferably S3A
D157A, C, E, F, G, H, I, K, L, M, N, P, Q, R, S, T, V, W or Y; preferably D157S, R, E, N, G, T, V, Q, K or C
S310A, C, D, E, F, G, H, I, K, L, M, N, P, Q, R, T, V, W or Y; preferably S310T -318 E
E309A, C, D, E, F, G, H, I, K, L, M, N, P, Q, R, T, V, W or Y; preferably E309 R, E, L, R or A
Y179A, C, D, E, F, G, H, I, K, L, M, N, P, Q, R, S, T, V or W; preferably Y179 D, T, E, R, N, V, K, Q or S, more preferably E, R, N, V, K or Q
N215A, C, D, E, F, G, H, I, K, L, M, P, Q, R, S, T, V, W or Y; preferably N215 S, L, R or Y
K22A, C, D, E, F, G, H, I, L, M, N, P, Q, R, S, T, V, W or Y; preferably K22 E, R, C or A
Q289A, C, D, E, F, G, H, I, K, L, M, N, P, R, S, T, V, W or Y; preferably Q289 R, E, G, P or N
M23A, C, D, E, F, G, H, I, K, L N, P, Q, R, S, T, V, W or Y; preferably M23 K, Q, L, G, T or S
H180A, C, D, E, F, G, I, K, L, M, P, Q, R, S, T, V, W or Y; preferably H180 Q, R or K
M209 A, C, D, E, F, G, H, I, K, L, N, P, Q, R, S, T, V, W or Y; preferably M209 Q, S, R, A, N, Y, E, V or L
L210A, C, D, E, F, G, H, I, K, M, N, P, Q, R, S, T, V, W or Y; preferably L210 R, A, V, S, T, I, W or M
R21A, C, D, E, F, G, H, I, K, L, M, N, P, Q, S, T, V, W or Y; preferably R211T
P81A, C, D, E, F, G, H, I, K, L, M, N, Q, R, S, T, V, W or Y; preferably P81G
V112A, C, D, E, F, G, H, I, K, L, M, N, P, Q, R, S, T, W or Y; preferably V112C
N80A, C, D, E, F, G, H, I, K, L, M, P, Q, R, S, T, V, W or Y; preferably N80 R, G, N, D, P, T, E, V, A or G
L82A, C, D, E, F, G, H, I, M, N, P, Q, R, S, T, V, W or Y; preferably L82N, S or E
N88A, C, D, E, F, G, H, I, K, L, M, P, Q, R, S, T, V, W or Y; preferably N88C
N87A, C, D, E, F, G, H, I, K, L, M, P, Q, R, S, T, V, W or Y; preferably N87M or G Preferred modification of one or more of the following residues results in a variant enzyme having an increased absolute transferase activity against phospholipid:
S3N, R, A, G
M23 K, Q, L, G, T, S
H180 R
L82 G
Y179 E, R, N, V, K or Q
E309R, S, L or A One preferred modification is N80D. This is particularly the case when using the reference sequence SEQ ID No. 74. Therefore in a preferred embodiment of the present invention the lipid acyltransferase according to the present invention comprises SEQ ID No. 74. or an amino acid sequence which has 75% or more, preferably 85% or more, more preferably 90% or more, even more preferably 95% or more, even more preferably 98% or more, or even more preferably 99% or more identity to SEQ ID No. 74.

As noted above, when referring to specific amino acid residues herein the numbering is that obtained from alignment of the variant sequence with the reference sequence shown as SEQ ID No. 73 or SEQ ID No. 74.

Much by preference, the lipid acyltransferase for use in the method and uses of the present invention may be a lipid acyltransferase comprising the amino acid sequence shown as SEQ ID No. 62 or the amino acid sequence shown as SEQ ID No. 90, or an amino acid sequence which has 75% or more, preferably 85% or more, more preferably 90% or more, even more preferably 95% or more, even more preferably 98% or more, or even more preferably 99% or more identity to SEQ ID No. 62 and/or SEQ ID No. 90. This enzyme may be considered a variant enzyme.

For the purposes of the present invention, the degree of identity is based on the number of sequence elements which are the same. The degree of identity in accordance with the present invention may be suitably determined by means of computer programs known in the art, such as GAP provided in the GCG program package (Program Manual for the Wisconsin Package, Version 8, August 1994, Genetics Computer Group, 575 Science Drive, Madison, Wis., US 53711) (Needleman & Wunsch (1970), J. of Molecular Biology 48, 443-45) using the following settings for polypeptide sequence comparison: GAP creation penalty of 3.0 and GAP extension penalty of 0.1. Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the lipid acyltransferase/lipid acyl transferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter*, Vibrionaceae, *Xylella, Sulfolobus, Aspergillus, Schizosaccharomyces, Listeria, Neisseria, Mesorhizobium, Ralstonia, Xanthomonas, Candida, Thermobifida* and *Corynebacterium*.

Suitably, the lipid acyltransferase/lipid acyl transferaseenzyme according to the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Streptomyces thermosacchari, Streptomyces avermitilis Lactobacillus helveticus, Desulfitobacterium dehalogenans, Bacillus*sp, *Campylobacter jejuni*, Vibrionaceae, *Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis Thermobifida fusca* and *Corynebacterium efficiens*.

In one aspect, preferably the lipid acyl transferase enzyme according to the present invention is obtainable, preferably obtained or derived from one or more of *Aeromonas* spp., *Aeromonas hydrophila* or *Aeromonas* salmonicida.

Preferably, when carrying out a method according to the present invention the product is produced without increasing or substantially increasing the free fatty acids in the foodstuff.

The term "transferase" as used herein is interchangeable with the term "lipid acyltransferase".

Suitably, the lipid acyltransferase as defined herein catalyses one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule. Acyl transfer which results from hydrolysis requires the separation of the water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity); however, the enzyme may transfer less than 100% of the acyl groups present in the lipid acyl donor to the acyl acceptor. In which case, preferably the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following protocol:

Protocol for the Determination of % Acyltransferase Activity:

A foodstuff to which a lipid acyltransferase according to the present invention has been added may be extracted following the enzymatic reaction with $CHCl_3:CH_3OH$ 2:1 and the organic phase containing the lipid material is isolated and analysed by GLC and HPLC according to the procedure detailed hereinbelow. From the GLC and HPLC analyses the amount of free fatty acids and one or more of sterol/stanol esters; carbohydrate esters, protein esters; diglycerides; or monoglycerides are determined. A control foodstuff to which no enzyme according to the present invention has been added, is analysed in the same way.

Calculation:

From the results of the GLC and HPLC analyses the increase in free fatty acids and sterol/stanol esters and/or carbohydrate esters and/or protein esters and/or diglycerides and/or monoglycerides can be calculated:

$\Delta$ % fatty acid=% Fatty acid(enzyme)−% fatty acid (control); Mv fatty acid=average molecular weight of the fatty acids;

$A=\Delta$ % sterol ester/Mv sterol ester (where $\Delta$ % sterol ester=% sterol/stanol ester(enzyme)−% sterol/stanol ester(control) and Mv sterol ester=average molecular weight of the sterol/stanol esters)–applicable where the acyl acceptor is a sterol and/or stanol;

$B=\Delta$ % carbohydrate ester/Mv carbohydrate ester (where $\Delta$ % carbohydrate ester=% carbohydrate ester(enzyme)−% carbohydrate ester(control) and Mv carbohydrate ester=average molecular weight of the carbohydrate ester)–applicable where the acyl acceptor is a carbohydrate;

$C=\Delta$ % protein ester/Mv protein ester (where $\Delta$ % protein ester=% protein ester(enzyme)−% protein ester(control) and Mv protein ester=average molecular weight of the protein ester)–applicable where the acyl acceptor is a protein; and $D$=absolute value of diglyceride and/or monoglyceride/Mv di/monoglyceride (where $\Delta$ % diglyceride and/or monoglyceride=% diglyceride and/or monoglyceride (enzyme)−% diglyceride and/or monoglyceride (control) and Mv di/monoglyceride=average molecular weight of the diglyceride and/or monoglyceride)–applicable where the acyl acceptor is glycerol.

The transferase activity is calculated as a percentage of the total enzymatic activity:

$$\% \text{ transferase activity} = \frac{A^* + B^* + C^* + D^* \times 100}{A^* + B^* + C^* + D^* + \Delta \% \text{ fatty acid}/(Mv \text{ fatty acid})}.$$

*delete as appropriate.

If the free fatty acids are increased in the foodstuff they are preferably not increased substantially, i.e. to a significant degree. By this we mean, that the increase in free fatty acid does not adversely affect the quality of the foodstuff.

In some aspects of the present invention, the term "without substantially increasing free fatty acids" as used herein means that the amount of free fatty acid in a foodstuff or composition treated with an lipid acyltransferase according to the present invention is less than the amount of free fatty acid produced in the foodstuff or composition when an enzyme other than a lipid acyltransferase according to the present invention had been used, such as for example as compared with the amount of free fatty acid produced when a conventional phospholipase enzyme, e.g. LipopanF® (Novozymes A/S, Denmark), had been used.

The term "in situ" as used herein means that the emulsifier(s) and/or the sterol/stanol esters and/or the carbohydrate esters and/or the protein esters and/or the mono- or diglycerides are produced within the foodstuff or fraction of the foodstuff. This contrasts the situation where the emulsifier(s) and/or the sterol/stanol esters and/or the carbohydrate esters and/or the protein esters and/or the mono- or diglycerides are produced separately of the foodstuff and are added as formed products to the foodstuff during preparation of the same. In other words, the term "in situ" as used herein means that by the addition of the lipid acyltransferase enzyme according to the present invention to a foodstuff, or to the food ingredients/materials constituting the foodstuff, an emulsifier and/or a sterol ester and/or a stanol ester and/or a carbohydrate ester and/or a protein ester and/or a mono- or diglyceride may be produced from components of the foodstuff. Suitably, the components of the foodstuff may be the substrate(s) for the enzyme. If necessary, the components of the foodstuff may be supplemented by addition of one or more further components which further components may be the same as those present in the foodstuff or may be additional to those components already present in the foodstuff. For the avoidance of doubt, in one embodiment, the method according to the present invention may be a method for the production of an emulsifier and/or a sterol ester and/or a stanol ester and/or a carbohydrate ester and/or a protein ester and/or a mono- or diglyceride in situ in a foodstuff and is not a method for preparing an emulsifier and/or a sterol ester and/or a stanol ester (for example is an isolated and/or purified form) for subsequent addition to a foodstuff.

In another embodiment the lipase acyl-transferase may be used during the food processing, but not remain in the foodstuff. For example, the lipase acyl transferase may be immobilised, allowing it to be reused.

Preferably, the lipid acyltransferase according to the present invention is capable of transferring an acyl group from a lipid to a sterol and/or stanol and/or a carbohydrate and/or a protein and/or glycerol when present in a polar environment, preferably in an aqueous environment, preferably a water containing foodstuff. Suitably, the aqueous environment may be an aqueous buffer or may be the aqueous phase in a foodstuff. The term "aqueous environment" as used herein preferably means an environment which is absent an organic solvent, preferably absent a polar organic solvent, more preferably absent an non-edible organic solvent. In particular, the term "aqueous environment" may refer to an environment to which no exogenous organic solvents, preferably no polar organic solvents, have been added. The term organic solvent as used herein does not encompass food oils, preferably does not encompass food oils that are high in non-polar lipids. In one embodiment the term organic solvent may exclude edible organic solvents, such as ethanol, propylene glycol and/or glycerol. Suitably, the aqueous environment according to the present invention may comprise less than 80% by volume organic solvents, less than 70% by volume organic solvents, less than 50% by volume organic solvents, less than 30% by volume organic solvents, more preferably less than 15% by volume organic solvents, more preferably less than 5%. Suitably the foodstuff may comprise between 1 and 5% organic solvent, for example ethanol. However, when the foodstuff comprises such an organic solvent, preferably it is produced endogenously within the foodstuff. That is to say, when the foodstuff comprises such an organic solvent, preferably the organic solvent is not an exogenous organic solvent.

The term "foodstuff" as used herein means a substance which is suitable for human and/or animal consumption.

Suitably, the term "foodstuff" as used herein may mean a foodstuff in a form which is ready for consumption. Alternatively or in addition, however, the term foodstuff as used herein may mean one or more food materials which are used in the preparation of a foodstuff. By way of example only, the term foodstuff encompasses both baked goods produced from dough as well as the dough used in the preparation of said baked goods. By way of further example, the term foodstuff encompasses both the final product, i.e. for example the final diary product such as cheese, as well as the milk (e.g. cheese milk), the cream and/or the butterfat for example used in the preparation of the said dairy product (e.g. the cheese).

The term "food material" as used herein means one or more materials used in the preparation of a foodstuff. The term foodstuff may be used herein to mean food material and vice versa. In some embodiments for example the food material may be the final foodstuff. By way of example only the final foodstuff may be an edible oil (such as a cooking oil); in such instances the food material may also be the edible oil. In some embodiments for example the food material may be one constituent of the final foodstuff. By way of example only the final foodstuff may be a dairy product, such as cheese for instance; in such instances the food material may be milk (e.g. cheese milk), cream and/or butterfat for example used in the preparation of said diary product (e.g. the cheese).

When the food material forms only on constituent of the final foodstuff for instance in some embodiments the final foodstuff may be comprised of less than 10 wt % of the food material, such as less than 5 wt %.

In some embodiments, suitably the final foodstuff may be comprised of from 0.01 to 4 wt % of the food material.

In some embodiments, suitably the final foodstuff may be comprised of from 0.01 to 2 wt % of the food material.

In some embodiments, suitably the final foodstuff may be comprised of from 0.01 to 1 wt % of the food material.

In some embodiments, suitably the final foodstuff may be comprised of from 0.01 to 0.5 wt % of the food material.

In some embodiments, suitably the final foodstuff may be comprised of from 0.01 to 0.3 wt % of the food material.

In a preferred aspect the present invention provides a foodstuff as defined above wherein the foodstuff is selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

Suitably the foodstuff in accordance with the present invention may be a "fine foods", including cakes, pastry, confectionery, chocolates, fudge and the like.

In one aspect the foodstuff in accordance with the present invention may be a dough product or a baked product, such as a bread, a fried product, a snack, cakes, pies, brownies, cookies, noodles, snack items such as crackers, graham crackers, pretzels, and potato chips, and pasta.

In a further aspect, the foodstuff in accordance with the present invention may be a plant derived food product such as flours, pre-mixes, oils, fats, cocoa butter, coffee whitener, salad dressings, margarine, spreads, peanut butter, shortenings, ice cream, cooking oils.

In another aspect, the foodstuff in accordance with the present invention may be a dairy product, including butter, milk, cream, cheese such as natural, processed, and imitation cheeses in a variety of forms (including shredded, block, slices or grated), cream cheese, ice cream, frozen desserts, yoghurt, yoghurt drinks, butter fat, anhydrous milk fat, other dairy products. The enzyme according to the present invention may improve fat stability in dairy products.

As used herein the term 'milk' may comprise milk from either animal or vegetable origin. It is possible to use milk from animal sources such as buffalo, (traditional) cow, sheep, goat etc. either individually or combined. Vegetable milks such as soya milk may also be used. The vegetable milk may be used in combination with the animal milk, for example at a low percentage (of vegetable milk) say below 15%, or below 20%, or below 25% v/v. The term milk may also comprise cheese milk and cream. One advantage of the present invention is that it may assist the incorporation of soy milk into cheese production at a higher concentration when blended with milk from an animal source. Without wishing to be bound by theory, this may be due to the emulsification properties of soy milk treated in accordance with the present invention.

In one aspect the foodstuff in accordance with the present invention may be ice cream.

In one aspect the foodstuff in accordance with the present invention may be or may comprise cheese or a cheese analogue.

In one embodiment the present invention relates to a method for the production of cheese using a lipid acyltransferase and/or the use of a lipid acyltransferase for the production of cheese. Preferably, the use leads to one or more of the technical effects in the cheese taught herein.

Suitably, in some embodiments the foodstuff may be a derivative of the foodstuff in accordance with the present invention. By way of example only the foodstuff may be a pizza comprising cheese produced in accordance with the present invention.

In the present application, the term cheese "refers to any kind of cheese, such as natural cheese, cheese analogues and processed cheese for example. The cheese may be obtained by any suitable process known in the art, such as, e.g. by enzymatic coagulation of the cheese milk and/or cream with rennet, or by acidic coagulation of the cheese milk and/or cream with food grade acid or acid produced by lactic acid bacteria growth.

In one embodiment, the cheese manufactured by the process of the invention is rennet-curd cheese. Rennet is commercially available, e.g. as Naturene (animal rennet), Chymaxe (fermentation produced chymosin), Microlane (Microbial coagulant produced by fermentation), all from Chr. Hansen A/S, Denmark). The cheese milk and/or cream may be subjected to a conventional cheese-making process.

A preferable coagulant is Marzyme®, a pure, microbial coagulant, provides the benefits of fermentation-produced chymosin (FPC) without affecting yield or taste.

Processed cheese is preferably manufactured from natural cheese or cheese analogues by cooking and emulsifying the cheese, such as, with emulsifying salts (e.g. phosphates and citrate). The process may further include the addition of spices/condiments.

The term "cheese analogues" refers to cheese-like products which contain fat (such as, e.g., milk fat (e.g. cream)) as a part of the composition, and, in which further contain, as part of the composition, a non-milk constituents, such as, e.g. vegetable oil. An example of a cheese analogue is cheese base. Cheese analogues may comprise soya milk or soya protein.

The cheeses produced by the process of the present invention comprise all varieties of cheese, such as, e.g. Campesino, Chester, Danbo, Drabant, Herregard, Manchego, Primativo, Provolone, Saint Paulin, Soft cheese, Svecia, Taleggio, White cheese, including rennet-curd cheese produced by rennet-coagulation of the cheese curd; ripened cheeses such as Cheddar, Colby, Edam, Muenster, Gryere, Emmenthal, Camembert, Parmesan and Romano; fresh cheeses such as Mozzarella and Feta; acid coagulated cheeses such as cream cheese, Neufchatel, Quarg, Cottage Cheese and Queso-Blanco; and pasta filata cheese.

One embodiment relates to the production of pizza cheese by the process of the invention.

In cheese manufacturing, the coagulation of the casein in milk is preferably performed in two ways: the so-called rennet-curd and acid-curd cheese. In cheese production these two types of curds makes up two major groups of cheese types. Fresh acid-curd cheeses refer to those varieties of cheese produced by the coagulation of milk, cream or whey via acidification or a combination of acid and heat, and which are ready for consumption once the manufacturing without ripening are completed. Fresh acid-curd cheeses generally differ from rennet-curd cheese varieties (e.g. Camembert, Cheddar, Emmenthal) where coagulation normally is induced by the action of rennet at pH values 6.4-6.6, in that coagulation normally occur close to the isoelectric point of casein, i.e. e.g. at pH 4.6 or at higher values when elevated temperatures are used, e.g. in Ricotta pH 6.0 and 80 C.

In one embodiment of the invention, the cheese belongs to the class of rennet curd cheeses.

Mozzarella is a member of the so-called pasta filata, or stretched curd, cheeses which are normally distinguished by a unique plasticising and kneading treatment of the fresh curd in hot water, which imparts the finished cheese its characteristic fibrous structure and melting and stretching properties, cf. e.g. "Mozzarella and Pizza cheese" by Paul S. Kindstedt, Cheese: Chemistry, physics and microbiology, Volume 2: Major Cheese groups, second edition, page 337-341, Chapman & Hall. Pizza cheese as used herein includes cheeses suitable for pizzas and they are usually pasta filata/stretched curd cheeses. In one embodiment, the process of the invention further comprises a heat/stretching treatment as for pasta filata cheeses, such as for the manufacturing of Mozzarella.

In one embodiment preferably the cheese according to the present invention is Mozzarella.

In further embodiments of the invention, the cheese milk is prepared, totally or in part, from dried milk fractions, such as, e.g., whole milk powder, skim milk powder, casein, caseinate, total milk protein or buttermilk powder, or any combination thereof.

In one embodiment, preferably the foodstuff and/or the food material in accordance with the present invention is butterfat.

In one embodiment, particularly when the foodstuff and/or the food material treated with the lipid acyltransferase in accordance with the present invention is butterfat, the enzyme treated butterfat may be then used to produce a further dairy product (particularly cheese) and/or margarine or spreads (including low fat and very low fat spreads).

In one embodiment, the enzyme treated butterfat in accordance with the present invention may be added to milk (e.g. cheese milk) and/or cream which may subsequently be used to prepare a further dairy product, such as cheese for example.

In another embodiment, the foodstuff and/or the food material in accordance with the present invention may be milk and/or cream.

In one embodiment, particularly when the foodstuff and/or the food material treated with the lipid acyltransferase in accordance with the present invention is milk (preferably cheese milk) and/or cream, the enzyme treated milk and/or cream may be then used to produce a further dairy product (such as one or more of cheese, ice cream, frozen desserts, yoghurt, yoghurt drinks for instance, particularly cheese and/or ice cream).

In one embodiment the foodstuff consists of or comprises a cheese foodstuff which is heated to above the melting temperature of the cheese. The use of cheese prepared in accordance with the invention in foodstuffs which are heated can lead to a reduced oiling off effect from the cheese. There may also be beneficial texture and flavour benefits in using cheese or cheese products prepared according to the present invention.

The present invention further relates to use of the cheese produced by the process of the present invention in pizza, ready-to-eat dishes, such as lasagna or processed cheese, or as an ingredient in other food products. Accordingly, the cheese produced according to the process of the invention may be used in further processed food products like processed cheese, pizza, burgers, toast, sauces, dressings, cheese powder, or cheese flavours.

In further embodiments, the process of the invention further comprises the step of subjecting the cheese, or foodstuff comprising the cheese, prepared in accordance with the present invention to a heating treatment, such as for example in the range of about 150-350° C., or in the range of about 155-345° C., or in the range of about 160-340° C. or in the range of about 170-330° C. or in the range of about 180-320° C. or in the range of about 200-300° C. Suitably the heating treatment may be for at least 2 minutes such as at least 5 minutes, including at least 10 minutes.

In one aspect of the present invention the cheese produced in accordance with the present invention has a melting temperature which does not significantly differ from that of a control cheese (i.e. one which has not been produced using a lipid acyltransferase).

In another aspect of the present invention the cheese produced in accordance with the present invention has a texture and consistency which is similar to (if not better than) that of a control cheese (i.e. one which has not been produced using a lipid acyltransferase).

It is particularly advantageous to utilise the present invention in cheese as the production of free fatty acids in cheese is associated with a "soapy" taste. Thus, the use of a lipid acyltransferase in accordance with the present invention advantageously produces cheese without a "soapy" taste.

The reduced "soapy" taste and/or reduced off-flavours and off-taste associated with the use of a lipid acyltransferase in accordance with the present invention provides a significant advantage compared with the use of a standard lipase and/or phospholipase (such as Lecitase™ for example). The reduced off-flavours and off-taste may advantageously be the result of a reduction in the production of free fatty acids during the enzyme reactions. Fatty acids enzymatically removed by the lipid acyltransferase from the acyl donor are transferred to an acyl acceptor molecule, and thus do not accumulate in the cheese.

In another aspect, the foodstuff in accordance with the present invention may be a food product containing animal derived ingredients, such as processed meat products, cooking oils, shortenings.

In a further aspect, the foodstuff in accordance with the present invention may be a beverage, a fruit, mixed fruit, a vegetable or wine. In some cases the beverage may contain up to 20 g/l of added phytosterols.

In another aspect, the foodstuff in accordance with the present invention may be an animal feed. The animal feed may be enriched with phytosterol and/or phytostanols, preferably with beta-sitosterol/stanol. Suitably, the animal feed may be a poultry feed. When the foodstuff is poultry feed, the present invention may be used to lower the cholesterol content of eggs produced by poultry fed on the foodstuff according to the present invention.

In one aspect preferably the foodstuff is selected from one or more of the following: eggs, egg-based products, including mayonnaise, salad dressings, sauces, ice cream, egg powder, modified egg yolk and products made therefrom.

Preferably the foodstuff according to the present invention is a water containing foodstuff. Suitably the foodstuff may be comprised of 10-98% water, suitably 14-98%, suitably of 18-98% water, suitably of 20-98%, suitably of 40-98%, suitably of 50-98%, suitably of 70-98%, suitably of 75-98%.

For some aspects, preferably the foodstuff in accordance with the present invention is not a pure plant derived oil, such as olive oil, sunflower oil, peanut oil, rapeseed oil for instance. For the avoidance of doubt, in some aspects of the present invention the foodstuff according to the present invention may comprise an oil, but preferably the foodstuff is not primarily composed of oil or mixtures of oil. For some aspects, preferably the foodstuff comprises less than 95% lipids, preferably less than 90% lipids, preferably less than 85%, preferably less than 80% lipids. Thus, for some aspects of the present invention oil may be a component of the foodstuff, but preferably the foodstuff is not an oil per se.

The claims of the present invention are to be construed to include each of the foodstuffs listed above.

When it is the case that a carbohydrate ester is produced in accordance with the present invention, the carbohydrate ester is preferably an oligosaccharide ester, a monosaccharide ester or a disaccharide ester.

Suitably, the carbohydrate ester when produced in accordance with the present invention may be one or more of the following: glucose ester, fructose ester, anhydrofructose ester, maltose ester, lactose ester, galactose ester, xylose ester, xylooligosaccharide ester, arabinose ester, maltooligosaccharide ester, tagatose ester, sucrose ester, microthecin ester, ascopyrone P ester, ascopyrone T ester or cortalcerone ester.

Preferably, the carbohydrate ester when produced in accordance with the present invention is one or more of the following: a carbohydrate mono-ester, a sugar mono-ester, an oligosaccharide mono-ester, a trisaccharide mono-ester, a disaccharide mono-ester, a monosaccharide mono-ester, a glucose mono-ester, a fructose mono-ester, anhydrofructose mono-ester, maltose mono-ester, lactose mono-ester, galactose mono-ester, xylose mono-ester, xylooligosacchride mono-ester, arabinose mono-ester, maltooligosaccharide mono-ester, tagatose mono-ester, sucrose mono-ester, microthecin ester, ascopyrone P ester, ascopyrone T ester or cortalcerone ester.

In one embodiment, the microthecin ester, ascopyrone P ester, ascopyrone T ester and/or cortalcerone ester may function as an antimicrobial agent. Alternatively or in addition thereto, the microthecin ester, ascopyrone P ester, ascopyrone T ester and/or cortalcerone ester may function as one or both of an antioxidant and/or emulsifier.

Preferably, the formation of the carbohydrate ester (if any) in accordance with the present invention is independent of UDP-glucose.

Preferably, the foodstuff according to the present invention does not comprise UDP-glucose, or only comprises UDP-glucose in insignificant amounts.

Suitably, the emulsifier in accordance with the present invention may be for example one or more of the following: a diglyceride, a monoglyceride, such as 1-monoglyceride or a lysolecithin, such as lysophosphatidylcholine for example, a digalactosyl monoglyceride (DGMG). The emulsifier is preferably produced from the lipid acyl donor following removal of one or more acyl groups from said lipid acyl donor. The term lysolecithin as used herein encompasses lysophosphatidylcholine, lysophosphatidylethanolamine, lysophosphatidylinositol, lysophosphatidylserine and lysophosphatidylglycerol Where one of the emulsifiers is a carbohydrate ester, the second emulsifier may be for example one or more of the following: a diglyceride, a monoglyceride, such as 1-monoglyceride, lysophosphatidylcholine, or digalactosyl monoglyceride (DGMG). The second emulsifier is preferably produced from the lipid acyl donor following removal of one or more acyl groups from said lipid acyl donor. The term lysophosphatidylcholine as used herein is synonymous with the term lysolecithin and these terms may be used herein interchangeably.

Preferably the second emulsifier is DGMG. Suitably, the DGMG is produced in situ by the removal of an acyl group from DGDG with the transfer of the removed acyl group onto a carbohydrate to form a carbohydrate ester.

Where one of the emulsifiers is a protein ester and/or a diglyceride and/or a monoglyceride, the second emulsifier may be for example one or more of the following: a diglyceride, a monoglyceride, such as 1-monoglyceride, lysophosphatidylcholine, or digalactosyl monoglyceride (DGMG). The second emulsifier is preferably produced from the lipid acyl donor following removal of one or more acyl groups from said lipid acyl donor. The term lysophosphatidylcholine as used herein is synonymous with the term lysolecithin and these terms may be used herein interchangeably.

In one embodiment the lipid acyl transferase of the invention can be used in a process for the preparation of a foodstuff such as a cooking (e.g. edible) oil, margarine or spread, butterfat (e.g. for subsequent use in cheese and/or margarine and/or spreads), whereby the foodstuff naturally contains, or has been supplemented with, glycerol and/or has been supplemented with at least one phospholipid (for example lecithin) and/or glycolipid (for example digalactosyl-diglyceride), and optionally a phytosterol or phytostanol.

In one embodiment the lipid acyl transferase of the invention can be used in a process for the preparation of a foodstuff such as margarine or spread, whereby the foodstuff naturally contains, or has been supplemented with, glycerol, at least one phospholipid (for example lecithin) and/or glycolipid (for example digalactosyl-diglyceride), and optionally a phytosterol or phytostanol.

In one embodiment, the present invention provides a process for the production of modified edible oil or fat (including butterfat) comprising i) lysophospholipid and/or one or more of the following, glycerophosphatylcholine, phosphatylethanolamine, phosphatylinositol and phosphatylserine, and ii) monoglyceride, said process comprising:
  a) selecting at least one edible oil or fat, or combination thereof, wherein said edible oil or fat comprises at least a phospholipid,
  b) supplementing said edible oil or fat selected in step a) with exogenous glycerol and optionally b) exogenous phospholipid; wherein when the modified edible oil or fat selected in step a) essentially consists of a vegetable oil, exogenous phospholipid is added during step b),
  c) contacting the supplemented edible oil or fat of step b) with at least one lipid acyl transferase, and optionally a further enzyme, to produce an edible oil/enzyme reaction mixture, and
  d) incubating said edible oil/enzyme reaction mixture at a temperature at which said at least one lipid acyl transferase is active in order to produce a modified edible oil or fat comprising i) lysophospholipid and/or one or more of the following glycerophosphatylcholine, phosphatylethanolamine, phosphatylinositol and phosphatylserine, and ii) monoglyceride, and
  e) optionally deactivating or removing said lipid acyl transferase and/or optional further enzyme.

When used as a cooking oil or margarine, the foodstuff may have enhanced anti-plattering properties. In addition or alternatively the foodstuff may have one or more beneficial technical properties, for example improved oxidative stability, improved emulsification properties, or health benefits.

In one embodiment the lipid acyl transferase of the invention can be in the preparation of low fat foodstuffs, such as low fat spreads, low fat salad dressings, low fat mayonnaise, low fat margarines etc. In such low fat food products, the fat content is typically reduced by the addition of emulsifiers and additional water compared to the higher fat equivalent.

The lipid acyl transferases used in the compositions and methods of the invention have been found to have unique properties when compared to lipolytic enzymes in that they have a marked preference for transfer of acyl groups from lipids to acceptors other than water, even in the presence of significant water. In a comparison with prior art enzymes, the lipid acyl transferase used in the invention were found to have a high relative transferase activity in the presence of 6% water, 54% water, 73% water, 89% water and approximately 95%. Lipolytic enzymes tested had virtually no significant relative transferase activity at these water concentrations.

The phospholipase activity of an enzyme may be evaluated using the following assays. In this way, a lipid acyltransferase having the enzyme characteristics defined herein may be obtained/identified.

Determination of Phospholipase Activity (Phospholipase Activity TIPU-K Assay):

Substrate 1.75% L-Phosphatidylcholine 95% Plant (Avanti #441601), 6.3% Triton-X 100 (Peroxide free) and 5 mM $CaCl_2$ is dissolved in 0.05M HEPES buffer pH 7.

Assay Procedure:

21 μL substrate is added to a cuvette (Kone-Lab. Robot) and incubated 30° C. for 5 minutes. At time t=0 min, 4 μL enzyme solution is added. Also a blank with water instead of enzyme was analyzed. At time t=10 min 75 μl NEFA A (Substrate A of NEFA Kit from Wako Chemicals, Germany) is added, mixed and incubated at 30° C. At time t=15 min 150 μl NEFA B (Substrate B of NEFA Kit from Wako Chemicals, Germany) is added and incubated at 30° C. At time t=20 min the Absorbance (OD 520 nm) is measured.

A calibration curve based on oleic acid is produced and used for the calculation of free fatty acid in the samples.

Enzyme activity TIPU-K is calculated as micromole fatty acid produced per minute under assay conditions.

Determination of Phospholipase Activity (Phospholipase Activity PLU-7 Assay):

Substrate 0.6% L-α Phosphatidylcholine 95% Plant (Avanti #441601), 0.4% Triton-X 100 (Sigma X-100) and 5 mM $CaCl_2$ is dispersed in 0.05M HEPES buffer pH 7.

Assay Procedure:

400 μL substrate is added to a 1.5 mL Eppendorf tube and placed in an Eppendorf Thermomixer at 37° C. for 5 minutes. At time t=0 min, 50 μL enzyme solution is added. Also a blank with water instead of enzyme is analyzed. The sample is mixed at 10×100 rpm in an Eppendorf Thermomixer at 37° C. for 10 minutes. At time t=10 min the Eppendorf tube is placed in another thermomixer at 99° C. for 10 minutes to stop the reaction.

Free fatty acid in the samples is analyzed by using the NEFA C kit from WAKO GmbH.

Enzyme activity PLU-7 at pH 7 is calculated as micromole fatty acid produced per minute under assay conditions.

The lipase and acyltransferase activity of an enzyme may be evaluated using the following assays. In this way, a lipid acyltransferase having the enzyme characteristics defined herein may be obtained/identified.

Transferase Assay in Buffered Substrate (see Example 12)

Enzymes which function as lipid acyltransferases for use in the compositions and methods of the invention can be routinely identified using the assay taught herein in Example 12. This assay will be hereinafter referred to as the 'Transferase Assay in Buffered Substrate'. In Example 12 the lipid acyltransferase enzyme from *Aeromonas salmonicida* in accordance with the present invention was analysed and compared with a range of lipolytic enzymes not encompassed by the present invention. As can be seen, of the lipolytic enzymes only LIPOPAN® F (Novozymes, Denmark) was found to have any transferase activity and then only a very low level (1.3%).

Enzymes suitable for use in the compositions and methods of the invention can be routinely identified using the Transferase Assay in Buffered Substrate. Using this assay, in which there is a very high water content—approximately 95%, lipid acyltransferases in accordance with the present invention are those which have at least 2% acyltransferase activity (relative transferase activity), preferably at least 5% relative transferase activity, preferably at least 10% relative transferase activity, preferably at least 15%, 20%, 25% 26%, 28%, 30%, 40% 50%, 60% or 75% relative transferase activity. Suitably, the lipid acyltransferase in accordance with the present invention may have less than 28%, less than 30%, preferably less than 40%, 50%, 60%, 70%, 80%, 90% or 100% acyltransferase activity.

Transferase Assay in High Water Egg Yolk (See Example 11)

As an alternative to (or in addition to) using the "Transferase Assay in Buffered Substrate" (see above), a lipid acyltransferase for use in accordance with the present invention may be identified using the "Transferase Assay in High Water Egg Yolk" taught in Example 11.

In one embodiment, the lipid acyltransferase suitable for use in the methods and/or compositions according to the present invention is one which when tested using the Transferase Assay in High Water Egg Yolk in an egg yolk with 54% water, has up to 100% relative transferase activity. Indeed, experiments in high water egg yolk have shown that at the start of the experiment the initial transferase rate was calculated to be 100% transferase activity, i.e. no hydrolytic activity was observed. In contrast, the lipolytic enzymes used as control, i.e. LIPOPAN® F and phospholipase A2, showed no detectable transferase activity in egg yolk with 54% water, or egg yolk with enriched water content (namely egg yolk with 73% water or 89% water). Preferably the increase in water content does not significantly decrease the percentage acyl transferase activity of a lipid acyltransferase for use in the methods or compositions according to the present invention.

In a preferable embodiment, with reference to the Transferase Assay in High Water Egg Yolk, with a water content of 54%, a lipid acyltransferase for use in the present invention will have an initial percentage acyltransferase activity (initial relative transferase activity) measured after 10% consumption of the donor molecule (i.e. phospholipid) of at least 0.1% relative transferase activity, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 50% relative transferase activity, preferably at least 60%, preferably at least 70%, preferably at least 80%, preferably at least 90%, preferably at least 95%, preferably at least 99%, preferably about 100% acyl transferase activity.

In a preferable embodiment, with reference to the Transferase Assay in High Water Egg Yolk, with a water content of 54%, and measured after 10% consumption of the donor molecule (i.e. phospholipid), the lipid acyltransferase for use in the compositions and methods of the invention has detectable transferase activity, i.e. relative transferase activity of between 0.1 and 100%, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 45%, 50%, 60%, 70%, 80%, or 90% relative transferase activity. Suitably, the lipid acyl transferase in accordance with the present invention may have, when using the Transferase Assay in High Water Egg Yolk with 54% water content and measured after 10% consumption of the donor molecule (i.e. phospholipid), a percentage acyl transferase activity (relative transferase activity) of less than 45%, 47%, 50%, 60%, 70%, 80%, 90% or 100%.

In a preferable embodiment, with reference to the Transferase Assay in High Water Egg Yolk, with a water content of 73%, measured after 10% consumption of the donor molecule (i.e. phospholipid), the lipid acyltransferase for use in the compositions and methods of the invention has detectable transferase activity, i.e. relative transferase activity of between 0.1 and 100%, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 45%, 50%, 58%, 60%, 70%, 80%, or 90% relative transferase activity. Suitably, the lipid acyl transferase in accordance with the present invention may have, when using the Transferase Assay in High Water Egg Yolk with 73% water content and measured after 10% consumption of the donor molecule (i.e. phospholipid), a percentage acyl transferase activity (relative transferase activity) of less than 45%, 47%, 50%, 58%, 60%, 70%, 80%, 90% or 100%.

In a preferable embodiment, with reference to the Transferase Assay in High Water Egg Yolk, with a water content of 89%, and measured after 10% consumption of the donor molecule (i.e. phospholipid), the lipid acyltransferase for use in the compositions and methods of the invention has detectable transferase activity, i.e. relative transferase activity of between 0.1 and 100%, preferably at least 1% relative transferase activity, preferably at least 5% relative transferase activity, preferable at least 10% relative transferase activity, preferably at least 20% relative transferase activity, preferably at least 30% relative transferase activity, preferably at least 40% relative transferase activity, preferably at least 45%, 50%, 60%, 70%, 80%, or 90% relative transferase activity. Suitably, the lipid acyl transferase in accordance with the present invention may have, when using the Transferase Assay in High Water Egg Yolk with 89% water content and measured after 10% consumption of the donor molecule (i.e. phospholipid), a percentage acyl transferase activity (relative transferase activity) of less than 45%, 47%, 50%, 60%, 70%, 80%, 90% or 100%.

In a preferable embodiment, with reference to the Transferase Assay in High Water Egg Yolk, a lipid acyltransferase for use in the compositions and methods of the invention has significant relative transferase activity (i.e. at least 0.1% at both water contents), and has an equivalent relative transferase activity in egg yolk with a water content of 54% as in an egg yolk with a water content of 73%, when measured after 10% consumption of the donor molecule (i.e. phospholipid).

In a preferable embodiment, with reference to the Transferase Assay in High Water Egg Yolk, a lipid acyltransferase for use in the compositions and methods of the invention has significant relative transferase activity (i.e. at least 0.1% at both water contents), and has an equivalent relative transferase activity in egg yolk with a water content of 54% as in an egg yolk with a water content of 89%, when measured after 10% consumption of the donor molecule (i.e. phospholipid).

In a preferable embodiment, with reference to the Transferase Assay in High Water Egg Yolk, a lipid acyltransferase for use in the compositions and methods of the invention has significant relative transferase activity (i.e. at least 0.1% at both water contents), and has an equivalent relative transferase activity in egg yolk with a water content of 73% as in an egg yolk with a water content of 89%, when measured after 10% consumption of the donor molecule (i.e. phospholipid).

The term "equivalent relative transferase activity" as referred to herein means that the enzyme has a relative transferase activity (% acyltransferase activity) which is at least 2% lower, preferably at least 5%, 10%, 20%, 30%, 40%, 50%, 60%, 70%, 80% or 90% lower, in the egg yolk with the higher water content compared with that in the egg yolk with the lower water content.

Transferase Assay in a Low Water Environment

As an alternative to (or in addition to) using the "Transferase Assay in High Water Egg Yolk" and/or the "Transferase Assay in Buffered Substrate", lipid acyltransferases for use in accordance with the present invention may be identified using the "Transferase Assay in a Low Water Environment".

In order to determine if an enzyme is a lipid acyltransferase according to the present invention, one may carry out a "Transferase Assay in a Low Water Environment", namely in an oily environment with 6% water as taught in Example 22. This example illustrates that in an oily environment with 6% water content the lipid acyltransferase of the invention has a high relative transferase activity, where the prior art lipolytic enzymes have hydrolytic activity.

In one embodiment, the lipid acyltransferase suitable for use in the methods and/or compositions according to the present invention is one which when tested using the "Transferase Assay in a Low Water Environment", measured after a time period selected from 30, 20 or 120 minutes, has a relative transferase activity of at least 1%, preferably at least 2%, preferably at least 5%, preferably at least 10%, preferably at least 20%, preferably at least 30%, preferably at least 40%, preferably at least 50%, preferably at least 60%, preferably at least 70%, preferably at least 75%. Suitably, the lipid acyl transferase in accordance with the present invention may have less than 30%, 40%, 50%, 60%, 70%, or 80% activity when measured after a time period of 10, 20, 30 or 120 minutes using the "Transferase Assay in a Low Water Environment".

As described above, the lipase acyltransferase of the invention can be identified using either the "Transferase Assay in Buffered Substrate" or in the "Transferase Assay in Low Water Environment" using cholesterol as the acyl acceptor. Of course, the skilled person would be readily aware that, with obvious amendments to the analytical methods the 'Transferase Assay in Buffered Substrate' or the 'Transferase Assay in Low Water Environment" may be used to determine the lipid acyltransferase activity for any lipid acyl donor or any acyl acceptor combination. The skilled person would, if necessary, simply replace the acyl donor substrate (e.g. phospholipid) with an alternative acyl donor substrate (e.g. glycolipid, triacylglyceride) and/or replace the acyl acceptor (e.g. cholesterol) with an alternative acyl acceptor substrate (e.g. a carbohydrate, a protein, another sterol, a stanol or glycerol).

The term "high water" as used herein means any substrate or foodstuff with more than 2% water content, preferably more than 3%, 4%, 5%, 6%, 7%, 8%, 9%, 10%, 20%, 30%, 40%, 50%, 60%, 70%, 80% or 90%.

The term "low water" as used herein means any substrate or foodstuff with less than 6% water content, preferably less than 5%, 4%, 3%, 2%, 1% or 0.5%.

LUS Assay

The ability to hydrolyse triglyeride (E.C. 3.1.1.3 activity) may be determined by lipase activity is determined according to Food Chemical Codex (3rd Ed., 1981, pp 492-493) modified to sunflower oil and pH 5.5 instead of olive oil and pH 6.5. The lipase activity is measured as LUS (lipase units sunflower) where 1 LUS is defined as the quantity of enzyme which can release 1 [mu]mol of fatty acids per minute from sunflower oil under the above assay conditions.

LUT Assay

Alternatively the LUT assay as defined in WO9845453 may be used. This reference is incorporated herein by reference.

The lipid acyl transferase lipid acyl transferase according to the present invention or for use in the method and/or uses of the present invention which is substantially incapable of acting on a triglyceride may have a LUS/mg of less than 1000, for example less than 500, such as less than 300, preferably less than 200, more preferably less than 100, more preferably less than 50, more preferably less than 20, more preferably less than 10, such as less than 5, less than 2, more preferably less than 1 LUS/mg. Alternatively LUT/mg activity is less than 500, such as less than 300, preferably less than 200, more preferably less than 100, more preferably less than 50, more preferably less than 20, more preferably less than 10, such as less than 5, less than 2, more preferably less than 1 LUT/mg.

The lipid acyl transferase lipid acyl transferase according to the present invention or for use in the method and/or uses of the present invention which is substantially incapable of acting on a monoglyceride may be determined by using monooleate (M7765 1-Oleoyl-rac-glycerol 99%) in place of the sunflower oil in the LUS assay. 1 MGHU is defined as the quantity of enzyme which can release 1 [mu]mol of fatty acids per minute from monoglyceride under the assay conditions.

The lipid acyl transferase lipid acyl transferase according to the present invention or for use in the method and/or uses of the present invention which is substantially incapable of acting on a triglyceride may have a MGHU/mg of less than 5000, for example less than 1000, for example less than 500, such as less than 300, preferably less than 200, more preferably less than 100, more preferably less than 50, more preferably less than 20, more preferably less than 10, such as less than 5, less than 2, more preferably less than 1 MGHU/mg.

Preferably the method and/or use according to the present invention may be carried out, for example, in foodstuff at a temperature of 15-60° C., preferably at a temperature of 20-60° C., preferably 20-50° C., preferably 20-45° C., preferably 20-40° C. For some aspects, for example in dough, preferably the temperature of the food during which the acyltransferase reaction takes place is between 20 and 40° C. For other aspects, for example with regard to dairy products, such as cheese, the temperature of the food may suitably be between 30° C. and 60° C. In yet other aspects, for example with regard to mayonnaise, the temperature of the food may suitably be between 20 and 40° C., more preferably between 25 and 30° C.

Preferably, the emulsifier produced according to the present invention comprises less than 5 wt % of the foodstuff.

Preferably, the emulsifier produced according to the present invention comprises from 0.01 to 4 wt % of the foodstuff.

Preferably, the emulsifier produced according to the present invention comprises from 0.01 to 2 wt % of the foodstuff.

Preferably, the emulsifier produced according to the present invention comprises from 0.01 to 1 wt % of the foodstuff.

Preferably, the emulsifier produced according to the present invention comprises from 0.01 to 0.5 wt % of the foodstuff.

Preferably, the emulsifier produced according to the present invention comprises from 0.01 to 0.3 wt % of the foodstuff.

Suitably, the method according to the present invention includes inactivating or denaturing the enzyme to provide a foodstuff comprising the enzyme in an inactive or denatured form. Suitably the enzyme may be denatured by either baking or by pasteurisation.

The present invention may further encompass the use of a lipid acyltransferase as defined herein in food and/or feed enzyme compositions, and may encompass food and/or feed enzyme compositions comprising a lipid acyltransferase as defined herein. Such compositions may contain one or more further enzymes, such as those listed herein. Alternatively, the enzyme composition of the invention may be used in combination with other food ingredients/additives, such as those listed herein, including other enzyme compositions. By formulation of the lipid acyl transferase of the invention within a food and/or feed composition, the enzyme can be stabilised to allow for prolonged storage (under suitable conditions) prior to use in food and/or feed production. In addition the enzyme composition of the present invention provides the enzyme in a suitable form for safe use for the 'in situ' application in the preparation of foodstuffs and/or feedstuffs, or ingredients for use in food and/or feed preparation. Such compositions may be in either liquid, semi-liquid or solid/granular form.

In one embodiment the food enzyme composition may suitable be a dough improving composition. The dough improving composition may comprise other beneficial components such as an emulsifier and/or other enzymes as listed herein.

Food enzymes are sold as stabilised liquid concentrates or as particulate solids. Formulation into food enzyme composition minimises losses in enzymatic activity during transport, storage, and use. Enzymes are often exposed to humid, hot, or oxidative environments in food and beverage processing. Formulations enhance stability by counteracting the primary forces of deactivation: denaturation, catalytic-site deactivation, and proteololysis. Denaturation occurs by physical unfolding of an enzyme's tertiary protein structure under thermal or chemical stress. Once an enzyme begins to unfold it becomes dramatically more vulnerable to deactivation and proteolysis. To minimise unfolding, the formulator can alter the protein's environment so as to induce a compact protein structure; this is done most effectively by "preferential exclusion" of water from the protein surface by adding water-associating compounds such as sugars, polyhydric alcohols, and lyotropic salts. The best ways to combat active site inactivation are to ensure sufficient levels of any required cofactors, to add reversible inhibitors, and to exclude oxidising or reactive species from the formulation.

Besides enzymatic stability, a formulation should meet several key secondary requirements, including preservation against microbial contamination, avoidance of physical precipitation or haze formation, minimising the formation of sensitising dusts or aerosols, and the optimisation of aesthetic criteria such as colour and odour. Many of these problems are best addressed by focusing as far "upstream" as possible, including the choice of raw materials in the fermentation or enzyme recovery process. Downstream operations such as diafiltration, adsorption, chromatography, crystallization, and extraction can be used to remove impurities responsible for colour, odour, and precipitation. The risk of physical precipitation is minimised by formulating near the isoelectric point of the enzyme with hydrophilic solvents such as glycerol or propylene glycol. One can effectively also add moderate levels of solvating salts to avoid either salting-out or "reverse salting-in". To prevent microbial contamination, one can use a combination of filtration, acidification, and the minimisation of free water; biocides can be effective, but the range of acceptable chemicals for controlling or killing microbes is increasingly circumscribed by health and safety regulations.

Two processes producing the most attrition-resistant granules to date are high-shear granulation and fluidised-bed spray coating, see for example T. Becker: "Separation and Purification Processes for Recovery of Industrial Enzymes" in R. K. Singh, S. S. H. Rizvi (eds.): *Bioseparation Processes in Foods*, Marcel Dekker, New York, pp. 427-445. These processes use various binders, coatings, and particle morphologies to produce nonfriable particles which still protect enzymes during storage but allow for their ready release in solution during use.

Food enzyme compositions containing the lipid acyl transferase of the invention may be made using standard formulation techniques, such as spray drying or liquid formulation.

The lipid acyl-transferase of the invention can be expressed in any suitable expression host. For example the lipid acyl-transferase of the invention may be expressed in *Bacillus subtilis* and may be purified by ultrafiltration and/or by precipitation in ethanol and/or centrifugation, and may be subsequently spray dried using starch (maltodextrin) as carrier for the enzyme. The spray dried enzyme may be standardised to specified PLU activity by adding further carrier in powder form. The techniques involved are well established and routine in the art.

Alternatively, lipid acyltransferase for use in accordance with the present invention, for example the heterologously produced lipid acyl-transferase of the invention, once purified, may be stabilised in a suitable liquid formulation, such as those based on glycerol. Other methods of making stabilised enzyme formulations are described in EP 0 770 037 and EP 0 702 712.

The acyl transferase in powder form can also be used in combination with other enzymes as listed herein, for the production of enzyme compositions with defined activity according to the product specification.

Typically the dosage of the food enzyme formulation is between 10 g and 1000 g per 1000 kg of foodstuff, preferably 50-200 g per 1000 kg of foodstuff, preferably, 75-125 gm per 1000 kg of foodstuff.

Preferably the enzyme according to the present invention is present in an inactive form or in a denatured form in the foodstuff.

In one embodiment, the enzyme according to the present invention is preferably not immobilised, in particular is not immobilised on a solid support.

In an alternative embodiment, the enzyme may be immobilised.

Immobilised lipid acyl transferase can be prepared using immobilisation techniques known in the art. There are numerous methods of preparing immobilised enzymes, which will be apparent to a person skilled in the art (for example the techniques referred to in EP 0 746 608; or Balcao V M, Paiva A L, Malcata F X., Enzyme Microb Technol. 1996 May 1; 18(6):392-416; or Reetz M T, Jaeger K E. Chem Phys Lipids. 1998 June; 93(1-2):3-14; or Bornscheuer U T, Bessler C, Srinivas R, Krishna S H. Trends Biotechnol. 2002 October; 20(10):433-7 (each of which is incorporated herein by reference).

In one embodiment, the foodstuff of the invention may contain food ingredients, which have been prepared using immobilised lipid acyltransferase, but do not contain the lipid acyltransferase in the food ingredient or foodstuff. For example the foodstuff may contain one or more of the following: an emulsifier, more than one emulsifier, one or more flavouring agents, one or more textural enhancers and/or one or more sterol esters, such as phytosterol esters or phytostanol esters.

The enzyme according to the present invention may be used with one or more conventional emulsifiers, including for example monoglycerides, diacetyl tartaric acid esters of mono- and diglycerides of fatty acids, and lecithins e.g. obtained from soya.

The enzyme according to the present invention may be used with one or more other suitable food grade enzymes. Thus, it is within the scope of the present invention that, in addition to the enzyme of the invention, at least one further enzyme is added to the foodstuff. Such further enzymes include starch degrading enzymes such as endo- or exoamylases, pullulanases, debranching enzymes, hemicellulases including xylanases, cellulases, oxidoreductases, e.g. peroxidases, phenol oxidases, glucose oxidase, pyranose oxidase, sulfhydryl oxidase, or a carbohydrate oxidase such as one which oxidises maltose, for example hexose oxidase (HOX), lipases, phospholipases, glycolipases, galactolipases and proteases.

In one embodiment the enzyme may be Dairy HOX™, which acts as an oxygen scavenger to prolong shelf life of cheese while providing browning control in pizza ovens. Therefore in a one aspect the present invention relates to the use of an enzyme capable of reducing the maillard reaction in a foodstuff (see WO02/39828 incorporated herein by reference), such as a dairy product, for example cheese, wherein the enzyme is preferably a maltose oxidising enzyme such as carbohydrate oxidae, glucose oxidase and/or hexose oxidase, in the process or preparing a food material and/or foodstuff according to the present invention.

In one preferred embodiment the lipid acyltransferase is used in combination with a lipase having one or more of the following lipase activities: glycolipase activity (E.C. 3.1.1.26, triacylglycerol lipase activity (E.C. 3.1.1.3), phospholipase A2 activity (E.C. 3.1.1.4) or phospholipase A1 activity (E.C. 3.1.1.32). Suitably, lipase enzymes are well know within the art and include by way of example the following lipases: LIPOPAN® F and/or LECITASE® ULTRA (Novozymes A/S, Denmark), phospholipase A2 (e.g. phospholipase A2 from LIPOMOD™ 22L from Biocatalysts, LIPOMAX™ from Genecor), LIPOLASE® (Novozymes A/S, Denmark), the lipases taught in WO03/97835, EP 0 977 869 or EP 1 193 314. This combination of a lipid acyl transferase as defined herein and a lipase may be particularly preferred in dough or baked products or in fine food products such as cakes and confectionary.

In some embodiments, it may also be beneficial to combine the use of lipid acyltransferase with a lipase such as rennet paste prepared from calf, lamb, kid stomachs, or Palatase A750L (Novo), Palatase M200L (Novo), Palatase M1000 (Novo), or Piccantase A (DSM), also Piccantase from animal sources from DSM (K, KL, L & C) or Lipomod 187, Lipomod 338 (Bioctalysts). These lipases are used conventionally in the production of cheese to produce cheese flavours. These lipases may also be used to produce an enzymatically-modified foodstuff, for example dairy product (e.g. cheese), particularly where said dairy product consists of, is produced from or comprises butterfat. A combination of the lipid acyltransferase with one or more of these lipases may have a beneficial effect on flavour in the dairy product (e.g. cheese for instance).

The use of lipases in combination with the enzyme of the invention may be particularly advantageous in instances where some accumulation of free fatty acids maybe desirable, for example in cheese where the free fatty acids can impart a desirable flavour, or in the preparation of fine foods. The person skilled in the art will be able to combine proportions of lipolytic enzymes, for example LIPOPAN® F and/or LECITASE® ULTRA (Novozymes A/S, Denmark), phospholipase A2 (e.g. phospholipase A2 from LIPOMOD™ 22L from Biocatalysts, LIPOMAX™ from Genecor), LIPOLASE® (Novozymes A/S, Denmark), the lipases taught in WO03/97835, EP 0 977 869 or EP 1 193, 314 and the lipid acyltransferase of the present invention to provide the desired ratio of hydrolytic to transferase activity which results in a preferred technical effect or combination of technical effects in the foodstuff (such as those listed herein under 'Technical Effects').

It may also be beneficial to combine the use of lipid acyltransferase with a phospholipase, such as phospholipase A1, phospholipase A2, phospholipase B, Phospholipase C and/or phospholipase D.

The combined use may be performed sequentially or concurrently, e.g. the lipid acyl transferase treatment may occur prior to or during the further enzyme treatment. Alternatively, the further enzyme treatment may occur prior to or during the lipid acyl transferase treatment.

In the case of sequential enzyme treatments, in some embodiments it may be advantageous to remove the first enzyme used, e.g. by heat deactivation or by use of an immobilised enzyme, prior to treatment with the second (and/or third etc.) enzyme.

Traditionally the cake industry uses cake improvers for the production of cakes and to secure high quality cakes in terms of taste, structure, eating quality and appearance. These cake improvers are normally based on emulsifiers spray dried on a carrier like starch and malto dextrin. Some cake improvers are also in a gel form based on emulsifiers, sugars and water. These cake improvers are very important for the cake industry in order to produce cake of high quality. Cake improvers however contain emulsifiers and other "non-natural" ingredients with an E-number. Because of demand for the consumers to reduce the numbers of E-numbers, the cake industry has asked for alternative ways to produce cakes of high quality without using emulsifiers.

An alternative way to produce cake is to use an enzyme, i.e. the lipid acyltransferase defined herein or an enzyme composition according to the present invention.

The lipid acyltransferase as defined herein and/or the food enzyme composition of the present invention may be used in the preparations of a fine food, such as a cake. In such instances, the following constituents may be formed in the fine food:

i) sugar esters and lysolecithin (from the carbohydrate in the cake recipe and the lecithin in egg which also form part of the cake recipe); and/or ii) acylated peptides and lysolecithin (by transferring a fatty acid from lecithin to a protein or peptide during formation of protein-fatty acid condensates, which are known to be highly efficient emulsifiers (Herstellung und Anvendungmöglichkeiten von Eiweiss-Fettsäurekondensaten. Andreas Sander, Eberhard Eilers, Andrea Heilemann, Edith von Kreis.Fett/lipid 99 (1997) Nr. 4, 115-120).

It is considered that in the production of some fine foods, particularly high fat fine foods, such as cakes, it may be desirable to have some accumulation of fatty acids. Therefore the combination of the use of lipolytic enzymes and the lipid acyl transferase as defined herein may be particularly beneficial for production of high fat fine foods. Alternatively, additional free fatty acids or fatty acid soap (E470a) may be selected and used in combination with the lipid acyl transferase.

The foodstuff according to the present invention may suitably comprise one or more of the following additives: soy protein material; carotenoids, flavenoids, antioxidant and phytochemical (especially anthocyanonide, carotenoid, bioflavinoid, glutathione, catechin, isoflavone, lycopene, ginsenoside, pycnogenol, alkaloid, pygeum phytosterol, sulphoraphone, resveretol, grape seed extract or food containing stanol esters), vitamin (especially vitamin C, vitamin A, vitamin B3, vitamin D, vitamin E, thiamine, riboflavin, niacin, pyridoxine, cyanocobalamin, folic acid, biotin, pantothenic acid or vitamin K), minerals (especially calcium, iodine, magnesium, zinc, iron, selenium, manganese, chromium, copper, cobalt, molybdenum or phosphorus), fatty acid (especially gamma-linoleic acid, ucospentaenoic acid or decosahexaenoic acid), oil (especially borage oil, high carotenoid canola oil or flax seed oil), amino acid (especially tryptophan, lysine, methionine, phenylalanine, threonine, valine, leucine, isoleucine, alanine, arginine, aspartic acid, cystine, cysteine, glutamic acid, glutamine, glycine, histidine, proline, hydroxyproline, serine, taurine or tyrosine), enzyme (especially bromelain, papain, amylase, cellulase or coenzyme Q), lignin, stanol ester or friendly bacteria (especially *Lactobacillus acidophilus, Lactobacillus bulgaricus, Lactobacillus bifidus, Lactobacillus plantarum* or *Streptococcus faecium*), folic acid, and soluble fibre.

Technical Effect

Surprisingly lipid acyltransferases have significant acyltransferase activity in foodstuffs. This activity has surprising beneficial applications in methods of preparing foodstuffs.

The present invention is predicated upon the surprising finding that the lipid acyltransferases according to the present invention can perform carbohydrate-esterification via alcoholosis, i.e. acyl transfer from a lipid, in a foodstuff with a significant water content. Prior art suggests that such enzymes if they would function at all in this manner would only function in a solvent environment (i.e. in environments with low or no water content).

The present invention may provide one or more of the following unexpected technical effects in egg products, particularly mayonnaise: an improved heat stability during pasteurization; improved organoleptic properties, an improved consistency.

The present invention may provide one or more of the following unexpected technical effects in dough and/or baked products: an improved specific volume of either the dough or the baked products (for example of bread and/or of cake); an improved dough stability; an improved crust score (for example a thinner and/or crispier bread crust), an improved crumb score (for example a more homogenous crumb distribution and/or a finer crumb structure and/or a softer crumb); an improved appearance (for example a smooth surface without blisters or holes or substantially without blisters or holes); a reduced staling; an enhanced softness; an improved odour; an improved taste.

The present invention may provide a beneficial effect from formation of highly surface-active materials in a foodstuff without formation of substantial amount of free fatty acids, which reduce the ability of the foodstuff to oxidize upon storage, because free fatty acids are more prone to oxidation than the corresponding fatty acid esters.

Suitably, the present invention may provide one or more of the following unexpected technical effects in a foodstuff: an improved appearance, an improved mouthfeel, an improved stability, in particular an improved thermal stability, an improved taste, an improved softness, an improved resilience, an improved emulsification.

Suitably, the present invention may provide one or more of the following unexpected technical effects in dairy products, such as ice cream for example: an improved mouthfeel (preferably a more creamy mouthfeel); an improved taste; an improved meltdown.

Suitably, the present invention may provide one or more of the following unexpected technical effects in egg or in egg products: improved stability of emulsion; thermal stability of emulsion; improved flavour; reduced mal-odour; improved thickening properties, improved consistency.

Specific technical effects associated with the use of a lipid acyltransferase as defined herein in the preparation of a foodstuff are listed in the table below:

| | Foodstuff | Effect |
|---|---|---|
| 1 | Bread, Muffins and Doughnuts | Strengthens dough and increases mechanical resistance and increases water absorption capacity. Increases volume of bakery products and maintains softness of crumb |
| 2 | Frozen dough | Prevents spoiling during refrigeration |
| 3 | Sponge cake | Makes good cake volume and a uniform soft texture |
| 4 | Biscuit, cracker and cookie | Makes stable emulsions of fat and prevents stickiness to the machine. Prevents blooming of high fat products |
| 5 | Batter and breading | Improves texture of fried products. |
| 6 | Noodles | Prevents dough from sticking to the machine. Increases water content, and decreases cooking loss |
| 7 | Instant noodles | Prevent noodles form adhering to each other |
| 8 | Pasta | Dough conditioner prevents adhesion on cooking. |
| 9 | Custard cream | Makes starch paste with a smooth and creamy texture, and prevents dehydration. |
| 10 | Coffee whitener | Prevent oil and water separation |
| 11 | Whipping cream | Provides stable emulsion |
| 12 | Chocolate | Prevents or reduced blooming |
| 13 | Caramel, candy and nougat | Improves emulsification of molten sugar and oil. Prevents separation of oil. |
| 14 | Processed meat, sausages | Improves water holding capacity of sausages and pressed ham, and prevents separation of oil phase of pastes and pâté. |

Suitably, the present invention may provide one or more of the following unexpected technical effects in cheese: a decrease in the oiling-off effect in cheese; an increase in cheese yield; an improvement in flavour; a reduced mal-odour; a reduced "soapy" taste.

Oiling-off is the tendency to form free oil upon storage and melting. Excessive oiling-off is a defect most often related to heated products wherein cheese is used, e.g. pizza and related foods (cf. e.g. Kindstedt J. S; Rippe J. K. 1990, J Dairy Sci. 73: 867873. It becomes more and more important to control/eliminate this defect, as the consumer concern about dietary fat levels increases. Free oil/fat in a product is perceived as a high fat content, and is generally undesirable. The oiling off effect can not only affect the appearance of the cheese, but in severe cases the oil released by the cheese may spread across the food product, and be absorbed by the food product. This is particularly detrimental to food products which contain a baked components, such as a pizza base, and the effect is not only seen in the undesirable appearance, but also detrimental texture and flavour may also result.

In foodstuffs the fat phase is often stabilised by mechanic emulsification, e.g. homogenisation. This technology is generally not applicable in cheese production as homogenisation of the cheese milk has a negative influence on the coagulation properties of the cheese milk and on the yield as well as the taste of the cheese produced therefrom.

The use of the enzyme modified foodstuff and/or food material of the present invention (including enzyme modified milk, cream and/or butter fat for example) can be used to produce foodstuffs such as cheese which have a reduced oiling-off effect and/or to improve the homogenization properties of the cheese milk, and/or reduce the negative influence of coagulation properties of homogenised cheese milk when made into cheese, and/or improve the flavour and/or texture of the cheese.

Oiling off effect and cheese yield and fat yield/content can be measured according to the protocols disclosed in WO00/54601.

In one embodiment the foodstuff (for example the dairy product, e.g. cheese) prepared in accordance with the present invention may have a higher yield.

Cheese yield increases may occur either when the cheese milk and/or cream is modified directly by enzyme treatment, and/or when the cheese milk is supplemented with the enzyme modified oil or fat, such as enzyme modified butterfat.

A further advantage of the present invention may be the reduction of off-flavours and/or off-tastes, preferably by reducing the amount of free fatty acids in the enzymatically treated foodstuffs (e.g. in the cheese).

One advantage of the present invention is that the lipid acyltransferase may be used in a lower dosage to produce the same (or better) effects compared with a phospholipase A2 (PLA2). Thus effectively enzyme may be necessary to achieve the same (or better) results.

Another advantage of the present invention is that the lipid acyltransferase for use in the present invention and particularly in cheese manufacture does not necessarily require pretreatment of the milk and/or cream. In fact the lipid acyltransferase when used in the present invention may be added directly to the cheese vat. This may advantageously simplify the cheese manufacture process for the end user.

Another advantage of the present invention is that the lipid acyltransferase may increase the moisture content of the foodstuff, such as for example a cheese (e.g. mozzarella) and/or butterfat, compared to when a phospholipase such as Lecitase™ is used for instance.

In one embodiment, the use of the enzyme modified foodstuff and/or food material of the present invention can be used to produce a foodstuff such as cheese that has an increased moisture content compared to when a phospholipase such as Lecitase™ is used for instance. This one embodiment may be particularly advantageous where the foodstuff and/or food material is a dairy product, for example milk, cream, butterfat, and/or cheese.

Another advantage of the present invention is that sterol esters and/or stanol esters may be produced in foodstuff. This one embodiment this may be particularly advantageous where the foodstuff and/or food material is a dairy product, for example milk, cream, butterfat, and/or cheese.

Advantageously the present invention may be used to reduce the cholesterol level of a foodstuff, particularly a dairy product, for example cheese.

In food production, in particular cheese production, the use of the lipid acyltransferase in accordance with the present invention provides a significant advantage in the ability to recover soluble proteins from dairy products. For example, in cheese production nearly 20% of all milk protein is removed in the whey (i.e. the watery part of the milk that remains after the formation of curds). The whey comprises the soluble milk proteins, whereas the hydrophobic proteins are maintained in the curd. By use of the lipid acyltransferase in accordance with the present invention it is possible to transfer an acyl group from a lipid (preferably from a glycolipid or a phospholipid), to a protein (in particular to a whey protein such as lactoglobulin) to from a protein fatty acid condensate. Thus, producing a product which is more hydrophobic and which will stay in the curd rather than being eluted in the whey. In this way, more of the milk protein can be maintained in the final foodstuff, i.e. the final dairy product such as the cheese.

In one aspect, the present invention is based in part on the realisation that yields of foods—such as cheese—may be improved by the use of a lipid acyl transferase. In addition or alternatively, the flavour, texture, oxidative stability and/or shelf life of the food may be improved. In addition or alternatively, the food may have a reduced cholesterol level or enhanced content of phytosterol/stanol esters.

Without wishing to be bound to a particular theory it is considered that the increase in yield may be the result of the transesterification of whey proteins and peptides, resulting in a significant increase in the hydrophobicity of the whey proteins and precipitation of the acylated whey proteins in the cheese curd.

In biological systems, for example, the deposition of membrane bound proteins and enzymes are achieved by two different mechanisms. The membrane bound proteins either possess a number of membrane-spanning or hydrophobic domains, or they have alternatively a fatty acid linked to the polypeptide chain. The fatty acids have normally a chain length of 14 or 16 carbon atoms. The fatty acids are covalently linked to the polypeptide chain at 3 different position, the N-terminal amino acid as an amide-bond, a cysteine residue as a thioester linkage, or a serine or threonine amino acid as an ester linkage. Only one fatty acid per polypeptide molecule is necessary to incorporate the protein into the cell membrane.

When a fatty acid is covalently linked to a non-membrane protein, the physical and functional properties will change drastically. WO97/14713 describes the transformed soy and gluten proteins into acyl derivatives by treatment with a lipase from *Mucor miehei* (Lipozyme™, Novozymes), and a fatty acid in organic solvent. The lipid acyl transferase according to the present invention may be used in the production of acylated proteins is a low or high water environment.

We note that acylated proteins form amphiphilic complexes that can be used for a number of cosmetic products. The acylated protein can form gels, bind water by retaining moisture, have emulsifying properties and is very active in the interphase between water and lipid.

Thus, the present invention may in one aspect provide a cosmetic composition comprising a lipid acyl transferase as defined herein.

In addition, the present invention may provide the use of an acyltransferase as defined herein to produce a cosmetic composition.

In a further aspect, the present invention provides a method of in situ production of a protein ester in a cosmetic composition, wherein the method comprises the step of adding to the cosmetic composition (or components thereof) a lipid acyltransferase as defined herein.

Many food proteins are soluble in aqueous solutions and are therefore suitable for in situ modification by the lipase acyl transferase. In the cheese production, β-lactoglobulin is lost to the whey fraction. After acylation with a lipase acyl transferase, or a lipase acyl transferase variant, initial results indicate that b-lactoglobulin may however, be deposited in the casein micelle surface during rennet coagulation. β-lactoglobulin has three potential acylation sites (serine residues) on three surface loops. Milk contains sufficient amounts of lecithin, a suitable substrate for a lipid acyl transferase enzyme to acylate the β-lactoglobulin. The lysolecithin formed may have an additional emulsifying effect.

The improvements observed with lipid acyltransferase according to the present invention are in comparison to when lipolytic enzymes without acyltransferase activity, such as triacylglycerol lipases and phospholipases, are used.

Advantages

The generation of an emulsifier and a sterol/stanol ester in situ from at least one constituent of the food material, means that the food material will contain at least one less additive material. This is advantageous because of the improvement in the ease of production. For example, no further processing or addition of ingredients or addition of emulsifiers may be required. Moreover, the foodstuff may contain less "additives". The reduction or elimination of "additives" is desirable to consumers and inclusion of additives often must be declared to the consumer in the ingredients listing on the foodstuff. Thus, the present invention is further advantageous.

An advantage of the present invention may be the production in situ of an emulsifier in a foodstuff without a detrimental increase in the free fatty acid content of the foodstuff.

The generation of two emulsifiers and/or a carbohydrate ester in situ from at least one constituent of the food material, means that the food material will contain at least one less additive material.

In addition, when the lipid acyltransferase acts on a glycolipid it is possible to advantageously produce the emulsifier DGMG in situ without a detrimental increase in the free fatty acid content of the foodstuff. Thus, reducing detrimental effects attributed to an increase in free fatty acids, including but not limited to a reduction in "soapy" taste in cheese, prevention of overdosing in dough and dough baked properties.

For some aspects, an advantage of the present invention is the reduction in free cholesterol levels in the foodstuff.

For other aspect, an advantage of the present invention is the increase in stanol and/or sterol esters in the foodstuff. Some sterol/stanol esters may be effective flavourants and/or texturisers. Thus, the present invention may not only results in the in situ production of an emulsifier in a foodstuff, but also the in situ production of a flavourant and/or a texturiser. Some sterol/stanol esters are known to reduce blood serum cholesterol and/or low density lipoproteins when consumed in a foodstuff. Thus, the present invention may be used to prepare a foodstuff with increased levels of sterol esters and/or stanol esters.

For some aspects, particularly when the enzyme according to the present invention is used in egg based products, an advantage is the removal of unwanted free carbohydrates.

Also advantageously the emulsification properties of the foodstuff are enhanced, leading to improved appearance and/or handling properties and/or structure and/or consistency and/or heat stability without a negative impact on taste.

In addition, for some embodiments advantageously the effect of "overdosing" observed when using lipases per se, is effectively overcome by the addition of an enzyme in accordance with the present invention. This is due at least in part to the fact that free fatty acids are not produced or only produced to an insignificant degree when using the enzyme according to the present invention.

Further and/or alternative advantages are taught in the section entitled "Tehnical Effects" above.

Isolated

In one aspect, preferably the polypeptide or protein for use in the present invention is in an isolated form. The term "isolated" means that the sequence is at least substantially free from at least one other component with which the sequence is naturally associated in nature and as found in nature.

Purified

In one aspect, preferably the polypeptide or protein for use in the present invention is in a purified form. The term "purified" means that the sequence is in a relatively pure state—e.g. at least about 51% pure, or at least about 75%, or at least about 80%, or at least about 90% pure, or at least about 95% pure or at least about 98% pure.

Cloning a Nucleotide Sequence Encoding a Polypeptide According To the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characterisitics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. Nos. 6,344,328, 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the lipid acyltransferase used in the invention may be a variant, i.e. may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx, GANDY (SEQ ID NO: 15) and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the lipid acyltransferase for use in the invention may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases for use in the invention may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme for use in the invention may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 Jan. 15: 266 (2): 997-1000; Robertson et al J. Biol. Chem. 1994 Jan. 21; 269(3):2146-50; Brumlik et al J. Bacteriol 1996 April; 178 (7): 2060-4; Peelman et al Protein Sci. 1998 March; 7(3):587-99.

Amino Acid Sequences

The present invention also encompasses amino acid sequences of polypeptides having the specific properties as defined herein.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 μg of the freeze-dried material may be dissolved in 50 μl of a mixture of 8 M urea and 0.4 M ammonium hydrogen carbonate, pH 8.4. The dissolved protein may be denatured and reduced for 15 minutes at 50° C. following overlay with nitrogen and addition of 5 μl of 45 mM dithiothreitol. After cooling to room temperature, 5 μl of 100 mM iodoacetamide may be added for the cysteine residues to be derivatized for 15 minutes at room temperature in the dark under nitrogen.

135 μl of water and 5 μg of endoproteinase Lys-C in 5 μl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 μm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387) or the Vector NTI (Invitrogen Corp.). Examples of software that can perform sequence comparisons include, but are not limited to, the BLAST package (see Ausubel et al 1999 Short Protocols in Molecular Biology, 4$^{th}$ Ed—Chapter 18), FASTA (Altschul et al 1990 J. Mol. Biol. 403-410) and Align X for example. Both BLAST and FASTA are available for offline and online searching (see Ausubel et al 1999, pages 7-58 to 7-60). A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs and GCG Wisconsin programs generally use either the public default values or a custom symbol comparison table if supplied (see user manual for further details). For some applications, it is preferred to use the public default values for the GCG package or Vector NTI, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Should Gap Penalties be used when determining sequence identity, then preferably the following parameters are used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

The nucleotide sequence of the present invention or coding for a polypeptide having the specific properties as defined herein may be present in a vector, in which the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence for use in the present invention or a nucleotide sequence encoding a polypeptide having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions.

Preferably, the nucleotide sequence of the present invention may be operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the ShI-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Host Cells

The term "host cell"—in relation to the present invention includes any cell that comprises either a nucleotide sequence encoding a polypeptide having the specific properties as defined herein or an expression vector as described above and which is used in the recombinant production of a polypeptide having the specific properties as defined herein.

Thus, a further embodiment of the present invention provides host cells transformed or transfected with a nucleotide sequence of the present invention or a nucleotide sequence that expresses a polypeptide having the specific properties as defined herein. The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus: 50 years on*. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit. Rev Biotechnol (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts, Vol 5*, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp. including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO01/39544).

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27), or in WO01/16308. The transgenic plant may produce enhanced levels of phytosterol esters and phytostanol esters, for example.

Therefore the present invention also relates to a method for the production of a transgenic plant with enhanced levels of phytosterol esters and phytostanol esters, comprising the steps of transforming a plant cell with a lipid acyltransferase as defined herein (in particular with an expression vector or construct comprising a lipid acyltransferase as defined herein), and growing a plant from the transformed plant cell.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (Bacillus).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and U.S. Pat. No. 4,366,241.

Also, recombinant immunoglobulins may be produced as shown in U.S. Pat. No. 4,816,567.

Fusion Proteins

A polypeptide having the specific properties as defined herein may be produced as a fusion protein, for example to aid in extraction and purification thereof. Examples of fusion protein partners include glutathione-S-transferase (GST), 6xHis (SEQ ID NO: 55), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

In another embodiment of the invention, the amino acid sequence of a polypeptide having the specific properties as defined herein may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The invention will now be described, by way of example only, with reference to the following Figures and Examples.

FIG. 1 shows a pfam00657 consensus sequence from database version 6 (SEQ ID No. 1);

FIG. 2 shows an amino acid sequence (SEQ ID No. 2) obtained from the organism *Aeromonas hydrophila* (P10480; GI:121051);

FIG. 3 shows an amino acid sequence (SEQ ID No. 3) obtained from the organism *Aeromonas salmonicida* (AAG098404; GI:9964017);

FIG. 4 shows an amino acid sequence (SEQ ID No. 4) obtained from the organism *Streptomyces coelicolor* A3(2) (Genbank accession number NP_631558);

FIG. 5 shows an amino acid sequence (SEQ ID No. 5) obtained from the organism *Streptomyces coelicolor* A3(2) (Genbank accession number: CAC42140);

FIG. 6 shows an amino acid sequence (SEQ ID No. 6) obtained from the organism *Saccharomyces cerevisiae* (Genbank accession number P41734);

FIG. 7 shows an alignment of selected sequences (SEQ ID NOS 61 & 91-94 disclosed respectively in order of appearance) to pfam00657 consensus sequence (SEQ ID NO: 1);

Figure 35:
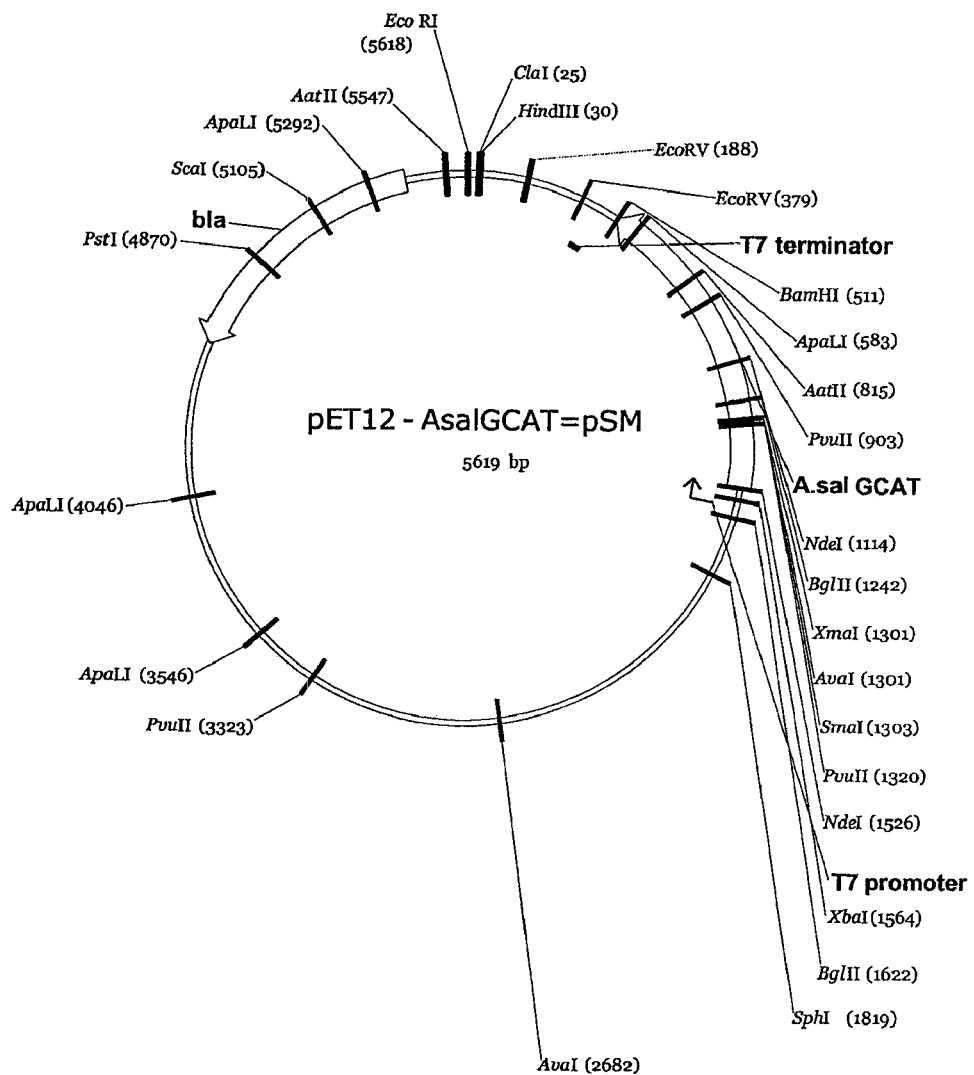

FIG. 8 shows a pairwise alignment of SEQ ID No. 3 (residues 1-335) with SEQ ID No. 2 showing 93% amino acid sequence identity. The signal sequence is underlined. +denotes differences. The GDSX motif containing the active site serine 16, and the active sites aspartic acid 116 and histidine 291 are highlighted (see shaded regions). Numbers after the amino acid is minus the signal sequence;

FIG. 9 shows a nucleotide sequence (SEQ ID No. 7) encoding a lipid acyl transferase according to the present invention obtained from the organism *Aeromonas hydrophila*;

FIG. 10 shows a nucleotide sequence (SEQ ID No. 8) encoding a lipid acyl transferase according to the present invention obtained from the organism *Aeromonas salmonicida*;

FIG. 11 shows a nucleotide sequence (SEQ ID No. 9) encoding a lipid acyl transferase according to the present invention obtained from the organism *Streptomyces coelicolor* A3(2) (Genbank accession number NC_003888.1: 8327480.8328367);

FIG. 12 shows a nucleotide sequence (SEQ ID No. 10) encoding a lipid acyl transferase according to the present invention obtained from the organism *Streptomyces coelicolor* A3(2) (Genbank accession number AL939131.1: 265480.266367);

FIG. 13 shows a nucleotide sequence (SEQ ID No. 11) encoding a lipid acyl transferase according to the present invention obtained from the organism *Saccharomyces cerevisiae* (Genbank accession number Z75034);

FIG. 14 shows an amino acid sequence (SEQ ID No. 12) obtained from the organism Ralstonia (Genbank accession number: AL646052);

FIG. 15 shows a nucleotide sequence (SEQ ID No. 13) encoding a lipid acyl transferase according to the present invention obtained from the organism Ralstonia;

FIG. 16 shows SEQ ID No. 20. Scoe1 NCBI protein accession code CAB39707.1 GI:4539178 conserved hypothetical protein [*Streptomyces coelicolor* A3(2)];

FIG. 17 shows a nucleotide sequence shown as SEQ ID No. 21 encoding NCBI protein accession code CAB39707.1 GI:4539178 conserved hypothetical protein [*Streptomyces coelicolor* A3(2)];

FIG. 18 shows an amino acid shown as SEQ ID No.22. Scoe2 NCBI protein accession code CAC01477.1 GI:9716139 conserved hypothetical protein [*Streptomyces coelicolor* A3(2)];

FIG. 19 shows a nucleotide sequence shown as SEQ ID No. 23 encoding Scoe2 NCBI protein accession code CAC01477.1 GI:9716139 conserved hypothetical protein [*Streptomyces coelicolor* A3(2)];

FIG. 20 shows an amino acid sequence (SEQ ID No.24) Scoe3 NCBI protein accession code CAB88833.1 GI:7635996 putative secreted protein. [*Streptomyces coelicolor* A3(2)];

FIG. 21 shows a nucleotide sequence shown as SEQ ID No. 25 encoding Scoe3 NCBI protein accession code CAB88833.1 GI:7635996 putative secreted protein. [*Streptomyces coelicolor* A3(2)];

FIG. 22 shows an amino acid sequence (SEQ ID No.26) Scoe4 NCBI protein accession code CAB89450.1 GI:7672261 putative secreted protein. [*Streptomyces coelicolor* A3(2)];

FIG. 23 shows an nucleotide sequence shown as SEQ ID No. 27 encoding Scoe4 NCBI protein accession code CAB89450.1 GI:7672261 putative secreted protein. [*Streptomyces coelicolor* A3(2)];

FIG. 24 shows an amino acid sequence (SEQ ID No.28) Scoe5 NCBI protein accession code CAB62724.1 GI:6562793 putative lipoprotein [*Streptomyces coelicolor* A3(2)];

FIG. 25 shows a nucleotide sequence shown as SEQ ID No. 29, encoding Scoe5 NCBI protein accession code CAB62724.1 GI:6562793 putative lipoprotein [*Streptomyces coelicolor* A3(2)];

FIG. 26 shows an amino acid sequence (SEQ ID No.30) Srim1 NCBI protein accession code AAK84028.1 GI:15082088 GDSL-lipase [*Streptomyces rimosus*];

FIG. 27 shows a nucleotide sequence shown as SEQ ID No. 31 encoding Srim1 NCBI protein accession code AAK84028.1 GI:15082088 GDSL-lipase [*Streptomyces rimosus*];

FIG. 28 shows an amino acid sequence (SEQ ID No.32) A lipid acyl transferase from *Aeromonas hydrophila* (ATCC #7965);

FIG. 29 shows a nucleotide sequence (SEQ ID No. 33) encoding a lipid acyltransferase from *Aeromonas hydrophila* (ATCC #7965);

FIG. 30 shows an amino acid sequence (SEQ ID No.34) of a lipid acyltransferase from *Aeromonas salmonicida* subsp. *Salmonicida* (ATCC#14174);

FIG. 31 shows a nucleotide sequence (SEQ ID No 35) encoding a lipid acyltransferase from *Aeromonas salmonicida* subsp. *Salmonicida* (ATCC#14174);

FIG. 32 shows that homologues of the *Aeromonas* genes can be identified using the basic local alignment search tool service at the National Center for Biotechnology Information, NIH, MD, USA and the completed genome databases. The GDSX motif was used in the database search and a number of sequences/genes potentially encoding enzymes with lipolytic activity were identified. Genes were identified from the genus *Streptomyces, Xanthomonas* and *Ralstonia*. As an example below, the *Ralstonia solanacearum* (SEQ ID NO: 96) was aligned to the *Aeromonas salmonicida* (satA) (SEQ ID NO: 95) gene. Pairwise alignment showed 23% identity. The active site serine is present at the amino terminus and the catalytic residues histidine and aspartic acid can be identified;

FIG. 33 shows the Pfam00657.11 [family 00657, database version 11] consensus sequence (hereafter called Pfam consensus) and the alignment of various sequences to the Pfam consensus sequence. The arrows indicate the active site residues, the underlined boxes indicate three of the homology boxes indicated by [Upton C and Buckley JT (1995) Trends Biochem Sci 20; 179-179]. Capital letters in the Pfam consensus indicate conserved residues in many family members. The — symbol indicates a position where the hidden Markov model of the Pfam consensus expected to find a residue but did not, so a gap is inserted. The . symbol indicates a residue without a corresponding residue in the Pfam consensus. The sequences are the amino acid sequences listed in FIGS. 16, 18, 20, 22, 24, 26, 28 and 30. (SEQ ID NOS 97, 30, 20, 22, 24, 26, 28, 32, 34& 36)

FIG. 34 shows the Pfam00657.11 [family 00657, database version 11] consensus sequence (hereafter called Pfam consensus) and the alignment of various sequences to the Pfam consensus sequence. The arrows indicate the active site residues, the underlined boxes indicate three of the homology boxes indicated by [Upton C and Buckley JT (1995) Trends Biochem Sci 20; 179-179]. Capital letters in the Pfam consensus indicate conserved residues in many family members. The — symbol indicates a position where the hidden Markov model of the Pfam consensus expected to find a residue but did not, so a gap is inserted. The . symbol indicates a residue without a corresponding residue in the Pfam consensus. The sequences are the amino acid sequences listed in FIGS. 2, 16, 18, 20, 26, 28 and 30. All these proteins were found to be active against lipid substrates. (SEQ ID NOS 98, 30, 20, 22, 32, 34 & 36)

Figure 36:
Figure 37:
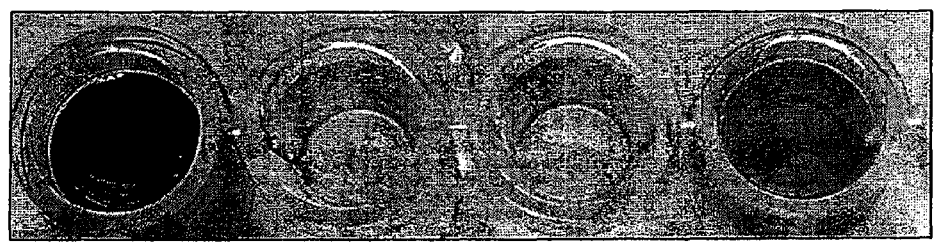
Figure 38:
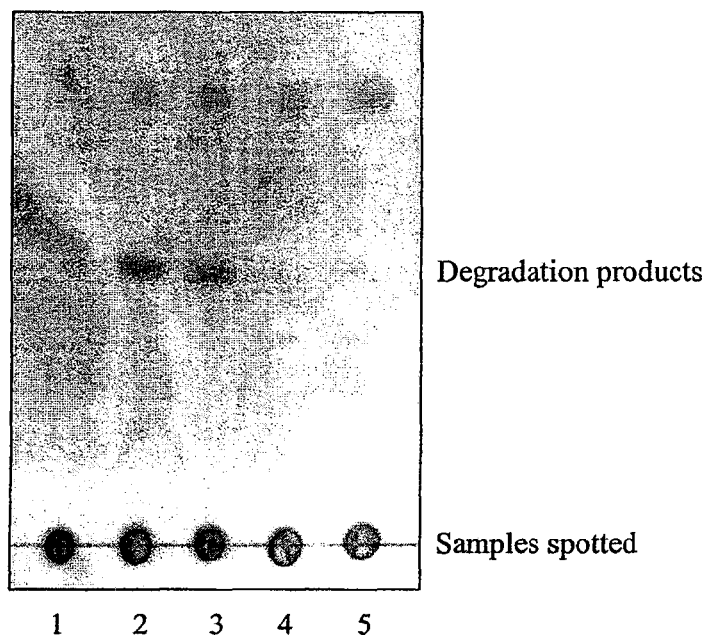
Figure 39:
Figure 40:
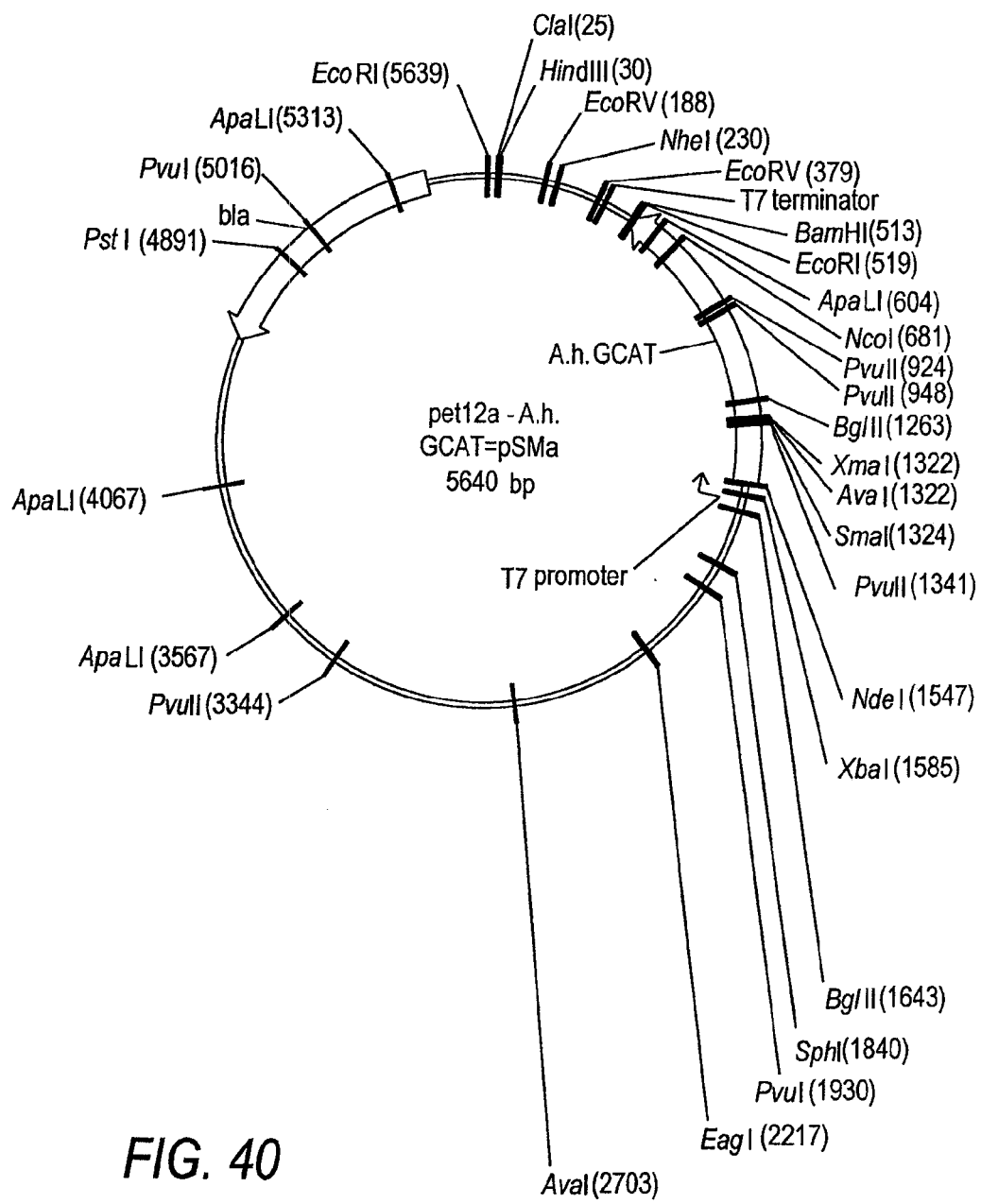
Figure 41:
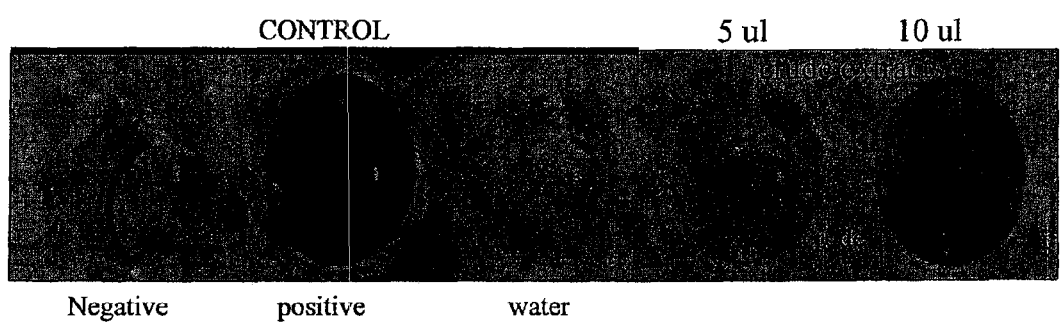
Figure 42:
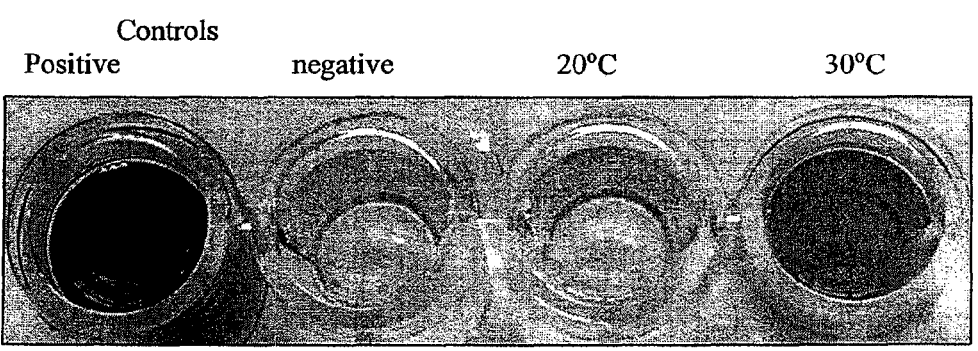
Figure 43:
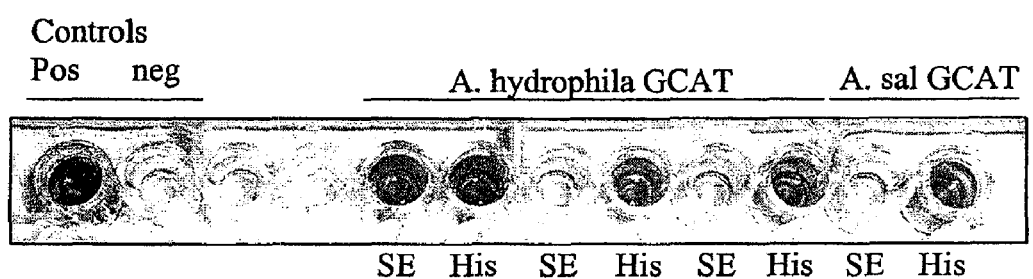
Figure 44:
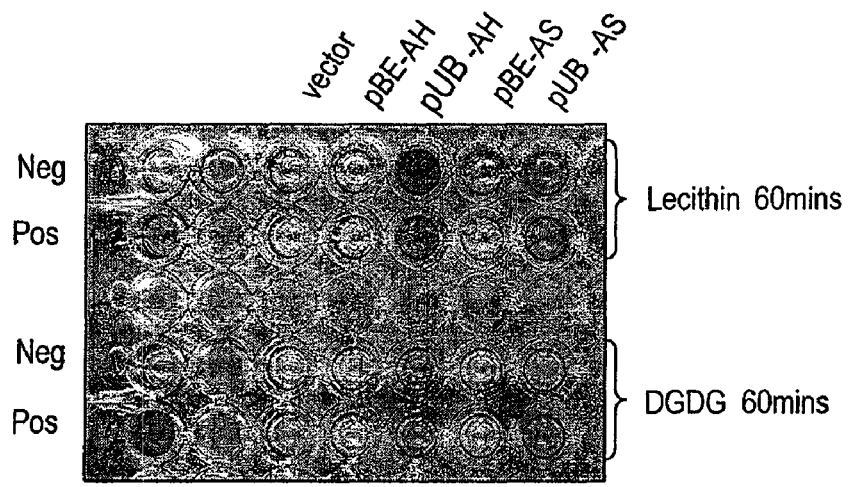

FIG. 35 shows a expression vector pet12-AsalGCAT=pSM containing the C-terminal His-tagged *Aeromonas salmonicida* lipid acyltransferase gene;

FIG. 36 shows the results of testing cell extracts in a NEFA Kit Assay, which depicts the activity of a recombinant, *A. salmonicida* lipid acyltransferase, towards lecithin. The wells from left to right indicate: a positive control, a negative control (i.e. extracts from empty plasmid) and samples collected after 0, 1, 2 and 3 hours cultivation after IPTG induction;

FIG. 37 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay. Wells from left to right: positive control; negative control; 20° C.; 30° C.;

FIG. 38 shows crude cell extracts from BL21(DE3)pLysS expressing active lipid acyltransferase incubated with the substrate lecithin and reaction mixture was analyzed using thin layer chromatography showing the presence of degradation products. Lanes: 1. No enzyme; 2. +A.sal-10 ul 37° C.; 3. +A.sal-20 ul 37° C.; 4. +A.sal-10 ul 24° C.; 5. +A.sal-20 u 24° C.;

FIG. 39 shows partial purification of the *Aeromonas salmonicida* Acyl Transferase showing the phospholipase activity associated with purified His-tag protein. SE=Sonicated extracts, His=Purified with Ni-NTA spin-kit from Qiagen;

FIG. 40 shows the expression vector pet12-A.h. GCAT=pSMa containing the C-terminal His-tagged *Aeromonas hydrophila* Glycerolipid Acyl Transferase (GCAT) gene was used to transform *E. coli* strain BL21(DE3)pLysS;

FIG. 41 shows the activity of the crude extracts (5 & 10 ul) containing the recombinant *Aeromonas hydrophila* GCAT enzyme was tested towards lecithin using Non-Esterified Fatty Acid (NEFA) kit (Roche, Switzerland), showing the presence of active enzyme towards the phospholipid, lecithin;

FIG. 42 shows growth optimisation of BL21(DE3)pLysS harboring the expression vector pet12-AsalGCAT=pSM showing cultivation at 30° C. resulted in the production of enzyme with high activity towards lecithin. Cell extracts were tested for phospholipase activity using the NEFA kit assay;

FIG. 43 shows the partial purification of the *Aeromonas hydrophila* & *A. salmonicida* Acyl Transferases showing the phospholipase activity associated with purified His-tag protein. SE=Sonicated extracts, His=Purified with Ni-NTA spin-kit from Qiagen);

FIG. 44 shows the expression of the *Aeromonas* genes in *Bacillus subtilis* 163 showing the production of secreted enzyme with activity towards both lecithin and DGDG. pUB-AH=construct containing the *A. hydrophila* gene and pUB-AS, construct with the *A. salmonicida* gene, Culture filtrate was incubated with the substrates for 60 minutes.

Figure 45:
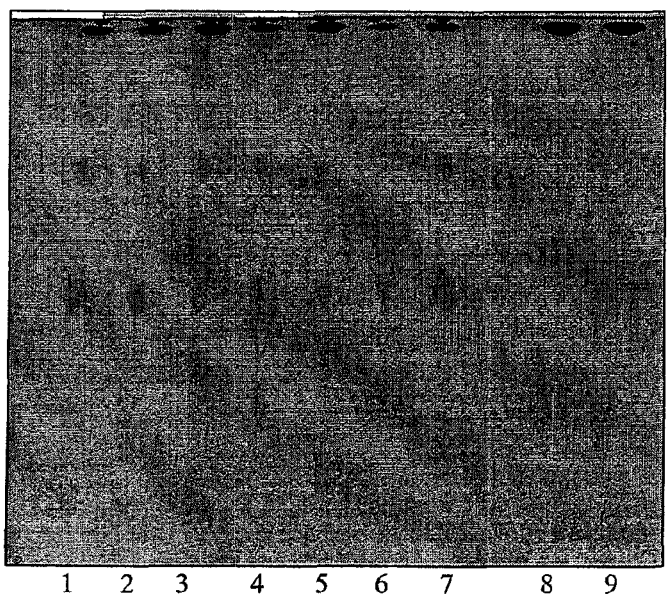
Figure 46:
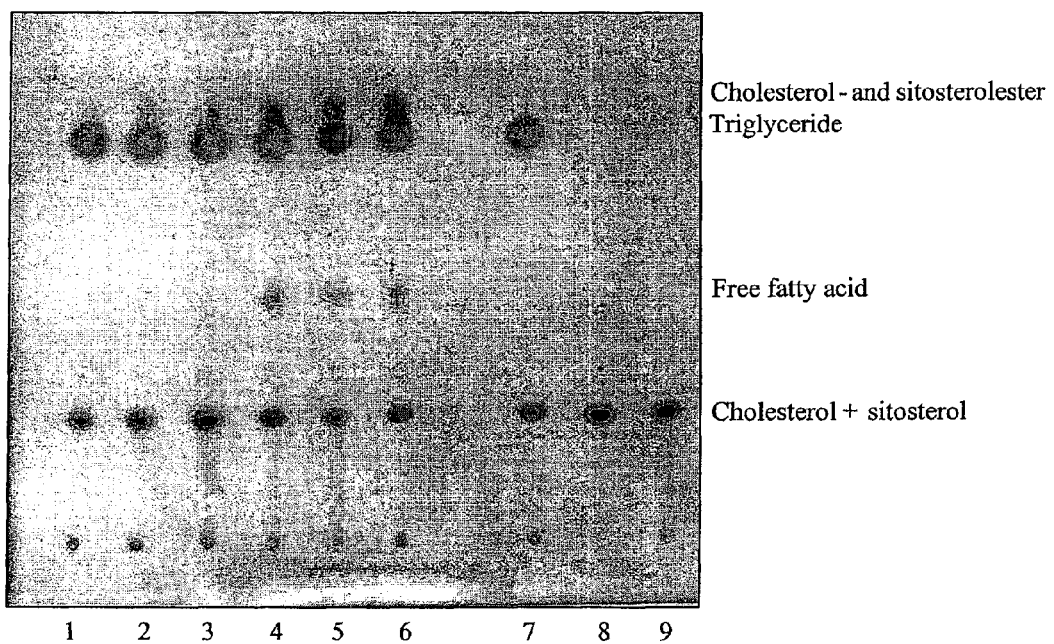
Figure 47:
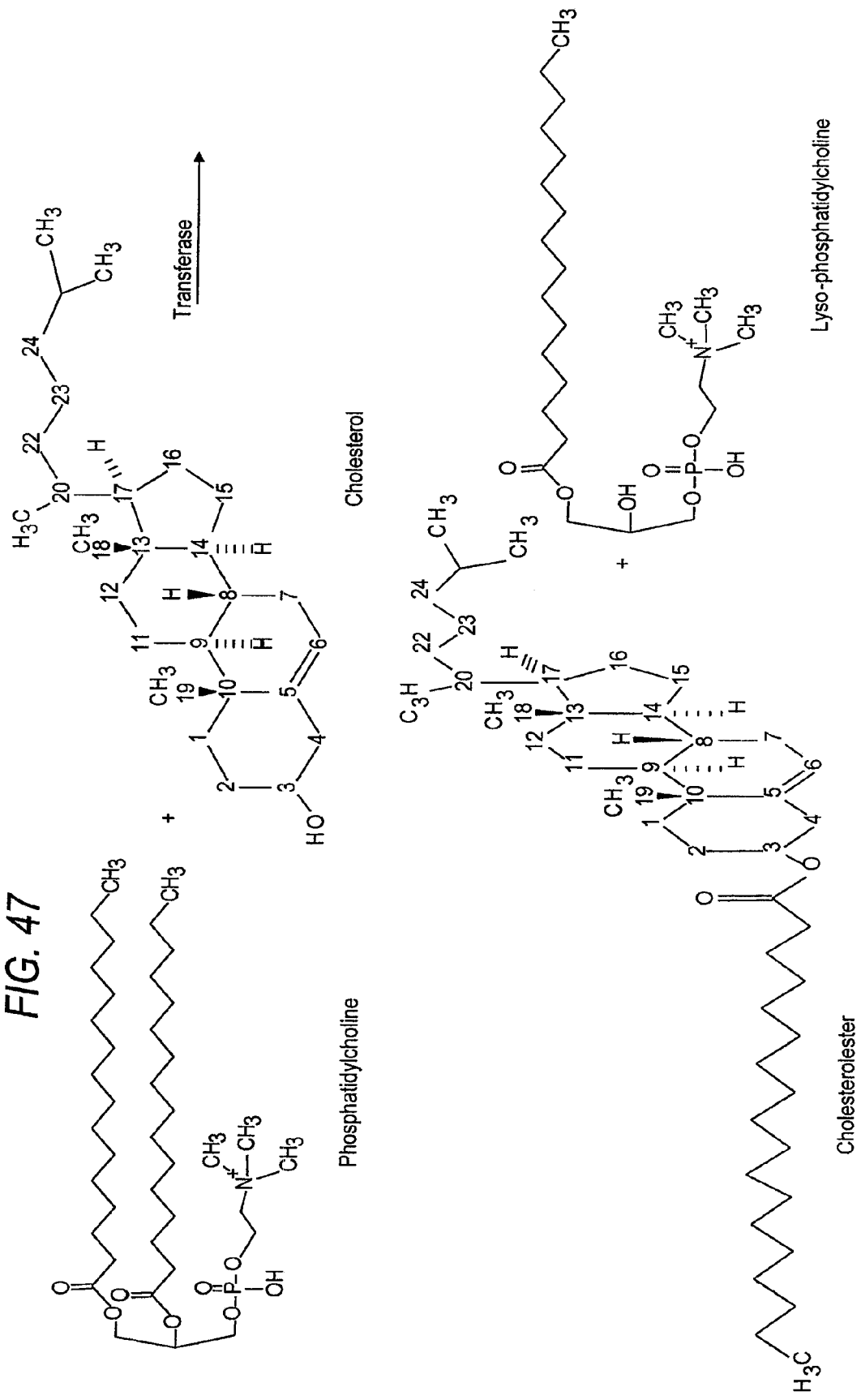
Figure 48:
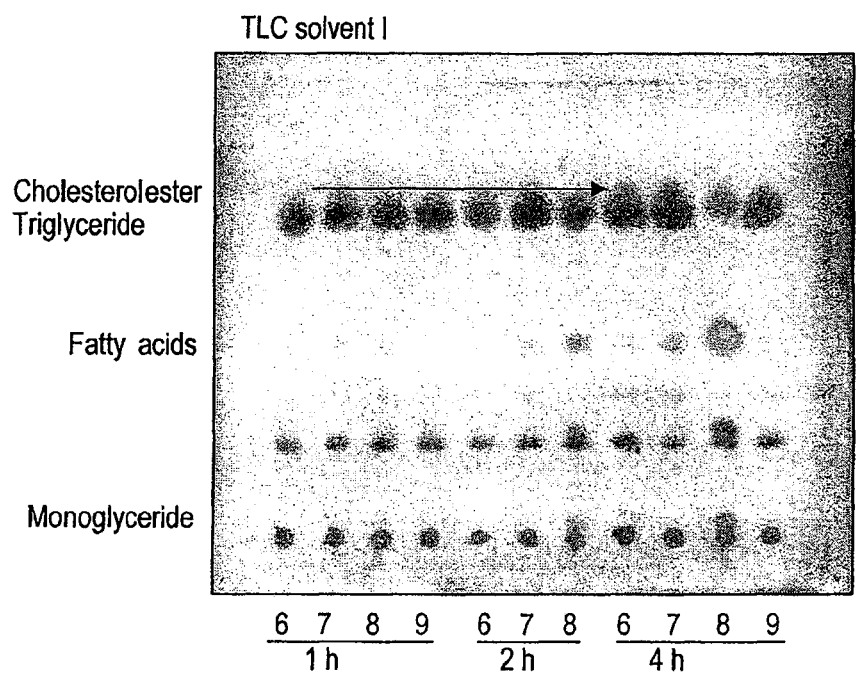

FIG. 45 and FIG. 46 show a TLC plate in developing solvent IV (chloroform:methanol:water (65:25:4)); Lane 1: 40 mg sitosterol 30 min: Lane 2: Transferase+40 mg sitosterol 30 min; Lane 3: Transferase+80 mg sitosterol 30 min; Lane 4: Transferase+40 mg sitosterol 120 min; Lane 5: Transferase+80 mg sitosterol 120 min; Lane 6: Transferase+40 mg sitosterol 300 min; Lane 7: 40 mg sitosterol 300 min; Lane 8: Cholesterol; Lane 9: Sitosterol;

FIG. 47 depicts the reaction between phosphatidylcholine and cholesterol which is catalysed by a lipid acyltransferase;

FIG. 48 shows a TLC analysis of lipids extracted from enzyme treated or untreated egg yolk., 6) 0.31PLU/g Transferase #179, 7) 1.25PLU/g Transferase #178-9., 8) 23.25 PLU/g Phospholipase #3108, 9) Control.

Figure 49:
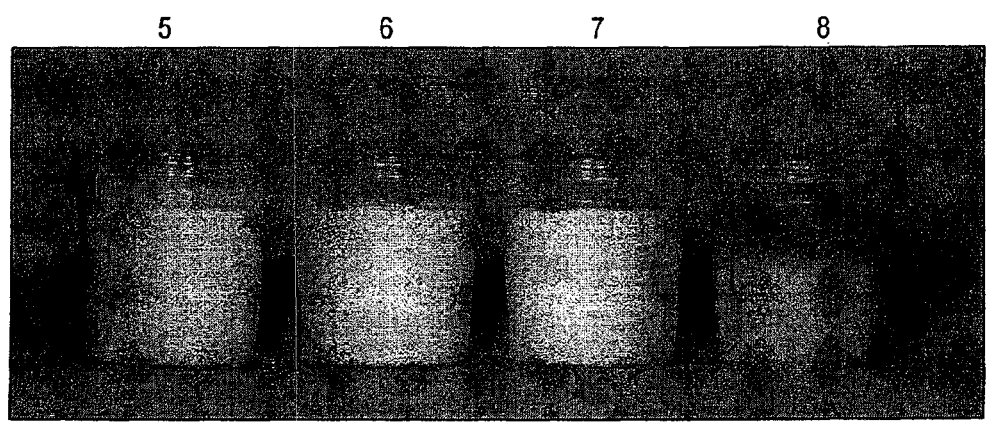
Figure 50:
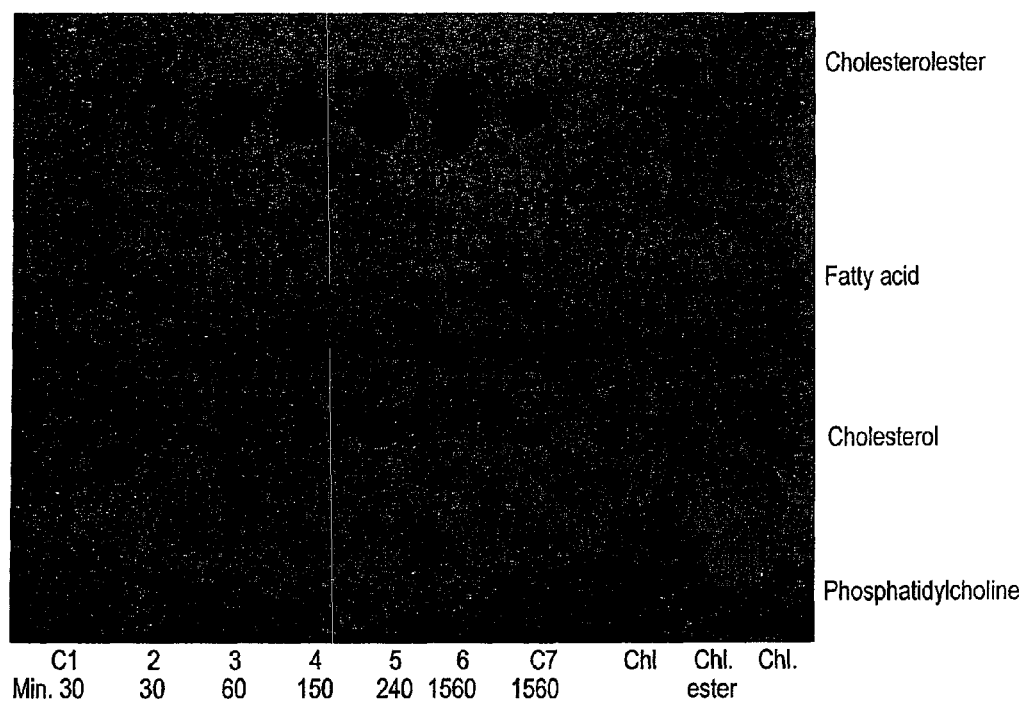
Figure 51:
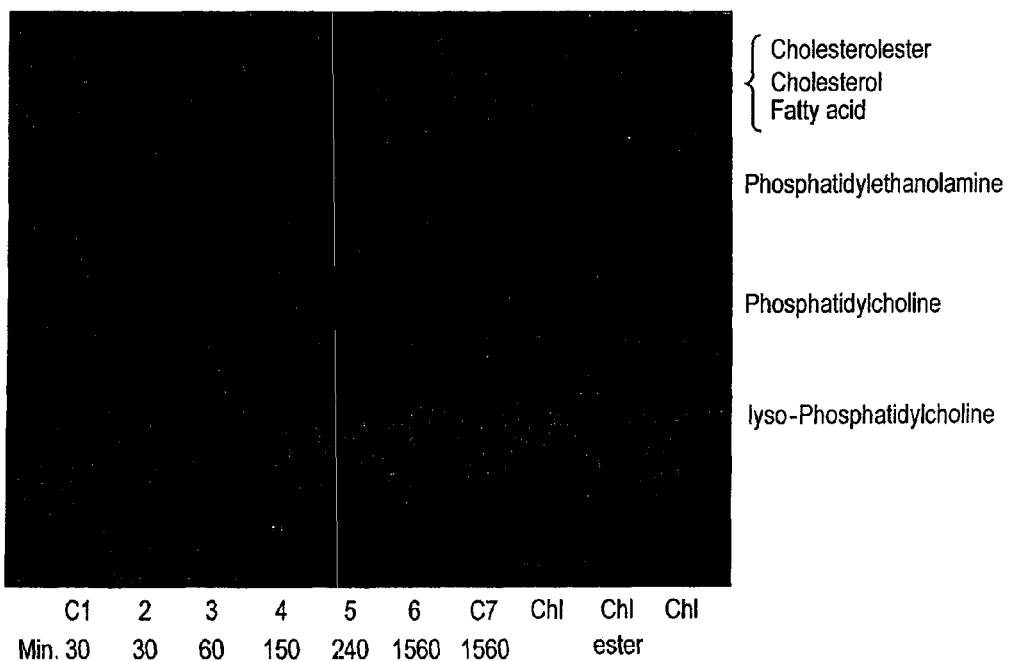
Figure 52:
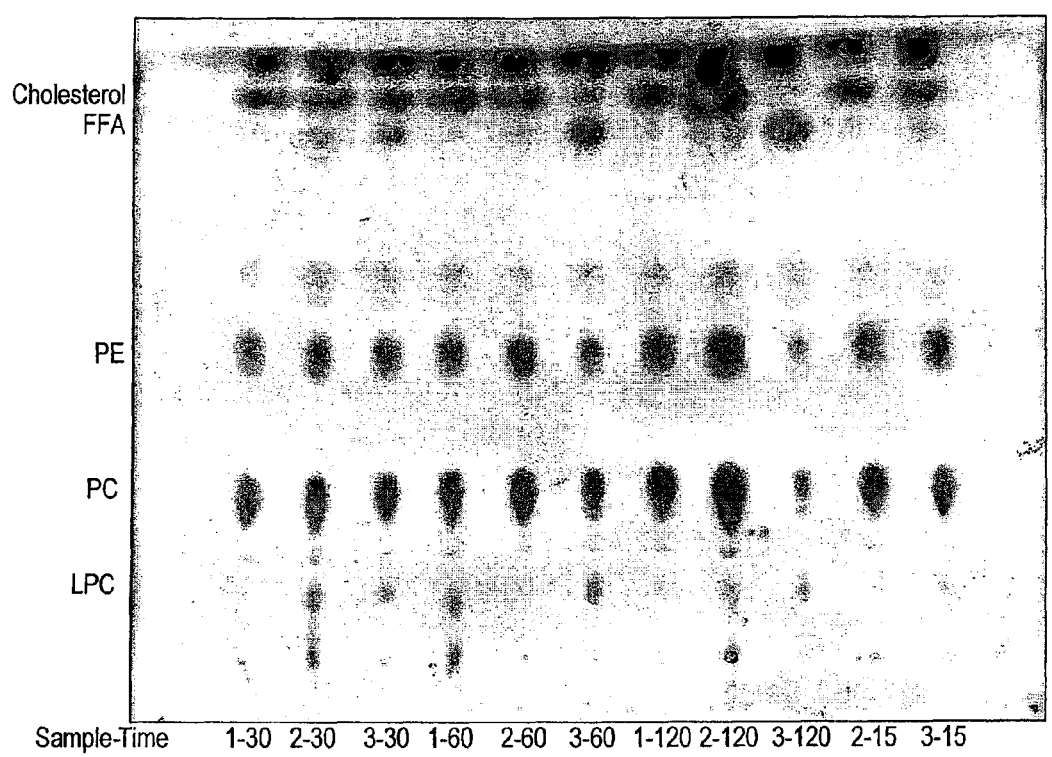
Figure 53:
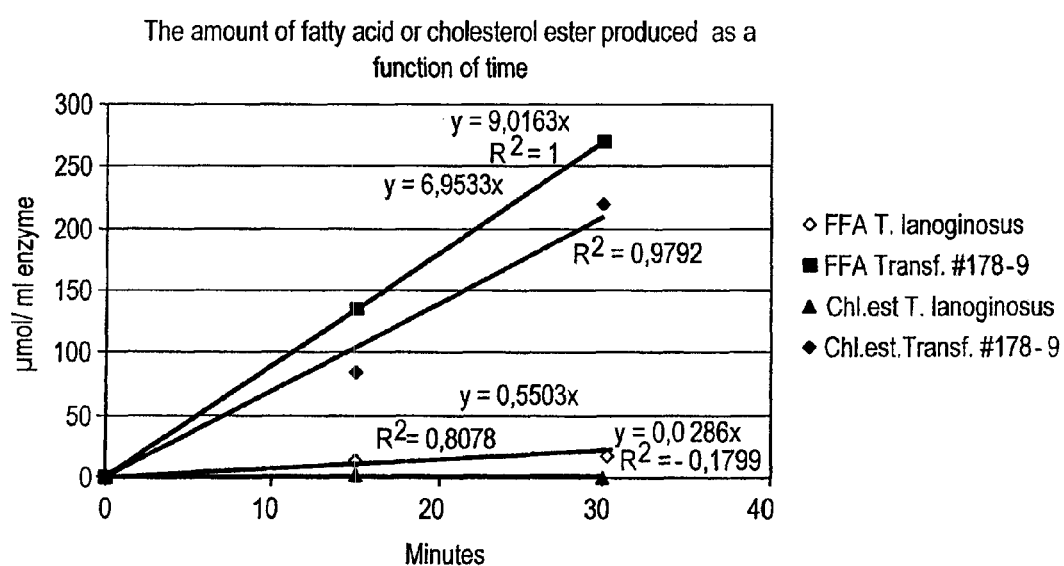

FIG. 49 shows mayonnaise test samples produced by enzyme treated or untreated egg yolk: 5) Transferase #179, 0.31 PLU/g. 6) Transferase #178-9, 1.25 PLU/g, 7) Phospholipase #3108, 23.3 PLU/g 8) Control, water FIG. 50 shows a TLC (in solvent I) of egg yolk lipid treated with a lipid acyl transferase from *A. hydrophila*;

FIG. 51 shows a TLC (in solvent IV) of egg yolk lipid treated with a lipid acyl transferase from *A. hydrophila*;

FIG. 52 shows a TLC analysis of transferase treated lipid from egg yolk over a time course;

FIG. 53 shows the amount of fatty acid and cholesterol ester produced as a function of time when using a lipid acyltransferase (Tranf #178-9) compared with when using a control lipolytic enzyme, *Thermomyces lanuginosus;*

Figure 54:
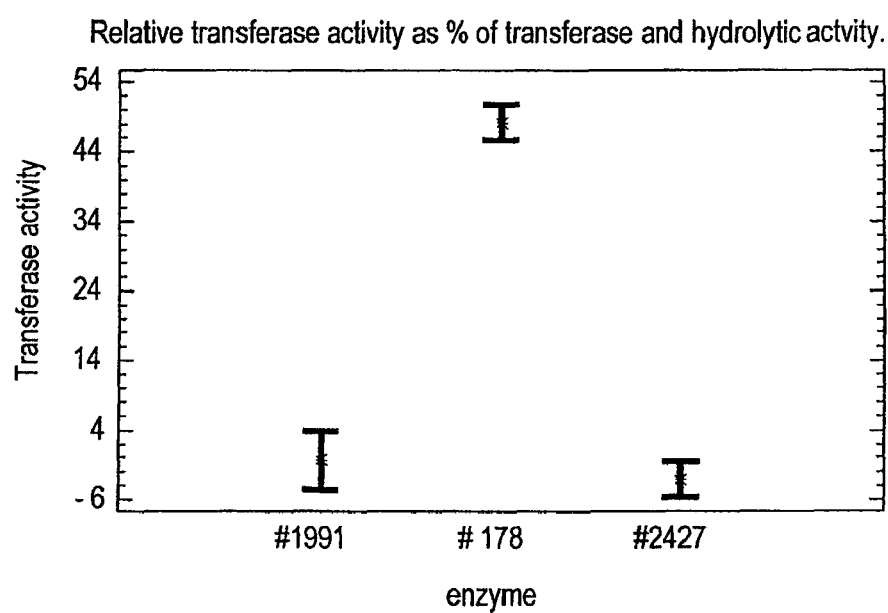
Figure 55:
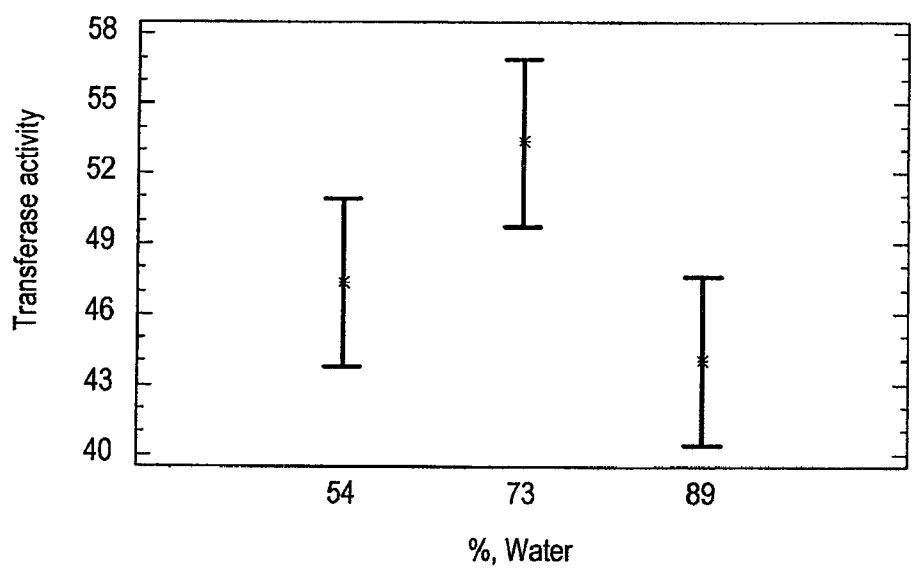
Figure 56:
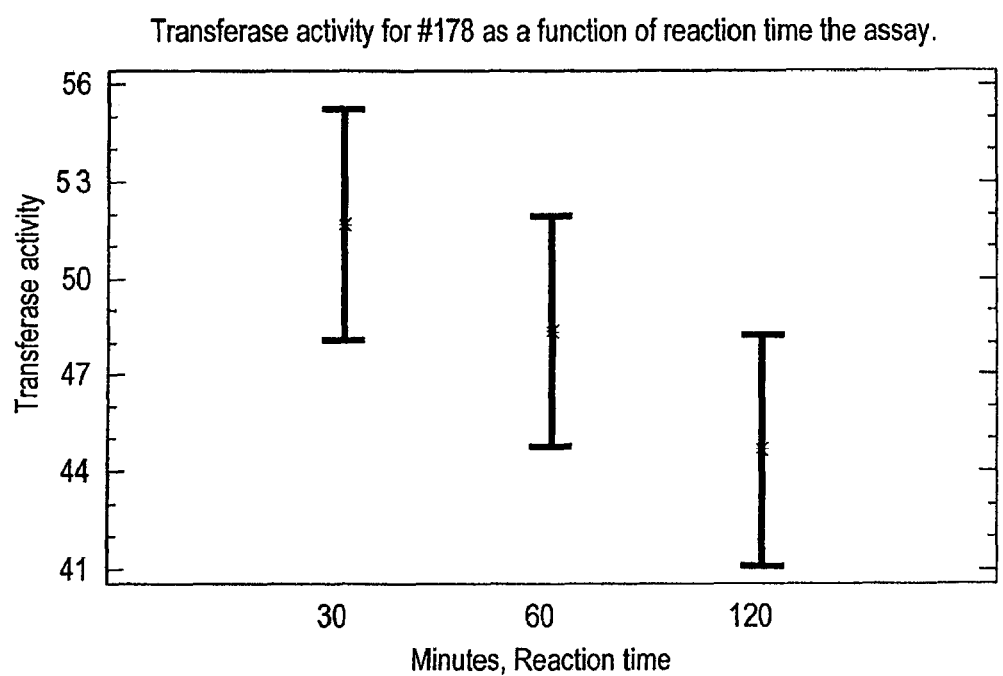
Figure 57:
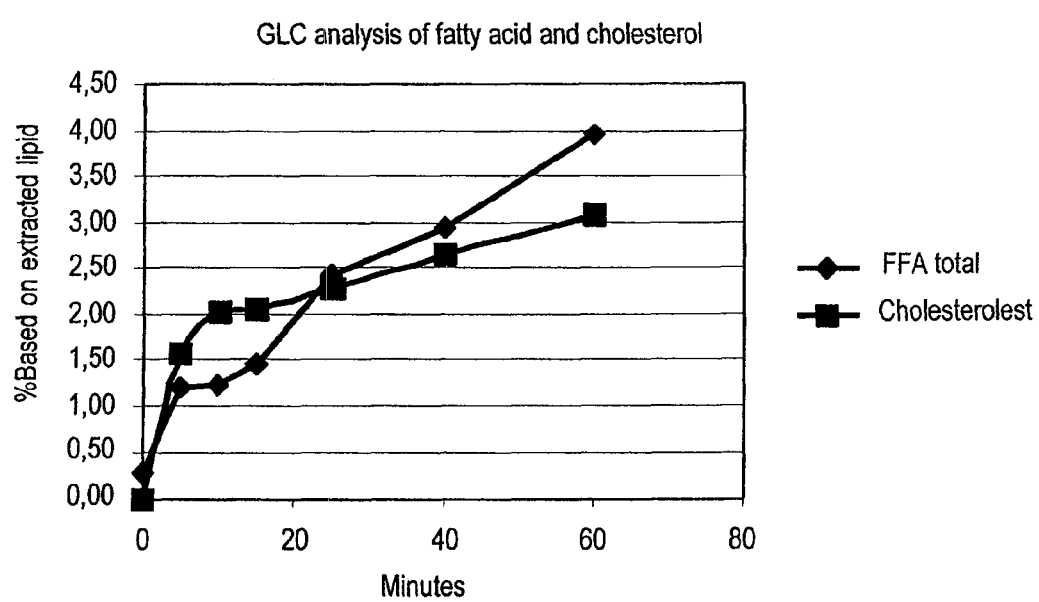
Figure 58:
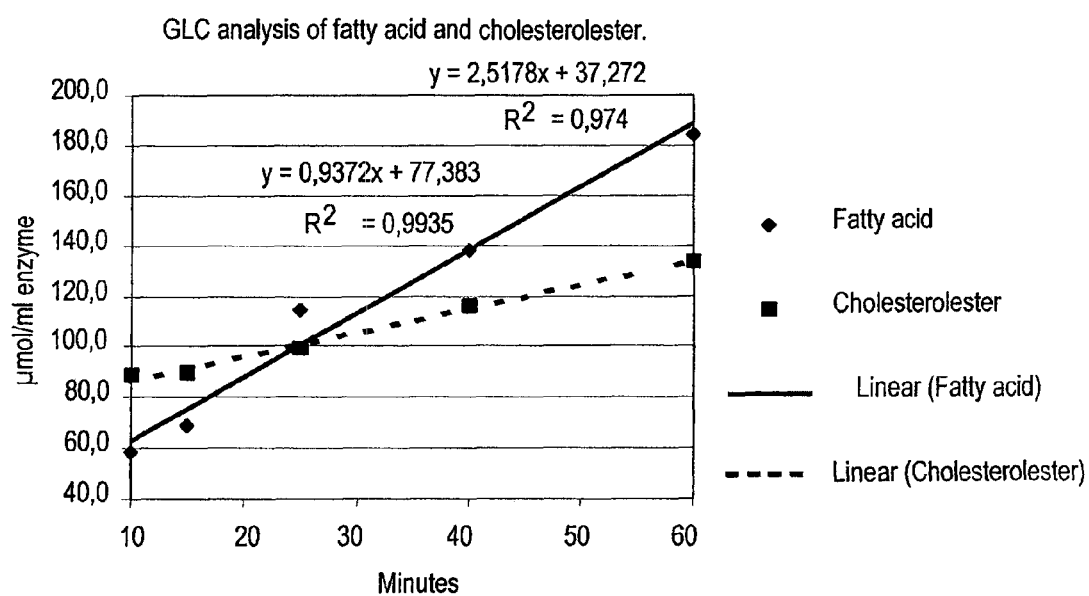
Figure 59:
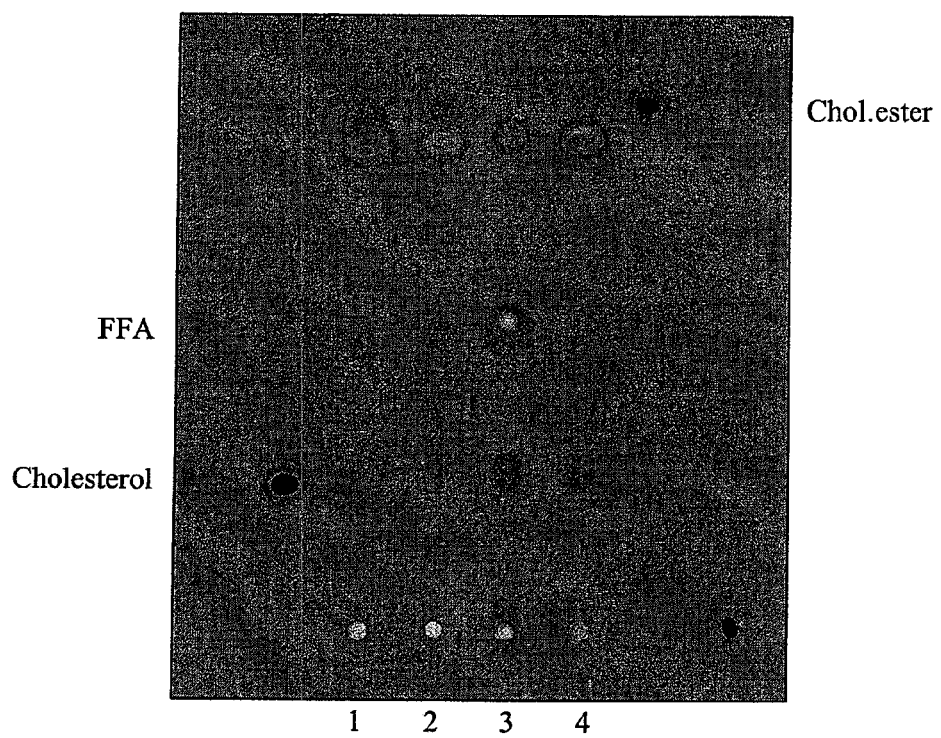
Figure 60:
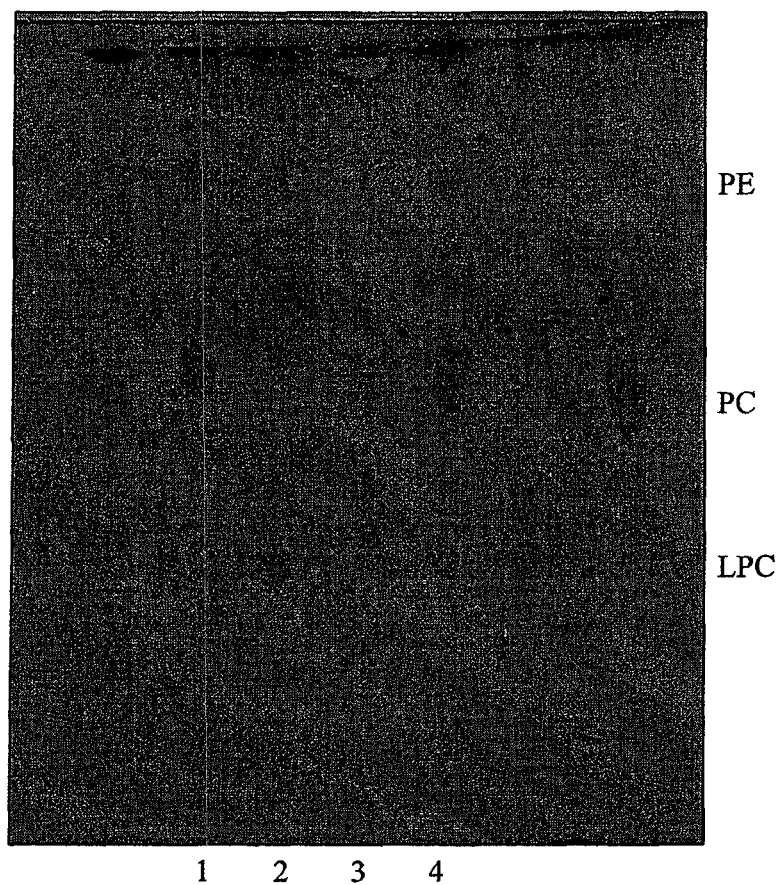
Figure 61:
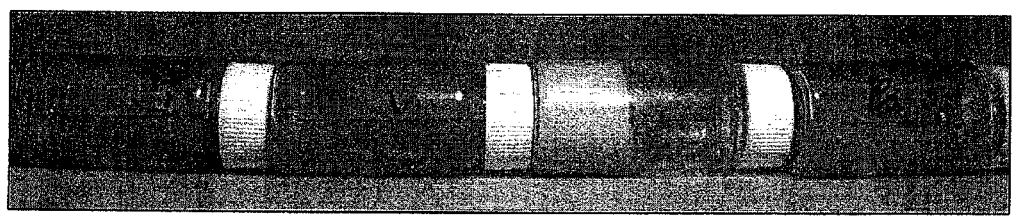
Figure 62:
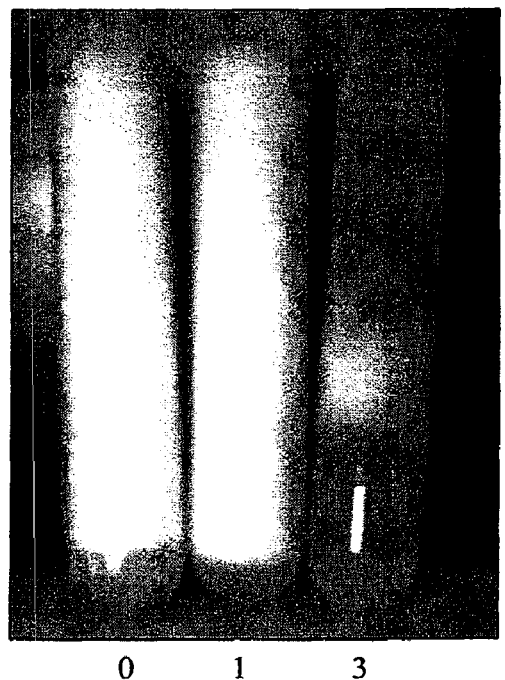
Figure 63:
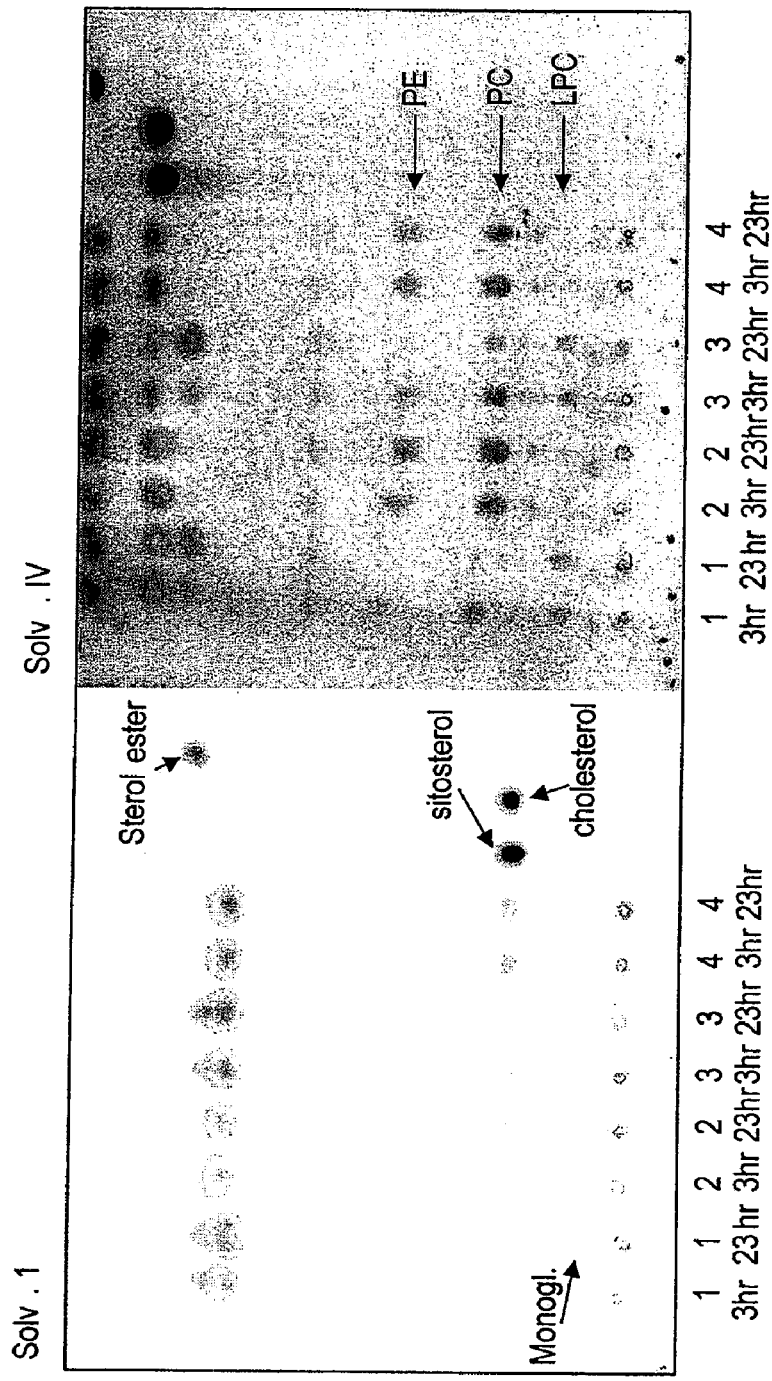
Figure 64:
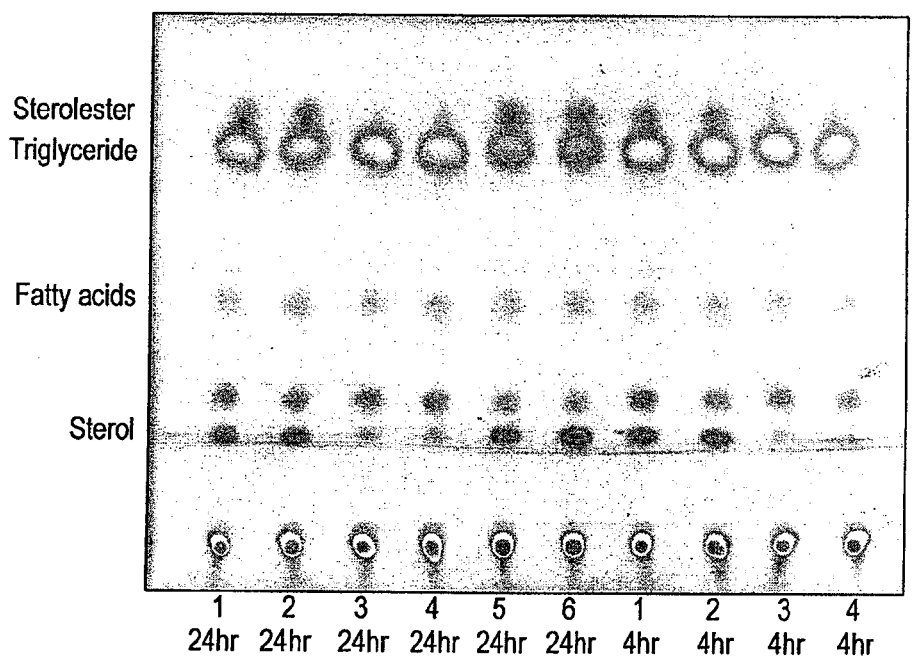
Figure 65:
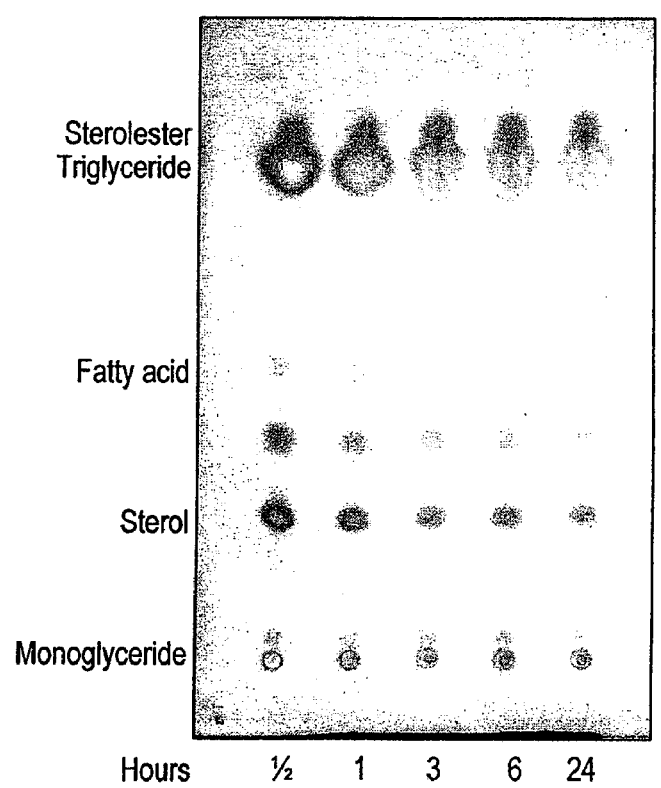
Figure 66:
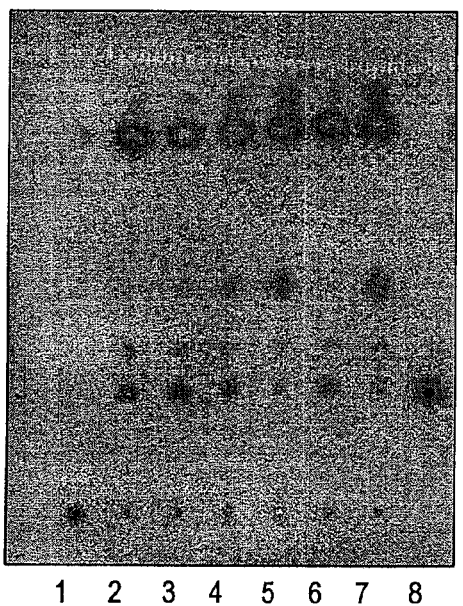
Figure 67:
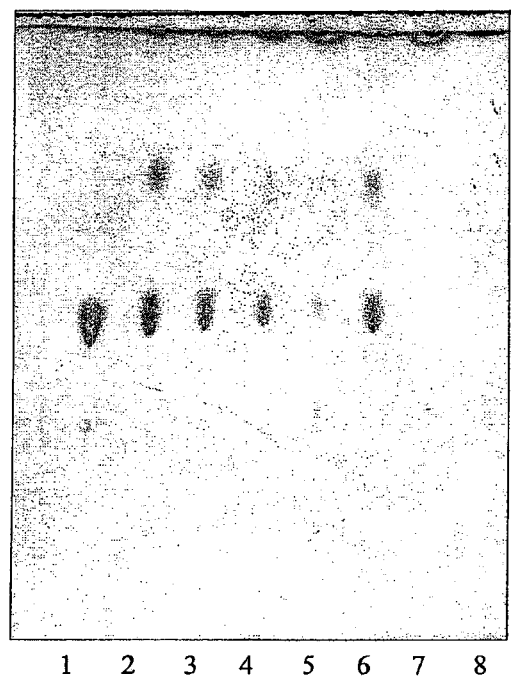
Figure 68:
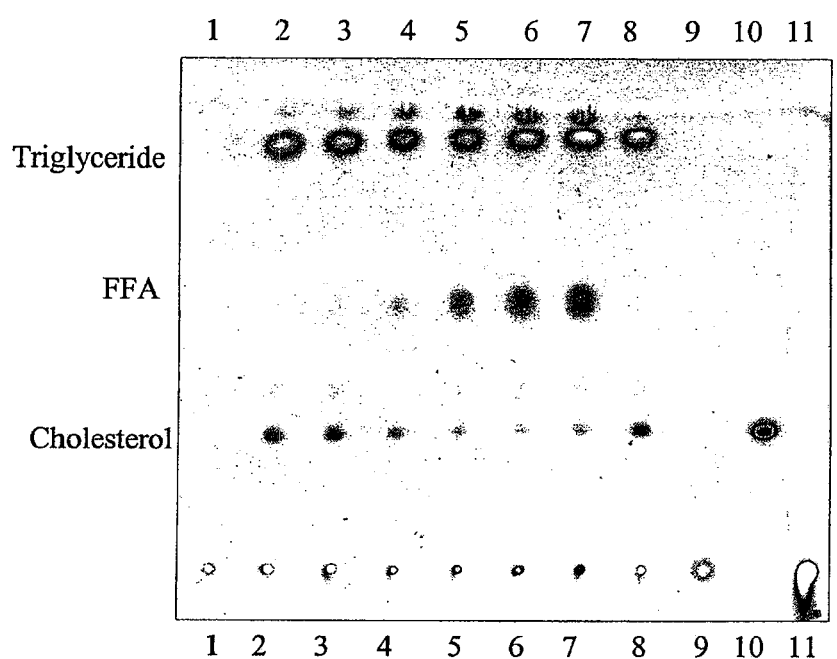
Figure 69:
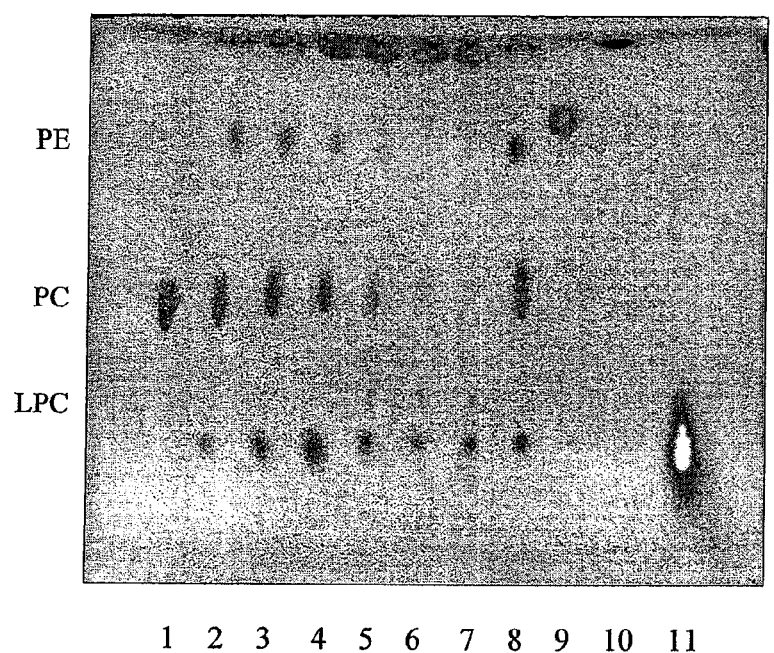
Figure 70:
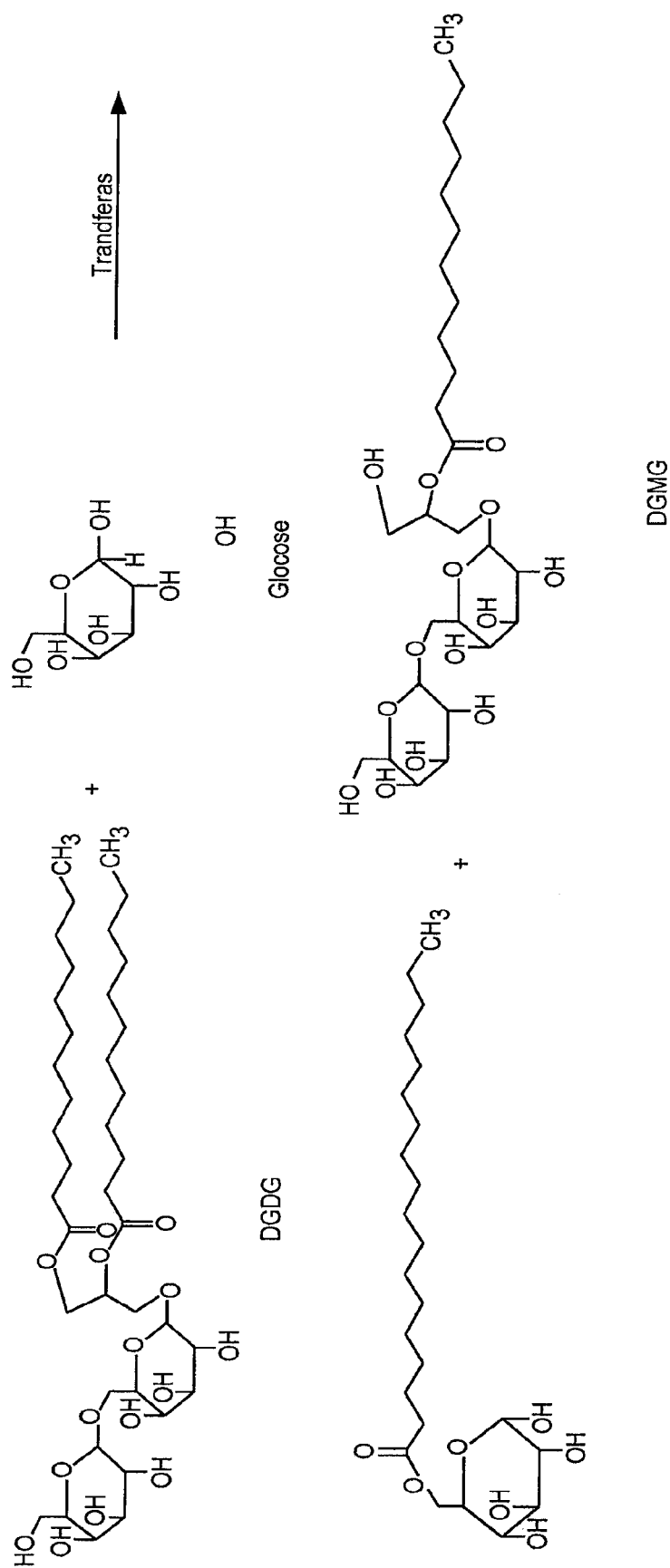
Figure 73:
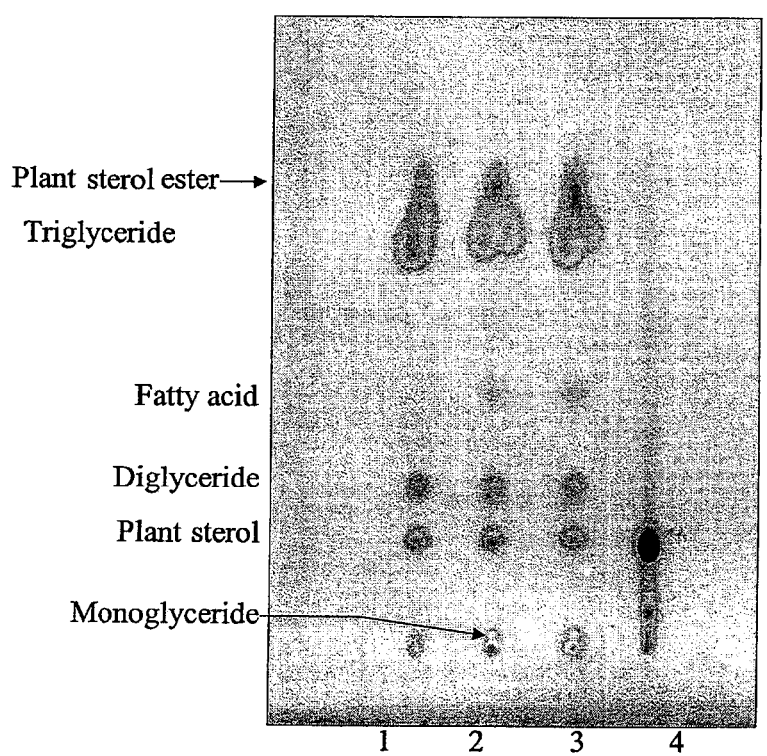

FIG. 54 shows relative transferase activity as % of transferase and hydrolytic activity in enzymatic reactions in egg yolk with high water content, #1991 (phospholipase A2) and #2427 (phospholipase A1) are control phospholipases, #178 is a lipid acyltransferase;

FIG. 55 shows the effect of water content in the assay on the transferase activity of the transferase #178 in transferase reactions in egg yolk with high water content;

FIG. 56 shows the transferase activity for a lipid acyltransferase (#178) as a function of reaction time in transferase reactions in egg yolk with high water;

FIG. 57 and FIG. 58 show graphs depicting fatty acid and cholesterol ester as a function of time. The graphs depict results obtained for GLC analysis in the assay for measurement of acyltransferase activity using lecithin and cholesterol in buffer as substrate;

FIG. 59 shows a TLC in solvent I. Egg yolk treated with lipid acyltransferase #138 from *Aeromonas salmonidica* (lane no. 1 and 2) or with a phospholipase #2938 (LIPOPAN® F) (lane no. 3) or Untreated egg yolk (lane no. 4);

FIG. 60 shows a TLC in solvent IV. Egg yolk treated with lipid acyltransferase #138 (lane no. 1 and 2) or with Phospholipase #2938 (lane no. 3). Untreated egg yolk (lane no. 4);

FIG. 61 shows egg yolk treated with lipid acyltransferase #138 (sample nos. 1 and 2) and with phospholipase #2938 (sample no. 3). Untreated egg yolk (sample no. 4);

FIG. 62 shows a food emulsion after 2 hours at 100° C., 0) Untreated egg yolk 1) Egg yolk treated with lipid acyl transferase #138 for 210 minutes. 3) Egg yolk treated with the control phospholipase #2938 for 210 minutes;

FIG. 63 shows TLC plates showing the screening of transferase activity on plant sterol and glycerol. PC=phosphatidylcholine, LPC=lysophosphatidylcholine; PE=phosphatidylethanolamine; monogl=monoglyceride;

FIG. 64 shows a TLC plate in solvent I, Samples 1 to 6 after 24 hours and samples 1 to 4 after 4 hours reaction time. The TLC analysis confirms the formation of sterol ester in samples 1, 2, 5 and 6;

FIG. 65 shows a TLC plate in solvent I where the transferase activity of an immobilised acyltransferase from *Aeromonas salmonicida* was tested in an oil mixture—with samples taken at 0.5, 1, 3, 6 and 24 h;

FIGS. 66 and 67 show TLC plates in solvent I and IV. Lane 1=lecithin; Lane 2=control—10 mins; Lane 3=0.75 PLU, 10 mins; Lane 4=0.75 PLU, 60 mins; Lane 5=0.75 PLU, 220 mins; Lane 6=control, 20 h; Lane 7=0.75 PLU, 20 h; and Lane 8=cholesterol ester;

FIGS. 68 and 69 show TLC plates in solvent IV. Lane 1=lecithin; Lane 2=control—10 mins; Lane 3=1 PLU, 10 mins; Lane 4=1 PLU, 60 mins; Lane 5=1 PLU, 180 mins; Lane 6=1PLU, 220 mins; Lane 7=1PLU, 1200 min; Lane 8=control, 1200 min; Lane 9=glucose ester; Lane 10=cholesterol; and Lane 11=glucose;

FIG. 70 shows the reaction between DGDG and glucose when catalysed by a lipid acyltransferase;

FIG. 71 shows an amino acid sequence (SEQ ID No. 36) of the fusion construct used for mutagenesis of the *Aeromonas hydrophila* lipid acyltransferase gene in Example 17. The underlined amino acids is a xylanase signal peptide;

FIG. 72 shows a nucleotide sequence (SEQ ID No. 54) encoding an enzyme from *Aeromonas hydrophila* including a xylanase signal peptide;

FIG. 73 shows a TLC plate clearly showing the formation of plant sterol ester and monoglyceride. Lane 1 is after 1 hour reaction time, Lane 2 is after 4 hours reaction time, Lane 3 is after 24 hours reaction time and Lane 4 is a plant sterol; and FIG. 74 shows the amino acid sequence of a mutant *Aeromonas salmonicida* mature lipid acyltransferase (GCAT) with a mutation of Asn80Asp (notably, amino acid 80 is in the mature sequence) (SEQ ID 62);

FIG. 75 shows SEQ ID No 63 which is the amino acid sequence of a lipid acyltransferase from *Candida parapsilosis;*

FIG. 76 shows SEQ ID No. 64 which is the amino acid sequence of a lipid acyltransferase from *Candida parapsilosis;*

FIG. 77 shows SEQ ID No. 65. Scoe1 NCBI protein accession code CAB39707.1 GI:4539178 conserved hypothetical protein [*Streptomyces coelicolor* A3(2)];

FIG. 78 shows a polypeptide sequence of a lipid acyltransferase enzyme from *Thermobifida* (SEQ ID No. 66);

FIG. 79 shows a polypeptide sequence of a lipid acyltransferase enzyme from *Thermobifida* (SEQ ID No. 67);

FIG. 80 shows a polypeptide of a lipid acyltransferase enzyme from *Corynebacterium efficiens* GDSx 300 amino acid-(SEQ ID No. 68);

FIG. 81 shows a polypeptide of a lipid acyltransferase enzyme from *Novosphingobium aromaticivorans* GDSx 284 amino acid-(SEQ ID No. 69);

FIG. 82 shows a polypeptide of a lipid acyltransferase enzyme from *Streptomyces coelicolor* GDSx 269 mino cid (SEQ ID No. 70);

FIG. 83 shows a polypeptide of a lipid acyltransferase enzyme from *Streptomyces avermitilis* GDSx 269 amino acid (SEQ ID No. 71);

FIG. 84 shows a polypeptide of a lipid acyltransferase enzyme from *Streptomyces* (SEQ ID No. 72);

FIG. 85 shows an amino acid sequence (SEQ ID No. 73) obtained from the organism *Aeromonas hydrophila* (P10480; GI:121051) (notably, this is the mature sequence);

FIG. 86 shows the amino acid sequence (SEQ ID No. 74) of a mutant *Aeromonas salmonicida* mature lipid acyltransferase (GCAT) (notably, this is the mature sequence);

FIG. 87 shows a nucleotide sequence (SEQ ID No. 75) from *Streptomyces thermosacchari;*

FIG. 88 shows an amino acid sequence (SEQ ID No 76) from *Streptomyces thermosacchari;*

FIG. 89 shows an amino acid sequence (SEQ ID No. 77) from *Thermobifida fusca*/GDSx 548 amino acid;

FIG. 90 shows a nucleotide sequence (SEQ ID No. 78) from *Thermobifida fusca;*

FIG. 91 shows an amino acid sequence (SEQ ID No. 79) from *Thermobifida fusca*/GDSx;

FIG. 92 shows an amino acid sequence (SEQ ID No. 80) from *Corynebacterium efficiens*/GDSx 300 amino acid;

FIG. 93 shows a nucleotide sequence (SEQ ID No. 81) from *Corynebacterium efficiens;*

FIG. 94 shows an amino acid sequence (SEQ ID No. 82) from *S. coelicolor*/GDSx 268 amino acid;

FIG. 95 shows a nucleotide sequence (SEQ ID No. 83) from *S. coelicolor;*

FIG. 96 shows an amino acid sequence (SEQ ID No. 84) from *S. avermitilis;*

FIG. 97 shows a nucleotide sequence (SEQ ID No. 85) from *S. avermitilis;*

Figure 104:
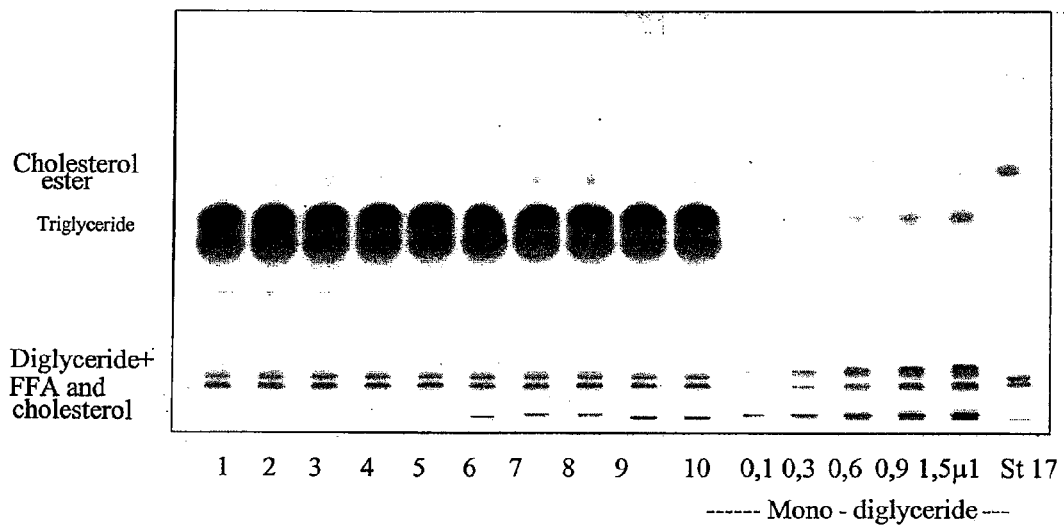
Figure 105:
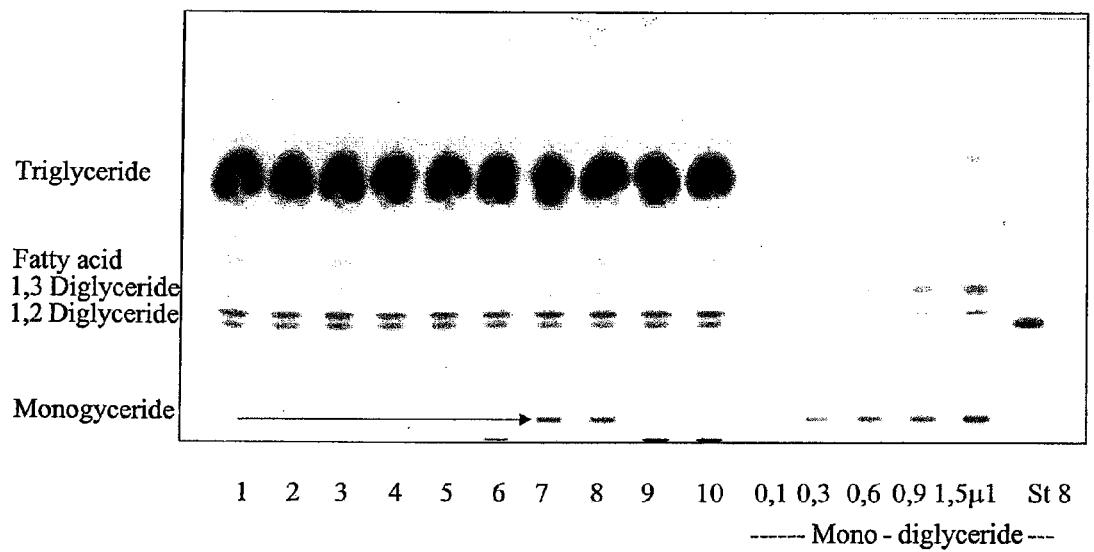
Figure 106:
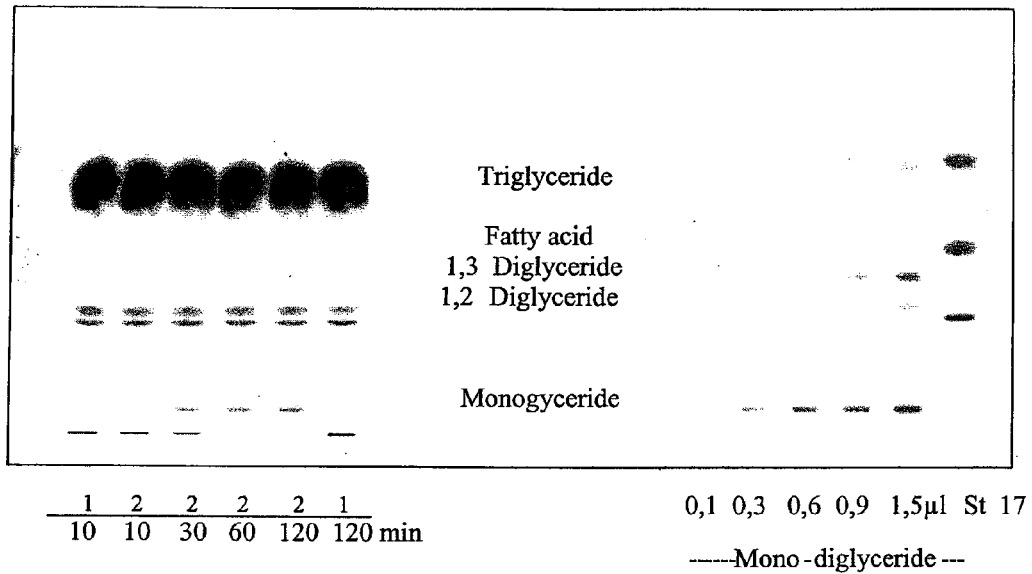
Figure 107:
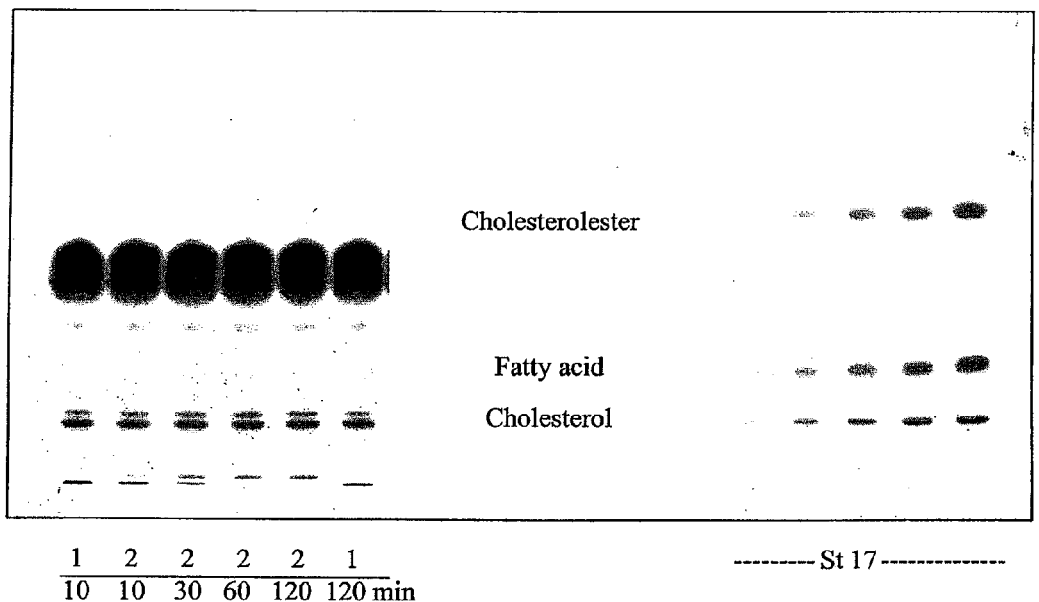
Figure 108:
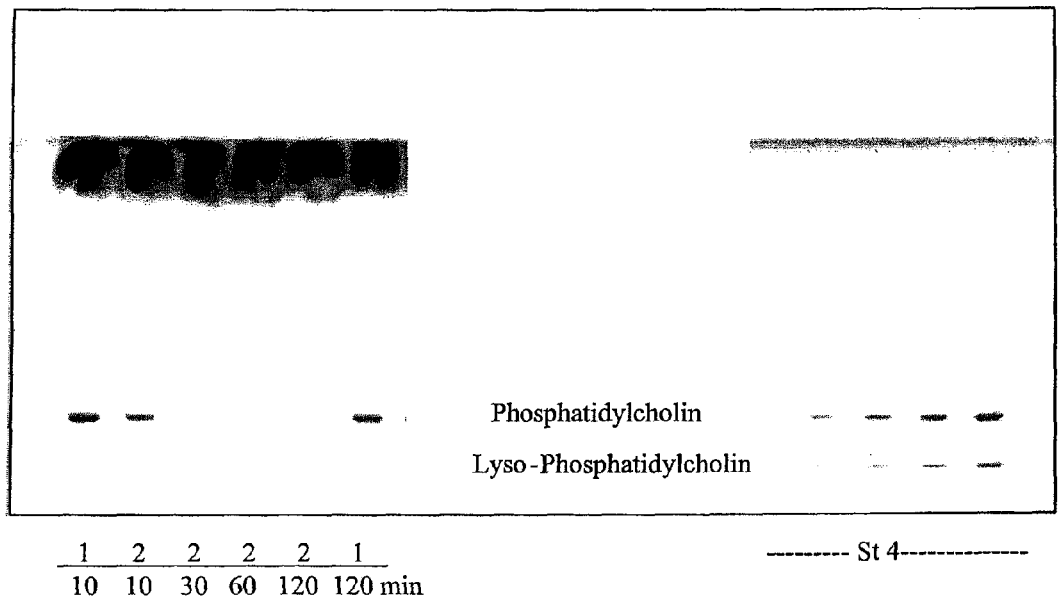
Figure 109:
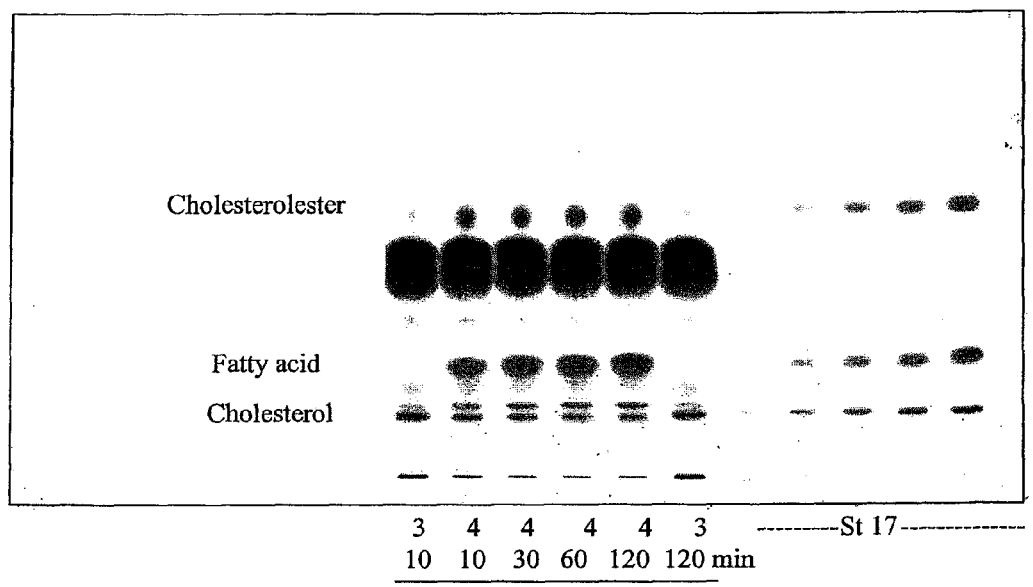
Figure 110:
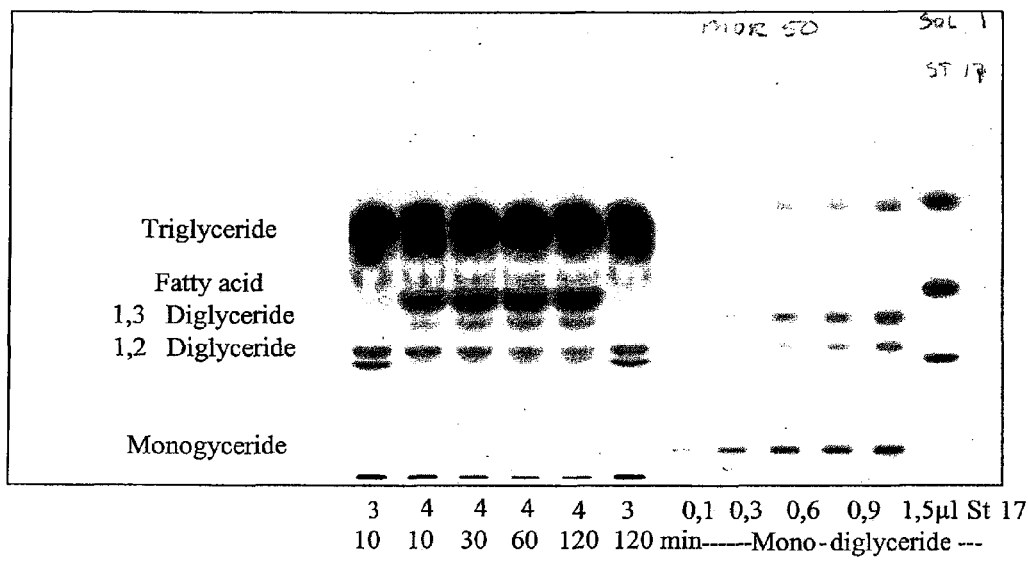
Figure 111:
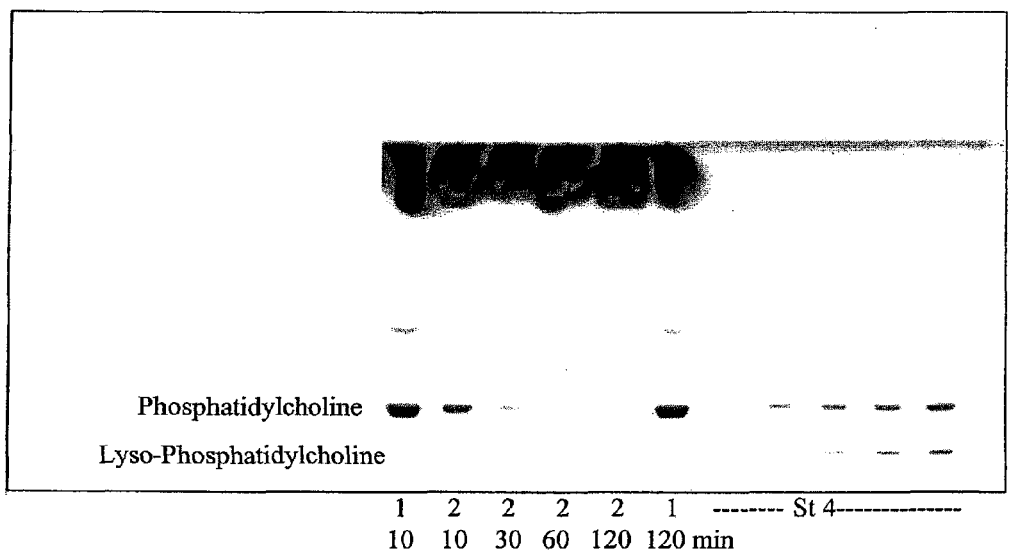
Figure 112:
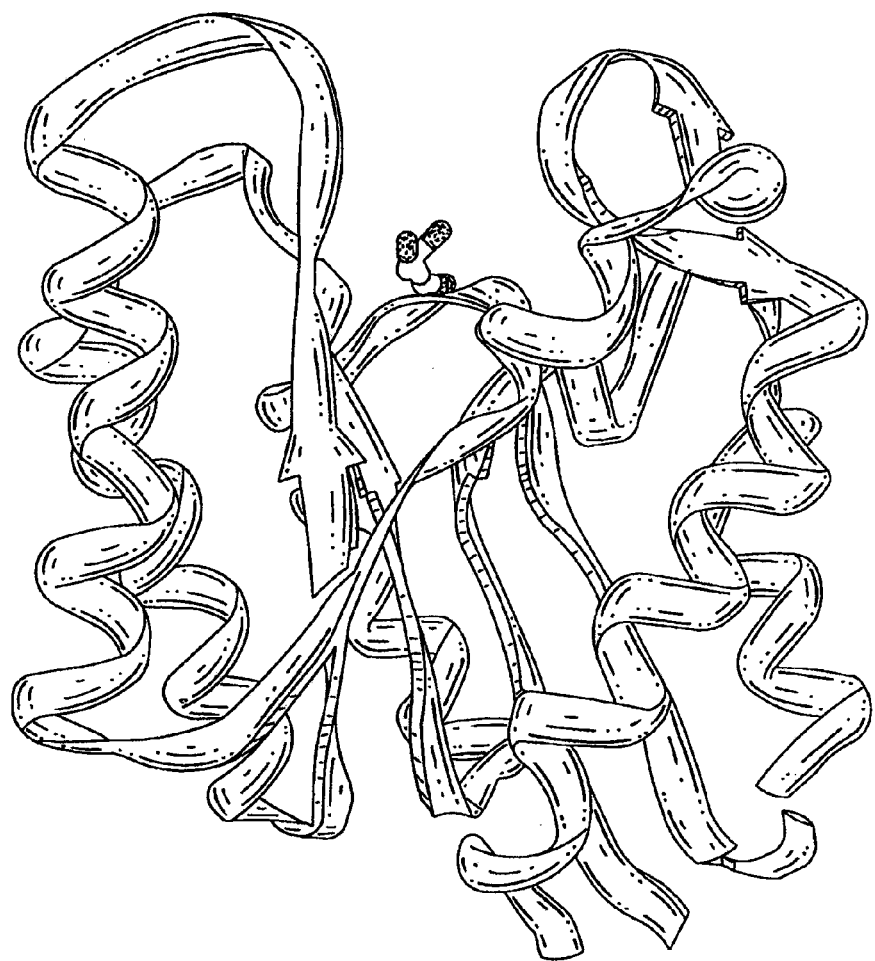
Figure 113:
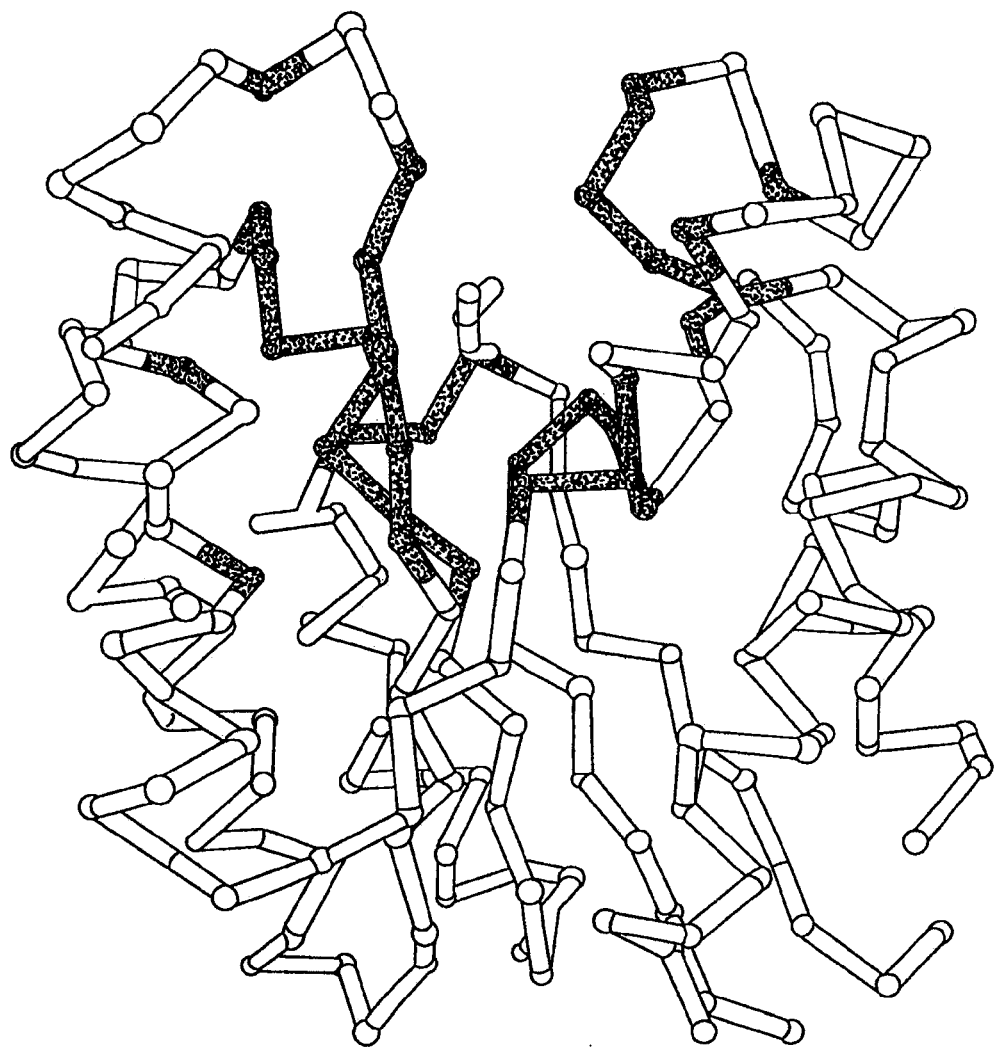
Figure 114:
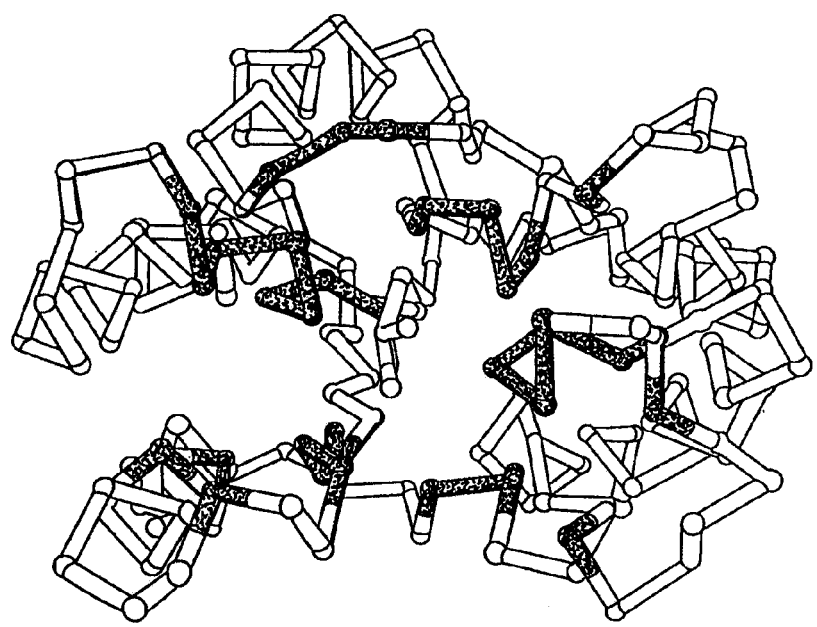
Figure 120:
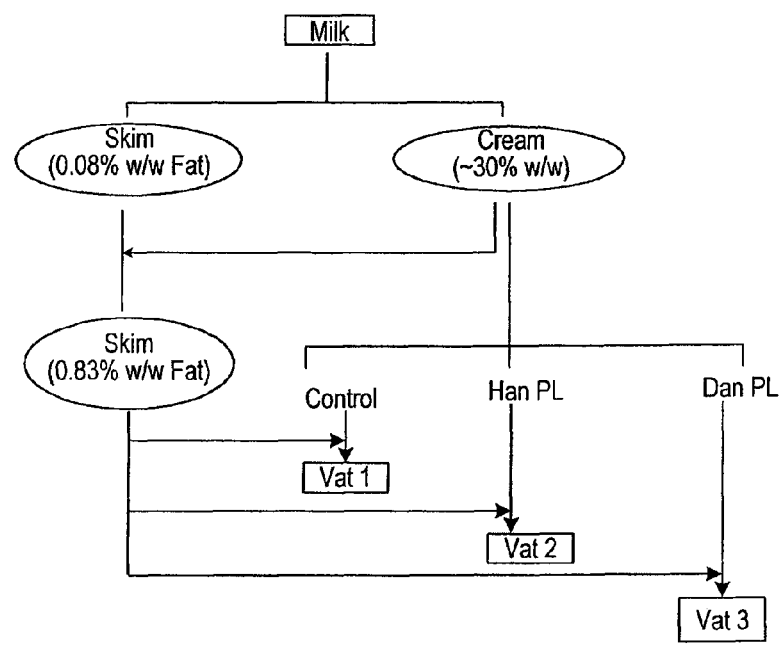
Figure 121:
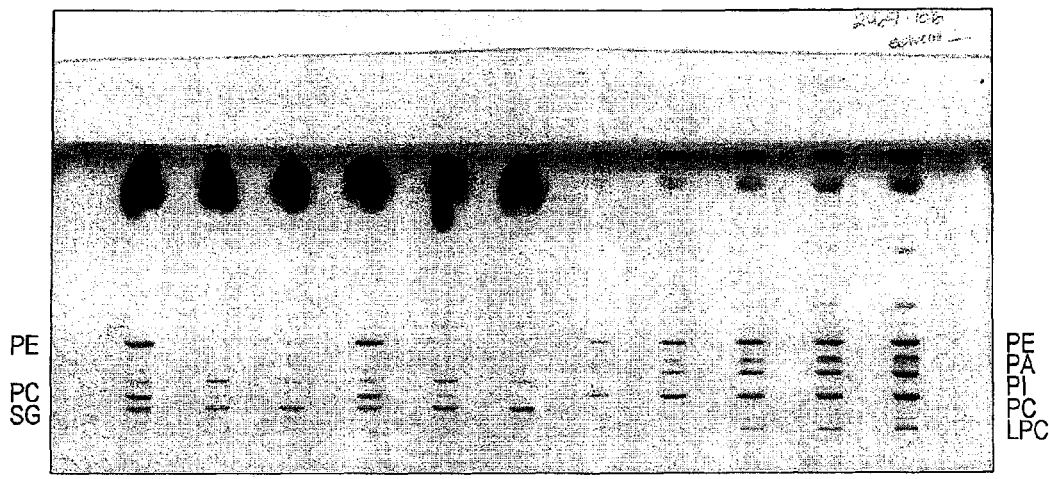
Figure 122:
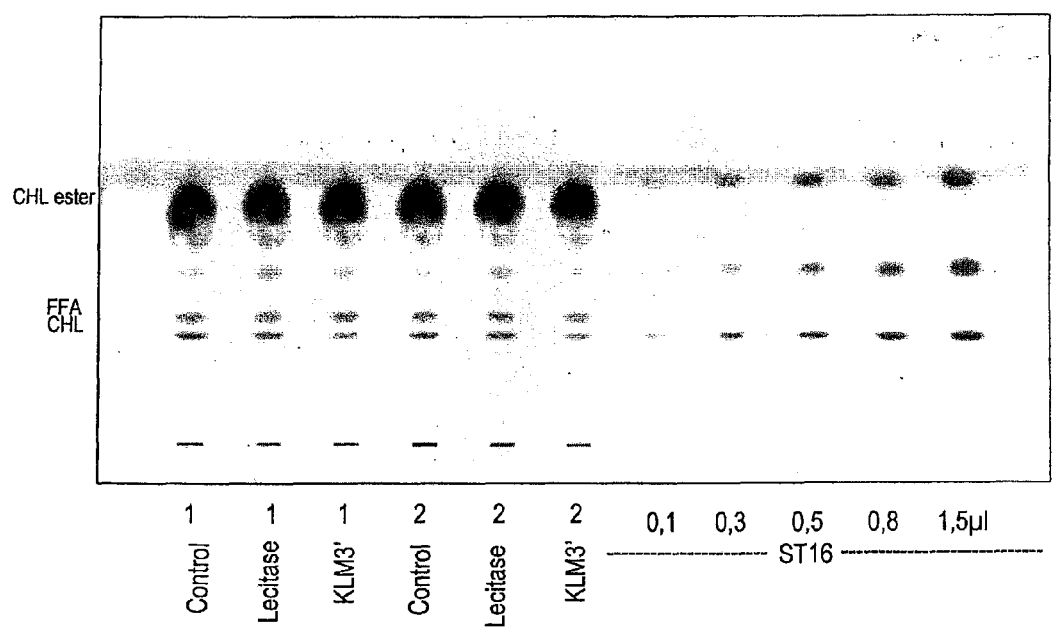
Figure 123:
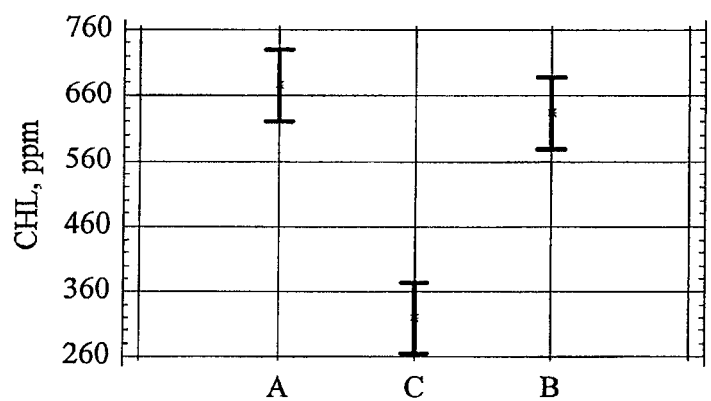
Figure 124:
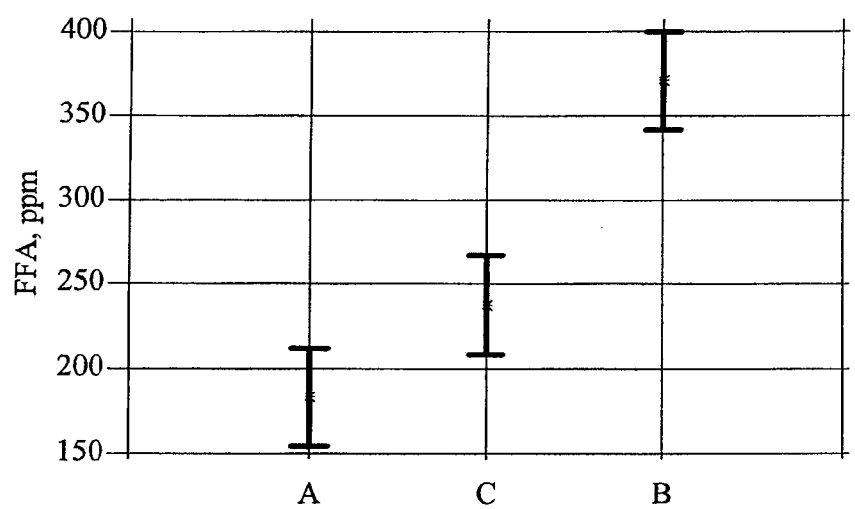
Figure 125:
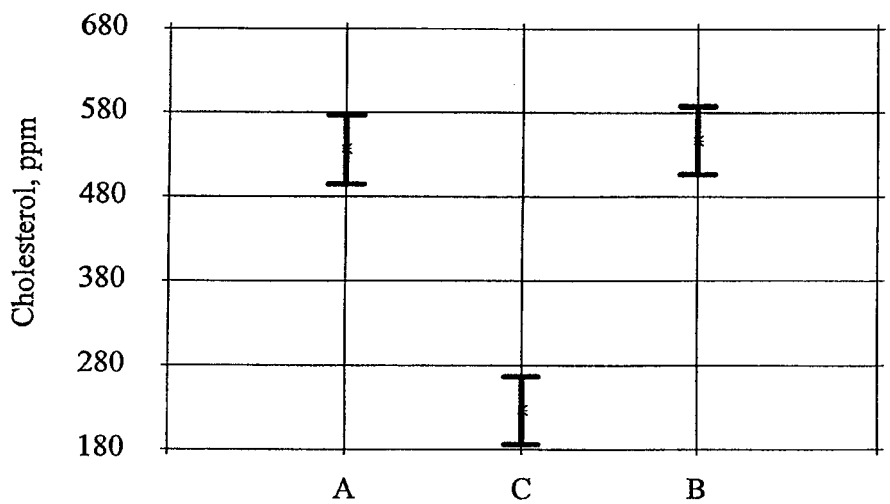
Figure 126:
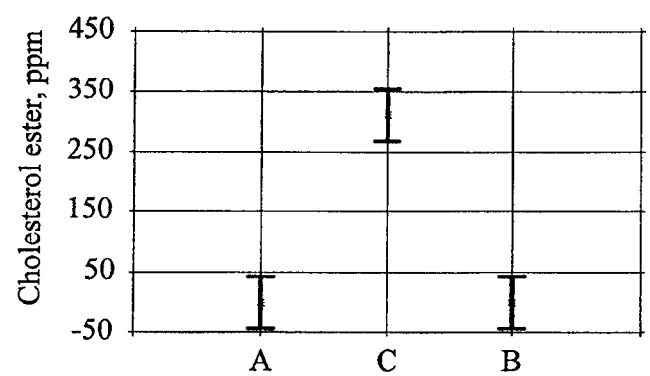
Figure 127:
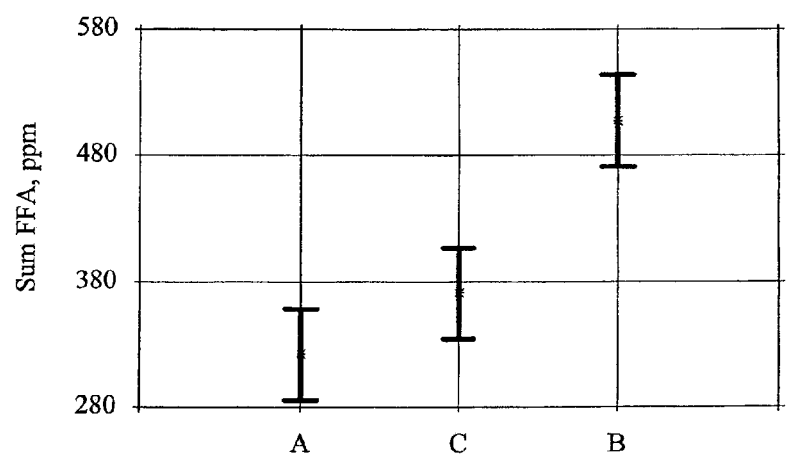
Figure 128:
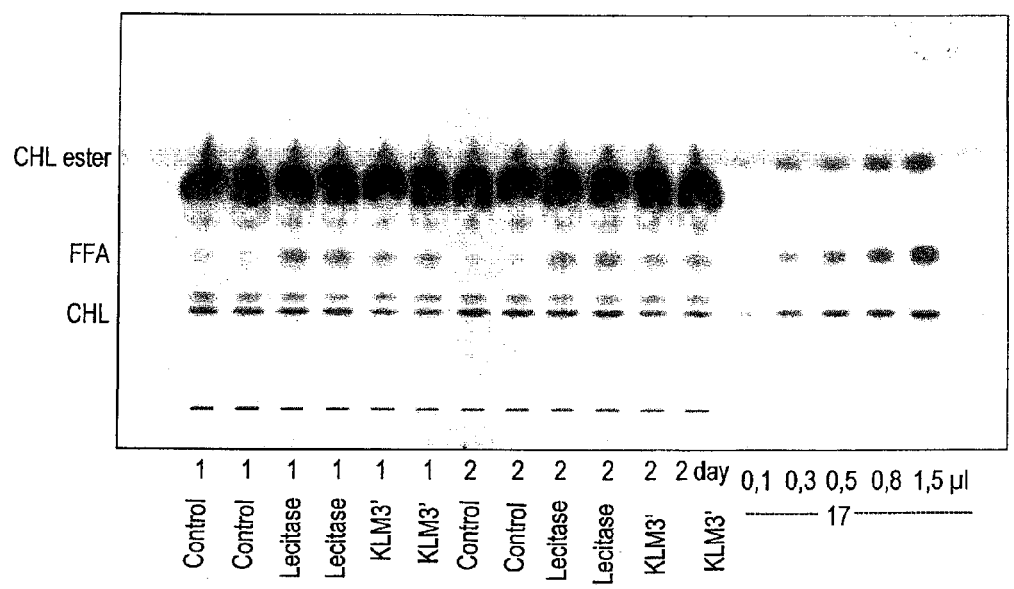
Figure 129:
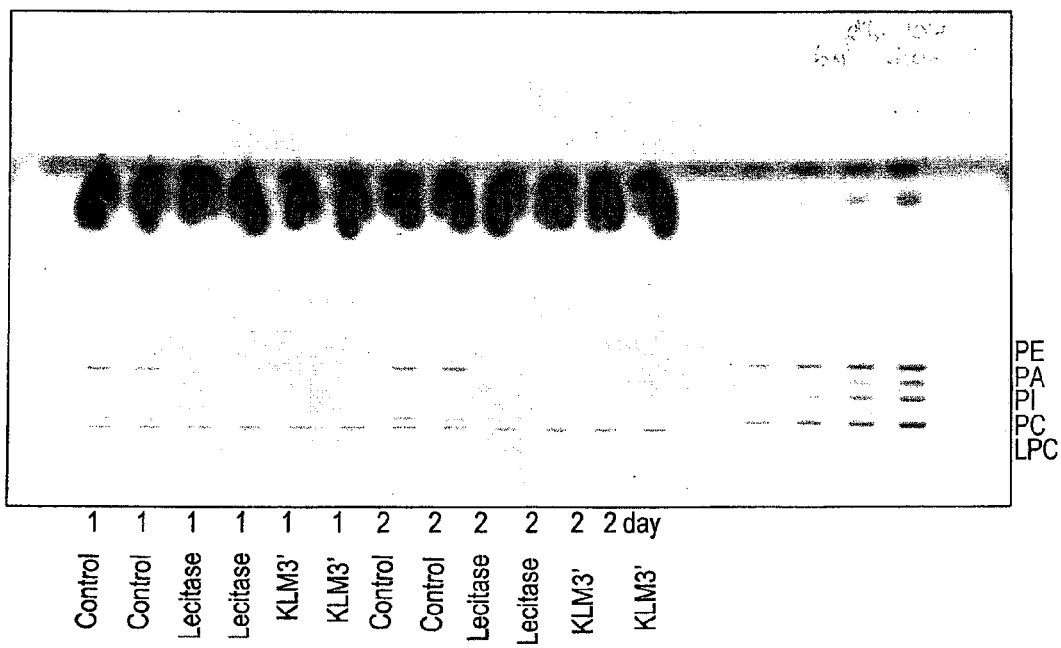
Figure 130:
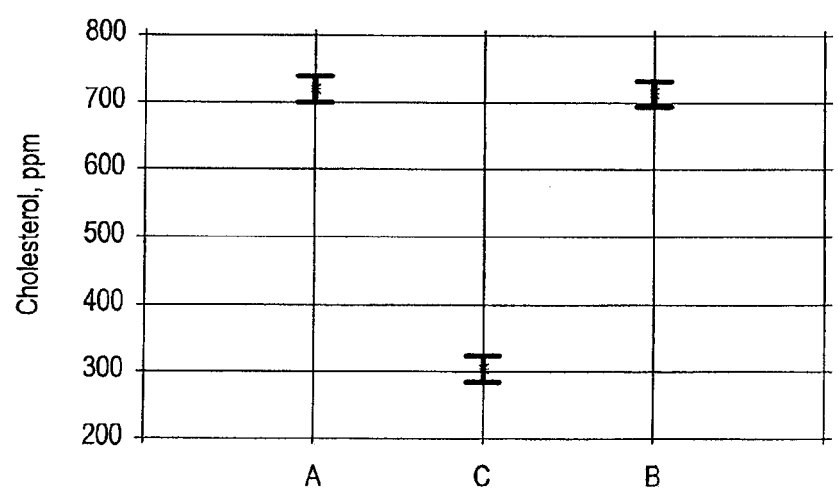
Figure 131:
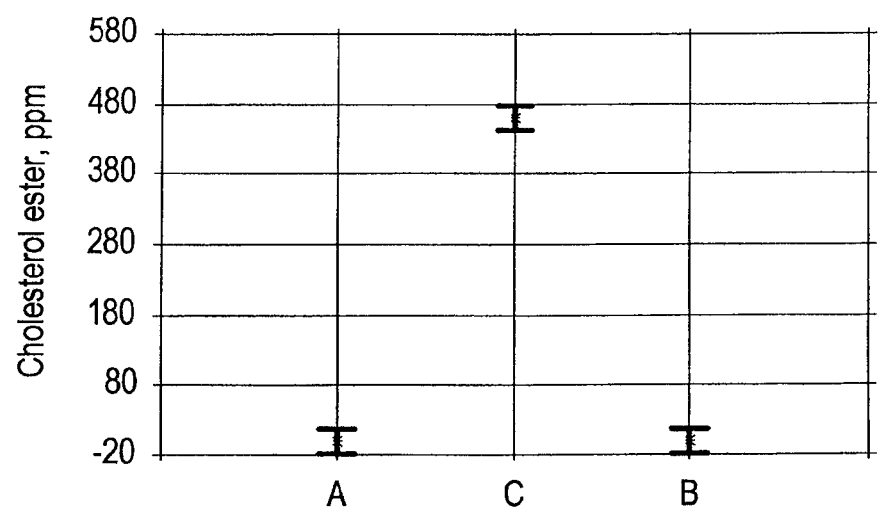
Figure 132:
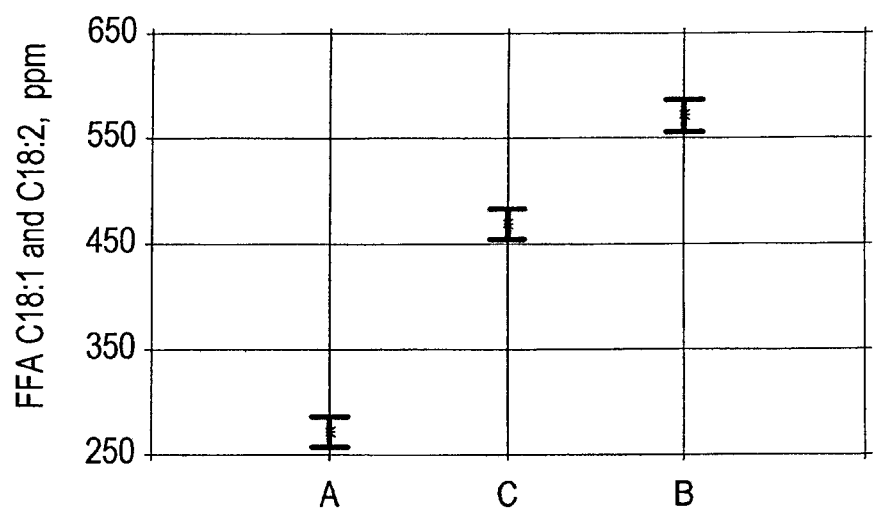
Figure 133:
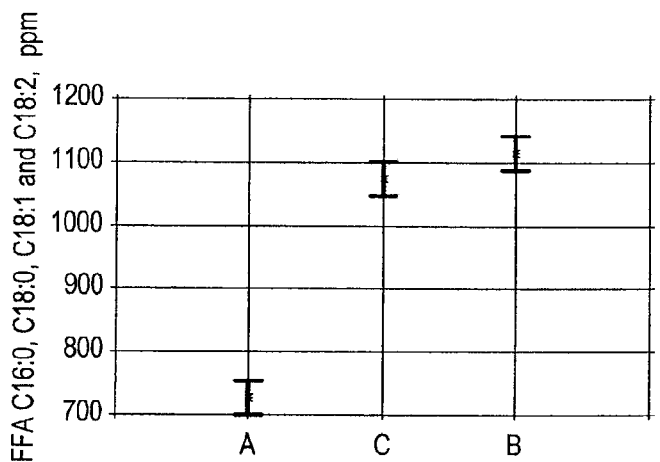
Figure 134:
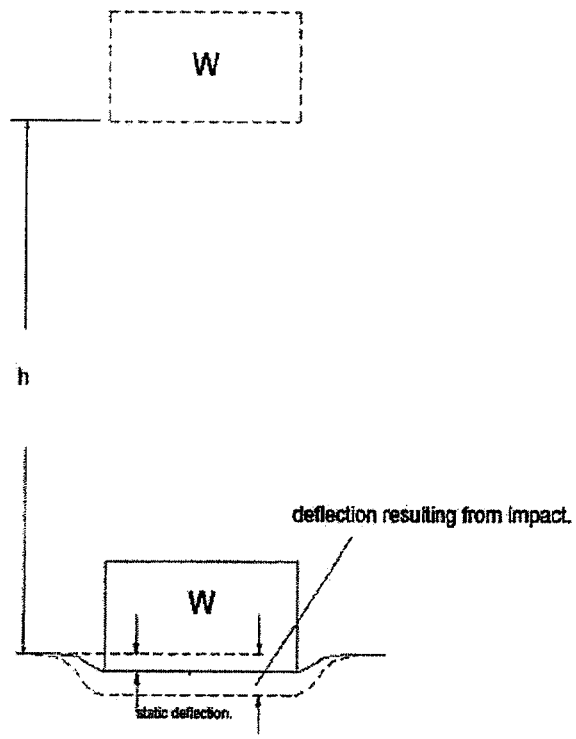
Figure 135:
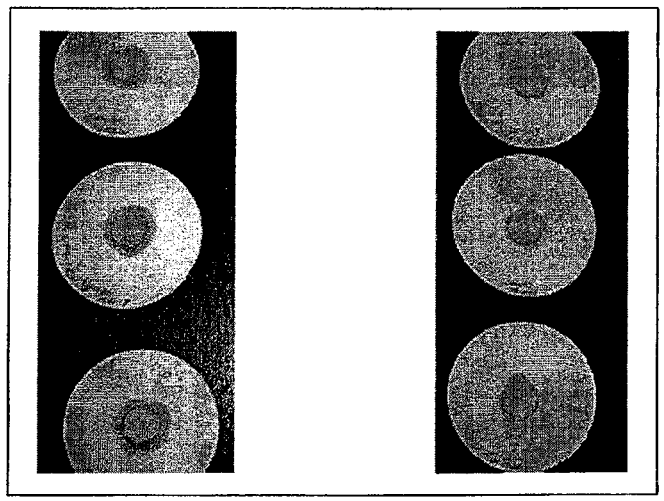
Figure 136:
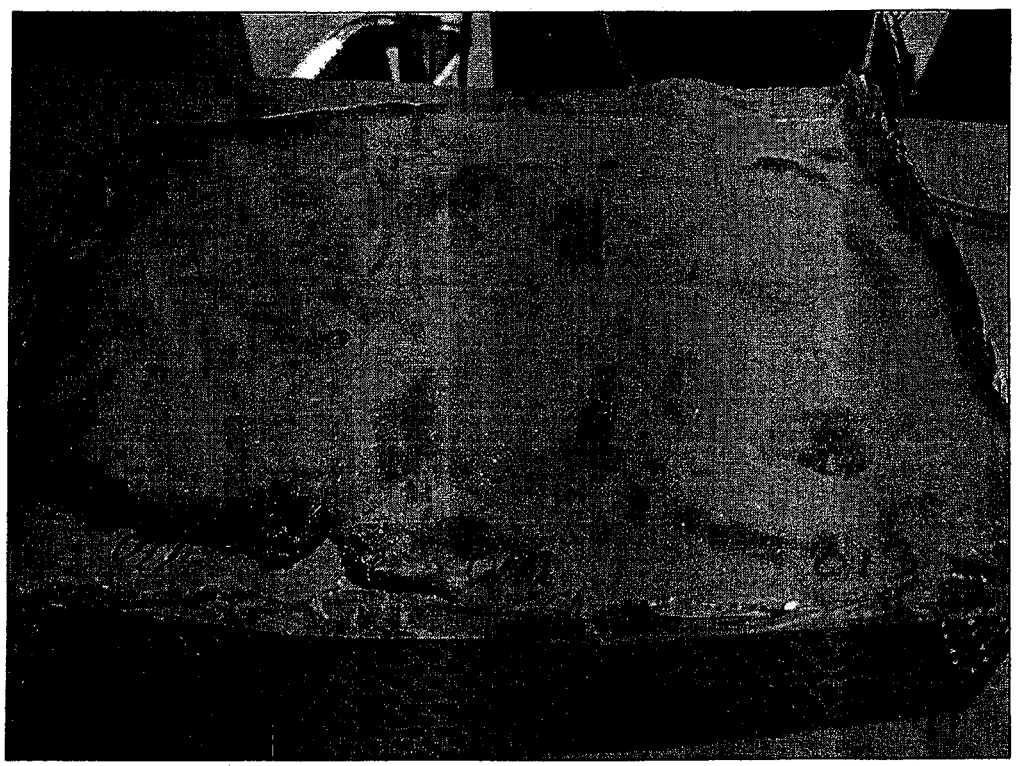

FIG. 98 shows an amino acid sequence (SEQ ID No. 86) from *Thermobifida fusca*/GDSx;

FIG. 99 shows a nucleotide sequence (SEQ ID No. 87) from *Thermobifida fusca*/GDSx;

FIG. 100 shows a nucleotide sequence from *Aeromonas salmonicida* (SEQ ID No. 88) including the signal sequence (preLAT —positions 1 to 87);

FIG. 101 shows a polypeptide sequence of a lipid acyltransferase enzyme from *Streptomyces* (SEQ ID No. 89);

FIG. 102 shows shows the amino acid sequence of a mutant *Aeromonas salmonicida* mature lipid acyltransferase (GCAT) with a mutation of Asn80Asp (notably, amino acid 80 is in the mature sequence) —shown herein as SEQ ID No. 62—after undergoing post-translational modification (SEQ ID No. 90);

FIG. 103 shows an alignment of the L131 and homologues from *S. avermitilis* and *T. fusca* illustrates that the conservation of the GDSx motif (GDSY (SEQ ID NO: 17) in L131 and *S.avermitilis* and *T. fusca*), the GANDY (SEQ ID NO: 15) box, which is either GGNDA (SEQ ID NO: 16) or GGNDL (SEQ ID NO: 18), and the HPT block (considered to be the conserved catalytic histadine). These three conserved blocks are highlighted (SEQ ID NOS 99-101 are disclosed respectively in order of appearance);

FIG. 104. TLC (running buffer 5) of 10 butterfat samples, mono-diglyceride and St 17 containing cholesterol, oleic acid and cholesterol ester;

FIG. 105 TLC (running buffer 1) of 10 butterfat samples, mono-diglyceride and St 8 containing cholesterol;

FIG. 106 TLC (running buffer 5) of butterfat samples 1(ref) and 2(enzyme). Reference St. 17 containing cholesterol, oleic acid and cholesterol ester;

FIG. 107 TLC (running buffer 1) of butterfat sample 1(reference), 2(enzyme), mono-diglyceride and St 17 containing cholesterol, fatty acid and cholesterol ester;

FIG. 108 TLC (running buffer 4) of butterfat sample 1 (reference), 2(enzyme) and St. 4 containing phosphatidylcholine (PC) and lyso-phosphatidylcholine;

FIG. 109 TLC (running buffer 5) of cream sample 3(ref), 4(enzyme) and reference St. 17 containing cholesterol, oleic acid and cholesterol ester;

FIG. 110 TLC (running buffer 1) of cream sample 3(reference), 4(enzyme), mono-diglyceride and St 17 containing cholesterol, fatty acid and cholesterol ester;

FIG. 111 TLC (running buffer 4) of cream sample 3(reference), 4(enzyme) and St. 4 containing phosphatidylcholine (PC) and lyso-phosphatidylcholine;

FIG. 112 shows a ribbon representation of the 1IVN.PDB crystal structure which has glycerol in the active site. The Figure was made using the Deep View Swiss-PDB viewer;

FIG. 113 shows 1IVN.PDB Crystal Structure—Side View using Deep View Swiss-PDB viewer, with glycerol in active site—residues within 10 Å of active site glycerol are coloured black;

FIG. 114 shows 1IVN.PDB Crystal Structure—Top View using Deep View Swiss-PDB viewer, with glycerol in active site—residues within 10 Å of active site glycerol are coloured black;

FIG. 115 shows alignment 1 (1DEO (SEQ ID NO: 102); 1IVN (SEQ ID NO: 103); P10480 (SEQ ID NO: 104);

FIG. 116 shows alignment 2 (1DEOm (SEQ ID NO: 105); 1IVNm (SEQ ID NO: 106); P10480m (SEQ ID NO: 107);

FIGS. 117 [1DEO (SEQ ID NO: 102); 1IVN (SEQ ID NO: 103); P10480 (SEQ ID NO: 104); 1DEOm (SEQ ID NO: 105); 1IVNm (SEQ ID NO: 106); P10480m (SEQ ID NO: 107)]and 118 (SEQ ID NOS 108 & 109) show an alignment of 1IVN to P10480 (P10480 is the database sequence for *A. hydrophila* enzyme), this alignment was obtained from the PFAM database and used in the model building process;

FIG. 119 shows an alignment where P10480 is the database sequence for *Aeromonas hydrophila*. This sequence is used for the model construction and the site selection. Note that the full protein (SEQ ID No. 36) is depicted, the mature protein (equivalent to SEQ ID No. 73) starts at residue 19. A.sal is *Aeromonas salmonicida* (SEQ ID No. 3) GDSX lipase, A. hyd is *Aeromonas hydrophila* (SEQ ID No. 73) GDSX lipase. The consensus sequence contains a * at the position of a difference between the listed sequences;

FIG. 120 shows a diagram which illustrates the addition of enzyme to each vat., Han PL is Lecitase, Dan PL is KLM3 a lipid acyltransferase according to the present invention;

FIG. 121 shows a TLC (solvent 6) of lipid extracted from cream and a standard mixture (ST16) of phospholipids; Phosphatidylcholine (PC); Lyso-phosphatidylcholine (LPC); Phosphatidylinisitol (PI); Phosphatidylethanolamine (PE); 5.13% Phosphatidic acid (PA); and Spingholipid (SG);

FIG. 122 shows a TLC (solvent 1) of lipid extracted from cream and a standard mixture of free fatty acids (FFA), cholesterol (CHL) and cholesterol ester (CHL-ester);

FIG. 123 shows the ANOVA evaluation of cholesterol in enzyme treated cream (30%) analyzed by TLC (Table 43), A=control, B=Lecitase and C=KLM3';

FIG. 124 shows the ANOVA evaluation of Fatty acids in enzyme treated cream (30%) analyzed by TLC (Table 43), A=control, B=Lecitase and C=KLM3';

FIG. 125 shows ANOVA evaluation of cholesterol analyzed by GLC (Table 44) A=control, B=Lecitase and C=KLM3';

FIG. 126 shows the ANOVA evaluation of cholesterol ester analyzed by GLC (Table 44) A=control, B=Lecitase and C=KLM3';

FIG. 127 shows the ANOVA evaluation of Sum FFA (palmetic acid, C:16:0+oleic acid, C18:1+Linoleic acid, C18:2+stearic acid, C18.0) analyzed by GLC (Table 44) A=control, B=Lecitase and C=KLM3';

FIG. 128 shows a TLC (solvent 6) of lipid extracted from cheese and a standard mixture of free fatty acids (FFA), cholesterol (CHL) and cholesterol ester (CHL-ester);

FIG. 129 shows a TLC (solvent 6) of lipid extracted from cheese and a standard mixture of phospholipids: Phosphatidylcholine (PC), Lyso-phosphatidylcholine (LPC), Phosphatidylinisitol (PI), Phosphatidylethanolamine (PE) and Phosphatidic acid (PA);

FIG. 130 shows the ANOVA evaluation of cholesterol in cheese analyzed by GLC (Table 45) A=control, B=Lecitase and C=KLM3';

FIG. 131 shows the ANOVA evaluation of cholesterol ester in cheese analyzed by GLC (Table 45) A=control, B=Lecitase and C=KLM3';

FIG. 132 shows the ANOVA evaluation of Oleic acid (C18: 1)+linoleic acid (C18:2) in cheese analyzed by GLC (Table 45) A=control, B=Lecitase and C=KLM3';

FIG. 133 shows the ANOVA evaluation of Palmetic acid (C16:0), Stearic acid (C18:0), Oleic acid (C18:1)+linoleic acid (C18:2) in cheese analyzed by GLC (Table 45) A=control, B=Lecitase and C=KLM3';

FIG. 134 shows a diagram depicting force as an outcome of mass, acceleration and deflection properties of target material;

FIG. 135 shows the photos of the control samples DAN011 (left) and the cheese produced with KLM3 DAN013 (right). 5 minutes standing after heating step;

FIG. 136 shows Pizza baked with cheese DAN011 (left), DAN012 (centre) and DAN013 (right).

Figure 137:
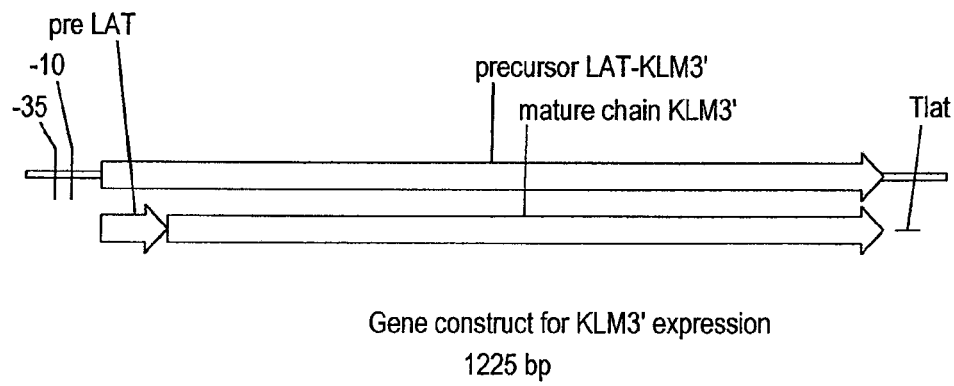
Figure 138:
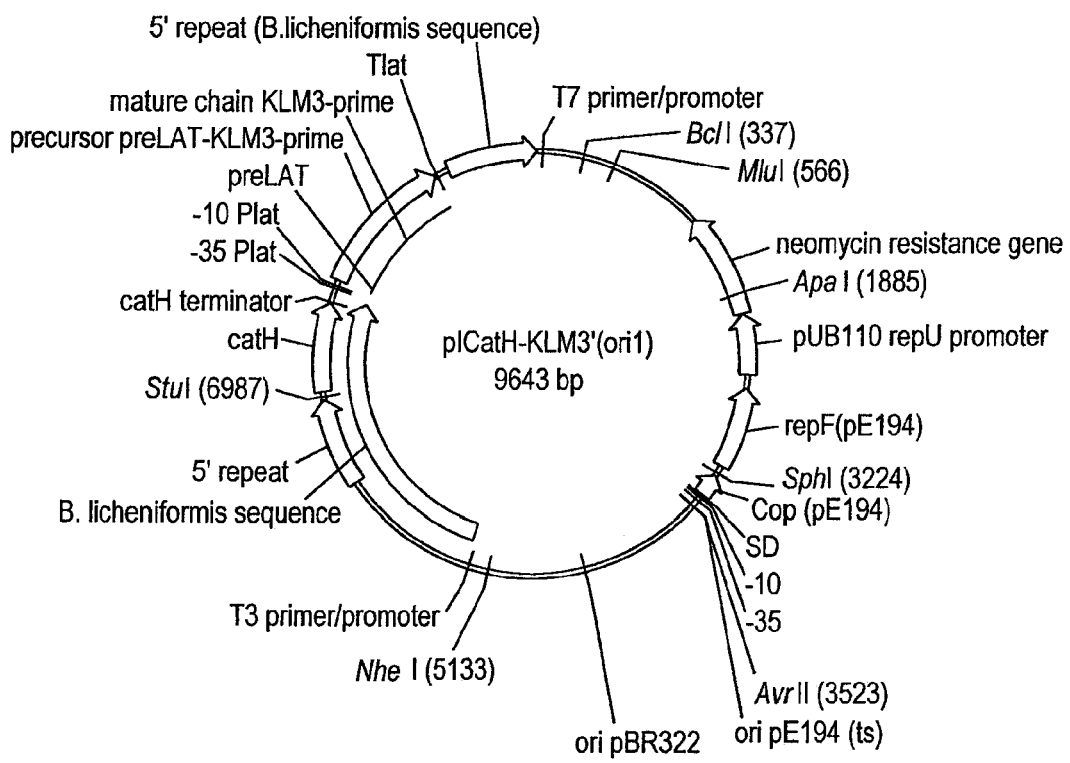
Figure 140:
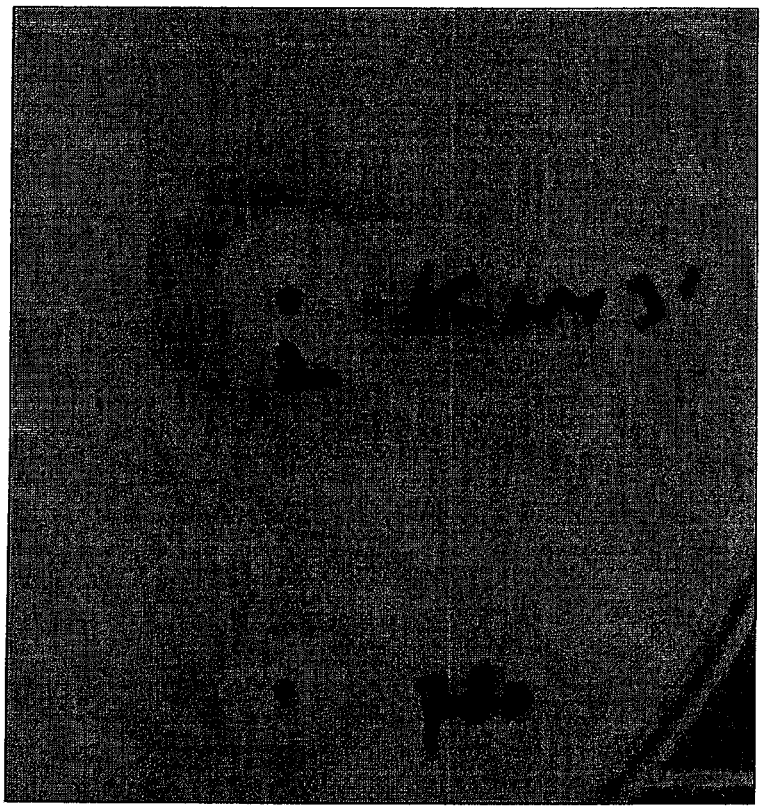

FIG. 137 shows a gene construct used in Example 32;

FIG. 138 shows a codon optimised gene construct (no. 052907) used in Example 32; and FIG. 139 shows the sequence of the XhoI insert containing the LAT-KLM3' precursor gene, the −35 and −10 boxes are underlined (SEQ ID NOS 110 & 111); and FIG. 140 shows BML780-KLM3'CAP50 (comprising SEQ ID No. 90—upper colony) and BML780 (the empty host strain—lower colony) after 48 h growth at 37° C. on 1% tributyrin agar.

EXAMPLES

Except where stated TLC analysis was performed as described in Example 6 and GLC analysis was performed as described in Example 11.

Example 1

The Cloning, Sequencing and Heterologous Expression of a Transferase from *Aeromonas salmonicida* subsp. *Salmonicida*

Strains Used:
*Aeromonas salmonicida* subsp. *Salmonicida* (ATCC 14174) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat. 19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12-AsalGCAT=pSM. Transformants containing the appropriate plasmid were grown at 37° C. in LB agar medium containing 100-ug ampicillin/ml.

Construction of Expression Vector pet12-AsalGCAT-pSM:

For all DNA amplifications of the transferase genes from *Aeromonas*, genomic DNA (0.2-1 ul) was used as template and pfu DNA polymerase (2.5 units) was used with 10 ul of 10× pfu buffer, 1 ul each primer (50 pmol/ul), 200 uMdNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. salmonicida* was carried in 2 separate PCR reactions. PCR reaction 1 was performed using primer pairs, as1USNEW (5'AGCATATGAAAA AATGGTTTGT TTGTTTATTG GGG 3' [SEQ ID No. 56]) and asls950new (5' GTG ATG GTG GGC GAG GAA CTC GTA CTG3' [SEQ ID No. 37]). A second PCR reaction was performed to incorporate a C-terminal Histidine tag using the PCR product from the first reaction and the primers: as1USNEW(5'AGCATATGAAAA AATGGTTTGT TTGTTTATTG GGG 3' [SEQ ID No. 38]) and AHLS1001(5'TTGGATCC GAATTCAT CAATG GTG ATG GTG ATG GTG GGC3' [SEQ ID No. 39]). The PCR product from the second reaction was purified and digested with restriction enzymes NdeI and BamHI. 2 ug of pET 12a vector DNA was also digested with restriction enzymes NdeI and BamHI and treated with phosphatase. The restriction enzyme-treated pet12a and PCR product from reaction 2 were purified and ligated using the Rapid Ligation Kit (Roche, Switzerland). The ligation mix was used to transform *E. coli* TOP10 cells. Transformants were plated on LB agar medium containing 100 ugml ampicillin.

The T7 promoter primer (5'TAATACGACTCACTATAG3' [SEQ ID No. 40]) and the T7 terminator primer (5'CTAGTTATTGCTCAGCGG3' [SEQ ID No. 41]) were used to verify the sequences and the orientation of the cloned transferase genes in pET12a vector. DNA sequencing was performed using ABI Prism® BigDye™ Terminators Cycle sequencing kit with 500 ng plasmid DNA as template and 3.2 pmol T7 promoter and terminator primers.

The construct shown in FIG. 35 was used to transform competent bacterial host strain BL21(DE3)pLysS (Novagen) and ampicillin resistant transformants were picked and used for expression analysis.

Expression of the Recombinant *Aeromonas salmonicida* Lipid Acyltransferase

Quantification of enzyme activity towards lecithin was determined on cell extracts using Non-Esterified Fatty Acid (NEFA) kit (Roche, Switzerland).

In FIG. 36, BL21(DE3)pLysS harboring the expression vector pet12-AsalGCAT=pSM was grown in LB medium+ 100 ug/ml ampicillin and incubated with shaking at 37° C. until $OD_{600}$=0.6 to1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate.

Growth Optimisation for the Production of More Active Enzymes

BL21(DE3)pLysS harboring the expression vector pet12-AsalGCAT=pSM was grown in LB medium+100 ug/ml ampicillin and incubated with shaking at different growth temperatures (37° C., 30° C., & 20° C.). The optimal condition for the production of active lipid acyltransferase enzyme was when cultures are grown at 30° C. as shown in FIG. 37.

Partial Purification of Recombinant *Aeromonas salmonicida* Transferase

Strain BL21(DE3)pLysS harboring the expression vector pet12-AsalGCAT=pSM was grown at 37° C. & crude cell extracts were prepared by sonication. The recombinant enzyme was further purified from the sonicated crude cell extracts using the Ni-NTA spin kit from Qiagen. Phospholipase activity using the NEFA kit & Lecithin as substrate. Crude cell extracts from BL21(DE3)pLysS expressing active transferase incubated with the substrate lecithin and reaction mixture was analysed using thin layer chromatography showing the presence of degradation products (see FIG. 38).

Partial Purification of Recombinant *Aeromonas salmonicidae* Transferase.

Strain BL21(DE3)pLysS harbouring the expression vector pet12-AsalGCAT=pSM was grown at 37° C. and crude cell extracts were prepared by sonication. The recombinant enzyme ware further purified from the sonicated crude cell extract using the Ni-NTA spin kit from Qiagen. Phospholipase activity using the NEFA kit and lecithin as substrate was tested (see FIG. 39).

Example 2

Cloning and Expression of *Aeromonas hydrophila* Transferase in *E. coli*

*Aeromonas hydrophila* (ATCC # 7965) was obtained from ATCC and grown overnight at 30° C. in Luria-Bertani medium (LB). The cells were centrifuged and genomic DNA was isolated using the procedures for genomic DNA isolation from Qiagen Ltd. Genomic DNA buffer set (cat. 19060), protease K (cat. 19131) and RNAse A (cat. 19101) were all obtained from Qiagen Ltd. (Boundary court Gatwick Court, West Sussex, RH10 2AX).

Host bacterial strain BL21(DE3)pLysS (Novagen) was used for production of the recombinant *Aeromonas* enzymes. Competent cells of BL21(DE3)pLysS were used as host for transformation with the expression vector pet12a-A.h.GCAT=pSMa. Transformants containing the appropriate plasmid were grown at 37° C. in LB agar medium containing 100-ug ampicillin/ml.

Construction of Expression Vector pet12a-A.h.GCAT-pSMa:

For all DNA amplifications of the transferase gene from *Aeromonas*, genomic DNA (0.2-1 ul) was used as template and pfu DNA polymerase (2.5 units) was used with 10 ul of 10×pfu buffer, 1 ul each primer (50 pmol/ul), 200 uMdNTP in a total reaction volume of 100 ul. PCR reactions were performed in a programmable thermal cycler using the following conditions: 95° C. for 30 seconds, 30 cycles of 95° C. for 30 seconds, 60° C. for 1 minute and 68° C. for 2 minutes. An additional extension of 5 minutes at 72° C. was applied.

The PCR amplification of the transferase gene from *A. hydrophila* (ATCC # 7965) was carried out in 2 separate PCR reactions.

PCR reaction 1 was performed using primer pairs, AHUS1 (5'GTCATATGAAAAAATGGTTTGTGTGTT-TATTGGGATTGGTC3', SEQ ID No. 42) and ahls950 (5'ATGGTGATGGTGGGCGAGGAACTCGTACTG3', SEQ ID No. 43).

A second PCR reaction was performed to incorporate a C-terminal Histidine tag using the PCR product from the first reaction and the primer pairs:
AHUS1(5'GTCATATGAAAAAATGGTTTGTGTGTT-
TATTGGGATTGGTC3' SEQ ID No. 44,) and AHLS1001
(5'TTGGATCCGAATTCATCAATGGTGATG-
GTGATGGTGGGC3' SEQIDNo. 45).

The PCR product from the second reaction was purified and digested with restriction enzymes Nde1 and BamHI. 2 ug of pET 12a vector DNA was also digested with restriction enzymes Nde1 and BamHI and treated with phosphatase. The restriction enzyme-treated pet12a and PCR product from reaction 2 were purified and ligated using the Rapid Ligation Kit (Roche, Switzerland). The ligation mix was used to transform *E. coli* TOP10 cells. Transformants were plated on LB agar medium containing 100 ug/ml ampicillin.

The T7 promoter primer (5'TAATACGACTCAC-TATAG3') (SEQ ID NO: 57) and the T7 terminator primer (5'CTAGTTATTGCTCAGCGG3') (SEQ ID NO: 58) were used to verify the sequences and the orientation of the cloned GCAT genes in pET12a vector. DNA sequencing was performed using ABI Prism® BigDye™ Terminators Cycle sequencing kit with 500 ng plasmid DNA as template and 3.2pmol T7 promoter and terminator primers.

The construct shown in FIG. 40 was used to transform competent bacterial host strain BL21 (DE3)pLysS (Novagen) and ampicillin resistant transformants were picked and used for expression analysis.

Expression of the *Aeromonas hydrophila* Transferase in BL21(DE3)pLysS

The *E. coli* strain BL21(DE3)pLysS harboring the expression vector pet12a-A.h.GCAT=pSMa was grown in LB medium+100 ug/ml ampicillin and incubated with shaking at 37° C. until $OD_{600}$=0.6 to 1.0 is reached. The cultures are then induced using IPTG (0.4 mM) and incubation was continued for the next 3 hours. Samples where taken at 0 hour, 1, 2, and 3 hours after IPTG induction. Enzyme Activity was tested using the NEFA kit and lecithin as substrate (FIG. 41).

Growth Optimisation for the Production of More Active Enzymes

BL21(DE3)pLysS harboring the expression vector pet12a-A.h.GCAT=pSMa was grown in LB medium+100 ug/ml ampicillin and incubated with shaking at different growth temperatures (37° C., 30° C., & 20° C.). The optimal condition for the production of active GCAT enzyme was when cultures are grown at 30° C. as shown in FIG. 42.

Partial Purification of Recombinant *A. hydrophila* Transferase (GCAT)

Strain BL21(DE3)pLysS harboring the expression vector pet12a-A.h.GCAT=pSMa was grown at 37° C. & crude cell extracts were prepared by sonication. The recombinant enzyme was further purified from the sonicated crude cell extracts using the Ni-NTA spin kit from Qiagen. Phospholipase activity assay using the NEFA kit & Lecithin as substrate. (FIG. 43).

Example 3

Expression of *Aeromonas* Transferases in *Bacillus subtilis* 163

Plasmid Construction

Two different *Bacillus subtilis* expression vectors (pUB 110 & pBE5) were used for the heterologous expression of the *Aeromonas* genes in *Bacillus subtilis*. The pUB110 vector contains the alpha amylase promoter while the pBE vector has the P32 promoter as the regulatory region for the expression of the fused *Aeromonas* genes. In pUB110, the first amino acid of the mature GCAT genes of *Aeromonas* were fused in frame with the last amino acid of the xylanase signal peptide sequence from *Bacillus subtilis* via the restriction site Nhe1, creating an additional 2 amino acids in front of the mature proteins. pBE5 contains the cgtase signal sequence fusion at the Nco1 site for secretion of the recombinant proteins into the culture filtrate.

PCR reactions were carried out to obtain the *Aeromonas* genes fuse in frame to the signal sequences of the pUB 110 and the pBE5 vectors. PCRs were performed using the following primer pairs for *A. hydrophila* gene:
PCR reaction 1: usAHncol (5'ATGCCATGGCCGA-CAGCCGTCCCGCC3', SEQ ID No. 46) and lsAH (5'TTG-GATCCGAATTCATCAATGGTGATG3', SEQ ID No. 47)
PCR reaction 2: US-Ahnhel (5'TTGCTAGCGCCGA-CAGCCGTCCCGCC3', SEQ ID No. 48) and lsAH (5'TTG-GATCCGAATTCATCAATGGTGATG3, SEQ ID No. 49)
PCRs were performed using the following primer pairs for *A. salmonicida* gene:
PCR reaction 3: US-Asncol (5'TTGCCATGGCCGA-CACTCGCCCCGCC3', SEQ ID No. 50) and lsAH (5'TTG-GATCCGAATTCATCAATGGTGATG3', SEQ ID No. 51)
PCR reaction 4: US-ASnhel (5'TTGCTAGCGCCGA-CACTCGCCCCGCC3', SEQ ID No. 52) and lsAH (5'TTG-GATCCGAATTCATCAATGGTGATG3', SEQ ID No. 53)

All the PCR products were cloned into PCR blunt II (TOPO vector) and sequenced with reverse & forward sequencing primers.

Clones from PCR reactions 1 & 3 were cut with Nco1 & Bam HI and used as inserts for ligation to the pBE5 vector cut with Nco1/BamH1/phosphatase. Clones from PCR reactions 2 & 4 were cut with Nhe1 & Bam H1 and used as inserts for ligation to the pUB vector that was cut with Nhe1/BamH1/phosphatase.

Expression of the *Aeromonas* Transferase genes in *Bacillus subtilis* and characterization of the Enzyme Activity.

The acyl transferases from the two *Aeromonas* species have been successfully expressed in *E. coli* (results above). The *Bacillus* pUB110 & pBE5 gene fusion constructs were used to transform *Bacillus subtilis* and transformants were selected by plating on kanamycin plates. The kanamycin resistant transformants isolated and grown in 2×YT are capable of heterologous expression of the *Aeromonas* genes in *Bacillus*. The culture filtrates have digalactosyldiacylglycerol (DGDG) galactolipase activity, in addition to having both acyl transferase and phospholipase activities. The activity towards digalactosyldiacylglycerol (DGDG) was measured after 60 minutes of incubation of culture supernatant with the substrate, DGDG from wheat flour (obtainable form Sigma) as well as the activity towards lecithin as shown in FIG. 44. *Bacillus* produced the enzyme after overnight (20-24 hours) to 48 hours of cultivation in the culture medium as a secreted protein. In some instances, the expression of the *Aeromonas* genes has been shown to interfere with cell viability and growth in *Bacillus* & *E. coli*, it is therefore necessary to carefully select expression strains and optimise the growth conditions to ensure expression. For example, several *Bacillus* host strains (B.s 163, DB104 and OS 21) were transformed with the expression vectors for growth comparison. B.s163 is transformable with the 2 *Aeromonas* genes and is capable of expressing active protein. DB104 is transformable with all the constructs but is only able to express *A. salmonicida* transferase.

Example 4

Fermentation and Purification of *Aeromonas* Lipid Acyltransferases Produced in *E. coli*

*E. coli* Fermentations:
Microorganisms

Two strains of Eschericia coli, one containing an *Aeromonas hydrophila* (Example 2) lipid acyltransferase and two containing *Aeromonas salmonicida* lipid acyltransferases, (Example 1) were used in this study.

The *E. coli* strain containing the *A. hydrophila* gene was named DIDK0124, and the *E. coli* strain containing the *A. salmonicida* gene was named DIDK0125. The fermentation with DIDK0124 was named HYDRO0303 and the fermentation with DIDKO125 was named SAL0302. The purified protein from HYDRO025 was named REF#138. The purified protein from HYDRO0303 was named REF#135.
Growth Media and Culture Conditions
LB-agar The LB agar plates used for maintaining the strains contained: 10 g/L tryptone, 5 g/L yeast extract, 5 g/L NaCl, 15 g/L agar, 100 mg/L ampicillin and 35 mg/L chloramphenicol. The agar plates were incubated at 30° C.
LB Shake Flask The LB medium (50 mL pr shake flask) used for production of inoculum material for the bioreactor cultivations contained: 10 g/L tryptone, 5 g/L yeast extract, 5 g/L NaCl, 100 mg/L ampicillin and 35 mg/L chloramphenicol. The shake flasks were inoculated from the LB agar plates, and incubated at 30° C. and 200 rpm.
Bioreactor Cultivation The bioreactor cultivations were carried out in 6 L in-house built bioreactors filled with 4 L medium containing: 10 g/L tryptone, 5 g/L yeast extract, 5 g/L NaCl, 8 g/L $KH_2PO_4$, 0.9 g/L $MgSO_4$, $7H_2O$, 40 g/L glucose monohydrate, 0.4 mL/ADD APT® Foamstop Sin 260 (ADD APT Chemicals AG, Helmond, The Netherlands), 10 mg/L $(NH_4)_2Fe(SO_4)_2.6H_2O$, 0.7 mg/L $CuSO_4.5H_2O$, 3 mg/L $ZnSO_4.7H_2O$, 3 mg/L $MnSO_4H_2O$, 10 mg/L EDTA, 0.1 mg/L $NiSO_4.6H_2O$, 0.1 mg/L $CoCl_2$, 0.1 mg/L $H_3BO_4$, 0.1 mg/L KI, 0.1 mg/L $Na_2MoO_4.2H_2O$, 1 g/L ampicillin and 35 mg/L chloramphenicol.

The bioreactors were inoculated with an amount of LB culture ensuring end of growth after approximately 20 hours of cultivation (calculated from the maximum specific growth rate of 0.6 h$^{-1}$, the $OD_{600}$ of the LB shake flask and the final $OD_{600}$ in the bioreactor of approximately 20).

SAL0302 was inoculated with 10 mL of LB culture, and HYDRO0303 was inoculated with 4 mL of LB culture.

The bioreactors were operated at the following conditions: temperature 30° C., stirring 800-1000 rpm (depending on experiment), aeration 5 L/min, pH 6.9, pH control 8.75% (w/v) $NH_3$-water and 2 M $H_2SO_4$. Induction was achieved by addition of isopropyl β-D-thiogalactoside to a final concentration of 0.6 mM, when 0.4 moles (HYDRO0303) and 0.7 moles $CO_2$ was produced respectively.
Harvest The following procedure was used for harvest and homogenisation of the biomass:
1) The fermentation broth from the fermentations was centrifuged at 5000×g and 4° C. for 10 minutes, and the supernatant was discharged. The biomass was stored at −20° C. until use. The biomass was thawed and resuspended in 500 mL of 20 mM $NaH_2PO_4$, pH 7.4, 500 mM NaCl, 10 mM Imidazole and Complete (EDTA-free) protease inhibitor (Roche, Germany).
2) The suspended biomass was homogenized at 2 kbar and 4° C. in a cell disrupter from Constant Systems Ltd (Warwick, UK).
3) The cell debris was removed by centrifugation at 10.000×g and 4° C. for 30 minutes followed by collection of the supernatant.
4) The supernatant was clarified further by centrifugation at 13.700×g and 4° C. for 60 minutes, followed by collection of the supernatant.
5) The supernatant was filtered through 0.2 μm Vacu Cap filters (Pall Life Sciences, UK) and the filtrate was collected for immediate chromatographic purification.
Chromatographic Purification of the Transferases A column (2.5×10 cm) was packed with 50 ml of Chelating Sepharose ff. gel and charged with Ni-sulphate (according to the method described by manufacturer, Amersham Biosciences). The column was equilibrated with 200 ml of 20 mM $NaH_2PO_4$, pH 7.4, 500 mM NaCl, 10 mM Imidazole. 400 ml of crude was applied to the column at a flow rate of 5 ml/min. The column was then washed with 20 mM $NaH_2PO_4$, pH 7.4, 500 mM NaCl, 10 mM Imidazole until the UV280 reached the base line. The GCAT was then eluted with 40 ml of 20 mM $NaH_2PO_4$, pH 7.4, 500 mM NaCl and 500 mM Imidazole.

Example 5

Fermentation and Purification of *Aeromonas* Lipid Acyltransferases Produced in *Bacillus subtilis*

Fermentations
BAC0318-19, BAC0323-24
Microorganism

The microorganisms used in this study originate from transformation of a *Bacillus subtilis* host strain, #163 with a plasmid containing the gene encoding the *Aeromonas salmonicida* transferase inserted in the vector pUB110OIS. The expression of the gene is controlled by an alpha-amylase promoter, and the secretion of the transferase is mediated by the *B. subtilis* xylanase signal sequence (Example 3). The strains were named DIDK0138 (fermentation BAC0318-19) and DIDK0153 (fermentation BAC0323-24).
Growth Media and Culture Conditions
Pre Culture Medium A shake flask (500 mL total volume, with baffles) was added 100 mL of a medium containing:

| | |
|---|---|
| NaCl | 5 g/L |
| $K_2HPO_4$ | 10 g/L |
| Soy flour | 20 g/L |
| Yeast extract, BioSpringer 106 | 20 g/L |
| Antifoam, SIN260 | 5 mL/L |

PH was adjusted to 7.0 before autoclaving

After autoclaving 6 mL 50% (w/w) Nutriose were added pr flask. Kanamycin was added at a concentration of 50 mg/L after autoclaving.
Inoculation A pre culture shake flask was inoculated with frozen culture directly from a 25% (w/v) glycerol stock. The shake flask was incubated at 33° C. and 175 rpm for approximately 16 hours, whereupon 50 mL was used to inoculate the fermentor.
Fermentations The fermentations were carried out in 6 L in house built fermentors.
The batch medium (3 L) contained:

| | |
|---|---|
| Corn steep liquor (50% dw) | 40 g/L |
| Yeast extract BioSpringer 153 (50% dw) | 10 g/L |
| NaCl | 5 g/L |
| $CaCl_2$, $2H_2O$ | 0.25 g/L |
| $Mn(NO_3)_2$, $H_2O$ | 0.2 g/L |
| Antifoam SIN260 | 1 mL/L |
| Kanamycin (filter sterilised to the fermentor after autoclaving) | 50 mg/L |

The feed contained:

| | |
|---|---|
| Glucose monohydrate | 540 g/kg |
| $MgSO_4$, $7H_2O$ | 4.8 g/kg |
| Antofoam SIN260 | 4 mL/kg |
| Yeast extract, BioSpringer 153 (50% dw) | 150 g/kg (autoclaved separately) |

The feed in fermentation BAC0318 and BAC0323 was started based on the accumulated $CO_2$, according to the equations below:

Feed-flow[g/h]=0, $AcCO_2$<0.15

Feed-flow[g/h]=2.85+t·1.54, $AcCO_2 \geq 0.15$ and t<12

Feed-flow[g/h]=21.3, t>12 t: time (hours) from the point when the accumulated $CO_2$ ($AcCO_2$) reached 0.15 moles.

The feed in fermentation BAC0319 and BAC0324 was started based on the accumulated $CO_2$, according to the equations below:

Feed-flow[g/h]=0, $AcCO_2$<0.15

Feed-flow[g/h]=2.0+t·1.08, $AcCO_2 \geq 0.15$ and t<12

Feed-flow[g/h]=15, t>12 t: time (hours) from the point when the accumulated $CO_2$ ($AcCO_2$) reached 0.15 moles.

The pH was controlled at 7.0 by adding 12.5% (w/v) $NH_3$-water or 2M phosphoric acid.

The aeration was 3 L/min corresponding to 1 vvm.

The temperature was 33° C.

The fermentor was equipped with two 8 cm Ø Rushton impellers placed with a distance of 10 cm.
Harvest The biomass was removed by centrifugation at 16,000×g for 10 minutes at room temperature. The supernatant was filter sterilized, and the filtrate was used for purification and application tests.

Example 6

Application Tests in Egg Yolk

In the following experiments the isolated transferase from *Aeromonas salmonicida* expressed in E-coli was tested in egg yolk alone and in egg yolk where a plant sterol had been added.
Material
Transferase from *Aeromonas salmonicida* REF#138
Egg yolk: from fresh egg (hens eggs)
Plant sterol: β-sitosterol, Sigma S 5753
TLC plates: Silica plates Merck nr. 1.05715.0001
TLC analysis.

TLC-plate was activated in a heat cupboard (110° C.) for ½ h.

100 ml developing solvent was poured into a chromatography camber with lid. The walls of the chamber were covered with filter paper (Whatman 2) in order to saturate the chamber with the solvent vapor.

The TLC-plate was placed in a frame and the sample was applied onto the TLC plate 2 cm from the bottom. The TLC plate was then placed in the TLC chamber with the developing solvent. When the developing solvent reached 14 cm from the bottom of the plate. The TLC plate was taken out and dried in fume board, and then placed in the heat cupboard at 110° C. for 10 minutes.

The TLC-plate was then immersed in the developing reagent, and dried in the heat cupboard at 110° C. for 15 minutes
Developing Solvent:
Nr. IV:Chloroform:Methanol:$H_2O$ (65:25:4)
Nr. I:P-ether:MTBE:Acetic acid (60:40:1)
Developing Buffer (Vanadate-Buffer):
32 g $Na_2CO_3$ ad 300 ml $H_2O$ (1M)
18.2 g vanadate pentoxide ($V_2O_5$) is added and dissolved during gentle heating.
The solution is cooled to ambient.
Carefully 460 ml 2.5 M $H_2SO_4$. (460 ml $H_2O$+61 ml $H_2SO_4$) is added
Water is added to 1000 ml.
Phospholipase Activity.
Substrate:
0.6% L-α Phosphatidylcholine 95% Plant (Avanti #441601)+ 0.4% Triton-X 100(Sigma X-100)+5 mM $CaCl_2$ is dissolved in 0.05M HEPES buffer pH 7.
Procedure.

400 µl substrate was added to an 1.5 ml Eppendorf tube and placed in a Eppendorf thermomixer at 30° C. for 5 minutes.

To the time T=0 50 µl enzyme solution was added. Also a blank with water instead of enzyme was analysed.

The sample was mixed at 1000 rpm on Eppendorf Termomixer at 30° C. for 10 minutes. To the time T=10 min. The Eppendorf tube was placed in another termomixer at 99° C. for 10 minutes to stops the reaction.

Free fatty acid in the samples were analyzed by using the NEFA kit from WAKO GmbH.

Enzyme activity PLU-7 pH 7 was calculated as micromole fatty acid produced per minute under assay conditions.

Lipid Extraction.

1 g egg yolk and 7.5 ml Chloroform:Methanol 2:1 was mixed on a Whirley and centrifuged at 750×g for 10 minutes.

3 ml of the chloroform phase was isolated and used for further lipid analysis.

Results:

The transferase (REF#138), from *Aeromonas salmonicida* expressed in *E-coli* was analysed for phospholipase activity as described above, and was also tested in egg yolk with and without β-sitosterol. The sample was stirred with a magnetic stirrer during the reaction. The experimental design is shown in Table 1

TABLE 1

| Test Nr | Reaction time at 37° C. Minutes | Egg yolk gram | Sitosterol mg | Transferase #138 Units |
|---|---|---|---|---|
| 1 | 30 | 1 | 40 | |
| 2 | 30 | 1 | 40 | 0.75 PLU |
| 3 | 30 | 1 | 80 | 0.75 PLU |
| 4 | 120 | 1 | 40 | 0.75 PLU |
| 5 | 120 | 1 | 80 | 0.75 PLU |
| 6 | 300 | 1 | 40 | 0.75 PLU |
| 8 | 300 | 1 | 40 | |

The reaction was stopped by adding 7.5 ml Chloroform: Methanol (2:1) and mixed on a Whirley mixer for 30 seconds. The chloroform phase was isolated by centrifugation and 2 µl of the chloroform phase was transferred to a pre-activated silica TLC plate and eluted with developing solvent nr. I, and another TLC-plate in developing solvent IV.

The results from the TLC analysis are shown in FIGS. 45 and 46.

Transferase reaction with a transferase from *Aeromonas salmonicida* in egg yolk where plant sterol was added has shown that the enzyme transfers fatty acid from lecithin in the egg yolk to the cholesterol during formation of cholesterol ester. The TLC chromatogram also indicated that part of the sterol added to egg yolk was transferred to sterol ester.

The amount of sterol ester relative to the amount of cholesterol ester formed during the reaction can be analysed by HPLC or GLC.

It is known that plant sterol esters reduce the absorption of cholesterol in the intestine. It is also indicated in the literature that cholesterol esters are absorbed less than free cholesterol in the intestine. When a transferase and plant sterol is added to egg yolk a product with causes reduced cholesterol absorption is obtained, and at the same time lysolecithin is produced which improves the emulsification properties of the egg yolk. A further advantage of adding transferase and plant sterol to egg yolk is that plant sterol ester is ingested together with the natural available cholesterol, which is expected to have the highest effect on the reduction of cholesterol absorption.

Example 7

Modification of Egg Yolk by Lipid Acyl Transferase from *Aeromonas salmonicida*

In accordance with the present invention it has now been shown that it is possible to produce lysolecithin from egg yolk without substantial free fatty acid formation by use of a transferase.

The lecithin content of egg yolk is an important emulsifier for the production of mayonnaise with the limitation that the mayonnaise is not heat stable. It has therefore been known for several years to use a phospholipase from pancreas to modify lecithin in egg yolk to lysolecithin, which is a more efficient emulsifier. The use of enzyme modified egg yolk in mayonnaise production contributes to better heat stability of the mayonnaise during pasteurisation. A limitation of using pancreas phospholipase in egg yolk is that the amount of free fatty acid also increases, which contributes to reduced oxidative stability because free fatty acids are more prone to oxidation than the corresponding ester. Free fatty acid may also contribute to a soapy off taste.

The transferase from *Aeromonas salmonicida* was successfully expressed in *B. subtilis* and fermented in lab scale as described in Example 5, purified by liquid chromatography and used to modify egg yolk lipids. The enzyme modified egg yolk was used to produce heat stable mayonnaise.

The transferase from *A. salmonicida* can be used to produce lysolecithin and cholesterol ester in egg yolk without production of significant amounts of free fatty acids. That is to say without increasing or substantially increasing the free fatty acids in the foodstuff.

The enzyme modified egg yolk produced by transferase showed improved emulsification properties and can be used for heat stable mayonnaise.

This enzyme was highly functional in modification of egg yolk by catalysing the lipid transfer reaction between lecithin and cholesterol FIG. 47.

This study further investigated the use of transferase for modification of egg yolk and the use of modified egg yolk in the production of heat stable mayonnaise.

This example describes the fermentation, isolation, and application of the transferase in egg yolks as well as the application of the enzyme modified egg yolk in mayonnaise. The example is divided into two parts:

A. Application of Transferase in Egg Yolk
B. Testing of Enzyme Modified Egg Yolk in Mayonnaise Experimental A. Application Enzyme and Substrate Transferase # 178-9 from *A. salmonicida*, purification 2554-100 C73, 15 PLU-7/ml.

Transferase # 179 from *A. salmonicida*, 18.5 PLU-7/ml.

Phospholipase A1 LECITAS™ Ultra (Novozymes A/S, Denamrk)

Egg yolk: Liquid egg yolk with 8% salt, SANOVA FOODS, DK

TLC analysis was performed as described previously (see above Example 6).

Phospholipase activity: See previous examples.

Lipid Extraction 1 g egg yolk and 7.5 ml Chloroform:Methanol 2:1 was mixed on a Whirley for 30 sec. and centrifuged at 750×g for 10 minutes.

4 ml of the chloroform phase was isolated and used for further lipid analysis.

Oxidation Stability Test

Oxidation stability of mayonnaise was measured in an ML OXIPRESS equipment where the sample is oxidative stressed by means of heat under pressure in an oxygen atmosphere.

After a certain time, called the induction period (IP), the oxidation of the sample causes a certain consumption of oxygen, which is registered as pressure change of a pressure transducer. Higher induction period indicates better oxidation stability.

Procedure.

5-gram mayonnaise is placed in a glass container and the glass container is closed with the pressure transducer. The container is filled with oxygen to 5 bars. The valve is opened to empty the container. This procedure is repeated twice and the sample with 5 bar oxygen atmosphere is placed at 80° C. The oxygen pressure as a function of time is measured and the induction period (IP) calculated in hours.

Results

Purified transferase from *Aeromonas salmonicide* sample no. #179 and #178-9 were used to treat egg yolk as outlined in Table 2. The initial test has shown that GCAT transferase should be added with much lower phospholipase (PLU) activity, than a commercial Phospholipase. This is explained by the fact that GCAT is a transferase and therefore has much lower hydrolytic activity than a normal phospholipase.

TABLE 2

| nr | Sanofo egg yolk 8% salt Egg yolk gram | 2344-44 C89 18.5 PLU-7/ml Transferase #179 gram | Transferase #178-9 18.5 PLU-7/ml gram | #3108, Lecitase Ultra 1500 PLU-7/ml ml | Water gram | PLU-7/ml |
|---|---|---|---|---|---|---|
| 6 | 120 | 2.00 | | | 8.00 | 0.31 |
| 7 | 120 | | 10 | | 0 | 1.25 |
| 8 | 120 | | | 1.86 | 8.14 | 23.25 |
| 9 | 120 | | | | 10 | 0 |

The enzymatic reactions were conducted by scaling the egg yolk and the enzyme in a beaker. The samples were placed in a heating cabinet at 37° C. during slow agitation. After 1, 2 and 4 hours reaction time a sample was taken out for TLC analysis. After 4 hours reaction time the product was stored at 5° C. and used for mayonnaise experiments.

The TLC analyses of lipids extracted from enzyme treated egg yolk is shown in FIG. 48.

The TLC analysis in FIG. 48 shows a clear hydrolytic effect of Phospholipase #3108 on triglyceride during formation of free fatty acids, as well as some mono- and diglyceride. Phospholipase #3108 seem to have no effect on cholesterol. Both transferase samples clearly contribute to the formation of cholesterol ester concomitant with the reduction of the cholesterol content.

D. Enzyme Modified Egg Yolk in Mayonnaise

In order to investigate the effect of the modification of the egg yolk samples mentioned in Table 2, application trials were performed on mayonnaise with a fat content of 50%. A mayonnaise containing untreated egg yolk was also produced.

The aim of the investigation was to determine the impact of enzymatically modified egg yolks' emulsification properties and the impact on heat stability. All mayonnaise samples contained the same oil level and were emulsified with only egg yolk.

The mayonnaise samples were all produced using a Koruma mixer (Disho V60/10) and heated during processing to 95° C. for 5 minutes.

Samples of the mayonnaises (FIG. 49) produced by enzyme treated egg yolk were nice and homogenous with no oil separation. The control sample separated in an oil and a water phase.

The particle size of oil droplet in the mayonnaise samples with enzyme treated egg yolk was measured on a Malvern Mastersizer. The sample was mixed with 0.1% SDS in 0.1 M phosphate buffer pH 7 prior to measurement. Reading was mean size of all particles as shown in Table 3.

TABLE 3

| Experiment | Enzyme | Mean particle size, μm |
|---|---|---|
| 6 | Transferase #179, 0.31 PLU-7/g | 12.9 |
| 7 | Transferase #178-9, 1.25 PLU-7/g | 7.2 |
| 8 | #3108, Lecitase Ultra, 23 PLU-7/g | 5.2 |

The results from the particle size measurement clearly show the effect of increased dosage of transferase from *A. salmonicida*. With the high dosage of transferase the particle size is close to the mayonnaise produced by Lecitase Ultra. It should however be kept in mind that Lecitase Ultra produces a lot of fatty acids, which might contribute to a finer particle distribution.

The oil droplet size of the mayonnaise prepared with the enzyme is significantly smaller than the oil droplet size of the mayonnaise prepared without the enzyme (i.e. the control mayonnaise).

Oxidation Stability

The oxidation stability of the mayonnaise samples 7 and 8 were analyzed on a ML OXIPRES with results shown in Table 4.

TABLE 4

| Sample | Induction period 1. determination hours | Induction period 2. determination hours |
|---|---|---|
| 7 | 37.44 | 38.08 |
| 8 | 35.68 | 35.52 |

Measurement of oxidation stability gave a clear significant difference in oxidation stability. The mayonnaise with transferase 179-8 treated egg yolk had a significant better oxidation stability than the mayonnaise with Lecitase Ultra treated egg yolk. This might be explained by the fact that Lecitase Ultra produces more free fatty acids which are more prone to oxidation that the corresponding fatty acid esters.

A sample of the egg yolks used for mayonnaise production were extracted with chloroform, and the lipids from the egg yolk were analysed by GLC with results shown in Table 5.

TABLE 5

| Experiment | Enzyme | Fatty acid | Cholesterol | Cholesterol ester | Triglyceride |
|---|---|---|---|---|---|
| 6 | Transferase #179 | 0.96 | 0.94 | 0.49 | 23.95 |
| 7 | Transferase #178-9 | 1.84 | 0.60 | 1.06 | 24.54 |
| 8 | #3108, Lecitase Ultra | 14.05 | 1.16 | 0.12 | 2.45 |
| 9 | Control | 0.48 | 1.16 | 0.13 | 22.87 |

The GLC results in Table 5 confirm the results form the TLC analysis that Lecitase Ultra produces a very high amount of free fatty acids and a large part of the triglyceride is hydrolysed. On the other hand the transferase produces only modest amount of free fatty acids and no triglycerides are hydrolysed. It is also clearly shown that transferase produce cholesterol ester from cholesterol.

The results indicate that the amount of PC in the "enzyme treated" mayonnaise is reduced as compared with the control mayonnaise, whilst the amount of LPC is increase in the enzyme treated mayonnaise as compared with the control mayonnaise. The increase in the amount of LPC may well explain the improved emulsification properties of the enzyme treated mayonnaise as compared with the control mayonnaise. The HPLC and GLC analyses also indicate a lower level of free cholesterol in the enzyme treated mayonnaise as compared with the control mayonnaise, probably due to the cholesterol being used as an acceptor molecule in the transferase reaction resulting in an increase in the amount of cholesterol esters in the enzyme treated mayonnaise as compared with the control mayonnaise. In addition, the results indicate that the amount of free fatty acids do not increases significantly when egg yolk is treated with the transferase. The results further indicate that the amount of free fatty acids produced in the foodstuff treated with the lipid acyltransferase is significantly lower than in the foodstuff treated with the control phospholipase, this is true even if the amount of lysolecithin formed in the foodstuffs is the same.

Example 8

Effect of *Aeromonas salmonicida* Transferase in Cakes

The effect of GCAT acyl-transferase form *Aeromonas salmonicida* is tested in a cake recipe. The enzyme is tested alone and in combination with other lipolytic enzymes. The enzymes are added to some of the cake ingredients or added together with the other cake ingredients before mixing the cake.

Preliminary results show that acyl-transferase combined with a triglyceride-hydrolysing enzyme improves the cake volume and crumb structure compared with a control.

In the following experiments a transferase from *A. salmonicida* and variants are tested alone and in combination with triglyceride hydrolysing enzymes. These enzymes are active on the lipid components in the egg and the shortening as well as on the carbohydrates, protein, glycerol and cholesterol (in egg), which forms part of the cake recipe.

Materials and Method

Enzyme

179, Acyl-transferase from *Aeromonas salmonicida* Grindamyl EXEL 16, Lipase from *Thermomyces lanuginisus*

Cake recipe:

| Ingredients | % | g |
|---|---|---|
| Sugar 35/20 | 20.37 | 204 |
| Cake flour, Albatros | 18.11 | 181 |
| Wheat starch | 5.21 | 52 |
| Baking powder | 0.36 | 4 |
| Pasteurised liquid whole egg | 22.63 | 226 |
| Shortening Vegao (Aarhus United) | 18.11 | 181 |
| Whey powder | 0.68 | 7 |
| Glucose sirup, 75% 42 DE | 4.53 | 45 |
| Glycerol | 1.36 | 14 |
| Salt | 0.32 | 3 |
| Rape seed oil | 6.34 | 63 |
| Potassium sorbate | 0.18 | 1.8 |

Equipment:
Mixer: Hobart N50 with a spatula
Oven: Simon cake oven
Procedure:
All ingredients must be tempered to room temperature.
1. Cream up sugar and shortening for 3 minutes—start at $2^{nd}$ speed and move to $3^{rd}$ speed within 30 sec
2. Add remaining ingredients—start at $1^{st}$ speed and move to $2^{nd}$ speed within 30 sec—mix total 5 min
3. Measure the volume of the batter in 1 dl cup
4. The pound cake tins are sprayed with "Babette" oil spread, and covered with paper
5. Scale 2×350 g into the pound cake tins
6. Spread out the mass evenly with a spatula
7. Before put in the oven—add a string of oil on top of the cake (lengthwise in the middle—to make the cake break in the middle
8. Bake for 50 min. at 180° C.
9. After baking take the tins out of the oven, and "drop" it on the table, before taking the cakes out of the tins
10. Take paper off the cakes and turn the right side up
11. The cakes are cooled on a grating for 60 min. before weighing and measuring of the volume Remarks:
The enzyme(s) used is/are added at the beginning of mixing or is/are added to some of the cake ingredients before added to the other cake ingredients.

The enzymes are only active during the mixing or reaction of cake components, and the enzymes are inactivated during baking of the cake.

Results.

The following experiments are conducted as shown in the following table:

| | | 1 | 2 | 3 | 4 |
|---|---|---|---|---|---|
| Whole egg | G | 250 | 250 | 250 | 250 |
| Glucose syrup, 75% DE 42 | G | 10 | 10 | 10 | 10 |
| #179 acyl-transferase, 26 PLU/ml | Ml | 25 | | 25 | |
| Grindamyl EXEL 16, | Mg | | 37.5 | 37.5 | |
| Water | | | | | 25 |

Egg, Glucose syrup and enzyme are reacted for 30 minutes at 37° C. and shortly after the eggs are use to produce cake according to the recipe mentioned above.

Preliminary results show that a combination of acyltransferase and a triglyceride hydrolysing lipase from *Thermomyces lanoginosus* improves the cake volume, and also the crumb structure, eating quality and appearance is improved compared with a water control. Preliminary results indicate in cake it may be preferably to use a combination of lipid acyltransferase and a lipase.

Example 9

The Purpose of these Experiments was to Test a Transferase from *A. hydrophila* Expressed in *E. coli*

The transferase reaction of *A. hydrophila* #135 (0.5 NEFA-PLU/ml) was tested in egg yolk. The experimental set-up is shown in Table 6.

TABLE 6

| Nr | Reaction time Minutes | Egg yolk Gram | #135 conc. Units, PLU-NEFA |
|---|---|---|---|
| 1 | 30 | 1 | 0.000 |
| 2 | 30 | 2 | 0.100 |
| 3 | 60 | 2 | 0.100 |
| 4 | 150 | 2 | 0.100 |
| 5 | 240 | 2 | 0.100 |
| 6 | 1560 | 2 | 0.100 |
| 7 | 1560 | 1 | 0.000 |

The egg yolk was heated to 37° C. and the enzyme added. After reaction time 7 ml CHCl$_3$:Methanol 2:1 was added and mixed on a Whirley for 30 sec.

The sample was centrifuged 800×g for 10 minutes and the lower solvent phase isolated. 2 μl of this sample was applied onto a TLC Silica plate and eluted in elution solvent IV. The results from the TLC analysis is shown in FIGS. 50 and 51.

The methods and materials mentioned in this Example are those detailed in Examples above.

Samples from this experiment was also analysed by GLC as TMS derivatives. The results from the GLC analysis are shown in Table 7.

TABLE 7

GLC analysis of lipid from egg yolk

| No. | Reaction time min | Transferase #135 conc. Units/g egg yolk | Free fatty acid % | Cholesterol % | Cholesterol-ester % |
|---|---|---|---|---|---|
| 7 | control | 0 | 0.25 | 2.88 | 0.34 |
| 3 | 60 | 0.025 | 0.25 | 2.68 | 0.56 |
| 4 | 150 | 0.025 | 0.29 | 1.85 | 1.72 |
| 5 | 240 | 0.025 | 0.53 | 1.42 | 3.54 |
| 6 | 1560 | 0.025 | 0.95 | 0.3 | 4.43 |

From the GLC analysis of free fatty acid, cholesterol and cholesterol ester it is possible to calculate the molar concentration of each component and calculate % transferase activity as shown in Table 7.

Calculation of % Transferase Activity

From the results the increase in free fatty acid, sterol esters are calculated

Δ % fatty acid=% Fatty acid(enzyme)−% fatty acid (control)

Δ % sterol ester=% sterol/stanol ester(enzyme)−% sterol/stanol ester(control)

The transferase activity is calculated as % of the total enzymatic activity:

$$\% \text{ transferase activity} = \frac{(\Delta \% \text{ sterol ester}/(Mv \text{ sterol ester}) \times 100}{\Delta \% \text{ sterol ester}/(Mv \text{ sterol ester}) + \Delta \% \text{ fatty acid}/(Mv \text{ fatty acid})}.$$

where:
Mv sterol ester=average molecular weight of the sterol esters
Mv fatty acid=average molecular weight of the fatty acids

TABLE 8

Transferase activity in egg yolk of *A. hydrophila* #135

| No. | Reaction Time min | Transferase #135 conc. Units/g egg yolk | Free fatty acid mM | Cholesterol mM | Cholesterol-ester mM | Transferase activity % |
|---|---|---|---|---|---|---|
| 7 | Control | 0 | 8.9 | 74.5 | 5.3 | — |
| 3 | 60 | 0.05 | 8.9 | 69.3 | 8.7 | 100 |
| 4 | 150 | 0.05 | 10.4 | 47.8 | 26.5 | 93 |
| 5 | 240 | 0.05 | 18.9 | 36.7 | 54.6 | 77 |
| 6 | 1560 | 0.05 | 33.9 | 7.8 | 68.4 | 48 |

Both TLC and GLC analysis confirm that initially the transferase reaction of *A. hydrophila* #135 is the dominating reaction. After 150 minutes reaction time some hydrolytic activity occurs. After 1560 minutes the transferase reaction and the hydrolytic reaction has almost reached the same level. The results also indicate that as long as the acceptor molecule cholesterol is available the transferase reaction is the dominating reaction. When the concentration of cholesterol decreases the hydrolytic activity becomes more dominant.

Example 10

Assay for Measurement of Transferase Activity Using Egg Yolk as Substrate—Hereinafter Referred to as the "Egg Yolk Assay"

A lipid acyltransferase was isolated from *Aeromonas salmonicida* and expressed in *Bacillus subtilis*. The purpose of this work is to develop an analytical method, which is able to measure both transferase and hydrolytic activity of enzymes and from these analyses it is possible to define both transferase and hydrolytic activity of enzymes using a substrate which contain lecithin and cholesterol.

In this work egg yolk was used as substrate for the enzyme assay because egg yolk contain both lecithin and cholesterol and it is known that transferases and phospholipases works very well in this substrate.

The drawback by using egg yolk is that this substrate is a complex mixture of water, lipids, and proteins. Lipid components include glycerides, 66.2%; phospholipids, 29.6%; and cholesterol, 4.2%. The phospholipids consist of 73% lecithin, 15% cephalin, and 12% other phospholipids. Of the fatty acids, 33% are saturated and 67% unsaturated, including 42% oleic acid and 7% linoleic acid (ref. Kirk-Othmer Encyclopedia of Chemical Technology, John Wiley & Sons, Inc.)

Some variations in the egg yolk composition might be expected. In the literature (Biochimica et Biophysica Acta, 1124 (1992) 205-222) it is however mentioned that "The mature egg yolk of the domestic hen possesses remarkably constant lipid and lipoprotein composition despite much variation in dietary and environmental conditions", and further it is quoted "As a result the egg yolk continues to provide a food product of nearly constant composition, which serves to maintain its chemical and physical-chemical properties for reliable utilization in the baking, cosmetic and pharmaceutical industries"

This reference indicates that egg yolk composition is very constant and it was therefore decided to use hens egg yolk as substrate for the Egg Yolk Assay.

Quantification of lipid reaction products from enzymatic treatment of egg yolk was made by extraction of lipids from the substrate followed by GLC analysis of the lipid components.

Procedure
Materials.
Egg yolk: Pasteurized liquid egg yolk from Danzg Products A/S, DK-4000 Roskilde.
HEPES buffer Sigma cat. no. H 3375
Chloroform, Analytical grade
Enzymes.
Purified lipid acyltransferase from *A. salmonicida* #178-9
*Thermomyces lanuginosus* lipase. GRINDAMYL EXEL 16, item nr. 147060 (Control)

Enzyme Assay with Egg Yolk Substrate.

5 gram liquid egg yolk was scaled in a 20 ml Wheaton glass and heated to 35° C.

0.25 ml enzyme solution was added and a stopwatch is started.

At regular intervals 0.5 g samples were transferred to a 10 ml Dram glass.

20 µl 4M HCl was added in order to stop the enzyme reaction and acidify the fatty acid soap.

3 ml Chloroform was added. And the sample was mixed on a Whirley mixer for 30 sec.

The sample was centrifuged at 3000 g for 10 min and 0.8 ml of the chloroform phase was transferred to a tarred Dram glass. Chloroform was evaporated at 60° C. under a steam of nitrogen. The dram glass was scaled again.

The isolated lipids were analysed by GLC and TLC.
TLC analysis—as described herein.
GLC analysis—as described herein.
Results For the Egg Yolk Assay using egg yolk as substrate the experiment shown in Table 9 was conducted.

TABLE 9

|  |  | 1 | 2 | 3 |
|---|---|---|---|---|
| Egg yolk, liquid. | gram | 5 | 5 | 5 |
| Transferase# 178-9, 32 PLU-7/ml* | ml |  |  | 0.25 |
| *T. lanuginosus* lipase, 200 LIPU/ml | ml |  | 0.25 |  |
| Water | ml | 0.25 |  |  |

0.5 g samples were taken out after 15, 30, 60 120 and 1080 minutes, and the lipid isolated by solvent extraction. The lipids were analysed by TLC using solvent I and IV respectively. Picture of the TLC plate is shown in FIG. 52.

The TLC analysis clearly indicates the activity of transferase #178-9 from *A. salmonicida* (sample 3). This can be seen from the decrease in the phospholipids PC and PE. The results also indicate that the amount of lysolecithin LPC is not as high as expected. This might indicate hydrolytic activity on lysolecithin or it might also be caused by insufficient extraction because lysolecithin is very polar and therefore could be partly distributed in the water phase.

The lipids isolated by solvent extraction was also analysed by GLC in order to quantify the amount of free fatty acid, cholesterol and cholesterol ester. The GLC results are shown in Table 10.

TABLE 10

| GLC analysis of lipid from enzyme treated egg yolk. Results are in % based on lipid content. | | | | | | | |
|---|---|---|---|---|---|---|---|
| | | | 15 Minutes | 30 Minutes | 60 Minutes | 120 Minutes | 1080 Minutes |
| Free fatty acids | Control | 1 | 0.328 | 0.304 | 0.332 | 0.333 | 0.369 |
|  | *T. lanuginosus* | 2 | 0.391 | 0.376 | 0.459 | 0.627 | 22.909 |
|  | *A. salmonicida* #178-9 | 3 | 1.007 | 1.668 | 4.013 | 6.761 | 15.098 |
| Cholesterol | Control | 1 | 3.075 | 2.968 | 3.103 | 3.056 | 3.099 |
|  | *T. lanuginosus* | 2 | 3.130 | 3.032 | 3.045 | 3.026 | 3.225 |
|  | *A. salmonicida* #178-9 | 3 | 2.835 | 1.912 | 0.356 | 0.220 | 0.206 |
| Cholesterol ester | Control | 1 | 0.416 | 0.397 | 0.422 | 0.408 | 0.437 |
|  | *T. lanuginosus* | 2 | 0.436 | 0.400 | 0.425 | 0.419 | 0.416 |
|  | *A. salmonicida* #178-9 | 3 | 1.414 | 2.988 | 6.107 | 6.694 | 5.760 |
| Triglyceride | Control | 1 | 76.153 | 73.505 | 75.565 | 79.344 | 77.382 |
|  | *T. lanuginosus* | 2 | 74.099 | 74.413 | 77.079 | 74.284 | 21.781 |
|  | *A. salmonicida* #178-9 | 3 | 73.781 | 73.342 | 77.857 | 82.040 | 72.117 |

From the results it was observed that almost all the cholesterol was esterified after 60 minutes in sample 3. It was concluded that for the first 30 minutes there was surplus substrate for the reaction. The results form samples taken out after 15 and 30 minutes were therefore used to calculate the activities of the enzymes.

Based on the information in table 10 and the fact that egg yolk contain 27% lipid the amount of micromole fatty acid and cholesterol ester produced per ml enzyme was calculated with results shown in Table 11 The results in Table 11 were obtained be the following calculations of the results from fatty acids in sample no. 3 (*A. salmonicida*, 15 min.)

Lipid in 5 g egg yolk=5*0.27=1.35 gram
1.35 gram lipid contain 1.007% fatty acids=1.35*1.007/100=0.01359 gram
Average molecular weight of fatty acids is 272
0.01359 gram=0.01359*1000000/272 μmol=49.9798 μmol
0.25 ml enzyme is added
μmol Fatty acid/ml enzyme=49.9798/0.25=199.9

TABLE 11

| Micromole/ml enzyme | | 0 min | 15 min | 30 min |
|---|---|---|---|---|
| Free fatty acid | Control | | 65.01 | 60.37 |
| | T. lanuginosa | | 77.61 | 74.71 |
| | Transferase #178-9 | | 199.86 | 331.06 |
| Cholesterol ester | Control | | 35.09 | 33.50 |
| | T. lanuginosa | | 36.77 | 33.73 |
| | Transf. #178-9 | | 119.29 | 252.15 |

From the results in Table 11 it is possible to calculate the change in amount of fatty acid and cholesterol ester caused by the enzyme relative to control as shown in Table 12.

TABLE 12

| Δ Micromole/ml enzyme | | 0 min | 15 min | 30 min |
|---|---|---|---|---|
| Free fatty acid | T. lanuginosus | 0 | 12.593 | 14.340 |
| | Transf. #178-9 | 0 | 134.843 | 270.691 |
| Cholesterol ester | T. lanuginosus | 0 | 1.677 | 0.235 |
| | Transf. #178-9 | 0 | 84.196 | 218.652 |

The amount of fatty acid or cholesterol ester produced as a function of time is shown in FIG. 53.

From the slope of the curve the hydrolytic activity (FFA formation) and the lipid acyltransferase activity (cholesterol ester formation) as a function of time was calculated. The relative transferase activity (% acyltransferase activity) and the relative hydrolytic activity were then calculated as shown in Table 13. The relative transferase activity was determined using the protocol for the determination of % acyltransferase activity as described hereinbefore. For example, calculation of relative activity for #178-9:Total activity is FFA activity+transferase activity=9,023+7,2884=16,311 μmol/min/ml, Relative transferase activity=7,2884*100/16,311=44.7, Relative hydrolytic activity=9,023*100/16,311=55.3

TABLE 13

| T. lanuginosus | FFA activity | 0.4780 | μmol/min/ml |
|---|---|---|---|
| A. salmonicida #178-9 | FFA activity | 9.0230 | μmol/min/ml |
| T. lanuginosus | Cholesterol ester. Activity | 0.0078 | μmol/min/ml |
| A. salmonicida #178-9 | Cholesterol ester. Activity | 7.2884 | μmol/min/ml |
| T. lanuginosus | Relative transferase activity | 1.6 | |
| A. salmonicida #178-9 | | 44.7 | |
| T. lanuginosus | Relative hydrolytic activity | 98.4 | |
| A. salmonicida #178-9 | | 55.3 | |

The results in Table 13 confirmed that the transferase enzyme from A. salmonicida has a significant transferase activity, but the results also confirmed that this enzyme has a significant hydrolytic activity.

The lipase from T. lanuginosus mainly has hydrolytic activity, and the relative transferase activity 1.6 was not a proof of any transferase activity but was explained by the uncertainty of the analysis.

Conclusion.

Egg yolk was used as substrate for the measurement of transferase and hydrolase activity of lipid acyltransferase from Aeromonas salmonicida and a lipase from Thermomyces lanuginosus. Under assay conditions there was initially a linear relation between cholestererol ester and free fatty acid formation and time for the lipid acyltransferase enzyme. Based on this linear relationship it was possible to calculate the hydrolytic activity (FFA formation) and the transferase activity (cholesterol ester formation). The relative hydrolytic and transferase activity was also calculated. The lipid acyltransferase (in this case a GCAT) from Aeromonas salmonicida showed almost equal hydrolytic and transferase activity under these assay conditions.

Lipase from Thermomyces lanuginosus showed very low hydrolytic activity and the transferase activity was not significant.

Example 11

Transferase Assay in High Water Egg Yolk

Introduction

A lipid acyltransferase in accordance with the present invention was isolated from Aeromonas salmonicida and expressed in Bacillus subtilis. Initial experiments have shown that this enzyme is very efficient in transferring fatty acid from lecithin to cholesterol using egg yolk as a substrate.

In the following experiments the transferase reaction was studied in further detail using egg yolk as a substrate with special focus on the water concentration in the substrate.
Procedure
Materials.
Egg yolk: Pasteurized liquid egg yolk from Danzg Products A/S, DK-4000 Roskilde.
HEPES buffer Sigma cat. no. H 3375
Chloroform, Analytical grade
Squalane, analytical grade
Enzymes.
178-9 Lipid acyl transferase in accordance with present invention from A. salmonicida #2427 Phospholipase A1 from Fusarium oxysporum. LIPOPAN® F from Novozymes, DK (comparative lipolytic enzyme)
1991 Phospholipase A2 from Pancreas, LIPOMOD 22L from Biocatalysts, UK (comparative lipolytic enzyme)
Enzyme Assay with Egg Yolk Substrate.

5 gram liquid egg yolk substrate was scaled in a 20 ml Wheaton glass and heated to 35° C.

Water and enzyme solution was added and a stopwatch is started.

At regular intervals 0.5 g samples was transferred to a 10 ml Dram glass.

20 μl 4M HCl was added in order to stop the enzyme reaction and acidify the fatty acid soap.

3 ml Chloroform was added. And the sample was mixed on a Whirley mixer for 30 sec.

The sample was centrifuged at 3000 g for 10 min and 0.8 ml of the chloroform phase was transferred to a tarred Dram glass. Chloroform was evaporated at 60° C. under a steam of nitrogen. The dram glass is scaled again.

The isolated lipids are analysed by GLC

GLC Analysis

Perkin Elmer Autosystem 9000 Capillary Gas Chromatograph equipped with WCOT fused silica column 12.5 m×0.25 mm ID×0.1μ film thickness 5% phenyl-methyl-silicone (CP Sil 8 CB from Chrompack).

Carrier gas: Helium.

Injector. PSSI cold split injection (initial temp 50° C. heated to 385° C.), volume 1.0 μl Detector FID: 395° C.

| Oven program: | 1 | 2 | 3 |
|---|---|---|---|
| Oven temperature, ° C. | 90 | 280 | 350 |
| Isothermal, time, min. | 1 | 0 | 10 |
| Temperature rate, ° C./min. | 15 | 4 | |

Sample preparation: 30 mg of sample was dissolved in 9 ml Heptane:Pyridin, 2:1 containing internal standard heptadecane, 0.5 mg/ml. 300 μl sample solution was transferred to a crimp vial, 300 μl MSTFA (N-Methyl-N-trimethylsilyl-trifluoraceamid) was added and reacted for 20 minutes at 60° C.

Calculation: Response factors for mono-di-triglycerides and free fatty acid were determined from Standard 2 (mono-di-triglyceride), for Cholesterol, Cholesteryl palmitate and Cholesteryl stearate the response factors were determined from pure reference material (weighing for pure material 10 mg).

Results

Egg yolk containing 2% squalane was used as substrate for the reactions. Squalane was added as an internal standard for the GLC analysis, in order to quantify the lipid components in egg yolk.

The experiment was set up as shown in Table 14.

TABLE 14

| | | 1 | 2 | 3 | 4 | 5 | 6 | 7 | 8 |
|---|---|---|---|---|---|---|---|---|---|
| Substrate, egg yolk with 2% squalane | g | 5 | 5 | 5 | 5 | 5 | 5 | 2.5 | 2.5 |
| Transferase # 178-9, 14 PLU-7/ml | ml | | 0.25 | | | 0.25 | | 0.13 | |
| LIPOPAN ® Fsolution, 200 PLU-7/ml | ml | | | 0.25 | | | | | 0.13 |
| #1991 Phospholipase A2, 6300 PLU/ml | ml | | | | 0.25 | | 0.25 | | |
| Water | ml | 0.25 | | | | 3.8 | 3.8 | 8.75 | 8.75 |

Samples were taken out after 30, 60 and 120 minutes and analysed according the method described above (0.5 ml (exp 1-4) 0.86 ml (exp. 5-6) and 2.2 ml (exp. 7-8) samples were taken).

The results from the GLC analysis are shown in Table 15. The GLC results were expressed in percent of the substrate (egg yolk). The table also indicate the reaction time and the total amount of water in the reaction mixture.

TABLE 15

| Enzyme | Reaction time minutes | Water % in reaction | GLC % Fatty acid | GLC % cholesterol | GLC % cholesterol ester |
|---|---|---|---|---|---|
| Control | 120 | 54 | 0.247 | 0.863 | 0.083 |
| #178 | 30 | 54 | 0.422 | 0.669 | 0.445 |
| #178 | 60 | 54 | 0.515 | 0.549 | 0.672 |
| #178 | 120 | 54 | 0.711 | 0.364 | 1.029 |
| #2427 | 30 | 54 | 2.366 | 0.848 | 0.090 |
| #2427 | 60 | 54 | 3.175 | 0.837 | 0.088 |
| #2427 | 120 | 54 | 3.926 | 0.833 | 0.082 |
| #1991 | 30 | 54 | 1.606 | 0.911 | 0.083 |
| #1991 | 60 | 54 | 1.701 | 0.838 | 0.080 |
| #1991 | 120 | 54 | 1.781 | 0.763 | 0.053 |
| #178 | 30 | 73 | 0.377 | 0.764 | 0.495 |
| #178 | 60 | 73 | 0.488 | 0.665 | 0.719 |
| #178 | 120 | 73 | 0.626 | 0.426 | 0.931 |
| #2427 | 30 | 73 | 2.471 | 0.853 | 0.092 |
| #2427 | 60 | 73 | 3.284 | 0.858 | 0.087 |
| #2427 | 120 | 73 | 4.176 | 0.837 | 0.081 |
| #178 | 30 | 89 | 0.344 | 0.720 | 0.308 |
| #178 | 60 | 89 | 0.443 | 0.725 | 0.446 |
| #178 | 120 | 89 | 0.610 | 0.597 | 0.607 |
| #2427 | 30 | 89 | 0.510 | 0.167 | 0.010 |
| #2427 | 60 | 89 | 0.602 | 0.133 | 0.010 |
| #2427 | 120 | 89 | 0.867 | 0.147 | 0.009 |

Based on the analyses of fatty acid, cholesterol and cholesterol ester it was possible to calculate the amount of free fatty acid, and cholesterol ester produced as a function of reaction time and water content. Based on these results it was then possible to calculate the total enzymatic activity as the sum of the fatty acid formation and the cholesterol ester formation. The relative hydrolytic activity and the relative transferase activity (i.e. % acyltransferase activity) were then calculated with the results shown in Table 16.

The results in Table 16. were also analysed statistically using a Statgraphic Multifactor ANOVA. The statistical results in FIG. 54 confirm that Phospholipase A1, #2427 and phospholipase A2, #1991 have no transferase activity whereas the transferase #178-9 showed almost 50% transferase activity under these assay conditions.

The effect of water content in the assay on the transferase activity of the transferase #178 was also analysed statistically as shown in FIG. 55. These results indicate that in the range from 54 to 89% water in the assay there was no strong effect of the water content on the relative transferase activity.

The impact of reaction time on transferase activity for transferase #178 was evaluated with results shown in Table 16 and FIG. 56. The results in FIG. 56 indicate that the relative transferase activity decreases as a function of reaction time. This might be explained by the fact that most of the acceptor molecule cholesterol is consumed and therefore the relative hydrolytic activity increases. The negative values for transferase reaction for #2427 only indicate no transferase activity within the variation for the analytical method.

TABLE 16

| Enzyme | Reaction time minutes | Water % in reaction mixture | Fatty acid Produced | Cholesterol Consumed | Cholesterol ester produced | Hydrolytic activity % | Transferase activity % |
|---|---|---|---|---|---|---|---|
| #178 | 30 | 54 | 0.175 | 0.194 | 0.362 | 53 | 47 |
| #178 | 60 | 54 | 0.268 | 0.314 | 0.589 | 52 | 48 |
| #178 | 120 | 54 | 0.464 | 0.499 | 0.946 | 53 | 47 |
| #2427 | 30 | 54 | 2.119 | 0.015 | 0.007 | 100 | 0 |
| #2427 | 120 | 54 | 2.928 | 0.026 | 0.005 | 100 | 0 |
| #2427 | 60 | 54 | 3.679 | 0.030 | −0.001 | 100 | 0 |
| #1991 | 30 | 54 | 1.359 | −0.048 | 0.000 | 100 | 0 |
| #1991 | 60 | 54 | 1.454 | 0.025 | −0.003 | 100 | 0 |
| #1991 | 120 | 54 | 1.534 | 0.100 | −0.030 | 101 | −1 |
| #178 | 30 | 73 | 0.130 | 0.099 | 0.412 | 42 | 58 |
| #178 | 60 | 73 | 0.241 | 0.198 | 0.636 | 47 | 53 |
| #178 | 120 | 73 | 0.379 | 0.437 | 0.848 | 51 | 49 |
| #2427 | 30 | 73 | 2.224 | 0.010 | 0.009 | 100 | 0 |
| #2427 | 60 | 73 | 3.037 | 0.005 | 0.004 | 100 | 0 |
| #2427 | 120 | 73 | 3.929 | 0.026 | −0.002 | 100 | 0 |
| #178 | 30 | 89 | 0.097 | 0.143 | 0.225 | 50 | 50 |
| #178 | 60 | 89 | 0.196 | 0.138 | 0.363 | 56 | 44 |
| #178 | 120 | 89 | 0.363 | 0.266 | 0.524 | 62 | 38 |
| #2427 | 30 | 89 | 0.263 | 0.696 | −0.073 | 113 | −13 |
| #2427 | 60 | 89 | 0.355 | 0.730 | −0.073 | 110 | −10 |
| #2427 | 120 | 89 | 0.620 | 0.716 | −0.074 | 105 | −5 |

Conclusion.

The lipid acyltransferase from *Aeromonas salmonicida* was tested in egg yolk as substrate and with different levels of water content. This enzyme was compared with control lipolytic enzymes, namely Phospholipase A1 from *Fusarium oxysporum* and a Phospholipase A2 from pancreas.

The results have proved that only the transferase catalysed the transferase reaction between lecithin and cholesterol during formation of cholesterol ester. The results showed that in the range from 54% to 89% water in the substrate the relative transferase activity was almost the same for transferase from *Aeromonas salmonicida*.

Example 12

The "Transferase Assay in Buffered Substrate" for Measurement of Acyltransferase Activity (e.g. for Use in a Foodstuff Using Lecithin and Cholesterol)

The lipid acyltransferase was isolated from *Aeromonas salmonicida* and expressed in *Bacillus subtilis*. This enzyme is very efficient in transferring fatty acid from lecithin to cholesterol during formation of cholesterol esters. It has also been shown that the enzyme has some hydrolytic activity, which is observed by the formation of free fatty acid. Traditional phospholipases (EC3.1.1.4 and EC3.1.1.32) have the ability to hydrolyse lecithin during formation of free fatty acids and lysolecithin, and no transferase reactions has been reported for these enzymes.

We detail herein an assay that is able to measure both transferase and hydrolytic activity of enzymes and thus to identify lipid acyltransferases in accordance with the present invention, the assay uses a substrate which contains lecithin and cholesterol. In this work a substrate based on phosphatidylcholine and cholesterol dispersed in a buffer was used. Quantification of reaction products was made by extraction of lipids from the substrate followed by GLC analysis of the lipid components.

Procedure
Materials
L-alpha-Phosphatidylcholine 95% (Plant) Avanti no. 441601
Cholesterol: Sigma cat. C 8503
Cholesteryl Palmitate, Sigma C 6072
Cholesteryl Stearate, Sigma C 3549
HEPES buffer Sigma cat. No. H 3375
Chloroform, Analytical grade.
Enzymes
Purified GCAT from *A. salmonicida* #178-9

TLC analysis was carried out as described in Example 6.
GLC analysis was carried out as described in Example 11.
Results: Transferase assay based on phosphatidylcholine and cholesterol as substrate.

In the following the transferase activity of the transferase was tested in a substrate based on phosphatidylcholine and cholesterol according to the following procedure. 450 mg phosphatidylcholine (>95% PC Avanti item no. 441601) and 50 mg cholesterol was dissolved in chloroform and evaporated to dryness under vacuum. 300 mg cholesterol/phosphatidylcholine mixture was transferred to a Wheaton glass and 15 ml 50 mM HEPES buffer pH 7 was added. The lipid was dispersed in the buffer during agitation.

The substrate was heated to 35° C. during mixing with a magnetic stirrer and 0.25 ml enzyme solution was added. This is a very high water environment of approximately 95% water.

Samples of 2 ml were taken out after 0, 5, 10, 15, 25, 40 and 60 minutes reaction time. Immediately 25 µl 4M HCl was added to acidify the free fatty acid and stop the enzyme reaction. 3.00 ml chloroform was added, and the sample was shaken vigorously on a Whirley for 30 seconds. The sample was centrifuged and 2 ml of the chloroform phase was isolated and filtered through 0.45-µm filters into a 10 ml tared Dram glass. The chloroform was evaporated under a stream of nitrogen at 60° C., and the samples were scaled again. The extracted lipid was analysed by GLC.

The results from the GLC analysis are shown in Table 17. The results are expressed in % calculated on extracted lipid. The amount of fatty acid and cholesterol ester formed as a function of time is illustrated in. FIG. 57 It can be concluded from FIG. 57 that the enzyme reaction is not linear as a function of time, because an initially strong both hydrolytic and transferase activity is observed. After approximately 10 minutes and until approximately 60 minutes the reaction shows an almost linear response of fatty acid and cholesterol ester formation as a function of time. It was therefore decided to look at the enzymatic reaction in this time interval.

TABLE 17

| | Minutes | | | | | | |
|---|---|---|---|---|---|---|---|
| | 0 | 5 | 10 | 15 | 25 | 40 | 60 |
| Cholesterol, % | 10.064 | 8.943 | 8.577 | 8.656 | 8.102 | 7.856 | 7.809 |
| Cholesterol ester, % | 0.000 | 1.571 | 2.030 | 2.058 | 2.282 | 2.659 | 3.081 |
| FFA total, % | 0.260 | 1.197 | 1.239 | 1.466 | 2.445 | 2.943 | 3.940 |

From the knowledge about the amount of lipid in the reaction mixture and the amount of enzyme added it was possible to calculate the formation of fatty acid and cholesterol ester expressed in μmol/ml enzyme (Table 18 and FIG. 58)

TABLE 18

| | Minutes | | | | |
|---|---|---|---|---|---|
| | 10 μmol/ml | 15 μmol/ml | 25 μmol/ml | 40 μmol/ml | 60 μmol/ml |
| FFA total | 58.1 | 68.7 | 114.6 | 138.0 | 184.7 |
| Cholesterol ester | 88.8 | 90.0 | 99.3 | 115.6 | 133.8 |

From the results in Table 18 and the slope of the curves in FIG. 58 it was possible to calculate the amount of fatty acid and cholesterol ester as a function of time expressed in gmol/min per ml enzyme.

The calculation of the hydrolytic activity and the transferase activity is shown in Table 19. The relative transferase activity was determined using the protocol for the determination of % acyltransferase activity as described hereinbefore.

TABLE 19

| Hydrolytic activity (fatty acid) | 2.52 | μmol/min per ml enzyme |
|---|---|---|
| Transferase activity (cholesterol ester) | 0.94 | μmol/min per ml enzyme |
| Total activity | 3.45 | μmol/min per ml enzyme |
| Relative Transferase activity | 27.1 | % |
| Relative hydrolytic activity | 72.9 | % |

Screening of Other Enzymes for Transferase Activity.

The method mentioned above was used to screen different lipolytic enzymes for transferase and hydrolytic activity. The enzymes were tested as shown in Table 20

TABLE 20

| | | 1 | 2 | 3 | 4 | 5 |
|---|---|---|---|---|---|---|
| Substrate | ml | 15 | 15 | 15 | 15 | 15 |
| #178-9Transferase *A. salmonicida* 32 PLU-7/ml | ml | 0.25 | | | | |
| 5% #3016, LIPOPAN ® F (*F. oxysporum*) | ml | | 0.25 | | | |
| 5%, *Thermomyces lanuginosus* | ml | | | 0.25 | | |
| 5% *Candida rugosa* #2983 | ml | | | | 0.25 | |
| 5% *Candida cylindracea* #3076 | ml | | | | | 0.25 |

The substrate containing 300 mg phosphatidylcholine/cholesterol dispersed in 50 mM HEPES buffer pH 7.0 was heated to 35° C. with agitation. Enzyme solution was added and the sample was kept at 35° C. with agitation. Samples were taken out with regular interval and extracted with Chloroform. The isolated lipids were analysed by GLC with results shown in Table 21.

TABLE 21

| Sample | | | | | | | | |
|---|---|---|---|---|---|---|---|---|
| 1 | Transferase 178-9 | | | | | | | |
| | Minutes | 0 | 5 | 10 | 15 | 25 | 40 | 60 |
| | FFA | 1.216 | 2.516 | 2.983 | 2.62 | 2.894 | 3.448 | 3.911 |
| | Cholesterol | 7.547 | 6.438 | 6.365 | 6.15 | 6.136 | 5.936 | 5.662 |
| | Chl. Ester | 0 | 1.835 | 2.177 | 2.44 | 2.58 | 2.851 | 3.331 |
| 2 | *Fusarium oxysporum* (LIPOPAN ® F) | 0 | 5 | 10 | 15 | 25 | 40 | 60 |
| | FFA | 1.216 | 1.345 | 1.796 | 1.95 | 2.487 | 2.424 | 2.977 |
| | Cholesterol | 7.547 | 7.309 | 7.366 | 7.33 | 7.429 | 7.341 | 7.326 |
| | Chl. Ester | 0 | 0.26 | 0.386 | 0.35 | 0.267 | 0.36 | 0.394 |
| 3 | *Thermomyces lanuginosus* | 0 | 5 | 10 | 15 | 25 | 40 | 60 |
| | FFA | 1.216 | 0.853 | 0.875 | 1 | 0.896 | 1.105 | 1.009 |
| | Cholesterol | 7.547 | 7.384 | 7.639 | 7.63 | 7.675 | 7.603 | 7.529 |
| | Chl. Ester | 0 | 0 | 0 | 0 | 0 | 0 | 0 |
| 4 | *Candida rugosa* (#2938) | 0 | 5 | 10 | 15 | 25 | 40 | 60 |
| | FFA | 1.216 | 0.982 | 0.987 | 1.02 | 1.135 | 1.131 | 1.15 |
| | Cholesterol | 7.547 | 7.438 | 7.656 | 7.66 | 7.638 | 7.575 | 7.585 |
| | Chl. Ester | 0 | 0 | 0 | 0 | 0 | 0 | 0 |
| 5 | *Candida cylandracea* (#3076) | 0 | 5 | 10 | 15 | 25 | 40 | 60 |
| | FFA | 1.216 | 1.032 | 1.097 | 1.07 | 1.203 | 1.131 | 1.43 |
| | Cholesterol | 7.547 | 7.502 | 7.425 | 7.65 | 7.619 | 7.502 | 7.411 |
| | Chl. Ester | 0 | 0 | 0 | 0 | 0 | 0 | 0 |

From the GLC analysis it was observed that only the lipid acyltransferase (178-9) produced significant amount of cholesterol ester and fatty acids. Phospholipase from *Fusarium oxysporum* also gave a steady increase in free fatty acid but only an initial small amount formation of cholesterol ester was formed but no increase in cholesterol ester as a function of time was observed.

Based on the knowledge about the amount of lipid substrate and the GLC analyses it was possible to calculate the relative transferase activity and the relative hydrolytic activity based on the results from 10 to 60 minutes reaction time.

The results from Transferase 178-9 and *Fusarium oxysporum* lipase are shown in Table 21. The other enzymes tested showed no activity.

TABLE 21

|  | Transferase 178-9 | Fusarium oxysporum |
|---|---|---|
| Hydrolytic activity, micromole/min per ml enzyme | 1.03 | 0.96 |
| Transferase activity, micromole/min per ml enzyme | 0.40 | 0.01 |
| Total activity, micromole/min per ml enzyme | 1.43 | 0.98 |
| Relative hydrolytic activity | 71.8 | 98.7 |
| Relative transferase activity | 28.2 | 1.3 |

The result shown in Table 21 confirm a significant transferase activity from the lipid acyltransferase (sample 178-9). It is also observed that the relative transferase activity is in good agreement with the experiment mentioned in Table 19

A very low transferase activity form *Fusarium oxysporum* phospholipase is however observed. This transferase level is so low that it falls within the uncertainty of the analysis. As expected *Fusarium oxysporum* phospholipase has a significant hydrolytic activity.

Conclusion.

Instead of egg yolk (shown in Example 11) an artificial substrate based on purified phosphatidylcholine and cholesterol was used as a substrate to measure the activity of transferase from *Aeromonas salmonicida*. Between 10 minutes and 60 minutes reaction time the assay gave an almost linear formation of free fatty acids and cholesterol ester as a function of time. Based on the activity between 10 and 60 minutes reaction time the hydrolytic activity and the transferase activity was calculated.

The concentration of substrates in this assay was relatively lower than in egg yolk, and the amount of water in the assay was relatively higher.

Based on the results from the assay of the lipid acyltransferase (in this instance a GCAT) from *Aeromonas salmonicida* in a artificial substrate of phosphatidylcholine/cholesterol in buffer it is concluded that this enzyme has very good transferase activity also in a system with a very high water content.

Both assays based on egg yolk (see Example 11) and phosphatidylcholine/cholesterol in buffer (Example 12), can be used to measure the transferase and hydrolytic activity of enzymes. The egg yolk is preferred from the point of view that the hydrolytic and the transferase activity is linear as a function of time, but the phosphatidylcholine/cholesterol in buffer is only linear within a certain time limit.

Example 13

Food Emulsions

The effect of enzyme modified liquid egg yolk was tested in a standard Food emulsion recipe with 60% oil.

Standard methods and materials are as per those detailed in the Examples above.

The egg yolk was treated with a lipid acyl transferase from *Aeromonas salmonicida* (#138) or phospholipase, namely a commercially available enzyme LipopanF® (Novozymes A/S, Denmark) (#2938) as shown in Table 22.

TABLE 22

Enzyme treatment of egg yolk.

|  |  | 1 | 2 | 3 | 4 |
|---|---|---|---|---|---|
| Egg Yolk, Sanofo product no 1123P2 | Gram | 10 | 10 | 10 | 10 |
| #138, 10 PLU/ml | Ml | 1 | 1 |  |  |
| #2938, 200 PLU/ml | Ml |  |  | 1 |  |
| Water | Ml |  |  |  | 1 |
| Reaction time | Minutes | 210 | 360 | 210 | 210 |

TLC analysis of the egg yolk lipids from enzyme treated egg yolk (Table 9) is shown in FIGS. 59 and 60.

In this experiment the dosage of #2938 was increased by a factor of 10 and this gave a very clear activity on egg yolk. The amount of free fatty acid increased significantly and lecithin (PC) was hydrolysed to lysolecithin (LPC). The transferase #138 gave a clear transferase reaction because free cholesterol was converted to cholesterol ester and part of the lecithin was converted to lysolecithin.

Another interesting aspect of the enzyme modification was the consistency of the product. The sample treated with Phospholipase #2938 became very solid, whereas the samples treated with the lipid acyltransferase #138 kept the same liquid consistency as the control sample (see FIG. 61).

These modified egg yolks were tested in a Food Emulsion recipe shown in Table 23.

TABLE 23

Mayonnaise with enzyme modified egg yolk.

|  | 0 % | 1a % | 2a % | 3a % | 4a % |
|---|---|---|---|---|---|
| Rapsolie | 60 | 60 | 60 | 60 | 60 |
| Egg yolk, Sanofo product no. 1123P2 | 2.8 |  |  |  |  |
| Enz. Modified egg yolk no. 1 |  | 2.8 |  |  |  |
| Enz. Modified egg yolk no. 2 |  |  | 2.8 |  |  |
| Enz. Modified egg yolk no. 3 |  |  |  | 2.8 |  |
| Control (untreated) egg yolk no. 4 |  |  |  |  | 2.8 |
| Water | 39 | 36.2 | 36.2 | 36.2 | 36.2 |
| Vinegar, 10% acetic acid | 1 | 1 | 1 | 1 | 1 |

Modified egg yolks 1 and 2 were treated with the lipid acyl transferase; and modified egg yolk 3 was treated with the commercially available phospholipase.

The food emulsion was produced as an oil in water emulsion according to the following procedure: Egg yolk and water was scaled in a beaker. The oil was scaled separately. A Turrax mixer (20000 rpm) was immersed in the water phase. Oil was pumped to the water phase at a constant speed over 2 minutes. The mixing continued for further 1 minute. The vinegar was then added and mixed for 5 seconds.

The stability of the emulsion was tested in a heating cabinet at 100° C. After 2 hours at 100° C. the emulsion was evaluated (see FIG. 62).

The emulsion stability of untreated egg yolk was quite good in this experiment. Treatment of egg yolk with the lipid acyltransferase #138 however improved the stability because the amount of water separation was reduced. Egg yolk treated with phospholipase #2938 gave a very unstable emulsion with almost complete separation of the oil- and the water phase at 100° C.

It is considered that in some applications the use of the compositions and methods of the invention can provide enhanced thermal stability of emulsions, such as oil in water salad dressings and the like. This is particularly important in food emulsions which are pasturised to ensure long shelf life and/or are heated prior to serving, e.g. in pre-prepared meals for re-heating prior to serving (e.g. microwave meals). Although not wishing to be bound by any particular theory, it is considered that in some applications the accumulation of free fatty acid may be detrimental to the thermal stability of such emulsions. It should be recognised that the enhanced thermal stability of the food emulsions produced using the methods of the invention, may not be found, or even desirable, in all food applications. It will be apparent to the person skilled in the art in which applications such characteristics are desirable, and the stability of the emulsions can be easily determined using a simple heat tests, equivalent to, for example pasteurization and or microwave reheating. The inventors have discovered that in a preferable embodiment the food emulsions obtained using the enzymes of the invention have enhanced thermal stability.

Example 14

Transferase Reaction in Plant Sterol Enriched Egg Yolk

Transferase form *Aeromonas salmonicida* was able to catalyse to formation of lysolecithin, monoglyceride and plant sterol esters in egg yolk enriched with plant sterol and glycerol. The same enzyme was also tested in a low water system containing palm oil, lecithin, plant sterol and glycerol By TLC and GLC analyses it was shown that monoglyceride, and plant sterol esters were produced under these reaction conditions.
Introduction:
The transferase from *Aeromonas salmonicida* was tested for transferase activity in almost water free system of lecithin, fat, plant sterol and glycerol.
Materials:
Egg yolk: Pasteurized liquid egg yolk from Danæg Products A/S, DK-4000 Roskilde
GCAT transferase purification 178-9, 32 PLU-7/ml (Journal 2254-100)
Soya lecithin. Yolkin from Aarhus United, Denmark.
Palm oil 43, from Aarhus United, Denmark.
L-α Phosphatidylcholine 95% Plant (Avanti #441601)
Sitosterol, Sigma no S5753
Plant Sterol Generol N122 from Cognis, Germany
Glycerol Item no. 085915
Results
Initial screening of transferase activity on plant sterol and glycerol was conducted in egg yolk as shown in Table 24.

TABLE 24

|  |  | 1 | 2 | 3 | 4 |
|---|---|---|---|---|---|
| Egg yolk | Gram | 1 | 1 | 1 | 1 |
| Glycerol | Gram | 0.1 | 0.1 |  |  |
| Sitosterol:olie 3:7 | Gram |  |  | 0.13 | 0.13 |
| Transferase #178-9 | Units | 1 |  | 1 |  |
| Water |  |  | * |  | * |

* Water corresponding to the amount of water in the enzyme solution = 83 μl

The ingredients were mixed and heated to 37° C. and kept at this temperature during agitation with a magnetic stirrer.
0.1 gram samples were taken out after 3 and 23 hours and analysed by TLC.
The results from the TLC analysis is shown in FIG. 63.
The result in FIG. 63 indicated that both cholesterol and plant sterols were esterified by the transferase reaction, concomitant with the formation of lysolecithin (sample 3 and 4), because almost all free sterol and cholesterol was converted to the corresponding ester in sample 3.

The results also indicated that the sample with only glycerol and egg yolk produced monoglyceride. The amount of monoglyceride needs to be confirmed by GLC analysis. When sterol was added together with glycerol (sample 3) the amount of monoglyceride was very low and not detectable by TLC. This indicated that as long as there were surplus of sterol or cholesterol the transferase reaction using glycerol was modest.

In another experiment the transferase enzyme 178-9 was added to a mixture soybean lecithin, glycerol and plant sterol, in order to study the catalytic activity of the enzyme in this reaction mixture.

The composition of the reaction mixtures in these experiments are shown in Table 25

TABLE 25

|  |  | 1 | 2 | 3 | 4 | 5 | 6 |
|---|---|---|---|---|---|---|---|
| Soya lecithin | gram | 1.875 | 2.25 | 1.875 | 2.5 | 3.5 | 3.5 |
| Plantesterol; Generol N 122 | gram | 0.225 | 0.225 | 0 | 0 | 0.225 | 0.5 |
| Palm oil 43 | gram | 2.675 | 2.25 | 2.8 | 2.125 | 1.062 | 0.831 |
| Glycerol | gram | 0.225 | 0.275 | 0.325 | 0.375 | 0.248 | 0.238 |
| Transferase #178-9, 32 PLU/ml | ml | 0.2 | 0.2 | 0.2 | 0.2 | 0.2 | 0.2 |

The experiment was conducted by mixing the lipid components during agitation at 46° C. The enzyme was added and samples were taken out after 4 and 24 hours.
The samples were analysed by TLC as shown in FIG. 64.
Sample from experiment 2, 4 and 5 after 24 hours reaction time were also analysed by GLC with results shown in Table 26

TABLE 26

|  |  | 2 | 4 | 5 |
|---|---|---|---|---|
| Glycerol | % | 3.16 | 5.71 | 4.17 |
| Fatty acids | % | 4.23 | 5.36 | 6.67 |
| Mono | % | 2.24 | 3.87 | 3.92 |
| Sterol | % | 2.13 |  | 2.62 |
| Sterolester | % | 2.89 |  | 2.14 |

The results confirmed that transferase 178-9 was able to catalyse to formation plant sterol esters and monoglyceride from a reaction mixture containing soybean lecithin, glycerol and plant sterol. Such reaction mixture could be of interest for use in margarine production where monoglyceride is wanted for their emulsification properties and plant sterol esters for their cholesterol lowering effect.

Conclusion

CGAT transferase from *Aeromonas salmonicida* was able to catalyse the formation of plant sterol esters and monoglyceride in egg yolk where plant sterol and glycerol was added. The same enzyme also catalysed the formation of plant sterol esters and monoglyceride in a mixture of palm oil, lecithin, plant sterol and glycerol. This enzyme therefore is of interest for use in margarine and other oil containing food products where monoglyceride and lysolecithin are needed for improved emulsification and the plant sterol ester for their cholesterol lowering effects.

Example 15

Immobilisation of a Lipid Acyltransferase from *Aeromonas salmonicida* and the Use in the Synthesis of Sterol Esters A lipid acyltransferase (in this instance a GCAT) from *A. salmonicida* was immobilised on Celite by acetone precipitation. 10 ml enzyme solution in 20 mM TEA buffer pH 7 was agitated slowly with 0.1 gram Celite 535 535 (from Fluka) for 2 hours at room temperature.

50 ml cool acetone was added during continued agitation. The precipitate was isolated by centrifugation 5000 g for 1 minute.

The precipitate was washed 2 times with 20 ml cold acetone.

The Celite was tried at ambient temperature for about 1 hour

The immobilised transferase was tested in a oil mixture containing 13% Phosphatidylcholin and 7% plant sterol. (Table 27)

TABLE 27

|  | % |
|---|---|
| Avanti lecithin | 12.0 |
| Plant sterol, Generol 122N | 6.6 |
| Palm 43 | 71.4 |
| Glycerol | 5.0 |
| Immobilised Transferase #178, 45 U/g | 2.0 |
| Water | 3.0 |

Lecithin, plant sterol and soybean oil was heated to 46° C. and the plant sterol was dissolved. The immobilised transferase was added.

The transferase reaction continued at 46° C. during gentle agitation with a magnetic stirrer. Samples were taken out for analyses after ½, 1 3 6 and 24 hours and analysed by TLC.

The reaction was stopped after 24 hours reaction time and the immobilised enzyme was filtered off.

The samples were analysed by TLC as shown in FIG. 65.

The TLC analysis clearly shows the effect of immobilised transferase from *A. salmonicida* in the transformation of cholesterol into cholesterol ester. It is also observed that small amount of monoglyceride is formed. The enzyme has also been shown to have a high activity in environments with high water content (6-89%) water environments, the use of the transferase, and other transferases for use in the invention can therefore also be used in immobilised enzyme applications with a significant water content. This allows the replacement of the solvents used by the current immobilised lipases in the bioconvertion of lipids using transferases.

Example 16

The *Aeromonas hydrophila* Transferase can Transfer from a Phospholipid to a Sterol to Form a Sterol Ester, and/or a Sugar Molecule to Form a Sugar Ester A lipid acyltransferase from *Aeromonas hydrophila* expressed in *E. coli* (Hydro 0303 HVP), labelled #139 was purified on a Chelating Sepharose FF, HR 2.5/10 column and analysed for Phospholipase activity. The transferase activity was evaluated in egg yolk for enzyme activity and functionality in egg yolk. The enzyme was also tested in egg yolk containing glucose.

Phospholipase Activity.

Transferase #139 isolated from a Chelating Sepharose FF, HR 2.5/10 column was assayed by NEFA-PLU(pH7) The activity was 1.15 Units NEFA-PLU/ml.

Egg Yolk

In an initial application test transferase #139 was tested in egg yolk according to the following procedure.

1-gram fresh egg yolk was scaled in a 10 ml flask with screw lid. The enzyme preparation was added and mixed on a Vortex mixer. The sample was placed at 37° C. and agitated with a magnetic stirrer.

The reaction was stopped by adding 7.5 ml Chloroform: Methanol (2:1) and mixed on a Whirley mixer for 30 seconds. The chloroform phase was isolated by centrifugation and 2 µl of the chloroform phase was transferred to a pre-activated silica TLC plate and eluted with running buffer nr. I and another TLC-plate in running buffer IV, The experimental set up is shown in table 28.

TABLE 28

| Test no. | Reaction time min. | Egg yolk gram | Transferase #139 units |
|---|---|---|---|
| 1 | 10 | 1 |  |
| 2 | 10 | 1 | 0.75 NEFA-PLU |
| 3 | 60 | 1 | 0.75 NEFA-PLU |
| 4 | 300 | 1 | 0.75 NEFA-PLU |
| 5 | 1200 | 1 |  |
| 6 | 1200 | 1 | 0.75 NEFA-PLU |

TLC analysis are shown in FIG. 66 and FIG. 67. The TLC analysis clearly demonstrates the transferase reaction of transferase #139. The cholesterol is converted to cholesterol ester and the amount of lecithin is reduced. The results however also indicate that lysolecithin are only accumulated in very small amount because transferase #139 also is active on lysolecithin. This observation is supported by the formation of free fatty acids (FFA).

Egg Yolk and Glucose

It was earlier shown that a transferase from *Aeromonas salmonicida* (#138) was able to use glucose as acceptor molecule in a transferase reaction. It has also been tested if transferase #139 can use glucose as acceptor molecule. The experimental set up is seen in Table 29.

TABLE 29

| Test no. | Reaction time Minutes | Egg yolk gram | Glucose, 70% mg | Transferase #139 units |
|---|---|---|---|---|
| 1 | 10 | 1 | 500 |  |
| 2 | 10 | 1 | 500 | 1 NEFA-PLU |
| 3 | 60 | 1 | 500 | 1 NEFA-PLU |
| 4 | 180 | 1 | 500 | 1 NEFA-PLU |
| 5 | 300 | 1 | 500 | 1 NEFA-PLU |
| 6 | 1200 | 1 | 500 | 1 NEFA-PLU |
| 7 | 1200 | 1 | 500 |  |

The reaction products were analysed by TLC (FIG. 68 and FIG. 69).

The TLC analysis indicates formation of glucose ester after 220 min. reaction time (FIG. 69 lane 6) but after 1200 min reaction time no glucose ester is seen.

It must therefore be concluded that transferase #139 has both transferase and hydrolytic activity. This is also supported by the fact that the amount of free fatty acids steadily increases as a function of reaction time.

Resume:

Transferase from *Aeromonas hydrophila* was tested in egg yolk. The results confirm that this enzyme catalyses the formation of cholesterol ester concomitant with the formation of lysolecithin. After extended reaction time when most of the cholesterol is consumed free fatty acid are also formed. It can therefore be concluded that the enzyme has primary transferase activity but also hydrolytic activity was observed when only water was available as donor molecule.

In an experiment with egg yolk and glucose it has been observed that transferase from *Aeromonas hydrophila* is able to catalyse the formation of glucose ester in situ in a high water food environment (FIG. 70).

Example 17

Variants of a Lipid Acyltransferase from *Aeromonas hydrophila* (Ahyd2)

SEQ ID No. 36 (see FIG. 71)

Mutations were introduced using the QuikChange® Multi-Site Directed Mutagenesis kit from Stratagene, La Jolla, Calif. 92037, USA following the instructions provided by Stratagene.

Variants at Tyr256 showed an increased activity towards phospholipids.

Variants at Tyr256 and Tyr260 showed an increased activity towards galactolipids.

Variants at Tyr265 show an increased transferase activity with galactolipids as the acyl donor.

The numbers indicate positions on the following sequence: An enzyme from *Aeromonas hydrophila* the amino acid sequence of which is shown as SEQ ID No. 36 in FIG. 71 (the underlined amino acids show a xylanase signal peptide). The nucleotide sequence is as shown as SEQ ID No 54 in FIG. 72.

Example 18

Use of Acyl-Transferase Reaction for the Production of Plant Sterol Ester and Monoglyceride for Margarine Production An acyltransferase from *Aeromonas salmonicida* expressed in *Bacillus subtilis* was tested in a palm oil mixture containing plant lecithin, plant sterol and glycerol. The acyltransferase showed the ability to utilise both plant sterol and glycerol as acceptor molecules during production of plant sterol ester and monoglyceride. The reaction mixture was used to produce table margarine of good quality based on the monoglyceride in the reaction mixture and at the same time the margarine was enriched with plant sterol ester, which has been shown to have a cholesterol lowering effect.

The aim of this work was to study to possibility to produce monoglyceride and plant sterol ester by enzymatic reaction of lecithin, plant sterol and glycerol dissolved in vegetable fat.

Initial experiments has shown that it was possible to use acyl-transferase from *Aeromonas salmonicida* to produce monoglyceride and plant sterol ester from lecithin, glycerol and plant sterol.

In this experiment such reaction mixture was used to produce table margarine.

Materials:
Lipid acyltransferase from *Aeromonas salmonicida*, # 196 C101, 18.6 PLU/g (Journal 2254-104)
Palm Oil 43, from Aarhus United, DK
L-α Phosphatidylcholine 95% Plant (Avanti #441601)
Plant Sterol Generol N122 from Cognis, Germany
Glycerol Item no. 085915
Distilled Monoglyceride, Dimodan HP from Danisco.

Margarine Production.
1. Blend the water phase ingredients. (If required, pasteurize the water phase by heating to approx. 80° C.). Adjust pH 5.5.
2. Melt the fat phase, and temper to approx. 40-45° C.
3. Heat the emulsifier with some of the oil in a ratio of 1 part emulsifier to 5 parts oil to a temperature (75-80°), which is 5-10° C. higher than the melting point of the emulsifier. When this blend is fully melted and well stirred, add it to the remaining heated oil, stirring continuously.
4. Add the flavouring.
5. Add the water phase to the fat phase, stirring continuously.
6. Cool in a tube chiller (normal capacity, normal cooling) to an outlet temperature of 8-10° C.

Results

Acyltransferase from *A. salmonicida* was tested in an palm oil mixture as shown in Table 30. Lecithin, plant sterol, glycerol and palm oil was heated to 60° C. during agitation in order to solubilize plant sterol and lecithin.

TABLE 30

| Substrate: | % |
|---|---|
| Avanti lecithin | 12 |
| Plant sterol, Generol 122N | 6.6 |
| Palm oil, melting point 43 | 76.4 |
| Glycerol | 5 |

The substrate was cooled to 48° C. and acyl-transferase #196 was added in the amount shown in Table 31. The reaction mixture was kept at 48° C. for 24 hours during slow agitation.

TABLE 31

|  | gram |
|---|---|
| Substrate | 220 |
| Transferase # 196 C101, 18.6 PLU/g | 15 |

Samples from the reaction mixture were taken out after 1, 4 and 24 hours reaction time, and analysed by TLC in solvent I (FIG. 73). The TLC results clearly show the formation of plant sterol ester and monoglyceride. In FIG. 73, the first lane is after 1 hour reaction time, Lane 2 is 4 hours reaction time, Lane 3 is 24 hours reaction time and Lane 4 is a plant sterol.

The reaction was stopped after 24 hours reaction time and residues of undissolved plant sterol was removed, and the clear solution was used to produce margarine.

Margarine.

The reaction mixture containing monoglyceride and plant sterol ester was used to produce table margarine according to the recipe shown in Table 32.

TABLE 32

|  | Jour. No 3734 | |
|---|---|---|
|  | 1 | 2 |
| Water phase | | |
| Water phase | 16 | 16 |
| Salt | 0.5 | 0.5 |

TABLE 32-continued

| | Jour. No 3734 | |
|---|---|---|
| | 1 | 2 |
| Skim milk powder | 1 | 1 |
| Potassium sorbate | 0.1 | 0.1 |
| EDTA | 0.015 | 0.015 |
| PH | 5.5 | 5.5 |
| Water phase total | 16.6 | 16.6 |
| Fat phase | | |
| Palm 43 | 25 | 25 |
| Rapeseed Oil | 75 | 75 |
| Fat phase total | 83.2 | 78.4 |
| Dimodan HP | 0.2 | |
| Reaction mixture | | 5 |

The margarine produced from the reaction mixture was evaluated of good quality with good spreadability, and good mouth feel and without any off flavour. The margarine was compared to be on quality level with the reference margarine produced by using distilled monoglyceride Dimodan HP.

The only difference observed was that the margarine jour. 3734 no 2 with the reaction mixture was slightly more firm, which was explained by the fact that this recipe contained more Palm 43 than the reference margarine.

Example 19

Use of a Lipid Acyltransferase During Bread Production

One of the limitations of using lipases in bread making is that free fatty acid is formed during the lipase reaction. It is well known that formation of too much free fatty acid will have a negative impact on the baking performance of flour, because the gluten gets too stiff and a bucky (i.e. less elastic) dough is formed which can not expand during fermentation and baking.

Formation of free fatty acid should also be avoided from the point of oxidative stability, because free fatty acids are more prone to lipid oxidation than the corresponding triglyceride.

In the present invention the problems with free fatty acid formation when adding a lipolytic enzyme to a dough has been overcome by using a lipid acyltransferase which, instead of producing free fatty acids, transfers one or more fatty acids from the lipid acyl donor to a non water acceptor molecule present in the dough, such as a carbohydrate, a protein or peptide, or if used in bread with milk fat, a sterol, alternatively or in combination other acceptors listed above mat be added to a dough, for example phytosterols or phytostanols. Preferably, the acceptor molecule in a dough may be one or more of glucose, sucrose or maltose and/or other carbohydrates normally available in a dough.

In the following experiments acyl transferase is tested in mini scale baking experiments. The formation of reaction products, and the lipid components in fully proved dough is extracted by water saturated butanol and analysed by HPLC and GLC analysis.

Materials and Methods
Enzymes:
Acyl Transferase, 550 PLU-7/ml
Lipopan™ F BG, a commercial lipase from Novozymes. 12000 LIPU/g or Grindamyl Exel 16. 12000 LIPU/g
Lecithin powder, 95% phospholipid (available from Danisco A/S Denmark)
Digalactosyldiglyceride from whole wheat flour (from Sigma D4651)
Flour: Sølvmel nr. 2001084 (Danish wheat flour, obtained from Havnemollerne, Odense, Denmark)
Mini baking test.

Flour, 50 gram, Dry yeast 10 gram, glucose 0.8 gram, salt 0.8 gram, 70 ppm ascorbic acid and, water 400 Brabender units was kneaded in a 50 g Brabender mixing bowl for 5 min at 30° C.

Resting time was 10 min. at 34° C. The dough was scaled 15 gram per dough. Then moulded on a special device where the dough is rolled between a wooden plate and a plexiglas frame. The doughs were proofed in tins for 45 min. at 34° C., and baked in a Voss household oven 8 min. 225° C.

After baking the breads are cooled to ambient temperature and after 20 min. the breads are scaled and the volume is determined by rape seed displacement method. The breads are also cut and crumb and crust evaluated.
Results and Conclusion:

Preliminary results indicate that the lipid acyltransferase clearly demonstrates a positive effect on both bread volume and bread appearance. In particular, preliminary results indicate that the use of the lipid acyltransferase results in increased specific bread volume as compared with that obtained with the control (no enzyme) and that obtained with the use of a commercially available lipolytic enzyme, namely Grindamyl Exel 16 or LipopanF™.

Example 20

Standard Ice Cream with Dairy Fat

The function of emulsifiers used in ice cream is to bring about controlled fat crystallisation and mild destabilization due to protein desorption during ageing of the ice cream. This change improves the ice cream quality. Mono-diglycerides are normally used for the production of ice cream, but is also known to use polar emulsifiers like polysorbate and sugar esters in ice cream production in combination with mono-diglyceride to facilitate controlled fat destabilization and produce ice cream with very good creamy and smooth eating texture.

Emulsifiers used for ice cream are normally added the ice cream mix as a powder. Recently it has however been shown that mono-diglyceride can bee produced by enzymatic reaction of the fat in the ice cream recipe using lipases. The problem by using lipases is however that lipases also catalyse the formation of free fatty acids, when water is available in the reaction mixture.

It has however surprisingly been shown that lipid acyltransferase overcomes the limitation by lipase because acyltransferase is able to transfer fatty acid from lecithin and other lipids to acceptor molecules like sterol, cholesterol, glucose, glycerol and proteins/peptides without formation of significant amount of free fatty acids.

One of the main ingredients in ice cream is dairy cream containing 38% milk fat. Dairy cream also contains smaller amount of lecithin, which is a donor molecule for acyl-transferase. ("Complex milk lipids account for about 1% of the total milk fat and are mainly composed of phospholipids". Ref. Ullmann's Encyclopedia of Industrial Chemistry Copyright © 2003 by Wiley-VCH Verlag GmbH & Co. KGaA.). Dairy cream also contains small amount of cholesterol, which is an acceptor molecule for acyl-transferase.

From the constituents of ice cream it is thus possible to produce both monoglyceride and polar emulsifiers like lysolecithin and sugar ester, which are known for the beneficial effects in ice cream production.

A further beneficial effect form the reaction of acyl-transferase in dairy cream is the formation of cholesterol ester, which might slow down the absorption of cholesterol in the intestine.

| Ice cream Recipe | | |
|---|---|---|
|  | With emulsifier | With enzyme |
| Dairy cream, 38% | 23.65 | 23.65 |
| Skimmed milk | 53.30 | 53.30 |
| Skimmed milk powder | 4.90 | 11.30 |
| Sugar | 12.00 | 12.00 |
| Glucose sirup, DE 42, 75% TS | 4.25 | 4.25 |
| Glycerol | 1.0 | 1.0 |
| Stabilizer blend | 0.2 | 0.2 |
| Cremodan SE 30 | 0.6 |  |
| Lipid acyl transferase, 500 PLU/g |  | 0.1 |
| Grindsted Flavouring 2976 | 0.1 | 0.1 |
| Colour | + | + |

Ice Cream Production Process.
1. Heat dairy cream, glucose syrup and glycerol to approx. 40° C. Add the lipid acyl transferase and let the mixture react for 30 minutes. A sample is taken out for analysis
2. Heat all the other liquid ingredients to approx. 40°
3. Add the other dry ingredients. (stabiliser blend is mixed with sugar before addition)
4. When the dry ingredients are dissolved add the dairy cream-glucose mixture.
5. Pasteurize at 80-85° C./20-40 seconds
6. Homogenize at 80° C. (190 bar for recipe 1 and 175 bar for recipe 2)
7. Cool to ageing temperature, 4° C.
8. Freeze in continuous freezer to desired overrun (100% recommended)
9. Harden in tunnel at −40° C.
10. Store below −25° C.

Results:

Uses of Acyl-transferase in the production of ice cream contribute to the production of ice cream with very good taste and excellent creamy mouth feel comparable the ice cream produced by using a commercial emulsifier Cremodan SE 30. The melt down of the ice cream produced by the lipid acyl transferase is also improved.

Example 21

Acyl Transferase in Cheese

Cheese is the fresh or matured solid or semisolid product obtained by coagulating milk, skimmed milk, partly skimmed milk, cream, whey cream, or buttermilk, or any combination of these materials, through the action of rennet or other suitable coagulating agents, and partially draining the whey that results from such coagulation.

The cheese yield depends primarily on the fat and protein contents of the milk. The salt (particularly calcium salts) and protein concentrations, as well as the acidity, are very important for coagulation. (ref. *Ullmann's Encyclopedia of Industrial Chemistry* Copyright © 2003 by Wiley-VCH Verlag GmbH & Co).

Such effort has been made in order to optimise and increase the cheese yield by optimisation of the cheese making procedure (U.S. Pat. No. 4,959,229) or by using improved clotting method (U.S. Pat. No. 4,581,240), which increase the amount of whey protein in the curd.

In the present invention the amount of whey protein in the curd is increased by enzymatic modification of the whey protein by treatment of the milk during cheese making with a lipid acyl transferase.

When a fatty acid is covalently linked to a non-membrane protein like 3-lactoglobulin, the physical and functional properties will change drastically.

For cheese production of the present invention acyl transferase is added to the milk before or at the same time as rennet is added to the milk.

During casein precipitation acyl transferase is able to use lecithin and other lipids in the milk as donor and peptides or protein as acceptor molecule during formation of acylated protein or acylated peptides.

The change in hydrophobic properties of milk protein contributes to increased protein precipitation in the curd during cheese production.

Since the increase in cheese yield obtained by the present invention originates from increased retention in the cheese coagulum of proteins that are normally lost in the whey, a suitable method, directly related to the mechanism of the invention, is based on determination of the amount of protein that ends up in the whey. Less protein in the whey necessarily means more protein in the curd, and higher cheese yield.

The test for the amount of protein in the whey can be performed in the following way. Skim or whole milk is warmed to a temperature suitable for rennet coagulation, typically 30-35 oC in a 100 ml beaker. Optionally 1% of a bulk lactic acid bacteria starter is added, and standard rennet is added in an amount corresponding to e.g. 0.03-0.05%. When the milk has turned into a coagulum solid enough to allow it to be cut into cubes with a side length of about 0.5 cm, such cutting is performed with a sharp knife. Syneresis is thereby initiated, and after 30 min holding period, that allows the curd to settle, a whey sample is withdrawn, and centrifuged in a laboratory centrifuge for 10 min. This sample is analyzed for protein content, using e.g. the Kjeldahl method. Alternatively, and/or as a supplement, the sample may be analyzed with methods that allow the type and quantity of the individual protein components to be established.

Example 22

Assay in Low Water Environment

Transferase reactions of lipolytic enzymes in low water environment.
Procedure
Materials.
Cholesterol Sigma cat. C 8503
L-alpha-Phosphatidylcholine 95% (Plant) Avanti #441601
Soybean oil, Aarhus United, DK.
Chloroform, Analytical grade
Enzymes.
179, GCAT from A salmonicida
2427, Phospholipase A1 from *Fusarium oxysporum*. LIPOPAN®F from Novozymes, Denmark
1991, Phospholipase A2 from Pancreas, LIPOMOD 22L from Biocatalyst, UK
2373, *Candida Antarctica* lipase, Novozyme 525 L from Novozymes Denmark.
Enzyme Assay
13.1% Lecithin and 6.6% cholesterol was dissolved in soybean oil by heating to 60° C. during agitation.

The substrate was scaled in a 20 ml Wheaton glass and heated to 46° C.

Water and enzyme solution was added and a stopwatch is started.

At regular intervals 50 mg samples ware transferred to a 10 ml Dram glass and frozen.

The isolated lipids were analysed by GLC
GLC Analysis
GLC analysis was carried out as described in Example 11

Results

The experiment was set up as shown in Table 33

The substrate based on soybean oil containing 13.1% lecithin and 6.6% cholesterol was heated to 46° C. The enzyme solution was added and a stopwatch started.

After 30, 60 and 120 minutes reaction time samples were taken out for GLC analysis.

TABLE 33

|  |  | 1 | 2 | 3 | 4 | 5 |
|---|---|---|---|---|---|---|
| Substrate | gram | 5 | 5 | 5 | 5 | 5 |
| Transferase #179-C72, 56 PLU-7/ml | ml |  | 0.3 |  |  |  |
| #2427, 200 PLU-7/ml | ml |  |  | 0.3 |  |  |
| Pancreas PLA 2 #1991 6300 PLU/ml | ml |  |  |  | 0.3 |  |
| Novozyme 525 L, #2373, 200 LIPU/ml | ml |  |  |  |  | 0.3 |
| Water | ml | 0.3 |  |  |  |  |
| % water |  | 6 | 6 | 6 | 6 | 6 |

The results from the GLC analysis is shown in Table 34. The results are expressed in percent based total sample composition. Based on the GLC results it was possible to calculate the amount of fatty acid and cholesterol ester produced by enzymatic reaction relative to the control sample without enzyme added. Under these experimental conditions the total enzymatic activity was estimated as the hydrolytic activity measured as free fatty acid formation and the transferase activity estimated as cholesterol ester formation. From these results and the information about molecular weight of fatty acid and cholesterol ester it was possible to calculate to relative molar hydrolytic activity and the relative molar transferase activity as shown in Table 35.

TABLE 34

| Enzyme | Reaction time minutes | Fatty acid % | cholesterol % | Cholesterol ester % |
|---|---|---|---|---|
| Control | 120 | 0.533 | 7.094 | 0.000 |
| #179 | 30 | 0.770 | 5.761 | 2.229 |
| #179 | 60 | 0.852 | 5.369 | 2.883 |
| #179 | 120 | 0.876 | 4.900 | 3.667 |
| #2427 | 30 | 3.269 | 7.094 | 0.000 |
| #2427 | 60 | 3.420 | 7.094 | 0.000 |
| #2427 | 120 | 3.710 | 7.094 | 0.000 |
| #1991 | 30 | 2.871 | 7.094 | 0.000 |
| #1991 | 60 | 3.578 | 7.094 | 0.000 |
| #1991 | 120 | 3.928 | 7.094 | 0.000 |
| #2373 | 30 | 1.418 | 7.094 | 0.000 |
| #2373 | 60 | 1.421 | 7.094 | 0.000 |
| #2373 | 120 | 1.915 | 7.094 | 0.000 |

TABLE 35

| Enzyme | Reaction time minutes | Fatty acid produced | Cholesterol Used | Cholesterol ester produced | Hydrolytic activity % | Transferase activity % |
|---|---|---|---|---|---|---|
| #179 | 30 | 0.238 | 1.334 | 2.229 | 20 | 80 |
| #179 | 60 | 0.319 | 1.725 | 2.883 | 21 | 79 |
| #179 | 120 | 0.343 | 2.195 | 3.667 | 18 | 82 |
| #2427 | 30 | 2.737 | 0.000 | 0.000 | 100 | 0 |
| #2427 | 60 | 2.887 | 0.000 | 0.000 | 100 | 0 |
| #2427 | 120 | 3.177 | 0.000 | 0.000 | 100 | 0 |
| #1991 | 30 | 2.338 | 0.000 | 0.000 | 100 | 0 |
| #1991 | 60 | 3.046 | 0.000 | 0.000 | 100 | 0 |
| #1991 | 120 | 3.395 | 0.000 | 0.000 | 100 | 0 |
| #2373 | 30 | 0.885 | 0.000 | 0.000 | 100 | 0 |
| #2373 | 60 | 0.888 | 0.000 | 0.000 | 100 | 0 |
| #2373 | 120 | 1.383 | 0.000 | 0.000 | 100 | 0 |

Conclusion

In these experiments it was observed that all the tested enzymes showed hydrolytic activity because the amount of fatty acid increased. However the only enzyme which showed transferase activity was GCAT from *A. salmonicida*. It is therefore concluded that in an oily system with lecithin and cholesterol containing 6% water phospholipase A1 from *Fusarium oxysporum*, phospholipase A2 from pancreas and a lipase from *Candida antarctica* only showed hydrolytic activity.

Example 23

Treatment of Butterfat

Lipid acyl transferase derived from *Aeromonas salmonicida* (SEQ ID No. 90, N80D variant) was expressed in *Bacillus licheniformis* (hereinafter referred to as KLM3) (see below).

The lipid acyl transferase was tested in butterfat with the aim to investigate the transfer reaction when 0.5% glycerol and 1% phospholipid was added to the butterfat.

The reaction products were analysed by TLC and the results clearly showed the formation of monoglyceride which confirm that lipid acyl transferase utilizes glycerol as acceptor molecule.

Experimental

Enzymes:
Lipid acyl transferase (LAT) expressed in *B. licheniformis*: 2005876 (5500 TIPU/ml) Lipomod 699L, pancreatic phospholipase from Biocatalysts. 10000 U/ml
Butterfat: Anhydrous Butterfat A0019659 lot 0130547 from Croman Belgium.
Glycerol:
Lecithin: Phosphatidylcholine 95% Plant (Avanti #441601), HPTLC
Applicator: LINOMAT 5, CAMAG applicator.
HPTLC plate: 10×10 cm (Merck no. 1.05633)
The plate was activated before use by drying in an oven at 160° C. for 20-30 minutes.
Application: 1.0 μl of a 15.0% solution of reacted butterfat dissolved in Chloroform:Methanol (2:1) was applied to the HPTLC plate using LINOMAT 5 applicator.
Running-buffer: 1: P-ether:MTBE:Acetic acid (60:40:1)
Application/Elution time: 14 minutes.
Running-buffer: 5: P-ether:MTBE:Acetic acid (70:30:1)
Application/Elution time: 12 minutes.

Running-buffer: 4: Chloroform:Methanol:water (75:25:4)
Application/Elution time: 20 minutes.
Developing fluid: 6% Cupriacetate in 16% $H_3PO_4$ After elution the plate was dried in an oven at 160° C. for 5 minutes, cooled and immersed in the developing fluid and then dried additional in 5 minutes at 160° C. The plate was evaluated visually and scanned (Camag TLC scanner).

Results

Samples of butterfat, glycerol, lecithin and enzyme were scaled in a 20 ml Wheaton glass as outlined in table 36.

TABLE 36

|  |  | 1 | 2 | 3 | 4 | 5 | 6 | 7 | 8 | 9 | 10 |
|---|---|---|---|---|---|---|---|---|---|---|---|
| Croman Anhydrous Butterfat | g | 10 | 10 | 10 | 10 | 10 | 9.9 | 9.9 | 9.9 | 9.9 | 9.9 |
| lecithin, | g |  |  |  |  |  | 0.1 | 0.1 | 0.1 | 0.1 | 0.1 |
| LAT, 500 | mg |  | 20 | 100 |  |  |  | 20 | 100 |  |  |
| Lipopmod 699L 1000 | mg |  |  |  | 20 | 100 |  |  |  | 20 | 100 |
| Glycero | mg | 50 | 30 |  | 30 |  | 50 | 30 |  | 30 |  |
| Units/g |  | 0 | 1 | 5 | 2 | 10 | 1 | 1 | 5 | 2 | 10 |

* LAT 2005876 (5000 TIPU/ml) dissolved in glycerol:enzyme 9:1
** Lipomod 699L (#3332) dissolved in glycerol:enzyme 9:1

The samples were placed in a heating block at 50° C. for 4 hours and then a sample was taken out for analysis and dissolved in chloroform:methanol 2:1.

The samples were analyzed by TLC in running buffer 5, 1 and 4 as shown in FIG. 104.

The TLC plate shown in FIG. 105 was scanned by a Camag Densiometric scanner and based on the amount of monoglyceride in the reference sample of mono-diglyceride the amount of monoglyceride in the butterfat is calculated as shown in table 37

TABLE 37

Monoglyceride in the butterfat samples calculated by dentiometric measurement of TLC plate.

| Sample Jour. 2390-67 | % Monoglyceride |
|---|---|
| 1 | 0.005 |
| 2 | 0.005 |
| 3 | 0.009 |
| 4 | 0.005 |
| 5 | 0.005 |
| 6 | 0.004 |
| 7 | 0.423 |
| 8 | 0.449 |
| 9 | 0.004 |
| 10 | 0.004 |

Conclusion

The TLC results from enzymatic treatment of butter oil containing glycerol/phospholipids with lipid acyltransferase conform the ability of the enzyme to convert cholesterol into cholesterol ester and glycerol to monoglyceride using phospholipid as acyl donor.

In the experiment conducted it was shown that all phospholipids both phosphatidylcholine (PC) and lyso-phosphatidylcholine (LPC) can be completely converted to glycerophosphocholine.

The experiments also indicated that the pancreatic phospholipase is less active in low water environment and had no significant acyltransferase activity.

The enzyme modified butterfat (samples 7 & 8 of Table 37) is added to skimmed milk to a final concentration of 3.6 wt % fat to produce a milk for use in the preparation of cheese.

Example 24

Treatment of Butterfat and Cream

The lipid acyl transferase was tested in butterfat and cream (38% fat) with the aim to investigate the transfer reaction when 0.5% glycerol and 1% phospholipid was added to the butterfat.

The reaction products was analysed by TLC and the results from butterfat clearly showed the formation of monoglyceride and lysophosphopholipid. The results from experiment with cream also confirmed the formation of monoglyceride although at lower level, possibly due to a competitive hydrolytic reaction causing the formation of free fatty acids. In the experiments with cream little increase in lysophospholipid was observed, but this might be explained by too high enzyme dosage.

Experimental

Enzymes:
Lipid acyl transferase (as per Example 23)
Butterfat: Anhydrous Butterfat A0019659 lot 0130547 from Croman Belgium.
Cream: 38% fat from ARLA, DK
Glycerol:
Lecithin: Phosphatidylcholine 95% Plant (Avanti #441601),
HPTLC
Applicator: LINOMAT 5, CAMAG applicator.
HPTLC plate: 10×10 cm (Merck no. 1.05633)
The plate was activated before use by drying in an oven at 160° C. for 20-30 minutes.
Application: 1.0 µl of a 15.0% solution of reacted butterfat dissolved in Chloroform:Methanol (2:1) was applied to the HPTLC plate using LINOMAT 5 applicator.
Running-buffer: 1: P-ether:MTBE:Acetic acid (60:40:1)
Application/Elution time: 14 minutes.
Running-buffer: 5: P-ether:MTBE:Acetic acid (70:30:1)
Application/Elution time: 12 minutes.
Running-buffer: 4: Chloroform:Methanol:water (75:25:4)
Application/Elution time: 20 minutes.
Developing fluid: 6% Cupriacetate in 16% $H_3PO_4$ After elution the plate was dried in an oven at 160° C. for 5 minutes, cooled and immersed in the developing fluid and then dried additional in 5 minutes at 160° C. The plate was evaluated visually and scanned (Camag TLC scanner).

Results

Samples of butterfat, glycerol, lecithin and enzyme were scaled in a 20 ml Wheaton glass as outlined in table 38

TABLE 38

|  | 1 | 2 |
|---|---|---|
| Croman, Anhydrous Butterfat A0019659 lot 0130547 g | 10 | 10 |
| Cream, 38% g |  |  |
| Lecithin, Avanti g | 0.1 | 0.1 |
| LAT, 500 TIPU/ml* mg |  | 50 |
| Glycerol mg | 50 |  |
| Units/g | 0 | 2.5 |

*LAT (5000 TIPU/ml) dissolved n glycerol:enzyme 9:1

The samples were placed in a heating block at 45° C. and samples were taken out after 10, 30, 60, and 120 minutes and dissolved in chloroform:methanol 2:1.

The samples were analyzed by TLC in running buffer 5, 1 and 4 as shown in FIG. 106, 107 and 108.

Conclusion. Butterfat Experiment.

The TLC results from enzymatic treatment of butter oil containing glycerol/phospholipids with lipid acyltransferase confirm the ability of this enzyme to convert cholesterol into cholesterolester and glycerol to monoglyceride using phospholipid as acyl donor.

In the experiment conducted it was shown that phospholipid (PC) was converted to lyso-phosphatidylcholine (LPC). By extended reaction time lyso-phospholipid (LPC) was further converted to glycophosphocholine. It is therefore possible to optimize enzyme dosage and reaction time in order to identify the optimum level of monoglyceride and lysophospholipid production for any particular application.

The enzyme modified butterfat is added to skimmed milk to a final concentration of 3.6 wt % fat to produce a milk for use in the preparation of cheese. Initial experiments indicate that the enzyme modified butter fat may be more easily incorporated into the skimmed milk when compared to non modified butter fat.

Results with Cream

Samples of cream, glycerol, lecithin and enzyme were scaled in a 20 ml Wheaton glass as outlined in table 39

TABLE 39

|  | 3 | 4 |
|---|---|---|
| Croman, Anhydrous Butterfat A0019659 lot 0130547 g |  |  |
| Cream, 38% g | 10 | 10 |
| lecithin, Avanti g | 0.1 | 0.1 |
| LAT, 500 TIPU/ml* mg |  | 50 |
| Glycerol mg | 50 |  |

*LAT (5000 TIPU/ml) dissolved in glycerol:enzyme 9:1

The samples were placed in a heating block at 45° C. and samples were taken out after 10, 30, 60, and 120 minutes and dissolved in chloroform:methanol 2:1.

The samples were analyzed by TLC in running buffer 5, 1 and 4 as shown in figures. 109, 110 and 111.

Conclusion. Cream Experiment.

The TLC results from treatment of cream containing phospholipid and glycerol with an enzyme lipid acyl transferase clearly confirm the transfer reaction of acyl groups from phospholipid (PC) to cholesterol during formation of cholesterol ester.

The transferase reaction of acyl groups to glycerol was also observed. There was also a noticeable hydrolytic activity. Further optimerization of to produce optimum level of monoglceyride via modulation of enzyme dosage, glycerol dosage and reaction time is therefore is therefore possible.

Example 25

Production of Mozzarella

Enzymes

EDS 188: Lipid acyltransferase in accordance with the present invention, (herein referred to KLM3) expressed in *B. lichiniformis:* 2005876 (1460 TIPU/ml) (SEQ ID No. 90, N80D variant).

Lecitase, pancreas phospholipase, Sigma P0861, 10,000 unit/ml.

Day 1.
1. Milk was separated at 55° C. into skim (0.075% w/w fat) and cream (30%, w/w) fat A "skim" (0.83%, w/w) fat was prepared by blending the skim milk and cream (see FIG. 120)
2. 0.4 g CaCl2 (50%, w/v) per kg of cream (30% fat) was added and the cream was divided into 3 equal lots—namely for control (Vat 1), Lecitase (Vat 2) and KLM3' (Vat 3)
3. 0.2% (w/w of fat content), Lecitase to Vat 2 equivalent to 0.06% (w/w of 30% fat cream) or equivalent to 0.6 g per kg of 30% fat cream was added.
4. KLM3' 25 TIPU/kg cream was added to Vat 3.
5. In the control (Vat 1), no enzyme solution (or water) was added.
6. All cream treatments (incl. control) were incubated at 50° C. for 30 min.
7. Immediately thereafter, the correct weight of each cream to the correct of cold (10° C.) "skim milk (0.83% w/w) fat was added to get the correct fat content (3.5%, w/w) in the mixtures, which are the standardized milks.
8. These were pasteurized at 72° C. for 26 seconds.
9. Cooled to 5 C and held overnight.

Day 2.
10. The milk was heated to 41° C. and kept it for 30 minutes (This was done so as to reverse the cold storage ageing effects on the milk).
11. The milk was cooled to 34.4° C.
12. Starter culture was added (Choozit Ta 61 100DCU, Choozit LH100 50 DCU in DAN 011, Dan 012, DAN 013; and Choozit Ta 61 100 DCU, Choozit LH100 23.3 DCU in DAN 021, DAN 022, DAN 023). DAN 021, DAN 022 and DAN 023 were dosed with a reduced amount of Choozit LH100 to reflect the addition rates of Helveticus culture normally used in industrial mozzarella production. The cultures were added directly to the cheese milk and left for 45 min. with agitation
13. The rennet was added ((145 ml Marzyme10 (140 imcu/ml) diluted to 1 liter with water),
14. The rennet was mixed in for 2 min. A sample of the rennet milk was taken and placed in a rheometer to measure the change in the elastic modulus, G', as a function of time.
15. The gel (curd) in the vat was cut when the firmness (G') reached 40 Pa as determined on a controlled stress rheometer.
16. The gel was cut using a wire grid—(speed 2-15 seconds, stand 1 min, cut speed 1-15 seconds, stand 1 min, Cut speed 1-10 seconds) and the curd whey mix was allowed to sit quiescently (heal). This healing step is incorporated in industrial cheese making to minimize fat losses to the whey.
17. The curd whey mixture was stirred (at 10 min from beginning of cut period) for 5 min, so as to get curd/whey mix in motion.
18. The curd/whey mix was heated to 41.1° C. in 30 min.

19. Stirring continued until curd pH (as measured on whey squeezed from the curd) reached 5.9.
20. The curd whey mixture was drained into finishing vat, and the whey removed by gravity flow.
21. The curd was trenched to sides of vat, leading to 2 curd trenches.
22. The curd trenchs were cut into slabs.
23. The curd slabs were turned every 15-20 min and held in the finishing vat until the pH (as measured by inserting pH probe into sample of curd) reached 5.25.
24. The curd was then milled into chips (0.75 cm×0.75 cm×7 cm long).
25. Covered with cold water (17° C.) for 15 mins.
26. The water drained for 10 mins.
27. The curd was weighed and salt added to the curd at a level of 0.2% (w/w) of cheese milk weight (0.9 kg to cheese curd from 450 kg of milk). The curd was left to absorb applied salt for 20 min
28. The curd was placed into a plasticization kneading/stretching unit (via the shredding unit built into the equipment).
29. The curd was kneaded/stretched while it is heated to 63° C. by circulating water at 80 C.
30. The curd was placed in 7° C. water for 30 min
31. The curd was then placed in 7° C. brine (23% NaCl) for 90 min.
32. The curd was remove from the brine and left to drain for 10 mins.
33. The brined curd was weighed
34. Vacuum packed, and placed at 4° C.

Results

TABLE 40

Cheese yield and fat content of whey

| Code | Wt Milk kg | wt curd in moulds kg | unmoulded curd kg | Curd ex brine kg | Total wt of salted cheese kg | Cheese yield kg/100 kg milk | Fat in whey %, w/w |
|---|---|---|---|---|---|---|---|
| DAN011 | 454.1 | 26.62 | 18.36 | 26.78 | 45.25 | 9.96 | 0.48 |
| DAN012 | 454.6 | 26.62 | 21.66 | 26.69 | 48.41 | 10.65 | 0.41* |
| DAN013 | 454.2 | 26.6 | 23.56 | 26.83 | 50.59 | 11.14* | 0.34* |
| DAN021 | 454.4 | 26.55 | 18.63 | 26.7 | 45.44 | 10.00 | 0.51 |
| DAN022 | 454.1 | 26.5 | 20.69 | 26.69 | 47.53 | 10.47 | 0.41* |
| DAN023 | 454.3 | 26.4 | 21.61 | 26.52 | 48.23 | 10.62* | 0.35* |

DAN011 and DAN021 = control,
DAN 012 and DAN022 = Lecitase,
DAN013 and DAN023 = KLM3
[*means statistically significant compared with the control]

Example 26

Pizza Made with Enzyme Modified Cheese

The cheese prepared according to Example 25 is used in the preparation of pizza.
Pizza Base
500 gms strong white flour
12 gms fresh yeast dissolved in 200-250 ml water containing 1 teaspoon of dissolved sugar, and allowed to stand at 20° C. for 10 minutes.
1 egg
1-2 tablespoons olive oil to taste.
Salt to taste
The above are mixed and subsequently kneaded by hand for 5 minutes to produce a dough. The dough is left, covered by a damp cloth, to rise until at least doubled in volume. The dough is then rolled until approximately 5 mm-1 cm thin depending on taste.

A tomato sauce is prepared by briefly frying finely chopped onion and garlic in a pan with olive oil and adding chopped tomatoes. The sauce is reduced to a desirable consistency. When cool, the sauce is added to the rolled out pizza dough.

The cheese prepared in Example 25 is added, vegetable, meat and seafood toppings may also be added. The pizza is baked at 200° C. on a stone base in a fan assisted oven.

The pizza made with the cheese comprising the edible oil/fat of the invention appears to have noticeably less surface oil and the baked pizza base appear to be less saturated with the oil, especially around the edges, and on the surface of the sauce and toppings (see FIG. 136). This makes the pizza more appetizing to handle and to eat.

The pizza has an improved over appearance with less visible oiling off.

Example 27

Lipid Analysis

Cream and cheese from the production of mozzarella as detailed in Example 25 were analysed as follows:
Lipid Analysis
Cream and cheese from the production of Mozzarella cheese as detailed in Example 25 were extracted with organic solvents and the isolated lipids were analysed by HPTLC and GLC. In the cheese experiment the cream used to produce the cheese was treated with a pancreatic phospholipase (Lecitase) or a lipid acyltransferase according to the present invention (KLM3). A control experiment without any enzyme treatment was also conducted. All three experiments were made in duplicate over two days.

Lipid analysis of isolated lipids from enzyme treated cream as well as the cheese produced from the creams showed that both Lecitase and KLM3 were active on the phospholipids in the products, and the main phospholipids, phosphatidylcholine (PC) and phosphadidylethanolamine (PE) were almost completely degraded.

In the Lecitase treated sample the degradation of PC and PE was followed by concomitant formation of free fatty acids, mainly oleic acid and linoleic acid. In the experiment with KLM3 the formation of free fatty acids were significantly lower than the degradation of phospholipids because this enzyme carried out a transfer reaction of fatty acids from phospholipids to cholesterol which resulted in the formation of cholesterol esters. In the cheese samples treated with KLM3 only 40% cholesterol was left compared with control and Lecitase treated cheeses. In the cheese treated with KLM3 small amounts of saturated free fatty acids were formed, because of unspecific activity on the saturated fatty acids in the sn-1 position of the phospholipids.

The enzyme treatment was made in a 30% cream which after enzymation was added to skim milk and adjusted to 3.5% fat for cheese production.

In this report the analyses of lipid components in the cream used for the cheese production as well as the cheese were analysed.

Materials and Methods

Enzymes:

EDS188: Lipid acyltransferase in accordance with the present invention, (hereinafter referred to KLM3) expressed in *B. lichiniformis*: 2005876 (1460 TIPU/ml), (SEQ ID No. 90, N80D variant).

Lecitase, pancreas phospholipase, Sigma P0861, 10,000 unit/ml.

TLC Standards:

ST16: 0.5% solution of phospholipids containing 14.76% Phosphatidylcholine (PC), 0.49% Lyso-phosphatidylcholine (LPC), 10.13% Phosphatidylinisitol (PI), 12.74% Phosphatidylethanolamine (PE) and 5.13% Phosphatidic acid (PA).

ST17: 0.1% solution of cholesterol, 0.1% cholesterolsteareate and 0.1% oleic acid.

Enzymation of Cream Used for Mozzarella Cheese Production

Was carried out as disclosed in Example 25.

HPTLC

Applicator: CAMAG applicator AST4.

HPTLC plate: 20×10 cm (Merck no. 1.05641)

The plate was activated before use by drying in an oven at 160° C. for 20-30 minutes.

Application: 3.0 µl of extracted lipids dissolved in Chloroform:Methanol (2:1) was applied to the HPTLC plate using AST4 applicator. 0.1, 0.3, 0.5, 0.8, 1.5 µl of a standard solution of standard components with known concentration are also applied to the HPTLC plate.

Running-buffer: 1: P-ether:MTBE:Acetic acid (50:50:1)

Application/Elution time: 12 minutes.

Running-buffer: 6: Methyl-acetate:Chloroform:Methanol: Tsopropanol: 0.25% KCl solution in water. (25:25:25:10: 9)

Application/Elution time: 20 minutes.

Developing fluid: 6% Cupriacetate in 16% $H_3PO_4$

After elution the plate was dried in an oven at 160° C. for 10 minutes, cooled and immersed in the developing fluid and then dried additional in 5 minutes at 160° C. The plate was evaluated visually and scanned (Camag TLC scanner).

After drying the TLC spots are quantified by scanning the plate in a TLC Scanner 3 from Camag. Based on the density of the standard component a calibration curve is constructed, and used for quantification of the components in the sample.

GLC Analysis

Perkin Elmer Autosystem 9000 Capillary Gas Chromatograph equipped with WCOT fused silica column 12.5 m×0.25 mm ID×0.1µ film thickness 5% phenyl-methyl-silicone (CP Sil 8 CB from Chrompack).

Carrier gas: Helium.

Injector. PSSI cold split injection (initial temp 50° C. heated to 385° C.), volume 1.0 µl Detector FID: 395° C.

| Oven program (used since 30.10.2003): | 1 | 2 | 3 |
|---|---|---|---|
| Oven temperature, ° C. | 90 | 280 | 350 |
| Isothermal, time, min. | 1 | 0 | 10 |
| Temperature rate, ° C./min. | 15 | 4 | |

Sample preparation: Lipid extracted from cheese or cream samples was dissolved in 0.5 ml Heptane:Pyridin, 2:1 containing internal standard heptadecane, 0.5 mg/ml. 300 µl sample solution is transferred to a crimp vial, 300 µl MSTFA (N-Methyl-N-trimethylsilyl-trifluoraceamid) is added and reacted for 20 minutes at 60° C.

Calculation: Response factors for Free Fatty Acid (FFA), Cholesterol, Cholesteryl palmitate and Cholesteryl stearate were determined from pure reference material.

Extraction Cream.

Cream samples in Eppendorph tubes were heated at 99° C. for 10 min. in order to inactivate the enzyme, and cooled to ambient temperature. 1 ml cream was transferred to a 10 ml dram glass with screw lid. 3 Ml Chloroform:Methanol 2:1 was added and mixe on a Whirley. The sample was extracted for 30 min on a Rotamix. The sample was centrifuged for 10 min. at 1700 g. The lower organics phase was isolated and used for TLC and GLC analysis.

Extraction Cheese 0.5 g cheese was scaled in a 12 ml centrifuge with screw lid. 2 ml 99% Ethanol was added and the sample was homogenized with a Ultra Turrax Mixer for 30 sec at 20000 rpm. The mixer was rinsed with 1.5 ml Ethanol. 5 ml Chloroform was added and mixed on a whirley. The sample was extracted for 30 min on a Rotamix 25 rpm. The sample was centrifuged for 10 min. at 1700 g.

The lower organics phase was isolated and used for TLC and GLC analysis

Samples

TABLE 41

Cream samples taken out after 30 min enzymation.

| Test No. | Enzyme | Dosage, ppm | Day |
|---|---|---|---|
| DAN011 | Control | 0 | 1 |
| DAN012 | Lecitase | 600 | 1 |
| DAN013 | KLM3 | 17.1 | 1 |
| DAN021 | Control | 0 | 2 |
| DAN022 | Lecitase | 600 | 2 |
| DAN023 | KLM3 | 17.1 | 2 |

TABLE 42

Labeliing of Mozzarella Cheese samples

| Test No. | Enzyme | Day |
|---|---|---|
| DAN011 | Control | 1 |
| DAN012 | Lecitase | 1 |
| DAN013 | KLM3 | 1 |
| DAN021 | Control | 2 |
| DAN022 | Lecitase | 2 |
| DAN023 | KLM3 | 2 |

Results

Cream Lipid Analysis.

Samples of cream used for the production of cheese were extracted with Chloroform methanol according to the procedure mentioned under Materials and Methods and analysed by HPTLC.

The results from TLC analysis of the cream samples are shown in FIGS. 121 and 122.

FIG. 121 shows the TLC (solvent 6) of lipid extracted from cream and a standard mixture (ST16) of phospholipids; Phosphatidylcholine (PC); Lyso-phosphatidylcholine (LPC); Phosphatidylinisitol (PI); Phosphatidylethanolamine (PE); 5.13% Phosphatidic acid (PA); and Spingholipid (SG)

FIG. 122 shows a. TLC (solvent 1) of lipid extracted from cream and a standard mixture of free fatty acids (FFA), cholesterol (CHL) and cholesterol ester (CHL-ester).

The density of the bands from the TLC chromatogram were determined, and based on the standard mixture of phospholipids the amount of PC and PE were calculated from the TLC chromatogram in FIG. 121 and based on the standard mixture of cholesterol and fatty acids the amount of free fatty acids and cholesterol in the samples were calculated from the TLC chromatogram. The results are shown in table 43.

TABLE 43

Analysis of Phosphatidylcholine(PC), phosphatidylethanolamine (PE), cholesterol (CHL) and free fatty acids (FFA) based on TLC chromatograms FIGS. 121 and 122

| Enzyme | Day | ppm PC | Ppm PE | ppm CHL | ppm FFA |
|---|---|---|---|---|---|
| Control | 1 | 149 | 278 | 713 | 201 |
| Lecitase | 1 | 23 | 17 | 638 | 396 |

TABLE 43-continued

Analysis of Phosphatidylcholine(PC), phosphatidylethanolamine (PE), cholesterol (CHL) and free fatty acids (FFA) based on TLC chromatograms FIGS. 121 and 122

| Enzyme | Day | ppm PC | Ppm PE | ppm CHL | ppm FFA |
|---|---|---|---|---|---|
| KLM3 | 1 | 11 | 24 | 328 | 274 |
| Control | 2 | 117 | 214 | 638 | 166 |
| Lecitase | 2 | 39 | 29 | 629 | 345 |
| KLM3 | 2 | 15 | 28 | 311 | 201 |

The results in table 43 were evaluated statistically by ANOVA using Statgraphic Plus for Windows 3.1. The statistical evaluation for cholesterol and free fatty acid are illustrated graphically in FIGS. 123 and 124.

TLC analysis of cream treated with Lecitase and KLM3 has shown a strong effect of phospholipases in the cream (FIG. 121) and it is seen that the two main phospholipid components PC and PE are almost completely hydrolyzed (table 43).

In FIG. 122 it is shown that KLM3 has a strong impact on the cholesterol compared to Lecitase. It is also observed that the amount of fatty acids produced in sample treated with Lecitase are clearly higher than the samples treated with KLM3 and control.

A statistical evaluation of the amount of fatty acids (FIG. 124) shows that KLM3 produces a small but not significant amount of free fatty acids compared with control. The amount of fatty acids in the sample treated with Lecitase is however significantly higher. This is explained by the fact that Lecitase hydrolyses phospholipids resulting in the formation of free fatty acids. KLM3 also degrades the phospholipids (Table 43) but results in the fatty acids from the phospholipids being transferred to cholesterol, thus resulting in the formation of cholesterol ester. This is also confirmed by the fact that the amount of cholesterol is significantly lower in the sample treated with KLM3 whereas control and Lecitase treated samples are on the same level (see FIG. 123).

On a molar ratio it can be calculated that the amount of degraded PC and PE is 0.6 mmol/kg for both Lecitase and KLM3 and the amount of fatty acids produced is 0.65 mmol/kg in Lecitase treated cream and 0.2 mmol/kg for the KLM3 treated cream, which confirms the observations that Lecitase hydrolyzes phospholipids, but KLM3 catalyses a transfer reaction.

The lipids extracted from cream after 30 minutes enzymation were also analyzed by GLC in order to quantify specific fatty acids, cholesterol and cholesterol ester.

The results from GLC analysis are shown in table 44

TABLE 44

GLC analysis of palmitic acid (FFA-16), oleic acid (C18:1), linoleic acid (C18:2), stearic acid (C:18:0), Sum FFA (C16:0, C18:0, C18:1 and C18:2), cholesterol and cholesterol ester.

| Enzyme | Day | FFA-16 ppm | FFA-18:1 and C:18:2 ppm | FFA-C18:0 ppm | Sum FFA ppm | Cholesterol ppm | Cholesterol ester Ppm |
|---|---|---|---|---|---|---|---|
| Control | 1 | 119 | 154 | 54 | 327 | 551 | 0 |
| Lecitase | 1 | 133 | 316 | 60 | 508 | 546 | 0 |
| KLM3 | 1 | 125 | 177 | 51 | 353 | 216 | 286 |
| Control | 2 | 111 | 152 | 54 | 317 | 520 | 0 |
| Lecitase | 2 | 130 | 314 | 62 | 507 | 547 | 0 |
| KLM3 | 2 | 130 | 195 | 63 | 388 | 238 | 335 |

The results in table 44 are evaluated statistically by ANOVA using Statgraphic Plus for Windows 3.1. The statistical evaluation for cholesterol, cholesterol ester and Sum free fatty acid (FFA) are illustrated in FIGS. 125 to 127.

The GLC analysis confirms what already was observed by TLC analysis, that KLM3 significantly reduces the amount of cholesterol (see FIG. 126) compared with control and Lecitase treated cream. The cholesterol in the KLM3 treated cream is converted to cholesterol ester (see FIG. 121), whereas cream treated with Lecitase and control contain no cholesterol ester. The formation of cholesterol ester also has an impact on the level of free fatty acid (see FIG. 127) where Lecitase produces a significant amount of free fatty acids by hydrolysis of phospholipids, and KLM3 only produces a small and not significant amount of free fatty acids. It is also observed that it is mainly the unsaturated fatty acid which increases during enzymation, because Lecitase is a sn-2 specific phospholipase and KLM3 is sn-2 specific with regard to transferase reaction. In naturally occurring phospholipids the sn-2 position contains mainly unsaturated fatty acids.

Cheese Lipids Analysis

Samples of cheese produced from enzyme modified cream were extracted with chloroform ethanol according to the procedure mentioned above and analyzed by HPTLC and GLC. Each sample was analyzed in duplicate.

The results from the HPTLC analysis are shown in FIGS. 128 and 129.

The TLC chromatogram shown in FIG. 129 indicates that both Lecitase and KLM3 has completely hydrolyzed the phospholipids phosphatidylcholine and phosphatidylethanolamine. The chromatogram in FIG. 128 illustrates that cheese treated with KLM3 has a reduced content of cholesterol compared with control and Lecitase treated cheese. It is also observed the amount of free fatty acids in cheese treated with KLM3 is lower than cheese treated with Lecitase although both enzymes completely hydrolysis phospholipids PC and PE.

GLC Analysis of Lipids from Mozzarella Cheese.

The lipids extracted from cheese were also analyzed by GLC in order to quantify specific fatty acids, cholesterol and cholesterol ester. Each cheese was extracted and analyzed in duplicate.

The results from the GLC analysis is shown in Table 45. The fatty acid analysis is split up in the amount of palmetic acid (C16:0), oleic acid (C18:1) and linoleic acid (C18.2) and stearic acid (C:18:0).

TABLE 45

GLC analysis of lipids from Mozzarella cheese.

| Enzyme | Day | FFA-16 | FFA-18:1 and 18:2 | FFA-18:0 | Sum FFA | Cholesterol | Cholesterol ester |
|---|---|---|---|---|---|---|---|
| Control | 1 | 291 | 291 | 158 | 740 | 689 | 0 |
| Control | 1 | 304 | 275 | 156 | 735 | 758 | 0 |
| Lecitase | 1 | 345 | 566 | 195 | 1105 | 688 | 0 |
| Lecitase | 1 | 336 | 546 | 180 | 1062 | 690 | 0 |
| KLM3 | 1 | 374 | 453 | 202 | 1030 | 296 | 440 |
| KLM3 | 1 | 399 | 481 | 228 | 1109 | 304 | 492 |
| Control | 2 | 285 | 259 | 160 | 703 | 726 | 0 |
| Control | 2 | 302 | 261 | 167 | 730 | 702 | 0 |
| Lecitase | 2 | 354 | 584 | 202 | 1140 | 728 | 0 |
| Lecitase | 2 | 357 | 591 | 202 | 1150 | 744 | 0 |
| KLM3 | 2 | 377 | 458 | 221 | 1056 | 302 | 419 |
| KLM3 | 2 | 388 | 485 | 227 | 1099 | 315 | 487 |

The results in table 45 showing the GLC analysis of lipids in Mozzarella cheese were evaluated statistically by ANOVA using Statgraphic Plus for Windows 3.1. The statistical evaluation for cholesterol, cholesterol ester, Oleic acid+linoleic acid and Sum FFA are illustrated in FIGS. 130 to 133.

GLC analysis of lipids in Mozzarella has confirmed the effect of KLM3 on cholesterol (see FIG. 130) and the formation of cholesterol ester (see FIG. 131). Cheese produced with KLM3 contains only 40% cholesterol compared with the control cheese. Lecitase did not show any affect on the cholesterol level and no cholesterol ester was formed in control and Lecitase treated cheese.

Because of the transfer reaction it is also seen that the amount of free fatty acids in the cheeses produced with KLM3 is lower than in cheese produced with Lecitase. This is clearly seen for the unsaturated fatty acids oleic acid and linoleic acids (see FIG. 132), which are lower in the trials with KLM3 compared with Lecitase. However the differences are less pronounced for Palmetic acid and Stearic acid (see Table 45). It is known that pancreas phospholipase—Lecitase is very specific for the sn-2 position of the phospholipids and thus primary produces unsaturated fatty acids. Some unspecific hydrolytic activity of KLM3 is known, which can explain the formation of saturated fatty acids from sn-1 position of phospholipids in milk fat.

In this experiment it is seen that almost all phospholipids are degraded after 30 minutes enzymation of the cream. However the enzyme reaction continues during the standardization of the cheese milk until the cheese milk was pasteurized. The ongoing enzyme reaction after enzymation of cream, until the cheese milk is pasteurized explains the formation saturated fatty acids C16:0 and C18:0 in the experiment with KLM3. This is also confirmed by the fact that no saturated fatty acids are formed in cream after 30 minutes enzymation with KLM3, but is only seen in the cheese. The formation of saturated fatty acids in the experiment with KLM3 can be reduced or prevented by reducing the incubation time of the cream.

Conclusion

Enzymation of cream for use in Mozzarella cheese production has shown that KLM3 and Lecitase were very active on phospholipids in milk fat. An almost complete conversion of the phospholipids phosphatidylcholine and phosphatidylethanolamine were observed.

The activity of Lecitase on phospholipids contributed to an increase in free fatty acids. The fatty acids produced were mainly the unsaturated fatty acids oleic acid and linoleic acid, because Lecitase is sn-2 specific and the unsaturated fatty acids are most abundant in the sn-2 position of the phospholipids.

KLM3 however produced less free fatty acids because this enzyme transfers fatty acids from phospholipids to cholesterol during formation of cholesterol ester.

Lipid analysis of lipid extracted from the final product Mozzarella cheese showed almost the same lipid profiles as observed for the cream used to produce the Mozzarella cheese.

Example 28

Moisture Analysis

Cheese from six experiments with the use of enzyme in pilot scale Mozzarella cheese production (see Example 25) were analyzed for moisture content by standard method IDF 4A, 1982 and the fat content was determined by the standard method IDF 5B, 1986 from International Dairy Federation.

Results:

TABLE 46

Analysis of moisture and fat content.

| Cheese | | % Moisture | % Fat |
|---|---|---|---|
| DAN011 | Control | 48.75 | 23.26 |
| DAN012 | Lecitase | 50.95 | 23.02 |
| DAN013 | KLM3 | 52.03 | 22.70 |
| DAN021 | Control | 48.67 | 24.69 |
| DAN022 | Lecitase | 49.60 | 24.25 |
| DAN023 | KLM3 | 51.66 | 23.67 |

The moisture content of the cheese was influenced by the enzyme treatment; the KLM3 acyl transferase significantly increased the moisture content of the cheese, both when compared to the lecitase as well as the control. This partly explains the increased yield obtained by the enzyme treatment. The percentage of fat in the cheese thus decreases slightly due to the total increase in yield.

Example 29

Oiling Off Analysis

Cheese from experiments with the use of enzyme in pilot scale Mozzarella cheese production (see Example 25) were analyzed for oiling off by a diffusion test. After production the cheeses matured for 8 days at 6° C.

Oiling Off Diameter Test:

Cheese samples (2 g) were ground up and pressed into a 2 cm wide ring using a weight of 16 g dropped from a 5 cm height, applied three times in order to make a compact mass. This is a key point for measuring the oiling off, unless the amount of force used to create the sample is known (along with the resistance of the material being compacted) it will be unclear as to the density of the final mass which has a direct effect on oiling off during heating (see FIG. 134).

The samples were placed on Whatman number 4 filter papers and heated together in a drying oven at 90.0° C. for 5 minutes.

Measurements of oiling off as determined by the diameter of translucent zones seen on the filter papers were measured after 10 minutes.

Results:

TABLE 47 oiling off

| Cheese | Mean | SD | Av. Area/mm2 | % of control area |
|---|---|---|---|---|
| DAN011 | 32.33 | 1.25 | 821.09 | |
| DAN013 | 25.00 | 2.16 | 490.87 | 59.78 |

DAN011 (left) and the cheese produced with KLM3 DAN013 (right). 5 minutes standing after heating step.

Conclusions:

As can be seen from the results, after 10 minutes the day the KLM3 cheese did indeed register significantly less oiling off than the control.

Example 30

Melting Test

Cheese from experiments with the use of enzyme in pilot scale Mozzarella cheese production (see Example 25) were analyzed for melting ability by the tube method described by Olsen (Olsen, N F. & W V. Price, Journal of Dairy Science 1958, Vol. 41: 999-1000). The cheese flow is measured as percentage change from the starting point before heating the tube (Olsen 1958).

Results:

TABLE 48 cheese flow results.

| Cheese | | Cheese flow (%) |
|---|---|---|
| DAN011 | Control | 211 |
| DAN012 | Lecitase | 217 |

TABLE 48-continued cheese flow results.

| Cheese | | Cheese flow (%) |
|---|---|---|
| DAN013 | KLM3 | 221 |
| DAN021 | Control | 168 |
| DAN022 | Lecitase | 200 |
| DAN023 | KLM3 | 200 |

No statistically significant difference was observed in the melting test for the cheese, thus neither Lecitase nor the acyl transferase KLM3 changed the melting properties of the cheese.

Melting properties was also determined by baking a pizza, to determine visual changes of the mozzarella cheese as compared to the control without enzyme. The cheese showed less oiling off on the pizza and normal melting properties.

Example 31

Expression of a Lipid Acyltransferase in *Bacillus licheniformis*

A nucleotide sequence (SEQ ID No. 100) encoding a lipid acyltransferase (SEQ. ID No. 90, hereinafter KLM3) was expressed in *Bacillus licheniformis* as a fusion protein with the signal peptide of *B. licheniformis* [alpha]-amylase (LAT) (see FIGS. 137 and 138). For optimal expression in *Bacillus*, a codon optimized gene construct (no. 052907) was ordered at Geneart (Geneart AG, Regensburg, Germany).

Construct no. 052907 contains an incomplete LAT promoter (only the −10 sequence) in front of the LAT-KLM3' precursor gene and the LAT transcription (Tlat) downstream of the LAT-KLM3' precursor gene (see FIGS. 137 and 139). To create a XhoI fragment that contains the LAT-KLM3' precursor gene flanked by the complete LAT promoter at the 5' end and the LAT terminator at the 3' end, a PCR (polymerase chain reaction) amplification was performed with the primers Plat5XhoI_FW and EBS2XhoI_RV and gene construct 052907 as template.

```
Plat5XhoI_FW:
                                       (SEQ ID NO: 59)
ccccgctcgaggcttttcttttggaagaaaatatagggaaaatggtactt gttaaaaattcggaatatttatacaatatcatatgtttcacattgaaagg gg EBS2XhoI_RV:
                                       (SEQ ID NO: 60)
tggaatctcgaggttttatcctttaccttgtctcc
```

PCR was performed on a thermocycler with Phusion High Fidelity DNA polymerase (Finnzymes OY, Espoo, Finland) according to the instructions of the manufacturer (annealing temperature of 55 [deg.] C.).

The resulting PCR fragment was digested with restriction enzyme XhoI and ligated with T4 DNA ligase into XhoI digested pICatH according to the instructions of the supplier (Invitrogen, Carlsbad, Calif. USA).

The ligation mixture was transformed into *B. subtilis* strain SC6.1 as described in U.S. Patent Application US20020182734 (International Publication WO 02/14490). The sequence of the XhoI insert containing the LAT-KLM3' precursor gene was confirmed by DNA sequencing (BaseClear, Leiden, The Netherlands) and one of the correct plasmid clones was designated pICatH-KLM3'(ori1) (FIG. 137). pICatH-KLM3'(ori1) was transformed into *B. licheniformis* strain BML780 (a derivative of BRA7 and BML612, see WO2005111203) at the permissive temperature (37 [deg.] C.).

One neomycin resistant (neoR) and chloramphenicol resistant (CmR) transformant was selected and designated BML780(pICatH-KLM3'(ori1)). The plasmid in BML780 (pICatH-KLM3'(ori1)) was integrated into the catH region on the *B. licheniformis* genome by growing the strain at a non-permissive temperature (50 [deg.] C) in medium with 5 [mu] g/ml chloramphenicol. One CmR resistant clone was selected and designated BML780-pICatH-KLM3'(ori1). BML780-pICatH-KLM3'(ori1) was grown again at the permissive temperature for several generations without antibiotics to loop-out vector sequences and then one neomycin sensitive (neoS), CmR clone was selected. In this clone, vector sequences of pICatH on the chromosome are excised (including the neomycin resistance gene) and only the catH-LATKLM3' cassette is left. Next, the catH-LATKLM3' cassette on the chromosome was amplified by growing the strain in/on media with increasing concentrations of chloramphenicol. After various rounds of amplification, one clone (resistant against 50 [mu]g/ml chloramphenicol) was selected and designated BML780-KLM3'CAP50. To verify KLM3'expression, BML780-KLM3'CAP50 and BML780 (the empty host strain) were grown for 48 h at 37 [deg.] C on a Heart Infusion (Bacto) agar plate with 1% tributyrin. A clearing zone, indicative for lipid acyltransferase activity, was clearly visible around the colony of BML780-KLM3'CAP50 but not around the host strain BML780 (see FIG. 140). This result shows that a substantial amount of KLM3' is expressed in *B. licheniformis* strain BML780-KLM3'CAP50 and that these KLM3' molecules are functional.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention will now be further described by the following numbered paragraphs:

1. A method for the in situ production of an emulsifier in a foodstuff, wherein the method comprises the step of adding a lipid acyltransferase to the foodstuff.

2. A method according to paragraph 1 wherein at least 2 emulsifiers are produced.

3. A method according to paragraph 1 or paragraph 2 wherein the emulsifier is produced without increasing or substantially increasing the free fatty acids in the foodstuff.

4. A method according to any one of paragraphs 1-3 wherein the lipid acyltransferase is one which is capable of transferring an acyl group from a lipid to one or more of the following acyl acceptors: a sterol, a stanol, a carbohydrate, a protein or a sub-unit thereof, glycerol.

5. A method according to paragraph 2 wherein at least one of the emulsifiers is a carbohydrate ester.

6. A method according to paragraph 2 wherein at least one of the emulsifiers is a protein ester.

7. A method according to any one of the preceding paragraphs wherein one or more of a sterol ester or a stanol ester or a protein ester or a carbohydrate ester or a diglyceride or a monoglyceride is produced in situ in the foodstuff.

8. A method according to paragraph 7 wherein the sterol ester is one or more of alpha-sitosterol ester, beta-sitosterol ester, stigmasterol ester, ergosterol ester, campesterol ester or cholesterol ester.

9. A method according to paragraph 6 wherein the stanol ester is one or more beta-sitostanol or ss-sitostanol.

10. A method according to any one of the preceding paragraphs wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

11. A method according to any one of the preceding paragraphs wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

12. A method according to any one of the preceding paragraphs wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter*, Vibrionaceae, *Xylella, Sulfolobus, Aspergillus, Schizosaccharomyces, Listeria, Neisseria, Mesorhizobium, Ralstonia, Xanthomonas* and *Candida*.

13. A method according to any one of the preceding paragraphs wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SEQ ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID No. 62, (xvi) the amino acid sequence shown as SEQ ID No. 90, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34, SEQ ID No. 62 or SEQ ID No. 90.

14. A method according to any one of the preceding paragraphs, wherein the emulsifier is one or more of the following: a monoglyceride, a lysophosphatidylcholine, DGMG.

15. Use of a lipid acyltransferase to prepare from a food material a foodstuff comprising an emulsifier, wherein the emulsifier is produced without increasing or without substantially increasing the free fatty acids in the foodstuff, and wherein the emulsifier is generated from constituents of the food material by the lipid acyltransferase.

16. Use according to paragraph 15 wherein at least two emulsifiers are produced.

17. Use according to paragraph 16 wherein at least one of the emulsifiers is a carbohydrate ester.

18. Use according to paragraph 16 wherein at least one of the emulsifiers is a protein ester.

19. Use according to any one of paragraphs 15-18 wherein one or more of a sterol ester or a stanol ester or a protein ester or a carbohydrate ester or a diglyceride or a monoglyceride is also produced in situ in the foodstuff.

20. Use according to paragraph 19 wherein the sterol ester is one or more of alpha-sitosterol ester, beta-sitosterol ester, stigmasterol ester, ergosterol ester, campesterol ester or cholesterol ester.

21. Use according to paragraph 20 wherein the stanol ester is one or more beta-sitostanol or ss-sitostanol.

22. Use according to any one of paragraphs 15 to 21 wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

23. Use according to any one of paragraphs 15-22 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

24. Use according to any one of paragraphs 15-23 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter*, Vibrionaceae, *Xylella, Sulfolobus, Aspergillus, Schizosaccharomyces, Listeria, Neisseria, Mesorhizobium, Ralstonia, Xanthomonas* and *Candida*.

25. Use according to any one of paragraphs 15-24 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SEQ ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID No. 62, (xvi) the amino acid sequence shown as SEQ ID No. 90, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34, SEQ ID No. 62 or SEQ ID No. 90.

26. Use according to any one of paragraphs 15-25, wherein the emulsifier is one or more of the following: a monoglyceride, a lysophosphatidylcholine, DGMG.

27. A food or feed enzyme composition which contains a lipid acyltransferase.

28. A food or feed enzyme composition according to paragraph 27 wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

29. A food or feed enzyme composition according to paragraph 27 or paragraph 28 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

30. A food or feed enzyme composition according to any one of paragraphs 27-29 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter*, Vibrionaceae, *Xylella, Sulfolobus, Aspergillus, Schizosaccharomyces, Listeria, Neisseria, Mesorhizobium, Ralstonia, Xanthomonas* and *Candida*.

31. A food or feed enzyme composition according to any one of paragraphs 27-30 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SEQ ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID No. 62, (xvi) the amino acid sequence shown as SEQ ID No. 90, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34, SEQ ID No. 62 or SEQ ID No. 90.

32. Use of a food or feed enzyme composition according to any one of paragraphs 27-31 in accordance with any one of paragraphs 15-26 or in the method according to any one of paragraphs 1-14.

33. A foodstuff obtainable by the method according to any one of paragraphs 1-14.

34. An immobilised lipid acyltransferase enzyme.

35. An immobilised lipid acyltransferase according to paragraph 34 wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

36. An immobilised lipid acyltransferase according to paragraph 34 or paragraph 35 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

37. An immobilised lipid acyltransferase according to any one of paragraphs 34-36 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter*, Vibrionaceae, Xylella, Sulfolobus, Aspergillus, Schizosaccharomyces, Listeria, Neisseria, Mesorhizobium, Ralstonia, Xanthomonas and Candida.

38. An immobilised lipid acyltransferase according to any one of paragraphs 34-37 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SEQ ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID No. 62, (xvi) the amino acid sequence shown as SEQ ID No. 90, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34, SEQ ID No. 62 or SEQ ID No. 90.

39. A method of identifying a suitable lipid acyltransferase for use in accordance with the present invention, comprising the steps of testing an enzyme of interest using one or more of the "Transferase Assay in a Low Water environment", the "Transferase Assay in High Water Egg Yolk" or the "Transferase Assay in Buffered Substrate", and selecting a lipid acyltransferase if it is one which has one or more of the following characteristics: (a) when tested using the "Transferase Assay in a Low Water Environment", measured after a time period selected from 30, 20 or 120 minutes, has a relative transferase activity of at least 1%; (b) when tested using the "Transferase Assay in High Water Egg Yolk" in an egg yolk with 54% water, has up to 100% relative transferase activity; or (c) when tested using the "Transferase Assay in Buffered Substrate" has at least 2% acyltransferase activity.

40. A method according to paragraph 39 wherein the lipid acyltransferase is selected if it is one which has more than two of the following characteristics (a) when tested using the "Transferase Assay in a Low Water Environment", measured after a time period selected from 30, 20 or 120 minutes, has a relative transferase activity of at least 1%; (b) when tested using the "Transferase Assay in High Water Egg Yolk" in an egg yolk with 54% water, has up to 100% relative transferase activity; or (c) when tested using the "Transferase Assay in Buffered Substrate" has at least 2% acyltransferase activity.

41. A method according to paragraph 39 wherein the lipid acyltransferase is selected if it is one which has more than three of the following characteristics (a) when tested using the "Transferase Assay in a Low Water Environment", measured after a time period selected from 30, 20 or 120 minutes, has a relative transferase activity of at least 1%; (b) when tested using the "Transferase Assay in High Water Egg Yolk" in an egg yolk with 54% water, has up to 100% relative transferase activity; or (c) when tested using the "Transferase Assay in Buffered Substrate" has at least 2% acyltransferase activity.

42. A method according to paragraph 39 wherein the lipid acyltransferase is selected if it is one which has all of the following characteristics (a) when tested using the "Transferase Assay in a Low Water Environment", measured after a time period selected from 30, 20 or 120 minutes, has a relative transferase activity of at least 1%; (b) when tested using the "Transferase Assay in High Water Egg Yolk" in an egg yolk with 54% water, has up to 100% relative transferase activity; or (c) when tested using the "Transferase Assay in Buffered Substrate" has at least 2% acyltransferase activity.

43. A lipid acyltransferase identified using a method according to any one of paragraphs 39-42.

---

The invention claimed is:

1. A method for the in situ production of an emulsifier in a foodstuff, wherein the method comprises the step of adding a lipid acyltransferase to the foodstuff wherein the lipid acyltransferase is one which is capable of transferring an acyl group from a lipid to one or more of the following acyl acceptors: a sterol, a stanol, a carbohydrate, a protein or a sub-unit thereof, glycerol; wherein one or more of a sterol ester or a stanol ester or a protein ester or a carbohydrate ester or a diglyceride or a monoglyceride is produced in situ in the foodstuff and wherein the lipid acyltransferase when tested using the Transferase Assay in Buffered Substrate has at least 5% acyltransferase activity (relative acyltransferase activity) wherein the Transferase Assay in Buffered Substrate comprises:
(a) heating to 35° C. a substrate solution comprising phosphatidylcholine, cholesterol, water and HEPES buffer, wherein the substrate solution comprises approximately 95% water and has pH 7.0;
(b) adding an enzyme to the substrate solution; and
(c) determining acyltransferase activity of the enzyme based upon cholesterol ester and fatty acids formed.

2. A method according to claim 1 wherein at least 2 emulsifiers are produced.

3. A method according to claim 1 wherein the emulsifier is produced without increasing or substantially increasing the free fatty acids in the foodstuff.

4. A method according to claim 2 wherein at least one of the emulsifiers is a carbohydrate ester.

5. A method according to claim 2 wherein at least one of the emulsifiers is a protein ester.

6. A method according to claim 1 wherein the sterol ester is one or more of alpha-sitosterol ester, beta-sitosterol ester, stigmasterol ester, ergosterol ester, campesterol ester or cholesterol ester.

7. A method according to claim 5 wherein the stanol ester is one or more beta-sitostanol or ss-sitostanol.

8. A method according to claim 1 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

9. A method according to claim 1 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

10. A method according to claim 1 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SED ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID No. 62, (xvi) the amino acid sequence shown as SEQ ID No. 90, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32 or SEQ ID No. 34, SEQ ID No. 62 or SEQ ID No. 90.

11. A method according to claim 1, wherein the emulsifier is one or more of the following: a monoglyceride, a lysophosphatidylcholine, DGMG.

12. A method of preparing a foodstuff comprising an emulsifier, comprising the step of contacting a food material with a lipid acyltransferase, wherein an emulsifier is thereby produced by reaction of the lipid acyltransferase with one or more consistuents of the food material, without increasing or without substantially increasing the free fatty acids in the foodstuff, wherein the lipid acyltransferase is one which is capable of transferring an acyl group from a lipid to one or more of the following acyl acceptors: a sterol, a stanol, a carbohydrate, a protein or a sub-unit thereof, glycerol; wherein one or more of a sterol ester or a stanol ester or a protein ester or a carbohydrate ester or a diglyceride or a monoglyceride is produced in situ in the foodstuff and wherein the lipid acyltransferase when tested using the Transferase Assay in Buffered Substrate has at least 5% acyltransferase activity (relative acyltransferase activity) wherein the Transferase Assay in Buffered Substrate comprises:
(a) heating to 35° C. a substrate solution comprising phosphatidylcholine, cholesterol, water and HEPES buffer, wherein the substrate solution comprises approximately 95% water and has pH 7.0;
(b) adding an enzyme to the substrate solution; and
(c) determining acyltransferase activity of the enzyme based upon cholesterol ester and fatty acids formed.

13. The method according to claim 12 wherein at least two emulsifiers are produced.

14. The method according to claim 13 wherein at least one of the emulsifiers is a carbohydrate ester.

15. The method according to claim 13 wherein at least one of the emulsifiers is a protein ester.

16. The method according to claim 12 wherein the sterol ester is one or more of alpha-sitosterol ester, beta-sitosterol ester, stigmasterol ester, ergosterol ester, campesterol ester or cholesterol ester.

17. The method according to claim 16 wherein the stanol ester is one or more beta-sitostanol or ss-sitostanol.

18. The method according to claim 12 wherein the lipid acyltransferase is characterised as an enzyme which possesses acyl transferase activity and which comprises the amino acid sequence motif GDSX, wherein X is one or more of the following amino acid residues L, A, V, I, F, Y, H, Q, T, N, M or S.

19. The method according to claim 12 wherein the lipid acyltransferase enzyme comprises H-309 or comprises a histidine residue at a position corresponding to His-309 in the amino acid sequence of the *Aeromonas hydrophila* lipolytic enzyme shown as SEQ ID No. 2 or SEQ ID No. 32.

20. The method according to claim 12 wherein the lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

21. The method according to claim 12 wherein the lipid acyltransferase comprises one or more of the following amino acid sequences: (i) the amino acid sequence shown as SEQ ID No. 2; (ii) the amino acid sequence shown as SEQ ID No. 3; (iii) the amino acid sequence shown as SEQ ID No. 4; (iv) the amino acid sequence shown as SED ID No. 5; (v) the amino acid sequence shown as SEQ ID No. 6; (vi) the amino acid sequence shown as SEQ ID No. 12, (vii) the amino acid sequence shown as SEQ ID No. 20, (viii) the amino acid sequence shown as SEQ ID No. 22, (ix) the amino acid sequence shown as SEQ ID No. 24, (x) the amino acid sequence shown as SEQ ID No. 26, (xi) the amino acid sequence shown as SEQ ID No. 28, (xii) the amino acid sequence shown as SEQ ID No. 30, (xiii) the amino acid sequence shown as SEQ ID No. 32, (xiv) the amino acid sequence shown as SEQ ID No. 34, (xv) the amino acid sequence shown as SEQ ID No. 62, (xvi) the amino acid sequence shown as SEQ ID No. 90, or an amino acid sequence which has 75% or more identity with any one of the sequences shown as SEQ ID No. 2, SEQ ID No. 3, SEQ ID No. 4, SEQ ID No. 5, SEQ ID No. 6, SEQ ID No. 12, SEQ ID No. 20, SEQ ID No. 22, SEQ ID No. 24, SEQ ID No. 26, SEQ ID No. 28, SEQ ID No. 30, SEQ ID No. 32, SEQ ID No. 34, SEQ ID No. 62 or SEQ ID No. 90.

22. The method according to claim 12, wherein the emulsifier is one or more of the following: a monoglyceride, a lysophosphatidylcholine, DGMG.

* * * * *